US008202865B2

(12) United States Patent
Quattropani et al.

(10) Patent No.: US 8,202,865 B2
(45) Date of Patent: Jun. 19, 2012

(54) OXADIAZOLE DERIVATIVES

(75) Inventors: Anna Quattropani, Geneva (CH); Cyril Montagne, Saint-Genis-Pouilly (FR); Wolfgang Sauer, Chambesy (CH); Stefano Crosignani, St. Genis-Pouilly (FR); Agnes Bombrun, Chambesy (CH); Mathilde Muzerelle, Gaillard (FR); Jermone Dorbais, Annecy (FR); Delphine Marin, Arthaz-Pont-Notre Dame (FR); Jerome Gonzalez, Ville la Grand (FR); Patrick Gerber, Etoy (CH)

(73) Assignee: Merck Serono SA, Coinsins, Vaud (CH)

( * ) Notice: Subject to any disclaimer, the term of this patent is extended or adjusted under 35 U.S.C. 154(b) by 0 days.

(21) Appl. No.: 12/675,235

(22) PCT Filed: Oct. 1, 2008

(86) PCT No.: PCT/EP2008/063180
§ 371 (c)(1),
(2), (4) Date: Feb. 25, 2010

(87) PCT Pub. No.: WO2009/043889
PCT Pub. Date: Apr. 9, 2009

(65) Prior Publication Data
US 2010/0240658 A1 Sep. 23, 2010

Related U.S. Application Data

(60) Provisional application No. 60/998,254, filed on Oct. 9, 2007.

(30) Foreign Application Priority Data

Oct. 4, 2007 (EP) .................................... 07117921

(51) Int. Cl.
A61K 31/5377 (2006.01)
A61K 31/454 (2006.01)
A61K 31/4439 (2006.01)
A61K 31/4245 (2006.01)
C07D 413/02 (2006.01)
C07D 271/06 (2006.01)

(52) U.S. Cl. .................... 514/236.2; 514/326; 514/340; 514/364; 544/138; 546/209; 546/269.1; 548/131

(58) Field of Classification Search ............... 514/236.2, 514/364, 340, 326; 548/131; 546/269.1; 546/209; 544/138
See application file for complete search history.

(56) References Cited

U.S. PATENT DOCUMENTS

| 4,135,910 A | 1/1979 | Howe |
| 2008/0200535 A1 | 8/2008 | Ohmori et al. |

FOREIGN PATENT DOCUMENTS

| DE | 4320801 | 1/1995 |
| GB | 1 584 716 | 2/1981 |
| WO | WO 00/64927 | 11/2000 |
| WO | WO 2004/091502 | 10/2004 |
| WO | WO 2005/032465 | 4/2005 |
| WO | WO 2005/058848 | 6/2005 |
| WO | WO 2005/115382 | 12/2005 |
| WO | WO 2006/131336 | 12/2006 |
| WO | WO 2007/043400 | 4/2007 |
| WO | WO 2008/023783 | 2/2008 |
| WO | WO 2008/037476 | 4/2008 |
| WO | WO 2008/076356 | 6/2008 |
| WO | WO 2008/152149 | 12/2008 |
| WO | WO 2009/043890 | 4/2009 |

OTHER PUBLICATIONS

Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Joel R. Huff, HIV Protease: A Novel Chemotherapeutic Target for AIDS, 1991, Journal of Medicinal Chemistry, vol. 34, No. 8, 2305-2314.*
Vippagunta et al., Crystalline solids, 2001, Advanced Drug Delivery Reviews, 48, pp. 3 and 18.*
Wolff et al., Burgers Medicinal Chemistry and Drug Discovery, 1994, Wiley-Interscience, Fifth Edition, vol. I: Principles and Practice, pp. 975-977.*
Cho, S. Y. et al. "Protein Tyrosine Phosphatase 1B Inhibitors: Heterocyclic Carboxylic Acids" *Bull. Korean Chem. Soc.*, 2003, pp. 1455-1464, vol. 24, No. 10, XP-002467994. Yan, L. et al. "Discovery of 3-arylpropionic acids as potent agonists of sphingosine-1-phosphate receptor-1 (S1P$_1$) with high selectivity against all other known S1P receptor subtypes" *Bioorganic & Medicinal Chemistry Letters*, 2006, pp. 3679-3683, vol. 16, XP-005477311.
Database Registry Chemical Abstracts Service, Columbus, Ohio, Accession No. RN 937669-94-8, Jun. 17, 2007, p. 1, XP-002467995.
Database Registry Chemical Abstracts Service, Columbus, Ohio, Accession No. RN 937669-95-9, Jun. 17, 2007, p. 1, XP-002467996.
Database Registry Chemical Abstracts Service, Columbus, Ohio, Accession No. RN 937670-06-9, Jun. 17, 2007, p. 1, XP-002467997.
Database Registry Chemical Abstracts Service, Columbus, Ohio, Accession No. RN 937681-49-7, Jun. 17, 2007, p. 1, XP-002467998.
Database Registry Chemical Abstracts Service, Columbus, Ohio, Accession No. RN 937697-96-6, Jun. 17, 2007, p. 1, XP-002467999.
Database Registry Chemical Abstracts Service, Columbus, Ohio, Accession No. RN 937681-63-5, Jun. 17, 2007, p. 1, XP-002468000.
Database Registry Chemical Abstracts Service, Columbus, Ohio, Accession No. RN 937681-77-1, Jun. 17, 2007, p. 1, XP-002468001.

(Continued)

*Primary Examiner* — Kamal Saeed
*Assistant Examiner* — Kristin Bianchi
(74) *Attorney, Agent, or Firm* — Saliwanchik, Lloyd & Eisenschenk

(57) ABSTRACT

The invention relates to compounds of formula I:

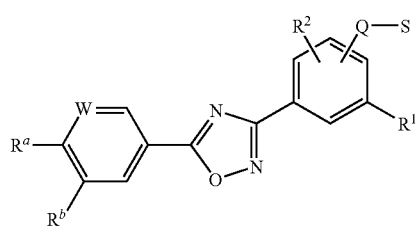

wherein $R^1$, $R^2$, $R^a$, $R^b$, W, Q and S have the meanings given in claim 16. The compounds are useful e.g. in the treatment of autoimmune disorders, such as multiple sclerosis.

37 Claims, No Drawings

OTHER PUBLICATIONS

Database Chemcats Chemical Abstracts Service, Columbus, Ohio, Accession No. 2037051069, Aug. 13, 2007, p. 1, XP-002468003.
Database Registry Chemical Abstracts Service, Columbus, Ohio, Accession No. RN 894518-34-4, Jul. 19, 2006, p. 1, XP-002531330.
Database Registry Chemical Abstracts Service, Columbus, Ohio, Accession No. RN 832683-65-5, Feb. 17, 2005, p. 1, XP-002531331.
Written Opinion in International Application No. PCT/EP2008/063180, Jun. 10, 2009, pp. 1-13.
Rosen, H. et al. "Tipping the gatekeeper: S1P regulation of endothelial barrier function" *Trends in Immunology*, 2007, pp. 102-107, vol. 28, No. 3.
Yoshida, M. et al. "Study of biodegradable copoly (L-lactic acid/glycolic acid) formulations with controlled release of Z-100 for application in radiation therapy" *International Journal of Pharmaceutics*, 1995, pp. 61-67, vol. 115.
Cyster, J. G. "Chemokines, Sphingosine-1-Phosphate, and Cell Migration in Secondary Lymphoid Organs" *Ann. Rev. Immunol.*, 2005, pp. 127-159, vol. 23.
Rosen, H. et al. "Sphingosine 1-Phosphate and its Receptors: An Autocrine and Paracrine Network" *Nature*, Jul. 2005, pp. 560-570, vol. 5.
Kappos, L. et al. "Oral Fingolimod (FTY720) for Relapsing Multiple Sclerosis" *N. Eng. J. Med.*, Sep. 14, 2006, pp. 1124-1140, vol. 355.
Massberg, S. et al. "Fingolimod and Sphingosine-1-Phosphate-Modifiers of Lympho-cyte Migration" *N. Eng. J. Med.*, Sep. 14, 2006, pp. 1088-1091, vol. 355, No. 2.
Yopp, A. C. et al. "Sphingosine 1-phosphate receptor modulators: a new class of immunosuppressants" *Clin Transplant*, 2006, pp. 788-795, vol. 20.
Tyle, P. "Iontophoretic Devices for Drug Delivery" *Pharmaceutical Research*, 1986, pp. 318-326, vol. 3, No. 6.
Database CHEMCATS, Accession No. 2028111707, Oxadiazole, Oct. 5, 2007, XP-002466530, p. 1.
Database CHEMCATS, Accession No. 2038041362, Piperazine, Sep. 6, 2007, XP-002466528, pp. 1-3.
Database CHEMCATS, Accession No. 2039084421, 1, 2, 4-Oxadiazole, Oct. 2, 2007, XP-002466529, p. 1.
Bulgarevich, S.B. et al. "Molecular Polarizability of Organic Compounds and Their Complexes. Part XIV.*Kerr Constants and Dipole Moments of Products of the Reaction of 4-Oxo-1,3-Benzoxazinium Salts with Hydroxylamine and Methylhydrazine" *Scientific Research Institute of Physical and Organic Chemistry*, Rostov-on-Don, Sep. 29, 1980, pp. 1418-1422.
Written Opinion in International Application No. PCT/EP2008/063185, Feb. 9, 2009, pp. 1-7.
Pending claims in U.S. Appl. No. 12/675,254, filed Feb. 25, 2010.
Liu, Q. et al. "FTY720 demonstrates promising preclinical activity for chronic lymphocytic leukemia and lymphoblastic leukemia/lymphoma" *Blood*, Jan. 1, 2008, pp. 275-284, vol. 111, No. 1.

* cited by examiner

OXADIAZOLE DERIVATIVES

CROSS-REFERENCE TO RELATED APPLICATION

This application is the U.S. national stage application of International Patent Application No. PCT/EP2008/063180, filed Oct. 1, 2008, which claims the benefit of U.S. Provisional Patent Application No. 60/998,254, filed Oct. 9, 2007, the disclosures of which are hereby incorporated by reference in their entirety, including all figures, tables and amino acid or nucleic acid sequences.

The present invention relates to oxadiazoles, their use as medicaments and their use for treating multiple sclerosis and other diseases.

In particular, the invention relates to compounds of formula (I):

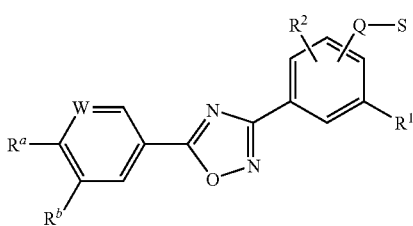

wherein
$R^1$, $R^2$ denote H, Hal, $CF_3$, $OCF_3$, CN, or $NO_2$, OH, A, OA,
S is $COOR^3$, $SO_2NH_2$, $CON(R^3)_2$ or Z
Q denotes $X(CH_2)_m$, $(CH_2)_mX(CH_2)_n$, or a single bond,
X is —O—, —$NR^3$—, —COO— or —$CONR^3$—
W denotes CH or N,
$R^a$ is Ar, Het, $NA_2$, $NO_2$, or if $R^1$ or $R^2$ is Hal, or if Q is $(CH_2)_mX(CH_2)_m$, also OA.
$R^b$ is, A, Hal, $OCF_3$, $(CH_2)_nOH$, $(CH_2)_nOA$, CN, $NO_2$, $N(R^3)_2$, $(CH_2)_nSO_2N(R^3)_2$, $SO_2N(R^3)_2$, $(CH_2)_n$ $NR^3SO_2A$, $(CH_2)_nSO_2A$, $(CH_2)_nN(SO_2A)_2$, $NR^3CON(R^3)_2$ or $NR^3COA$, $NR^3SO_2N(R^3)_2$, or if $R^1$ or $R^2$ is Hal, also $CF_3$, $OR^3$.
A is branched or linear alkyl having 1 to 12 C-atoms, wherein one or more, preferably 1 to 7 H-atoms may be replaced by Hal, $OR^3$, $COOR^3$, CN, $N(R^3)_2$ or Het and wherein one or more, preferably 1 to 7 non-adjacent $CH_2$-groups may be replaced by O, $NR^3$, CO or S and/or by —CH=CH— or —C≡C— groups or cycloalkylene groups having 3 to 7 carbon atoms, or denotes cycloalkyl or cycloalkylalkylen having 3-7 ring C atoms
Z is branched or linear alkyl chain having 1 to 12 C-atoms, wherein one or more, preferably 1 to 7 H-atoms are replaced by $OR^3$, $COOR^3$, $CON(R^3)_2$, CN, $SO_2A$, $N(R^3)_2$ or Het and/or wherein one or more, preferably 1 to 7 non-adjacent $CH_2$-groups are replaced by —O—, —COO—, —$NR^3$—, —NBoc-, —CO— or —S—, —$SO_2$— and/or by —CH=CH— or —C≡C— groups or cycloalkylene groups having 3 to 7 carbon atoms, or denotes cycloalkyl or cycloalkylalkylen having 3-7 ring C atoms
Hal is F, Cl, Br or I,
Ar denotes a monocyclic or bicyclic, saturated, unsaturated or aromatic carbocyclic ring having 6 to 14 carbon atoms, which may be monosubstituted, disubstituted or trisubstituted by Hal, A, $OR^3$, $N(R^3)_2$, $NO_2$, CN, $COOR^3$, $CF_3$, $OCF_3$, $CON(R^3)_2$, $NR^3COA$, $NR^3CON$ $(R^3)_2$, $NR^3SO_2A$, $COR^3$, $SO_2N(R^3)_2$, SOA or $SO_2A$, phenyl, pyridyl —$[C(R^3)_2]_n$—$COOR^3$ and/or —O[C $(R^3)_2$], —$CON(R^3)_2$, such that at least one atom adjacent to the atom linking the group Ar to the rest of the molecule bears one of said substituents.
Het denotes a monocyclic or bicyclic, saturated, unsaturated or aromatic heterocyclic ring having 1 to 4 N, O and/or S atoms which may be monosubstituted, disubstituted or trisubstituted by Hal, A, —$[C(R^3)_2]_n$—Ar, —$[C(R^3)_2]_n$-cycloalkyl, $OR^3$, $CF_3$, $OCF_3$, $N(R^3)_2$, $NR^3CON(R^3)_2$, $NO_2$, CN, —$[C(R^3)_2]_n$—$COOR^3$, —[C $(R^3)_2$], —$CON(R^3)_2$, $NR^3COA$, $NR^3SO_2A$, $COR^3$, $SO_2N(R^3)_2$, SOA, phenyl, pyridyl and/or $SO_2A$, such that at least one atom adjacent to the atom linking the group Het to the rest of the molecule bears one of said substituents.
$R^3$ is H or A; 2 geminal groups $R^3$ together may form a ring with the atom they are attached to.
n is 0, 1, 2, 3, 4, 5, 6, 7 or 8,
and
m is 1, 2, 3, 4, 5, 6, 7 or 8
and pharmaceutically acceptable derivatives, solvates, tautomers, salts and stereoisomers thereof, including mixtures thereof in all ratios.

The compounds of formula (I) are preferably binding on receptors for sphingosine 1-phosphate (S1P). S1P is a bioactive sphingolipid metabolite that is secreted by hematopoietic cells and stored and released from activated platelets. It acts as an agonist on a family of G protein-coupled receptors (GPCR). Five sphingosine 1-phosphate receptors have been identified ($S1P_1$, $S1P_2$, $S1P_3$, $S1P_4$, and $S1P_5$, also known as endothelial differentiation genes, which are Edg1, Edg5, Edg3, Edg6 and Edg8 respectively), that have widespread cellular and tissue distribution and are well conserved in human and rodent species.

S1P is involved in a number of cellular functions such as survival, proliferation and immunological responses. The compounds of the present invention are preferably acting as $S1P_1$/Edg1 receptor agonists and thus have immunosuppressive activities by modulating leukocyte trafficking, sequestering lymphocytes in secondary lymphoid tissues, and interfering with cell-cell interactions required for an efficient immune response. The invention is also directed to pharmaceutical compositions containing such compounds and methods of treatment or prevention.

FTY720 or fingolimod, a non selective $S1P_1$ agonist, exerts immunosuppressive activity and shows therapeutic effects in the treatment of relapsing-remitting multiple sclerosis. Numerous publications have been already published using this compound: Cyster J G Annu Rev Immunol 23:127-59, 2005, Rosen H Nat Rev Immunol 5:560-570, 2005, Rosen H Trends Immunol 28:102-107, 2007, Yopp A C Clin Transplant 20:788-795, 2006, Kappos L N Engl J Med 355:1124-1140, 2006, Massberg S N Engl J Med 355:1088-1089, 2006.

Immunosuppressive agents are further useful in a wide variety of autoimmune and chronic inflammatory diseases, including systemic lupus erythematosus, chronic rheumatoid arthritis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves opthalmopathy, atopic dermatitis and asthma. They are also useful as part of chemotherapeutic regimens for the treatment of cancers, lymphomas and leukemias.

Patent application WO2006/131336 describes oxadiazoles derivatives containing a biphenyl ring. Further oxadiazole derivatives containing a phenyl group substituted with a cycloalkyl group are known from Bioorg Med. Chem. Lett. 16 (2006) 3679-3683.

It has been found that the compounds of the present invention are selective $S1P_1$ agonists with improved pharmacological and/or other properties.

The present invention uses compounds of Formula (I) and pharmaceutically usable derivatives, salts, tautomers, solvates and stereoisomers thereof, including mixtures thereof in all ratios, for the preparation of a medicament for the treatment and/or prophylaxis of diseases in which the inhibition, activation, regulation, and/or modulation of $S1P_1$ receptor signal transduction plays a role.

Thus, the present invention preferably comprises compounds which are agonists of the $S1P_1$/Edg1 receptor, especially having selectivity over the $S1P_3$/Edg3 receptor. An $S1P_1$/Edg1 receptor selective agonist has advantages over current therapies and extends the therapeutic window of lymphocyte sequestration agents, allowing better tolerability with higher dosing and thus improving efficacy.

The invention further relates to the manufacture of a medicament for the improvement of vascular function, either alone or in combination with other active compounds or therapies.

The oxadiazole compounds according to formula (I) may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The following abbreviations refer respectively to the definitions below:

aq (aqueous), h (hour), g (gram), L (liter), mg (milligram), MHz (Megahertz), μM (micromolar) min. (minute), mm (millimeter), mmol (millimole), mM (millimolar), m.p. (melting point), eq (equivalent), mL (milliliter), μL (microliter), ACN (acetonitrile), BINAP (2,2'-bis(disphenylphosphino)-1,1'-binaphthalene, BOC (tert-butoxycarbonyl), CBZ (carbobenzoxy), $CDCl_3$ (deuterated chloroform), $CD_3OD$ (deuterated methanol), $CH_3CN$ (acetonitrile), c-hex (cHex), DCC (dicyclohexyl carbodiimide), DCM (DCM), dppf (1,1'-bis(diphenylphosphino)ferrocene), DIC (diisopropyl carbodiimide), DIEA (diisopropylethyl-amine), DMF (dimethylformamide), DMSO (dimethylsulfoxide), DMSO-d6 (deuterated dimethylsulfoxide), EDC (1-(3-dimethyl-aminopropyl)-3-ethylcarbodiimide), ESI (Electro-spray ionization), EtOAc (EtOAc), Et2O (diethyl ether), EtOH (ethanol), FMOC (fluorenylmethyloxycarbonyl), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), K2CO3 (potassium carbonate), LC (Liquid Chromatography), MD Autoprep (Mass directed Autoprep), MeOH (methanol), MgSO4 (magnesium sulfate), MS (mass spectrometry), MTBE (Methyl tert-butyl ether), Mtr. (4-Methoxy-2,3, 6-trimethylbenzensulfonyl), MW (microwave), NBS (N-bromo succinimide), NaHCO3 (sodium bicarbonate), NaBH4 (sodium borohydride), NMM (N-methyl morpholine), NMR (Nuclear Magnetic Resonance), POA (phenoxyacetate), Py (pyridine), PyBOPO (benzotriazole-1-yl-oxy-tris-pyrrolidino-phosphonium hexafluorophosphate), RT (RT), Rt (retention time), SPE (solid phase extraction), TBTU (2-(1-H-benzotriazole-1-yl)-1,1,3,3-tetramethyluromium tetrafluoroborate), TEA (triethylamine), TFA (trifluoroacetic acid), THF (THF), TLC (Thin Layer Chromatography), UV (Ultraviolet).

Depending on the nature of $R^1$, $R^2$, $R^a$, $R^b$, W, Q, and S, different synthetic strategies may be selected for the synthesis of compounds of formula (I). In the process illustrated in the following schemes $R^1$, $R^2$, $R^a$, $R^b$, W, Q, and S, are as above-defined in the description.

In general, the oxadiazole compounds according to formula (I) of this invention may be prepared from readily available starting materials. If such starting materials are not commercially available they may be prepared by standard synthetic techniques. The following general methods and procedures described hereinafter in the examples may be employed to prepare compounds of formula (I). Reaction conditions depicted in the following schemes, such as temperatures, solvent, or co-reagents, are given as examples only and are not restrictive.

Generally, compounds of formula (I'), wherein $R^1$, $R^2$, $R^a$, $R^b$, W and Q are defined as above, can be prepared by hydrolysis of the ester derivatives of formula (I''), wherein $R^3$ is as above defined and more preferably $R^3$ is a methyl or tertbutyl group, using conditions well known to those skilled in the art, such as a metal hydroxide, e.g. lithium hydroxide, sodium hydroxide or potassium hydroxide, in a suitable solvent such as THF, methanol, ethanol or water or mixtures thereof, or using an acid, e.g. HCl or TFA, in a suitable solvent such as dioxane, DCM, at a temperature between about 20° C. to about 50° C., preferably at RT, for a few hours, e.g. one hour to 24 h (Scheme 1).

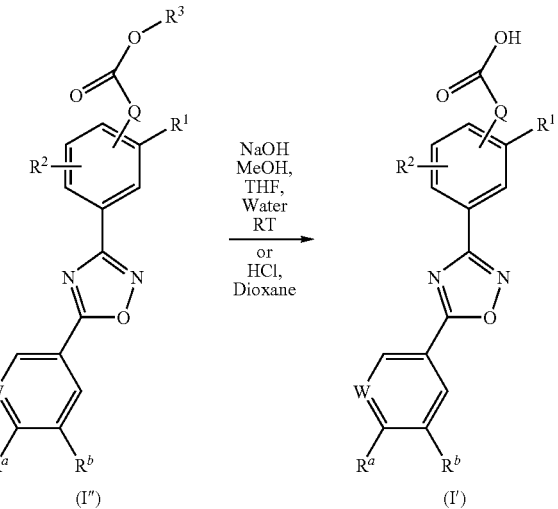

The compounds of formula (I), wherein $R^1$, $R^2$, $R^a$, $R^b$, W, Q, and S are defined as above, can be obtained in a 2-step protocol as outlined in Scheme 2. The first step consists in the coupling of a carboxylic acid of formula (VII) with an amidoxime of formula (VI), wherein $R^1$, $R^2$, $R^a$, $R^b$, W, Q, and S are defined as above. General protocols for such coupling are given below in the examples, using conditions and methods well known to those skilled in the art to prepare an O-substituted amidoximes (V) from a carboxylic acid (VII) and an aryl amidoxime (VI), with standard coupling agents, such as but not limited to EDC, HATU, TBTU, in the presence or absence of bases such as TEA, DIEA, NMM in a suitable solvent such as DCM, ACN, THF or DMF, at a temperature rising from about 20° C. to about 50° C., preferably at RT, for a few hours, e.g. one hour to 24 h. Alternatively, a carboxylic acid derivative (e.g. acyl chloride VIIa) may be coupled with the amidoxime (VI), using conditions and methods well known to those skilled in the art, in the presence of bases such as TEA, DIEA, NMM in a suitable solvent such as DCM, THF or DMF, at a temperature rising from about 20° C. to about 50° C., preferably at RT, for a few hours, e.g. one hour to 24 h (Scheme 3). The second step consists of the cyclization and dehydration of the O-substituted amidoximes (V) to form oxadiazole (I). Conditions are given below in the examples, using methods well known to those skilled in the art to prepare oxadiazole, such as thermolysis at temperature rising from RT to about 150° C., typically 150° C., using possibly a microwave oven, for a time comprised between 15 minutes and 24 hours, preferably for 30 min, in a suitable solvent or mixture of solvents such as ACN, THF, Pyridine, DMF, in the presence or absence of a base such as DIEA, TEA, or tetrabutyl ammonium fluoride.

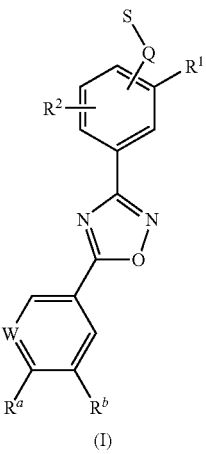

(I)

Scheme 2

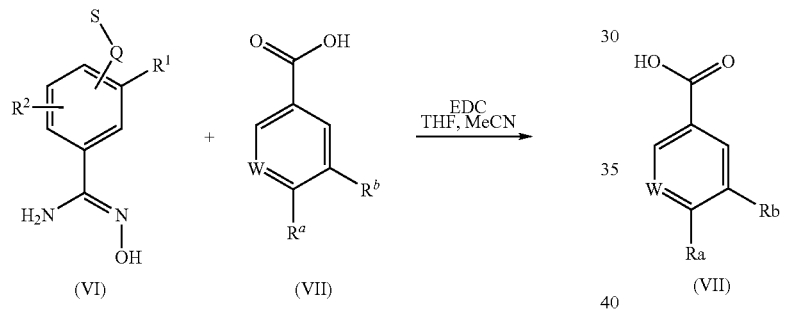

(VII)

Scheme 3

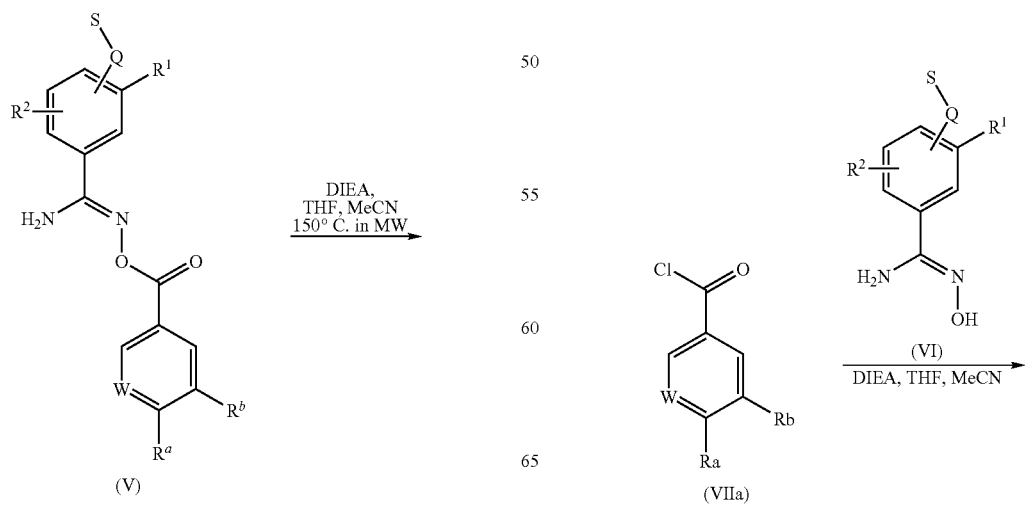

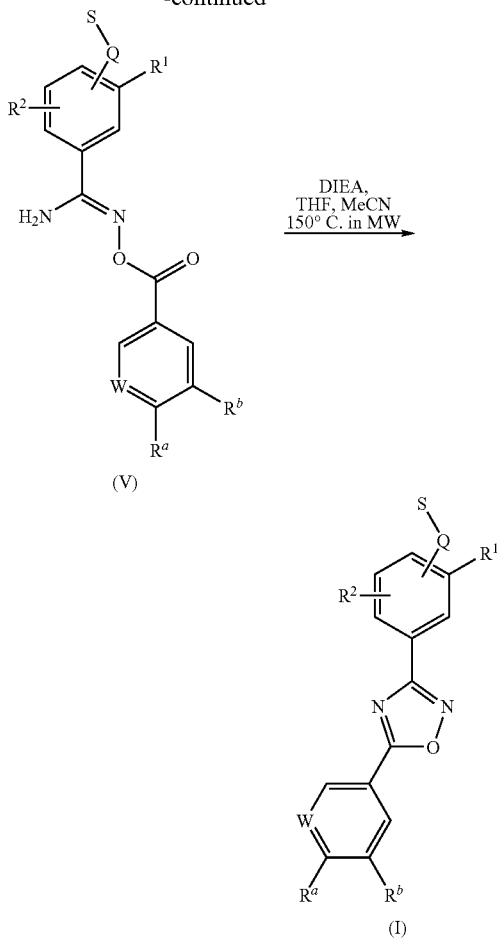

The method for preparing the compounds of formula (I") selected below:

methyl 2-fluoro-4-{5-[2'-(trifluoromethyl)biphenyl-4-yl]-1,2,4-oxadiazol-3-yl}benzoate
methyl 4-[5-(2'-chlorobiphenyl-4-yl)-1,2,4-oxadiazol-3-yl]-2-fluorobenzoate
methyl 4-[5-(2',6'-dimethylbiphenyl-4-yl)-1,2,4-oxadiazol-3-yl]-2-fluorobenzoate
methyl 4-[5-(2,2'-dimethylbiphenyl-4-yl)-1,2,4-oxadiazol-3-yl]-2-fluorobenzoate
methyl 2-fluoro-4-[5-(2'-methylbiphenyl-4-yl)-1,2,4-oxadiazol-3-yl]benzoate
methyl 2-fluoro-4-[5-(2-methylbiphenyl-4-yl)-1,2,4-oxadiazol-3-yl]benzoate
methyl 2-fluoro-4-[5-(2'-methoxy-2-methylbiphenyl-4-yl)-1,2,4-oxadiazol-3-yl]benzoate
methyl 2-fluoro-4-{5-[2-methyl-2'-(trifluoromethyl)biphenyl-4-yl]-1,2,4-oxadiazol-3-yl}benzoate
methyl 2-fluoro-4-{5-[3-methyl-4-(4-methyl-3-thienyl)phenyl]-1,2,4-oxadiazol-3-yl}benzoate
methyl 4-[5-(2,2'-dimethylbiphenyl-4-yl)-1,2,4-oxadiazol-3-yl]-3-fluorobenzoate
methyl 2-fluoro-4-[5-(2'-methyl-2-nitrobiphenyl-4-yl)-1,2,4-oxadiazol-3-yl]benzoate
methyl 2-fluoro-4-{5-[3-methoxy-4-(4-methyl-3-thienyl)phenyl]-1,2,4-oxadiazol-3-yl}benzoate
methyl 2-fluoro-4-[5-(2-methoxy-2'-methylbiphenyl-4-yl)-1,2,4-oxadiazol-3-yl]benzoate
methyl 2-fluoro-4-[5-(3-nitro-4-piperidin-1-ylphenyl)-1,2,4-oxadiazol-3-yl]benzoate
methyl 2-fluoro-4-{5-[4-(2-methylpiperidin-1-yl)-3-nitrophenyl]-1,2,4-oxadiazol-3-yl}benzoate
methyl 2-fluoro-4-[5-(3-methyl-4-piperidin-1-ylphenyl)-1,2,4-oxadiazol-3-yl]benzoate
methyl 2-fluoro-4-{5-[4-morpholin-4-yl-3-(trifluoromethyl)phenyl]-1,2,4-oxadiazol-3-yl}benzoate
methyl 2-fluoro-4-[5-(3-methyl-4-morpholin-4-ylphenyl)-1,2,4-oxadiazol-3-yl]benzoate
methyl 2-fluoro-4-{5-[4-(2-methylpiperidin-1-yl)-3-(trifluoromethyl)phenyl]-1,2,4-oxadiazol-3-yl}benzoate
methyl 4-[5-(2',4'-dimethoxy-2-methylbiphenyl-4-yl)-1,2,4-oxadiazol-3-yl]-2-fluorobenzoate
methyl 2-fluoro-4-[5-(4-nitro-3-piperidin-1-ylphenyl)-1,2,4-oxadiazol-3-yl]benzoate
methyl 2-fluoro-4-{5-[2'-methyl-2-(trifluoromethyl)biphenyl-4-yl]-1,2,4-oxadiazol-3-yl}benzoate
methyl 2-fluoro-4-{5-[4-(4-methyl-3-thienyl)-3-(trifluoromethyl)phenyl]-1,2,4-oxadiazol-3-yl}benzoate
methyl 4-[5-(2',5'-dimethoxy-2-methylbiphenyl-4-yl)-1,2,4-oxadiazol-3-yl]-2-fluorobenzoate
methyl 4-{5-[4-(3,5-dimethylisoxazol-4-yl)-3-methylphenyl]-1,2,4-oxadiazol-3-yl}-2-fluorobenzoate
methyl 3-fluoro-4-{5-[3-methyl-4-(4-methyl-3-thienyl)phenyl]-1,2,4-oxadiazol-3-yl}benzoate
methyl 3-fluoro-4-{5-[4-(2-methylpiperidin-1-yl)-3-(trifluoromethyl)phenyl]-1,2,4-oxadiazol-3-yl}benzoate
methyl 2-fluoro-4-{5-[4-(2-methoxypyridin-3-yl)-3-methylphenyl]-1,2,4-oxadiazol-3-yl}benzoate
methyl 4-{5-[3-cyano-4-(2-methylpiperidin-1-yl)phenyl]-1,2,4-oxadiazol-3-yl}-2-fluorobenzoate
methyl 2-fluoro-4-(5-{4-(2-methylpiperidin-1-yl)-3-[(methylsulfonyl)amino]phenyl}-1,2,4-oxadiazol-3-yl)benzoate
methyl 2-fluoro-4-[5-(2-methyl-1,1':2',1"-terphenyl-4-yl)-1,2,4-oxadiazol-3-yl]benzoate
methyl 2-fluoro-4-[5-(2'-hydroxy-2-methylbiphenyl-4-yl)-1,2,4-oxadiazol-3-yl]benzoate
methyl 2-fluoro-5-{5-[4-(2-methylpiperidin-1-yl)-3-(trifluoromethyl)phenyl]-1,2,4-oxadiazol-3-yl}benzoate
methyl 4-[5-(5,6-dichloropyridin-3-yl)-1,2,4-oxadiazol-3-yl]-2-fluorobenzoate
Methyl 2-fluoro-4-{5-[2-(methoxymethyl)-2'-methylbiphenyl-4-yl]-1,2,4-oxadiazol-3-yl}benzoate
methyl 4-[5-(2,2'-dimethylbiphenyl-4-yl)-1,2,4-oxadiazol-3-yl]benzoate
methyl 5-[5-(2,2'-dimethylbiphenyl-4-yl)-1,2,4-oxadiazol-3-yl]-2-hydroxybenzoate
methyl 2-hydroxy-5-{5-[3-methyl-4-(4-methyl-3-thienyl)phenyl]-1,2,4-oxadiazol-3-yl}benzoate
methyl 4-[5-(2,2'-dimethylbiphenyl-4-yl)-1,2,4-oxadiazol-3-yl]-3-methoxybenzoate
methyl 4-[5-(2,2'-dimethylbiphenyl-4-yl)-1,2,4-oxadiazol-3-yl]-2-methoxybenzoate
tert-butyl (2-fluoro-4-{5-[4-(2-methylpiperidin-1-yl)-3-(trifluoromethyl)phenyl]-1,2,4-oxadiazol-3-yl}phenoxy)acetate
tert-butyl {4-[5-(2,2'-dimethylbiphenyl-4-yl)-1,2,4-oxadiazol-3-yl]-2-fluorophenoxy}acetate
tert-butyl {4-[5-(5,6-dichloropyridin-3-yl)-1,2,4-oxadiazol-3-yl]-2-fluorophenoxy}acetate
methyl N-{4-[5-(2,2'-dimethylbiphenyl-4-yl)-1,2,4-oxadiazol-3-yl]-2-fluorobenzoyl}glycinate
methyl N-{4-[5-(2,2'-dimethylbiphenyl-4-yl)-1,2,4-oxadiazol-3-yl]-2-fluorobenzoyl}-beta-alaninate
tert-butyl N-{4-[5-(2,2'-dimethylbiphenyl-4-yl)-1,2,4-oxadiazol-3-yl]-2-fluorophenyl}glycinate tert-butyl N-methyl-N-[3-(5-{4-(2-methylpiperidin-1-yl)-3-[(methylsulfonyl)amino]phenyl}-1,2,4-oxadiazol-3-yl)benzyl]glycinate
methyl 2-fluoro-4-{5-[2-(hydroxymethyl)-2'-methylbiphenyl-4-yl]-1,2,4-oxadiazol-3-yl}benzoate
methyl 2-fluoro-4-[5-(2'-methyl-2-{[(methylsulfonyl)oxy]methyl}biphenyl-4-yl)-1,2,4-oxadiazol-3-yl]benzoate
methyl 4-{5-[2-(ethoxymethyl)-2'-methylbiphenyl-4-yl]-1,2,4-oxadiazol-3-yl}-2-fluorobenzoate
methyl 2-fluoro-4-(5-{4-isobutoxy-3-[(methylsulfonyl)amino]phenyl}-1,2,4-oxadiazol-3-yl)benzoate
methyl 4-{5-[3-(acetylamino)-4-(2-methylpiperidin-1-yl)phenyl]-1,2,4-oxadiazol-3-yl}-2-fluorobenzoate
methyl 2-fluoro-4-(5-{4-[isobutyl(propyl)amino]-3-[(methylsulfonyl)amino]phenyl}-1,2,4-oxadiazol-3-yl)benzoate
methyl 4-{5-[3-[(ethylsulfonyl)amino]-4-(2-methylpiperidin-1-yl)phenyl]-1,2,4-oxadiazol-3-yl}-2-fluorobenzoate
methyl 2-chloro-4-[5-(2,2'-dimethylbiphenyl-4-yl)-1,2,4-oxadiazol-3-yl]benzoate
methyl 2-chloro-4-{5-[2-(methoxymethyl)-2'-methylbiphenyl-4-yl]-1,2,4-oxadiazol-3-yl}benzoate
methyl 2-chloro-4-(5-{4-(2-methylpiperidin-1-yl)-3-[(methylsulfonyl)amino]phenyl}-1,2,4-oxadiazol-3-yl)benzoate
methyl 4-{5-[3-(propionylamino)-4-(2-methylpiperidin-1-yl)phenyl]-1,2,4-oxadiazol-3-yl}-2-fluorobenzoate
methyl 2-fluoro-4-{5-[4-(2-methylpiperidin-1-yl)-3-nitrophenyl]-1,2,4-oxadiazol-3-yl}benzoate
methyl 4-{5[3-[(propylsulfonyl)amino]-4-(2-methylpiperidin-1-yl)phenyl]-1,2,4-oxadiazol-3-yl}-2-fluorobenzoate
methyl 2-fluoro-4-{5-[2-methyl-2-(morpholin-4-ylmethyl)biphenyl-4-yl]-1,2,4-oxadiazol-3-yl}benzoate
methyl 2-fluoro-4-{5-[2'-methoxy-2-(methoxymethyl)biphenyl-4-yl]-1,2,4-oxadiazol-3-yl}benzoate
methyl 2-fluoro-4-{5-[2'-fluoro-2-(methoxymethyl)biphenyl-4-yl]-1,2,4-oxadiazol-3-yl}benzoate
methyl 4-{5-[2',3'-dimethoxy-2-(methoxymethyl)biphenyl-4-yl]-1,2,4-oxadiazol-3-yl}-2-fluorobenzoate
methyl 2-fluoro-4-{5-[2'-methyl-2-(methylsulfonyl)biphenyl-4-yl]-1,2,4-oxadiazol-3-yl}benzoate
methyl 2-fluoro-4-{5-[5'-fluoro-2-(methoxymethyl)-2'-methylbiphenyl-4-yl]-1,2,4-oxadiazol-3-yl}benzoate
methyl 4-{5-[2,2'-bis(methoxymethyl)biphenyl-4-yl]-1,2,4-oxadiazol-3-yl}-2-fluorobenzoate
methyl 2-fluoro-4-{5-[2-(methoxymethyl)-2'-(trifluoromethyl)biphenyl-4-yl]-1,2,4-oxadiazol-3-yl}benzoate
methyl 2-fluoro-4-{5-[2'-(methoxymethyl)-2-methylbiphenyl-4-yl]-1,2,4-oxadiazol-3-yl}benzoate
methyl 2-chloro-4-(5-{2'-methyl-2-[(methylsulfonyl)methyl]biphenyl-4-yl}-1,2,4-oxadiazol-3-yl)benzoate
methyl 2-fluoro-4-{5-[5'-fluoro-2'-methoxy-2-(methoxymethyl)biphenyl-4-yl]-1,2,4-oxadiazol-3-yl}benzoate
methyl 4-{5-[2'-ethoxy-2-(methoxymethyl)biphenyl-4-yl]-1,2,4-oxadiazol-3-yl}-2-fluorobenzoate
methyl 4-{5-[2',5'-difluoro-2-(methoxymethyl)biphenyl-4-yl]-1,2,4-oxadiazol-3-yl}-2-fluorobenzoate
methyl 3-{5-[2-(methoxymethyl)-2'-methylbiphenyl-4-yl]-1,2,4-oxadiazol-3-yl}benzoate
methyl 2-fluoro-4-{5-[3-(methoxymethyl)-4-(4-methyl-3-thienyl)phenyl]-1,2,4-oxadiazol-3-yl}benzoate
methyl 2-fluoro-4-{5-[4'-fluoro-2-(methoxymethyl)-2'-methylbiphenyl-4-yl]-1,2,4-oxadiazol-3-yl}benzoate
methyl 2-fluoro-4-{5-[2-(methoxymethyl)-2',3'-dimethylbiphenyl-4-yl]-1,2,4-oxadiazol-3-yl}benzoate
methyl 2,5-difluoro-4-{5-[2-(methoxymethyl)-2'-methylbiphenyl-4-yl]-1,2,4-oxadiazol-3-yl}benzoate
methyl 4-{5-[2'-chloro-2-(methoxymethyl)biphenyl-4-yl]-1,2,4-oxadiazol-3-yl}-2-fluorobenzoate
methyl 2-fluoro-4-[5-(2-hydroxy-2'-methylbiphenyl-4-yl)-1,2,4-oxadiazol-3-yl]benzoate
methyl 2-chloro-5-{5-[2-(methoxymethyl)-2'-methylbiphenyl-4-yl]-1,2,4-oxadiazol-3-yl}benzoate
methyl 2-chloro-5-fluoro-4-{5-[2-(methoxymethyl)-2'-methylbiphenyl-4-yl]-1,2,4-oxadiazol-3-yl}benzoate
methyl 2-fluoro-5-methoxy-4-{5-[2-(methoxymethyl)-2'-methylbiphenyl-4-yl]-1,2,4-oxadiazol-3-yl}benzoate
methyl 2-chloro-5-methoxy-4-{5-[2-(methoxymethyl)-2'-methylbiphenyl-4-yl]-1,2,4-oxadiazol-3-yl}benzoate
tert-butyl N-(3-{5-[2-(methoxymethyl)-2'-methylbiphenyl-4-yl]-1,2,4-oxadiazol-3-yl}benzyl)-N-methylglycinate
tert-butyl N-(3-{5-[2'-ethyl-2-(methoxymethyl)biphenyl-4-yl]-1,2,4-oxadiazol-3-yl}benzyl)-N-methylglycinate
tert-butyl N-(2-fluoro-5-{5-[2-(methoxymethyl)-2'-methylbiphenyl-4-yl]-1,2,4-oxadiazol-3-yl}benzyl)-N-methylglycinate
tert-butyl N-(5-{5-[2'-ethyl-2-(methoxymethyl)biphenyl-4-yl]-1,2,4-oxadiazol-3-yl}-2-fluorobenzyl)-N-methylglycinate
tert-butyl N-(3-{5-[4-isopropoxy-3-(methoxymethyl)phenyl]-1,2,4-oxadiazol-3-yl}benzyl)-N-methylglycinate
tert-butyl N-(2-fluoro-5-{5-[2-(methoxymethyl)-2'-methylbiphenyl-4-yl]-1,2,4-oxadiazol-3-yl}benzyl)-N-methyl-beta-alaninate
tert-butyl N-(2-fluoro-5-{5-[3-(methoxymethyl)-4-(2-methylpiperidin-1-yl)phenyl]-1,2,4-oxadiazol-3-yl}benzyl)-N-methylglycinate
tert-butyl N-(2-fluoro-5-{5-[2-(methoxymethyl)-2'-methylbiphenyl-4-yl]-1,2,4-oxadiazol-3-yl}benzyl)-N-methyl-beta-alaninate
tert-butyl N-(5-{5-[2'-ethyl-2-(methoxymethyl)biphenyl-4-yl]-1,2,4-oxadiazol-3-yl}-2-fluorobenzyl)-N-methyl-beta-alaninate
tert-butyl N-(2-fluoro-5-{5-[4-isopropoxy-3-(methoxymethyl)phenyl]-1,2,4-oxadiazol-3-yl}benzyl)-N-methyl-beta-alaninate
tert-butyl N-(2-fluoro-5-{5-[4-isopropoxy-3-(methoxymethyl)phenyl]-1,2,4-oxadiazol-3-yl}benzyl)-N-methylglycinate
tert-butyl [(3-{5-[2-(methoxymethyl)-2'-methylbiphenyl-4-yl]-1,2,4-oxadiazol-3-yl}benzyl)oxy]acetate
tert-butyl [2-(3-{5-[2-(methoxymethyl)-2'-methylbiphenyl-4-yl]-1,2,4-oxadiazol-3-yl}phenyl)ethoxy]acetate
ethyl 4-(4-{5-[2'-ethyl-2-(methoxymethyl)biphenyl-4-yl]-1,2,4-oxadiazol-3-yl}-2-fluorophenoxy)butanoate
ethyl 4-(3-{5-[3-(methoxymethyl)-4-(2-methylpiperidin-1-yl)phenyl]-1,2,4-oxadiazol-3-yl}phenoxy)butanoate
tert-butyl (2-fluoro-4-{5-[2-(methoxymethyl)-2'-methylbiphenyl-4-yl]-1,2,4-oxadiazol-3-yl}phenoxy)acetate
ethyl 4-(2-fluoro-4-{5-[2-(methoxymethyl)-2'-methylbiphenyl-4-yl]-1,2,4-oxadiazol-3-yl}phenoxy)butanoate
tert-butyl (2-fluoro-4-{5-[3-(methoxymethyl)-4-(2-methylpiperidin-1-yl)phenyl]-1,2,4-oxadiazol-3-yl}phenoxy)acetate
is more particularly described in the examples.

Compounds of formula (VII), wherein $R^a$, $R^b$ and W are defined as above, are either commercially available or may be prepared by standard synthetic techniques, as hereinafter described in the examples, for example by metal catalyzed coupling reaction or aromatic nucleophilic substitution on the corresponding halogenated benzoic acid or alkyl benzoate. Alternatively, compounds of formula (VII), wherein $R^a$, $R^b$ and W are defined as above, may be obtained by metal catalyzed cross-coupling reaction followed by hydrolysis of the resulting ester (XI), as shown in Scheme 4 below. More particularly, they may be obtained by Suzuki-Miyura coupling reaction between an alkyl benzoate (VIII), where $R^c$ may preferably be Br, I or a sulfonate ester such as triflate, and a boronic acid (Xa) or ester (Xb), using well known Suzuki-Miyura reaction conditions such as shown in Scheme 4 (Miyaura, N.; Suzuki, A. *Chem. Rev.* 1995, 95, 2457; Takahiro I. and Toshiaki M., *Tetrahedron Lett.* 2005, 46, 3573-3577). In a typical procedure, alkyl benzoate (VIII) and boronic acid (Xa) or ester (Xb) are heated at various temperature by traditional thermic methods or using microwave technology in the presence of a base such as but not limited to a carbonate salt, e.g. $K_2CO_3$, $Na_2CO_3$, $Cs_2CO_3$, and a catalytic amount of palladium catalyst such as $Pd(PPh_3)_4$, $PdCl_2(PPh_3)_2$, $Pd(OAc)_2$, with the possible addition of phosphine ligands such as $PPh_3$, S-Phos, X-Phos in an appropriate solvent or mixture of solvents such as THF, Toluene, Dioxane, MeOH, ACN, DMF, water. All the different combinations described above may be used. Alternatively, alkyl benzoate (IX) wherein $R^c$ is as above defined and boronic acid (Xc) or ester (Xd) may be coupled under the same palladium catalyzed procedure as described above. The resulting ester (XI) can then be hydrolyzed using conditions well known to those skilled in the art, such as but not limited to the use of a metal hydroxide, e.g. lithium hydroxide, sodium hydroxide or potassium hydroxide, in a suitable solvent such as THF, methanol, ethanol or water or mixtures thereof, at a temperature rising from about 20° C. to about 60° C., preferably at RT, for a few hours, e.g. one hour to 24 h.

Scheme 4

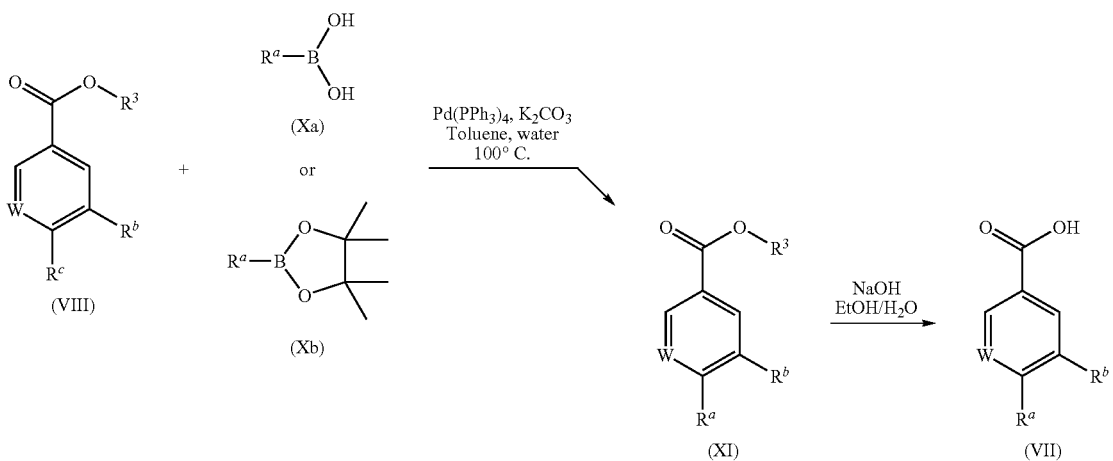

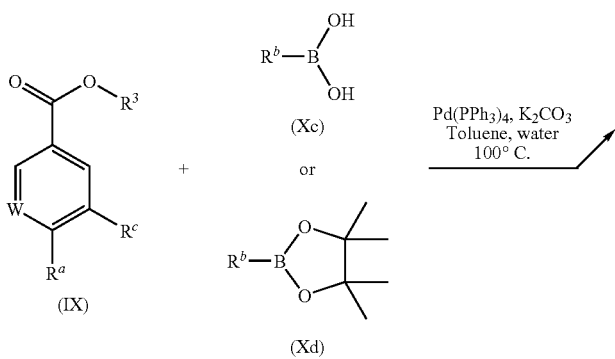

An alternative route for the preparation of compounds of formula (VII), wherein $R^a$, $R^b$ and W are defined as above, maybe via Suzuki-Miyura coupling reaction between an alkyl benzoate boronic acid or ester derivative of formula (XII) or (XIII), where $R^d$ is a boronic acid or tetramethyl-dioxaborolane, with an optionally substituted aryl, respectively (Xe) and (Xf), where $R^c$ is preferably Br, I or a sulfonate ester such as triflate, using well known Suzuki-Miyura reaction conditions such as shown in Scheme 5 below and described above. The resulting ester can be hydrolyzed into compounds of formula (VII) under conditions described above and in the examples below.

(VII) under conditions described above and in the examples below. Alternatively, an amino derivative of formula (Xg) and (Xh) can be added respectively to benzonitrile (XIVa) and (XIVb) under similar conditions as the one described above and in the examples below. The resulting benzonitrile of formula (XIV) can be hydrolyzed into the corresponding ester (XI), using conditions well known to those skilled in the art, such as but not limited to the use of an acid, e.g. HCl, in a suitable solvent such as THF, methanol or water or mixtures thereof, at a temperature rising from about 20° C. to about 100° C., preferably at 78° C., for 12 h to 48 h.

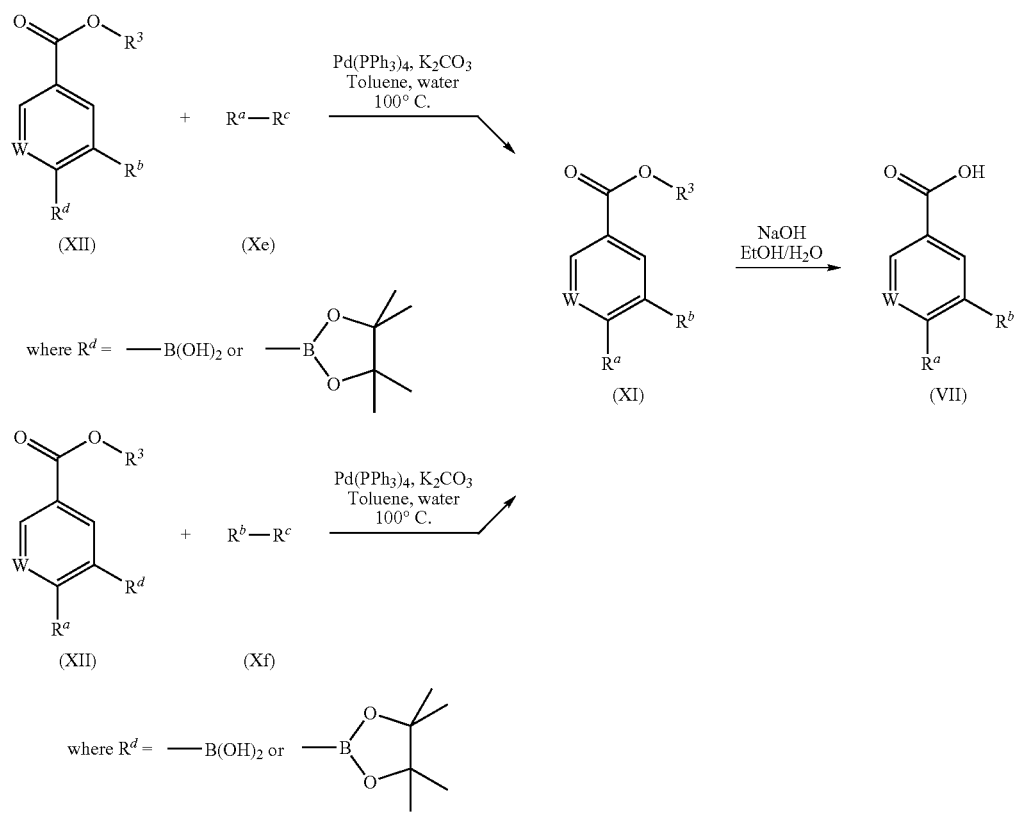

An alternative route for the preparation of compounds of formula (VII), wherein $R^a$, $R^b$ and W are defined as above, may be the addition of an amino derivative $R^aH$ of formula (Xg) to an alkyl benzoate of formula (VIIIa) or a benzoic acid of formula (VIIIb), as outlined in Scheme 6, in the optional presence of a suitable base, such as TEA, DIEA, NMM in a solvent such as THF or DMF, at a temperature rising from about 20° C. to about 100° C., preferably at RT, for a few hours, e.g. one hour to 24 h. An amino derivative $R^aH$ of formula (Xg) can be also used neat, as solvent. Alternatively, compounds of formula (VII) may be obtained by addition of an amino derivative $R^bH$ of formula (Xh) to an alkyl benzoate (IXa) or a benzoic acid (IXb), as outlined in Scheme 6, under reaction conditions described above and in the examples below. In the cases where ester of formula (XI) is first obtained, it can be hydrolyzed into compounds of formula

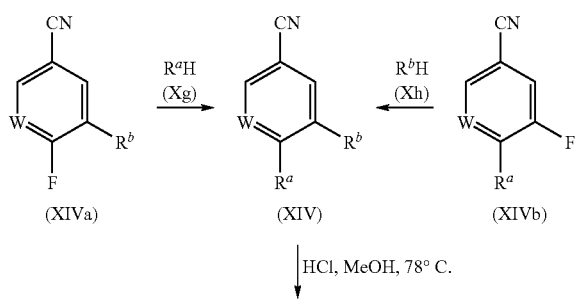

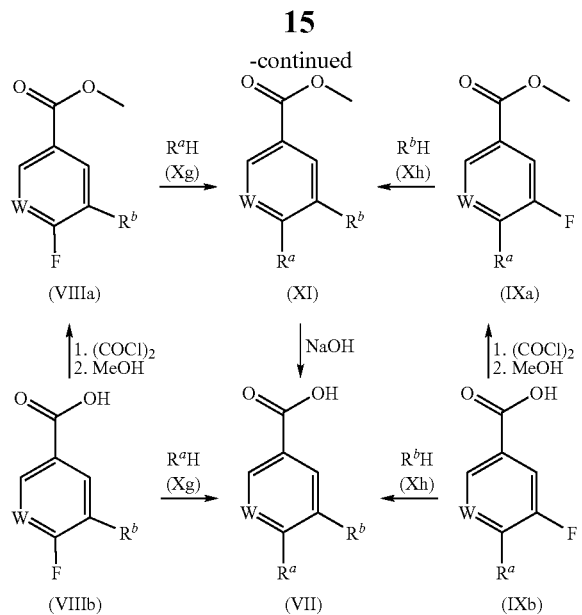

Compounds of formula (VIIIa) and (IXa), wherein $R^a$, $R^b$ and W are defined as above, are either commercially available or may be prepared by standard synthetic techniques, as hereinafter described in the examples. Typically, they may be prepared by esterification of the corresponding benzoic acid, (VIIIb) and (IXb) respectively, such as but not limited to the formation of the corresponding acid chloride with oxalyl chloride, followed by the addition of the suitable alcohol, such as MeOH for methyl carboxylate, at temperatures ranging from about 0° C. to about 50° C., preferably at RT for a few hours, e.g. one hour to 24 hours.

Alternatively, compounds of formula (VII), wherein $R^a$, $R^b$ and W are defined as above, may be obtained by metal catalyzed cross-coupling reaction followed by hydrolysis of the resulting ester of formula (XI), as shown in Scheme 7 below. More particularly, they may be obtained by Buchwald-Hartwig cross-coupling reaction between an alkyl benzoate of formula (VIII) or (IX), where $R^c$ may preferably be Br, I or a sulfonate ester such as triflate, and an amino derivative, respectively (Xg) or (Xh), using well known Buchwald-Hartwig reaction conditions such as shown in Scheme 7 below (Muci, A. R.; Buchwald, S. L. *Top. Curr. Chem.* 2002, 219, 131-209; Jiang, L.; Buchwald, S. L. *Metal-Catalyzed Cross-Coupling Reactions* (2$^{nd}$ Edition) 2004, 2, 699-760). In a typical procedure, alkyl benzoate of formula (VIII) and (IX), and respectively amino derivatives (Xg) and (Xh) are heated at various temperature by traditional thermic methods or using microwave technology in presence of a base such as but not limited to a carbonate salt, e.g. $K_2CO_3$, $Na_2CO_3$, $Cs_2CO_3$, and a catalytic amount of palladium catalyst such as $Pd(PPh_3)_4$, $PdCl_2(PPh_3)_2$, $Pd(OAc)_2$, with the possible addition of phosphine ligands such as BINAP, X-phos, in an appropriate solvent or mixture of solvents such as THF, Toluene, Dioxane, MeOH, ACN, DMF, water. All the different combinations described above may be used. The resulting ester of formula (XI) can be then hydrolyzed using conditions well known to those skilled in the art, such as but not limited to the use of a metal hydroxide, e.g. lithium hydroxide, sodium hydroxide or potassium hydroxide, in a suitable solvent such as THF, methanol, ethanol or water or mixtures thereof, at a temperature rising from about 20° C. to about 60° C., preferably at RT, for a few hours, e.g. one hour to 24 h.

Scheme 7

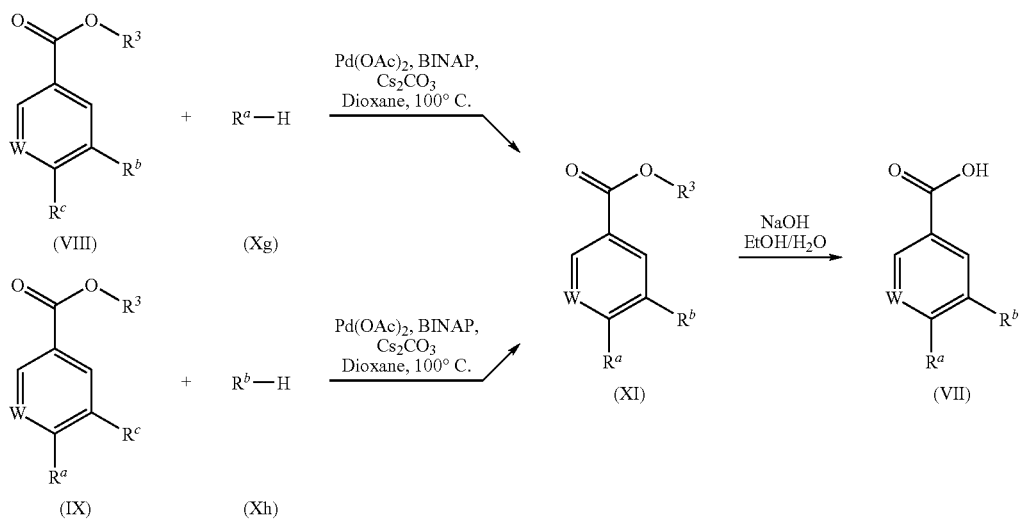

Alternatively, compounds of formula (VII) wherein W is as defined above and wherein $R^a$ or $R^b$ is OA can be prepared by adding alkyl bromide (XI) or (Xj) to the corresponding intermediates of formula (VIIIp) or (IXc) respectively, in the presence of a base, e.g $K_2CO_3$ in DMF at about 90° C. Such transformation can also be performed on compounds of formula (I), wherein $R^a$ or $R^b$ is OH, as it is described hereinafter in the examples.

Scheme 8

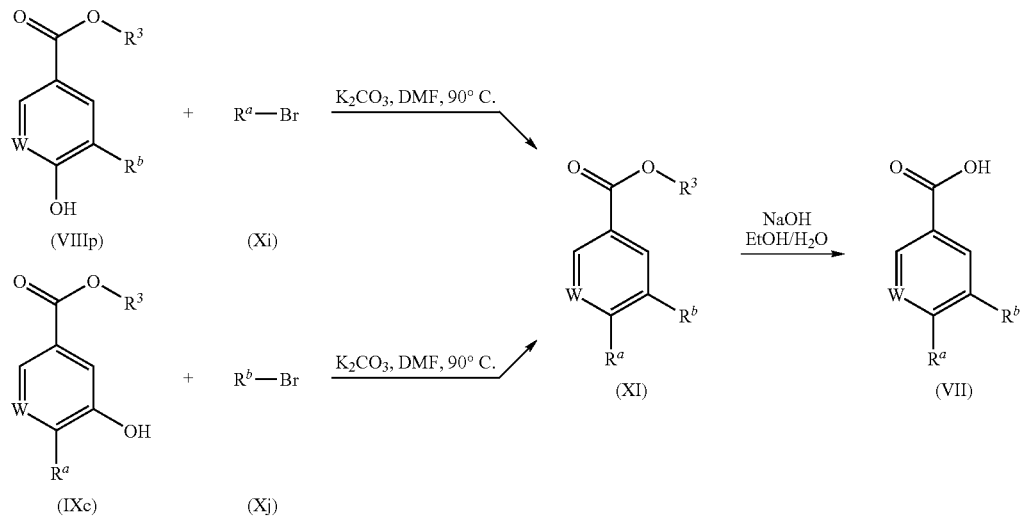

The method for preparing the compounds of formula (VII) selected below:
2,2'-dimethyl-1,1'-biphenyl-4-carboxylic acid
2'-methoxy-2-methylbiphenyl-4-carboxylic acid
2-methyl-2'-(trifluoromethyl)biphenyl-4-carboxylic acid
3-methyl-4-(4-methyl-3-thienyl)benzoic acid
2'-methyl-2-nitro-1,1'-biphenyl-4-carboxylic acid
3-methoxy-4-(4-methyl-3-thienyl)benzoic acid
2-methoxy-2'-methylbiphenyl-4-carboxylic acid
3-nitro-4-piperidin-1-ylbenzoic acid
4-(2-methylpiperidin-1-yl)-3-nitrobenzoic acid
3-methyl-4-piperidin-1-ylbenzoic acid
4-morpholin-4-yl-3-(trifluoromethyl)benzoic acid
3-methyl-4-morpholin-4-ylbenzoic acid
4-(2-methylpiperidin-1-yl)-3-(trifluoromethyl)benzoic acid
4-(2,6-dimethylphenyl)benzoic acid
2',4'-dimethoxy-2-methyl biphenyl-4-carboxylic acid
4-nitro-3-piperidin-1-ylbenzoic acid
2'-methyl-2-(trifluoromethyl) biphenyl-4-carboxylic acid
4-(4-methyl-3-thienyl)-3-(trifluoromethyl)benzoic acid
2',5'-dimethoxy-2-methyl biphenyl-4-carboxylic acid
4-(3,5-dimethylisoxazol-4-yl)-3-methylbenzoic acid
4-(2-methoxypyridin-3-yl)-3-methylbenzoic acid
3-cyano-4-(2-methylpiperidin-1-yl)benzoic acid
4-(2-methylpiperidin-1-yl)-3-[(methylsulfonyl)amino]benzoic acid
2-methyl-1,1':2,1''-terphenyl-4-carboxylic acid
2'-hydroxy-2-methylbiphenyl-4-carboxylic acid
2-(methoxymethyl)-2'-methyl biphenyl-4-carboxylic acid
6-[2-(methoxymethyl)pyrrolidin-1-yl]-5-methylnicotinic acid
2-(hydroxymethyl)-2'-methylbiphenyl-4-carboxylic acid
4-isobutoxy-3-[(methylsulfonyl)amino]benzoic acid
3-(acetylamino)-4-(2-methylpiperidin-1-yl)benzoic acid
4-[isobutyl(propyl)amino]-3-[(methylsulfonyl)amino]-benzoic acid
4-(dimethylamino)-3-nitrobenzoic acid
2'-ethyl-2-(methoxymethyl)-1,1'-biphenyl-4-carboxylic acid
4-bromo-3-(methoxymethyl)benzoic acid
2'-methyl-2-(methylsulfonyl)biphenyl-4-carboxylic acid
2'-(methoxymethyl)-2-methyl biphenyl-4-carboxylic acid
2'-methyl-2-[(methylsulfonyl)methyl]biphenyl-4-carboxylic acid
2-(3-methoxyprop-1-yn-1-yl)-2'-methylbiphenyl-4-carboxylic acid
2-(ethoxymethyl)-2'-methylbiphenyl-4-carboxylic acid
2-hydroxy-2'-methyl-1,1'-biphenyl-4-carboxylic acid
2-(3-methoxypropyl)-2'-methylbiphenyl-4-carboxylic acid
4-isopropoxy-3-(methoxy methyl)benzoic acid
3-(methoxymethyl)-4-(2-methylpiperidin-1-yl)benzoic acid
is more particularly described in the examples.

Compounds of formula (VIII) are either commercially available or may be prepared by standard synthetic techniques, as hereinafter described in the examples. Typically, when $R^b$ is $(CH_2)OH$, $(CH_2)OA$, $(CH_2)N(R^3)_2$ or $(CH_2)SO_2Me$, $R^c$ is F, Cl, Br, I or a sulfonate ester such as triflate and $R^3$ is as defined above, compounds of formula (VIII), respectively (VIIIf), (VIIIg), (VIIIh) and (VIIIj), may be prepared by bromination of the corresponding toluoyl derivative (VIIIc) followed by an $S_N2$ reaction on the benzyl bromine derivative (VIIId) with a suitable group, such as but not exclusively, an acetate salt, e.g. NaOAc in HOAc, an alcoholate salt, e.g. NaOA in the corresponding alcohol, THF or DMF, an alcohol, e.g. HOA, that can be used as solvent, an amine, e.g. $HN(R^3)_2$ or a thiolate salt, e.g. NaSA, in a suitable solvent, such as but not exclusively THF, MeCN, DMF, at a temperature ranging from RT to 130° C., with the possible use of the microwave (see Scheme 9). Hydrolysis of the acetate group on compounds of formula (VIIIe), using conditions well known to those skilled in the art, such as but not limited to sodium hydroxide in EtOH at about 60° C., afforded compounds of formula (VIIIf). Sulfide oxidation of compounds of formula (VIIIi), using conditions well known to those skilled in the art, such as but not limited to mCPBA, afforded compounds of formula (VIIIj). Compounds of formula (VIIIf), when $R^b$ is $(CH_2)OH$, can be further transformed into the corresponding alkyl sulfonate (VIIIk) that can be used as starting material for $S_N2$ reactions similarly to (VIIIb), as it illustrated on Scheme 9. Such diversification can also be performed at a later stage, on compounds of formula (I) wherein $R^b$ is $(CH_2)OH$, as described hereinafter in the examples.

Scheme 9
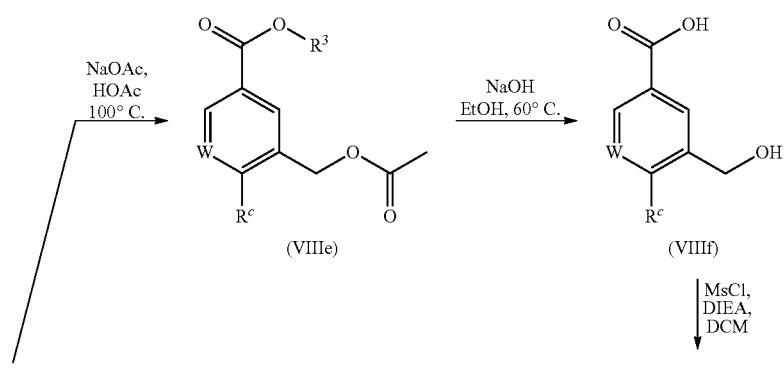
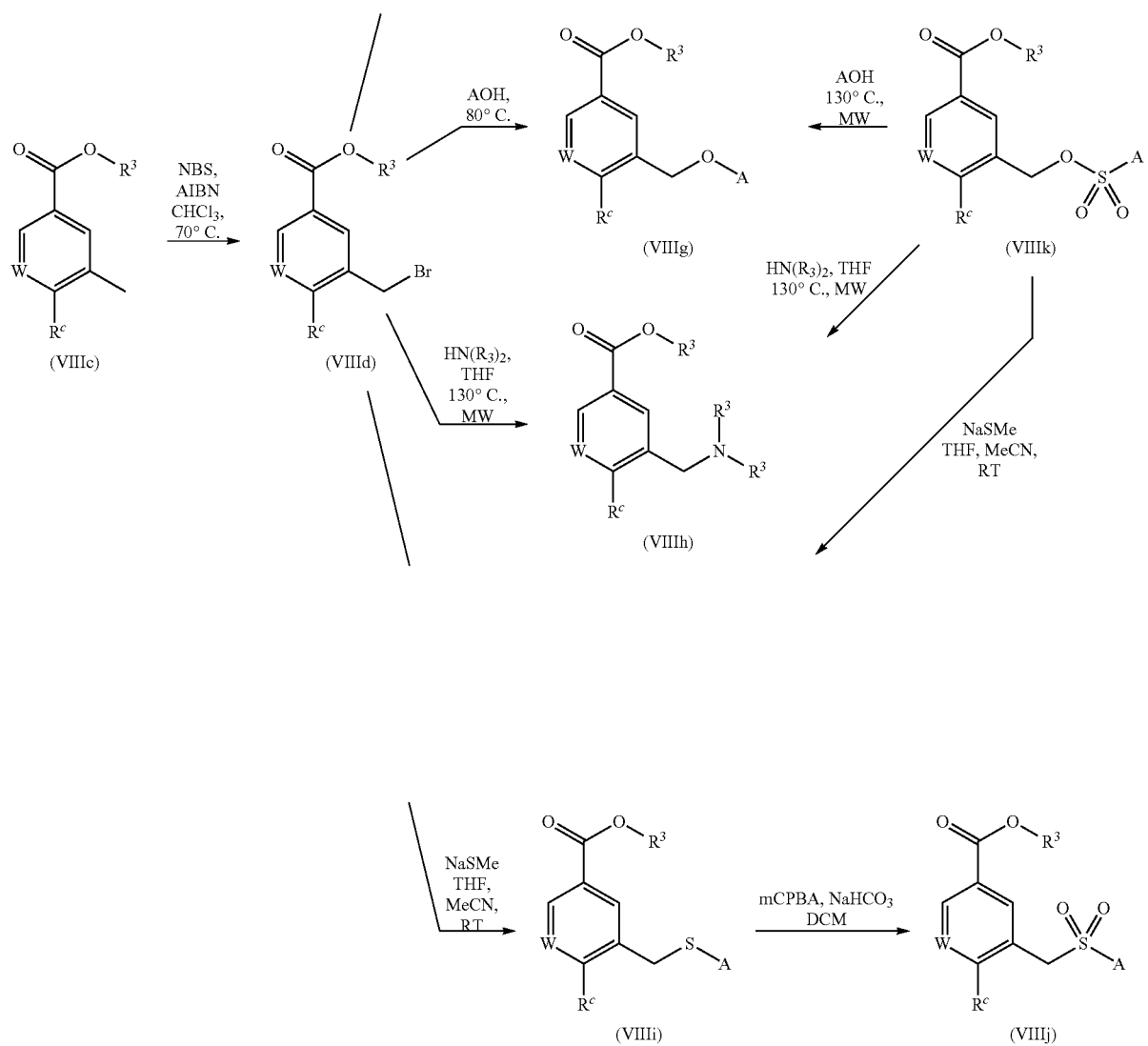

Alternatively, compounds of formula (VIIIf) can be prepared by double bromination of (VIIIc), followed by hydrolysis of (VIIIm), as it is described in Scheme 10. The reduction of the resulting benzaldehyde derivative of formula (VIIIn), with a suitable reducing agent, such as but not limited to NaBH₄, yields the benzylic alcohol of (VIIIf), compound (VIIIo). Transformation of compounds of formula (VIIIn) into compounds of formula (XIa) by metal catalyzed cross coupling reaction or $S_NAr$ reaction can be performed first. Then the reduction gives the corresponding alcohol of formula (XIa), as outlined in Scheme 10.

Scheme 10

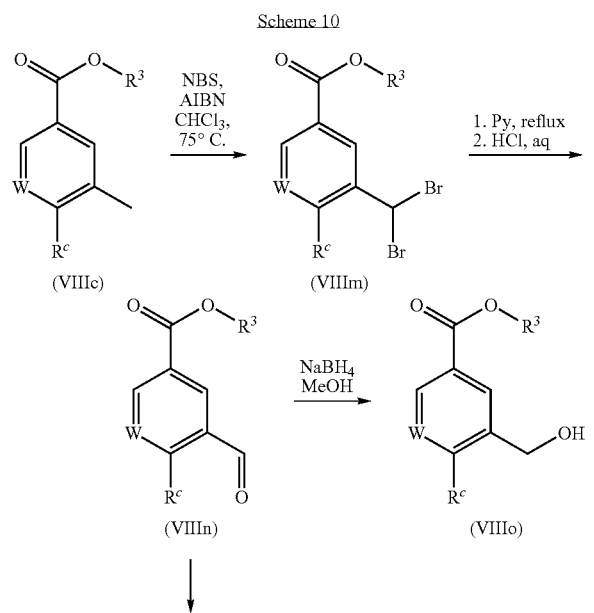

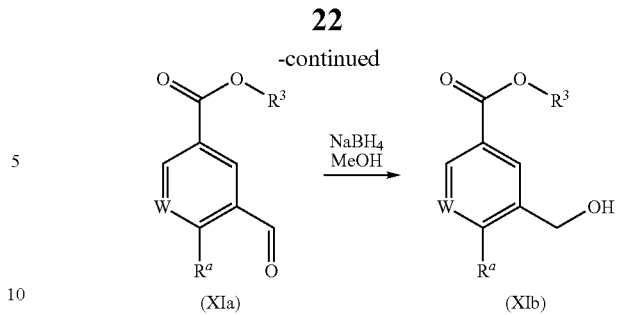

When $R^b$ is $(CH_2)_nNR^3SO_2A$ or $(CH_2)_nNR^3COA$, wherein n=0 and $R^a$, $R^3$ and W are defined as above, compounds of formula (XIe) or (XIf) respectively can be synthesized from compounds of formula (XIc), as it is outlined in Scheme 11. After reduction of nitro group, the resulting aniline (XId) can be transformed into a sulphonamide (XIe) with $ASO_2Cl$ addition or into an amide (XIf) with ACOCl addition, in the presence of a base, such as but not limited to TEA, DIEA, NMM, pyridine, in a solvent or a mixture of solvents such as DCM, DMF, Pyridine. Such diversification can also be performed on a later stage, on compounds of formula (I) where $R^b$ is $NH_2$, as it is described hereinafter in the examples.

Scheme 11

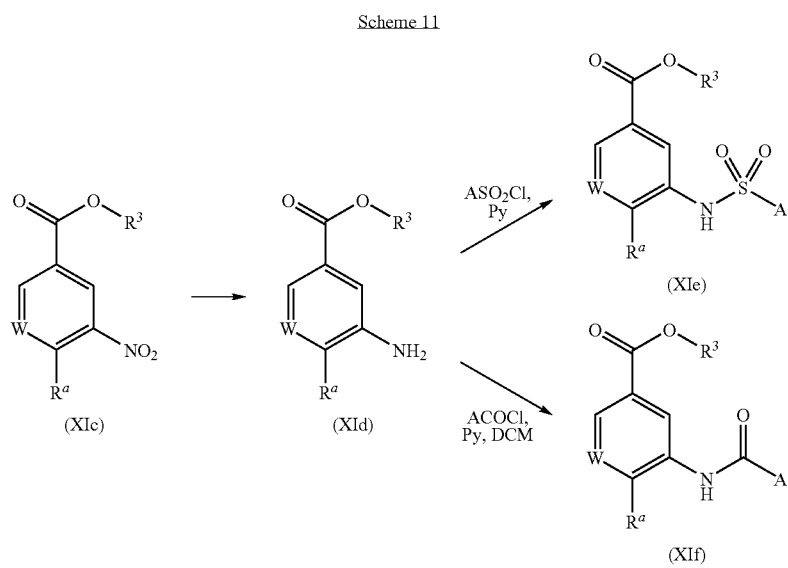

Compounds of formula (VIIb), where $R^b$ is $(CH_2)_3OA$, can be synthesized from compound (VIIIp) via the sequential Sonogashira and Suzuki-Miyura cross-coupling reactions, as it is outlined in Scheme 12. The resulting compounds of formula (VIIa) can be then reduced by standard techniques well known to those skilled in the art, such as but not limited to Pd/C in $H_2$ atmosphere, affording compounds of formula (VIIb).

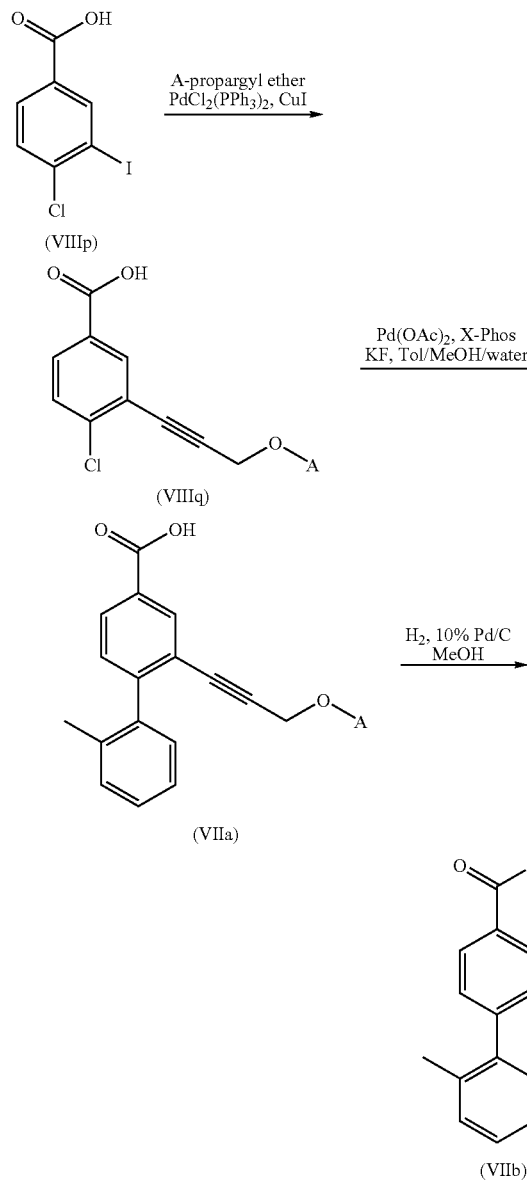

Alternatively, compounds of formula (VII), wherein $R^a$, $R^b$ and W are defined as above, may be prepared from compounds of formula (XV) in a two steps process, as outlined in Scheme 13. The first step is an halogen-metal exchange with, typically but not exclusively, an alkyl lithium salt, such as nBuLi or tBuLi. The second step is the addition of CO2, at gas or solid state, as electrophile.

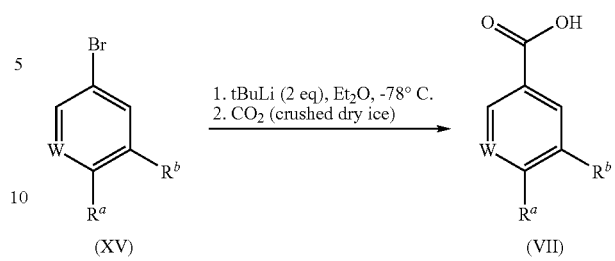

Compounds of formula (VI), wherein, $R^1$, $R^2$, Q and S are defined as above, can be prepared according to Scheme 14 by addition of hydroxylamine to the corresponding substituted benzonitrile of formula (XVI) in a solvent or a mixture of solvents, such as EtOH, water, at a temperature ranging from about 20° C. to about 50° C., preferably at RT, for a few hours, e.g. one hour to 24 h.

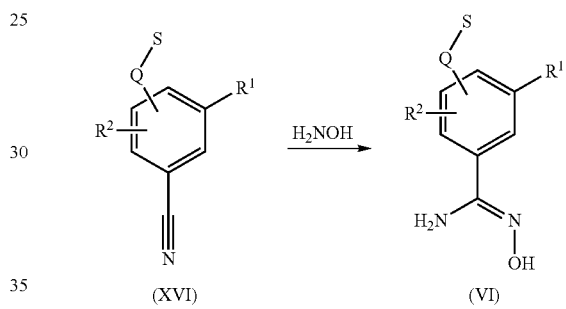

The method for preparing the compounds of formula (VI) selected below:
Methyl 4-[amino(hydroxyimino)methyl]-2-fluorobenzoate
Methyl 4-[amino(hydroxyimino)methyl]-3-fluorobenzoate
Methyl 4-[amino(hydroxyimino)methyl]-2-chlorobenzoate
Methyl 2-fluoro-5-[(hydroxyamino)(imino)methyl]benzoate
Methyl 2-hydroxy-5-[(hydroxyamino)(imino)methyl]benzoate
Methyl 4-[(hydroxyamino)(imino)methyl]-3-methoxybenzoate
Methyl 4-[(hydroxyamino)(imino)methyl]-2-methoxybenzoate
Tert-butyl {4-[amino(hydroxy imino)methyl]-2-fluorophenoxy}acetate
Tert-butyl N-{4-[amino(hydroxyimino)methyl]-2-fluorophenyl}glycinate
Tert-butyl [{3-[amino(hydroxyimino)methyl]benzyl}(methyl)amino]acetate
Methyl 4-[amino(hydroxyimino)methyl]-2,5-difluorobenzoate
Methyl 3-[amino(hydroxyimino)methyl]-4-methoxybenzoate
Methyl 5-[amino(hydroxyimino)methyl]-2-chlorobenzoate
Methyl 2-chloro-5-fluoro-4-[(hydroxylamino)(imino)methyl]benzoate
Methyl 4-[amino(hydroxyimino)methyl]-2-fluoro-5-methoxybenzoate
Methyl 4-[amino(hydroxyimino)methyl]-2-chloro-5-methoxybenzoate Tert-butyl N-{5-[amino(hydroxyimino)methyl]-2-fluorobenzyl}-N-methylglycinate {Tert-Butoxycarbonyl-[3-(N-hydroxycarbamimidoyl)-benzyl]-amino}-acetic acid tert-butyl ester Tert-butyl 3-[{3-[amino(hydroxyimino)methyl]benzyl}(methyl)amino]propanoate Tert-butyl N-{5-[amino(hydroxyimino)methyl]-2-fluorobenzyl}-N-methyl-beta-alaninate N'-hydroxy-3-(methylsulfonyl)benzenecarboximidamide tert-butyl (2-{3-[amino(hydroxyimino)methyl]phenyl}ethoxy)acetate Ethyl 4-{4-[amino (hydroxyimino)methyl]-2-fluorophenoxy}butanoate Ethyl 4-{3-[amino(hydroxy imino)methyl]phenoxy}butanoate 3-(1,3-dioxolan-2-yl)-N'-hydroxybenzenecarboximidamide (Tert-butyl {3-[(Z)-amino(hydroxyimino)methyl]benzyl}(2-hydroxyethyl)carbamate (Tert-butyl {3-[(Z)-amino(hydroxyimino)methyl]benzyl}(2-methoxyethyl)carbamate 4-[Amino(hydroxyimino)methyl]benzamide N'-hydroxy-3-(hydroxymethyl)benzenecarboximidamide N'-hydroxy-3-(2-hydroxyethyl)benzenecarboximidamide N'-hydroxy-4-(hydroxymethyl)benzenecarboximidamide N'-hydroxy-3-[(2-methoxyethoxy)methyl]benzenecarboximidamide N'-hydroxy-3-[(2-hydroxyethoxy)methyl]benzenecarboximidamide N-Hydroxy-3-{[(2-methoxy-ethyl)-methyl-amino]-methyl}-benzamidine N-Hydroxy-3-{[(2-methoxy-ethyl)-methyl-amino]-methyl}-benzamidine is more particularly described in the examples.

Scheme 15

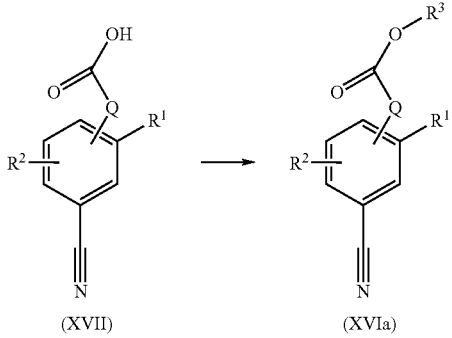

Compounds of formula (XVI), wherein $R^1$, $R^2$, Q and S are defined as above, are either commercially available or may be prepared by standard synthetic techniques well known to those skilled in the art. Typically, when S is $COOR^3$ as defined above, compounds of formula (XVIa) may be prepared by coupling the corresponding carboxylic acid of formula (XVII) to an alcohol, using conditions such as but not limited to the formation of the corresponding acid chloride of compounds of formula (XVII) with oxalyl chloride, followed by the addition of the suitable alcohol, such as MeOH at temperatures ranging from about 0° C. to about 50° C., preferably at RT for few hours, e.g. one hour to 24 hours, as it is outlined on Scheme 15. It may be also prepared with standard coupling agents, such as but not limited to EDC, HATU, TBTU, in the presence or absence of bases such as TEA, DIEA, NMM in the suitable alcohol, such as MeOH, at a temperature between about 20° C. to about 50° C., preferably at RT, for a few hours, e.g. one hour to 24 h.

Alternatively compounds of formula (XVIb) wherein Q=$(CH_2)_mX(CH_2)_m$, X=—O—, and $R^1$, $R^2$, m and S are defined as above, may be prepared from alcohol (XVIII), by addition of an electrophile, LG-$(CH_2)_m$S, where LG- is a leaving group, such as but not exclusively Br, I, OMs, in the presence of a base such as LiHMDS, NaH, NaOH, in a solvent or a mixture of solvent such as THF or Toluene-water in the presence of a phase transfer agent, such as but not limited to $(Bu_4N)HSO_4$ at temperatures ranging from RT to about 100° C., as it is outlined in Scheme 16. Alternatively, alcohol (XVIII) can be transformed into the corresponding mesyl or tosyl groups, which can then react with an alcohol (for X=—O—) or an amine (for X=—$NR^3$—), affording compounds of formula (XVIb) and (XVIc) respectively, wherein Q=$(CH_2)_mX(CH_2)_m$ and $R^1$, $R^2$, m and S are defined as above (Scheme 16). Alcohol (XVIII) can be oxidized into the corresponding aldehyde (XVIIIb), according to Scheme 16.

Then a reductive amination of the compounds of formula (XVIIIb) with a suitable amine, affords compounds of formula (XVIc), wherein Q=$(CH_2)_mX(CH_2)_m$ with X=—$NR^3$—, and $R^1$, $R^2$, m and S are defined as above, according to Scheme 16. The different transformations described in Scheme 16 may be performed on compounds of formula (I) with the suitable substitution pattern, as it is described in the examples.

Scheme 16

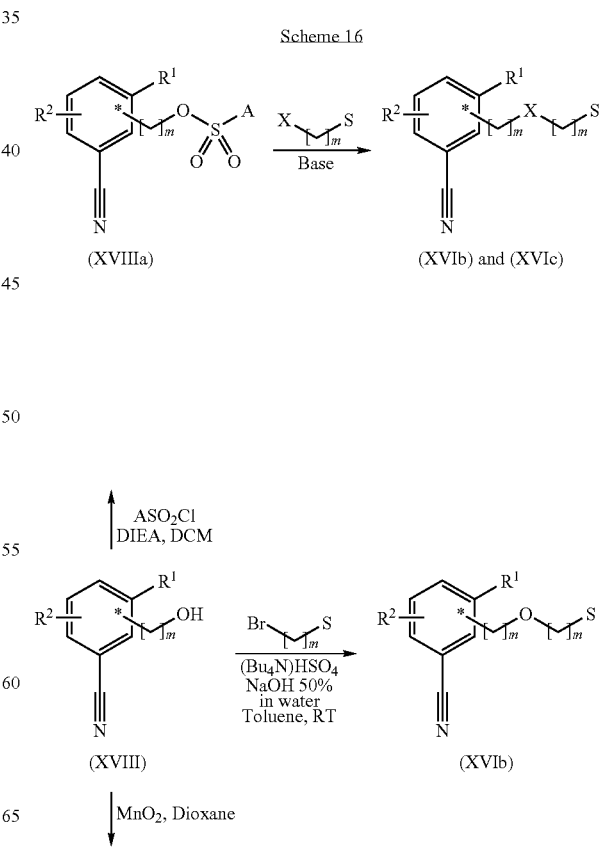

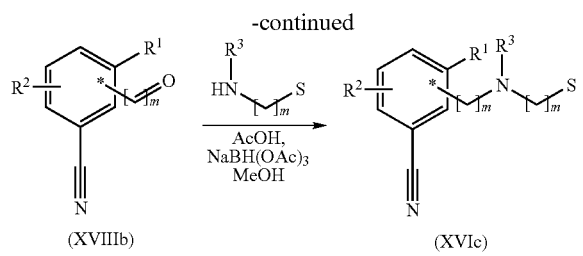

Alternatively, addition of an alcohol or an amine to benzyl bromide of formula (XVIIIc), as outlined in Scheme 17, in the presence of a base, such as but not limited to DIEA, TEA, $K_2CO_3$, $Cs_2CO_3$, in a suitable solvent such as MeCN, THF, DMF, yields compounds of formula (XVIb) and (XVIc), wherein Q=$(CH_2)X(CH_2)_m$, X=—O— or —$NR^3$— respectively, and $R^1$, $R^2$, m and S are defined as above.

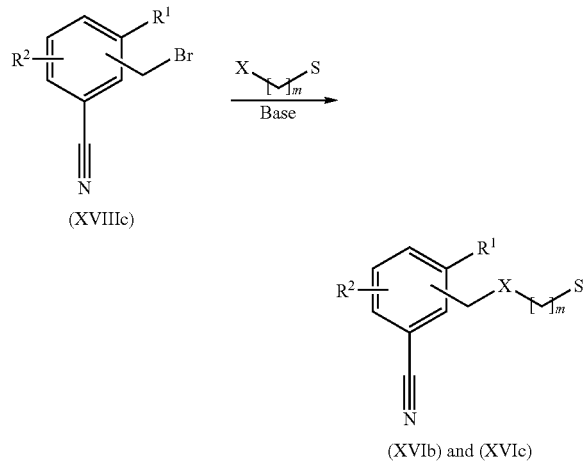

Phenol derivative of formula (XIX) may be transformed into compounds of formula (XVId) by Mitsunobu or alkylation reaction, using conditions known to the person skilled in the art and as described below in the examples. Typically, phenol alkylation with LG-$(CH_2)_m$S, where LG- is a leaving group, such as but not limited to Br, I, OMs, is performed in a solvent such as THF or DMF, in the presence of a base such as DIEA, TEA, $K_2CO_3$ or $Cs_2CO_3$, at temperature ranging from RT to about 100° C.

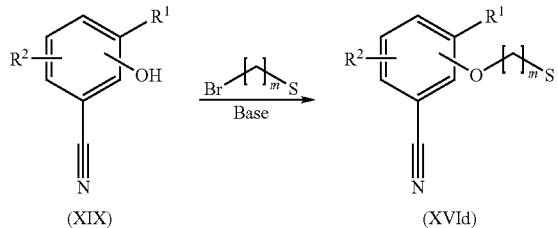

Alternatively, aniline derivative of formula (XX) may be transformed into compounds of formula (XVIe) by alkylation reaction, using conditions known to the person skilled in the art and as described below in Scheme 19 and in the examples.

Typically, aniline alkylation with LG-$(CH_2)_m$S, where LG- is a leaving group, such as but not exclusively Br, I, OMs, is performed in a solvent such as THF or DMF, in the presence of a base such as DIEA, TEA, $K_2CO_3$ or $Cs_2CO_3$, at temperature ranging from RT to about 100° C.

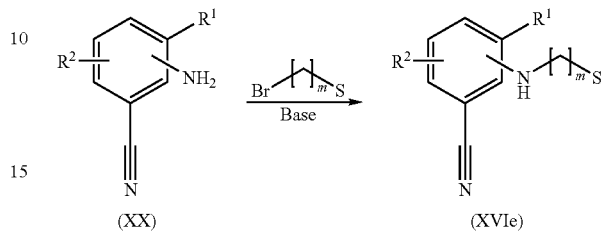

Alternatively, compounds of formula (XVI), wherein Q, S, $R^1$, and $R^2$ are defined as above, may be obtained from the corresponding aryl fluoride (XIII) by aromatic nucleophilic substitution with a cyanide salt, typically but not exclusively sodium cyanide in the presence of tetrabutylammonium bromide, in a solvent such as DMF and at a temperature ranging from about 20° C. to about 100° C., preferably at about 60° C., for few hours, e.g. 12 h, as it is described in Scheme 20, according to Jenkins, T. J. et al. *J. Med. Chem.* 2007, 50, 566. Metal catalyzed cyanation of aryl bromide of formula (XIV) can be used as alternative strategy, as shown on Scheme 20. Addition of $Zn(CN)_2$ in the presence of a palladium catalyst, such as but not limited to $Pd_2(dba)_3$ or $Pd(PPh_3)_4$, with the optional addition of a ligand such as dppf (according to Maligres, P. E. et al *Tetrahedron Lett.* 1999, 40, 8193-8195), and zinc derivatives such as but not limited to Zn dust and $Zn(OAc)_2$ (according to Chidambaram, R. et al *Tetrahedron Lett.* 2004, 45, 1441-1444) in a solvent such as DMF and at temperature raising from RT to 150° C., typically 100° C., yields the formation of compounds of formula (XI). The cyanation of aryl bromide of formula (XIV) can be also performed in the absence of palladium, with the use of CuCN in DMF (according to Couture. C.; Paine, A. J. *Can. J. Chem.* 1985, 63, 111-120).

Cyanide group may be introduced by Sandmeyer reaction, starting from an aniline of formula (XXI), as outlined in Scheme 20. Its transformation into the corresponding diazonium salt can be achieved with sodium nitrite in the presence of a mineral acid, such as HCl in water. It can then further react with copper cyanide, prepared from a mixture of CuCN and KCN, in water at a temperature ranging from about 20° C. to about 100° C., affording compounds of formula (XI) (according to Barraclough, P. et al. *Arch. Pharm.* 1990, 323, 507-512). The starting analine derivatives of formula (XXI) are either commercially available or can be obtained by reduction of the corresponding nitro group by Pd/C catalyzed hydrogenation, as described hereafter in the examples.

Scheme 20

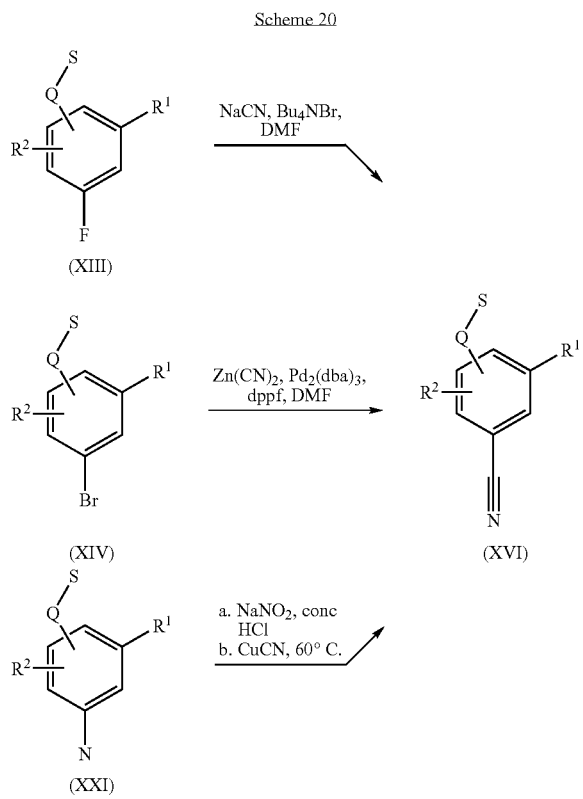

If the above set out general synthetic methods are not applicable to obtain the compounds of formula (I), suitable methods of preparation known by a person skilled in the art should be used.

The pharmaceutically acceptable cationic salts of compounds of the present invention are readily prepared by reacting the acid forms with an appropriate base, usually one equivalent, in a co-solvent. Typical bases are sodium hydroxide, sodium methoxide, sodium ethoxide, sodium hydride, potassium hydroxide, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

According to a further general process, compounds of formula (I), and any subformulae can be converted to alternative compounds of formula (I) and any subformulae, employing suitable inter-conversion techniques well known by a person skilled in the art.

In general, the synthesis pathways for any individual compounds of formula (I) will depend on the specific substitutents of each molecule and upon the ready availability of Intermediates necessary; again such factors being appreciated by those of ordinary skill in the art. For all the protection and de-protection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, 3$^{rd}$ Edition 1999.

Compounds of this invention can be isolated in association with solvent molecules by crystallization from evaporation of an appropriate solvent. The pharmaceutically acceptable acid addition salts of the compounds of formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compounds of formula (I), which contain an acid center, with a suitable base. Both types of salts may be formed or interconverted using ion-exchange resin techniques.

Depending on the conditions used, the reaction times are generally between a few minutes and 14 days, and the reaction temperature is between about −30° C. and 140° C., normally between −10° C. and 90° C., in particular between about 0° C. and about 70° C.

Compounds of the formula (I) can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula (I), but contain corresponding protected amino and/or hydroxyl groups instead of one or more free amino and/or hydroxyl groups, preferably those which carry an amino-protecting group instead of an H atom bound to an N atom, in particular those which carry an R'—N group, in which R' denotes an amino-protecting group, instead of an HN group, and/or those which carry a hydroxyl-protecting group instead of the H atom of a hydroxyl group, for example those which conform to the formula (I), but carry a —COOR" group, in which R" denotes a hydroxyl protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxy-carbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-carbonyl, ethoxycarbonyl, 2,2,2-trichloroethoxycarbonyl, BOC (tert-butoxy-carbonyl) and 2-iodoethoxycarbonyl; aralkoxycarbonyl, such as CBZ ("carbo-benz-oxy"), 4-methoxybenzyloxycarbonyl and FMOC; and aryl-sulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitro-benzoyl, p-toluenesulfonyl, tert-butyl and acetyl, where benzyl and tert-butyl are particularly preferred.

The compounds of the formula (I) are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as THF or dioxane, amides, such as DMF, halogenated hydrocarbons, such as DCM, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (RT).

The BOC, OBut and Mtr groups can, for example, preferably be cleaved off using TFA in DCM or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, tri-fluoro-methylbenzene, chloroform or DCM; alcohols, such as methanol, ethanol, isopropanol, n-propanol, n-butanol or tert-butanol; ethers, such as diethyl ether, diisopropyl ether, tetrahydrofurane (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as EtOAc, or mixtures of the said solvents.

Esters can be saponified, for example, using LiOH, NaOH or KOH in water, water/THF, water/THF/ethanol or water/dioxane, at temperatures between 0 and 100° C. Furthermore, ester can be hydrolysed, for example, using acetic acid, TFA or HCL.

Free amino groups can furthermore be acylated in a conventional manner using an acid chloride or anhydride or alkylated using an unsubstituted or substituted alkyl halide or reacted with $CH_3$—C(=NH)—OEt, advantageously in an inert solvent, such as DCM or THF and/or in the presence of a base, such as triethylamine or pyridine, at temperatures between −60° C. and +30° C.

Therefore, the invention also relates to the preparation of the compounds of formula (I), and salts thereof, characterized in that
a) a compounds of formula A

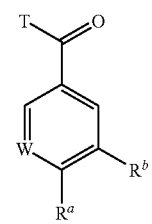

wherein W, $R^a$ and $R^b$ have the meanings given above, and T is OH, or a leaving group, such as Cl, Br, I, imidazolyl, pentafluorophenoxy or the product of the reaction of isobutyl chloroformate with formula A, wherein T is OH, is reacted with
a compounds of formula B

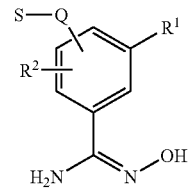

wherein $R^1$ and $R^2$ Q and S have the meanings given above preferably in the presence of a solvent and of a suitable base, such as an amine like TEA, DIEA or NMM, or in case T is OH, in the presence of a suitable condensation reagent, such as EDC, HATU, and the resulting product is cyclized, preferably in the presence of an amine, such as DIEA, TEA or tetrabutylammonium fluoride
and optionally a base or acid of the formula I is converted into one of its salts.

Throughout the specification, the term leaving group preferably denotes Cl, Br, I or a reactively modified OH group, such as, for example, an activated ester, an imidazolide or alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N-hydroxysuccinimide.

The formula (I) also encompasses the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the formula I and so-called prodrug compounds.

The term "prodrug derivatives" is taken to mean compounds of the formula I which have been modified with, for example, alkyl or acyl groups, sugars or oligopeptides and which are rapidly cleaved in the organism to form the active compounds.

These also include biodegradable polymer derivatives of the compounds according to the invention, as described, for example, in Int. J. Pharm. 115, 61-67 (1995).

The formula (I) also encompasses mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention also encompasses compounds of Formula (I) wherein $R^a$ is cycloalkyl having 3-7 atoms, OA, $NA_2$, or $NO_2$, $R^b$ is H, CN, $CF_3$, or $OR^3$, and wherein Ar and Het can be unsubstituted or substituted elsewhere than at the atom adjacent to the atom linking the Ar or Het group to the rest of the molecule.

In a preferred embodiment, the invention relates to compounds of Formula (I) wherein $R^1$, $R^2$, W, Q, S and $R^b$ are as defined above, and wherein $R^a$ is Ar or Het monosubstituted at the carbon adjacent to the carbon linked to the rest of the molecule.

In another preferred embodiment, the invention relates to compounds of Formula (I) wherein Q is on meta position with regards to the oxadiazole moiety.

Very particularly, preferred embodiments of formula (I) are the compounds of formula IA, IB, IC and ID:

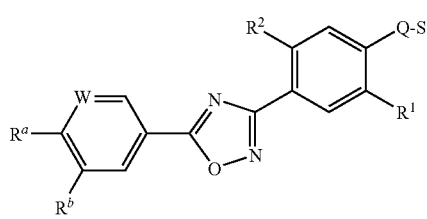

IA

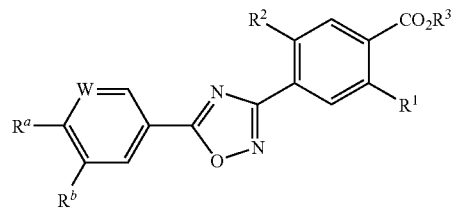

IB

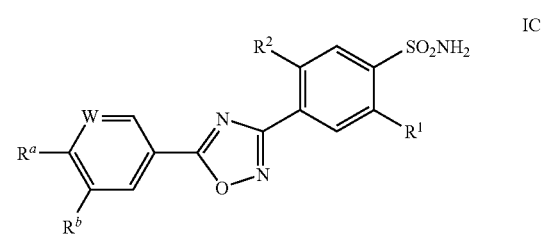

IC

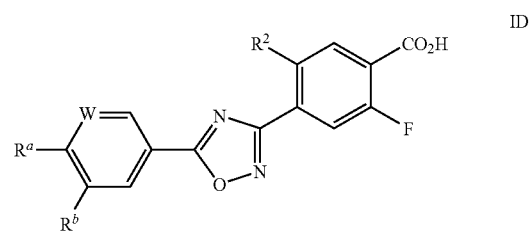

ID wherein $R^1$, $R^2$, $R^3$, $R^a$, $R^b$, Q, S and W are defined as above. formula ID is especially preferred. Preferably, W in formula ID is CH.

A Preferred embodiment of formula (I) relates also to compounds of formula (IE)

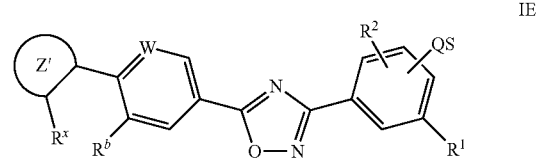

IE

Wherein W, $R^b$, $R^1$, $R^2$, Q, S are as defined above and wherein Z' denotes Ar or Het, $R^x$ denotes Hal, A, $OR^3$, $N(R^3)_2$, $NO_2$, CN, $COOR^3$, $CF_3$, $OCF_3$, $CON(R^3)_2$, $NR^3COA$, $NR^3CON(R^3)_2$, $NR^3SO_2A$, $COR^3$, $SO_2N(R^3)_2$, SOA or $SO_2A$, phenyl, pyridyl, $-[C(R^3)_2]_n-COOR^3$ or $-O[C(R^3)_2]_n-CON(R^3)_2$. Preferably $R^x$ is in such position that it limits the rotation of the ring Z' with respect to the ring bearing $R^b$, by the meaning of steric hindrance or electrostatic interactions with $R^b$. $R^x$ is preferably an alkyl or an alkoxy chain containing 1 to 5 carbon atoms. $R^x$ is most preferably attached to the atom adjacent to the atom which links the ring Z to the rest of the molecule. $R^x$ is most preferably $-CH_3$, $-C_2H_5$, F, Cl, $-OCH_3$, $-OC_2H_5$, $-CH_2OCH_3$ and $R^b$ is simultaneously $-CH_3$, $-C_2H_5$, F, Cl, $-OCH_3$, $-OC_2H_5$, $-CH_2OCH_3$, $-CH_2OH$, $-CH_2N(CH_3)_2$, $CF_3$.

An other preferred embodiment of Formula (I) relates to compounds of Formula (IF)

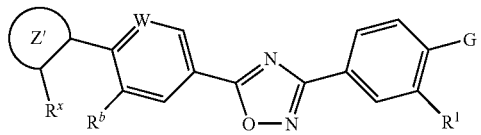

Wherein W, $R^x$, $R^b$, $R^1$ and Z' are as defined above, and wherein G denotes a linear or branched carbon chain terminated with carboxylic acid, carboxylic ester, amide, amine or alcohol function, and optionally containing 1 or 2 oxygen and/or nitrogen atoms, or a —$CONR^3$— group, or a $C_3$-$C_6$cycloalkyl group. G preferably denotes —$CH_2OH$, —$OCH_2COOH$, —CO—NH—$(CH_2)_n$—$CO_2R^3$, —CO—$NR^3$—$(CH_2)_n$—$CO_2R^3$, —CO—$NR^3$—$(C_3$-$C_6$cycloalkyl)-$CO_2H$, —CO—$NR^3$—$(C_3$-$C_6$cycloalkyl)-$CO_2CH_3$, —CO—$NR^3$—$(C_3$-$C_6$cycloalkyl)—$CO_2C_2H_5$, —$CH_2NR^3$—$(C_3$-$C_6$cycloalkyl)-$CO_2H$, —$CH_2NR^3$—$(C_3$-$C_6$cycloalkyl)-$CO_2CH_3$, —$CH_2NR^3$—$(C_3$-$C_6$cycloalkyl)-$CO_2C_2H_5$, —$CONH(CH_2)_nCN$, —$CH_2NH(CH_2)_nCN$, —$CONH(CH_2)_nOCH_3$, —$CONH(CH_2)_nOH$, —$CON(CH_3)(CH_2)_nOCH_3$, —$CON(CH_3)(CH_2)_nOH$, —$CONH(CH_2)_nNHCOCH_3$, —$NH(CH_2)_nCO_2H$, —$CH_2N(CH_3)$—$(CH_2)_nCO_2H$, —$CON(CH_3)$—$(CH_2)_nCO_2CH_3$, —$CH_2N(CH_3)$—$(CH_2)_nCO_2CH_3$, —$CH_2N(CH_3)$—$(CH_2)_nCO_2C(CH_3)_3$, —$CON(CH_3)$—$(CH_2)_nCO_2CH_3$, —$CONH(CH_2)_nCO_2CH_3$, —$CONHCH(CH_3)(CH_2)_nCO_2CH_3$, —$CONHCH(CH_3)(CH_2)_nCO_2C_2H_5$, —$CONHCH(CH_3)(CH_2)_nCO_2H$, —$CONHC(CH_3)_2(CH_2)_nCO_2CH_3$, $CONHC(CH_3)_2(CH_2)_nCO_2C_2H_5$, —$CONHC(CH_3)_2(CH_2)_nCO_2H$, —$CH_2$—O—$(CH_2)_nCO_2H$, —$CH_2$—O—$(CH_2)_nCO_2CH_3$, —$CH_2$—O—$(CH_2)_nCO_2C_2H_5$, —$CH_2$—O—$(CH_2)_nCO_2C(CH_3)_3$, —$O(CH_2)_nCO_2H$, —$O(CH_2)_nCO_2CH_3$, —$O(CH_2)_nCO_2C_2H_5$, —$O(CH_2)_nCO_2C(CH_3)_3$, Wherein n and $R^3$ are as above defined.

An other preferred embodiment of Formula (I) relates to compounds of Formula (IG)

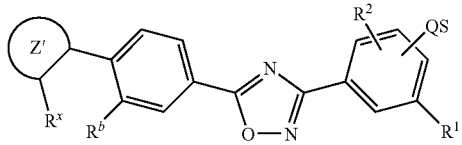

Wherein $R^b$, $R^1$, $R^2$, Q, S, Z' and $R^x$ are as above defined

An other preferred embodiment of Formula (I) relates to compounds of Formula (IH)

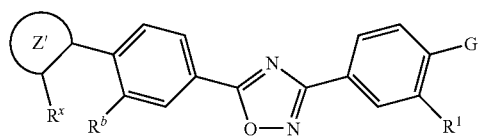

Wherein $R^b$, $R^x$, $R^1$, Z' and G are as above defined

Other preferred embodiments of Formula (I) are compounds of Formula (IJ) and (IK)

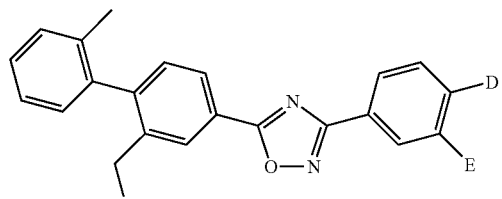

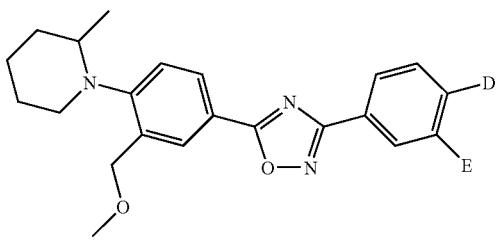

Wherein
D denotes $R^2$ or Q-S, more preferably D is H, F, Cl, —$CO_2H$, —$CO_2CH_3$, —$CO_2C_2H_5$, —$SO_2NH_2$, —$CH_2OH$, —OH, —$OCH_2COOH$, —$CONH_2$, —CO—NH—$(CH_2)_n$—$CO_2R^3$, —CO—$NR^3$-alkyl-$CO_2R^3$, —CO—$NR^3$—$(C_3$-$C_6$cycloalkyl)-$CO_2H$, —CO—$NR^3$—$(C_3$-$C_6$cycloalkyl)-$CO_2CH_3$, —CO—$NR^3$—$(C_3$-$C_6$cycloalkyl)-$CO_2C_2H_5$, —$CH_2NR^3$—$(C_3$-$C_6$cycloalkyl)-$CO_2H$, —$CH_2NR^3$—$(C_3$-$C_6$cycloalkyl)-$CO_2CH_3$, —$CH_2NR^3$—$(C_3$-$C_6$cycloalkyl)-$CO_2C_2H_5$, —$CONH(CH_2)_nCN$, —$CH_2NH(CH_2)_nCN$, —$CONH(CH_2)_nOCH_3$, —$CONH(CH_2)_nOH$, —$CON(CH_3)(CH_2)_nOCH_3$, —$CON(CH_3)(CH_2)_nOH$, —$CONH(CH_2)_nNHCOCH_3$,

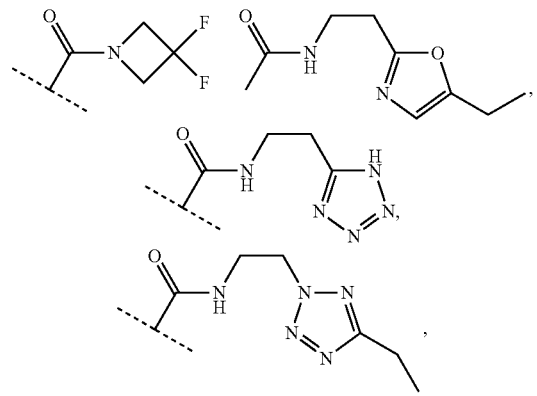

—$NH(CH_2)_nCO_2H$, —$CH_2N(CH_3)$—$(CH_2)_nCO_2H$, —$CON(CH_3)$—$(CH_2)_nCO_2H$, —$CH_2N(CH_3)$—$(CH_2)_n$—$CO_2CH_3$, —$CH_2N(CH_3)$—$(CH_2)_nCO_2C(CH_3)_3$, —$CON(CH_3)$—$(CH_2)_nCO_2CH_3$, —$CONH(CH_2)_nCO_2CH_3$, —$CONHCH(CH_3)(CH_2)_nCO_2CH_3$, —$CONHCH(CH_3)(CH_2)_nCO_2C_2H_5$, $CONHCH(CH_3)(CH_2)_nCO_2H$, —$CONHC(CH_3)_2(CH_2)_nCO_2CH_3$, $CONHC(CH_3)_2(CH_2)_nCO_2C_2H_5$, —$CONHC(CH_3)_2(CH_2)_nCO_2H$, —$CH_2$—O—$(CH_2)_nCO_2H$, —$CH_2O$ (CH$_2$)$_n$ CO$_2$CH$_3$, —CH$_2$—O—(CH$_2$)$_n$CO$_2$C$_2$H$_5$, —CH$_2$O(CH$_2$)$_n$CO$_2$C(CH$_3$)$_3$, —O(CH$_2$)$_n$CO$_2$, —O(CH$_2$)$_n$CO$_2$CH$_3$, —O(CH$_2$)$_n$CO$_2$C$_2$H$_5$, —O(CH$_2$)$_n$CO$_2$C(CH$_3$)$_3$,

E denotes R$^1$, more preferably, E is H, F, Cl, —CO$_2$H, —CO$_2$CH$_3$, —CO$_2$C$_2$H$_5$, —SO$_2$NH$_2$, —CH$_2$OH, —OH, —OCH$_2$COOH, —CONH$_2$, —CO—NH—(CH$_2$)$_n$—CO$_2$R$^3$, —CO—NR$^3$-alkyl-CO$_2$R$^3$, —CO—NR$^3$—(C$_3$-C$_6$cycloalkyl)-CO$_2$H, —CO—NR$^3$—(C$_3$-C$_6$cycloalkyl)-CO$_2$CH$_3$, —CO—NR$^3$—(C$_3$-C$_6$cycloalkyl)-CO$_2$C$_2$H$_5$, —CH$_2$NR$^3$—(C$_3$-C$_6$cycloalkyl)-CO$_2$H, —CH$_2$NR$^3$—(C$_3$-C$_6$cycloalkyl)-CO$_2$CH$_3$, —CH$_2$NR$^3$—(C$_3$-C$_6$cycloalkyl)-CO$_2$C$_2$H$_5$, —CONH(CH$_2$)$_n$CN, —CH$_2$NH(CH$_2$)$_n$CN, —CONH(CH$_2$)$_n$OCH$_3$, —CONH(CH$_2$)$_n$OH, —CON(CH$_3$)(CH$_2$)$_n$OCH$_3$, —CON(CH$_3$)(CH$_2$)$_n$OH, —CONH(CH$_2$)$_n$NHCOCH$_3$,

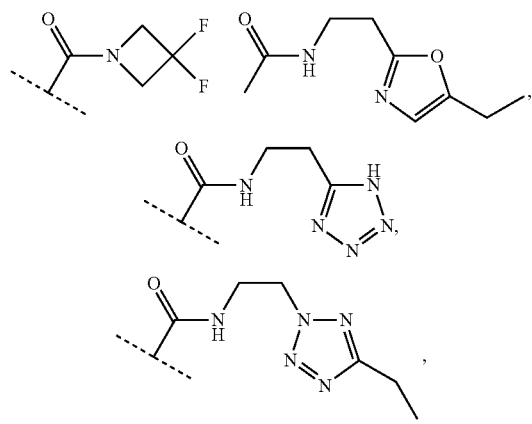

—NH(CH$_2$)$_n$CO$_2$H, —CH$_2$N(CH$_3$)—(CH$_2$)$_n$CO$_2$H, —CON(CH$_3$)—(CH$_2$)$_n$CO$_2$H, —CH$_2$N(CH$_3$)—(CH$_2$)$_n$CO$_2$CH$_3$, —CH$_2$N(CH$_3$)—(CH$_2$)$_n$CO$_2$C(CF$_{13}$)$_3$, —CON(CH$_3$)(CH$_2$)$_n$CO$_2$CH$_3$, —CONH(CH$_2$)$_n$CO$_2$CH$_3$, —CONHCH(CH$_3$)(CH$_2$)$_n$CO$_2$CH$_3$, —CONHCH(CH$_3$)(CH$_2$)$_n$CO$_2$C$_2$H$_5$, CONHCH(CH$_3$)(CH$_2$)$_n$CO$_2$H, —CONHC(CH$_3$)$_2$(CH$_2$)$_n$CO$_2$CH$_3$, CONHC(CH$_3$)$_2$(CH$_2$)$_n$CO$_2$C$_2$H$_5$, —CONHC(CH$_3$)$_2$(CH$_2$)$_n$CO$_2$H, —CH$_2$—O—(CH$_2$)$_n$CO$_2$H, —CH$_2$—O—(CH$_2$)$_n$CO$_2$CH$_3$, —CH$_2$—O—(CH$_2$)$_n$CO$_2$C$_2$H$_5$, —CH$_2$—O—(CH$_2$)$_n$CO$_2$C(CH$_3$)$_3$, —O(CH$_2$)$_n$CO$_2$H, —O(CH$_2$)$_n$CO$_2$CH$_3$, —O(CH$_2$)$_n$CO$_2$C$_2$H$_5$, —O(CH$_2$)$_n$CO$_2$C(CF$_{13}$)$_3$,

Wherein R$^3$ and n are as above defined.

An other preferred embodiment of Formula (I) are compounds of Formula IL

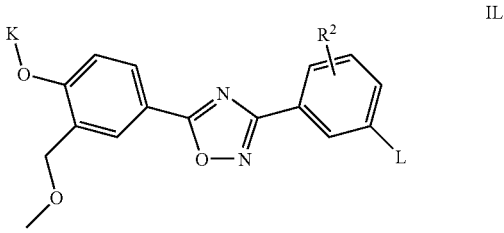

wherein R$^2$ is as defined above, K denotes A, and L denotes —(CH$_2$)$_m$X(CH$_2$)$_m$S wherein m and S are as above defined and X denotes —COO— or —CONR$^3$, wherein R$^3$ is as above defined. More preferably, K denotes C1-C6 alkyl group. More preferably K is a branched C1-C6 alkyl. Most preferably, K is —CH$_3$, ethyl, propyl, isopropyl, butyl, isobutyl, tert-butyl, pentyl, methylbutyl. L preferably denotes —CH$_2$—N(CH$_3$)CH$_2$CO$_2$H, —(CH$_2$)$_2$—N(CH$_3$)CH$_2$CO$_2$H, —CH$_2$—N(CH$_3$)(CH$_2$)$_2$CO$_2$H, —(CH$_2$)$_2$—N(CH$_3$)(CH$_2$)$_2$CO$_2$H, —CH$_2$—NHCH$_2$CO$_2$H, —(CH$_2$)$_2$—NHCH$_2$CO$_2$H, —CH$_2$—NH(CH$_2$)$_2$CO$_2$H, —(CH$_2$)$_2$—NH(CH$_2$)$_2$CO$_2$H, —CH$_2$—N(CH$_3$)CH$_2$CO$_2$Me, —(CH$_2$)$_2$—N(CH$_3$)CH$_2$CO$_2$Me, —CH$_2$—N(CH$_3$)(CH$_2$)$_2$CO$_2$Me, —(CH$_2$)$_2$—N(CH$_3$)(CH$_2$)$_2$CO$_2$Me, —CH$_2$—NHCH$_2$CO$_2$Me, —(CH$_2$)$_2$—NHCH$_2$CO$_2$Me, —CH$_2$—NH(CH$_2$)$_2$CO$_2$Me, —(CH$_2$)$_2$—NH(CH$_2$)$_2$CO$_2$Me, —CH$_2$—N(CH$_3$)CH$_2$CO$_2$Et, —(CH$_2$)$_2$—N(CH$_3$)CH$_2$CO$_2$Et, —CH$_2$—N(CH$_3$)(CH$_2$)$_2$CO$_2$Et, —(CH$_2$)$_2$—N(CH$_3$)(CH$_2$)$_2$CO$_2$Et, —CH$_2$—NHCH$_2$CO$_2$Et, —(CH$_2$)$_2$—NHCH$_2$CO$_2$Et, —CH$_2$—NH(CH$_2$)$_2$CO$_2$Et, —(CH$_2$)$_2$—NH(CH$_2$)$_2$CO$_2$Et, —CH$_2$—N(CH$_3$)CH$_2$CO$_2$tBu, —(CH$_2$)$_2$—N(CH$_3$)CH$_2$CO$_2$tBu, —CH$_2$—N(CH$_3$)(CH$_2$)$_2$CO$_2$tBu, —(CH$_2$)$_2$—N(CH$_3$)(CH$_2$)$_2$CO$_2$tBu, —CH$_2$—NHCH$_2$CO$_2$tBu, —(CH$_2$)$_2$—NHCH$_2$CO$_2$tBu, —CH$_2$—NH(CH$_2$)$_2$CO$_2$tBu, —(CH$_2$)$_2$—NH(CH$_2$)$_2$CO$_2$tBu.

In another preferred embodiment, compounds of Formula (I) exhibit a selectivity on S$_1$P$_1$ receptor over S$_1$P$_3$ receptor of more than 20 fold, preferably more than 50 fold, more preferably more than 100 fold, even more preferably more than 1000 fold.

Preference is given to the compounds of the present invention selected from the following group 1 to I27:

| Example Nb | structures |
|---|---|
| 1 | 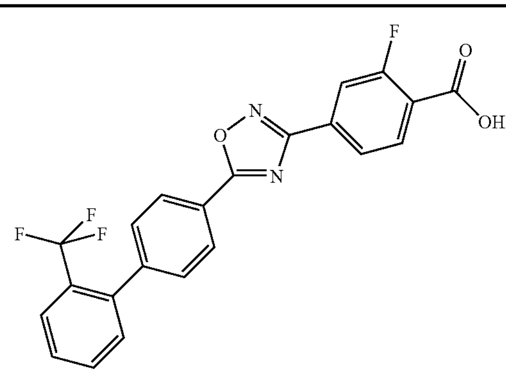 |

| Example Nb | structures |
|---|---|
| 2 | 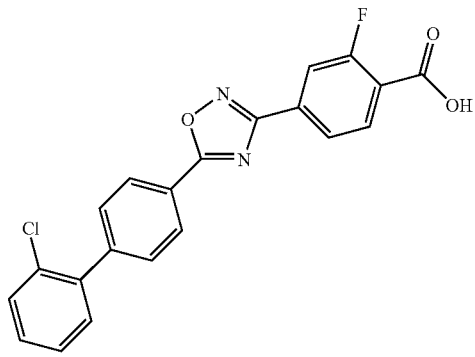 |
| 3 | 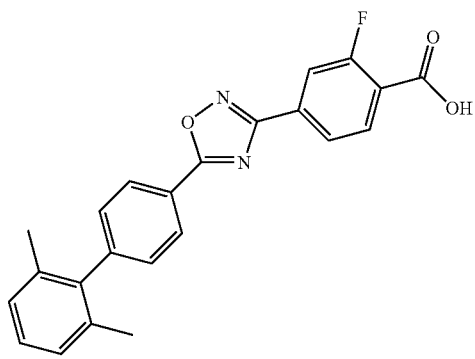 |
| 4 | 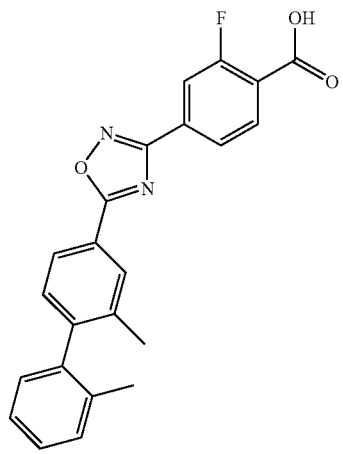 |

-continued
| Example Nb | structures |
|---|---|
| 5 | 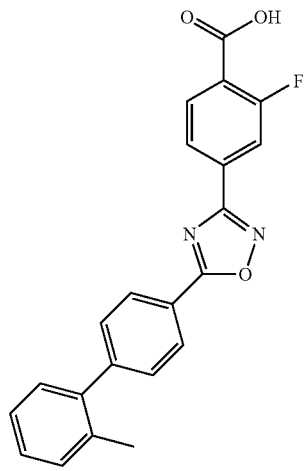 |
| 6 | 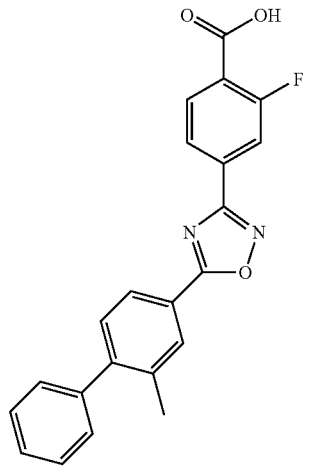 |
| 7 | 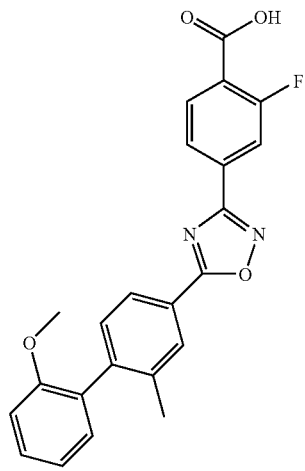 |

-continued
| Example Nb | structures |
|---|---|
| 8 | 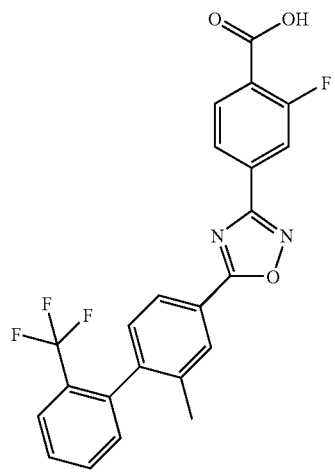 |
| 9 | 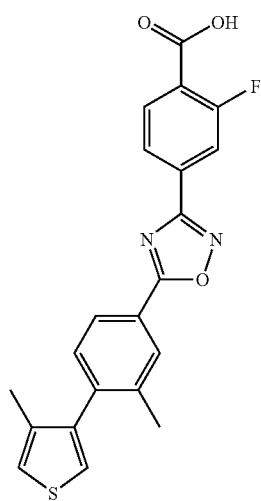 |
| 10 | 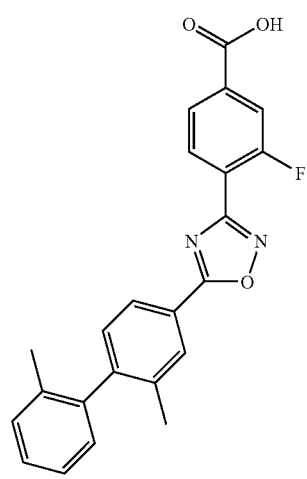 |

-continued
| Example Nb | structures |
|---|---|
| 11 | 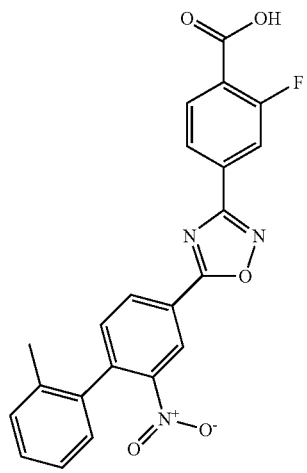 |
| 12 | 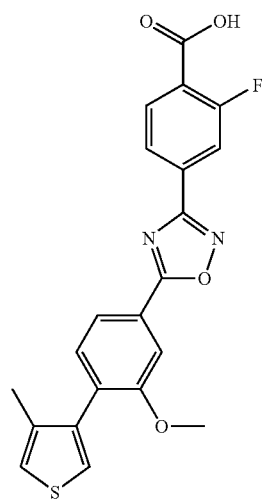 |
| 13 | 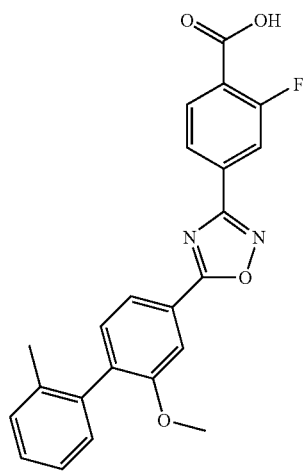 |

-continued
| Example Nb | structures |
|---|---|
| 14 | 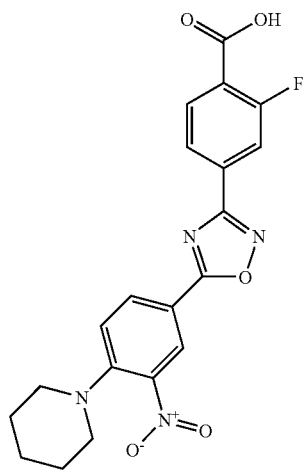 |
| 15 | 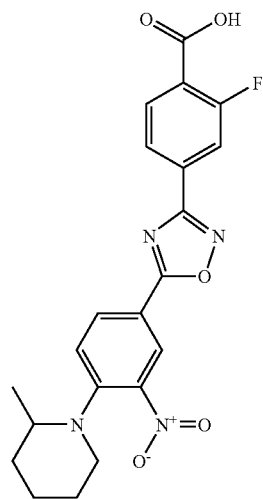 |
| 16 | 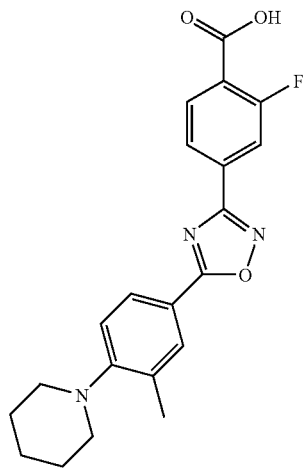 |

| Example Nb | structures |
|---|---|
| 17 | 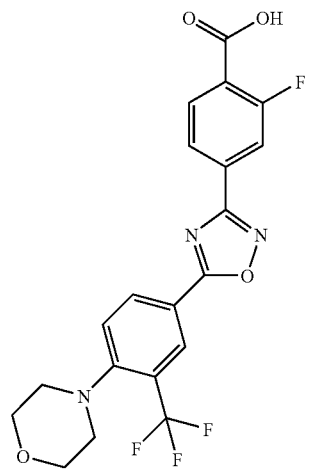 |
| 18 | 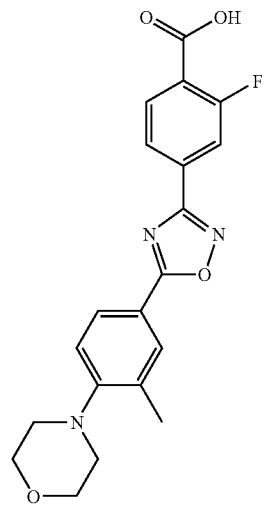 |
| 19 | 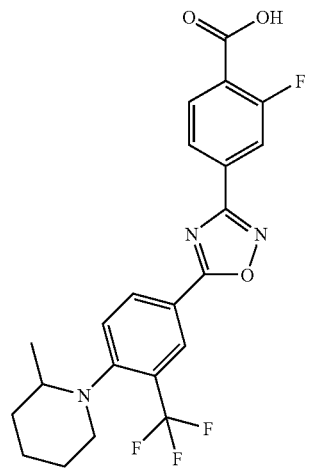 |

-continued

| Example Nb | structures |
|---|---|
| 20 | (structure: 2-fluoro-4-carboxyphenyl-1,2,4-oxadiazole linked to 2-methyl-2',4'-dimethoxybiphenyl) |
| 21 | (structure: 2-fluoro-4-carboxyphenyl-1,2,4-oxadiazole linked to 4-nitro-3-piperidinylphenyl) |
| 22 | (structure: 2-fluoro-4-carboxyphenyl-1,2,4-oxadiazole linked to 2-trifluoromethyl-2'-methylbiphenyl) |

| Example Nb | structures |
|---|---|
| 23 | 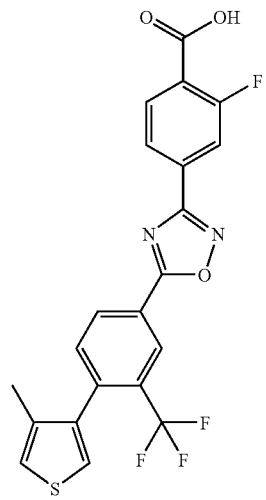 |
| 24 | 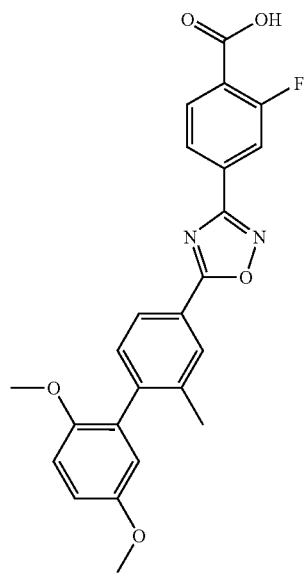 |
| 25 | 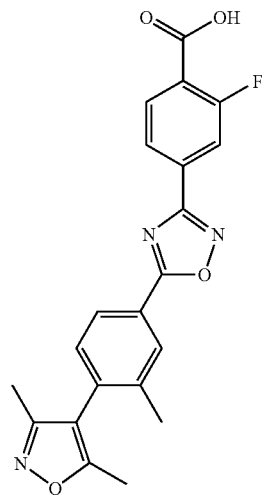 |

-continued
| Example Nb | structures |
|---|---|
| 26 | 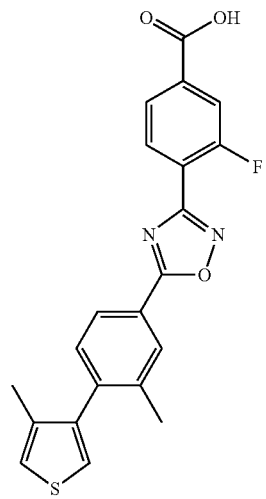 |
| 27 | 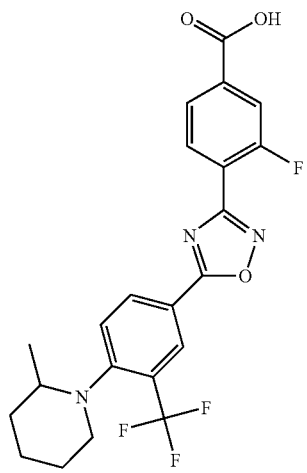 |
| 28 | 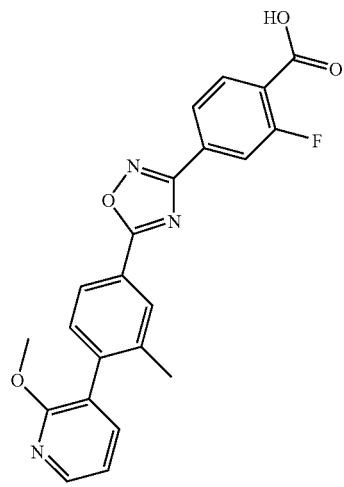 |

-continued
| Example Nb | structures |
|---|---|
| 29 | 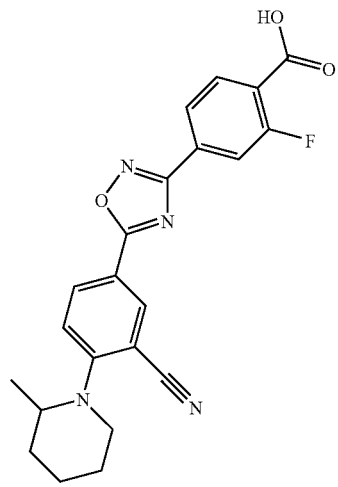 |
| 30 | 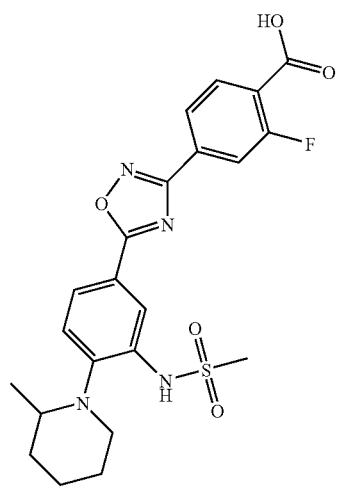 |
| 31 | 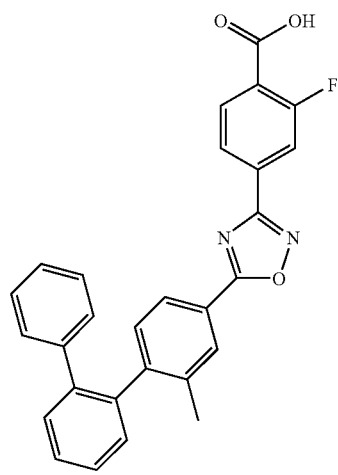 |

-continued
| Example Nb | structures |
|---|---|
| 32 | 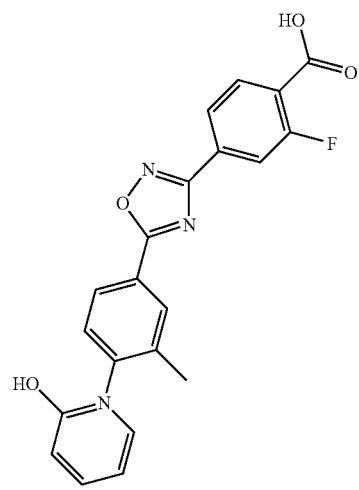 |
| 33 | 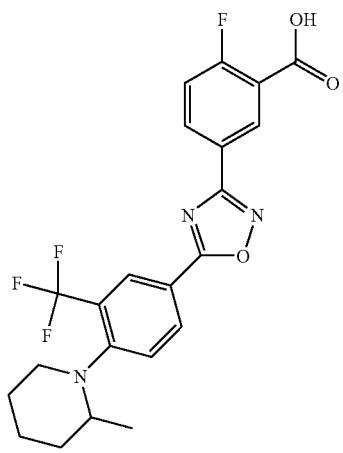 |
| 34 | 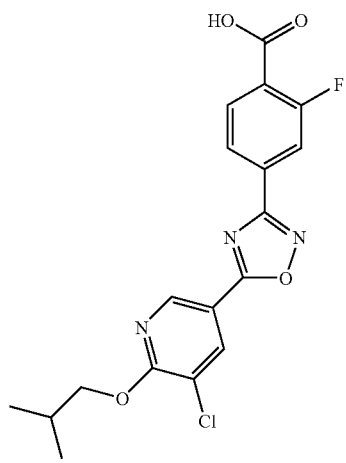 |

| Example Nb | structures |
|---|---|
| 35 | 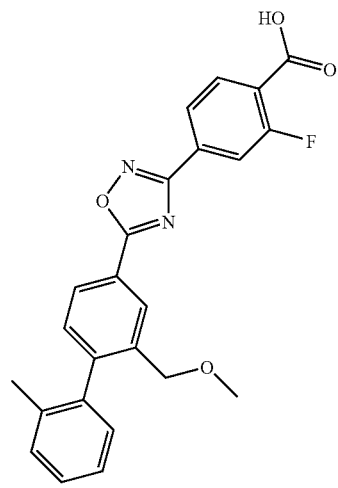 |
| 36 | 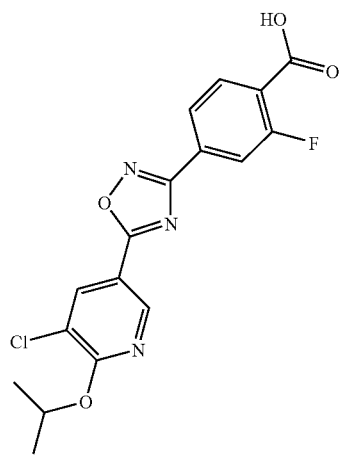 |
| 37 | 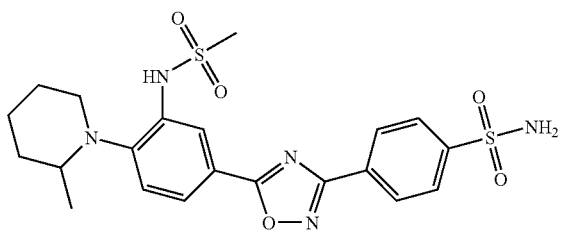 |
| 38 | 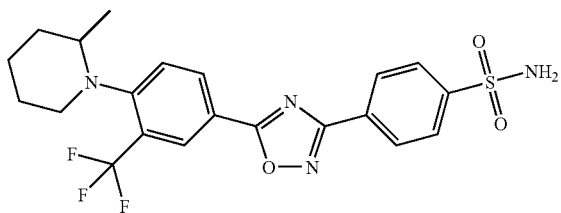 |

| Example Nb | structures |
|---|---|
| 39 | 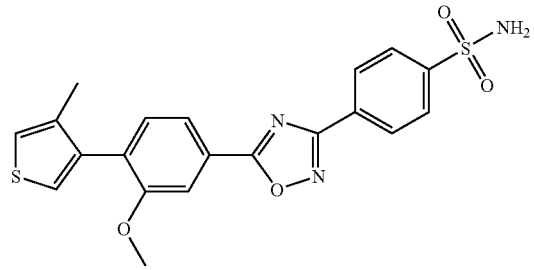 |
| 40 | 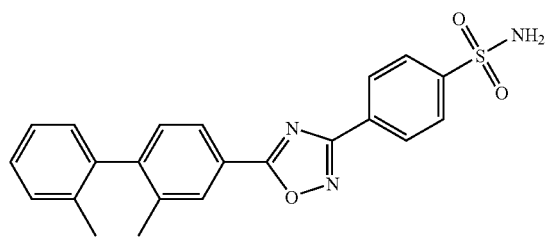 |
| 41 | 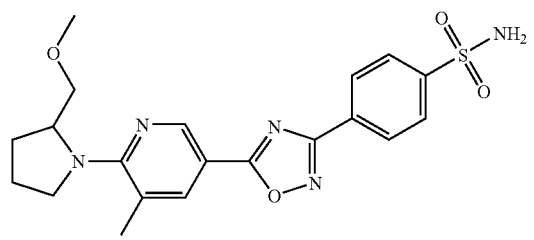 |
| 42 | 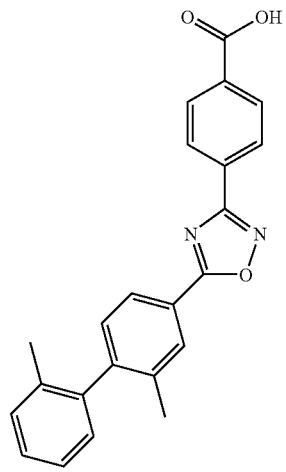 |

-continued
| Example Nb | structures |
|---|---|
| 43 | 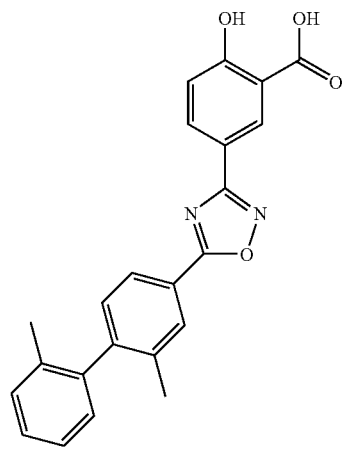 |
| 44 | 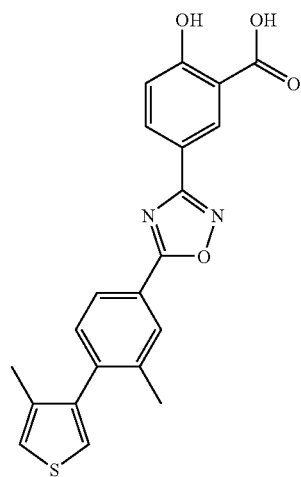 |
| 45 | 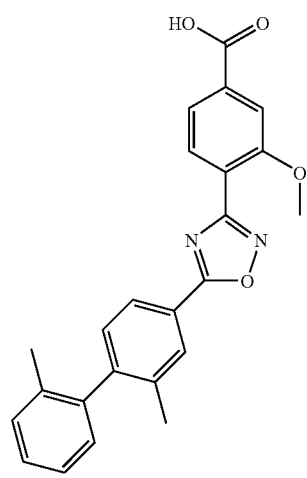 |

-continued
| Example Nb | structures |
|---|---|
| 46 | 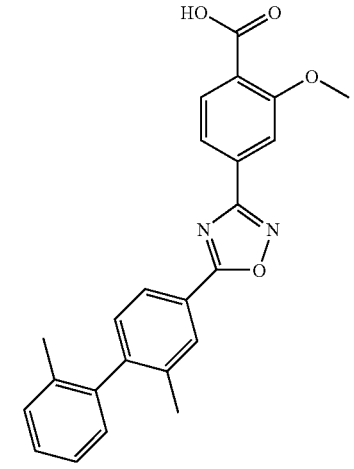 |
| 47 | 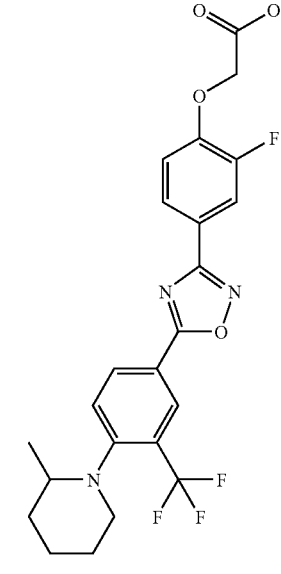 |
| 48 | 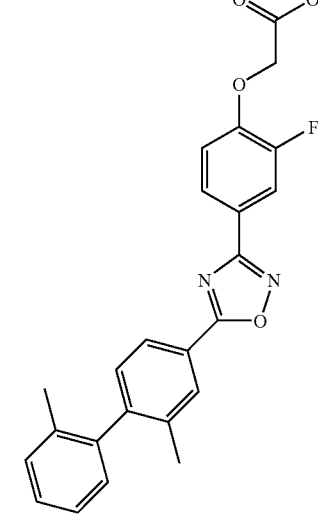 |

| Example Nb | structures |
|---|---|
| 49 | 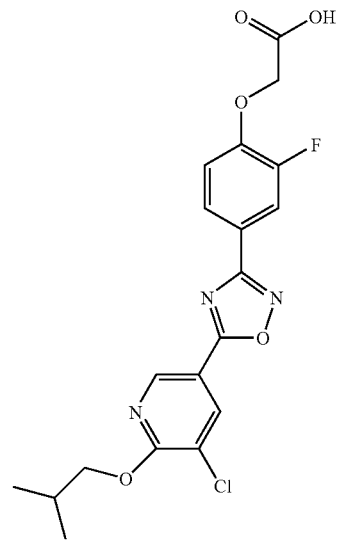 |
| 50 | 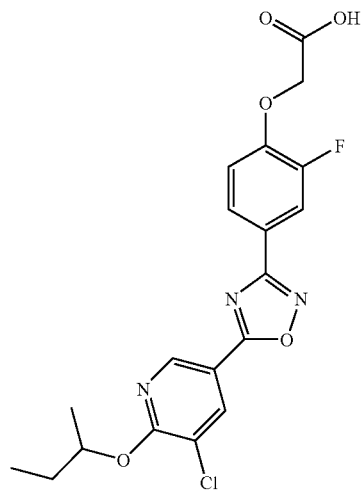 |
| 51 | 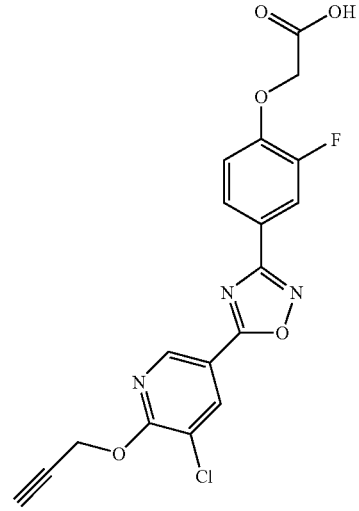 |

-continued
| Example Nb | structures |
|---|---|
| 52 | 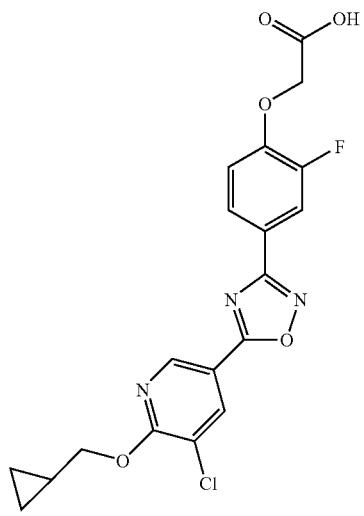 |
| 53 | 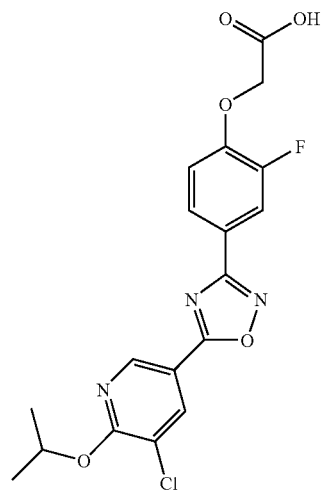 |
| 54 | 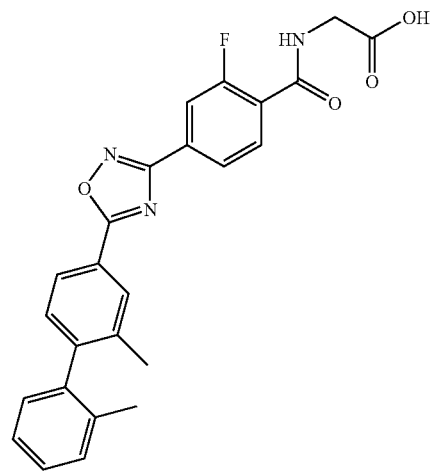 |

| Example Nb | structures |
|---|---|
| 55 | 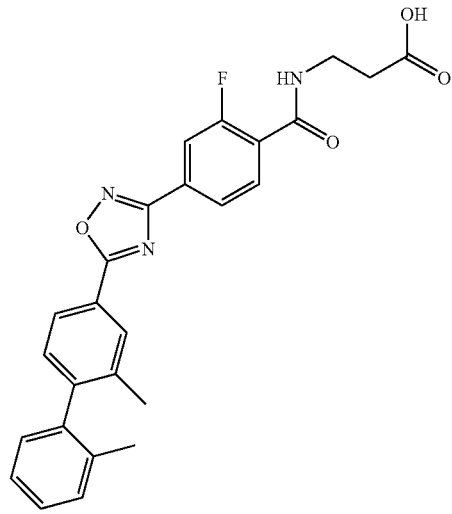 |
| 56 | 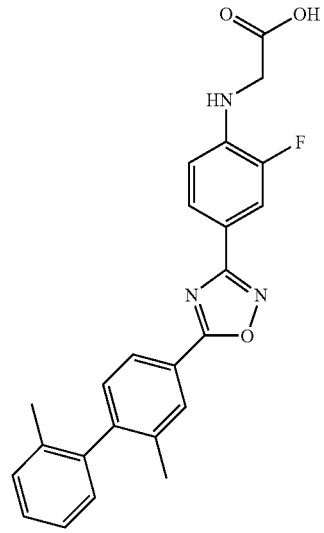 |
| 57 | 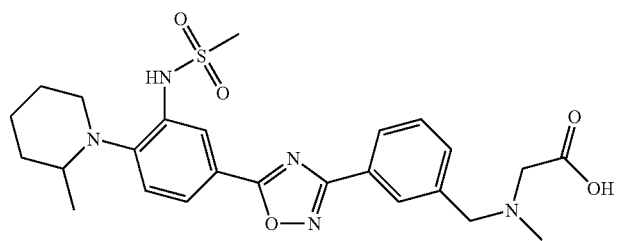 |

-continued
| Example Nb | structures |
|---|---|
| 58 | 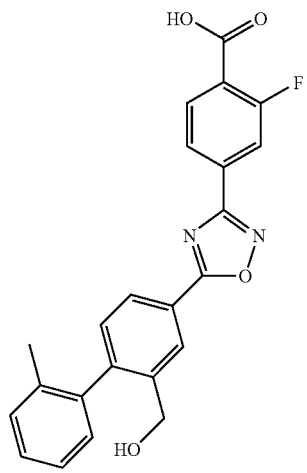 |
| 59 | 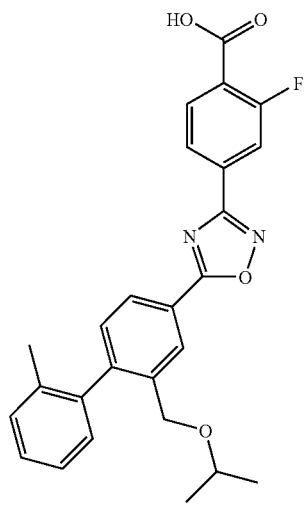 |
| 60 | 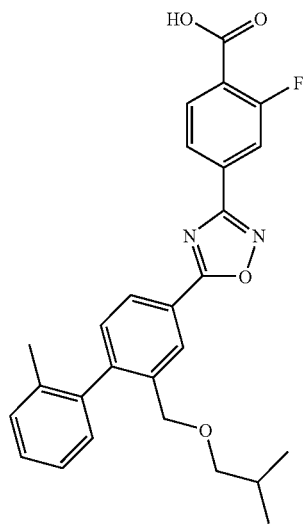 |

| Example Nb | structures |
|---|---|
| 61 | 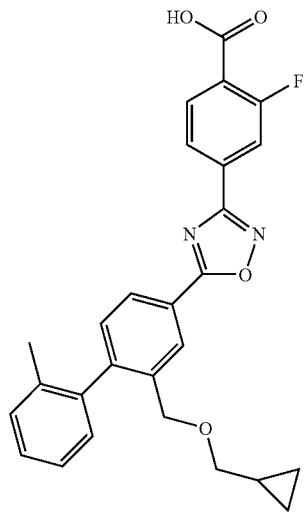 |
| 62 | 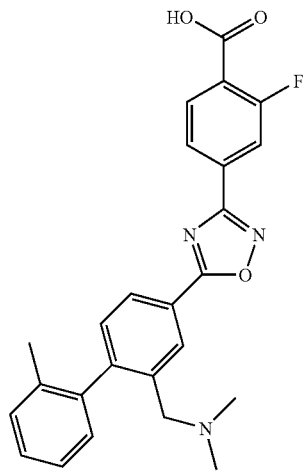 |
| 63 | 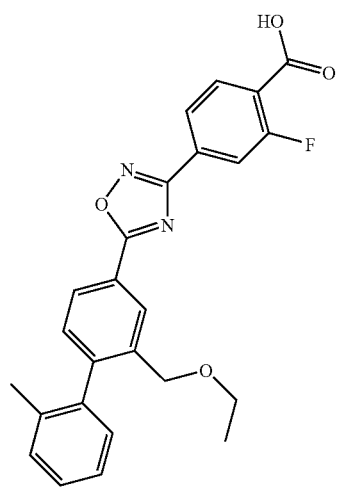 |

-continued
| Example Nb | structures |
|---|---|
| 64 | 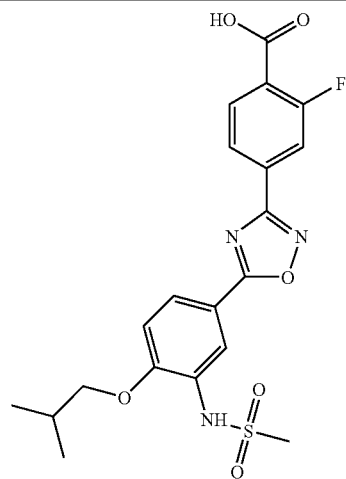 |
| 65 | 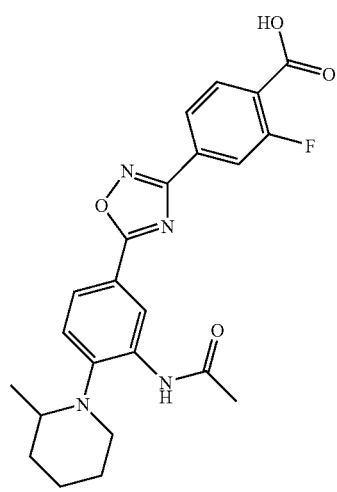 |
| 66 | 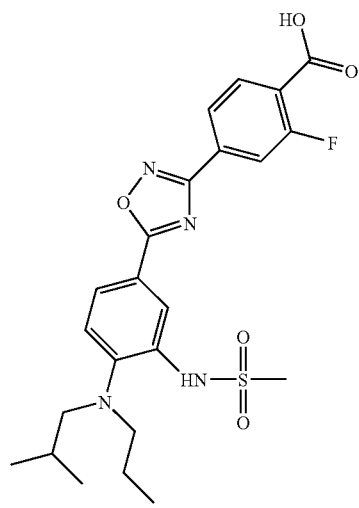 |

-continued
| Example Nb | structures |
|---|---|
| 67 | 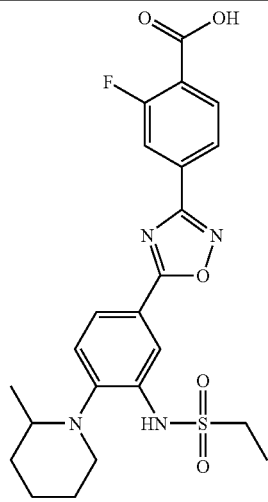 |
| 68 | 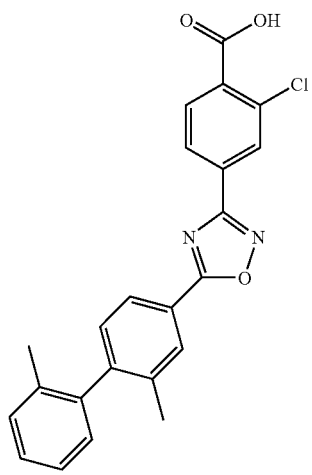 |
| 69 | 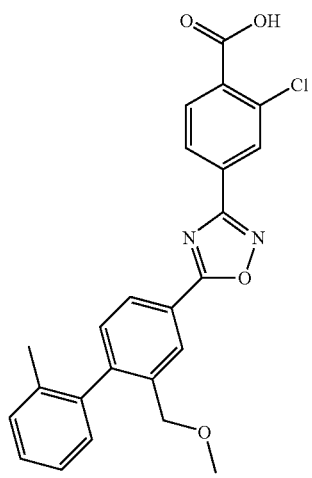 |

-continued
| Example Nb | structures |
|---|---|
| 70 | 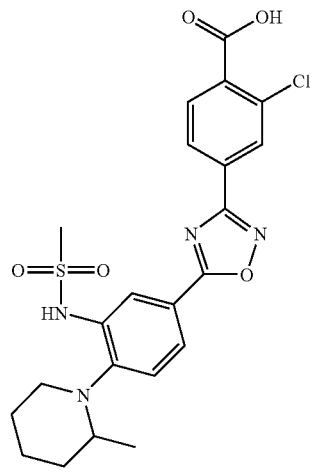 |
| 71 | 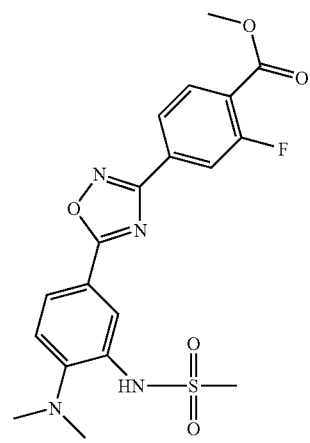 |
| 72 | 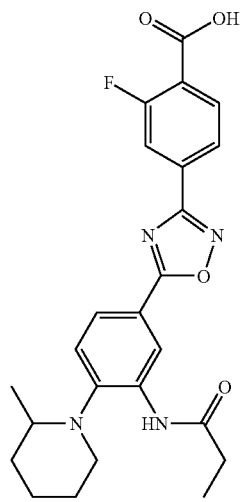 |

-continued
| Example Nb | structures |
|---|---|
| 73 | 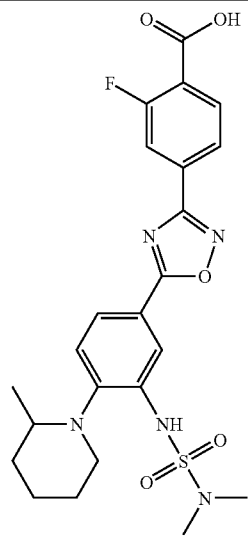 |
| 74 | 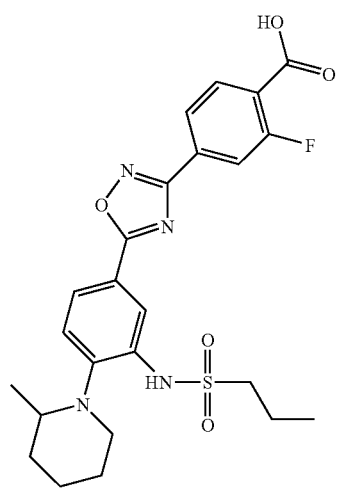 |
| 75 | 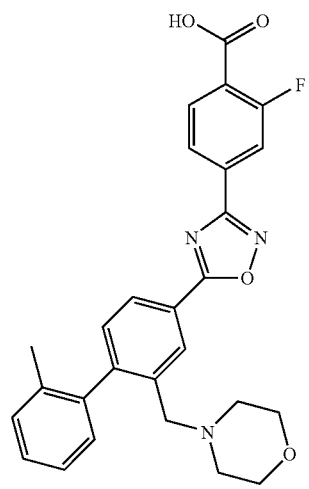 |

-continued
| Example Nb | structures |
|---|---|
| 76 | 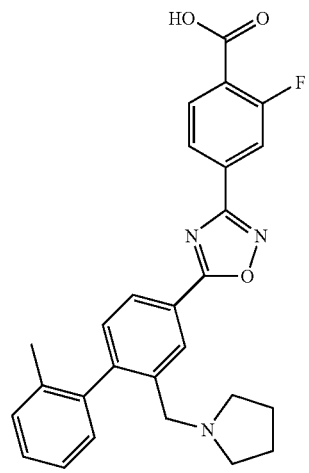 |
| 77 | 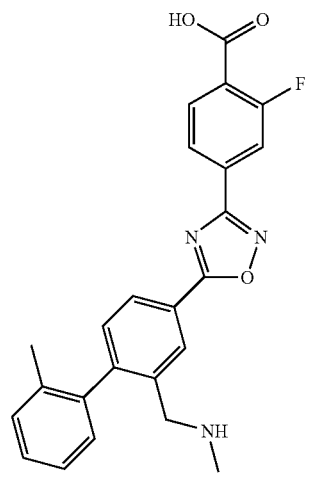 |
| 78 | 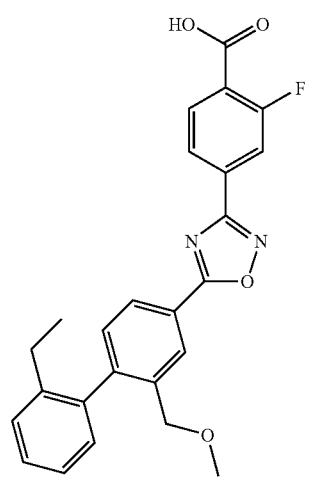 |

| Example Nb | structures |
|---|---|
| 79 | 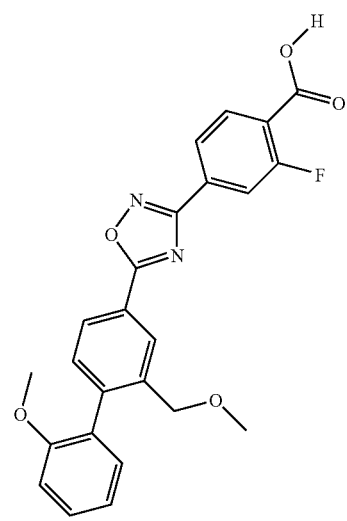 |
| 80 | 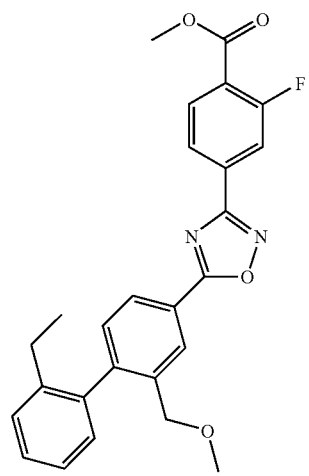 |
| 81 | 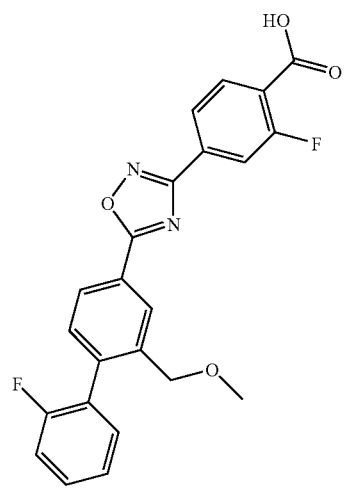 |

-continued
| Example Nb | structures |
|---|---|
| 82 | 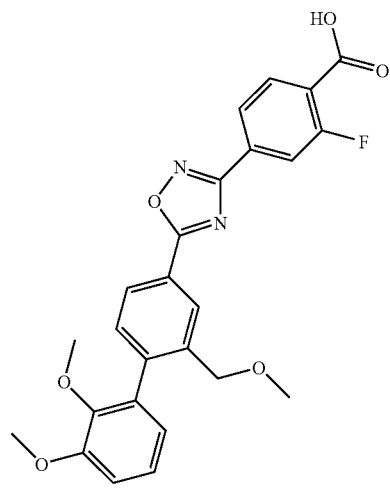 |
| 83 | 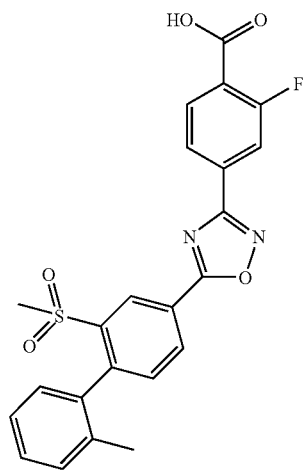 |
| 84 | 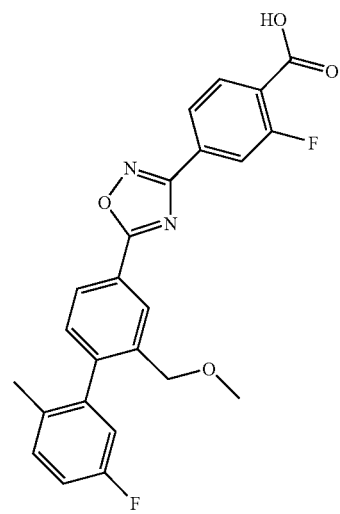 |

-continued
| Example Nb | structures |
|---|---|
| 85 | 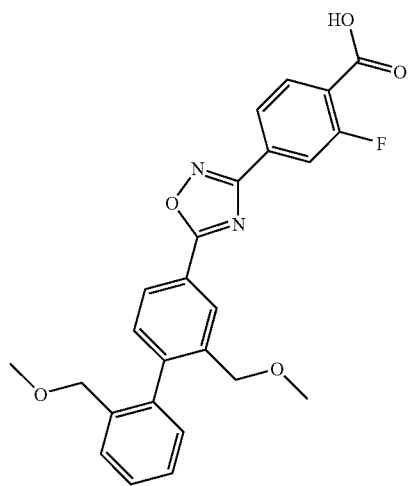 |
| 86 | 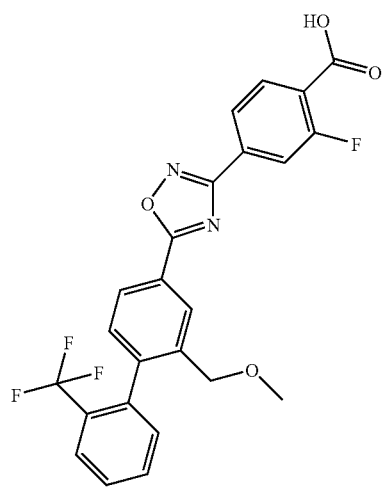 |
| 87 | 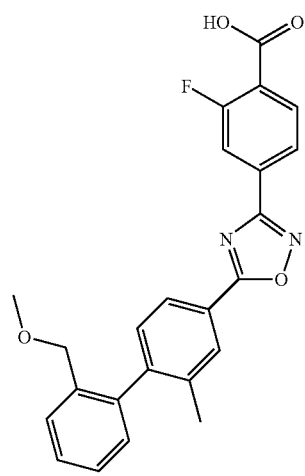 |

-continued
| Example Nb | structures |
|---|---|
| 88 | 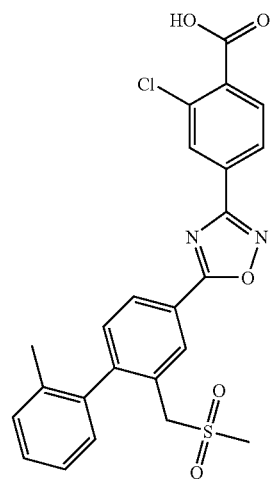 |
| 89 | 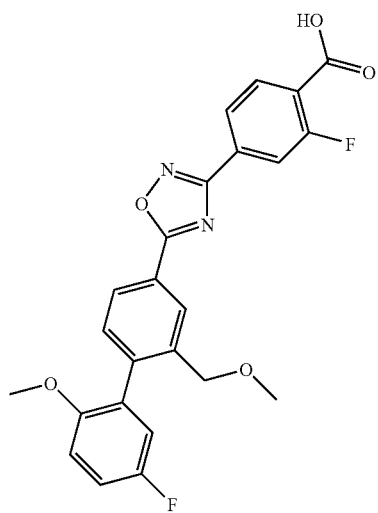 |
| 90 | 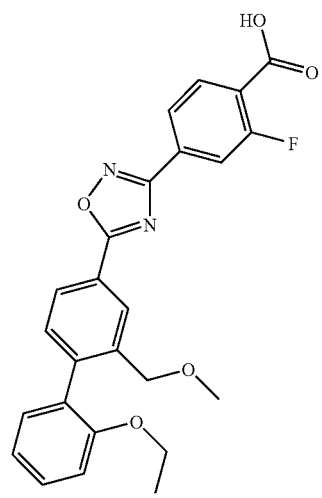 |

-continued
| Example Nb | structures |
|---|---|
| 91 | 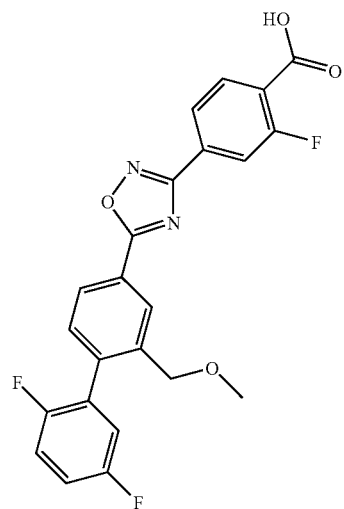 |
| 92 | 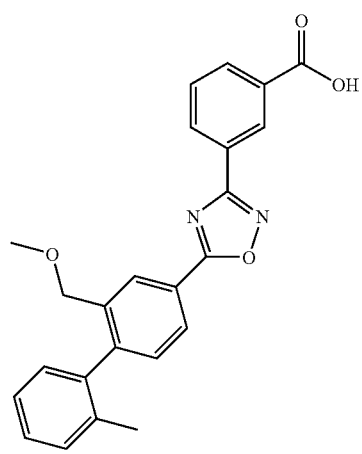 |
| 93 | 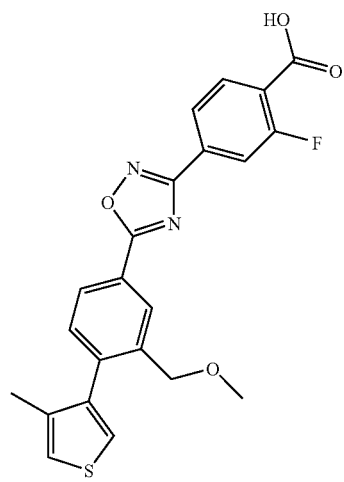 |

-continued
| Example Nb | structures |
|---|---|
| 94 | 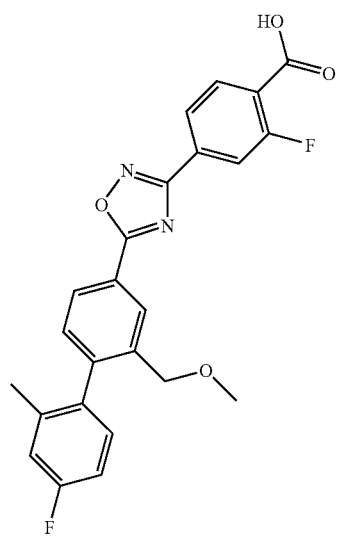 |
| 95 | 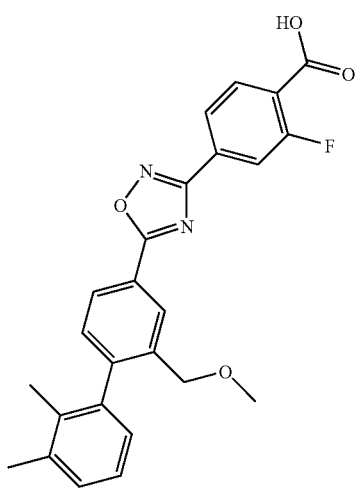 |
| 96 | 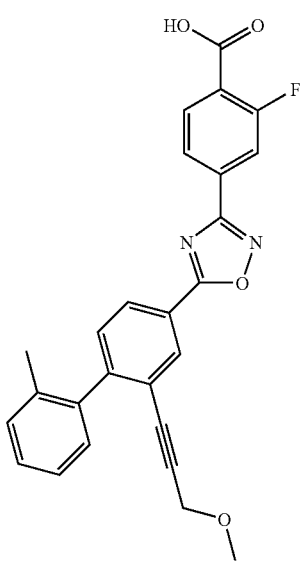 |

-continued
| Example Nb | structures |
|---|---|
| 97 | 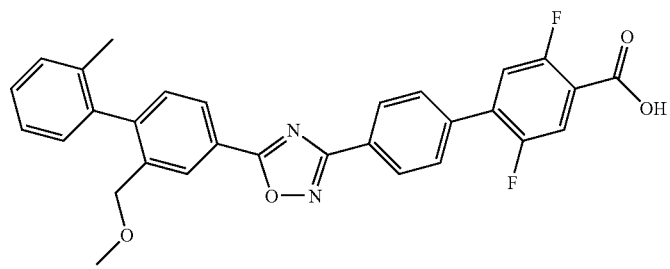 |
| 98 | 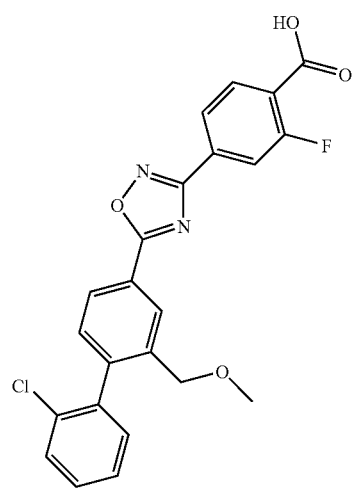 |
| 99 | 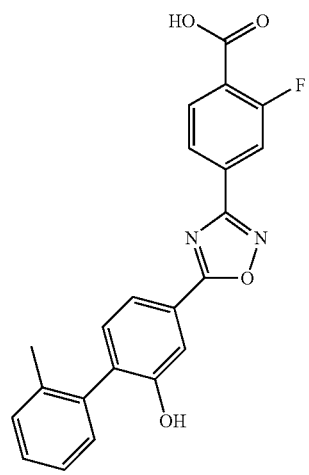 |

-continued
| Example Nb | structures |
|---|---|
| 100 | 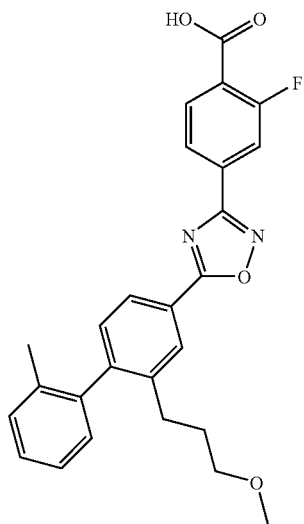 |
| 101 | 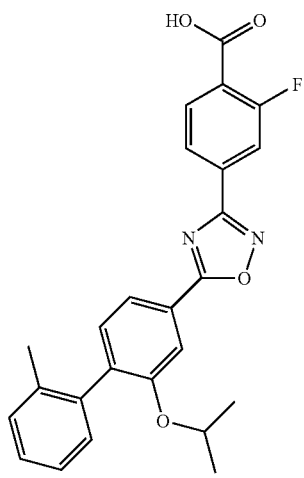 |
| 102 | 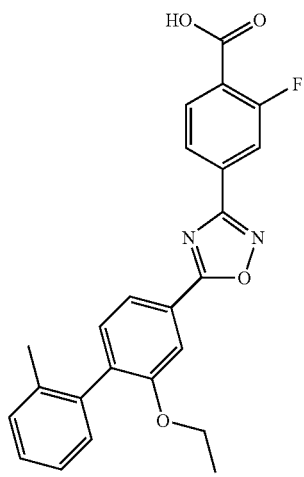 |

| Example Nb | structures |
|---|---|
| 103 | 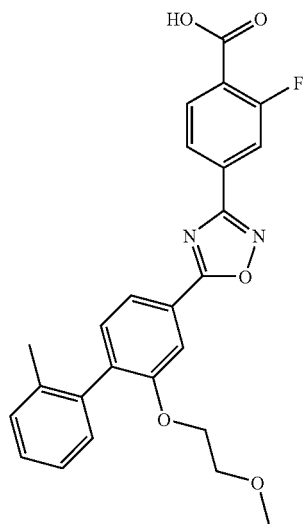 |
| 104 | 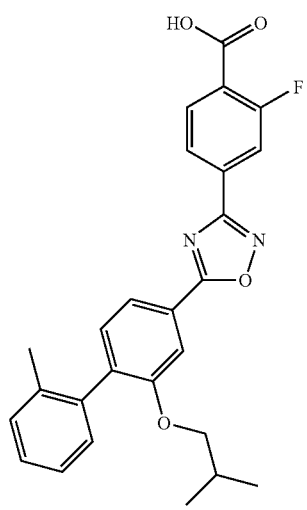 |
| 105 | 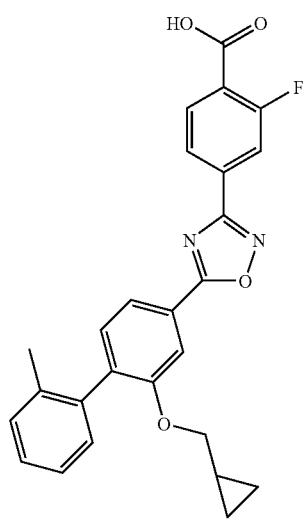 |

-continued
| Example Nb | structures |
|---|---|
| 106 | 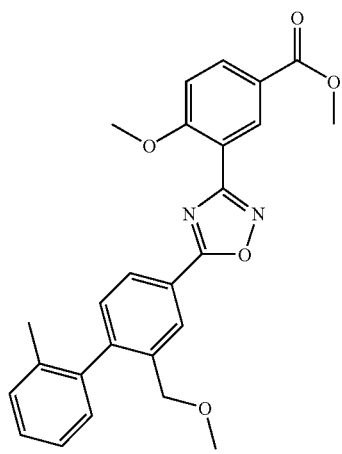 |
| 107 | 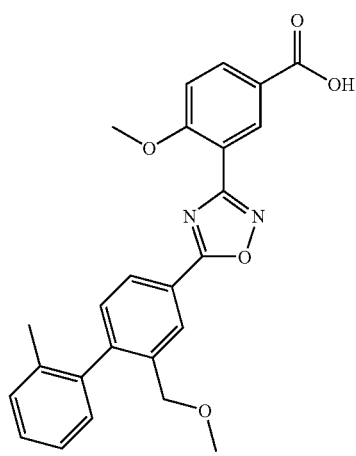 |
| 108 | 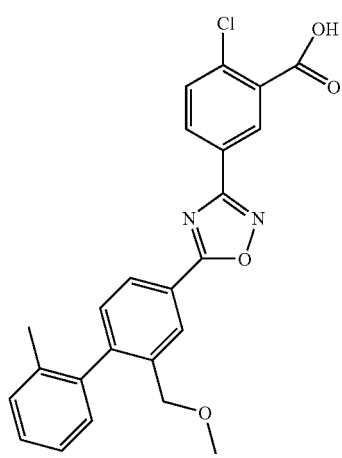 |

-continued
| Example Nb | structures |
|---|---|
| 109 | 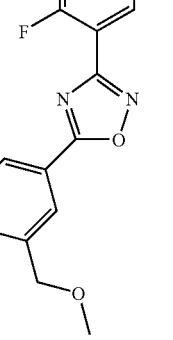 |
| 110 | 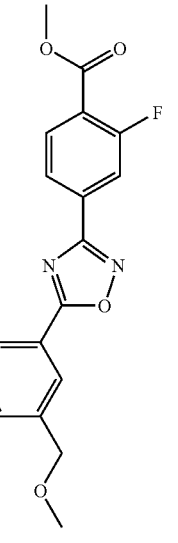 |
| 111 | 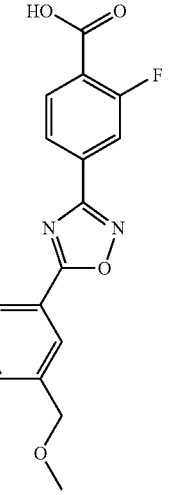 |

-continued
| Example Nb | structures |
|---|---|
| 112 | 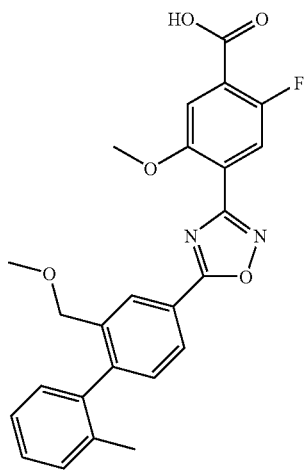 |
| 113 | 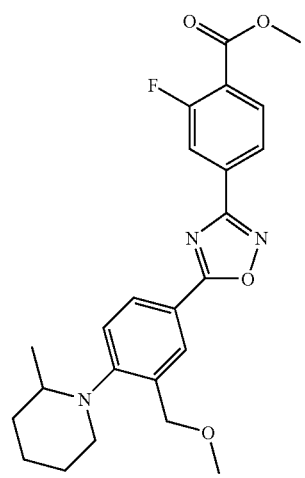 |
| 114 | 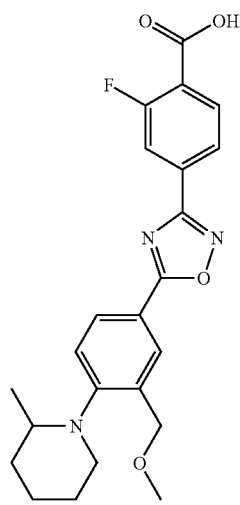 |

| Example Nb | structures |
|---|---|
| 115 | 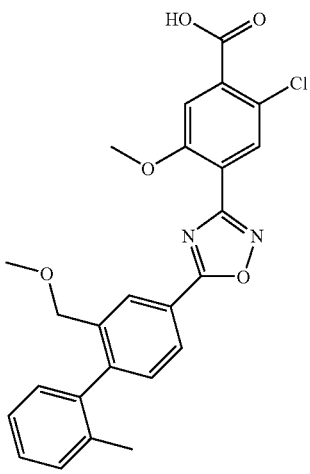 |
| 116 | 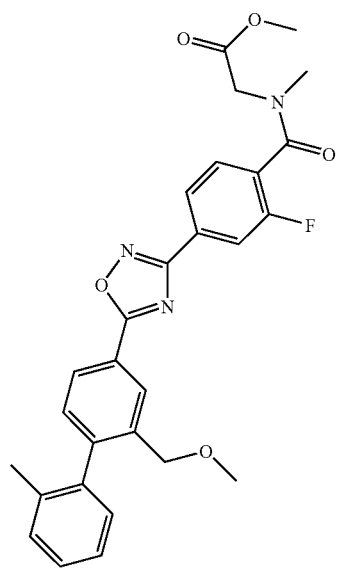 |
| 117 | 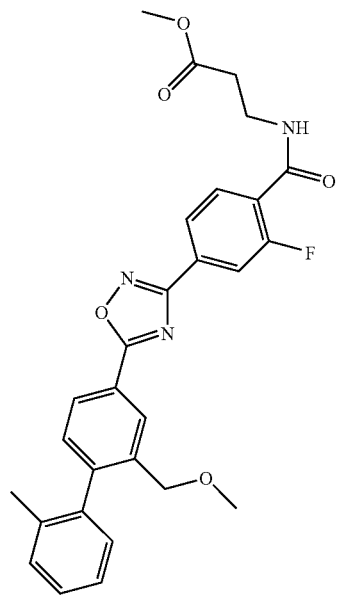 |

-continued
| Example Nb | structures |
|---|---|
| 118 | 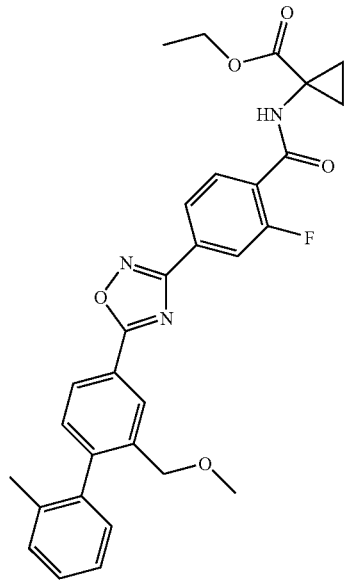 |
| 119 | 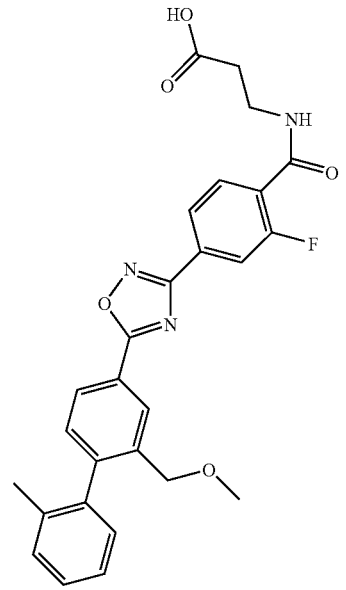 |

-continued
| Example Nb | structures |
|---|---|
| 120 | 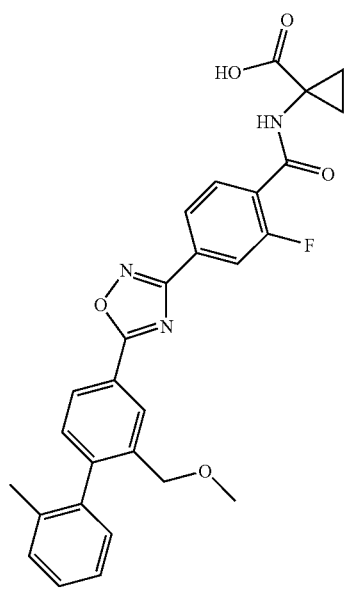 |
| 121 | 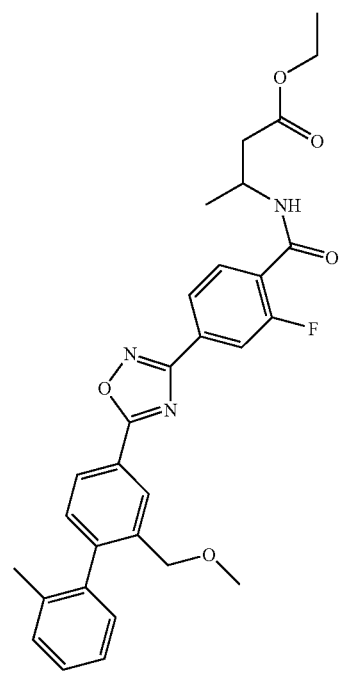 |

-continued
| Example Nb | structures |
|---|---|
| 122 | 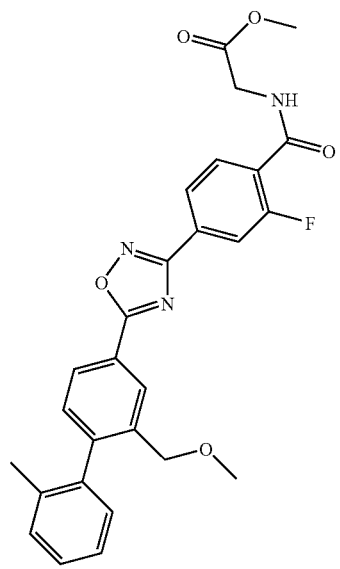 |
| 123 | 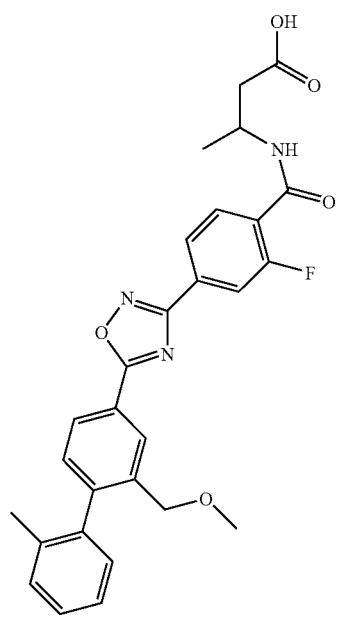 |

-continued
| Example Nb | structures |
|---|---|
| 124 | 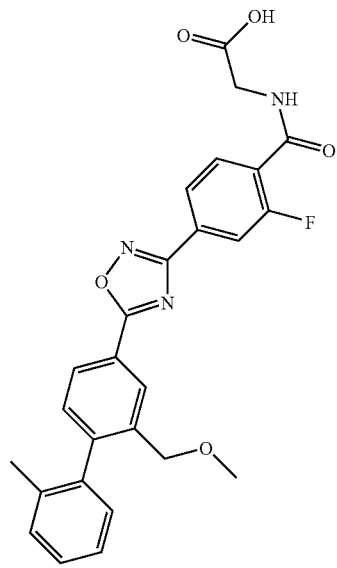 |
| 125 | 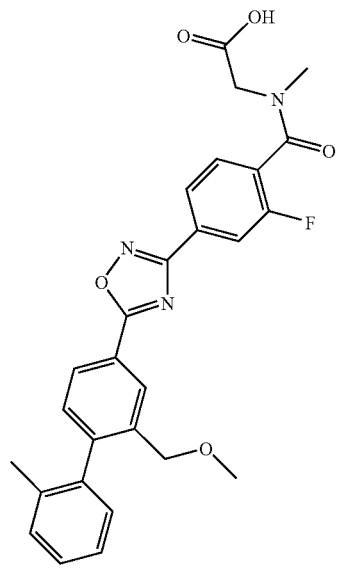 |

-continued
| Example Nb | structures |
|---|---|
| 126 | 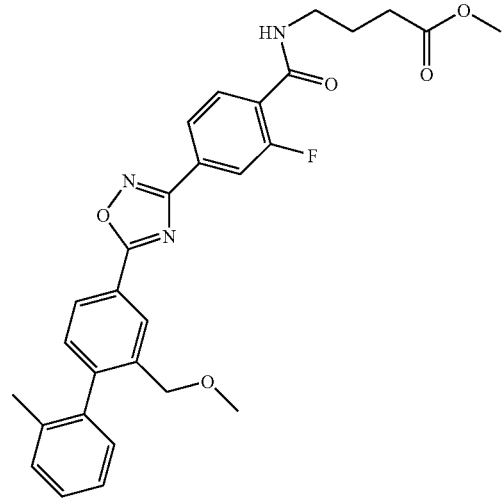 |
| 127 | 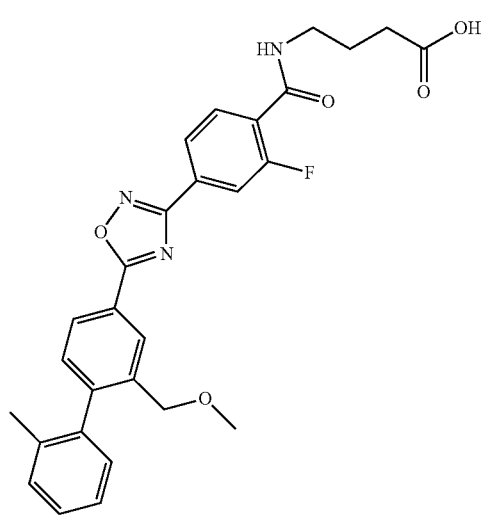 |
| 128 | 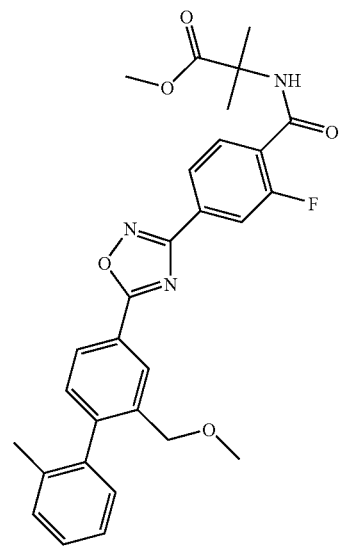 |

-continued
| Example Nb | structures |
|---|---|
| 129 | 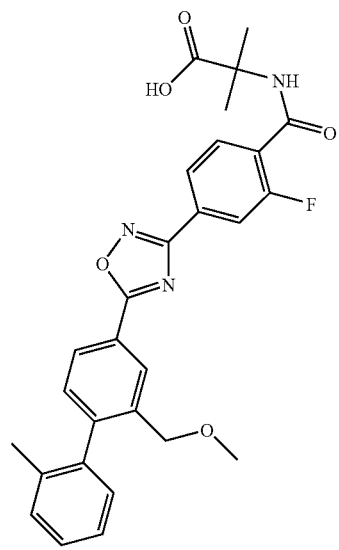 |
| 130 | 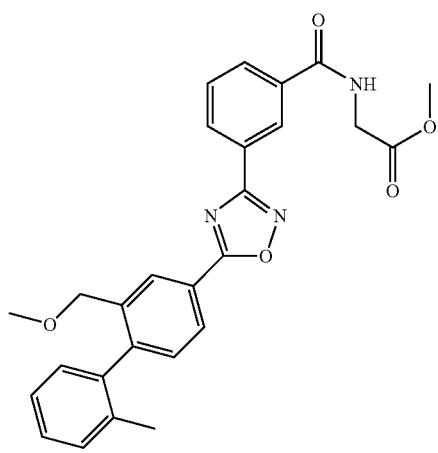 |
| 131 | 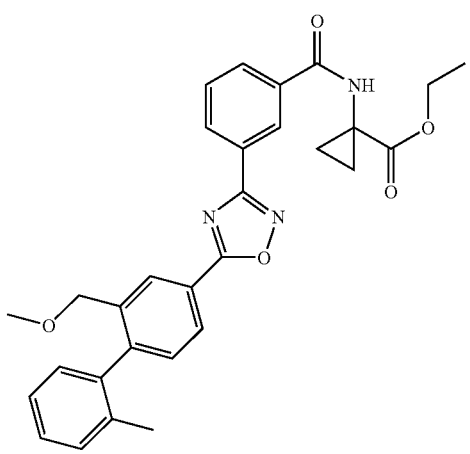 |

-continued
| Example Nb | structures |
|---|---|
| 132 | 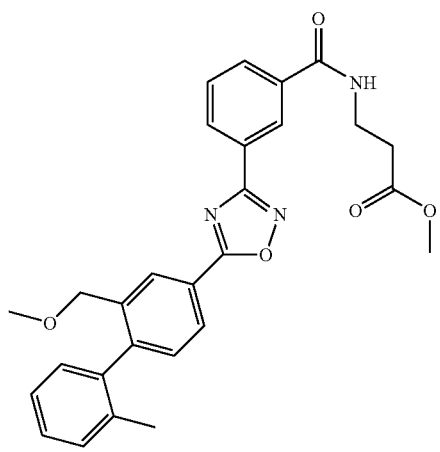 |
| 133 | 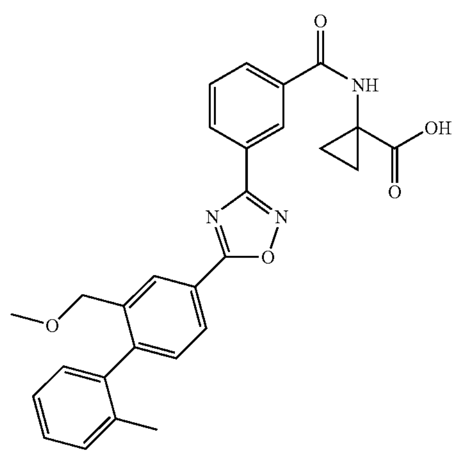 |
| 134 | 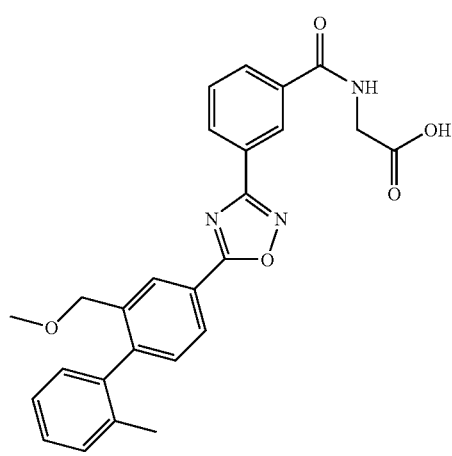 |

-continued
| Example Nb | structures |
|---|---|
| 135 | 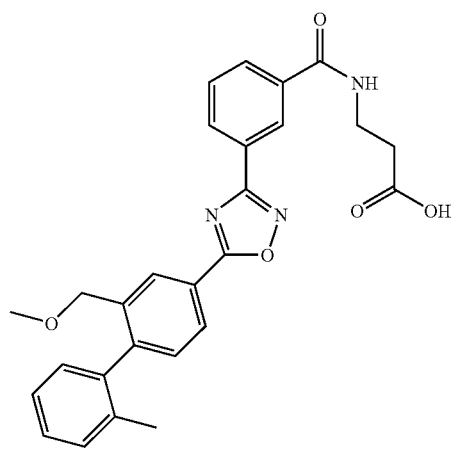 |
| 136 | 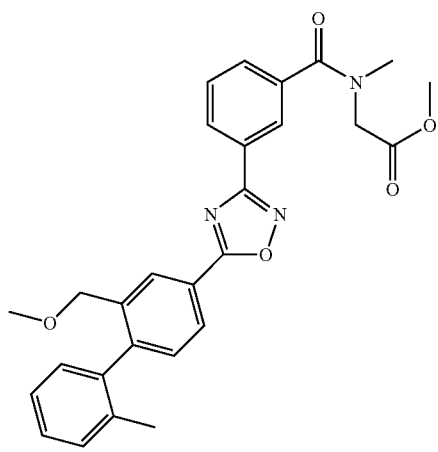 |
| 137 | 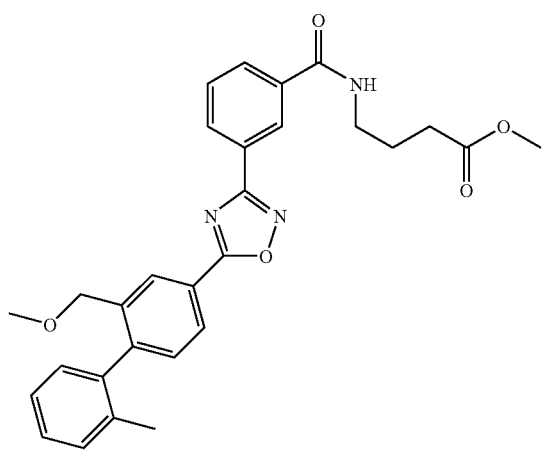 |

-continued
| Example Nb | structures |
|---|---|
| 138 | 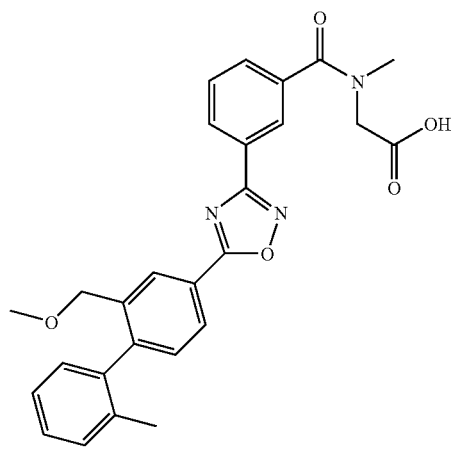 |
| 139 | 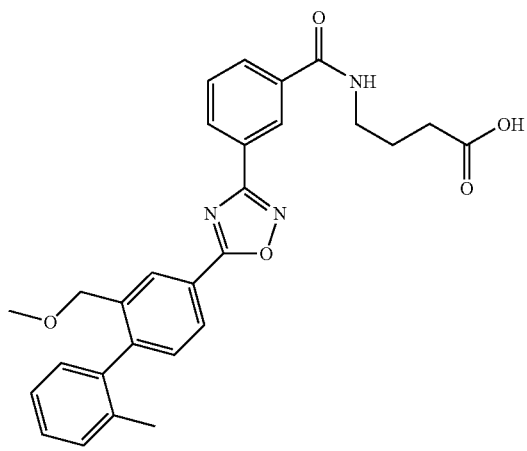 |
| 140 | 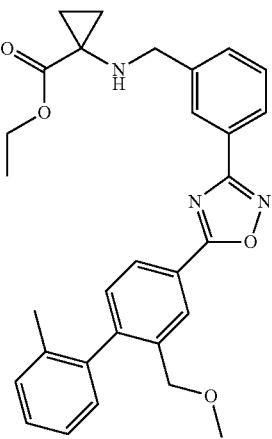 |

| Example Nb | structures |
| --- | --- |
| 141 | 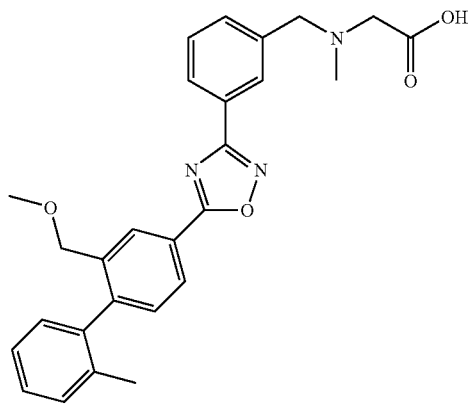 |
| 142 | 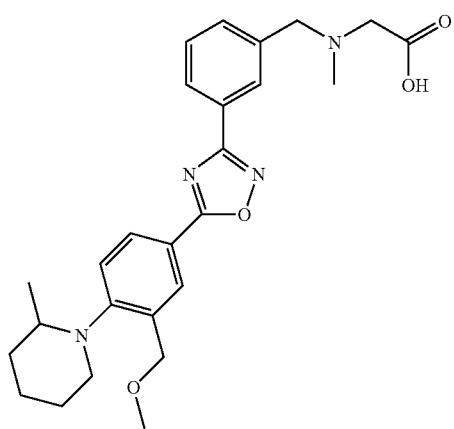 |
| 143 | 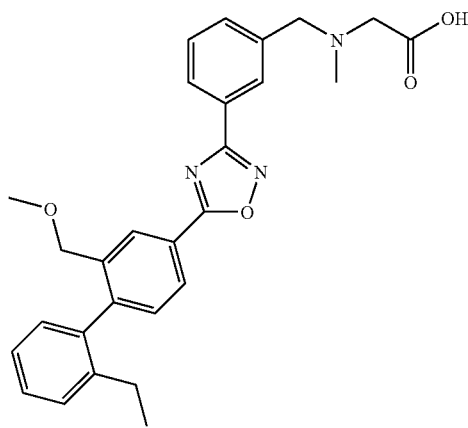 |

-continued
| Example Nb | structures |
|---|---|
| 144 | 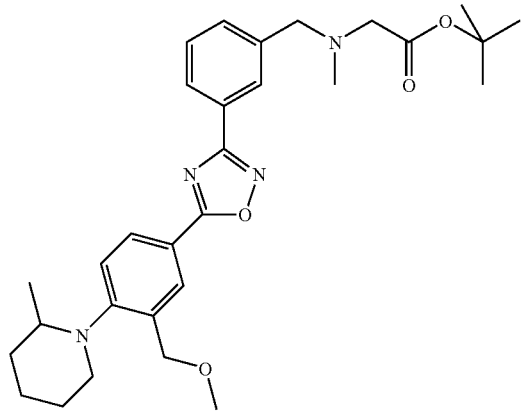 |
| 145 | 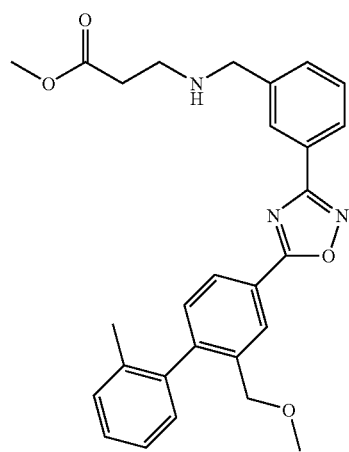 |
| 146 | 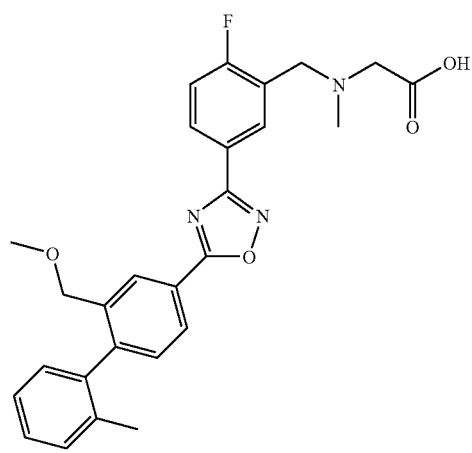 |

| Example Nb | structures |
|---|---|
| 147 | 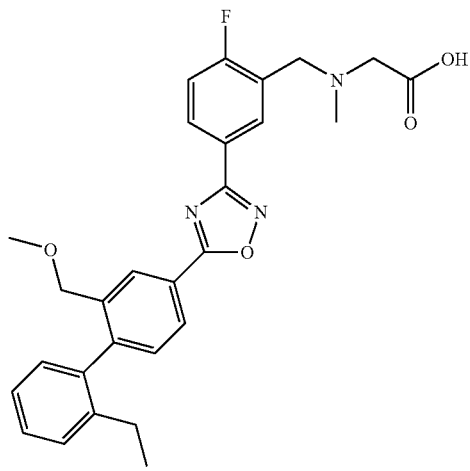 |
| 148 | 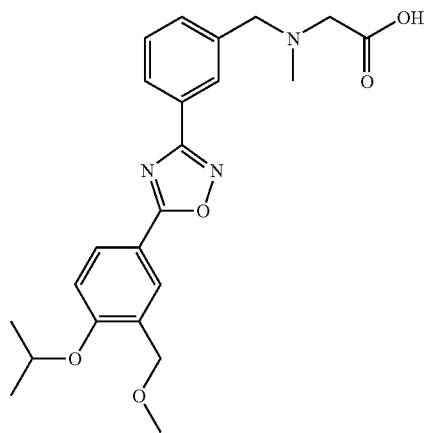 |
| 149 | 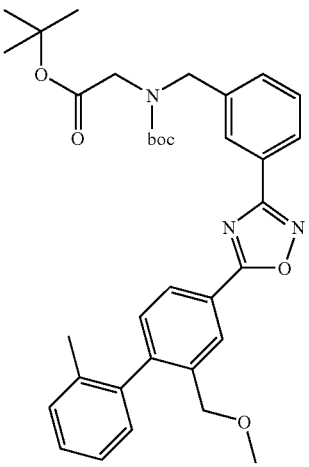 |

| Example Nb | structures |
|---|---|
| 150 | 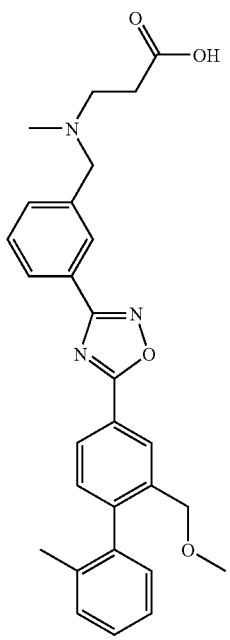 |
| 151 | 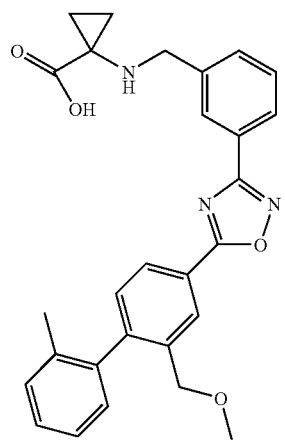 |
| 152 | 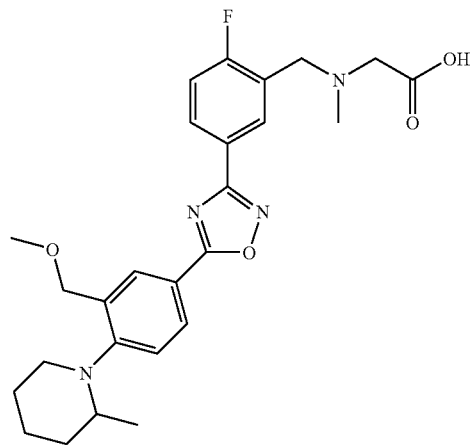 |

| Example Nb | structures |
|---|---|
| 153 | 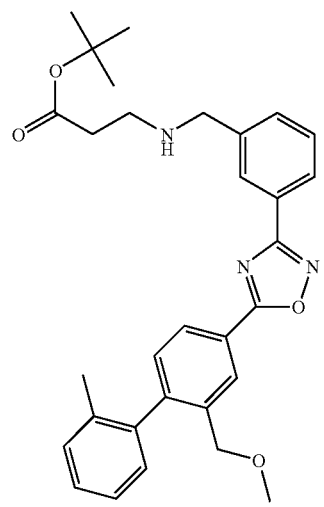 |
| 154 | 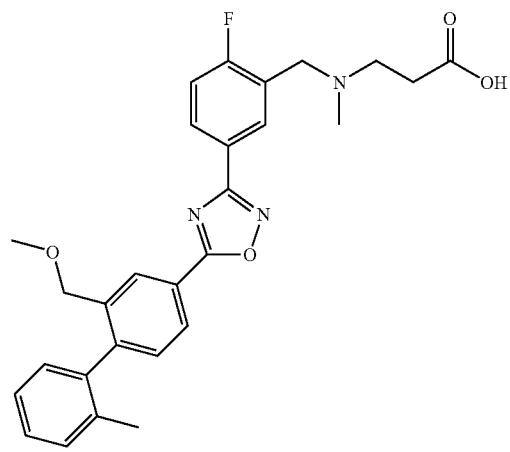 |
| 155 | 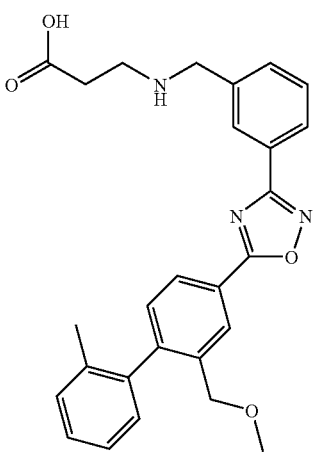 |

-continued
| Example Nb | structures |
|---|---|
| 156 | 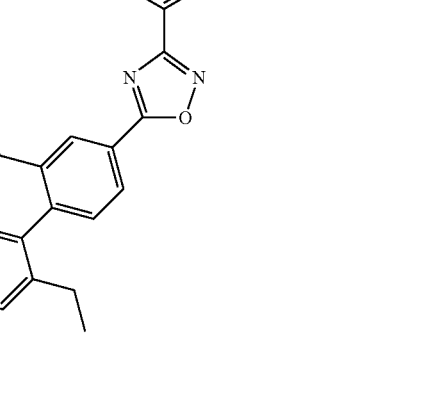 |
| 157 | 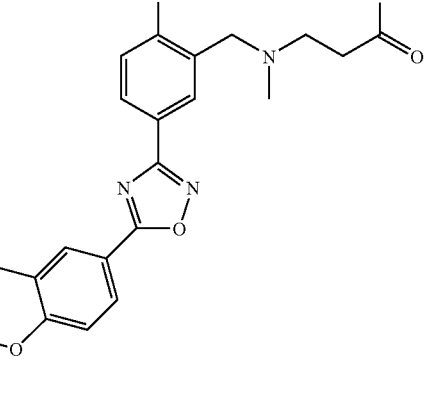 |
| 158 | 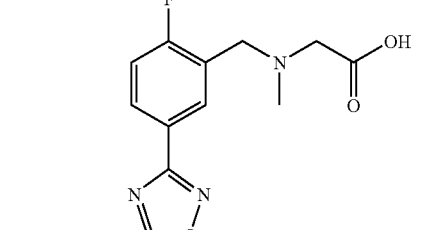 |

| Example Nb | structures |
|---|---|
| 159 | 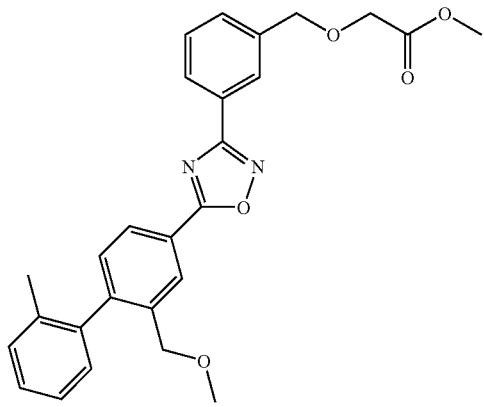 |
| 160 | 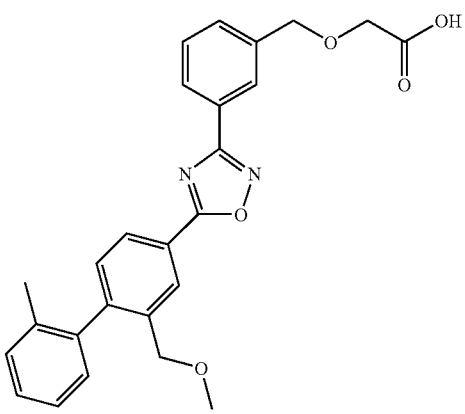 |
| 161 | 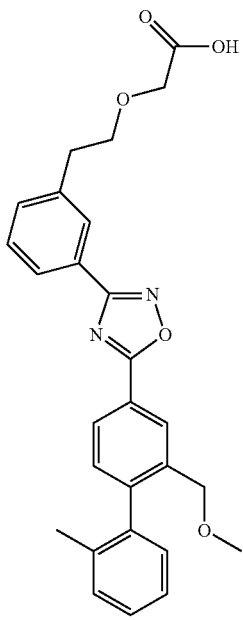 |

-continued
| Example Nb | structures |
|---|---|
| 162 | 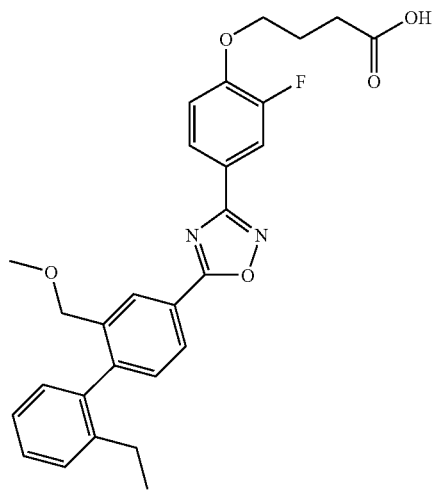 |
| 163 | 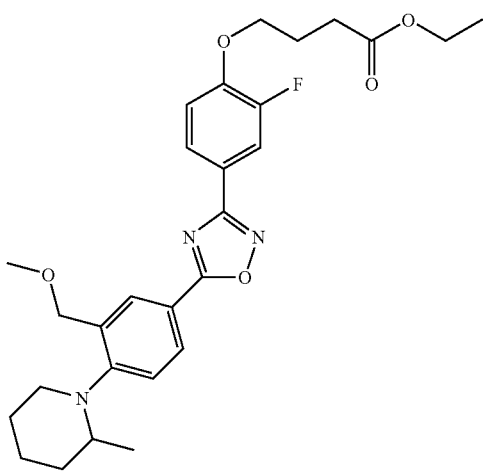 |
| 164 | 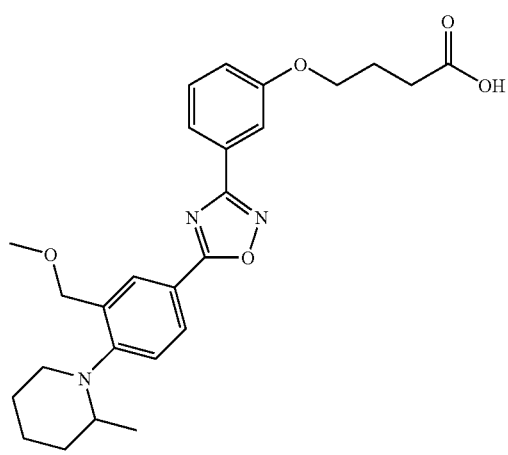 |

| Example Nb | structures |
|---|---|
| 165 | 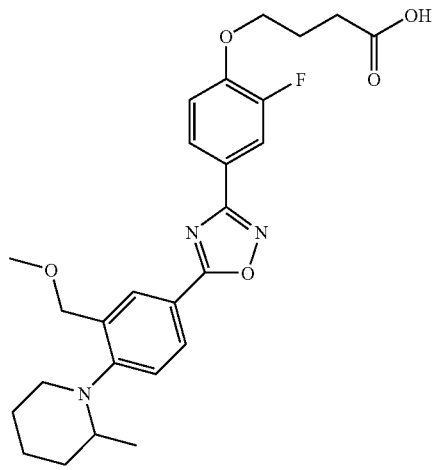 |
| 166 | 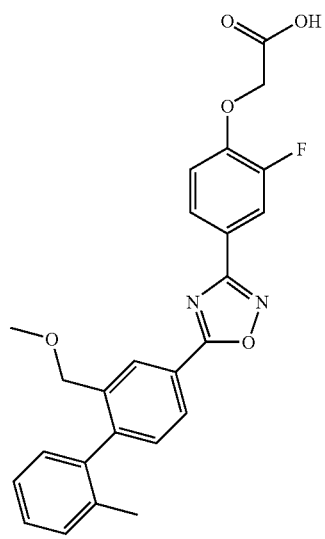 |
| 167 | 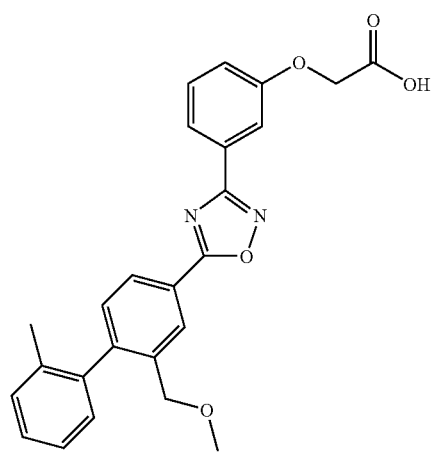 |

-continued
| Example Nb | structures |
|---|---|
| 168 | 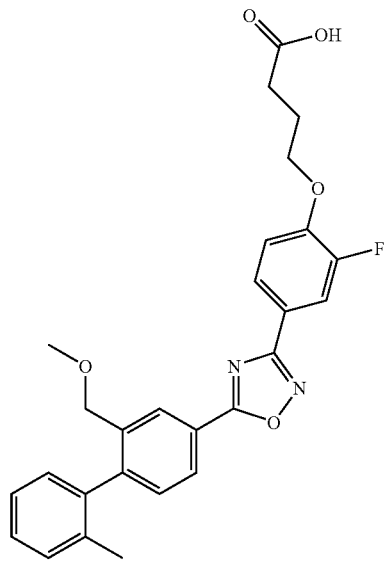 |
| 169 | 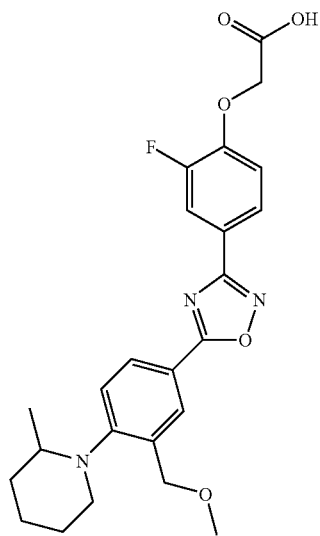 |
| 170 | 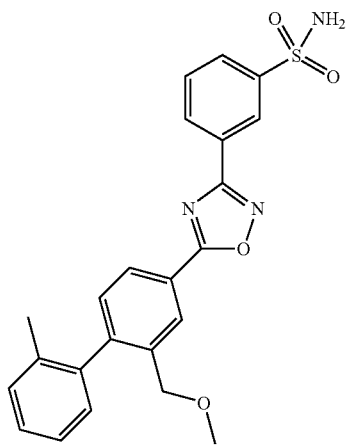 |

| Example Nb | structures |
|---|---|
| 171 | 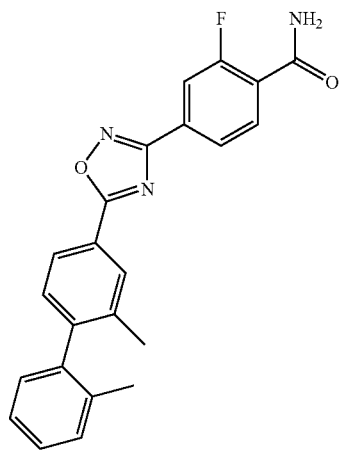 |
| 172 | 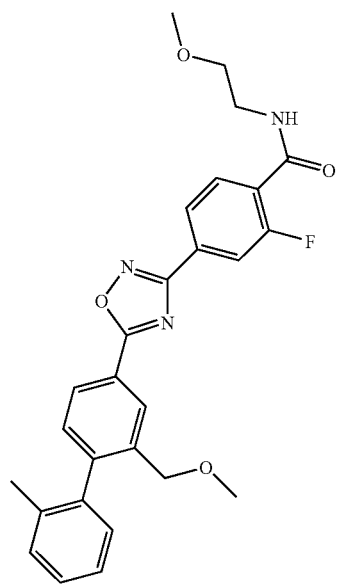 |
| 173 | 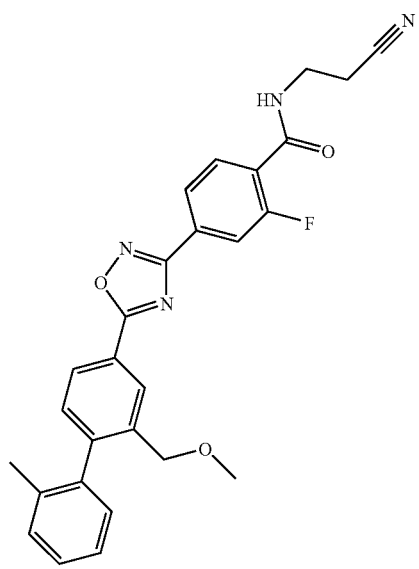 |

-continued
| Example Nb | structures |
|---|---|
| 174 | 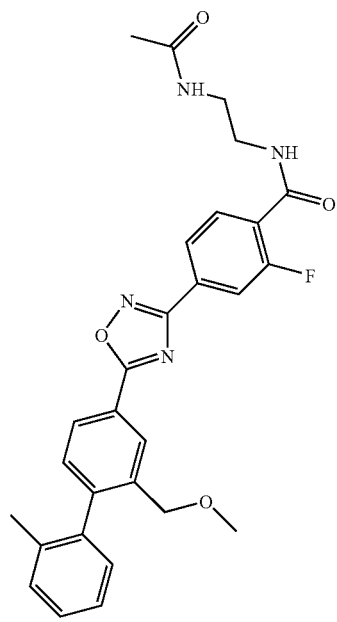 |
| 175 | 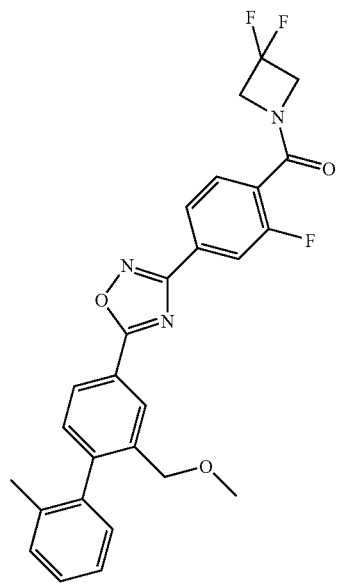 |

-continued
| Example Nb | structures |
|---|---|
| 176 | 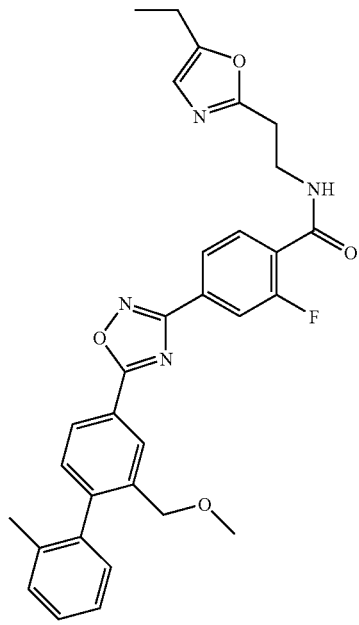 |
| 177 | 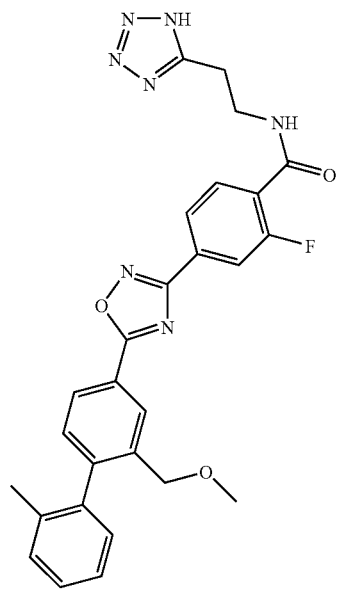 |

| Example Nb | structures |
|---|---|
| 178 | 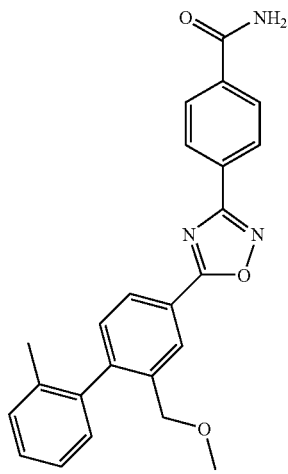 |
| 179 | 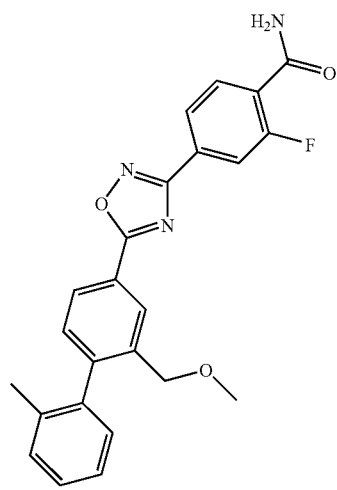 |
| 180 | 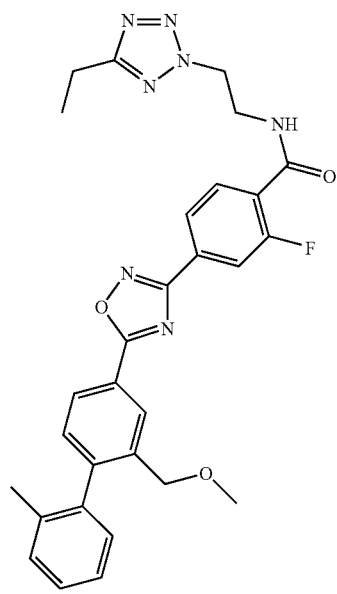 |

| Example Nb | structures |
|---|---|
| 181 | 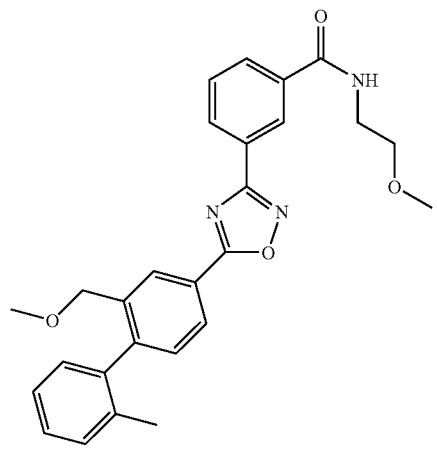 |
| 182 | 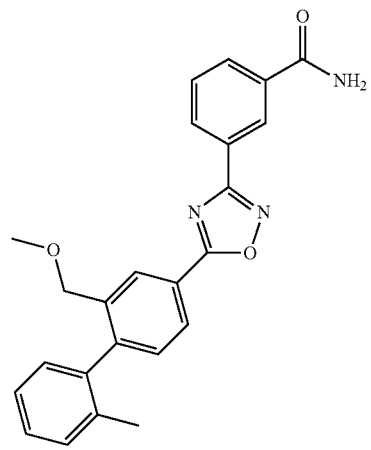 |
| 183 | 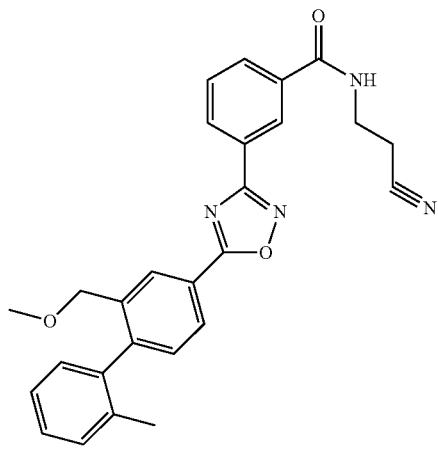 |

| Example Nb | structures |
|---|---|
| 184 | 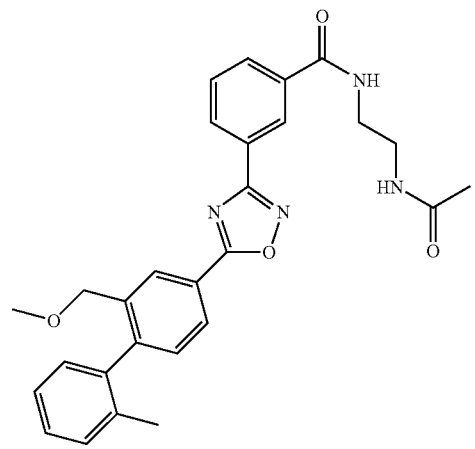 |
| 185 | 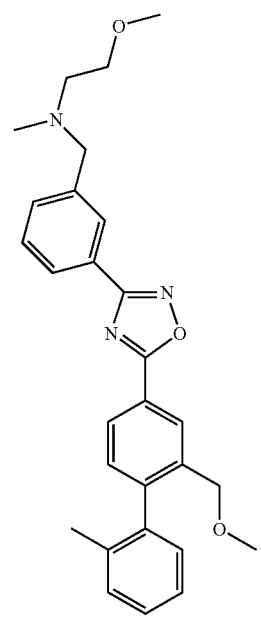 |

-continued

| Example Nb | structures |
|---|---|
| 186 | (structure) |
| 187 | (structure) |
| 188 | (structure) |

| Example Nb | structures |
|---|---|
| 189 | 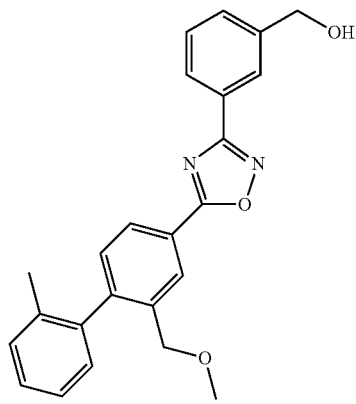 |
| 190 | 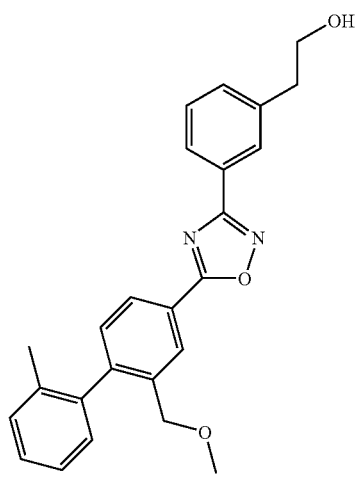 |
| 191 | 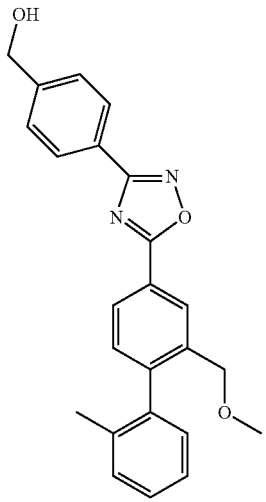 |

| Example Nb | structures |
|---|---|
| 192 | 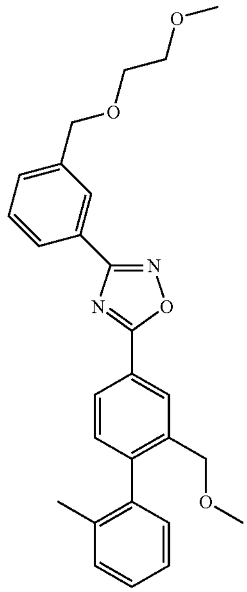 |
| 193 | 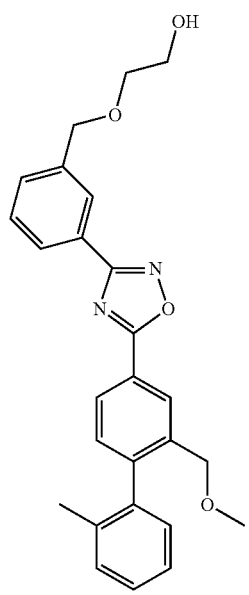 |
| 194 | 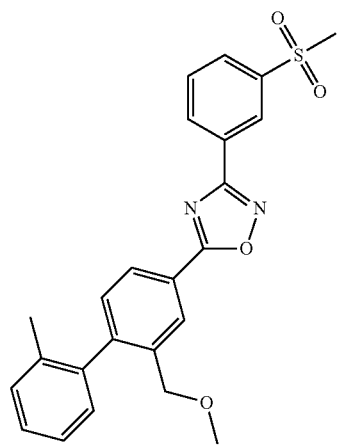 |

-continued
| Example Nb | structures |
|---|---|
| 195 | 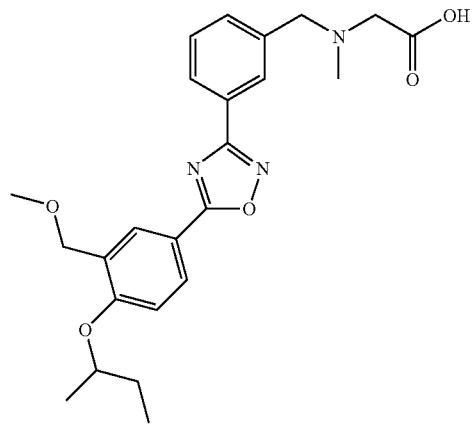 |
| I1 | 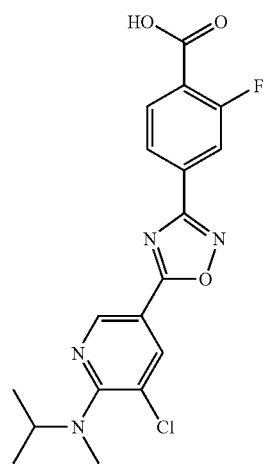 |
| I2 | 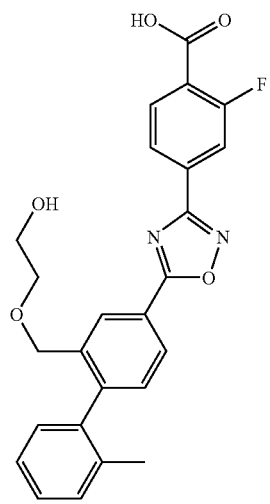 |

-continued
| Example Nb | structures |
|---|---|
| I3 | 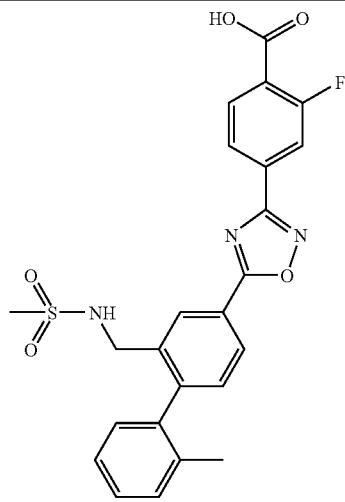 |
| I4 | 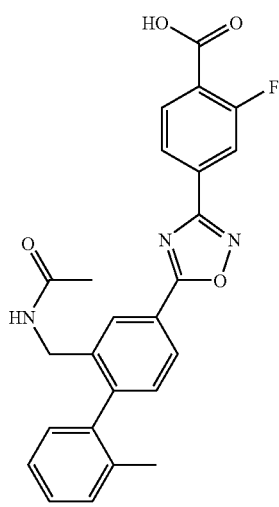 |
| I5 | 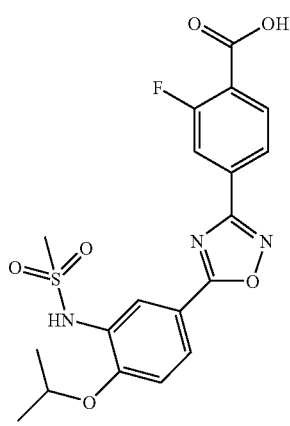 |

-continued
| Example Nb | structures |
|---|---|
| I6 | 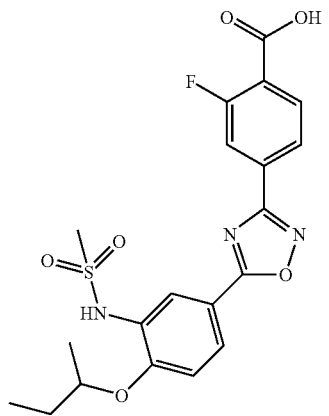 |
| I7 | 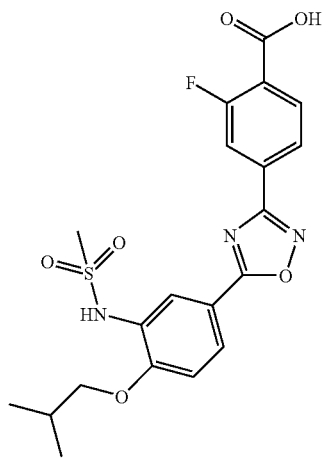 |
| I8 | 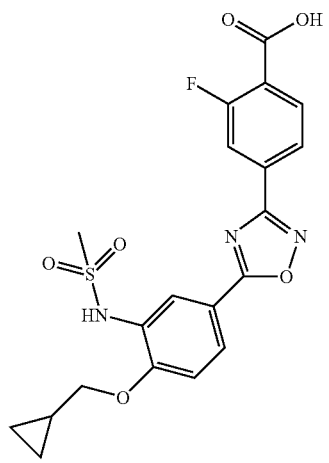 |

-continued

| Example Nb | structures |
|---|---|
| I9 | 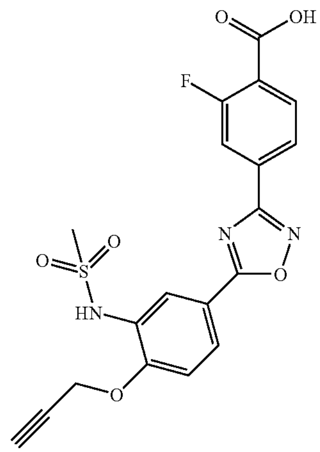 |
| I10 | 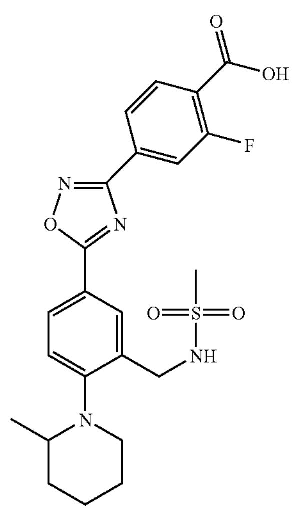 |
| I11 | 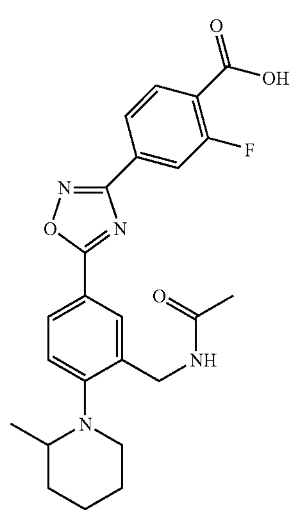 |

-continued
| Example Nb | structures |
|---|---|
| I12 | 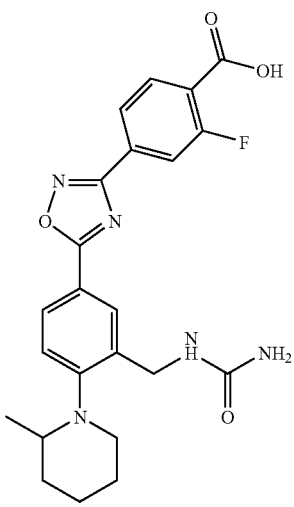 |
| I13 | 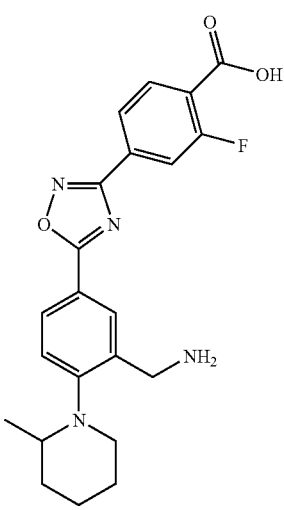 |
| I14 | 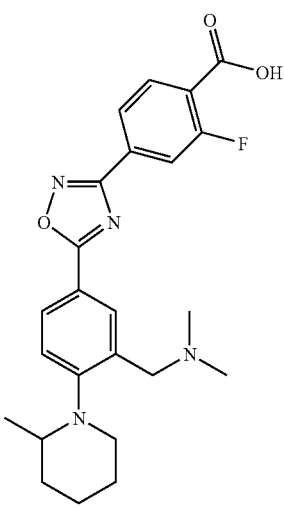 |

-continued
| Example Nb | structures |
|---|---|
| I15 | 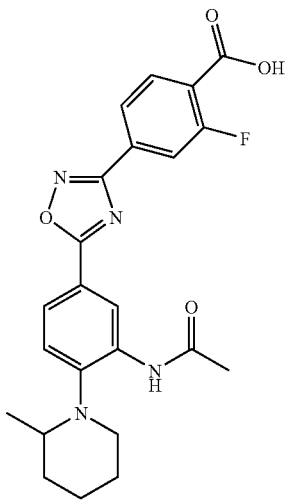 |
| I16 | 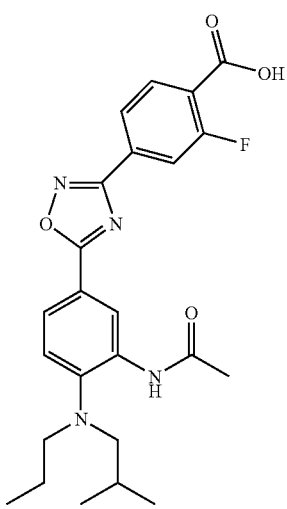 |
| I17 | 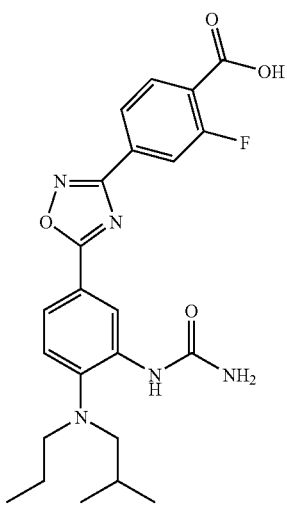 |

-continued
| Example Nb | structures |
|---|---|
| I18 | 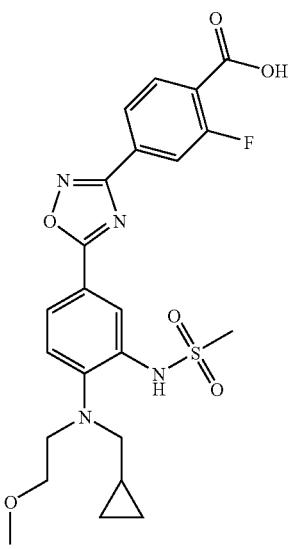 |
| I19 | 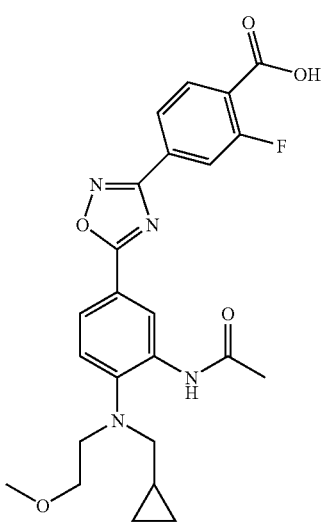 |
| I20 | 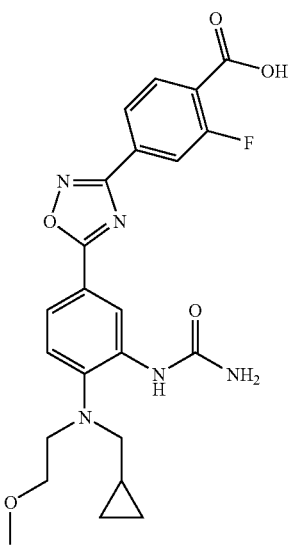 |

| Example Nb | structures |
|---|---|
| I21 | 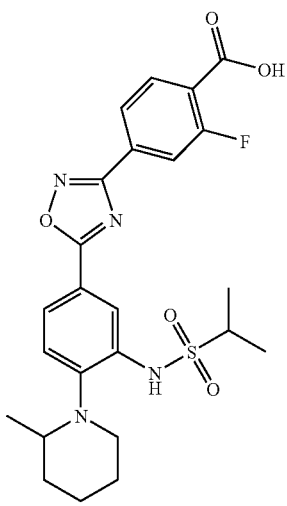 |
| I22 | 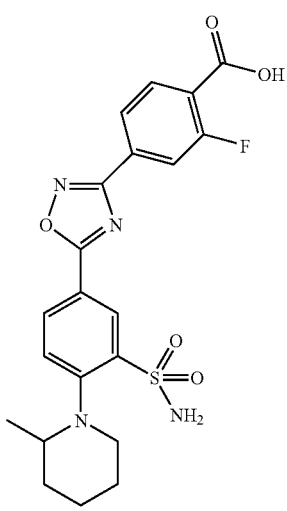 |
| I23 | 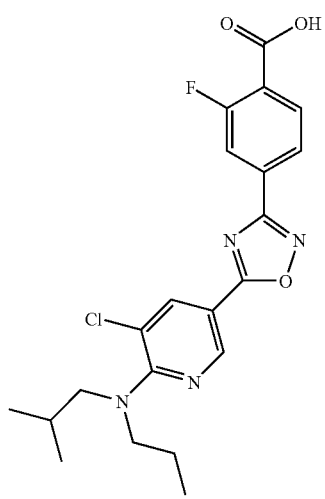 |

-continued
| Example Nb | structures |
|---|---|
| I24 | 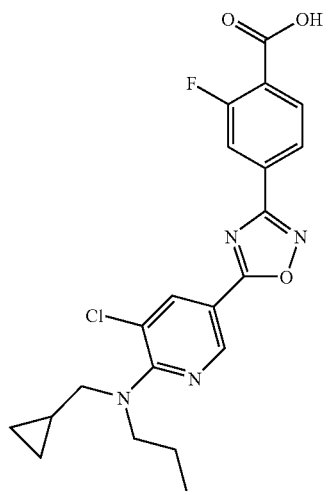 |
| I25 | 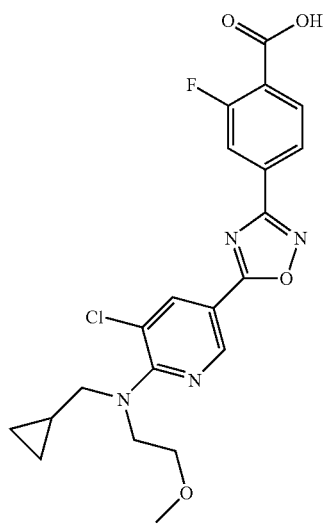 |
| I26 | 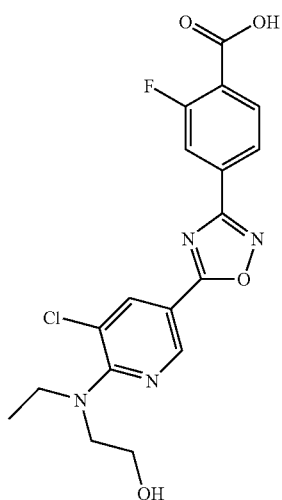 |

| Example Nb | structures |
|---|---|
| I27 | 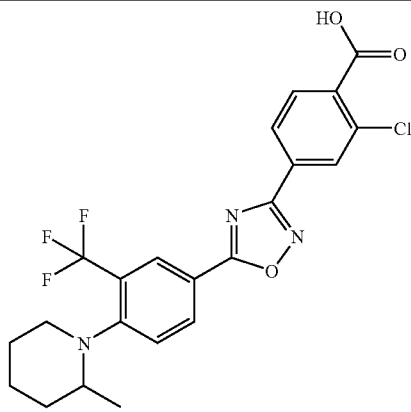 | and pharmaceutically usable derivatives, solvates, salts and stereoisomers thereof, including mixtures thereof in all ratios.

For all radicals and indices such as m which occur more than once within the same chemical structure, their meanings are independent of one another.

Above and below, the radicals or parameters $R^a$, $R^b$, $R^1$, $R^2$, $R^3$, W, Q, S, T, X, $X^1$, $X^2$, A, Ar, Het, m and n have the meaning indicated under the formula (I) and subformulae, unless expressly stated otherwise.

A denotes alkyl, is unbranched (linear) or branched, and has 1, 2, 3, 4, 5, 6, 7, 8, 9, 10, 11 or 12 carbon atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl. A very particularly preferably denotes alkyl having 1, 2, 3, 4, 5 or 6 carbon atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. A furthermore denotes $(CH_2)_nO(CH_2)_nOR^3$, $(CH_2)_nNR^3(CH_2)_2N(R^3)_2$, especially $(CH_2)_2O(CH_2)_2OR^3$ or $(CH_2)_2NH(CH_2)_2N(R^3)_2$.

Cycloalkyl is a cyclic alkyl containing 3 to 12 carbon atoms. Cycloalkyl preferably denotes cyclopropyl, cyclobutyl, cyclopentyl, cyclohexyl or cycloheptyl.

Cycloalkylalkylene is a cycloalkyl group bond to the rest of the molecule via a carbon chain and having 1, 2, 3, 4, 5, 6, 7, 8, 9, 10, 11, 12, 13, 14, 15, 16, 17, or 18 carbon atoms. Cycloalkylalkylene preferably denotes cyclopropylmethylene, cyclobutylmethylene, cyclopentylmethylene, cyclohexylmethylene or cycloheptylmethylene.

Alkylene is a bivalent carbon chain having 1, 2, 3, 4, 5, 6, 7, 8, 9, 10, 11, or 12 carbon atoms. Alkylene is preferably methylene, ethylene, propylene, butylene, pentylene or hexylene, furthermore branched alkylene.

$R^a$ is preferably Ar, Het or OA especially Ar or Het.

Ar or Het is preferably substituted with methyl, trifluoromethyl methoxy or $NO_2$.

If Het denotes a N-Atom bearing saturated heterocycle, Het is preferably linked to the rest of the molecule via an N-Atom. The alpha position is next to this N-Atom.

$R^a$ very preferrably denotes one of the following groups:

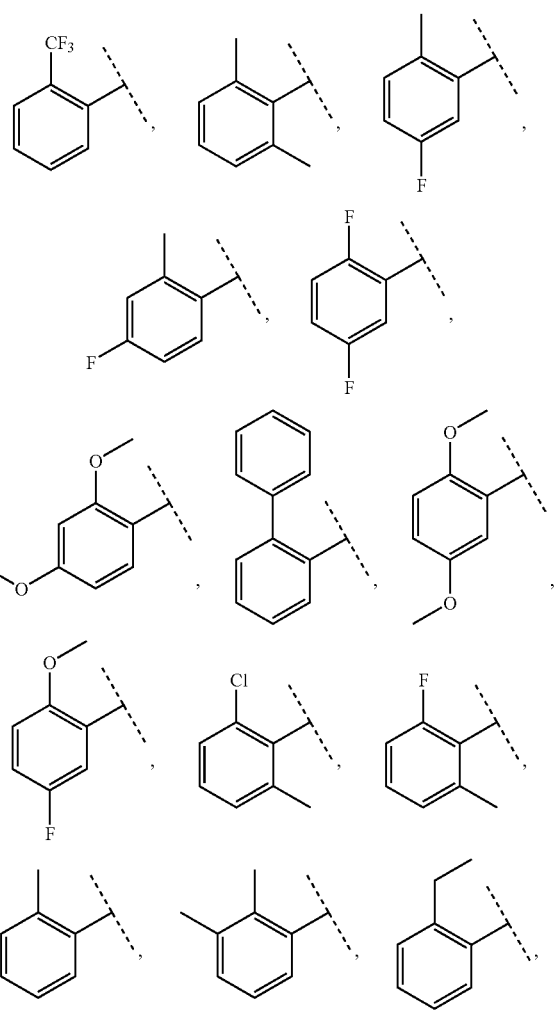

$R^b$ is preferably H, A, $OR^3$, $NO_2$, $NH_3$, Hal, $CH_2OR^3$, $(CH_2)_mOA$, especially $CH_2OCH_3$, $CH_2NHSO_2A$, $NHSO_2A$, such as $NHSO_2CH_3$, $CH_2NHCOCH_3$, $CH_2N(CH_3)_2$, $CH_2NH_2$, $NHCONH_2$ or $CF_3$. Very preferably, $R^b$ is one of the following groups: —$CH_3$, —OH, $NO_2$, —$CH_2OH$, —$CH_2OCH_3$, —$CH_2OC_2H_5$, —$CH_2OCH(CH_3)_2$, —$CH_2NHCH_3$, —$CH_2N(CH_3)_2$, —$CH_2SO_2CH_3$, —$(CH_2)_3OCH_3$, —$OCH_3$, —$O(CH_2)_2OCH_3$, —$OCH_2CH(CH_3)_2$, —$CF_3$, CN, —$NHCOCH_3$, —$NHCOC_2H_5$, —$NHSO_2CH_3$, —$NHSO_2C_2H_5$, —$NHSO_2C_3H_7$, —$NHSO_2N(CH_3)_2$, Cl, $R^3$ preferrably denotes H, ($C_1$-$C_6$ alkyl), ($C_1$-$C_6$ fluoroalkyl), more preferably, $R^3$ is H. 2 germinal groups $R^3$ linked to a N atom particularly denote wherein n is 0, 1, 2 or 3.

Hal is preferably F, Cl or Br and especially F or Cl.
Preferably, at least one of $R^1$ and $R^2$ denotes F or Cl.
$R^1$ preferably denotes F or 0 alkyl, especially F or $OCH_3$,
$R^2$ is preferably H.
W preferably denotes CH.
Q is preferably in para-position to the oxadiazole moiety.
Q is preferably a single bond.
S is preferably $COOR_3$ and especially COOH.
Most preferably, the group Q-S denotes COOH, $SO_2NH_2$ or $OCH_2COOH$.
If the group Q-S denotes $SO_2NH_2$, $R^1$ is preferably H. More preferably, $R^1$ and $R^2$ are H in this case
n is preferably 0, 1, 2, 3, 4 or 5 and more preferably 0, 1, 2, 3 or 4.
m is preferably 1, 2 or 3.
An aromatic carbocyclic ring preferably denotes phenyl, naphthyl or biphenyl.
Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o, m or p amino-sulfanyl-phenyl, o-, m- or p-phenoxyphenyl, further preferably 2,3-, 2,4-, 2,5-, 2,6-, 3,4- or 3,5-dimethylphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichloro-phenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxy-phenyl, 3-chloro-4- acetamidophenyl, 3-fluoro-4-methoxyphenyl, 3-amino-6-methylphenyl, 3-chloro-4-acetamidophenyl or 2,5-dimethyl-4-chlorophenyl.

Ar preferably denotes, for example, phenyl which is unsubstituted or monosubstituted, disubstituted or trisubstituted by A, Hal, $OR^3$, $CF_3$, $OCF_3$, $NO_2$ and/or CN. If Ar is phenyl, it is preferably substituted in ortho-position to the C-atom linking Ar to the rest of the molecule. The ortho-position is also indicated by the figure "2" in chemical nomenclature. Ar is preferably substituted by, —$CH_3$, —$(CH_2)_nOR^3$, —$(CH_2)_n NR^3SO_2A$.

Ar particularly preferably denotes, for example, phenyl which is unsubstituted or monosubstituted or disubstituted preferably monosubstituted, by $OCH_3$, OH, $CH_3$, $CF_3$, such as, for example, 2'-methoxy-phenyl-, 2'-trifluoromethyl-phenyl- preferably, aryl bearing at least a 2' substituent, 2'-chlorophenyl, 2',6'-dimethyl-phenyl- or 2'-alkyl-phenyl-, preferably 2'-methyl-phenyl-.

Ar very particularly preferably denotes one of the following groups:

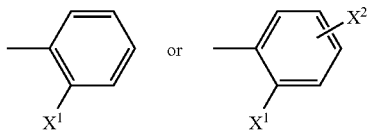

preferably

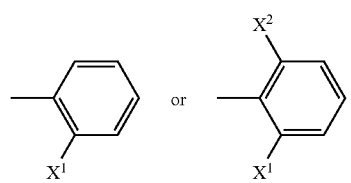

wherein $X^1$, and $X^2$ denote independently of one another F, Cl, —$OCH_3$, —$CH_3$, —$C_2H_5$, —$CF_3$, —$OCF_3$, —O-isoPropyl, —O-isobutyl, —OCH2CN, —OCH2cyclopropyl, —CH2OH, —CH2O-isoPropyl, —CH2O-isobutyl, —$CH_2OCH_2$cyclopropyl, —$CH_2NMe_2$, —$CH_2OC_2H_5$, —NHCOMe, —NHCOEt, —$NHSO_2NMe_2$, —$NHSO_2$propyl, —$CH_2$-morpholine, —$CH_2$pirolidine, —$CH_2NHMe$, —$SO_2Me$, —$CH_2SO_2Me$, —C≡C—$CH_2OMe$, —$(CH_2)_3OMe$, —$O(CH_2)_2OMe$, —$CO_2H$, —OH, —$NO_2$, —CN, —$NHSO_2CH_3$, and/or phenyl or pyridyl or piperidine, or morpholine which is preferably unsubstituted.

Het is preferably a 6 to 14 membered ring system and denotes, not withstanding further substitutions, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, indazolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxa-diazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxane-6-yl, 2,1,3-benzothiadiazol-4- or -5-yl or 2,1,3-benzoxadiazol-5-yl.

The heterocyclic radicals may also be partially or fully hydrogenated.

Het can thus also denote, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het very particularly denotes one of the following groups:

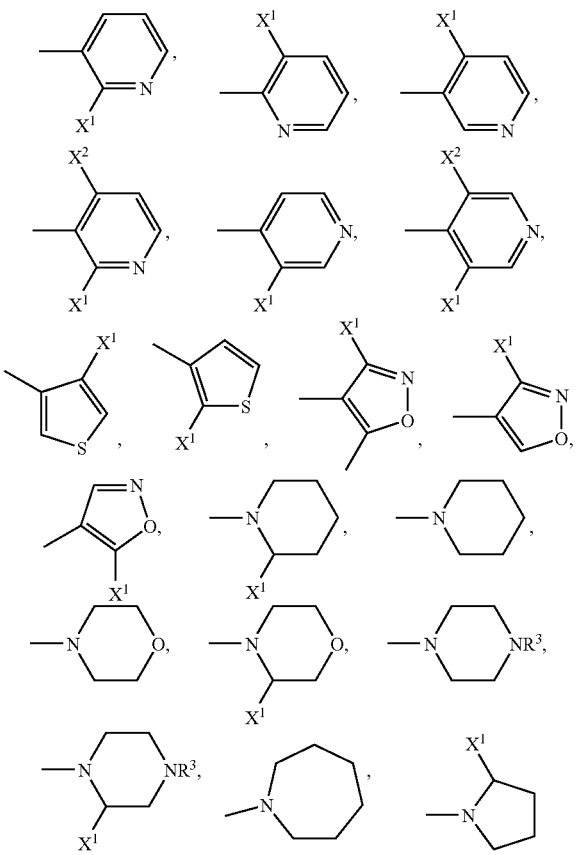

-continued

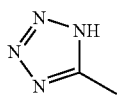 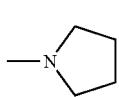 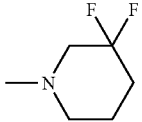

wherein $X^1$, $X^2$, and $R^3$ are as defined above.

The compounds of the formula I can have one or more centres of chirality and can therefore occur in various stereoisomeric forms. The formula I covers all these forms.

Accordingly, the invention relates, in particular, to Formula (I) and its use, in which at least one of the said radicals has one of the preferred meanings indicated above. Some preferred groups of compounds can be expressed by the following sub-formula Ia to Io, which conform to the formula (I) and in which the radicals not designated in greater detail have the meaning indicated under the formula I, but in which in Ia $R^a$ Ar or Het.

in Ib $R^a$ is phenyl which is unsubstituted or monosubstituted or disubstituted, preferably monosubstituted, by F, $OCH_3$, $CH_3$, $CF_3$, such as, for example, 2'-methoxyphenyl-, 2'-trifluoromethyl-phenyl-, 2'-chlorophenyl, 2',6'-methyl-phenyl-, 2'-alkyl-phenyl-, or pyridyl, in Ic $R^1$ denotes F, in Id $R^2$ denotes H, in Ie Q denotes a single bond in para-position to the oxadiazole-moiety,
S denotes COOH, in If $R^a$ denotes heterocyloalkyl preferably bearing at least an alpha-substituent, such as 2-methyl-piperidin-1-yl, in Ig $R^1$ is F,
$R^2$ is H,
$R^a$ denotes heterocyloalkyl, preferably bearing at least an alpha-substituent, such as 2-methyl-piperidin-1-yl,
$R^b$ is trifluoroalkyl, in Ih $R^1$ is F,
$R^2$ is H,
$R^a$ denotes heterocyloalkyl, preferably bearing at least an alpha-substituent, such as 2-methyl-piperidin-1-yl,
$R^b$ is nitro, in Ii $R^1$ is F,
$R^2$ is H,
$R^a$ is Ar, preferably bearing at least a 2' substituent, such as 2'-methyl-phenyl-, 2'-methoxy-phenyl-, 2'-trifluoromethyl-phenyl-
$R^b$ is alkyl, nitro, alkoxy, in Ij $R^1$ is F,
$R^2$ is H,
$R^a$ is Het, such as 4-methyl-3-thienyl-
$R^b$ is alkyl, alkoxy, in Ik $R^1$ is F,
$R^2$ is H,
$R^a$ is Ar, such as 2'-trifluoromethyl-phenyl-, 2'-chlorophenyl, 2',6'-methyl-phenyl-, 2'-methyl-phenyl,
$R^b$ is H, in Il $R^1$ is F,
$R^2$ is H,
$R^a$ is heterocycloalkyl, preferably non-substituted heterocycloakyl, such as piperidin-1-yl, morpholinyl $R^b$ is nitro, methyl, trifluoromethyl, in Im $R^1$ is F,
$R^2$ is H,
$R^a$ is Ar such as 2'-alkyl-phenyl-,
$R^b$ is alkyl, in In $R^1$ is F,
$R^2$ is H,
$R^a$ is A or heterocycloalkyl, preferably unsubstituted such as phenyl, piperidin-1-yl,
$R^b$ is methyl, In Io $R^1$ is F
$R^2$ is H
$R^a$ is ortho substituted Ar or orthosubstituted Het such as 2-methylphenyl, 2-methylpiperidine, 2-methylmorpholine, 2-methylthienyl.
$R^b$ is $CH_2OCH_3$.

Alternatively, in Formula Ig, Ih, Ii, Ij, Ik, Il, Im, In, and Io, W is CH, Q is a single bond in para position to the oxadiazole moiety and S is COOH.

Alternatively, in Formula Ig, Ih, Ii, Ij, Ik, Il, Im, In, and Io, QS denotes
—$COOR^3$, —$CON(R^3)(CH_2)_nCO_2R^3$, —$CONR^3(C_3$-$C_6cycloalkyl)CO_2R^3$, —$CH_2N(R^3)(CH_2)_nCO_2R^3$, —$CH_2NR^3(C_3$-$C_6cycloalkyl)CO_2R^3$, —$CH_2$—O—$(CH_2)_nCO_2R^3$, —$CH_2O(C_3$-$C_6cycloalkyl)CO_2R^3$, —$O(CH_2)_nCO_2R^3$, —$O(C_3$-$C_6cycloalkyl)CO_2R^3$
wherein n and $R^3$ are as above defined.

and pharmaceutically usable derivatives, solvates, salts and stereoisomers thereof, including mixtures thereof in all ratios.

The compounds of the formula I and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), under reaction conditions which are known and suitable for the said reactions. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, 3$^{rd}$ Edition 1999.

Use can also be made here of variants which are known per se, but are not mentioned here in greater detail.

If desired, the starting materials can also be formed in situ so that they are not isolated from the reaction mixture, but instead are immediately converted further into the compounds of the formula I.

The starting compounds for the preparation of compounds of formula I are generally known. If they are novel, they can, however, be prepared by methods known per se.

The reactions are preferably carried out in an inert solvent.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or DCM; alcohols, such as methanol, ethanol, isopropanol, n-propanol, n-butanol or tert-butanol; ethers, such as diethyl ether, diisopropyl ether, THF (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as EtOAc, or mixtures of the said solvents.

Pharmaceutical Salts and Other Forms

The said compounds of the formula I can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains an acidic center, such as a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example sodium- or potassiumethoxide and sodium or potassiumpropoxide, alkalihydrides, such as sodium- or potassiumhydride; and various organic bases, such as piperidine, diethanolamine and N-methyl-glutamine, benzathine, choline, diethanolamine, ethylenediamine, meglumine, benethamine, diethylamine, piperazine and tromethamine. The aluminium salts of the compounds of the formula I are likewise included. In the case of certain compounds of the formula I, which contain a basic center, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoaryl-sulfonates, such as ethanesulfonate, toluenesulfonate and benzene-sulfonate, and other organic acids and corresponding salts thereof, such as acetate, trifluoro-acetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzene-sulfonate (besylate), bisulfate, bisulfite, bromide, butyrate, camphorate, camphorsulfonate, caprylate, chloride, chlorobenzoate, citrate, cyclopentane-propionate, digluconate, dihydrogen-phosphate, dinitrobenzoate, dodecyl-sulfate, ethanesulfonate, fumarate, galacterate (from mucic acid), galacturonate, glucoheptanoate, gluconate, glutamate, glycerophosphate, hemi-succinate, hemisulfate, heptanoate, hexanoate, hippurate, hydrochloride, hydrobromide, hydroiodide, 2-hydroxy-ethanesulfonate, iodide, isethionate, isobutyrate, lactate, lactobionate, malate, maleate, malonate, mandelate, metaphosphate, methanesulfonate, methylbenzoate, mono-hydrogen-phosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula I include aluminium, ammonium, calcium, copper, iron (III), iron(II), lithium, magnesium, manganese(III), manganese(II), potassium, sodium and zink salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylen-ediamine (benzathine), dicyclohexylamine, diethanol-amine, diethylamine, 2-diethyl-amino-ethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lidocaine, lysine, meglumine (N-methyl-D-glucamine), morpholine, piperazine, piperidine, polyamine resins, procaine, purines, theobromine, triethanol-amine, triethylamine, trimethylamine, tripropylamine and tris(hydroxy-methyl)-methylamine (tromethamine), but this is not intended to represent a restriction.

Compounds of the formula I of the present invention which contain basic $N_2$-containing groups can be quaternised using agents such as (C1-C4)-alkyl halides, for example methyl, ethyl, isopropyl and tert-butyl chloride, bromide and iodide; di(C1-C4)alkyl sulfates, for example dimethyl, diethyl and diamyl sulfate; (C10-C18)alkyl halides, for example decyl, do-decyl, lauryl, myristyl and stearyl chloride, bromide and iodide; and aryl-(C1-C4)alkyl halides, for example benzyl chloride and phenethyl bromide. Both water- and oil-soluble compounds of the formula I can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tro-meth-amine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine.

The base-addition salts of acidic compounds of the formula I are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound of the formula I contains more than one group which is capable of forming pharmaceutically acceptable salts of this type, the formula I also encompasses multiple salts. Typical multiple salt forms include, for example, bitartrate, diacetate, difumarate, dimeglumine, di-phosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula I can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the Intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of compounds of formula I, in combination with at least one further medicament active ingredient, preferably medicaments used in the treatment of multiple sclerosis such as cladribine or another co-agent, such as interferon, e.g. pegylated or non-pegylated interferons, preferably interferon beta and/or with compounds improving vascular function. These further medicaments, such as interferon beta, may be administered concomitantly or sequentially, e.g. by subcutaneous, intramuscular or oral routes.

These compositions can be used as medicaments in human and veterinary medicine.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or drypressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a sphingosine 1-phosphate associated disorder, comprising administering to said subject an effective amount of a compounds of formula I. The present invention preferably relates to a method, wherein the sphingosine 1-phosphate-1 associated disorder is an autoimmune disorder or condition associated with an overactive immune response.

The present invention furthermore relates to a method of treating a subject suffering from an immunoregulatory abnormality, comprising administering to said subject a compounds of formula I in an amount that is effective for treating said immunoregulatory abnormality. The present invention preferably relates to a method wherein the immunoregulatory abnormality is an autoimmune or chronic inflammatory disease selected from the group consisting of: amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Preferred compounds of formula (I) exhibit a EC50 in GTPγS for the binding to the $S1P_1$ receptor of less than about 10 µM, preferably less than about 5 µM, more preferably less than about 1 µM and even more preferred less than about 0.1 µM. Most preferably, compounds of Formula (I) exhibit a EC50 for the binding of S1P1 less than 0.01 µM.

Preferred compounds of Formula (I) exhibit a selectivity on S1P1 receptor over the S1P3 receptor of a magnitude of more than about 20. More preferably, compounds of formula (I) are 50 fold selective for S1P1 compare to S1P3, more preferably, 100 fold.

The compounds of invention have been named according the standards used in the program "ACD/Name Batch" from Advanced Chemistry Development Inc., ACD/Labs (7.00 Release). Product version: 7.10, build: 15 Sep. 2003.

In the following the present invention shall be illustrated by means of some examples, which are not construed to be viewed as limiting the scope of the invention.

EXAMPLES

The oxadiazole compounds according to formula (I) can be prepared from readily available starting materials by several synthetic approaches, using both solution-phase and solid-phase chemistry protocols or mixed solution and solid phase protocols. Examples of synthetic pathways are described below in the examples.

The commercially available starting materials used in the following experimental description were purchased from Aldrich or Fluka unless otherwise reported.

The HPLC, NMR and MS data provided in the examples described below are obtained as followed:

HPLC data:

Method A: HPLC columns: Xbridge™ C8 column 50 mm×4.6 mm at a flow of 2 mL/min; 8 min gradient from 0.1% TFA in H₂O to 0.07% TFA in ACN.

Method B: HPLC columns: ATLANTIS C18 75×4.6 mm 5 U at a flow of 1 mL/min; A-0.1% HCOOH B-ACN.

Method C: HPLC columns: C18 BDS, 50×4.6 mm, SC\307 at a flow of 0.8 mL/min; A-0.1% TFA, B-ACN: Flow-0.8 mL/min.

UV detection (maxplot) for all methods.

Mass spectrum:

Method A: LC/MS Waters ZMD (ESI); GC/MS: GC Agilent 6890N & MS Agilent 5973.

Method B: HPLC/MS: Waters Acquity, column Waters Acquity HPLC BEH C18 1.7 m 2.1×50 mm, conditions: solvent A (10 mM ammonium acetate in water+5% ACN), solvent B (ACN), gradient 5% B to 100% B over 3 min, UV detection (PDA, 230-400 nm) and MS detection (SQ detector, positive and negative ESI modes, cone voltage 30 V).

¹H-NMR Data:

Bruker DPX-300 MHz unless otherwise reported.

Preparative HPLC Purifications:

Preparative HPLC purifications were performed with HPLC waters Prep LC 4000 System equipped with columns ®PrepMS C18 10 m, 50×300 mm, unless otherwise reported. All HPLC purifications were performed with a gradient of ACN/H₂O or ACN/H₂O/TFA (0.1%).

Mass Directed Autoprep Purifications:

Preparative HPLC purifications are performed with a mass directed autopurification Fractionlynx from Waters equipped with a Sunfire Prep C18 OBD column 19×100 mm 5 m, unless otherwise reported. All HPLC purifications were performed with a gradient of ACN/H₂O or ACN/H₂O/HCOOH (0.1%).

The microwave chemistry was performed on a single mode microwave reactor Emrys™ Optimiser from Personal Chemistry.

Intermediate 1: methyl 4-[amino(hydroxyimino)methyl]-2-fluorobenzoate

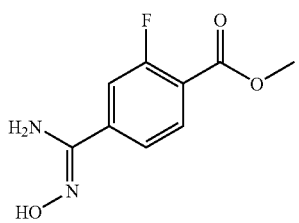

Step 1: methyl 4-cyano-2-fluorobenzoate

4-Cyano-2-fluorobenzoic acid (ABCR, 16 g; 96.90 mmol) was suspended in 300 mL of DCM. Oxalyl chloride (9 mL; 106.59 mmol) was added, followed by DMF (0.5 mL). After 3 hours at RT the yellow solution was evaporated under reduced pressure and the resulting yellow oil was taken up in anhydrous THF (150 mL) and added dropwise to a 4° C. solution of methanol (50 mL) and triethylamine (25.80 mL; 193.79 mmol; 2 eq.). An HCl solution (0.1 N, 200 mL) was added and the product was extracted with EtOAc (3×100 mL). The combined organic phases were washed with a semi-saturated NaHCO₃ solution (200 mL), water (200 mL) and dried over MgSO₄. Evaporation under reduced pressure gave the title compound as a light yellow solid (17.84 g, quantitative). HPLC (Method A) Rt 2.81 min (Purity: 93.9%).

Step 2: methyl 4-[amino(hydroxyimino)methyl]-2-fluorobenzoate

Methyl 4-cyano-2-fluorobenzoate, obtained in step 1 (17.76 g; 99.13 mmol) was suspended in EtOH (200 mL). Hydroxylamine (50% in water, 30 mL; 495.67 mmol) was added and the resulting yellow suspension was heated at 75° C. for 1 hour and stirred at RT overnight. The suspension was filtered, the remaining residue was rinsed twice with ethanol (50 mL) and dried under vacuum, affording the title compound as a colorless solid. ¹H NMR: (DMSO-d₆, 300 MHz) δ 10.09 (s, 1H), 7.95-7.89 (m, 1H), 7.70-7.62, m, 2H), 6.05 (s, 2H), 3.89 (s, 3H). LC/MS (Method A): 210.9 (M−H)⁻; 212.9 (M+H)⁺. HPLC (Method A), Rt: 0.97 min (purity: 100%).

Intermediate 2: methyl 4-[amino(hydroxyimino)methyl]-3-fluorobenzoate

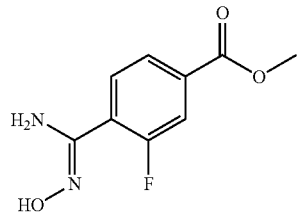

Step 1: methyl 4-cyano-3-fluorobenzoate

4-Cyano-3-fluorobenzoic acid (Carbocore, 1 g; 6.06 mmol) was dissolved in MeOH (12.50 mL) to which 1-(3-Dimethylaminopropyl)-3-ethylcarbodiimide hydrochloride (1.39 g; 7.27 mmol) followed by 4-dimethylaminopyridine (0.07 g; 0.61 mmol) were added. The mixture was stirred at RT overnight after which it was concentrated, taken up in EtOAc and washed with 0.1N HCl, 0.1 N NaOH and brine (2×50 mL each) and dried over MgSO₄ to give the title compound as an off-white solid (0.95 g; 87%). ¹H NMR: (DMSO-d₆, 300 MHz) δ 8.16 (dd, J=6.40 Hz, J=7.91 Hz, 1H), 8.02 (dd, J=1.50 Hz, J=9.80 Hz, 1H), 7.97 (dd. J=1.50 Hz, J=7.91, 1H), 3.95 (s, 3H). GC/MS (M⁺): 179 (EI). HPLC (Method A) Rt 3.17 min (Purity: 87.3%).

Step 2: methyl 4-[amino(hydroxyimino)methyl]-3-fluorobenzoate

To a solution of methyl 4-cyano-3-fluorobenzoate obtained in Step 1 (834.5 mg; 4.66 mmol) in EtOH (9 mL) was added hydroxylamine (50% in water, 1.37 mL; 23.29 mmol). The solution was stirred at 74° C. for 4 h. The solvents were evaporated and the residue was taken in EtOAc (20 mL), washed with brine (3×15 mL), dried over MgSO₄ and evaporated, affording the title compound as a yellow solid. $^1$H NMR: (DMSO-d₆, 300 MHz) δ 9.89 (s, 1H), 7.92 (t, J=7.91 Hz, 1H), 7.69 (dd, J=1.70 Hz, J=8.10 Hz, 1H), 7.64 (dd, J=1.51 Hz, J=12.81 Hz, 1H), 5.97 (s, 2H), 3.92 (s, 3H). HPLC (Method A) Rt 2.90 min (Purity: 90.3%).

Intermediate 3: 2,2'-dimethyl-1,1'-biphenyl-4-carboxylic acid

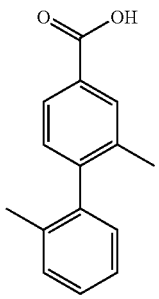

Step 1: methyl 2,2'-dimethyl-1,1'-biphenyl-4-carboxylate

To a solution of methyl 4-bromo-3-methylbenzoate (ABCR, 15 g, 65 mmol) in toluene (200 mL) and water (200 mL), was added o-tolylboronic acid (10.68 g, 78 mmol) followed by potassium carbonate (45.25 g, 32.7 mmol) and tetrakis(triphenylphosphine)palladium(0) (3.78 g, 3.3 mmol). The mixture was degassed with N₂ and refluxed at 120° C. for 6 hours. After the completion of reaction, the reaction mixture was cooled to RT. The organic phase was separated and evaporated under reduced pressure. The crude compound was passed through a silica column (60-120) using hexane as eluent to get the title compound as a white solid (15 g, 95%). $^1$H NMR: (DMSO-d₆, 400 MHz) δ 7.91 (s, 1H), 7.83-7.81 (m, 1H), 7.33-7.30 (m, 2H), 7.28-7.26 (m, 1H), 7.25-7.22 (m, 1H), 7.07-7.05 (d, 1H), 3.86-3.81 (s, 3H), 2.09-2 (s, 3H), 1.97-1.92 (s, 3H). HPLC (Method B), Rt: 3.01 min (purity: 98.71%).

Step 2: 2,2'-dimethyl-1,1'-biphenyl-4-carboxylic acid

To a solution of methyl 2,2'-dimethyl-1,1'-biphenyl-4-carboxylate, prepared in Step 1 (15 g, 62.2 mmol) in THF (100 mL) was added 10% sodium hydroxide (100 mL) and the mixture was heated to 100° C. overnight. THF was removed under reduced pressure and the aqueous residue was washed with EtOAc. The aqueous layer was then acidified with 3N HCl to pH 2-3 and extracted with DCM. The organic phase was washed with water and dried over sodium sulfate and concentrated under reduced pressure to obtain get the title compound as a white solid (13.5 g, 95%). $^1$H NMR: (DMSO-d₆, 400 MHz) δ 12.89 (bs, 1H), 7.89 (s, 1H), 7.82-7.80 (d, 1H), 7.32-7.23 (m, 3H), 7.19-7.11 (d, 1H), 7.07-7.05 (d, 1H), 2.04 (s, 3H), 1.98 (s, 3H). LC/MS (Method A): 227.0 (M+H)⁺. HPLC (Method B), Rt: 4.1 min (purity: 99.6%).

Intermediate 4: 2'-methoxy-2-methylbiphenyl-4-carboxylic acid

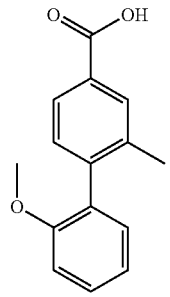

Step 1: methyl 2'-methoxy-2-methylbiphenyl-4-carboxylate

Methyl 4-bromo-3-methylbenzoate (ABCR, 4.90 g; 21.39 mmol; 1 eq.), 2-methoxyphenylboronic acid (3.575 g; 23.53 mmol; 1.10 eq.), potassium carbonate (14.781 mg; 107 mmol; 5 eq.), tetrakis(triphenylphosphine)palladium(0) (2.5 mg; 2.14 mmol; 0.10 eq.) were mixed in toluene (24.5 mL) and water (24.5 mL) under N₂ atmosphere. The reaction mixture was degassed with N₂ for 10 min and was heated under reflux for 6 hours. The reaction mixture was cooled to RT, filtered over a pad of celite and washed with toluene (500 mL). The filtrate was concentrated under vacuum to afford brown oil. It was taken in EtOAc (500 mL). The organic layer was washed with a saturated aqueous solution of NaHCO₃ (200 mL), water (200 mL) and brine (200 mL). It was dried over MgSO₄, filtered off and concentrated under vacuum giving a brown oil. It was purified by flash chromatography (cHex/EtOAc 9:1), affording the title compound as a colorless oil (4.38 g, 80%). $^1$H NMR: (DMSO-d₆, 300 MHz) δ 7.94 (s, 1H), 7.89-7.86 (dd, J=8.06 Hz, J=1.61 Hz, 1H), 7.51-7.46 (m, 1H), 7.34-7.31 (d, J=8.13 Hz, 1H), 7.21-7.09 (m, 3H), 3.95 (s, 3H), 3.79 (s, 3H), 2.19 (s, 3H). LC/MS (Method A): 257.0 (M+H)⁺. HPLC (Method A) Rt 4.85 min (Purity: 98.9%).

Step 2: 2'-methoxy-2-methylbiphenyl-4-carboxylic acid

To solution of methyl 2'-methoxy-2-methylbiphenyl-4-carboxylate, prepared in Step 1 (2 g; 7.80 mmol; 1 eq.) in EtOH (60 mL), was added at RT an aqueous solution of sodium hydroxide (4.68 mL; 5 M; 23.41 mmol; 3 eq.). The reaction mixture was stirred at 60° C. for one hour. The reaction mixture was concentrated under vacuum to give an orange solid. It was taken up in water (400 mL) and the aqueous phase was washed twice with EtOAc (200 mL). Aqueous phase was acidified with concentrated HCl (2 mL) to pH 2. Then it was concentrated under vacuum until a precipitate was formed. (⅕ of volume). The suspension was filtered off and dried under vacuum to afford the title compound as a brown solid. $^1$H NMR: (DMSO-d₆, 300 MHz) δ 12.89 (s, 1H), 7.86 (s, 1H), 7.82-7.79 (dd, J=7.99 Hz, J=1.23 Hz, 1H), 7.46-7.40 (m, 1H), 7.26-7.23 (d, J=7.68 Hz, 1H), 7.16-7.04 (m, 3H), 3.75 (s, 3H), 2.13 (s, 3H). LC/MS (Method A): 240.9 (M−H)⁻. HPLC (Method A) Rt 4.05 min (Purity: 98.5%).

Intermediate 5: 2-methyl-2'-(trifluoromethyl)biphenyl-4-carboxylic acid

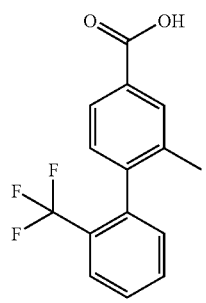

Step 1: methyl 2-methyl-2'-(trifluoromethyl)biphenyl-4-carboxylate

Methyl 4-bromo-3-methylbenzoate (ABCR. 3 g; 13.10 mmol; 1 eq.), 2-(trifluoromethyl)phenylboronic acid (2.736 g; 14.41 mmol; 1.10 eq.), potassium carbonate (9.049 g; 65.48 mmol; 5 eq.), tetrakis(triphenylphosphine)palladium (0) (1.51 g; 1.31 mmol; 0.10 eq.) were mixed in Toluene (15 mL) and water (15 mL) under $N_2$ atmosphere. The reaction mixture was degassed with $N_2$ for 10 min and was heated under reflux for 3 hours. The reaction mixture was cooled to RT, filtered over a pad of celite and washed with toluene (500 mL). The filtrate was concentrated under vacuum to afford brown oil. It was taken in EtOAc (500 mL). The organic layer was washed with a saturated aqueous solution of $NaHCO_3$ (200 mL), water (200 mL) and brine (200 mL). It was dried over $MgSO_4$, filtered off and concentrated under vacuum giving a brown oil (3.7 g, 96%). It was used in the next step without further purification. LC/MS (Method A): 294.5 (M+H)⁺. HPLC (Method A) Rt 5.34 min.

Step 2: 2-methyl-2'-(trifluoromethyl)biphenyl-4-carboxylic acid

To a solution of methyl 2-methyl-2'-(trifluoromethyl)biphenyl-4-carboxylate, prepared in step 1 (3 g; 10.19 mmol; 1 eq.) in EtOH (90 mL), was added at RT an aqueous solution of sodium hydroxide (6.12 mL; 5 M; 30.58 mmol; 3 eq.). The reaction mixture was stirred at 60° C. for one hour. The reaction mixture was concentrated under vacuum to give a brown solid. It was taken up in water (400 mL) and the aqueous phase was washed twice with EtOAc (200 mL). Aqueous phase was acidified with concentrated HCl (2 mL) to pH 2. Then it was concentrated under vacuum until a precipitate was formed (⅓ of volume). The suspension was filtered off and dried under vacuum, affording the title compound as a beige solid (2.41 g, 84%). ¹H NMR: (DMSO-d₆, 300 MHz) δ 13.03 (s, 1H), 7.91-7.68 (m, 5H), 7.38-7.36 (d, J=8.27 Hz, 1H), 7.27-7.25 (d, J=8.24 Hz, 1H), 2.05 (s, 3H). LC/MS (Method A): 279.0 (M−H)⁻. HPLC (Method A) Rt 4.49 min (Purity: 95.7%).

Intermediate 6: 3-methyl-4-(4-methyl-3-thienyl)benzoic acid

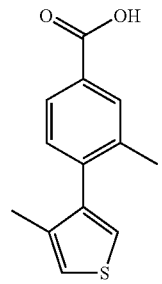

Step 1: methyl 3-methyl-4-(4-methyl-3-thienyl)benzoate

The title compound was prepared following procedure described for Intermediate 5, step 1, but starting from 4-methyl-3-thiopheneboronic acid (5.11 g; 36.01 mmol; 1.10 eq.). It was isolated as a brown oil (2.96 g, 92%) and was used in the next step without further purification. LC/MS (Method A): 246.8 (M+H)⁺. HPLC (Method A) Rt 5.14 min (Purity: 58.3%).

Step 2: 3-methyl-4-(4-methyl-3-thienyl)benzoic acid

The title compound was prepared following procedure described for Intermediate 5, step 2, but starting from methyl 3-methyl-4-(4-methyl-3-thienyl)benzoate (2.0 g; 8.12 mmol; 1 eq.), affording Intermediate 6 as a beige solid. ¹H NMR: (DMSO-d₆, 300 MHz) δ 12.97 (s, 1H), 7.91 (s, 1H), 7.84-7.81 (dd, J=8.12 Hz, J=1.87 Hz; 1H), 7.41 (d, J=3.20 Hz, 1H), 7.35-7.34 (m, 1H), 7.28-7.26 (d, J=7.80 Hz, 1H), 2.18 (s, 3H), 2 (s, 3H). LC/MS (Method A): 232.9 (M+H)⁺; 231.0 (M−H)⁻. HPLC (max plot) Rt 4.26 min (Purity: 99.6%).

Intermediate 7: 2'-methyl-2-nitro-1,1'-biphenyl-4-carboxylic acid

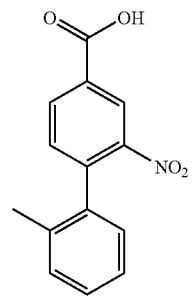

Step 1: methyl 2'-methyl-2-nitro-1,1'-biphenyl-4-carboxylate

To a solution of methyl 4-bromo-3-nitrobenzoate (Chess, 3 g, 11.53 mmol) in toluene (100 mL) and water (100 mL) was added o-tolylboronic acid (1.88 g, 13.84 mmol) followed by potassium carbonate (7.972 g, 57.68 mmol), tetrakis(triphenylphosphine)palladium(0) (0.668 g, 0.577 mmol). The reaction mixture was refluxed at 120° C. for 14 h. After the completion of reaction, it was cooled to RT and organic layer was separated and evaporated under reduced pressure. The crude compound was passed through silica pad (60-120 mesh) using hexane as eluent to give the title compound as a white solid (2.5 g, 79%). $^1$H NMR: (DMSO-d$_6$, 400 MHz) δ 8.52 (s, 1H), 8.29-8.26 (m, 1H), 7.63-7.61 (m, 1H), 7.34-7.33 (m, 2H), 7.23 (m, 1H), 7.13 (m, 1H), 3.94 (s, 3H), 2.04 (s, 3H).

Step 2: 2'-methyl-2-nitro-1,1'-biphenyl-4-carboxylic acid

Methyl 2'-methyl-2-nitro-1,1'-biphenyl-4-carboxylate, prepared in step 1 (2.5 g, 9.2 mmol) was dissolved in dry THF (20 mL) and cooled to 0° C. To this solution was added lithium hydroxide (1.15 g, 27.6 mmol) in water (5 mL) and the mixture was stirred at RT for 4 h. The solvents were concentrated and the aqueous residue was washed with EtOAc. The aqueous layer was separated and acidified with 1.5N HCl to pH 2-3 and extracted with DCM. DCM was washed with water and dried over sodium sulphate and evaporated under reduced pressure to obtain the title compound as a yellow solid (1.6 g, 70%). $^1$H NMR: (DMSO-d$_6$, 400 MHz) δ 13.67 (bs, 1H), 8.49 (s, 1H), 8.26-8.24 (d, 1H), 7.58-7.56 (m, 1H), 7.35-7.32 (m, 2H), 7.27-7.12 (d, 1H), 7.10 (d, 1H), 2.09-1.99 (s, 3H). LC/MS (Method A): 255.9 (M−H)$^−$. HPLC (Method B) Rt 1.79 min (Purity: 99.16%).

Intermediate 8:
3-methoxy-4-(4-methyl-3-thienyl)benzoic acid

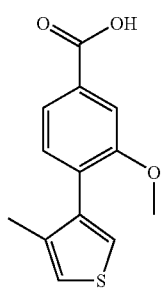

Step 1: methyl 3-methoxy-4-(4-methyl-3-thienyl)benzoate

The title compound was prepared following procedure described for Intermediate 5, step 1, but starting from methyl 4-bromo-3-methoxybenzoate (Combi-Blocks, 2.50 g; 10.20 mmol; 1 eq.) and 4-methyl-3-thiopheneboronic acid (1.59 g; 11.22 mmol; 1.10 eq.), and was isolated as a brown oil. It was used in the next step without further purification. LC/MS (Method A): 262.8 (M+H)$^+$. HPLC (Method A) Rt 4.79 min.

Step 2: 3-methoxy-4-(4-methyl-3-thienyl)benzoic acid

The title compound was prepared following procedure described for Intermediate 5, step 2, but starting from methyl 3-methoxy-4-(4-methyl-3-thienyl)benzoate (2.30 g; 8.77 mmol; 1 eq.), affording the title compound as a brown solid (1.81 g, 83%). $^1$H NMR: (DMSO-d$_6$, 300 MHz) δ 13.05 (s, 1H), 7.62-7.59 (m, 2H), 7.40-7.39 (d, J=3.23 Hz, 1H), 7.32-7.29 (d, J=7.48 Hz, 1H), 7.25-7.23 (m, 1H), 3.82 (s, 3H), 2.99 (s, 3H). LC/MS (Method A): 248.8 (M+H)$^+$; 246.9 (M−H)$^−$. HPLC (Method A) Rt 3.99 min (Purity: 97.4%).

Intermediate 9:
2-methoxy-2'-methylbiphenyl-4-carboxylic acid

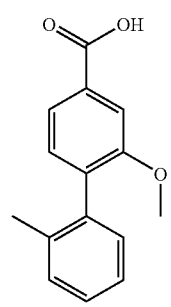

Step 1: methyl 2-methoxy-2'-methylbiphenyl-4-carboxylate

The title compound was prepared following procedure described for Intermediate 5, step 1, but starting from methyl 4-bromo-3-methoxybenzoate (Combi-Blocks, 2.50 g; 10.20 mmol; 1 eq.) and o-tolylboronic acid (1.53 g; 11.22 mmol; 1.10 eq.), and was isolated as a brown oil. It was used in the next step without further purification. LC/MS (Method A): 256.9 (M+H)$^+$. HPLC (Method A) Rt 4.93 min.

Step 2: 2-methoxy-2'-methylbiphenyl-4-carboxylic acid

The title compound was prepared following procedure described for Intermediate 5, step 2, but starting from methyl 2-methoxy-2'-methylbiphenyl-4-carboxylate (2.50 g; 9.75 mmol; 1 eq.), affording the title compound as a beige solid (1.95 g, 83%). $^1$H NMR: (DMSO-d$_6$, 300 MHz) δ 13.06 (s, 1H), 7.66-7.61 (m, 2H), 7.31-7.23 (m, 4H), 7.15-7.13 (d, J=7.28 Hz, 1H), 3.80 (s, 3H), 2.07 (s, 3H). LC/MS (Method A): 240.9 (M−H)$^−$. HPLC (Method A) Rt 4.05 min (Purity: 97.3%).

Intermediate 10: 3-nitro-4-piperidin-1-ylbenzoic acid

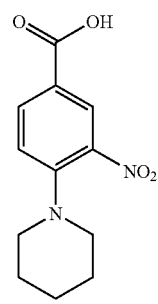

A mixture of ethyl 4-fluoro-3-nitrobenzoate (Clontech 01072, 500 mg; 2.35 mmol; 1 eq.) and piperidine (599.2 mg;

7.04 mmol; 3 eq.) in DMF (2 mL) was heated to 50° C. for 3 hours. The reaction was then allowed to return to RT and diluted with water. It was extracted with EtOAc and the organic phase was dried over sodium sulfate and concentrated in vacuo, affording ethyl 3-nitro-4-piperidin-1-ylbenzoate as a yellow oil. The residue was taken up in THF (15 mL) and lithium hydroxide (280.86 mg; 11.73 mmol; 5 eq.) was added, followed by water (15 mL). The reaction mixture was then stirred at RT for 5 hours. It was concentrated and the residue was diluted with water. The aqueous phase was washed with Et$_2$O and acidified to pH 5 with acetic acid. It was extracted with Et$_2$O and the organic phase was dried over magnesium sulfate and concentrated, affording the title compound as a yellow solid (562 mg, 96%). $^1$H NMR: (DMSO-d$_6$, 300 MHz) δ 13.07 (s, 1H), 8.29-8.28 (d, J=2.11 Hz, 1H), 8.03-8 (dd, J=8.91 Hz, J=2.20 Hz, 1H), 7.35-7.33 (d, J=8.91 Hz, 1H), 3.15-3.13 (m, 4H), 1.64-1.60 (m, 6H). LC/MS (Method A): 252.9 (M+H)$^+$; 250.9 (M−H)$^−$. HPLC (Method A) Rt 3.69 min (Purity: 99.7%).

Intermediate 11:
4-(2-methylpiperidin-1-yl)-3-nitrobenzoic acid

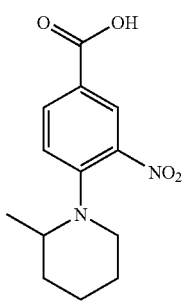

A mixture of ethyl 4-fluoro-3-nitrobenzoate (Clontech 01072, 1 g; 4.69 mmol; 1 eq.) and 2-methylpiperidine (1.395 g; 14.07 mmol; 3 eq.) in DMF (4 mL) was heated to 50° C. for 3 hours. The reaction was then allowed to return to RT and diluted with water. It was extracted with EtOAc and the organic phase was dried over sodium sulfate and concentrated in vacuo, affording ethyl 4-(2-methylpiperidin-1-yl)-3-nitrobenzoate as a yellow oil. The residue was taken up in THF (10 mL) and lithium hydroxide (561.73 mg; 23.46 mmol; 5 eq.) was added followed by water (10 mL). The reaction mixture was stirred at RT for 16 hours. It was concentrated and the residue was diluted with water and washed with Et$_2$O. The aqueous layer was acidified to pH 5 with acetic acid. It was extracted with Et$_2$O and the organic phase was dried over magnesium sulfate and concentrated, affording the title compound as a yellow solid (1.17 g, 94%). $^1$H NMR: (DMSO-d$_6$, 300 MHz) δ 13.07 (s, 1H), 8.23-8.22 (d, J=2.13 Hz, 1H), 8.04-8 (dd, J=8.96 Hz, J=2.28 Hz, 1H), 7.44-7.41 (d, J=8.88 Hz, 1H), 3.64-3.60 (m, 1H), 3.25-3.17 (m, 1H), 2.90-2.84 (m, 1H), 1.82-1.43 (m, 6H), 1.06-1.04 (d, J=6.43 Hz, 3H). LC/MS (Method A): 265.0 (M+H)$^+$; 263.0 (M−H)$^−$.

Intermediate 12: 3-Methyl-4-piperidin-1-ylbenzoic acid

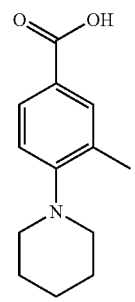

Step 1: Methyl 3-methyl-4-piperidin-1-ylbenzoate

To a stirred solution of methyl 4-bromo-3-methylbenzoate (ABCR, 5 g, 21.8 mmol) in dry 1,4-dioxane (100 mL), were added dry Cs$_2$CO$_3$ (10.65 g, 32.7 mmol) and piperidine (2.2 g, 26 mmol). The mixture was degassed with N$_2$ for 10 min. BINAP (0.67 g, 1.1 mmol) and palladium(II)acetate (0.24 g, 1.1 mmol) were added under N$_2$ and the resulting mixture was refluxed for 15 h. The reaction mixture was filtered through a pad of celite and the filtrate was evaporated. The crude product was purified by flash chromatography, affording the title product as a off-white solid (4.9 g, 96%). $^1$H NMR (CDCl$_3$, 400 MHz) δ 7.82-7.84 (m, 2H), 6.97-6.99 (d, 1H), 3.92 (s, 3H), 2.90-2.93 (m, 4H), 1.67-1.76 (m, 4H), 1.62-1.63 (m, 2H). LC/MS (Method A): 233.9 (M+H)$^+$. HPLC (Method B) Rt 4.18 min (Purity: 95.4%).

Step 2: 3-Methyl-4-piperidin-1-ylbenzoic acid

To a stirred solution of methyl 3-methyl-4-piperidin-1-ylbenzoate, obtained in step 1 (4.8 g, 20.6 mmol) in THF (100 mL) and water (5 mL) was added lithium hydroxide (2.5 g, 10.3 mmol). The resulting mixture was heated at 50° C. for 12 h. Solvents were removed under vacuum and the resulting mass was diluted with water. The aqueous layer was washed with DCM (2×50 mL) and was acidified with conc HCl (pH=4). It was extracted with EtOAc (2×100 mL). The EtOAc layer was washed with brine and dried over sodium sulfate, affording the title compound as a yellow solid (4.0 g, 88%). $^1$H NMR (DMSO-d$_6$, 400 MHz) δ 7.70-7.71 (m, 2H), 6.99-7.01 (m, 1H), 2.82-2.84 (m, 4H), 2.25 (s, 3H), 1.59-1.64

(m, 4H), 153-1.54 (m, 2H). LC/MS (Method A): 219.9 (M+H)⁺. HPLC (Method B) Rt 2.41 min (Purity: 92.3%).

Intermediate 13: 4-Morpholin-4-yl-3-(trifluoromethyl)benzoic acid

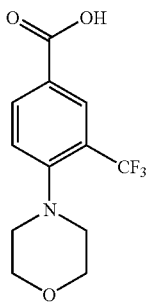

Step 1: 4-Morpholin-4-yl-3-(trifluoromethyl)benzonitrile

A mixture of 4-fluoro-3-trifluoro-methylbenzonitrile (Fluorochem2223, 10 g, 52.8 mmol) and morpholine (9.25 mL, 105.7 mmol) was heated at 60° C. under $N_2$ for 8 hours. The mixture was cooled and diluted with water (100 mL). The precipitate was filtered affording the title compound as a white solid (12.9 g, 95%). ¹H NMR (CDCl₃, 400 MHz) δ 7.92 (s, 1H), 7.78-7.81 (d, 1H), 7.32-7.35 (d, 1H), 3.84-3.87 (m, 4H), 3.04-3.06 (m, 4H). LC/MS (Method A): 257.1 (M+H)⁺. HPLC (Method B) Rt 3.61 min (Purity: 99.1%).

Step 2: Methyl 4-morpholin-4-yl-3-(trifluoromethyl)benzoate

A mixture of 4-morpholin-4-yl-3-(trifluoromethyl)benzonitrile, obtained in Step 1 (5 g, 19.5 mmol) and HCl in methanol (250 mL) was heated at 60° C. for 24 h. The reaction mixture evaporated to dryness and the residue was partitioned between EtOAc (200 mL) and 10% aqueous NaHCO₃ solution (100 mL). The organic layer was washed with water, brine and concentrated under vacuum to afford the title compound as yellow oil (4.45 g, 97%). It was used in the next step without further purification. ¹H NMR (CDCl₃, 400 MHz) δ 8.32 (s, 1H), 8.17-8.19 (d, 1H), 7.31-7.33 (d, 1H), 3.94 (s, 1H), 3.85-3.89 (m, 4H), 3.02-3.07 (m, 4H).

Step 3: 4-Morpholin-4-yl-3-(trifluoromethyl)benzoic acid

To a stirred solution of methyl 4-morpholin-4-yl-3-(trifluoromethyl)benzoate, obtained in Step 2 (5 g, 17.2 mmol) in THF (50 mL) and water (5 mL) was added lithium hydroxide (1.5 g, 34.4 mmol). The resulting mixture was stirred at RT for 12 h. Solvents were removed under vacuum and the resulting residue was diluted with water. The aqueous layer was washed with DCM (2×50 mL) and was acidified with concentrated HCl (pH=4). It was extracted with EtOAc (2×100 mL). The EtOAc layer was washed with brine and dried over sodium sulfate, affording the title compound as a white solid. ¹H NMR (DMSO-d₆, 400 MHz) δ 13.5 (bs, 1H), 8.13-8.16 (m, 2H), 7.55-7.57 (d, 1H), 3.69-3.71 (m, 4H), 2.94-2.96 (m, 4H). LC/MS (Method A): 275.9 (M+H)⁺. HPLC (Method B) Rt 2.97 min (Purity: 99.7%).

Intermediate 14: 3-Methyl-4-morpholin-4-ylbenzoic acid

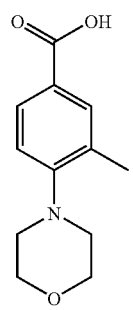

Step 1: Methyl 3-methyl-4-morpholin-4-ylbenzoate

To a stirred solution of methyl 4-bromo-3-methylbenzoate (5 g, 21.8 mmol) in dry 1,4-dioxane (100 mL), were added dry Cs₂CO₃ (10.65 g, 32.7 mmol) and morpholine (2.3 g, 26 mmol). The mixture was degassed for 10 min. BINAP (0.67 g, 1.1 mmol) and palladium(II)acetate (0.24 g, 1.1 mmol) were added under $N_2$ and the resulting mixture was refluxed for 15 h. The reaction mixture was filtered through a pad of celite and the filtrate was evaporated. The crude product was purified by flash chromatography, affording the title compound as a yellow solid (4.3 g, 84%). ¹H NMR (CDCl₃, 400 MHz) δ 7.86-7.90 (m, 2H), 7.13-7.16 (d, 1H), 3.98-4.0 (m, 4H), 3.91 (3H, s), 3.10-312 (m, 4H), 2.45 (3H, s). LC/MS (Method A): 236.0 (M+H)⁺. HPLC (Method B) Rt 2.24 min (Purity: 95.3%).

Step 2: 3-Methyl-4-morpholin-4-ylbenzoic acid

To a stirred solution of methyl 3-methyl-4-morpholin-4-ylbenzoate obtained in step 1 (4 g, 169.3 mmol) in THF (100 mL) and water (5 mL) was added lithium hydroxide (2 g, 84.6 mol). The resulting mixture was heated at 50° C. for 12 h. Solvents were removed under vacuum and the resulting mass was diluted with water. The aqueous layer was washed with DCM (2×50 mL) and was acidified with conc HCl (pH=4). It was extracted with EtOAc (2×100 mL). The EtOAc layer was washed with brine and dried over sodium sulfate, affording the title compound as a yellow solid (3.6 g, 97%). ¹H NMR (DMSO-d₆, 400 MHz) δ 12.5 (bs, 1H), 7.72-7.74 (m, 2H), 7.04-7.06 (m, 1H), 3.72-3.75 (m, 4H), 2.88-2.90 (m, 4H), 2.33 (s, 3H). LC/MS (Method A): 222.1 (M+H)⁺. HPLC (Method B) Rt 1.42 min (Purity: 98.3%).

Intermediate 15: 4-(2-Methylpiperidin-1-yl)-3-(trifluoromethyl)benzoic acid

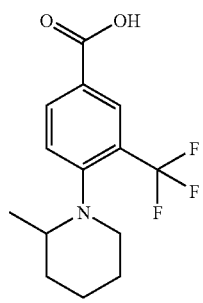

Step 1: 4-(2-methylpiperidin-1-yl)-3-(trifluoromethyl)benzonitrile

A mixture of 4-fluoro 3-trifluoro-methylbenzonitrile (5 g, 26.4 mmol) and 2-methylpiperidine (6.25 mL, 52.9 mmol) was heated at 100° C. under $N_2$ for 12 h. The reaction mixture was diluted with water (100 mL) and was extracted with EtOAc (2×100 mL). The organic layer was washed with water (2×100 mL) and brine solution (100 mL). The solvent was dried over sodium sulphate and concentrated. The residue was purified by flash chromatography using silica-gel (60-120 mesh) and pet-ether/EtOAc as eluent to afford the title compound as an off-white solid. $^1$H NMR (CDCl$_3$, 400 MHz) δ 7.87 (s, 1H), 7.71-7.74 (d, 1H), 7.50 (bs, 1H), 2.95-3.03 (m, 2H), 2.49-2.54 (m, 1H), 1.71-1.77 (m, 3H), 1.58-1.59 (m, 1H), 1.36-1.39 (m, 2H), 0.75-0.77 (d, 3H). HPLC (Method C) Rt 5.09 min (Purity: 98.8%).

Step 2: Methyl 4-(2-methylpiperidin-1-yl)-3-(trifluoromethyl)benzoate

A mixture of 4-(2-methylpiperidin-1-yl)-3-(trifluoromethyl)benzonitrile obtained in Step 1 (7.4 g, 27.6 mmol) and HCl in Methanol (250 mL) was heated at 75° C. for 48 h. The reaction mixture evaporated to dryness and the residue was partitioned between EtOAc (200 mL) and 10% NaHCO$_3$ solution (100 mL). The organic layer was washed with water, brine and concentrated under vacuum to afford the title compound as yellow liquid. It was used in the next step without further purification. $^1$H NMR (CDCl$_3$, 400 MHz) δ 8.38 (s, 1H), 8.21-8.25 (d, 1H), 7.45-7.47 (d, 1H), 3.94 (s, 3H), 2.99-3.04 (m, 3H), 2.50 (t, 1H), 1.78-1.81 (m, 3H), 1.72-1.77 (m, 3H), 1.42-1.45 (m, 3H).

Step 3: 4-(2-Methylpiperidin-1-yl)-3-(trifluoromethyl)benzoic acid

To a stirred solution of methyl 4-(2-methylpiperidin-1-yl)-3-(trifluoromethyl)benzoate obtained in step 2 (6.6 g, 21.9 mmol) in THF (50 mL) and water (5 mL) was added lithium hydroxide (1.84 g, 43.8 mmol). The resulting mixture was stirred at RT for 12 h. Solvents were removed under vacuum and the resulting mass was diluted with water. The aqueous layer was washed with DCM (2×50 mL) and was acidified with conc HCl (pH=4). It was extracted with EtOAc (2×100 mL). The EtOAc layer was washed with brine and dried over sodium sulfate, affording the title compound as a white solid. $^1$H NMR (DMSO-d$_6$, 400 MHz) δ 13.30 (bs, 1H), 8.15-8.19 (m, 2H), 7.67-7.70 (d, 1H), 3.08 (m, 1H), 2.86-2.89 (m, 1H), 2.49-2.50 (m, 1H), 1.89-1.90 (m, 2H), 1.74-1.76 (m, 2H), 1.43-1.46 (m, 1H), 1.40-1.41 (m, 1H), 0.77 (d, 3H). LC/MS (Method A): 288.1 (M+H)⁺. HPLC (Method B) Rt 3.71 min (Purity: 98.3%).

Intermediate 16: 4-(2,6-Dimethylphenyl)benzoic acid

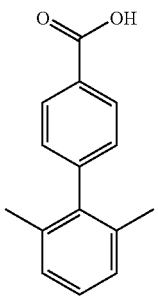

A mixture of 2,6-dibromobenzene (20 g, 0.10 mol), 4-carboxybenzeneboronic acid (15 g, 0.1 mol), Pd(OAc)$_2$ (5 g, 0.02 mol), PPh$_3$ (5 g, 0.02 mol) and TEA (100 mL) in dry DMF (400 mL) were refluxed at 150° C. for 20 h. The reaction mixture was filtered through celite, diluted with water and acidified to pH=2. The solid precipitate was filtered, washed with water and dried under vacuum, affording the title compound as an off-white solid. $^1$H NMR (DMSO-d$_6$, 400 MHz) δ 8.05 (d, J=8.62 Hz, 2H), 7.31-7.17 (m, 5H), 1.98 (s, 6H). LC/MS (Method A): 224.1 (M–H)⁻. HPLC (Method B) Rt 4.38 min (Purity: 97.2%).

Intermediate 17: 2',4'-dimethoxy-2-methyl biphenyl-4-carboxylic acid

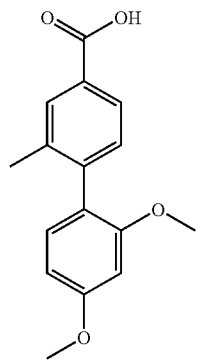

Step 1: Methyl 4-bromo-3-methylbenzoate

To a solution of 4-bromo-3-methylbenzoic acid (Aldrich 532819, 30 g; 139.5 mmol) in MeOH (600 mL), under $N_2$ was added dropwise thionyl chloride (40.5 mL; 558.0 mmol) over 10 min. The reaction mixture was stirred at RT for 12 hours. The solvents were concentrated and the crude residue was dissolved in EtOAc (700 mL). The organic layer was washed with a saturated aqueous solution of NaHCO$_3$ (200 mL), water (200 mL), brine (200 mL), dried over MgSO$_4$ and concentrated affording the title compound as an orange solid (31.3 g, 98%). $^1$H NMR (DMSO-d$_6$, 300 MHz) δ 7.96-7.95 (m, 1H), 7.79-7.69 (m, 2H), 3.89 (s, 3H), 2.45 (s, 3H). HPLC (Method A) Rt 4.37 min (Purity: 96.4%).

Step 2: Methyl 2',4'-dimethoxy-2-methylbiphenyl-4-carboxylate

Methyl 4-bromo-3-methylbenzoate obtained in step 1 (3 g; 13.10 mmol), 2,4-dimethoxyphenylboronic acid (2.62 g; 14.4 mmol), potassium carbonate (9.05 g; 65.48 mmol), tetrakis(triphenylphosphine)palladium(0) (1.51 g; 1.31 mmol) were taken in toluene (15 mL) and water (15 mL) under N$_2$ atmosphere. The reaction mixture was purged with vacuum and degassed with N$_2$ and then refluxed for 6 hours. The reaction mixture was cooled to RT, filtered over a pad of celite and washed with toluene (200 mL). The filtrate was concentrated to afford a brown oil which was taken in EtOAc (300 mL). The organic layer was washed with a saturated aqueous solution of NaHCO$_3$ solution (100 mL), water (100 mL) and brine (100 mL), dried over MgSO$_4$ and concentrated affording the title compound as a brown oil that was used without further purification (3.7 g, 98%). HPLC (Method A) Rt 4.74 min (Purity: 59.9%).

Step 3: 2',4'-dimethoxy-2-methylbiphenyl-4-carboxylic acid

A solution of methyl 2',4'-dimethoxy-2-methylbiphenyl-4-carboxylate obtained in step 2 (2 g; 6.99 mmol) in EtOH (60 mL) at RT was treated with sodium hydroxide (4.19 mL; 5 M; 20.96 mmol). The reaction mixture was stirred at 60° C. for 1 hour. The reaction mixture was concentrated to give a brown solid that was taken up in water (40 mL) and the aqueous phase was washed twice with EtOAc and then acidified with HCl to pH 2. Then it was concentrated until precipitation (⅕ of the volume). The suspension was filtered off and dried under vacuum affording the title compound as an orange solid. $^1$H NMR (DMSO-d$_6$, 300 MHz) δ 12.59 (br s, 1H), 7.58-7.51 (m, 2H), 6.97-6.95 (d, J=8.03 Hz, 1H), 6.81-6.79 (d, J=8.39 Hz, 1H), 6.44-6.37 (m, 2H), 3.59 (s, 3H), 3.49 (s, 3H), 1.88 (s, 3H). LC/MS (Method A): 272.9 (M+H)$^+$; 270.9 (M−H)$^−$. HPLC (Method A) Rt 3.87 min (Purity: 99.7%).

Intermediate 18: 4-nitro-3-piperidin-1-ylbenzoic acid

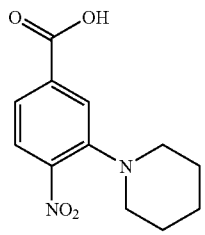

3-Fluoro-4-nitrobenzoic acid (Combi-Blocks CA-4022, 5 g; 27.01 mmol) was dissolved in EtOH (30 mL) to which was added piperidine (8.02 mL; 81.03 mmol). The reaction mixture was stirred at RT for 24 hours, then concentrated and the residue was taken up in water (300 mL). The aqueous phase was washed with Et$_2$O then the aqueous phase was acidified with acetic acid until pH 5. The aqueous phase was extracted with Et$_2$O (900 mL). The combined organic phases were dried over MgSO$_4$ and concentrated affording the title compound as an orange solid (6.18 g, 91%). $^1$H NMR (DMSO-d$_6$, 300 MHz) δ 13.55 (br s, 1H), 7.89-7.86 (d, J=8.42 Hz, 1H), 7.77-7.76 (d, J=1.40 Hz, 1H), 7.60-7.57 (dd, J=8.42 Hz, 1.50 Hz, 1H), 3.23-2.98 (m, 2H), 3.21-3.05 (m, 4H), 1.63-1.58 (m, 6H). HPLC (Method A) Rt 3.88 min (Purity: 99.9%).

Intermediate 19: 2'-methyl-2-(trifluoromethyl)biphenyl-4-carboxylic acid

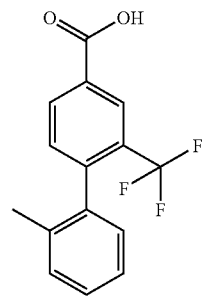

Step 1: Methyl 4-bromo-3-(trifluoromethyl)benzoate

To a suspension of 4-bromo-3-(trifluoromethyl)benzoic acid (Acceledev 000625, 15 g; 55.76 mmol) in MeOH (300 mL) at RT was added dropwise thionyl chloride (16.18 mL; 223.04 mmol) over 15 min. The reaction mixture was stirred at RT for 12 hours. The solvent was concentrated and the crude residue was diluted with EtOAc (500 mL). The organic layer was washed with a saturated aqueous solution of NaHCO$_3$ (200 mL), water (200 mL), brine (200 mL), dried over MgSO$_4$ and concentrated affording the title compound as an orange solid (14.80 g, 94%). $^1$H NMR (DMSO-d$_6$, 300 MHz) δ 8.26 (m, 1H), 8.14-8.13 (m, 2H), 3.93 (s, 3H). HPLC (Method A) Rt 4.71 min (Purity: 99.0%).

Step 2: Methyl 2'-methyl-2-(trifluoromethyl)biphenyl-4-carboxylate

Methyl 4-bromo-3-(trifluoromethyl)benzoate (6 g; 21.20 mmol; 1 eq.), o-tolylboronic acid (3.17 g; 23.32 mmol; 1.10 eq.), potassium carbonate (14.65 g; 105.99 mmol; 5 eq.), tetrakis(triphenylphosphine)palladium(0) (2.45 g; 2.12 mmol; 0.10 eq.) were taken up in Toluene (30 mL) and water (30 mL) under N$_2$ atmosphere. The reaction mixture was purged with vacuum for 5 minutes, then degassed with N$_2$ and then refluxed for 3 hours. The reaction mixture was cooled to RT, filtered over a pad of celite and washed with toluene (200 mL). The filtrate was concentrated to afford brown oil which was taken in EtOAc (200 mL). The organic layer was washed with a saturated aqueous solution of NaHCO$_3$ solution (50 mL), water (50 mL) and brine (50 mL), dried over MgSO$_4$ and concentrated affording the title compound as a brown oil (6.4 g, quantitative). HPLC (Method A) Rt 5.33 min (Purity: 60.0%).

Step 3: 2'-methyl-2-(trifluoromethyl)biphenyl-4-carboxylic acid

A solution of methyl 2'-methyl-2-(trifluoromethyl)biphenyl-4-carboxylate (5 g; 16.99 mmol; 1 eq.) in EtOH (150 mL) at RT was treated with sodium hydroxide (10.19 mL; 5 M; 50.97 mmol; 3 eq.). The reaction mixture was stirred at 60° C.

for 2 hours. The reaction mixture was concentrated to give a brown solid which was taken up in water (300 mL) and the aqueous phase was washed twice with EtOAc. The aqueous phase was acidified with HCl cc to pH 2, then it was concentrated until precipitation (half of the volume). The suspension was filtered affording the title compound as a beige solid. $^1$H NMR (DMSO-d$_6$, 300 MHz) δ 13.55 (br s, 1H), 8.31 (s, 1H), 8.26-8.23 (d, J=7.90 Hz, 1H), 7.51-7.48 (d, J=7.90 Hz 1H), 7.37-7.12 (m, 4H), 1.99 (s, 3H). LC/MS (Method A): 278.9 (M−H)$^−$. HPLC (Method A) Rt 4.57 min (Purity: 98.7%).

Intermediate 20:
4-(4-methyl-3-thienyl)-3-(trifluoromethyl)benzoic acid

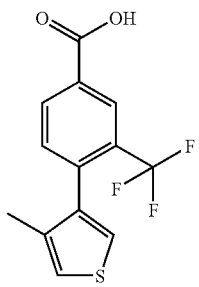

Step 1: Methyl
4-(4-methyl-3-thienyl)-3-(trifluoromethyl)benzoate

Methyl 4-bromo-3-(trifluoromethyl)benzoate (Intermediate 19, step 1) (3.50 g; 12.37 mmol; 1 eq.), 4-methyl-3-thiopheneboronic acid (1.93 g; 13.60 mmol; 1.10 eq.), potassium carbonate (8.54 g; 61.83 mmol; 5 eq.), tetrakis(triphenylphosphine)palladium(0) (1.43 g; 1.24 mmol; 0.10 eq.) were taken up in Toluene (17.50 mL) and water (17.50 mL) under N$_2$ atmosphere. The reaction mixture was purged with vacuum, then degassed with N$_2$ for 5 minutes and then refluxed for 24 hours. The reaction mixture was cooled to RT, filtered over a pad of celite and washed with toluene (200 mL). The filtrate was concentrated affording a brown oil that was taken in EtOAc (300 mL). The organic layer was washed with a saturated aqueous solution of NaHCO$_3$ solution (100 mL), water (100 mL) and brine (100 mL), dried over MgSO$_4$ and concentrated affording the title compound as a brown oil (3.7 g, 99%). HPLC (Method A) Rt 5.21 min (Purity: 68.1%).

Step 2:
4-(4-methyl-3-thienyl)-3-(trifluoromethyl)benzoic acid

A solution of methyl 4-(4-methyl-3-thienyl)-3-(trifluoromethyl)benzoate (3 g; 9.99 mmol; 1 eq.) in EtOH (90 mL) at RT was treated with sodium hydroxide (5.99 mL; 5 M; 29.97 mmol; 3 eq.). The reaction mixture was stirred at 60° C. for 2 hours. The reaction mixture was concentrated to give a brown solid which was taken up in water (300 mL) and the aqueous phase was washed twice with EtOAc. The aqueous phase was acidified with HCl cc to pH 2 and extracted with EtOAc (250 mL). The organic layer was dried over MgSO$_4$ and concentrated affording the title compound as a brown oil (2.60 g, 90%). $^1$H NMR (DMSO-d$_6$, 300 MHz) δ 13.07 (br s, 1H), 8.34-8.24 (m, 2H), 7.57-7.54 (m, 1H), 7.47-7.46 (m, 1H), 7.34-7.33 (m, 1H), 1.98 (s, 3H). LC/MS (Method A): 284.9 (M−H)$^−$. HPLC (Method A) Rt 4.53 min (Purity: 95.5%).

Intermediate 21: 2',5'-dimethoxy-2-methyl biphenyl-4-carboxylic acid

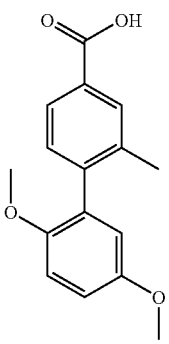

Methyl 4-bromo-3-methylbenzoate (Intermediate 17, step 1) (4 g; 17.46 mmol; 1 eq.), 2,5-dimethoxyphenylboronic acid (3.50 g; 19.21 mmol; 1.10 eq.), potassium carbonate (12.07 g; 87.31 mmol; 5 eq.), tetrakis(triphenylphosphine)palladium(0) (2.02 g; 1.75 mmol; 0.10 eq.) were taken in Toluene (20 mL) and water (20 mL) under N$_2$ atmosphere. The reaction mixture was degassed with N$_2$ and then refluxed for 24 hours. The reaction mixture was cooled to RT, filtered over a pad of celite and washed with toluene (200 mL). The filtrate was concentrated to afford a brown oil which was taken up in EtOAc (300 mL). The organic layer was washed with a saturated aqueous solution of NaHCO$_3$ solution (100 mL), water (100 mL) and brine (1000 mL), dried over MgSO$_4$ and concentrated affording methyl 2',5'-dimethoxy-2-methylbiphenyl-4-carboxylate as a brown oil (5.1 g) used without further purification (HPLC (Method A) Rt 4.73 min (Purity: 59.7%)). A solution of methyl 2',5'-dimethoxy-2-methylbiphenyl-4-carboxylate (4.50 g; 15.72 mmol; 1 eq.) in EtOH (135 mL) at RT was treated with sodium hydroxide (9.43 mL; 5 M; 47.15 mmol; 3 eq.). The reaction mixture was stirred at 60° C. for 2 hours. The reaction mixture was concentrated to give a beige solid which was taken up in water (100 mL) and the aqueous phase was washed twice with EtOAc. The aqueous phase was acidified with HCl cc to pH 2. Then it was concentrated until precipitation (volume divided by 2). The suspension was filtered affording the title compound as a beige solid (3.43 g, 80%). $^1$H NMR (DMSO-d$_6$, 300 MHz) δ 12.91 (br s, 1H), 7.85-7.78 (m, 2H), 7.27-7.24 (d, J=7.17 Hz, 1H), 7.08-6.96 (m, 2H), 6.72-6.71 (d, J=3.01 Hz, 1H), 3.76 (s, 3H), 3.68 (s, 3H), 2.14 (s, 3H). LC/MS (Method A): 270.9 (M−H)⁻. HPLC (Method A) Rt 3.84 min (Purity: 97.8%).

Intermediate 22:
4-(3,5-dimethylisoxazol-4-yl)-3-methylbenzoic acid

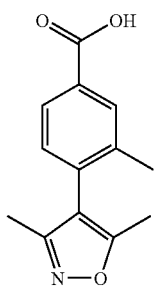

Methyl 4-bromo-3-methylbenzoate (Intermediate 17, step 1) (4 g; 17.46 mmol; 1 eq.), 3,5-dimethyl-4-(4,4,5,5-tetramethyl-1,3,2-dioxaborolane-2-yl)isoxazole (4.28 g; 19.21 mmol; 1.10 eq.), potassium carbonate (12.07 g; 87.31 mmol; 5 eq.), tetrakis(triphenylphosphine)palladium(0) (2.02 g; 1.75 mmol; 0.10 eq.) were taken in Toluene (20 mL) and water (20 mL) under N₂ atmosphere. The reaction mixture was degassed with N₂ and then refluxed for 4 hours. The reaction mixture was cooled to RT, filtered over a pad of celite and washed with toluene (200 mL). The filtrate was concentrated to afford a brown oil which was taken up in EtOAc (250 mL). The organic layer was washed with a saturated aqueous solution of NaHCO₃ solution (100 mL), water (100 mL) and brine (100 mL), dried over MgSO₄ and concentrated affording methyl 4-(3,5-dimethylisoxazol-4-yl)-3-methylbenzoate (4.2 g, 99%, HPLC (Method A) Rt 3.93 min) as an orange solid, which was used without further purification. A solution of methyl 4-(3,5-dimethylisoxazol-4-yl)-3-methylbenzoate (3 g; 12.23 mmol; 1 eq.) in EtOH (90 mL) at RT was treated with sodium hydroxide (7.34 mL; 5 M; 36.69 mmol; 3 eq.). The reaction mixture was stirred at 60° C. for 1 hour. The reaction mixture was concentrated to give a brown solid which was taken up in water (100 mL) and the aqueous phase was washed twice with EtOAc. The aqueous phase was acidified with HCl cc to pH 2. Then it was concentrated until precipitation (volume divided by 2). The suspension was filtered affording the title compound as a brown solid. It was washed with diethyl ether affording the title compound as a beige solid. ¹H NMR (DMSO-d₆, 300 MHz) δ 13.03 (br s, 1H), 7.95 (s, 1H), 7.86-7.84 (dd, J=7.88, 1.31 Hz, 1H), 7.34-7.32 (d, J=7.88 Hz, 1H), 2.26 (s, 3H), 2.19 (s, 3H), 2.07 (s, 3H). HPLC (Method A) Rt 3.13 min (Purity: 97.1%).

Intermediate 23:
4-(2-methoxypyridin-3-yl)-3-methyl benzoic acid

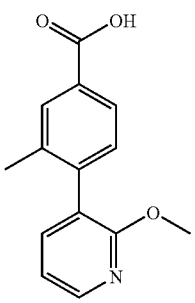

Methyl 4-bromo-3-methylbenzoate (Intermediate 17, step 1) (2 g; 8.73 mmol; 1 eq.), 2-methoxypyridin-3-ylboronic acid (1.47 g; 9.60 mmol; 1.10 eq.), K2CO3 (6.03 g; 43.65 mmol; 5 eq.), Pd(PPh3)4 (1.01 g; 0.87 mmol; 0.10 eq.) were taken up in toluene (10 mL) and water (10 mL) under N₂ atmosphere. The reaction mixture was purged with vacuum, then degassed with N₂ and refluxed for 24 hours. The reaction mixture was cooled to RT, filtered over a pad of celite and washed with toluene (100 mL). The filtrate was concentrated to afford a yellow oil which was taken in EtOAc (100 mL). The organic layer was washed with a saturated aqueous solution of NaHCO₃ solution, water and brine, dried over MgSO₄ and concentrated affording methyl 4-(2-methoxypyridin-3-yl)-3-methyl benzoate as a yellow oil (2.4 g, HPLC (Method A) Rt 4.02 min). A solution of methyl 4-(2-methoxypyridin-3-yl)-3-methylbenzoate (2.50 g; 9.72 mmol; 1 eq.) in EtOH (75 mL) at RT was treated with sodium hydroxide (5.83 mL; 5 M; 29.15 mmol; 3 eq.). The reaction mixture was stirred at 60° C. for 2 hours. The reaction mixture was concentrated to give a brown solid, which was taken up in water (50 mL) and the aqueous phase was washed twice with EtOAc. The aqueous phase was acidified with HCl cc to pH 2. Then it was concentrated (volume divided by 3) and the suspension was filtered affording the title compound as a beige solid. ¹H NMR (DMSO-d₆, 300 MHz) δ 12.96 (br s, 1H), 8.28-8.26 (dd, J=5.07 Hz, 1.86 Hz, 1H), 7.89 (m, 1H), 7.84-7.82 (dd, J=7.94 Hz, 1.52 Hz, 1H), 7.64-7.62 (dd, J=7.26 Hz, 1.86 Hz, 1H), 7.31-7.29 (d, J=7.94 Hz, 1H), 7.16-7.12 (m, 1H), 3.90 (s, 3H), 2.15 (s, 3H). LC/MS (Method A): 241.9 (M−H)⁻. HPLC (Method A) Rt 3.19 min (Purity: 99.1%).

Intermediate 24:
3-cyano-4-(2-methylpiperidin-1-yl)benzoic acid

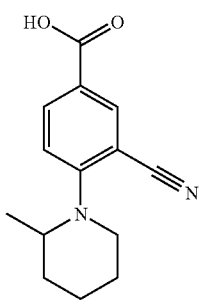

Step 1: 3-cyano-4-(2-methylpiperidin-1-yl)benzoic acid

2-Methylpiperidine (2.38 mL; 20.29 mmol; 5 eq.) was added to a solution of methyl 3-cyano-4-fluorobenzoate, prepared as described in *J. Med. Chem.* 2004, 47, 1339-1350 from 2-fluoro-5-formylbenzonitrile (Aldrich; 49, 408-9), (727 mg; 4.06 mmol; 1 eq.) in DMF (4 mL). The resulting mixture was stirred at RT for 2 days. The solution was partitioned between EtOAc and water and the phases separated. The organic layer was washed with 0.1M HCl then with NaCl sat. solution, dried over magnesium sulfate. Evaporation under reduced pressure afforded a greenish oil. The latter was taken up in THF (10 mL), LiOH (340.57 mg; 8.12 mmol; 2 eq.) then water (10 mL) were added and the reaction mixture was stirred at RT for 16 hours. The resulting solution was diluted with water and washed with Et₂O. The aqueous layer was made acidic (pH 2) by addition of 1M HCl and extracted with EtOAc. The organic phase was dried over magnesium sulfate and concentrated in vacuo to give a slightly yellow oil. The oil was triturated in a mixture of EtOAc and n-pentane and the resulting precipitate was filtered and dried to afford the title compound as an off-white solid. ¹H NMR (DMSO-d₆, 300 MHz) δ 13 (hr s, 1H), 8.08 (d, J=2.1 Hz, 1H), 8.01 (dd, J=8.8, 2.1 Hz, 1H), 7.18 (d, J=8.9 Hz, 1H), 4.12-4.08 (m, 1H), 3.35-3.25 (m, 2H), 1.84-1.53 (m, 6H), 1.09 (d, J=6.6 Hz, 3H). LC/MS (Method B): 243.2 (M−H)⁻; 245.2 (M+H)⁺.

Intermediate 25: 4-(2-methylpiperidin-1-yl)-3-[(methylsulfonyl)amino]benzoic acid

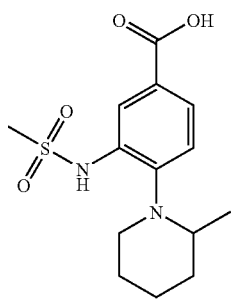

Step 1: 4-(2-methylpiperidin-1-yl)-3-nitrobenzoic acid

A mixture of ethyl 4-fluoro-3-nitrobenzoate (Clontech 01072, 25 g; 117.28 mmol; 1 eq.) and 2-methylpiperidine (41.54 mL; 351.84 mmol; 3 eq.) in DMF (100 mL) was heated to 50° C. for 2 hours The reaction was cooled to RT and diluted with water (100 mL), extracted with EtOAc, dried over MgSO₄ and concentrated giving a yellow oil. The residue was taken up in THF (250 mL) and lithium hydroxide (14.04 g; 586.41 mmol; 5 eq.) was added followed by water (250 mL). The reaction mixture was stirred at RT for 2 days. After evaporation of THF, the solution was diluted with water and washed with Et₂O. The aqueous layer was acidified to pH 5 with AcOH, extracted with Et₂O, dried over MgSO₄ and concentrated affording the title compound as a yellow solid (24.81 g, 80%). ¹H NMR (DMSO-d₆, 300 MHz) δ 13.09 (br s, 1H), 8.23-8.22 (d, J=2.14 Hz, 1H), 8.04-8.01 (dd, J=8.72 Hz, 2.19 Hz, 1H), 7.44-7.41 (d, J=8.94 Hz, 1H), 3.63-3.61 (m, 1H), 3.22-3.18 (m, 1H), 2.89-2.85 (m, 1H), 1.78-1.44 (m, 6H), 1.06-1.04 (d, J=6.65 Hz, 3H). LC/MS (Method B): 265.2 (M+H)⁺; 263.2 (M+H)⁻. HPLC (Method A) Rt 3.96 min (Purity: 97.9%)

Step 2: Ethyl 3-amino-4-(2-methylpiperidin-1-yl)benzoate

Ethyl 4-(2-methylpiperidin-1-yl)-3-nitrobenzoate (5 g; 17.10 mmol; 1 eq.) in a solution of MeOH/EtOAc 1:1 (340 mL, 0.05 M) was injected on a flow hydrogenation reactor (H-Cube), adapted with a Pd/C cartridge (44 mm), a flow of 1 mL/min, no heating and the full H₂ option enabled, affording after evaporation of the solvents the title compound as a white solid (4.34 g, 96%). ¹H NMR (DMSO-d₆, 300 MHz) δ 7.34-7.33 (d, 1H), 7.21-7.18 (dd, J=8.28 Hz, 1.81 Hz, 1H), 7.06-7.03 (d, J=8.18 Hz 1H), 5.09 (br s, 2H), 4.28-4.26 (q, J=7.43 Hz, 2H), 3.11-3.07 (m, 1H), 2.97-2.88 (m, 1H), 2.47-2.3 (m, 1H), 1.83-1.65 (m, 6H), 1.32 (t, J=7.43 Hz, 3H). LC/MS (Method B): 263.2 (M+H)⁺. HPLC (Method A) Rt 2.60 min (Purity: 97.8%).

Step 3: 4-(2-methylpiperidin-1-yl)-3-[(methylsulfonyl)amino]benzoic acid

Methanesulfonyl chloride (1.68 mL; 21.72 mmol; 1.10 eq.) was added dropwise (addition took 5 min) to a cold (0° C.) solution of Py (10 mL) and ethyl 3-amino-4-(2-methylpiperidin-1-yl)benzoate (5.18 g; 19.74 mmol; 1 eq.) in DCM (40 mL) and the reaction mixture was allowed to return to RT over one hour. The reaction mixture was stirred at RT for 3 hours. The reaction mixture was concentrated and the residue was taken up in water. The aqueous phase was extracted with EtOAc. The combined organic phases were washed with 1M HCl then brine, dried over MgSO₄ and concentrated giving a yellow oil. This oil was taken up in THF (30 mL) and lithium hydroxide (2.36 g; 98.72 mmol; 5 eq.) was added, followed by water (30 mL). The resulting mixture was stirred at RT for 2 days. THF was removed under vacuum and the solution diluted with water. This solution was washed with Et2O and acidified to pH 2 with conc HCl. The aqueous phase was extracted with EtOAc, washed with brine, dried over MgSO₄ and concentrated affording the title compound as a beige solid (5.48 g, 88%). ¹H NMR (DMSO-d₆, 300 MHz) δ 12.98 (br s, 1H), 8.53 (br s, 1H), 8.07-8.06 (d, J=1.91 Hz, 1H), 7.77-7.73 (dd, J=8.34 Hz, 1.97 Hz, 1H), 7.47-7.45 (d, J=8.34 Hz, 1H), 3.43-2.58 (m, 6H), 1.84-1.46 (m, 6H), 0.83-0.81 (d, J=6.09 Hz, 3H). HPLC (Method A) Rt 2.29 min (Purity: 99.0%).

Intermediate 26: 2-methyl-1,1':2',1''-terphenyl-4-carboxylic acid

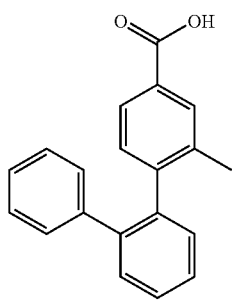

Step 1: Methyl 2-methyl-1,1':2',1''-terphenyl-4-carboxylate

Methyl 4-bromo-3-methylbenzoate (Intermediate 17, step 1) (3 g; 13.10 mmol; 1 eq.), 2-biphenylboronic acid (2 852.77 mg; 14.41 mmol; 1.10 eq.), potassium carbonate (9.05 g; 65.48 mmol; 5 eq.), tetrakis(triphenylphosphine)palladium (0) (1.51 g; 1.31 mmol; 0.10 eq.) were taken in Toluene (15 mL) and water (15 mL) under $N_2$ atmosphere. The reaction mixture was purged with vacuum, then degassed with $N_2$ and then refluxed for 3 hours. The reaction mixture was cooled to RT, filtered over a pad of celite and washed with toluene (200 mL). The filtrate was concentrated to afford brown oil, which was taken in EtOAc (200 mL). The organic layer was washed with a saturated aqueous solution of $NaHCO_3$ solution (70 mL), water (70 mL) and brine (70 mL), dried over $MgSO_4$ and concentrated affording methyl 2-methyl-1,1':2',1''-terphenyl-4-carboxylate as a brown oil (3.9 g, 98%, HPLC (Method A) Rt 5.51 min), which was used further without purification. A solution of methyl 2-methyl-1,1':2',1''-terphenyl-4-carboxylate (3.50 g; 11.58 mmol; 1 eq.) in EtOH (105 mL) at rt was treated with sodium hydroxide (6.95 mL; 5 M; 34.73 mmol; 3 eq.). The reaction mixture was stirred at 60° C. for 1 hour. The reaction mixture was concentrated giving a brown solid. It was taken up in water (400 mL) and the aqueous phase was washed twice with EtOAc. The aqueous phase was acidified with HCl cc (2 mL) to pH 2, then it was concentrated until precipitation (volume divided /5). The suspension was filtered affording the title compound as an orange solid (2.41 g, 72%). $^1$H NMR (DMSO-$d_6$, 300 MHz) δ 12.71 (br s, 1H), 7.54-6.91 (m, 12H), 1.76 (s, 3H). LC/MS (Method A): 286.9 (M−H)$^-$. HPLC (Method A) Rt 4.85 min (Purity: 97.1%).

Intermediate 27: 2'-hydroxy-2-methylbiphenyl-4-carboxylic acid

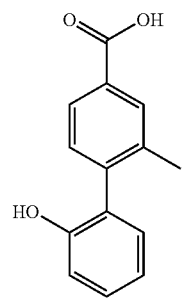

Step 1: Methyl 7-hydroxy-2-methylbiphenyl-4-carboxylate

Methyl 4-bromo-3-methylbenzoate (Intermediate 17, step 1) (3 g; 13.10 mmol; 1 eq.), 2-hydroxybenzeneboronic acid (1.99 g; 14.41 mmol; 1.10 eq.), potassium carbonate (9.05 g; 65.48 mmol; 5 eq.), tetrakis(triphenylphosphine)palladium (0) (1.51 g; 1.31 mmol; 0.10 eq.) were taken up in Toluene (15 mL) and water (15 mL) under $N_2$ atmosphere. The reaction mixture was purged with vacuum, then degassed with $N_2$ and then refluxed for 2 days. The reaction mixture was cooled to RT, filtered over a pad of celite and washed with toluene (200 mL). The filtrate was concentrated to afford a brown oil which was taken in EtOAc (200 mL). The organic layer was washed with a saturated aqueous solution of $NaHCO_3$ solution (75 mL), water (75 mL) and brine (75 mL), dried over $MgSO_4$ and concentrated affording the title compound as an orange oil used without further purification (3.0 g, 94%). LC/MS (Method B): 241.2 (M−H)$^-$.

Step 2: 2'-hydroxy-2-methylbiphenyl-4-carboxylic acid

A solution of methyl 2'-hydroxy-2-methylbiphenyl-4-carboxylate (3 g; 12.38 mmol; 1 eq.) in EtOH (90 mL) at RT was treated with sodium hydroxide (7.43 mL; 5 M; 37.15 mmol; 3 eq.). The reaction mixture was stirred at 60° C. for 2 hours. The reaction mixture was concentrated to give a brown solid. It was taken up in water (250 mL) and the aqueous phase was washed twice with EtOAc. The aqueous phase was acidified with HCl cc to pH 2. Then it was concentrated and extracted with EtOAc giving the title compound as an orange oil. It was purified by flash chromatomatography eluting with EtOAc: cHex (1:1) affording the title compound as a white solid. $^1$H NMR (DMSO-$d_6$, 300 MHz) δ 12.88 (br s, 1H), 9.49 (s, 1H), 7.81-7.75 (m, 2H), 7.24-7.18 (m, 2H), 7.05-7.02 (m, 1H), 6.94-6.84 (m, 2H), 2.16 (s, 3H). LC/MS (Method B): 227.2 (M−H)⁻. HPLC (Method A) Rt 3.26 min (Purity: 95.1%).

Intermediate 28: 2-(methoxymethyl)-2'-methyl biphenyl-4-carboxylic acid

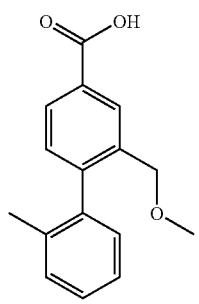

Step 1: Methyl 4-bromo-3-(bromomethyl)benzoate

Under $N_2$, to a solution of methyl 4-bromo-3-methylbenzoate (Aldrich 532878, 50 g; 218.27 mmol; 1 eq.) in CHCl3 (1 000 mL) were added NBS (46.62 g; 261.93 mmol; 1.20 eq.) in one portion and α,α'-azoisobutyronitrile (0.72 g; 4.37 mmol; 0.02 eq.). The mixture was stirred at 70° C. for 2 days. The reaction mixture was cooled to RT and water (500 mL) was added. The organic layer was washed with 50 mL NaHCO₃ sat. solution, water (340 mL), then brine (500 mL), dried over MgSO₄ and concentrated affording the title compound as a yellow solid. It was washed with pentane (2×500 mL) affording the title compound as a yellow solid. ¹H NMR (DMSO-$d_6$, 300 MHz) δ 8.24 (d, J=1.91 Hz, 1H), 7.88-7.82 (m, 2H), 4.87 (s, 2H), 3.91 (s, 3H). HPLC (Method A) Rt 4.44 min (Purity: 97.9%).

Step 2: Methyl 4-bromo-3-(methoxymethyl)benzoate

A solution of methyl 4-bromo-3-(bromomethyl)benzoate (37.50 g; 121.77 mmol; 1 eq.) in MeOH (1 125 mL) was refluxed for 4 days. After concentration, the mixture was partitioned between EtOAc (500 mL) and water (200 mL). The organic layer was washed with a 5% NaHCO₃ aqueous solution (200 mL), brine (200 mL), dried over MgSO₄ and concentrated affording the title compound as a beige solid (29.8 g, 94%). ¹H NMR (DMSO-$d_6$, 300 MHz) δ 8.06-8.05 (m, 1H), 7.83 (d, J=1.23 Hz, 2H), 4.54 (m, 2H), 3.90 (s, 3H), 3.45 (s, 3H). LC/MS (Method B): 227.2 (M−H)⁻. HPLC (Method A) Rt 4.42 min (Purity: 93.0%).

Step 3: Methyl 2-(methoxymethyl)-2'-methylbiphenyl-4-carboxylate

Methyl 4-bromo-3-(methoxymethyl)benzoate (40 g; 154.38 mmol; 1 eq.), o-tolylboronic acid (23.09 g; 169.82 mmol; 1.10 eq.), K2CO3 (106.68 g; 771.90 mmol; 5 eq.), tetrakis(triphenylphosphine)palladium (0) (1.78 g; 1.54 mmol; 0.01 eq.) were taken up in Toluene (200 mL) and water (200 mL) under $N_2$ atmosphere. The reaction mixture was purged with vacuum, then degassed with $N_2$ and then refluxed for 1 hour. The reaction mixture was cooled to RT, filtered over a pad of celite and washed with EtOAc (1000 mL). The filtrate was concentrated to afford a yellow oil which was taken in EtOAc (800 mL). The organic layer was washed with a saturated aqueous solution of NaHCO₃ solution (250 mL), water (250 mL) and brine (250 mL), dried over MgSO₄ and concentrated affording the title compound as a yellow oil used without further purification (41.9 g, quantitative). HPLC (Method A) Rt 5.34 min (Purity: 89.4%).

Step 4: 2-(methoxymethyl)-2'-methylbiphenyl-4-carboxylic acid

A solution of methyl 2-(methoxymethyl)-2'-methylbiphenyl-4-carboxylate (40 g; 147.97 mmol; 1 eq.) in EtOH (1 200 mL) at RT was treated with NaOH (88.78 mL; 5 M; 443.90 mmol; 3 eq.). The reaction mixture was stirred at 60° C. for 1 hour. The reaction mixture was cooled to RT and concentrated to give a yellow solid which was taken up in water (800 mL) and the aqueous phase was washed twice with EtOAc. The aqueous phase was acidified with HCl cc (40 mL) to pH 2 and it was extracted with EtOAc (2×400 mL). The combined organics were washed with brine, dried over MgSO₄ and concentrated affording the title compound as a yellow solid (35.1 g, 92%). ¹H NMR (DMSO-$d_6$, 300 MHz) δ 12.99 (br s, 1H), 8.09 (s, 1H), 7.92-7.89 (m, 1H), 7.33-7.22 (m, 4H), 7.10-7.08 (m, 1H), 4.11 (m, 2H), 3.18 (s, 3H), 1.99 (s, 3H). LC/MS (Method B): 255.2 (M−H)⁻. HPLC (Method A) Rt 4.52 min (Purity: 96.4%).

Intermediate 29: 6-[2-(methoxymethyl)pyrrolidin-1-yl]-5-methylnicotinic acid

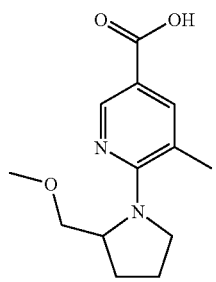

Step 1: 6[2-(methoxymethyl)pyrrolidin-1-yl]-5-methylnicotinonitrile 2-(Methoxymethyl)pyrrolidine (406 mg; 3.53 mmol; 1.2 eq.) and DIEA (1.52 mL; 8.82 mmol; 3 eq.) were added to a solution of 5-cyano-2-fluoro-3-methylpyridine (400 mg; 2.94 mmol; 1 eq.) in 1-butanol (1 mL) and the reaction mixture was stirred at 90° C. for 16 hours. The reaction mixture was allowed to return to RT then diluted with EtOAc, washed with water, dried over MgSO₄ and concentrated in vacuo to afford the title compound as a yellow oil (0.59 g, 87%). LC/MS (Method A): 200.1 (M+H)⁺. HPLC (Method A) Rt 2.42 min (Purity 99.1%).

Step 2: 6-[2-(methoxymethyl)pyrrolidin-1-yl]-5-methylnicotinic acid

A mixture of 6-[2-(methoxymethyl)pyrrolidin-1-yl]-5-methylnicotinonitrile (591 mg; 2.56 mmol; 1 eq.) and potassium hydroxide (717 mg; 12.8 mmol; 5 eq.) in water (20 mL) was stirred at reflux for 16 hours. The pH was adjusted to 5-6 with HCl 1M and the aqueous layer extracted with EtOAc. The combined organic phase was dried over MgSO₄ and concentrated in vacuo to afford the title compound as a white solid (0.63 g, 99%). LC/MS: 219.1 (M+H)⁺. HPLC (Method A): Rt 1.44 min (purity 96.6%).

Intermediate 30: 2-(hydroxymethyl)-2'-methylbiphenyl-4-carboxylic acid

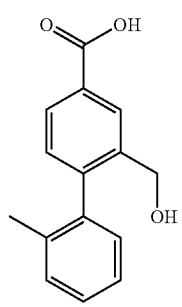

Step 1: Methyl 4-bromo-3-(bromomethyl)benzoate

To a solution of methyl 4-bromo-3-methylbenzoate (Aldrich 532878, 50 g; 218 mmol; 1 eq.) in CHCl₃ (1 L) were added NBS (46.6 g; 262 mmol; 1.2 eq.) in one portion and α,α'-azoisobutyronitrile (0.72 g; 4.37 mmol; 0.02 eq.). The reaction mixture was stirred at 70° C. for 2 days. It was cooled down to RT and water (500 mL) was added. The organic layer was washed with aq. NaHCO₃ (400 mL), then brine (500 mL), dried over MgSO₄ and concentrated in vacuo. The residue was washed with n-pentane (2×500 mL) to afford the title compound as a yellow solid. ¹H NMR (DMSO-d₅, 300 MHz) δ 8.24 (d, J=1.9 Hz, 1H), 7.88-7.82 (m, 2H), 4.87 (s, 2H), 3.91 (s, 3H). HPLC (Method A): Rt 4.44 min (purity 97.9%).

Step 2: Methyl 3-[(acetyloxy)methyl]-4-bromobenzoate

To a solution of methyl 4-bromo-3-(bromomethyl)benzoate (6.5 g; 21 mmol; 1 eq.) in AcOH (32.5 mL) was added sodium acetate (3.46 g; 42 mmol; 2 eq.) and the reaction mixture was stirred at 100° C. for 12 hours. After concentration in vacuo, the residue was partitioned between EtOAc and water. The organic layer was washed with 5% aq. NaHCO₃ then brine, dried over MgSO₄ and concentrated in vacuo. Purification by column chromatography (c-hexane/EtOAc, 5/1) afforded the title compound as a white solid (4.78 g, 79%). ¹H NMR (DMSO-d₆, 300 MHz) δ 8.03 (m, 1H), 7.85-7.84 (d, J=1.3 Hz, 1H), 5.18 (s, 2H), 3.87 (s, 3H), 2.11 (s, 3H). HPLC (Method A) Rt 4.37 min (purity 98.1%).

Step 3: Methyl 2-[(acetyloxy)methyl]-2'-methylbiphenyl-4-carboxylate

A mixture of methyl 3-[(acetyloxy)methyl]-4-bromobenzoate (4.7 g; 16.4 mmol; 1 eq.), o-tolylboronic acid (2.45 g; 18 mmol; 1.1 eq.), potassium carbonate (11.3 g; 82 mmol; 5 eq.) and Pd(PPh₃)₄ (1.89 g; 1.64 mmol; 0.1 eq.) in toluene (23.5 mL) and water (23.5 mL) was refluxed for 2 hours. After cooling to RT, the reaction mixture was filtered through a pad of Celite® which was further washed with toluene (50 mL). The filtrate was concentrated in vacuo, the residue taken up in EtOAc (250 mL) and washed with sat. aq. NaHCO₃ (100 mL), water (100 mL) and brine (100 mL), dried over magnesium sulphate and concentrated in vacuo to afford the title compound (4.9 g, quantitative) as a brown oil. HPLC (Method A) Rt 5.23 min (Purity 62.3%).

Step 4: 2-(hydroxymethyl)-2'-methylbiphenyl-4-carboxylic acid

Sodium hydroxide (5M; 12.1 mL; 60.3 mmol; 3 eq.) was added to a solution of methyl 2-[(acetyloxy)methyl]-2'-methylbiphenyl-4-carboxylate (6 g; 20 mmol; 1 eq.) in EtOH (180 mL) and the reaction mixture was stirred at 60° C. for 2 hours. After concentration in vacuo, the residue was taken up in water (500 mL) and washed with EtOAc (2×100 mL). The aqueous phase was acidified to pH 2 with conc. HCl and extracted with EtOAc (2×100 mL). The combined organic layer was dried over MgSO₄ and concentrated in vacuo to afford the title compound as a yellow solid (3.46 g, 71%). ¹H NMR (DMSO-d₆, 300 MHz) δ 12.97 (br s, 1H), 8.20-8.19 (m, 1H), 7.87-7.84 (dd, J=8.0 Hz, 1.86 Hz, 1H), 7.37-7.06 (m, 5H), 5.23-5.19 (m, 1H), 4.25-4.09 (m, 2H), 2.01 (s, 3H). LC/MS (Method A): 241.2 (M−H)⁻. HPLC (Method A) Rt 3.77 min (purity 96.1%).

Intermediate 31: 4-isobutoxy-3-[(methylsulfonyl)amino]benzoic acid

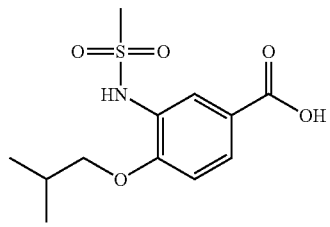

Step 1: isobutyl 4-isobutoxy-3-nitrobenzoate

Lithium bis(trimethylsilyl)amide (30 mL; 1 M; 30 mmol; 3 eq.) was added to a solution of ethyl 4-fluoro-3-nitrobenzoate (CLONTECH; 01072; 2 131.63 mg; 10 mmol; 1 eq.) and 2-methyl-1-propanol (2.78 mL; 30 mmol; 3 eq.) in THF (12 mL). The resulting mixture was stirred at RT for 2 h. Water and HCl 0.1N were further added to obtain a pH=6-7. The mixture was then extracted with EtOAc and washed with NaCl sat. solution to afford the title compound as a orange oil (2.6 g; 89%). It was used without further purification. HPLC (Method A), Rt 6.11 min (purity: 66.4%).

Step 2: isobutyl 3-amino-4-isobutoxybenzoate

Isobutyl 4-isobutoxy-3-nitrobenzoate, obtained in step 1 (2 510.35 mg; 8.50 mmol; 1 eq.) was dissolved in MeOH (200 mL). It was injected on a flow hydrogenation reactor (H-Cube), adapted with a Pd/C cartridge (70 mm), a flow of 1.7 mL/min, no heating and the full H₂ option enabled. After evaporation of the solvents, the title compound was isolated as an orange solid (2.2 g; 95%). HPLC (Method A), Rt 4.05 min (purity: 65.4%).

Step 3: 4-isobutoxy-3-[(methylsulfonyl)amino]benzoic acid

Methanesulfonyl chloride (690 µL; 8.91 mmol; 1.10 eq.) was added dropwise to a cold (0° C.) solution of pyridine (5 mL) and isobutyl 3-amino-4-isobutoxybenzoate, obtained in step 2 (2 150 mg; 8.10 mmol; 1 eq.) in DCM (20 mL) and the reaction mixture was allowed to warm to RT. After three hours, solvents were evaporated in vacuo and the residue was partitioned between water and EtOAc. The two phases were separated and the aqueous layer was extracted with EtOAc. The combined organic phase was washed with 1M HCl then NaCl sat. solution, dried over MgSO$_4$ and concentrated in vacuo to give a yellow oil.

The latter was taken up in THF (15 mL) and lithium hydroxide (970.2 mg; 40.51 mmol; 5 eq.) was added, followed by water (15 mL). The resulting mixture was stirred at RT for 2 days. Solvent was evaporated in vacuo and the mixture was diluted with water. This aqueous solution was washed twice with Et$_2$O and acidified to pH=2 with HCl 5N and then extracted with EtOAc, washed with NaCl sat. solution, dried over MgSO$_4$ and concentrated under vacuum. The compound was then solubilized in THF and purified by preparative HPLC to afford the title compound as a white powder. $^1$H NMR (DMSO-d$_6$, 300 MHz) δ 12.76 (br s, 1H), 9.04 (br s, 1H), 7.84 (d, J=2.1 Hz, 1H), 7.76 (dd, J=8.5, 2.2 Hz, 1H), 7.14 (d, J=8.6 Hz, 1H), 3.86 (d, J=6.6 Hz, 2H), 2.95 (s, 3H), 2.17-2.04 (m, 1H), 1.02 (d, J=6.8 Hz, 6H). HPLC (Method A) Rt 3.24 min (Purity: 99.2%).

Intermediate 32:
3-(acetylamino)-4-(2-methylpiperidin-1-yl)benzoic acid

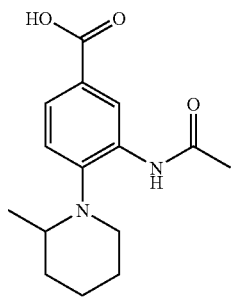

Step 1: 4-(2-methylpiperidin-1-yl)-3-nitrobenzoic acid

A mixture of ethyl 4-fluoro-3-nitrobenzoate (25 g; 117.28 mmol) and 2-methylpiperidine (41.54 mL; 351.84 mmol) in DMF (100 mL) was heated to 50° C. for 2 h. The reaction was allowed to cool to RT and diluted with water (100 mL). Extraction with EtOAc, drying over sodium sulfate and concentration under vacuum gave a yellow oil that was taken up in THF (250 mL) followed by the addition of an aqueous solution of lithium hydroxide (14.0 g; 586.4 mmol, 2.3 M). The reaction mixture was stirred at RT for 48 h. After evaporation of the THF, the solution was diluted with water and washed with Et$_2$O. The aqueous layer was acidified to pH 5 with AcOH, extracted with Et$_2$O, dried over MgSO$_4$ and concentrated under vacuum to give the title compound as a yellow solid (24.8 g, 80%). $^1$H NMR (DMSO-d$_6$, 300 MHz) δ 13.1 (bs, 1H), 8.23 (d, J=2 Hz, 1H), 8.02 (dd, J=8.7, 2 Hz, 1H), 7.41 (d, J=8.7 Hz, 1H), 3.63-3.61 (m, 1H), 3.23-3.18 (m, 1H), 2.89-2.85 (m, 1H), 1.79-1.54 (m, 6H), 1.47 (d, J=6 Hz, 3H). LC/MS (Method B): 265.2 (M+H)$^+$. HPLC (Method A) Rt 3.96 min (Purity: 97.9%).

Step 2: 3-amino-4-(2-methylpiperidin-1-yl)benzoic acid

A methanolic solution of 4-(2-methylpiperidin-1-yl)-3-nitrobenzoic acid obtained in step 1 (500 mg; 1.89 mmol; 0.01 M) was pumped through an H-Cube (1 mL/min) fitted with a 10 mol % Pd/C catalyst cartridge (30×4 mm) and heated to 25° C. with the full hydrogen option enabled. Solvent was evaporated under vacuum to give the title compound as a pinkish oil (443 mg, 99%). $^1$H NMR (DMSO-d$_6$, 300 MHz) δ 12.39 (bs, 1H), 7.28 (d, J=1.86 Hz, 1H), 7.14 (dd, J=8.1, 2.1 Hz, 1H), 6.99 (d, J=8.1 Hz, 1H), 5.01 (bs, 1H), 3.07-3.03 (m, 1H), 2.91-2.88 (m, 1H), 2.43-2.35 (m, 1H), 1.79-1.70 (m, 2H), 1.62-1.61 (m, 2H), 1.41-1.31 (m, 2H), 0.79 (d, J=6 Hz, 3H). HPLC (Method A) Rt 1.66 min (Purity: 99.2%).

Step 3:
3-(acetylamino)-4-(2-methylpiperidin-1-yl)benzoic acid

To a suspension of 3-amino-4-(2-methylpiperidin-1-yl)benzoic acid obtained in step 2 (100 mg; 0.43 mmol) in pyridine (69.04 μL, 0.85 mmol) and DCM (4 mL), was added acetyl chloride (36.42 μL; 0.51 mmol). The reaction mixture was then stirred at 40° C. for 5 h after which solvents were evaporated under vacuum, solid residue was triturated with ethylacetate and re-evaporated. Finally, water was added to the reaction mixture which was sonicated, filtered, dried under vacuum to give the title compound as a white solid (95 mg, 81%). $^1$H NMR (DMSO-d$_6$, 300 MHz) δ 12.76 (bs, 1H), 8.97 (s, 1H), 8.66 (s, 1H), 7.64 (dd, J=8.2, 2.1 Hz, 1H), 7.29 (d, J=8.2 Hz, 1H), 3.07-3.01 (m, 1H), 2.86-2.82 (m, 1H), 2.57-2.51 (m, 1H), 2.15 (s, 3H), 1.82-1.77 (m, 4H), 1.47-1.42 (m, 2H), 0.78 (d, J=6 Hz, 3H). LC/MS (Method B): 277.2 (M+H)$^+$. HPLC (Method A) Rt 1.77 min (purity: 91.3%).

Intermediate 33: 4-[isobutyl(propyl)amino]-3-[(methylsulfonyl)amino]-benzoic acid

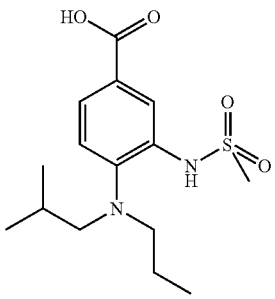

Step 1: Ethyl 4-[isobutyl(propyl)amino]-3-nitrobenzoate

To a solution of ethyl 4-fluoro-3-nitrobenzoate (7.4 g, 0.035 mol) in ethanol (100 mL) was added N-isobutyl-N-propylamine (11.98 g, 0.104 mol) at RT. The reaction mixture was heated at 60° C. for 12 h. It was then concentrated under reduced pressure. The residue was dissolved in water (40 mL) and was acidified to pH=4 with 1 M HCl solution. It was extracted with EtOAc (2×75 mL). The combined organic phases were washed with brine, dried over sodium sulphate and evaporated to afford the title compound (10 g, 93%) as a yellow oil. $^1$H NMR (DMSO-$d_6$, 400 MHz) δ 8.20 (s, 1H), 7.92 (m, 1H), 7.38 (m, 1H), 4.28 (m, 2H), 3.15 (m, 2H), 3.03 (m, 2H), 1.86 (m, 1H), 1.51 (m, 2H) 1.28 (m, 3H), 0.78 (m, 9H). LC/MS (Method A): 309.0 (M+H)$^+$. HPLC (Method B) Rt 5.05 min (purity: 99.4%).

Step 2: Ethyl 3-amino-4-[isobutyl(propyl)amino]benzoate

A solution of ethyl 4-[isobutyl(propyl)amino]-3-nitrobenzoate (6 g, 0.0194 mol) in EtOAc (100 mL) was added Pd/C (600 mg). The reaction mixture was hydrogenated with hydrogen gas under 5 kg pressure for 3 h. The reaction mixture was filtered off Pd/C and filtrate was concentrated under reduced pressure to afford the title compound as yellow oil (5 g, 92%). $^1$H NMR (DMSO-$d_6$, 400 MHz) δ 7.29 (s, 1H), 7.16 (d, 1H), 7.01 (d, 1H), 4.93 (s, 2H), 4.23 (q, 2H), 2.80 (t, 2H), 2.71 (t, 3H), 1.65 (m, 1H) 1.40 (m, 2H), 1.28 (t, 3H), 0.82 (m, 9H). LC/MS (Method A): 279.0 (M+H)$^+$. HPLC (Method B) Rt 3.94 min (purity: 97.9%).

Step 3: Ethyl-4-[isobutyl(propyl)amino]-3-[(methylsulfonyl)amino]benzoate

To a solution of ethyl 3-amino-4-[isobutyl(propyl)amino] benzoate (5 g, 0.0179 mol) in dry DCM (50 mL) was added triethyl amine (7.24 g, 0.0716 mol) at RT. Methane sulphonyl chloride (2.67 g, 0.0233 mol) was added in drops at 0° C. The reaction mixture was stirred at RT for 4 h. The reaction mixture was concentrated under reduced pressure. The residue was dissolved in water, extracted with ethylacetate (2×75 mL), washed with 0.5M HCl, brine, dried over sodium sulphate and evaporated to afford the title compound as a yellow oil (6 g, 93%). $^1$H NMR (DMSO-$d_6$, 400 MHz) δ 8.45 (s, 1H), 7.86 (s, 1H), 7.65 (m, 1H), 7.28 (m, 1H), 4.28 (m, 2H), 3.09 (s, 3H) 3.01 (m, 2H), 2.86 (m, 2H), 1.68 (m, 1H), 1.42 (m, 2H), 1.28 (m, 3H), 0.80 (m, 9H). LC/MS (Method A): 357.0 (M+H)$^+$. HPLC (Method B) Rt 5.09 min (purity: 94.40%).

Step 4: 4-[Isobutyl(propyl)amino]-3-[(methylsulfonyl)amino]benzoic acid

To a solution of ethyl-4-[isobutyl(propyl)amino]-3-[(methylsulfonyl)amino]benzoate (7 g, 0.0196 mol) in THF (70 mL) was added lithium hydroxide (4.12 g, 0.098 mol) and water (70 mL). The reaction mixture was heated at 70° C. for 5 h. The reaction mixture was diluted with water (30 mL), washed with diethyl ether (50 mL). The aqueous layer was acidified with 1M HCl until pH=2, extracted with EtOAc (2×75 mL), washed with brine, dried over sodium sulphate and evaporated to afford the title compound as an off white solid (5.6 g, 86%). $^1$H NMR: (DMSO-$d_6$, 400 MHz), δ 12.78 (s, 1H), 8.39 (s, 1H), 7.87 (s, 1H), 7.65 (m, 1H), 7.28 (m, 1H), 3.09 (s, 3H), 2.97 (m, 2H) 2.84 (m, 2H), 1.67 (m, 1H), 1.41 (m, 2H), 0.84 (m, 9H). LC/MS (Method A): 329.0 (M+H)$^+$. HPLC (Method B) Rt 4.53 min (purity: 99.12%).

Intermediate 34: methyl 4-[amino(hydroxyimino)methyl]-2-chlorobenzoate

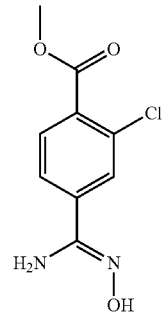

Step 1: methyl 4-bromo-2-chlorobenzoate

4-Bromo-2-chlorobenzoic acid (COMBI-BLOCK; CA-4187; 1 000 mg; 4.25 mmol; 1 eq.) was dissolved in MeOH (20 mL). The resulting solution was cooled down to 0° C. and thionyl chloride (1.23 mL; 16.99 mmol; 4 eq.) was added dropwise. After addition, the reaction mixture was stirred at RT. As the reaction was complete, solvents were evaporated. The crude mixture was dissolved in EtOAc and washed with NaHCO$_3$ sat. and NaCl sat. solutions. The organic phase was dried over MgSO$_4$, filtrated and evaporated to give the title compound (871 mg, 82%). $^1$H NMR (CDCl$_3$, 300 MHz) δ 7.72 (d, J=8.3 Hz, 1H), 7.64 (d, J=1.9 Hz, 1H), 7.46 (dd, J=8.5, 1.9 Hz, 1H), 3.93 (s, 3H). HPLC (Method A) Rt 4.22 min (Purity: 98.5%).

Step 2: methyl 2-chloro-4-cyanobenzoate

Triphenylphosphine polymer bound (238.69 mg; 0.72 mmol; 0.15 eq.), palladium (II) acetate (75.02 mg; 0.33 mmol; 0.07 eq.) and DMF (12 mL) were first mixed, purged with N$_2$ and let stirring at RT for 2 h. The vial was then opened, zinc cyanide (560.56 mg; 4.77 mmol; 1 eq.) and methyl 4-bromo-2-chlorobenzoate, obtained in step 1 (1 191 mg; 4.77 mmol; 1 eq.) were added and the resulting mixture was purged once more before heating under microwave irradiation at 140° C. for 50 min. The reaction mixture was then filtrated through a glass frit and the resin was washed with Et$_2$O (3×10 mL). The combined organic solutions were washed with water (3×5 mL), once with NaCl sat. solution (10 mL) and then dried over MgSO$_4$. Evaporation of the solvent gave the title compound as a white powder (543 mg; 58%). $^1$H NMR (DMSO-$d_6$, 300 MHz) δ 8.23-8.22 (m, 1H), 7.96-7.95 (m, 2H), 3.90 (s, 3H). HPLC (Method A) Rt 3.39 min (Purity: 97.6%).

Step 3: methyl 4-[amino(hydroxyimino)methyl]-2-chlorobenzoate

Methyl 2-chloro-4-cyanobenzoate, obtained in step 2 (543 mg; 2.78 mmol; 1 eq.) was dissolved in MeOH (30 mL). Hydroxylamine (50% in water) (409.33 μL; 13.88 mmol; 5 eq.) was added and the mixture was stirred at room temperature overnight. Solvents were evaporated, affording the title compound (631 mg; 99%). $^1$H NMR (DMSO-$d_6$, 300 MHz) δ

10.02 (br s, 1H), 7.84 (d, J=1.4 Hz, 1H), 7.81 (s, 1H), 7.75 (dd, J=8.2, 1.6 Hz, 1H), 6.03 (br s, 2H), 3.86 (s, 3H). LC/MS (Method B): 227.2 (M−H)⁻, 229.1 (M+H)⁺. HPLC (Method A) Rt 1.44 min (Purity: 63.4%).

Intermediate 35: 4-(dimethylamino)-3-nitrobenzoic acid

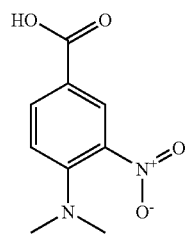

To a solution of 4-fluoro-3-nitrobenzoic acid (1 g; 5.4 mmol) in EtOH (5 mL) was added dimethylamine (730 mg; 16.2 mmol). The resulting mixture was stirred at RT for 18 h and 4 h at 70° C. The reaction mixture was then partitioned between water (10 mL) and Et₂O (15 mL), washed with Et₂O (10 mL). The aqueous phase was acidified to pH ~5 with AcOH and washed with Et₂O (2×15 mL). The combined organic layers were dried over MgSO₄, filtered and concentrated to give the title compound as a yellow powder (1.02 g, 90%). ¹H NMR (DMSO-d₆, 300 MHz) δ 12.9 (bs, 1H), 8.24 (d, J=2 Hz, 1H), 7.92 (dd, J=8.9, 2 Hz, 1H), 7.20 (d, J=8.9 Hz, 1H), 2.92 (s, 6H). HPLC (Method A) Rt 2.44 min (purity: 97.2%).

Intermediate 36: 2'-Ethyl-2-(methoxymethyl)-1,1'-biphenyl-4-carboxylic acid

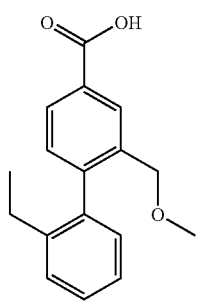

Step 1: Methyl 2'-ethyl-2-(methoxymethyl)-1,1'-biphenyl-4-carboxylate

To a solution of methyl 4-bromo-3-(methoxymethyl)benzoate, (Intermediate 28, step 2) (12 g, 0.0463 mol) in toluene (150 mL) and water (35 mL) under N₂, was added 2-ethyl benzene boronic acid (9.02 g, 0.0601 mol) followed by potassium carbonate (19 g, 0.1389 mol) and Pd(PPh₃)₄ (2.67 g, 023). The reaction mixture was degassed with N₂ for 10 min before heating. After 12 hours at 100° C., the reaction mixture was diluted with EtOAc. The organic layer was washed with sodium bicarbonate sat. solution (1×100 mL), water (2×100 mL) and finally with brine (1×100 mL). It was then dried over sodium sulphate and concentrated under reduced pressure. The residue was purified by chromatography (silica gel, 60-120 mesh, eluting with pet ether/EtOAc) to afford the title compound as a pale yellow liquid (12 g, 83%). ¹H NMR (CDCl₃, 400 MHz) δ 8.24-8.26 (1H, s), 7.99-8.01 (1H, d), 7.32-7.38 (2H, m), 7.22-7.27 (2H, m), 7.07-7.09 (1H, d), 4.12-4.21 (2H, d), 3.93-3.95 (3H, s), 3.28-3.30 (3H, s), 2.28-2.43 (2H, m), 1.01-1.05 (3H, t).

Step 2: 2'-Ethyl-2-(methoxymethyl)-1,1'-biphenyl-4-carboxylic acid

To a solution of methyl 2'-ethyl-2-(methoxymethyl)-1,1'-biphenyl-4-carboxylate (12 g, 0.0422 mol) in THF (150 mL) and water (30 mL), was added lithium hydroxide monohydrate (5.31 g, 0.1266 mol) in portions. After 12 h at RT, the reaction mixture was concentrated and the aqueous phase was acidified using conc. HCl and extracted with EtOAc. Then the organic layers were washed with water and brine solution. The solvents were dried over sodium sulphate and concentrated under reduced pressure to afford the title compound as a white solid (9 g, 80%). ¹H NMR (DMSO-d₆, 300 MHz) δ 12.9 (1H, bs), 8.08 (1H, s), 7.88-7.90 (1H, m), 7.34-7.35 (2H, m), 7.21-7.25 (2H, m), 7.03-7.05 (1H, m), 4.04-4.13 (2H, m), 3.16-3.18 (3H, s), 2.29-2.38 (1H, m), 2.19-2.24 (1H, m), 0.92-0.95 (3H, m). LC/MS (Method A): 269.0 (M−H)⁻. HPLC (Method B) Rt 5.06 min (Purity: 97.4%).

Intermediate 37: 4-bromo-3-(methoxymethyl)benzoic acid

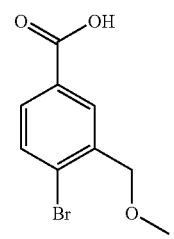

To a solution of methyl 4-bromo-3-(methoxymethyl)benzoate (Intermediate 28, step 2), (7 g; 27.02 mmol) in EtOH (210 mL) was added NaOH (16.21 mL; 5 M; 81.05 mmol). The resulting reaction mixture was heated at 60° C. for one hour. It was then cooled to RT and concentrated under vacuum to give a yellow solid. Water was added and the aqueous phase was washed with EtOAc. The aqueous phase was then acidified with HCl (1 M) and extracted with EtOAc. Organic phase was dried over MgSO4, filtered and concentrated under vacuum to give the title compound as a yellow solid (5.81 g, 87%). 1H NMR (DMSO-d6, 300 MHz) 13.19

(br s, 1H), 8 (m, 1H), 7.77-7.76 (m, 2H), 4.49 (s, 2H), 3.40 (s, 3H). LC/MS (Method B): 245.0 (M−H)−. HPLC (Method A) Rt 3.63 min (purity: 97.4%).

Intermediate 38: 2'-methyl-2-(methylsulfonyl)biphenyl-4-carboxylic acid

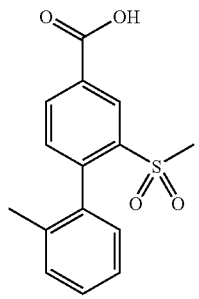

Step 1: methyl 4-chloro-3-(methylsulfonyl)benzoate 4-chloro-3-(methylsulfonyl)benzoic acid (Enamine, 500 mg; 2.13 mmol; 1 eq.) was dissolved in MeOH (10 mL) The solution was cooled down to 0° C. Thionyl chloride (0.62 mL; 8.52 mmol; 4 eq.) was added dropwise.

After addition, the reaction mixture was stirred at RT overnight.

As the reaction was complete, solvents were evaporated. The crude mixture was dissolved in EtOAc and washed with NaHCO$_3$ sat and brine. The organic phase was dried over MgSO$_4$, filtrated and evaporated, affording the title compound as an off-white solid (482 mg, 91%). $^1$H NMR (CDCl$_3$, 300 MHz) δ 8.72 (d, J=2.1 Hz, 1H), 8.16 (dd, J=2.1, 8.4 Hz, 1H), 7.59 (d, J=8.4 Hz, 1H), 3.90 (s, 3H), 3.22 (s, 3H).

Step 2: methyl 2'-methyl-2-(methylsulfonyl)biphenyl-4-carboxylate

In a schlenk flushed with Argon were added methyl 4-chloro-3-(methylsulfonyl)benzoate (124.34 mg; 0.50 mmol; 1 eq.), o-tolylboronic acid (84.97 mg; 0.62 mmol; 1.25 eq.), palladium(II) acetate (22.45 mg; 0.10 mmol; 0.20 eq.), 2-dicyclohexylphosphino-2',6'-dimethoxy-1,1'-biphenyl (82.11 mg; 0.20 mmol; 0.40 eq.), potassium fluoride (87.14 mg; 1.50 mmol; 3 eq.), toluene (2.49 mL), MeOH (2.49 mL) and water (5.40 µl). The reaction was degassed with Ar and heated under reflux for 2 hours. Then, it was cooled down to RT. The solvents were evaporated and the crude mixture was dissolved in EtOAc, washed with water and brine and dried over MgSO$_4$. The resulting crude product was purified by flash chromatography (c-hex/EtOAc 9:1 to 5:5), affording the title compound as a light yellow oil (135 mg; 88%). $^1$H NMR (DMSO-d$_6$, 300 MHz) δ 8.89 (d, J=1.77 Hz, 1H), 8.32 (dd, J=1.77, 7.90 Hz, 1H), 7.43-7.19 (m, 5H), 4 (s, 3H), 2.76 (s, 3H), 2.09 (s, 3H). LC/MS (Method B): 305.1 (M+H)+. HPLC (max plot) 99.2%; Rt 4.51 min.

Step 3: 2'-methyl-2-(methylsulfonyl)biphenyl-4-carboxylic acid

Methyl 2'-methyl-2-(methylsulfonyl)biphenyl-4-carboxylate (270 mg; 0.89 mmol; 1 eq.) was dissolved in THF (5 mL) and MeOH (5 mL). sodium hydroxide (0.89 mL; 5 M; 4.44 mmol; 5 eq.) was added and the mixture was stirred at RT overnight. Solvents were evaporated and the crude mixture was partitioned between EtOAc and water. Aqueous phase was acidified with HCl 5N solution. The two phases were separated and the organic phase was washed with brine and dried over MgSO$_4$. After filtration and evaporation of the solvents, the title compound was isolated as a beige solid (215 mg, 83%). $^1$H NMR (DMSO-d$_6$, 300 MHz) δ 13.53 (br s, 1H), 8.64 (d, J=1.8 Hz, 1H), 8.28 (dd, J=1.8, 8.0 Hz, 1H), 7.49 (d, J=7.91 Hz, 1H), 7.42-7.23 (m, 4H), 2.90 (s, 3H), 2.02 (s, 3H). LC/MS (Method B): 289.2 (M−H)−. HPLC (max plot) 97.9%; Rt 3.83 min.

Intermediate 39: 2'-(methoxymethyl)-2-methyl biphenyl-4-carboxylic acid

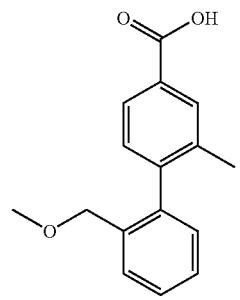

Step 1: methyl 2'-(methoxymethyl)-2-methylbiphenyl-4-carboxylate

Methyl 4-bromo-3-methylbenzoate (Aldrich 532878, 2 g; 8.73 mmol; 1 eq.), (2-methoxymethylphenyl)boronic acid (1.59 g; 9.60 mmol; 1.10 eq.), K2CO3 (6.03 g; 43.65 mmol; 5 eq.), tetrakis(triphenylphosphine)palladium (0) (1.01 g; 0.87 mmol; 0.10 eq.) were taken up in Toluene (10 mL) and water (10 mL) under N$_2$ atmosphere. The reaction mixture was purged with vacuum, then degassed with N$_2$ and then for 2 hours. The reaction mixture was cooled to RT, filtered over a pad of celite and washed with EtOAc (500 mL). The filtrate was concentrated to afford a yellow oil which was taken in EtOAc (100 mL). The organic layer was washed with a saturated aqueous solution of NaHCO$_3$ solution (30 mL), water (30 mL) and brine (30 mL), dried over MgSO$_4$ and concentrated affording the title compound as a brown oil used without further purification (3 g, quantitative). HPLC (Method A) Rt 5.20 min (Purity: 64.5%).

Step 2: 2'-(methoxymethyl)-2-methylbiphenyl-4-carboxylic acid

A solution of methyl 2'-(methoxymethyl)-2-methylbiphenyl-4-carboxylate (3 g; 11.10 mmol; 1 eq.) in EtOH (90 mL) at RT was treated with NaOH (6.66 mL; 5 M; 33.29 mmol; 3 eq.). The reaction mixture was stirred at 60° C. for 2 hours. The reaction mixture was concentrated to give a brown solid which was taken up in water (100 mL) and the aqueous phase was washed twice with EtOAc. The aqueous phase was acidified with HCl cc to pH 2 and it was extracted with EtOAc. The combined organics were washed with brine, dried over MgSO$_4$ and concentrated affording the title compound as a beige solid. $^1$H NMR (DMSO-d$_6$, 300 MHz) δ 12.95 (br s, 1H), 7.92-7.91 (m, 1H), 7.84-7.81 (dd, J=7.83 Hz, 1.91 Hz, 1H), 7.55-7.52 (m, 1H), 7.47-7.38 (m, 2H), 7.25-7.22 (d, J=7.86 Hz, 1H), 7.15-7.14 (m, 1H), 4.09 (m, 2H), 3.17 (s, 3H), 2.07 (s, 3H). LC/MS (Method B): 255.2 (M−H)⁻. HPLC (Method A) Rt 4.35 min (Purity: 96.8%).

Intermediate 40: 2'-methyl-2-[(methylsulfonyl)methyl]biphenyl-4-carboxylic acid

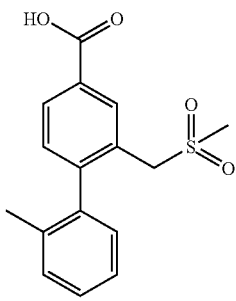

Step 1: methyl 4-bromo-3-[(methylthio)methyl]benzoate

To a solution of methyl 4-bromo-3-(bromomethyl)benzoate, which preparation is described above, under Intermediate 28, Step 1, (2 g; 6.49 mmol; 1 eq.) in CH₃CN (10 mL) and THF (10 mL) was added sodium thiomethoxide (0.50 g; 7.14 mmol; 1.10 eq.) and the mixture was stirred at reflux for 1 hour and at RT overnight. After concentration under vacuum, the mixture was partitioned between EtOAc and water. The organic layer was washed with NaCl sat. solution, dried over magnesium sulfate, filtered off and dried under vacuum to give the title compound as a yellow oil (1.7 g, 94%). ¹H NMR (CDCl₃) δ 7.99 (d, J=2.3 Hz, 1H), 7.77 (dd, J=8.3, 2.1 Hz, 1H), 7.65 (d, J=8.3 Hz, 1H), 3.92 (s, 3H), 3.83 (s, 2H), 2.06 (s, 3H). HPLC (Method A) Rt 4.31 min (Purity: 87.4%).

Step 2: methyl 4-bromo-3-[(methylsulfonyl)methyl]benzoate

3-Chloroperoxybenzoic acid (2 985.17 mg; 17.30 mmol; 3.50 eq.) was added to a suspension of methyl 4-bromo-3-[(methylthio)methyl]benzoate, obtained in step 1 (1 360 mg; 4.94 mmol; 1 eq.) and NaHCO₃ (2 075.98 mg; 24.71 mmol; 5 eq.) in DCM (100 mL) and the resulting mixture was stirred at RT for 16 hrs. DCM and water were added. The organic extract was washed with aq. NaHCO₃ dried over magnesium sulfate and concentrated in vacuo. It was purified by flash chromatography (cHex/EtOAc gradient), affording title compound as a white solid (1.4 g; 95%). ¹H NMR (CDCl₃) δ 8.24 (d, J=2.1 Hz, 1H), 7.92 (dd, J=8.3, 2.1 Hz, 1H), 7.74 (d, J=8.4 Hz, 1H), 4.56 (s, 2H), 3.93 (s, 3H), 2.86 (s, 3H). HPLC (Method A) Rt 2.88 min (Purity: 96.4%).

Step 3: methyl 2'-methyl-2-[(methylsulfonyl)methyl]biphenyl-4-carboxylate

Methyl 4-bromo-3-[(methylsulfonyl)methyl]benzoate, obtained in step 2 (1 449 mg; 4.72 mmol; 1 eq.), o-tolylboronic acid (705.49 mg; 5.19 mmol; 1.10 eq.), potassium carbonate (3 259.77 mg; 23.59 mmol; 5 eq.), tetrakis(triphenylphosphine)palladium (0) (545.13 mg; 0.47 mmol; 0.10 eq.) were taken up in toluene (7.24 mL) and water (7.24 mL) under N₂ atmosphere. The reaction mixture was purged with vacuum, then degassed with N₂ for 5 minutes and then refluxed for 45 min. The reaction mixture was cooled to RT, filtered over a pad of celite and washed with toluene (50 mL). The filtrate was concentrated affording a brown oil which was taken in EtOAc (50 mL). The organic layer was washed with a saturated aqueous solution of NaHCO₃ solution (10 mL), water (10 mL) and NaCl sat. solution (10 mL), dried over magnesium sulfate and concentrated affording the title compound as a yellow oil (2.1 g; 91%). HPLC (Method A) Rt 3.97 min (Purity: 64.5%).

Step 4: 2'-methyl-2-[(methylsulfonyl)methyl]biphenyl-4-carboxylic acid

To a solution of methyl 2'-methyl-2-[(methylsulfonyl)methyl]biphenyl-4-carboxylate, obtained in step 3 (1 502.82 mg; 4.72 mmol; 1 eq.) in EtOH (45 mL) was added NaOH (5.66 mL; 5 M; 28.32 mmol; 3 eq.) and the reaction mixture was stirred at 60° C. for 1 h30. The reaction mixture was concentrated under vacuum to give an orange oil. It was taken up in water and the aqueous phase was washed twice with EtOAc. The aqueous phase was then acidified with HCl 5N to pH=2 and it was extracted with EtOAc. The combined organics were dried over magnesium sulfate, filtered off and concentrated under vacuum to afford the title compound (1.3 g, 87%). ¹H NMR (DMSO-d₆, 300 MHz) δ 8.22 (d, J=1.7 Hz, 1H), 7.98 (dd, J=7.8, 1.7 Hz, 1H), 7.34-7.25 (m, 4H), 7.17 (d, J=7.2 Hz, 1H), 4.49 (d, J=13.8 Hz, 1H), 4.15 (d, J=13.7 Hz, 1H), 2.83 (s, 3H), 1.99 (s, 3H). HPLC (Method A) Rt 3.38 min (Purity: 90.5%).

Intermediate 41: 2-(3-methoxyprop-1-yn-1-yl)-2'-methylbiphenyl-4-carboxylic acid

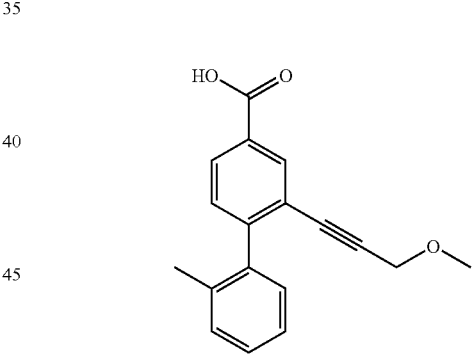

Step 1: 4-chloro-3-(3-methoxyprop-1-yn-1-yl)benzoic acid

Methyl propargyl ether (Fluka; 68898; 1.27 mL; 15 mmol; 1.50 eq.) was added dropwise to a suspension of 4-chloro-3-iodobenzoic acid (ABCR; TWC2211-D1; 2 824.60 mg; 10 mmol; 1 eq.), dichlorobis(triphenylphosphine)palladium(II) (701.91 mg; 1 mmol; 0.10 eq.) and cuprous iodide (190.45 mg; 1 mmol; 0.10 eq.) in a mixture of THF (20 mL) and triethylamine (10 mL). The reaction was stirred at RT for 2 h. The reaction mixture was quenched with saturated aqueous NH₄Cl, and extracted twice with EtOAc. The combined extract were evaporated under vacuo to afford an orange solid. The latter was dissolved in EtOAc and extracted 4 times with NaOH 0.1M. Then the aqueous layer was filtered, acidified to pH=3-4 with HCl 1M, and extracted with EtOAc. The combined organic layers were dried over magnesium sulfate, filtered and concentrated to afford the title compound as a slightly orange powder. $^1$H NMR (DMSO-$d_6$, 300 MHz) δ 13.42 (br. s., 1H), 8.03 (d, J=2.07 Hz, 1H), 7.92 (dd, J=2.17, 8.38 Hz, 1H), 7.71 (d, J=8.48 Hz, 1H), 4.41 (s, 2H), 3.19-3.37 (m, 3H). LC/MS (Method B): 223.0 (M−H)⁻. HPLC (Method A) Rt 3.51 min (Purity: 98.8%).

Step 2: 2-(3-methoxyprop-1-yn-1-yl)-2'-methylbiphenyl-4-carboxylic acid

A mixture of 4-chloro-3-(3-methoxyprop-1-yn-1-yl)benzoic acid, obtained in step 1 (336.97 mg; 1.50 mmol; 1 eq.), o-tolylboronic acid (254.92 mg; 1.88 mmol; 1.25 eq.), palladium(II) acetate (67.35 mg; 0.30 mmol; 0.20 eq.), 2-dicyclohexylphosphino-2',4',6'-triisopropylbiphenyl (286.03 mg; 0.60 mmol; 0.40 eq.), potassium fluoride (261.43 mg; 4.50 mmol; 3 eq.), toluene (6.7 mL), MeOH (6.7 mL) and water (16.2 μL) was degassed with N₂. The reaction was stirred at RT for 1 h and then heated at 50° C. for 1 h30. The mixture was filtrated over celite, rinsed with EtOAc and MeOH. Solvent were evaporated. HCl 0.1 M and EtOAc were added to the residue. The organic layer was then washed twice with NaOH 0.1 M. Combined aqueous layers were then acidified with HCl 5 M to pH=1 and finally extracted with EtOAc. The combined organic layers were dried over magnesium sulfate, filtered and concentrated to afford the title compound as an orange oil (307 mg; 73%). LC/MS (Method B): 279.1 (M−H)⁻. HPLC (Method A) Rt 4.19 min (Purity: 70.9%).

Intermediate 42: 2-(ethoxymethyl)-2'-methylbiphenyl-4-carboxylic acid

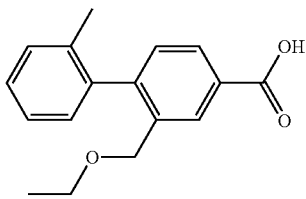

Step 1: ethyl 4-bromo-3-(ethoxymethyl)benzoate

To a solution of methyl 4-bromo-3-(bromomethyl)benzoate (Intermediate 28, Step 1), (2.50 g; 8.12 mmol; 1 eq.) in EtOH (12.50 mL) was added sodium ethylate (1 104.83 mg; 16.24 mmol; 2 eq.) and the mixture was stirred overnight at 80° C. After evaporation of the solvent, the mixture was partitioned between EtOAc and water. The organic layer was washed with a 5% NaHCO₃ aqueous solution, NaCl sat. solution, dried over magnesium sulfate, filtered off and dried under vacuum to afford a yellow oil. Purification by flash chromatography (cHex/ethyle acetate) afforded the title compound as a yellow oil. $^1$H NMR (CDCl₃) δ 8.13 (d, J=2.1 Hz, 1H), 7.80 (dd, J=8.3, 2.1 Hz, 1H), 7.61 (d, J=8.3 Hz, 1H), 4.58 (s, 2H), 4.38 (q, J=7.2 Hz, 2H), 3.64 (q, J=7.0 Hz, 2H), 1.39 (t, J=7.2 Hz, 3H), 1.30 (t, J=7.0 Hz, 3H). LC/MS (Method B): 382.2 ((M−H)+ACN)⁻; 330.2 ((M+H)+ACN)⁺. HPLC (Method A), Rt 4.90 min (purity: 78.5%).

Step 2: (ethoxymethyl)-2'-methylbiphenyl-4-carboxylic acid

Ethyl 4-bromo-3-(ethoxymethyl)benzoate, obtained in step 2 (495 mg; 1.72 mmol; 1 eq.), o-tolylboronic acid (257.80 mg; 1.90 mmol; 1.10 eq.), potassium carbonate (1 191.19 mg; 8.62 mmol; 5 eq.), tetrakis(triphenylphosphine) palladium (0) (199.20 mg; 0.17 mmol; 0.10 eq.) were taken in toluene (2.5 mL) and water (2.5 mL) under N₂ atmosphere. The reaction mixture was purged with vacuum and degassed with N₂ and then refluxed for 3 h30. The reaction mixture was cooled to RT, filtered over a pad of celite and washed with EtOAc (100 mL). The filtrate was concentrated to afford a brown oil which was taken in EtOAc (100 mL). The organic layer was washed with a saturated aqueous solution of NaHCO₃ solution (20 mL), water (20 mL) and NaCl sat. solution (20 mL), dried over magnesium sulfate and concentrated affording methyl 2-(ethoxymethyl)-2'-methylbiphenyl-4-carboxylate. The latter was dissolved in EtOH (5 mL) and THF (5 mL). Sodium hydroxide (500 μL; 5 M) was added and the solution was let stirred at RT for 6 h. HCl (500 μL; 5 M) was added and solvent were removed under reduce pressure. To the white solid water (20 mL) was added and the organic layer was extracted with EtOAc (2×20 mL). The combined organic layers were then dried over magnesium sulfate, filtered and concentrated to afford the title compound as a white solid (256 mg; 30%). LC/MS (Method B): 269.3 (M−H)⁻. HPLC (Method A), Rt 4.42 min (purity: 54.7%).

Intermediate 43: 2-Hydroxy-2'-methyl-1,1'-biphenyl-4-carboxylic acid

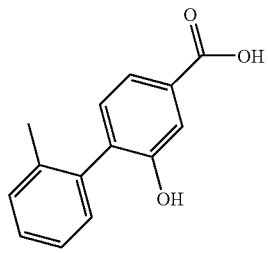

Step 1: Methyl 2-hydroxy-2'-methyl-1,1'-biphenyl-4-carboxylate

To a mixture of methyl 4-bromo-3-hydroxybenzoate (25 g, 0.108 mol) and o-tolylboronic acid (22 g, 0.162 mol) in a toluene (500 mL) water (100 mL) mixture, was added anhydrous potassium carbonate (44 g, 0.324 mol) followed by tetrakis (triphenylphosphine) palladium (0) (6.25 g, 0.054 mol). The reaction mixture was degassed with N₂ and heated at 110° C. for 12 h. After cooling to RT, the reaction mixture was filtered through a celite pad that was washed further with ethyl acetate. Combined filtrates were washed with 10% solution of NaHCO₃, water and brine solution. The solvents were dried over Na₂SO₄ and evaporated under vacuum. The residue was purified by chromatography (pet ether/EtOAc as an eluent) to afford the title compound as pale yellow solid (20 g, 77%). $^1$H NMR (DMSO-$d_6$, 400 MHz) δ 9.85 (1H, s), 7.52 (1H, s), 7.44-7.46 (1H, m), 7.20-7.25 (3H, m), 7.14-7.16 (1H, m), 7.09-7.11 (1H, m), 3.84 (3H, s), 2.09 (3H, s).

Step 2: 2-Hydroxy-2'-methyl-1,1'-biphenyl-4-carboxylic acid

To a stirred solution of methyl 2-hydroxy-2'-methyl-1,1'-biphenyl-4-carboxylate (12 g, 0.05 mol) in a mixture of THF/water (150 mL:15 mL) was added lithium hydroxide (6.23 g, 0.1485 mol) in portions. After being stirred at RT for 24 h, the reaction mass was evaporated to dryness and the residue diluted with little amount of water. The aqueous phase was acidified with conc.hydrochloric acid and extracted with EtOAc. Organic layer was washed with brine solution and was dried over $Na_2SO_4$. Evaporation of the solvents afforded the title compound as a white solid (10 g, 89%). $^1$H NMR (DMSO-$d_6$, 400 MHz) δ 12.72 (1H, bs), 9.78 (1H, bs), 7.50 (1H, s), 7.41-7.43 (1H, m), 7.08-7.24 (5H, m), 2.09 (3H, s). LC/MS (Method A): 227 (M−H)$^-$. HPLC (Method B), Rt 4.09 min (purity: 99.69%).

Intermediate 44: 2-(3-methoxypropyl)-2'-methylbiphenyl-4-carboxylic acid

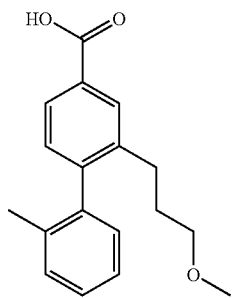

Intermediate 41 (625.12 mg; 2.23 mmol; 1 eq.) was dissolved in MeOH (50 mL). The solution was injected on a flow hydrogenation reactor (H-cube), adapted with 10% Pd/C cartridge, a flow of 0.5 mL/min, a temperature of 60° C. and the full $H_2$ option enabled. Evaporation of the solvent afforded the title compound as a yellow oil. $^1$H NMR (DMSO-$d_6$, 300 MHz) δ 7.99 (d, J=1.5 Hz, 1H), 7.92 (dd, J=7.9, 1.7 Hz, 1H), 7.23-7.14 (m, 4H), 7.02 (d, J=7.1 Hz, 1H), 3.25 (t, J=6.5 Hz, 2H), 3.20 (s, 3H), 2.56-2.47 (m, 1H), 2.41-2.31 (m, 1H), 1.97 (s, 3H), 1.65 (quintuplet, J=7.2 Hz, 2H). LC/MS (Method B): 281.2 (M−H)$^-$. HPLC (Method A) Rt 4.25 min (Purity: 97.7%).

Intermediate 45: methyl 5-[amino(hydroxyimino)methyl]-2-fluorobenzoate

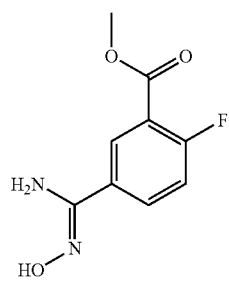

Step 1: methyl 3-cyano-4-fluorobenzoate

Triphenylphosphine polymer bound (200 mg; 0.60 mmol; 0.15 eq.), palladium (II) acetate (60.17 mg; 0.27 mmol; 0.07 eq.) and DMF (12 mL) were first mixed in a microwave vial, purged with $N_2$ and let stirring at RT for 2 h. The vial was then opened, zinc cyanide (469.70 mg; 4 mmol; 1 eq.) and methyl 5-bromo-2-fluorobenzoate, prepared from literature procedure starting from 5-bromo-2-fluorobenzoic acid (COMBI-BLOCKS; CA-4097) (932.15 mg; 4 mmol; 1 eq.), were added and the resulting mixture was purged once more and sealed. It was then heated in the microwave at 140° C. for 50 min. The reaction mixture was filtrated through a glass frit and the resin was washed with $Et_2O$ (3×10 mL). The combined organic solutions were washed with water (3×5 mL), once with NaCl sat. solution (10 mL) and then dried over magnesium sulfate. Evaporation of the solvents gave the title compound as a white solid (638 mg; 89%). $^1$H NMR (DMSO-$d_6$, 300 MHz) δ 8.35 (dd, J=6.8, 2.2 Hz, 1H), 8.2-8.17 (m, 1H), 7.63 (dd, J=10.6. 8.6 Hz, 1H), 3.89 (s, 3H). GC/MS: 179. HPLC (Method A), Rt 2.74 min (purity: 93.9%).

Step 2: methyl 5-[amino(hydroxyimino)methyl]-2-fluorobenzoate

To a suspension of methyl 5-cyano-2-fluorobenzoate, obtained in step 2 (804.60 mg; 4.49 mmol; 1 eq.) in EtOH (8.05 mL) was added hydroxylamine (50% in water) (1.35 mL; 22.46 mmol; 5 eq.). The reaction mixture was stirred at RT for 1 h40. Water (25 mL) was added followed by $Et_2O$ (25 mL). Aqueous layer was extracted with $Et_2O$ (2×25 mL). The combined organic layers were then washed with NaCl sat. solution and dried over magnesium sulfate, filtered and concentrated to afford the title compound as a yellow solid (931 mg; 98%). $^1$H NMR (DMSO-$d_6$, 300 MHz) δ 9.78 (br s, 1H), 8.21 (dd, J=7.1, 2.4 Hz, 1H), 7.96-7.91 (m, 1H), 7.38 (dd, J=10.8, 8.8 Hz, 1H), 5.97 (br s, 2H), 3.87 (s, 3H). HPLC (Method A), Rt 0.92 min (purity: 90.6%). LC/MS (Method B): 211.1 (M−H)$^-$; 213.0 (M+H)$^+$.

Intermediate 46: methyl 5-[amino(hydroxyimino)methyl]-2-hydroxybenzoate

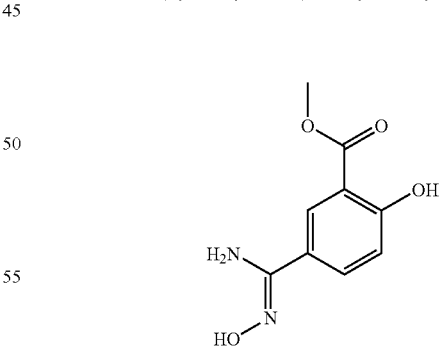

To a suspension of methyl 5-cyano-2-hydroxy-benzoate (ASTATECH; 63806; 1 g; 5.64 mmol; 1 eq.) in EtOH (10 mL) was added hydroxylamine (50% in water) (1.69 mL; 28.22 mmol; 5 eq.). The reaction mixture was stirred at 60° C. for 30 min. While cooling to RT a white precipitate was formed. Solvents were removed to dryness and the white solids were washed with EtOH to afford title compound pure at 66% as a white powder. $^1$H NMR (DMSO-$d_6$, 300 MHz) δ 8.12 (d, J=2.2 Hz, 1H), 7.81 (dd, J=8.4, 2.2 Hz, 1H), 6.99 (d, J=8.7 Hz, 1H), 5.82 (br s, 2H), 5.69 (br s, 1H), 3.91 (s, 3H). LC/MS (Method A): 210.8 (M+H)+.

Intermediate 47: methyl 4-[amino(hydroxyimino)methyl]-3-methoxybenzoate

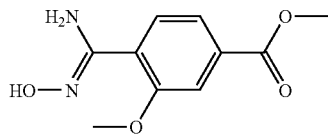

Step 1: methyl 4-cyano-3-methoxybenzoate

Triphenylphosphine polymer bound (50 mg; 0.15 mmol; 0.15 eq.), palladium (II) acetate (15.04 mg; 0.07 mmol; 0.07 eq.) and DMF (3 mL) were first mixed, purged with $N_2$ and let stirring at RT for 2 h. The vial was then opened, zinc cyanide (117.43 mg; 1 mmol; 1 eq.) and methyl 4-bromo-3-methoxybenzoate (COMBI-BLOCKS; CA-4192; 245.07 mg; 1 mmol; 1 eq.) were added and the resulting mixture was purged once more before heating at 140° C. for 50 min. The reaction mixture was then filtrated through a glass frit and the resin was washed with $Et_2O$ (3×10 mL). The combined organic solutions were washed with water (3×5 mL), once with NaCl sat. solution (10 mL) and then dried over magnesium sulfate. Evaporation of the solvent gave the title compound as a white solid (137 mg; 72%). $^1H$ NMR (DMSO-$d_6$, 300 MHz) δ 7.91 (d, J=7.9 Hz, 1H), 7.66-7.62 (m, 2H), 4 (s, 3H), 3.90 (s, 3H). LC/MS (Method A): 232.8 (M+ACN)+. GC/MS: 191. HPLC (Method A), Rt 3.14 min (purity: 99.3%).

Step 2: methyl 4-[amino(hydroxyimino)methyl]-3-methoxybenzoate

To a suspension of methyl 4-cyano-3-methoxybenzoate, obtained in step 1 (135 mg; 0.71 mmol; 1 eq.) in EtOH (1.35 mL) was added hydroxylamine (50% in water) (0.21 mL; 3.53 mmol; 5 eq.). The reaction mixture was stirred at 60° C. for 3 h. Solvent were removed to dryness, to afford the title compound as a white powder (191 mg; quantitative). $^1H$ NMR (DMSO-$d_6$, 300 MHz) δ 9.58 (br s, 1H), 7.56-7.51 (m, 3H), 5.71 (br s, 2H), 3.87-3.85 (m, 6H). HPLC (Method A), Rt 1.17 min (purity: 95.0%).

Intermediate 48: methyl 4-[amino(hydroxyimino)methyl]-2-methoxybenzoate

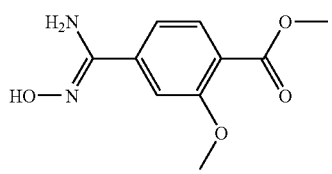

Step 1: methyl 4-cyano-2-methoxybenzoate

Triphenylphosphine polymer bound (50 mg; 0.15 mmol; 0.15 eq.), palladium (II) acetate (15.04 mg; 0.07 mmol; 0.07 eq.) and DMF (3 mL) were first mixed, purged with $N_2$ and let stirring at RT for 2 h. The vial was then opened, zinc cyanide (117.43 mg; 1 mmol; 1 eq.) and 4-bromo-2-methoxybenzoate (ALDRICH; 653098-10G; 245.07 mg; 1 mmol; 1 eq.) were added and the resulting mixture was purged once more before heating at 140° C. for 50 min. The reaction mixture was then filtrated through a glass frit and the resin was washed with $Et_2O$ (3×10 mL). The combined filtrates were washed with water (3×5 mL), once with NaCl sat. solution (10 mL) and then dried over magnesium sulfate. Evaporation of the solvent gave the title compound as a white powder (157 mg; 82%). $^1H$ NMR (DMSO-$d_6$, 400 MHz) δ 7.76 (d, J=7.9 Hz, 1H), 7.68 (d, J=1.4 Hz, 1H), 7.50 (dd, J=7.9, 1.4 Hz, 1H), 3.88 (s, 3H), 3.82 (s, 3H). LC/MS (Method A): 190.8 (M−H)−; 191.8 (M+H)+. HPLC (Method A), Rt 2.67 min (purity: 94.8%).

Step 2: methyl 4-[amino(hydroxyimino)methyl]-2-methoxybenzoate

To a suspension of methyl 4-cyano-2-methoxybenzoate, obtained in step 1 (155 mg; 0.81 mmol; 1 eq.) in EtOH (1.55 mL) was added hydroxylamine (50% in water) (0.24 mL; 4.05 mmol; 5 eq.). The reaction mixture was stirred at 60° C. for 60 min. Solvents were removed to dryness, to afford the title compound as a yellow powder. $^1H$ NMR (DMSO-$d_6$, 400 MHz) δ 10.62 (br s, 1H), 9.85 (s, 1H), 7.64 (d, J=7.9 Hz, 1H), 7.40 (s, 1H), 7.35-7.31 (m, 2H), 5.95 (br s, 2H), 3.85 (s, 3H), 3.78 (s, 3H).

Intermediate 49: Tert-butyl {4-[amino(hydroxyimino)methyl]-2-fluorophenoxy}acetate

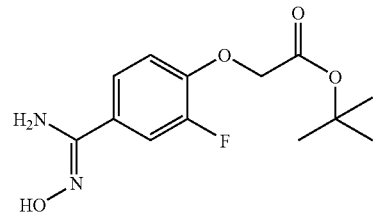

Step 1: Tert-butyl (4-cyano-2-fluorophenoxy)acetate 3-fluoro-4-hydroxybenzonitrile (ABCR F03756F.AB, 2 g; 14.59 mmol; 1 eq.) was dissolved in $CH_3CN$ (120 mL). cesium carbonate (5.70 g; 17.50 mmol; 1.20 eq.) and methyl bromoacetate (2.26 mL; 15.32 mmol; 1.05 eq.) were added and the mixture was stirred at RT for 12 hours. The reaction mixture was concentrated and the crude mixture was diluted with EtOAc and washed with water (3×) then with brine, dried over $MgSO_4$ and concentrated affording the title compound as a yellow solid (3.58 g, 97%). $^1H$ NMR (DMSO-$d_6$, 300 MHz) δ 7.91-7.84 (m, 1H), 7.68-7.65 (m, 1H), 7.37-7.24 (m, 1H), 4.92 (s, 2H), 1.42 (s, 9H). HPLC (Method A) Rt 4.72 min (Purity: 97.6%).

Step 2: Tert-butyl {4-[amino(hydroxyimino)methyl]-2-fluoro phenoxy}acetate

Tert-butyl (4-cyano-2-fluorophenoxy)acetate (3.50 g; 13.93 mmol; 1 eq.) was suspended in EtOH (70 mL). hydroxylamine (2.05 mL; 69.65 mmol; 5 eq.) was added in one portion. The reaction mixture was stirred at RT for 12 hours. The reaction mixture was concentrated affording the title compound as a white solid (3.57 g, 90%). $^1$H NMR (DMSO-d$_6$, 300 MHz) δ 9.61 (br s, 1H), 7.51-7.41 (m, 2H), 7.09-7.03 (t, J=8.84 Hz 1H), 5.81 (br s, 2H), 4.78 (s, 2H), 1.42 (s, 9H). LC/MS (Method 13): 285.1 (M+H)$^+$. HPLC (Method A) Rt 2.91 min (Purity: 94.3%).

Intermediate 50: tert-butyl N-{4-[amino(hydroxy-imino)methyl]-2-fluorophenyl}glycinate

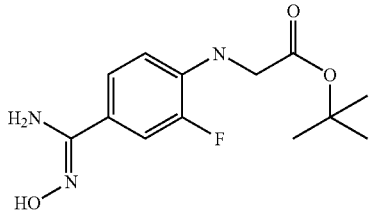

Step 1: tert-Butyl N-(4-cyano-2-fluorophenyl)glycinate 4-amino-3-fluorobenzonitrile (FLROCHEM, 500 mg; 3.67 mmol; 1 eq.) was dissolved in CH$_3$CN (4 mL). Cesium carbonate (1.44 g; 4.41 mmol; 1.50 eq.) was added and the mixture was stirred at RT for 1 h. Methyl bromoacetate (504.76 µl; 3.42 mmol; 0.93 eq.) was added and the mixture was stirred in the microwave at 150° C. for 15 min. As the reaction was not complete, it was relaunched for 15 min at 150° C. A mixture of starting material, desired product and double addition product was obtained (48%, 33% and 14% respectively). It was purified by flash chromatography (c-hex/EtOAc 95:5 to 50:50), affording the title product. HPLC (Method A) Rt 4.33 min (Purity: 72.2%).

Step 2: tert-Butyl N-{4-[amino(hydroxyimino)methyl]-2-fluorophenyl}glycinate tert-Butyl N-(4-cyano-2-fluorophenyl)glycinate obtained in Step 1 (290 mg; 1.16 mmol; 1 eq.) was dissolved in MeOH (1 mL) and hydroxylamine (0.34 mL; 5.79 mmol; 5 eq.) was added. The mixture was stirred at RT overnight. Solvents were evaporated off, affording the title product as an off-white solid, which was used further without purification (302 mg, 92%). HPLC (Method A) Rt 2.23 min (Purity: 74.2%).

Intermediate 51: tert-butyl [{3-[amino(hydroxy-imino)methyl]benzyl}(methyl)amino]acetate

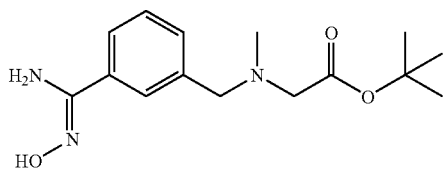

Step 1: tert-butyl [(3-cyanobenzyl)(methyl)amino]acetate

To a stirred solution of sarcosine tert-butyl ester hydrochloride (8.1 g, 44.9 mmol) and triethylamine (17 mL, 122.4 mmol) in acetonitrile (100 mL) under N$_2$, was added 3-(bromomethyl)benzonitrile (8 g, 40.8 mmol) portionwise over a period of 10 min at 0° C. After being stirred at RT for 3 h, the reaction mixture was poured into water and extracted with DCM. Then the organic layer was washed with brine and dried over sodium sulphate and concentrated under reduced pressure to afford the title compound as a pale green liquid (9 g, 85%). $^1$H NMR (DMSO-d$_6$, 400 MHz) δ 7.71-7.72 (2H, m), 7.63-7.65 (1H, m), 7.53-7.55 (1H, m), 3.66 (2H, s), 3.18 (2H, s), 2.22 (3H, s), 1.41 (9H, s).

Step 2: tert-butyl [{3-[amino(hydroxyimino)methyl]benzyl}(methyl)amino]acetate

To a solution of tert-butyl [(3-cyanobenzyl)(methyl)amino]acetate (9 g, 34.6 mmol) in ethanol (60 mL) under N$_2$, was added hydroxylamine (6 g, 178.8 mmol) in one portion. After being stirred at RT for 12 h, the reaction mixture was concentrated under reduced pressure to afford a colorless oil. It was triturated in diisopropyl ether, affording the title product as a white solid that was filtrated and dried under vacuo (8.5 g, 84%). $^1$H NMR (DMSO-d$_6$, 300 MHz) δ 9.57 (1H, s), 7.59 (1H, s), 7.52-7.53 (1H, m), 7.29-7.31 (2H, m), 5.75 (2H, s), 3.61 (2H, s), 3.15 (2H, s), 2.23 (3H, s), 1.41 (9H, s). LC/MS (Method A): 294.0 (M+H)$^+$. HPLC (Method B) Rt 3.31 min (Purity: 97.5%).

Intermediate 52: methyl 4-[amino(hydroxyimino)methyl]-2,5-difluorobenzoate

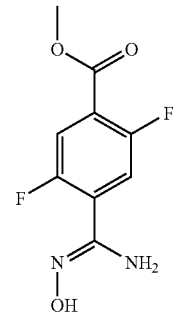

Step 1: methyl 4-cyano-2,5-difluorobenzoate

Methyl 2,4,5-trifluorobenzoate (DSL Chemicals; 950.61 mg; 5 mmol; 1 eq.), sodium cyanide (306.30 mg; 6.25 mmol; 1.25 eq.) and tetrabutylammonium bromide (2 014.82 mg; 6.25 mmol; 1.25 eq.) were dissolved in DMF (10 mL). The resulting mixture was heated at 60° C. overnight. As the reaction was not complete, sodium cyanide (306.30 mg; 6.25 mmol; 1.25 eq.) was added and the mixture was stirred at 60° C. for additional 24 h. The resulting dark pink solution was diluted with EtOAc and washed with brine several times. It was dried over MgSO$_4$, filtrated and evaporated, resulting into a sticky dark red oil, which was purified by flash chromatography (SiO$_2$ 100 g, EtOAc/c-hex 1:9 until 1:1), affording the title product. $^1$H NMR (DMSO-d$_6$, 300 MHz) δ 7.77 (dd, J=5.45, 8.41 Hz, 1H), 7.42 (dd, J=4.99, 8.88 Hz, 1H), 3.96 (s, 3H). LC/MS (Method A): 463.2 (M−H)$^-$; 465.2 (M+H)$^+$. HPLC (Method A) Rt 3.63 min (Purity: 99.9%).

Step 2: methyl 4-[amino(hydroxyimino)methyl]-2,5-difluorobenzoate

Methyl 4-cyano-2,5-difluorobenzoate (265 mg; 1.34 mmol; 1 eq.) was dissolved in MeOH. Hydroxylamine (0.40 mL; 6.72 mmol; 5 eq.) was added and the mixture was stirred at RT. After one night, the reaction was complete and the solvents were evaporated, affording the title product as a white solid (304 mg; 98%). LC/MS (Method A): 229.0 (M−H)⁻; 231.0 (M+H)⁺. HPLC (Method A) Rt 1.08 min (Purity: 98.7%)

Intermediate 53: methyl 3-[amino(hydroxyimino)methyl]-4-methoxybenzoate

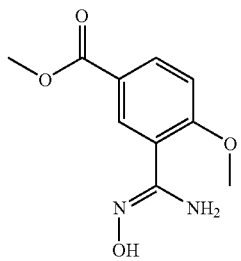

A solution of methyl 3-cyano-4-methoxybenzoate (518 mg, 2.71 mmol), hydroxylamine (810 µL, 50% in water, 13.55 mmol) in EtOH (20 mL) was heated for 18 h at 60° C. after which time solvents were removed under vacuum, solid residue was triturated with water filtered and dried under vacuum overnight to give the title compound as an off-white solid (600 mg, quant). $^1$H NMR (DMSO-$d_6$, 300 MHz) δ 9.48 (s, 1H), 7.97-7.95 (m, 2H), 7.20-7.17 (m, 1H), 5.70 (bs, 2H), 3.87 (s, 3H), 3.82 (s, 3H). LC/MS (Method B): 225.1 (M+H)⁺.

Intermediate 54: methyl 5-[amino(hydroxylimino)methyl]-2-chlorobenzoate

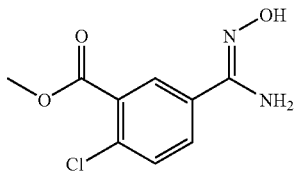

Step 1: Methyl 5-bromo-2-chlorobenzoate 5-bromo-2-chlorobenzoic acid (E-Merck 8.14989.0101, 20 g; 84.94 mmol; 1 eq.) was dissolved in MeOH (400 mL). The solution was cooled down to 0° C. SOCl2 (18.49 mL; 254.82 mmol; 3 eq.) was added dropwise (addition took 30 min and IT increased to 9° C.). After addition, the reaction mixture was stirred at RT for 2 days. The reaction mixture was concentrated and the crude mixture was dissolved in EtOAc (400 mL) and washed with a saturated aqueous solution of NaHCO₃ (100 mL), brine (100 mL), dried over MgSO₄ and concentrated affording the title compound as a white solid (20.15 g, 95%). $^1$H NMR (DMSO-$d_6$, 300 MHz) δ 7.98-7.97 (d, J=2.40 Hz, 1H), 7.80-7.67 (dd, J=8.74 Hz, 2.40 Hz, 1H), 7.56-7.54 (d, J=8.23 Hz, 1H), 3.86 (s, 3H). HPLC (Method A) Rt 4.15 min (Purity: 99.9%).

Step 2: Methyl 2-chloro-5-cyanobenzoate

Methyl 5-bromo-2-chlorobenzoate (2 g; 8.02 mmol; 1 eq.), zinc cyanide (564.79 mg; 4.81 mmol; 0.60 eq.), tris(diben- zylideneacetone)dipalladium(0) (58.73 mg; 0.06 mmol; 0.01 eq.), 1,1'-bis(diphenylphosphino)ferrocene (71.11 mg; 0.13 mmol; 0.02 eq.), zinc (20.97 mg; 0.32 mmol; 0.04 eq.) and zinc acetate (58.83 mg; 0.32 mmol; 0.04 eq.) were put in dry DMF (20 mL). The reaction mixture was purged with N₂ and then heated to 90° C. for 3 hours. The reaction mixture was cooled to RT, filtered over a pad of celite and washed with EtOAc. The organic phase was washed with water, brine, dried over MgSO₄ and concentrated to afford a brown solid purified by flash chromatography eluting with cHex-EtOAc 8:2 affording the title compound as a yellow solid. It was washed with EtOH and dried under vacuum affording the title compound as a yellow solid (1.55 g, 98%). $^1$H NMR (DMSO-$d_6$, 300 MHz) δ 8.29 (m, 1H), 8.09-8.06 (m, 1H), 7.83-7.81 (m, 1H), 3.89 (s, 3H). LC/MS (Method B): 197.0 (M+H)⁺. HPLC (Method A) Rt 3.70 min (Purity: 83.7%)

Step 3: Methyl 5-[amino(hydroxyimino)methyl]-2-chlorobenzoate

Methyl 2-chloro-5-cyanobenzoate (1.55 g; 7.92 mmol; 1 eq.) was suspended in EtOH (31 mL). Hydroxylamine (1.17 mL; 39.62 mmol; 5 eq.) was added in one portion. The reaction mixture was stirred at RT for 6 hours. The mixture was concentrated affording the title compound as a beige solid (1.65 g, 91%). $^1$H NMR (DMSO-$d_6$, 300 MHz) δ 9.92 (br s, 1H), 8.19-8.18 (m, 1H), 7.92-7.90 (m, 1H), 7.68-7.65 (m, 1H), 6.04 (br s, 2H), 3.95 (s, 3H). LC/MS (Method B): 229.0 (M+H)⁺; 227.0 (M−H)⁻.

Intermediate 55: Methyl 4-[amino(hydroxyimino)methyl]-2-chloro-5-fluorobenzoate

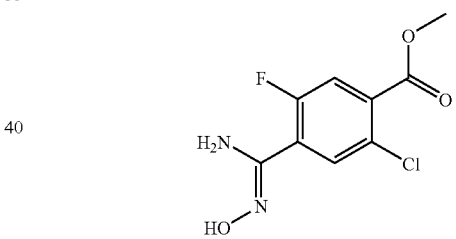

Step 1: Methyl 4-bromo-2-chloro-5-fluorobenzoate 4-bromo-2-chloro-5-fluorobenzoic acid (Apollo PC9723, 5 g; 19.73 mmol; 1 eq.) was dissolved in MeOH (100 mL). The solution was cooled down to 0° C. SOCl2 (4.29 mL; 59.18 mmol; 3 eq.) was added dropwise (addition took 15 min and IT increased to 9° C.). The reaction mixture was stirred at RT for 3 days. The reaction mixture was concentrated and the crude mixture was dissolved in EtOAc (200 mL) and washed with a saturated aqueous solution of NaHCO₃(50 mL), brine (50 mL), dried over MgSO₄ and concentrated affording the title compound as a white solid (5.04 g, 95%). $^1$H NMR (DMSO-$d_6$, 300 MHz) δ 8.10-8.08 (d, J=6.30 Hz), 1H), 7.86-7.83 (d, J=8.82 Hz, 1H), 3.87 (s, 3H). HPLC (Method A) Rt 4.32 min (Purity: 99.7%).

Step 2: Methyl 2-chloro-4-cyano-5-fluorobenzoate

Methyl 4-bromo-2-chloro-5-fluorobenzoate (1.80 g; 6.73 mmol; 1 eq.), zinc cyanide (474.13 mg; 4.04 mmol; 0.60 eq.), tris(dibenzylideneacetone)dipalladium(0) (49.30 mg; 0.05 mmol; 0.01 eq.), 1,1'-bis(diphenylphosphino)ferrocene (59.69 mg; 0.11 mmol; 0.02 eq.), zinc (17.60 mg; 0.27 mmol; 0.04 eq.) and zinc acetate (49.39 mg; 0.27 mmol; 0.04 eq.) were put in dry DMF (18 mL). The reaction mixture was purged with $N_2$ and then heated to 90° C. for 12 hours. The reaction mixture was cooled to RT, filtered over a pad of celite and washed with EtOAc. The organic phase was washed with water, brine, dried over $MgSO_4$ and concentrated affording a brown solid. It was purified by washing with EtOH affording the title compound as a beige solid. $^1$H NMR (DMSO-$d_6$, 300 MHz) δ 8.37-8.35 (d, J=5.86 Hz, 1H), 8-7.97 (d, J=9.18 Hz, 1H), 3.91 (s, 3H).

Step 3: methyl 4-[amino(hydroxyimino)methyl]-2-chloro-5-fluorobenzoate

Methyl 2-chloro-4-cyano-5-fluorobenzoate (1.65 g; 7.72 mmol; 1 eq.) was suspended in EtOH (33 mL). Hydroxylamine (1.14 mL; 38.62 mmol; 5 eq.) was added in one portion. The reaction mixture was stirred at RT for 6 hours. The obtained suspension was filtered affording the title compound as a beige solid. $^1$H NMR (DMSO-$d_6$, 300 MHz) δ 9.98 (br s, 1H), 7.74-7.67 (m, 2H), 6 (hrs, 2H), 3.87 (s, 3H). LC/MS (Method B): 247.0 (M+H)$^+$; 245.1 (M−H)$^−$. HPLC (Method A) Rt 1.80 min (Purity: 90.4%).

Intermediate 56: 4-isopropoxy-3-(methoxymethyl)benzoic acid

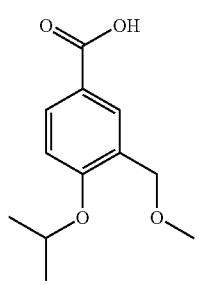

Step 1: Methyl 3-formyl-4-hydroxybenzoate 3-formyl-4-hydroxybenzoic acid (Aldrich 633488, 20 g; 120.39 mmol; 1 eq.) was dissolved in MeOH (400 mL). The solution was cooled down to 0°. SOCl2 (26.20 mL; 361.16 mmol; 3 eq.) was added dropwise (addition took 60 min and the temperature of the reaction mixture increased to 7.6° C.). The reaction mixture was stirred at RT for 24 hours. The reaction mixture was concentrated and the crude mixture was dissolved in EtOAc (500 mL) and washed with a saturated aqueous solution of $NaHCO_3$ (300 mL), HCl 1N (300 mL) and brine (300 mL), dried over $MgSO_4$ and concentrated affording the title compound as a beige solid (19.86 g, 91%). $^1$H NMR (DMSO-$d_6$, 300 MHz) δ 8.25-8.24 (d, J=2.33 Hz, 1H), 8.08-8.03 (dd, J=8.79 Hz, 2.33 Hz, 1H), 7.12-7.09 (d, J=8.75 Hz, 1H), 3.83 (s, 3H). LC/MS (Method B): 179.1 (M−H)$^−$. HPLC (Method A) Rt 3.04 min (Purity: 91.6%).

Step 2: Methyl 4-hydroxy-3-(hydroxymethyl)benzoate

A solution of methyl 3-formyl-4-hydroxybenzoate (19.80 g; 109.90 mmol; 1 eq.) in MeOH (396 mL) was added at 0° C. NaBH4 (6.24 g; 164.85 mmol; 1.50 eq.) in several portions (portions over 20 min). The reaction mixture was stirred at RT for 2 hours. The reaction mixture was concentrated and the residue was suspended in EtOAc (500 mL). The organic layer was washed with a saturated aqueous solution of NH4Cl (2×200 mL), water (200 mL), then brine (200 mL). The aqueous layer contained a lot of the desired compound so it was saturated with NaCl and extracted with EtOAc (4×600 mL). Organics were combined, dried over $MgSO_4$ and concentrated affording the title compound as a beige solid (10.52 g, 52%). LC/MS (Method B): 181.1 (M−H)$^−$.

Step 3: Methyl 4-hydroxy-3-(methoxymethyl)benzoate

To MeOH (100 mL) was added methyl 4-hydroxy-3-(hydroxymethyl)benzoate (10 g; 54.89 mmol; 1 eq.) and PTSA (1.89 g; 10.98 mmol; 0.20 eq.). The resulting suspension was heated to 130° C. for 1 hour. The reaction mixture was concentrated giving a yellow solid. It was dissolved in EtOAc (400 mL), washed with a saturated aqueous solution of $NaHCO_3$ (200 mL), brine (200 mL), dried over $MgSO_4$ and concentrated affording the title compound as an orange solid (9.59 g, 89%). $^1$H NMR (DMSO-$d_6$, 300 MHz) δ 10.48 (br s, 1H), 7.87-7.86 (d, J=2.11 Hz, 1H), 7.76-7.28 (dd, J=8.44 Hz, 2.31 Hz, 1H), 6.91-6.88 (d, J=8.48 Hz, 1H), 4.39 (s, 2H), 3.79 (s, 3H), 3.33 (s, 3H). LC/MS (Method B): 195.2 (M−H)$^−$.

Step 4: Methyl 4-isopropoxy-3-(methoxymethyl)benzoate

Methyl 4-hydroxy-3-(methoxymethyl)benzoate (9.50 g; 48.42 mmol; 1 eq.) was dissolved in DMF (142.50 mL). Then $K_2CO_3$ (26.77 g; 193.68 mmol; 4 eq.) and 2-bromopropane (18.18 mL; 193.68 mmol; 4 eq.) were added to the reaction mixture. It was heated to 90° C. for 3 hours. The reaction mixture was cooled to RT and diluted with EtOAc. It was washed with water (3×), brine, dried over $MgSO_4$ and concentrated affording the title compound as a yellow oil (11.35 g, 98%). $^1$H NMR (DMSO-$d_6$, 300 MHz) δ 7.95-7.84 (m, 2H), 7.13-7.11 (d, J=8.63 Hz, 1H), 4.81-4.69 (sept, J=6.07 Hz, 1H), 4.39 (s, 2H), 3.81 (s, 3H), 3.36 (s, 3H), 1.31-1.29 (d, J=6.01 Hz, 6H). LC/MS (Method B): 239.2 (M+H)$^+$. HPLC (Method A) Rt 4.25 min (Purity: 95.8%).

Step 5: 4-isopropoxy-3-(methoxymethyl)benzoic acid

A solution of methyl 4-isopropoxy-3-(methoxymethyl)benzoate (11.30 g; 47.42 mmol; 1 eq.) in EtOH (339 mL) at RT was treated with NaOH (47.42 mL; 5 M; 237.11 mmol; 5 eq.). The reaction mixture was stirred at RT for 12 hours. The reaction mixture was concentrated to give a yellow solid. It was taken up in water and the aqueous phase was washed with EtOAc and then acidified with HCl cc to pH 2. The aqueous layer was extracted with EtOAc (twice). The combined organics were washed with brine, dried over $MgSO_4$ and concentrated affording the title compound as a beige solid (9.71 g, 91%). $^1$H NMR (DMSO-$d_6$, 300 MHz) δ 12.39 (br s, 1H), 7.89-7.82 (m, 2H), 7.11-7.07 (d, J=8.75 Hz, 1H), 4.79-

4.67 (sept, J=5.92 Hz, 1H), 4.39 (s, 2H), 3.35 (s, 3H), 1.31-1.28 (d, J=6.06 Hz, 6H). LC/MS (Method B): 223.2 (M−H)⁻. HPLC (Method A) Rt 3.71 min (Purity: 92.8%).

Intermediate 57: methyl 4-[amino(hydroxyimino)methyl]-2-fluoro-5-methoxybenzoate

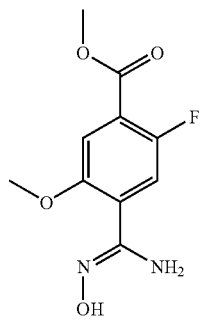

Step 1: methyl 2-fluoro-5-methoxy-4-nitrobenzoate

Methyl 2,5-difluoro-4-nitrobenzoate (Apollo, 500 mg; 2.30 mmol; 1 eq.) was dissolved in MeOH (10 mL). The solution was cooled down to 0° C. Lithium bis(trimethylsilyl)amide (2.30 mL; 1 M; 2.30 mmol; 1 eq.) was added as solution in THF. After addition, the reaction mixture was stirred at RT overnight. Solvents were evaporated and the crude mixture was dissolved in EtOAc, washed with water, brine and dried over MgSO₄. The resulting crude product was purified by flash chromatography (c-hex/EtOAc 90:10), affording the title product as a yellow solid. ¹H NMR (CDCl₃, 300 MHz) δ 7.60-7.52 (m, 2H), 3.93 (s, 3H), 3.91 (s, 3H). HPLC (Method A) Rt 3.88 min (Purity: 88.6%).

Step 2: Methyl 4-amino-2-fluoro-5-methoxybenzoate

Methyl 2-fluoro-5-methoxy-4-nitrobenzoate (549 mg; 1.13 mmol; 1 eq.) was dissolved in MeOH (50 mL). The resulting solution was injected on a flow hydrogenation reactor (H-Cube), adapted with Pd/C cartridge (44 mm), a flow of 1 mL/min, a temperature of 60° C. and the full H₂ option enabled. Solvents were evaporated, affording the title product as an off-white solid (220 mg; 97%). LC/MS (Method B): 200.0 (M+H)⁺. HPLC (Method A) Rt 3 min (Purity: 91.9%).

Step 3: 4-amino-2-fluoro-5-methoxybenzoic acid

Methyl 4-amino-2-fluoro-5-methoxybenzoate (100 mg; 0.50 mmol; 1 eq.) was dissolved in MeOH (2 mL). NaOH (0.50 mL; 5 M; 2.51 mmol; 5 eq.) was added and the mixture was heated at 50° C. overnight. The solvents were evaporated. EtOAc was added and the resulting solution was washed with NH₄Cl sat. The aqueous phase was extracted with EtOAc. Combined organic phases were dried over MgSO₄, filtrated and evaporated, affording the title compound (92 mg; 99%). HPLC (Method A) Rt 1.92 min (Purity: 96.4%).

Step 4: 4-cyano-2-fluoro-5-methoxybenzoic acid

A solution of sodium nitrite (29.51 mg; 0.43 mmol; 1.10 eq.) in water (1 mL) was added dropwise to a stirred mixture of 4-amino-2-fluoro-5-methoxybenzoic acid (72 mg; 0.39 mmol; 1 eq.), hydrochloric acid (388.86 μl; 1 M; 0.39 mmol; 1 eq.) and water (1.5 mL) at 0-5° C. The mixture was then stirred at 0-5° C. for 1 h and the resulting diazonium salt solution added in portions to a freshly prepared CuCN solution at 50° C. CuCN solution was prepared with copper(I) cyanide (43.54 mg; 0.49 mmol; 1.25 eq.) dissolved in a solution of potassium cyanide (63.30 mg; 0.97 mmol; 2.50 eq.) in water (500 uL). After addition was complete the mixture was stirred and heated at reflux for 2 h. The dark red solution was diluted with HCl 1N and was extracted with EtOAc. Organic phase was washed with brine, dried over MgSO₄, filtered and concentrated, affording (75 mg; 99%). ¹H NMR (DMSO-d₆) δ 13.9 (br s, 1H), 7.95-7.85 (m, 1H), 7.56-7.47 (m, 1H), 3.96 (s, 3H). LC/MS (Method B): 193.9 (M−H)⁻. HPLC (Method A) Rt 2.40 min (Purity: 99.2%).

Step 5: methyl 4-cyano-2-fluoro-5-methoxybenzoate

4-Cyano-2-fluoro-5-methoxybenzoic acid (75 mg; 0.38 mmol; 1 eq.) was dissolved in MeOH (1 mL). The solution was cooled down to 0° C. SOCl₂ (0.11 mL; 1.54 mmol; 4 eq.) was added dropwise. After addition, the reaction mixture was stirred at RT overnight. As the reaction was complete, solvents were evaporated. The crude mixture was dissolved in EtOAc and washed with NaHCO₃ sat and brine. The organic phase was dried over MgSO₄, filtrated and evaporated, affording the title product as an orange solid (64 mg; 80%). HPLC (Method A) Rt 3.68 min (Purity: 94.5%).

Step 6: methyl 4-[amino(hydroxyimino)methyl]-2-fluoro-5-methoxybenzoate

Methyl 4-cyano-2-fluoro-5-methoxybenzoate (64 mg; 0.31 mmol; 1 eq.) was dissolved in MeOH. Hydroxylamine (90.23 μl; 1.53 mmol; 5 eq.) was added and the mixture was stirred at RT overnight. As the reaction was not complete, it was heated at 50° C. for one more day. The solvents were then evaporated, affording the title product as an orange oil, which was used without further purification (74 mg; 100%). LC/MS (Method B): 243.1 (M+H)⁺. HPLC (Method A) Rt 1.24 min (Purity: 80.3%).

Intermediate 58: 3-(methoxymethyl)-4-(2-methylpiperidin-1-yl)benzoic acid

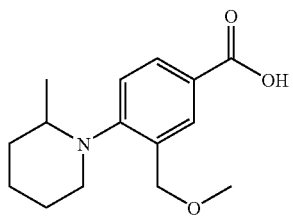

Step 1:
5-bromo-2-(2-methylpiperidin-1-yl)benzaldehyde

To a solution of 5-bromo-2-fluorobenzaldehyde (13.20 g; 65.02 mmol) in DMSO (160 mL) and water (40 mL) were added 2-methylpiperidine (15.35 mL; 130.04 mmol) and anhydrous sodium carbonate (13.78 g; 130.04 mmol). The resulting mixture was heated at 120° C. for 16 h after which it was allowed to cool to RT. Reaction mixture was partitioned between $H_2O$ (1 L) and Et2O (2×750 mL) and the combined organic layers were washed with brine (500 mL, pH 5-6 adjusted with HCl), dried over $MgSO_4$, filtered and dried under vacuum to give the title compound as a brown yellow oil (16.3 g, 89%). LC/MS (Method B): 282.1 $(M+H)^+$. HPLC (Method A): Rt 2.20 min (Purity: 93.7%).

Step 2:
[5-bromo-2-(2-methylpiperidin-1-yl)phenyl]methanol

To a solution of 5-bromo-2-(2-methylpiperidin-1-yl)benzaldehyde (16.30 g; 57.76 mmol) in MeOH (300 mL) was added sodium borohydride (2.19 g; 57.76 mmol) at 5° C. in a portion-wise fashion and stirred for 30 min. After this time, reaction mixture was diluted with a saturated aqueous solution of NH4Cl (300 mL), extracted with EtOAc. The org layers were washed with aqueous solution of NH4Cl (150 mL), brine (300 mL), dried over $MgSO_4$ and evaporated under vacuum to give the title compound as a yellow oil (15.9 g, 97%). LC/MS (Method A): 285.6 $(M+H)^+$. HPLC (Method A): Rt 2.13 min (Purity: 94.9%).

Step 3: 1-[4-bromo-2-(methoxymethyl)phenyl]-2-methylpiperidine

To a solution of solution of [5-bromo-2-(2-methylpiperidin-1-yl)phenyl]methanol (7.9 g; 27.8 mmol) and n-ethyldiisopropylamine (10.40 mL; 61.15 mmol) in anhydrous DCM (150 mL) cooled to 0° C., was added methanesulfonyl chloride (2.36 mL; 30.57 mmol). The reaction mixture was diluted with MeOH (150 mL) and heated to 50° C. for 3 h after which time solvents were removed under vacuum to give a brown oil. Residue was taken up with Et2O (450 mL), washed with water (150 mL, pH 8 adjusted with aqueous NaOH), saturated aqueous solution of NH4Cl (2×150 mL) and brine (150 mL). The combined organic layers were dried over $MgSO_4$, filtered and the solvent was removed under reduced pressure to give the title compound as a brown yellow oil (12.97 g, 92%). LC/MS (Method B): 298.1 $(M+H)^+$.

Step 4: 3-(methoxymethyl)-4-(2-methylpiperidin-1-yl)benzoic acid

To anhydrous Et2O (130 mL) at −78° C. was added tert-butyllithium (63.79 mL; 1.50 M; 95.68 mmol) (solution in pentane) which was followed by the slow addition of a solution of 1-[4-bromo-2-(methoxymethyl)phenyl]-2-methylpiperidine (12.97 g; 43.49 mmol) in anhydrous Et2O (20 mL). After 40 min, the reaction mixture was poured on an excess of freshly crushed dry ice and stirred for 30 min after which time it was diluted with Et2O/EtOAc (1:1, 800 mL), water (200 mL, pH 4-5). The organic layers were combined, dried over $MgSO_4$ and the solvents were removed under reduced pressure to give a yellow oil that was triturated in iPr2O (~20 mL) and pentane (~20 mL), filtered off and washed with pentane to give the title compound as a beige powder. LC/MS (Method B): 264.1 $(M+H)^+$.

Intermediate 59: methyl 4-[amino(hydroxyl imino)methyl]-2-chloro-5-methoxybenzoate

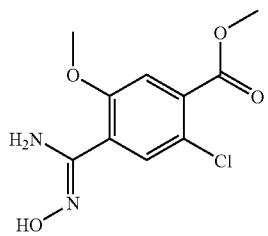

Step 1: Methyl 4-bromo-2-chloro-5-fluorobenzoate 4-bromo-2-chloro-5-fluorobenzoic acid (Apollo PC9723, 5 g; 19.73 mmol; 1 eq.) was dissolved in MeOH (100 mL). The solution was cooled down to 0° C. SOCl2 (4.29 mL; 59.18 mmol; 3 eq.) was added dropwise (addition took 15 min and IT increased to 9° C.). The reaction mixture was stirred at RT for 2 days. The reaction mixture was concentrated and the crude mixture was dissolved in EtOAc (100 mL) and washed with a saturated aqueous solution of $NaHCO_3$ (30 mL) and brine (30 mL), dried over $MgSO_4$ and concentrated under vacuum affording the title compound as a white powder (5.26 g, 99%), $^1H$ NMR (DMSO-$d_6$, 300 MHz) δ 8.10-8.08 (d, J=6.28 Hz, 1H), 7.86-7.83 (d, J=8.63 Hz, 1H), 3.87 (s, 3H). HPLC (Method A) Rt 4.32 min (Purity: 99.6%).

Step 2: Methyl 2-chloro-4-cyano-5-fluorobenzoate

Methyl 4-bromo-2-chloro-5-fluorobenzoate (2.10 g; 7.85 mmol; 1 eq.), zinc cyanide (553.15 mg; 4.71 mmol), tris(dibenzylideneacetone)dipalladium(0) (57.52 mg; 0.06 mmol), 1,1'-bis(diphenylphosphino)ferrocene (69.64 mg; 0.13 mmol; 0.02 eq.), zinc (20.54 mg; 0.31 mmol; 0.04 eq.) and zinc acetate (57.62 mg; 0.31 mmol; 0.04 eq.) were put in dry DMF (21 mL). The reaction mixture was purged with $N_2$ and then heated to 90° C. for 12 hours. The reaction mixture was cooled to RT, filtered over a pad of celite and washed with EtOAc. The organic phase was washed with water, brine, dried over $MgSO_4$ and concentrated affording the title compound as a brown solid. It was purified by washing with EtOH affording the title compound as a beige solid used without further purification. $^1H$ NMR (DMSO-$d_6$, 300 MHz) δ 8.36-8.35 (m, 1H), 8-7.97 (m, 1H), 3.90 (s, 3H). HPLC (Method A) Rt 4.02 min (Purity: 92.5%).

Step 3: 2-chloro-4-cyano-5-methoxybenzoic acid

A mixture of methyl 2-chloro-4-cyano-5-fluorobenzoate (840 mg; 3.93 mmol; 1 eq.) and K2CO3 (2 717.55 mg; 19.66 mmol; 5 eq.) in MeOH (16.80 mL) was stirred at RT for 24 hours. The reaction mixture was concentrated and the residue was taken up in water. The aqueous layer was washed with EtOAc then the aqueous phase was acidified with HCl cc and extracted with EtOAc. The combined organic phases were washed with water, brine, dried over $MgSO_4$ and concentrated affording the title compound as a yellow solid used without further (0.63 g, 75%). $^1H$ NMR (DMSO-$d_6$, 300

MHz) δ 14.05 (br s, 1H), 8.04 (s, 1H), 7.51 (s, 1H), 3.96 (s, 3H). HPLC (Method A) Rt 3.11 min (Purity 88.5%).

Step 4: Methyl 2-chloro-4-cyano-5-methoxybenzoate 2-chloro-4-cyano-5-methoxybenzoic acid (600 mg; 2.84 mmol; 1 eq.) was dissolved in MeOH (12 mL). The solution was cooled down to 0° C. $SOCl_2$ (0.62 mL; 8.51 mmol; 3 eq.) was added dropwise. The reaction mixture was stirred at RT for 24 hours. The reaction mixture was concentrated and the residue was taken up in EtOAc. The organic layer was washed with a saturated aqueous solution of $NaHCO_3$, then brine, dried over $MgSO_4$, concentrated affording the title compound as a yellow solid (0.58 g, 90%). $^1$H NMR (DMSO-$d_6$, 300 MHz) δ 8.09 (s, 1H), 7.57 (s, 1H), 3.96 (s, 3H), 3.89 (s, 3H). HPLC (Method A) Rt 4.08 min (Purity: 94.3%).

Step 5: Methyl 4-[amino(hydroxyimino)methyl]-2-chloro-5-methoxy benzoate

Methyl 2-chloro-4-cyano-5-methoxybenzoate (580 mg; 2.57 mmol; 1 eq.) was dissolved in EtOH (11.60 mL). hydroxylamine (0.38 mL; 12.85 mmol; 5 eq.) was added in one portion. The reaction mixture was stirred at RT for 24 hours. The reaction mixture was concentrated affording the title compound as a yellow solid (0.65 g, 97%). $^1$H NMR (DMSO-$d_6$, 300 MHz) δ 9.67 (br s, 1H), 7.49 (s, 1H), 7.43 (s, 1H), 5.77 (br s, 2H), 3.88 (s, 3H), 3.85 (s, 3H). LC/MS (Method B): 259.0 (M+H)$^+$. HPLC (Method A) Rt 1.91 min (Purity: 95.9%).

Intermediate 60: tert-butyl N-{5-[amino(hydroxyimino)methyl]-2-fluorobenzyl}-N-methylglycinate

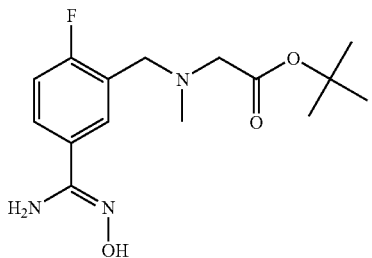

Step 1: tert-butyl N-(5-cyano-2-fluorobenzyl)-N-methylglycinate

A mixture of 5-cyano-2-fluorobenzylbromide (CARBOCORE; CO-0137; 1.50 g; 7.01 mmol; 1 eq.), sarcosine tert-butyl ester hydrochloride (BACHEM; F-1135; 1 527.73 mg; 8.41 mmol; 1.20 eq.) and potassium carbonate (2.91 g; 21.02 mmol; 3 eq.) in CH3CN (25 mL) was stirred at 60° C. for 6 hours then at RT for one night. The acetonitrile was evaporated in vacuo and the resulting mixture diluted with water. Extraction with EtOAc, washing with NaCl sat. solution, drying over magnesium sulfate and concentration in vacuo gave the title compound as a slightly yellow oil (1.9 g; 97%). $^1$H NMR (CDCl$_3$) δ 7.86 (dd, J=6.5, 2.0 Hz, 1H), 7.59-7.53 (m, 1H), 7.13 (t, J=9.0 Hz, 1H), 3.78 (s, 2H), 3.23 (s, 2H), 2.38 (s, 3H), 1.49 (s, 9H). $^{19}$F NMR (CDCl$_3$) δ-108.3. GC/MS: 278. LC/MS (Method B): 279.1 (M+H)$^+$. HPLC (Method A) Rt 2.25 min (Purity: 91.4%).

Step 2: tert-butyl N-{5-[amino(hydroxyimino)methyl]-2-fluorobenzyl}-N-methylglycinate Hydroxylamine (50% in water) (539.42 µL; 8.98 mmol; 5 eq.) was added to a solution of tert-butyl N-(5-cyano-2-fluorobenzyl)-N-methylglycinate, obtained in step 1 (500 mg; 1.80 mmol; 1 eq.) in EtOH (20 mL) and the resulting mixture was stirred at RT for 24 hours. Solvent was evaporated in vacuo and the resulting oily residue was freeze-dried to afford the title compound as a colourless oil (602 mg; quantitative). $^1$H NMR (DMSO-$d_6$, 300 MHz) δ 9.61 (br s, 1H), 7.73 (dd, J=7.3, 2.3 Hz, 1H), 7.62-7.56 (m, 1H), 7.20-7.12 (m, 1H), 5.81 (s, 2H), 3.71 (s, 2H), 3.20 (s, 2H), 2.28 (s, 3H), 1.43 (s, 9H). LC/MS (Method B): 310.1 (M−H)$^−$, 312.2 (M+H)$^+$.

Intermediate 61: {tert-Butoxycarbonyl-[3-(N-hydroxycarbamimidoyl)-benzyl]-amino}-acetic acid tert-butyl ester

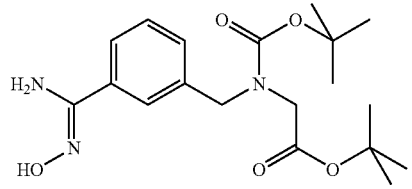

Step 1: tert-Butyl [(3-cyanobenzyl)amino]acetate

To a stirred solution of glycine-ter-butyl ester (5 g, 0.038 mol) in toluene (100 mL). was added 3-cyanobenzaldehyde (5 g, 0.0381 mol) under $N_2$ and refluxed at 140° C. for 2 h. After complete evaporation of the toluene, the reaction mass was cooled to RT and dissolved in dry methanol. Sodium borohydride (2.17 g, 0.0571 mol) was added in portions at 0° C. After 12 h, the reaction mass was evaporated under vacuum, washed with water (100 mL), extracted in DCM (100 mL), dried over sodium sulphate and concentrated under reduced pressure to afford the title compound as a yellow liquid (8.1 g, 86%). $^1$H NMR (DMSO-$d_6$, 400 MHz) δ 7.71-7.72 (m, 2H), 7.63-7.65 (m, 1H), 7.53-7.55 (m, 1H), 5.40-5.41 (m, 1H), 4.53-4.54 (m, 2H), 3.17 (s, 2H), 1.39 (s, 9H).

Step 2: {tert-Butoxycarbonyl-[3-cyanobenzyl]-amino}-acetic acid tert-butyl ester To a stirred solution of tert-butyl [(3-cyanobenzyl)amino] acetate (8.1 g, 0.0329 mol) in dry THF (100 mL), was added di-tert-butyl dicarbonate (15.79 mL, 0.0724 mol) and N,N-dimethylaminopyridine (0.1 g, 0082 mol) and the mixture was refluxed at 50° C. for a period of 12 hours. The reaction mixture was then concentrated under reduced pressure. The obtained crude product was purified by column using neutral silica gel (60-120 mesh) and pet ether/EtOAc as eluent to afford the title compound as a pale yellow liquid. $^1$H NMR (DMSO-$d_6$, 400 MHz) δ 7.71-7.73 (m, 2H), 7.61-7.63 (m, 1H), 7.53-7.55 (m, 1H), 4.40-4.42 (s, 2H), 3.84 (s, 2H), 1.35-1.37 (m, 18H).

Step 3: {tert-Butoxycarbonyl-[3-(N-hydroxycarbamimidoyl)-benzyl]-amino}-acetic acid tert-butyl ester To a solution of {tert-butoxycarbonyl-[3-cyanobenzyl]-amino}-acetic acid tert-butyl ester (3.5 g, 0.010 mol) in Ethanol (100 mL) under N₂, was added hydroxylamine (1.66 mL, 0.0505 mol) in one portion. After being stirred at RT for 12 h, the reaction mixture was concentrated under reduced pressure to afford the title compound as a pale yellow viscous liquid (3.8 g, 99%). ¹H NMR (DMSO-d₆, 400 MHz) δ 9.59 (s, 1H), 7.53-7.56 (m, 2H), 7.29-7.33 (m, 1H), 7.24-7.26 (m, 1H), 5.76 (s, 2H), 4.37-4.39 (s, 2H), 3.74 (s, 2H), 1.35-1.37 (s, 18H). LC/MS (Method A): 380.0 (M+H)⁺. HPLC (Method B) Rt 5.91 min (Purity: 90.3%).

Intermediate 62: tert-butyl 3-[{3-[amino(hydroxyimino)methyl]benzyl}(methyl)amino]propanoate

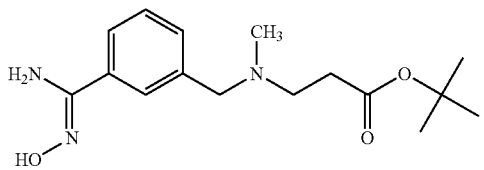

Step 1: 3-[(Methylamino)methyl]benzonitrile

To a stirred solution of methylamine (40% in water) (200 mL) under N₂, was added 3-(bromomethyl)benzonitrile (10 g, 0.051 mol) slowly in small portions over a period of 10 min at 0° C. After being stirred at RT for 3 h, the reaction mixture was extracted with DCM. Then the organic layer was washed with brine and dried over sodium sulphate and concentrated under reduced pressure. The obtained crude was purified using column chromatography on silica gel (pet ether/ethyl acetate) to afford the title compound as a pale yellow liquid (6.1 g, 82%). ¹H NMR (DMSO-d₆, 400 MHz) δ 7.74 (s, 1H), 7.63-7.68 (m, 2H), 7.48-7.52 (m, 1H) 3.66 (s, 2H), 2.22 (s, 3H).

Step 2: tert-Butyl 3-[(3-cyanobenzyl)(methyl)amino]propanoate

To a stirred solution of 3-[(methylamino)methyl]benzonitrile (6.1 g, 0.0417 mol) and sodium bicarbonate (7 g, 0.0834 mol) in acetonitrile (70 mL) under N₂, was added tert-butyl-3-bromo-propanoate (7 mL, 0.0417 mol) in dropwise. After being stirred at RT for 12 h, the reaction mixture was filtered and the filterate was concentrated under reduced pressure. The obtained crude was purified using column chromatography on neutral silica gel (pet ether/EtOAc) to afford the title compound as a pale yellow liquid. ¹H NMR (DMSO-d₆, 400 MHz) δ 7.69-7.70 (s, 2H), 7.59-7.61 (m, 1H), 7.49-7.53 (m, 1H), 3.49 (s, 2H), 2.56-2.59 (m, 2H), 2.34-2.38 (m, 2H), 2.09 (s, 3H), 1.38 (s, 9H).

Step 3: tert-butyl 3-[{3-[amino(hydroxyimino)methyl]benzyl}(methyl)amino]propanoate To a solution of tert-butyl 3-[(3-cyanobenzyl)(methyl) amino]propanoate (4.5 g, 0.0164 mol) in ethanol (60 mL) under N₂, was added hydroxylamine (2.5 mL, 0.082 mol) in one portion. After being stirred at RT for 12 h, the reaction mixture was concentrated under reduced pressure to afford the title compound as a white gummy solid (4.5 g, 84%). ¹H NMR (DMSO-d₆, 400 MHz) δ 9.56 (s, 1H), 7.51-7.53 (m, 2H), 7.27-7.31 (m, 2H), 5.74 (s, 2H), 3.44 (s, 2H), 2.55-2.59 (m, 2H), 2.34-2.38 (m, 2H), 2.09 (s, 3H), 1.37 (s, 9H). LC/MS (Method A): 308.2 (M+H)⁺. HPLC (Method B) Rt 5.18 min (Purity: 96.5%).

Intermediate 63: tert-butyl N-{5-[amino(hydroxyimino)methyl]-2-fluorobenzyl}-N-methyl-beta-alaninate

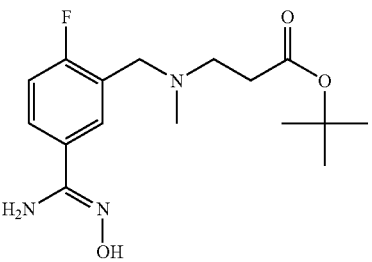

Step 1: tert-butyl N-(5-cyano-2-fluorobenzyl)-N-methyl-beta-alaninate

A mixture of 5-cyano-2-fluorobenzylbromide (CARBOCORE; CO-0137; 1.50 g; 7.01 mmol; 1 eq.), tert-butyl N-methyl-beta-alaninate (1.34 g; 8.41 mmol; 1.20 eq.) (prepared as described by Howard N., I. et al. in Bioorg. Med. Chem. 11 (2003), 3083-3099) and potassium carbonate (1.94 g; 14.02 mmol; 2 eq.) in CH3CN (25 mL) was stirred at 60° C. for 6 hours then at RT for 16 hours. The acetonitrile was evaporated in vacuo and the resulting mixture diluted with water. Extraction with EtOAc, washing with NaCl sat. solution, drying over sodium sulfate and concentration in vacuo gave title compound as a slightly yellow oil (1.9 g; 92%). ¹H NMR (CDCl₃) δ 7.79 (dd, J=6.7, 2.1 Hz, 1H), 7.57-7.52 (m, 1H), 7.11 (t, J=8.9 Hz, 1H), 3.57 (s, 2H), 2.74 (t, J=7.1 Hz, 2H), 2.43 (t, J=7.1 Hz, 2H), 2.22 (s, 3H), 1.45 (s, 9H). LC/MS (Method B): 293.2 (M+H)⁺. HPLC (Method A) Rt 2.44 min (Purity: 86.4%).

Step 2: tert-butyl N-{5-[amino(hydroxyimino)methyl]-2-fluorobenzyl}-N-methyl-beta-alaninate Hydroxylamine (50% in water) (513.54 μL; 8.55 mmol; 5 eq.) was added to a solution of tert-butyl N-(5-cyano-2-fluorobenzyl)-N-methyl-beta-alaninate, obtained in step 1 (500 mg; 1.71 mmol; 1 eq.) in EtOH (20 mL) and the resulting mixture was stirred at RT for 24 hours. Solvent was evaporated in vacuo and the resulting oily residue was freeze-dried to afford the title compound as a colourless oil (560 mg; quantitative). ¹H NMR (CDCl₃) δ 7.74 (dd, J=6.6, 2.2 Hz, 1H), 7.58-7.53 (m, 1H), 7.03 (t, J=9.1 Hz, 1H), 5.10 (s, 2H), 3.59 (s, 2H), 2.69 (t, J=7.0 Hz, 2H), 2.44 (t, J=6.9 Hz, 2H), 2.28 (s, 3H), 1.46 (s, 9H). LC/MS (Method B): 326.2 (M+H)⁺. HPLC (Method A) Rt 2.18 min (Purity: 86.2%).

Intermediate 64: N'-hydroxy-3-(methylsulfonyl)benzenecarboximidamide

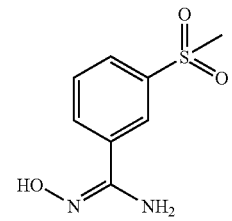

The title compound was obtained following procedure described for Intermediate 1 step 2 but starting from 3-methylsulfonylbenzonitrile (3.03 g; 16.72 mmol) to give the title compound as a white powder (2.69 g, 75%). $^1$H NMR (DMSO-d$_6$, 300 MHz) δ 9.88 (s, 1H), 8.21 (t, J=1.68 Hz, 1H), 8.00 (dt, J=1.44, 7.93 Hz, 1H), 7.91 (dt, J=1.49, 7.80 Hz, 1H), 7.66 (t, J=7.84 Hz, 1H), 6.03 (s, 2H), 3.23 (s, 3H).

Intermediate 65: tert-butyl (2-{3-[amino(hydroxyimino)methyl]phenyl}ethoxy)acetate

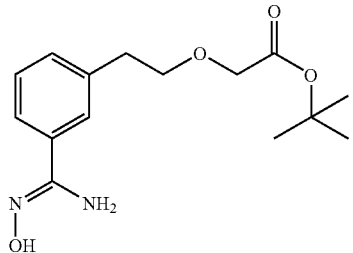

Step 1: tert-butyl [2-(3-cyanophenyl)ethoxy]acetate

To a solution of 3-(2-hydroxy-ethyl)-benzonitrile (1 g; 6.79 mmol) in toluene (20 mL), was added tetrabutylammonium hydrogen sulfate (230.70 mg; 0.68 mmol; 0.10 eq.) and NaOH (20 mL; 5 M; 10 mmol) followed by the addition of tert-butyl bromoacetate (2 mL; 13.59 mmol). Reaction mixture was stirred at RT under vigorous stirring for 9 h. After this time, the aqueous phase was removed and the organic phase was diluted with EtOAc (50 mL), washed with water (50 mL) and brine (50 mL). The combined organic layers were dried over magnesium sulfate, filtered and concentrated to give the title compound as a yellow powder (1.42 g; 80%). $^1$H NMR (DMSO-d$_6$, 300 MHz) δ 7.74-7.73 (m, 1H), 7.68-7.65 (m, 1H), 7.63-7.59 (m, 1H), 7.51-7.46 (m, 1H), 3.97 (s, 2H), 3.69 (t, J=6.5 Hz, 2H), 2.88 (t, J=6.5 Hz, 2H), 1.40 (s, 9H). LC/MS (Method B): 262.1 (M+H)$^+$.

Step 2: tert-butyl (2-{3-[amino(hydroxyimino)methyl]phenyl}ethoxy)acetate tert-butyl [2-(3-cyanophenyl)ethoxy]acetate obtained in step 1 (1.42 g; 5.43 mmol) was dissolved in EtOH (28.40 mL) to which was added hydroxylamine (401.26 μL; 50%, 27.17 mmol). Reaction mixture was stirred at RT for 18 h after which solvents were removed under vacuum, solubilized in a water/ACN mixture (1:1) and lyophilized to give the desired compound as a sticky colorless oil (1.32 g; 82%). $^1$H NMR (DMSO-d6, 300 MHz) δ 9.56 (bs, 1H), 7.53-7.48 (m, 2H), 7.27-7.25 (m, 2H), 5.76 (bs, 2H), 3.96 (s, 2H), 3.67 (t, J=6.9 Hz, 2H), 2.83 (t, J=6.5 Hz, 2H). LC/MS (Method B): 295.2 (M+H)$^+$.

Intermediate 66: Ethyl 4-{4-[amino (hydroxyimino)methyl]-2-fluorophenoxy}butanoate

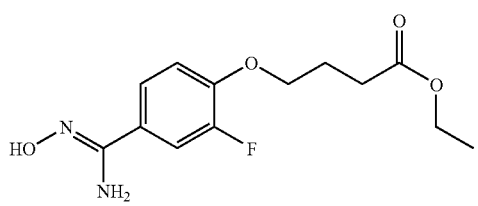

Step 1: Ethyl 4-(4-cyano-2-fluorophenoxy)butanoate 3-fluoro-4-hydroxybenzonitrile (ABCR F03756F.AB, 2 g; 14.59 mmol; 1 eq.) was dissolved in DMF (40 mL). Then ethyl 4-bromobutyrate (4.27 g; 21.88 mmol; 1.50 eq.) and potassium carbonate (3.02 g; 21.88 mmol; 1.50 eq.) were added to the reaction mixture and it was heated to 80° C. for 2 hours. The reaction mixture was cooled to RT and diluted with EtOAc. The organic layer was washed with water (3×), brine, dried over MgSO$_4$ and concentrated affording the title compound as a yellow solid (3.56 g, 97%). $^1$H NMR (DMSO-d$_6$, 300 MHz) δ 7.86-7.83 (d, J=11.43 Hz, 1H), 7.68-7.66 (d, J=8.73 Hz, 1H), 7.37-7.32 (m, 1H), 4.20-4.03 (m, 4H), 2.46-2.44 (m, 2H), 2.03-1.99 (m, 2H), 1.19-1.15 (t, J=6.62 Hz, 3H). HPLC (Method A) Rt 4.47 min (Purity: 98.8%).

Step 2: Ethyl 4-{4-[amino(hydroxyimino)methyl]-2-fluorophenoxy}butanoate

Ethyl 4-(4-cyano-2-fluorophenoxy)butanoate (3.50 g; 13.93 mmol; 1 eq.) was dissolved in EtOH (70 mL). Hydroxylamine (2.05 mL; 69.65 mmol; 5 eq.) was added in one portion. The reaction mixture was stirred at RT for 12 hours. The reaction mixture was concentrated under vacuum affording the title compound as a white solid. (3.82 g, 96%). $^1$H NMR (DMSO-d$_6$, 300 MHz) δ 9.59 (br s, 1H), 7.49-7.43 (m, 2H), 7.18-7.12 (m, 1H), 5.80 (br s, 2H), 4.11-4.02 (m, 4H), 2.46-2.43 (m, 2H), 2.03-1.94 (quint., J=6.97 Hz, 2H), 1.20-1.15 (t, J=7.11 Hz, 3H). LC/MS (Method B): 285.1 (M+H)$^+$. HPLC (Method A) Rt 2.67 min (Purity: 99.1%).

Intermediate 67: Ethyl 4-{3-[amino(hydroxy imino)methyl]phenoxy}butanoate

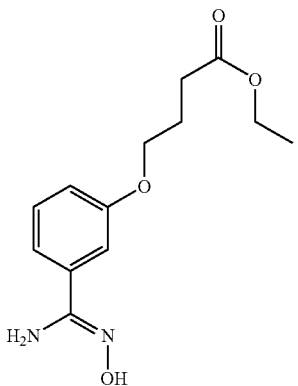

Step 1: Ethyl 4-(3-cyanophenoxy)butanoate 3-cyanophenol (2 000 mg; 16.79 mmol; 1 eq.) was dissolved in DMF (40 mL). Then ethyl 4-bromobutyrate (3 602.35 mg; 18.47 mmol; 1.10 eq.) and K2CO3 (3 480.55 mg; 25.18 mmol; 1.50 eq.) were added to the reaction mixture. The reaction mixture was heated to 80° C. for 2 hours. The reaction mixture was cooled to RT and diluted with EtOAc. The organic layer was washed with water (3×), brine, dried over MgSO$_4$ and concentrated affording the title compound as a colourless liquid (3.92 g, 96%). $^1$H NMR (DMSO-d$_6$, 300 MHz) δ 7.51-7.38 (m, 3H), 7.29-7.26 (m, 1H), 4.10-4.03 (m, 4H), 2.48-2.43 (t, J=7.37 Hz, 2H), 2.02-1.93 (m, 2H), 1.20-1.15 (t, J=7.10 Hz, 3H). HPLC (Method A) Rt 4.49 min (Purity: 97.9%).

Step 2: Ethyl 4-{3-[amino(hydroxyimino)methyl]phenoxy}butanoate

Ethyl 4-(3-cyanophenoxy)butanoate (3.79 g; 16.25 mmol; 1 eq.) was suspended in EtOH (75.80 mL). Hydroxylamine (2.40 mL; 81.24 mmol; 5 eq.) was added in one portion and the reaction mixture was stirred at RT for 24 hours. The reaction mixture was concentrated affording the title compound as a white solid (4.29 g, 99%). $^1$H NMR (DMSO-$d_6$, 300 MHz) δ 9.61 (br s, 1H), 7.27-7.20 (m, 3H), 6.94-6.90 (m, 1H), 5.79 (br s, 2H), 4.11-3.98 (m, 4H), 2.48-2.44 (t, J=7.15 Hz, 2H), 2.01-1.93 (m, 2H), 1.20-1.15 (t, J=7.03 Hz, 3H). LC/MS (Method A): 266.8 (M+H)$^+$. HPLC (Method A) Rt 2.62 min (Purity: 98.8%).

Intermediate 68: 3-(1,3-dioxolan-2-yl)-N'-hydroxybenzenecarboximidamide

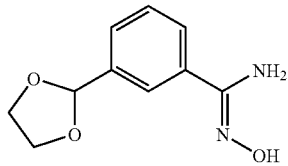

Step 1: 3-(1,3-dioxolan-2-yl)benzonitrile

To a solution of 3-formyl-benzonitrile (2 g, 15.25 mmol, 1 eq) in dry toluene (30 mL), paratoluenesulfonic acid (262 mg, 1.5 mmol, 0.1 eq) and ethylene glycol (12.8 mL, 228 mmol, 15 eq) were added and the mixture was heated to reflux in a Dean-Stark apparatus overnight. The toluene was concentrated and the reaction mixture purified by flash chromatography (EtOAc/cHex) to afford the title compound as a colorless liquid (2000 mg, 74%). $^1$H NMR: (CDCl$_3$, 300 MHz) δ 7.78 (m, 1H), 7.69 (m, 1H), 7.64 (m, 1H), 7.48 (t, J=7.7 Hz, 1H), 5.81 (s, 1H), 4.08 (m, 4H). HPLC (Method A) Rt: 2.45 min (purity: 92.1%).

Step 2: 3-(1,3-dioxolan-2-yl)-N-hydroxybenzenecarboximidamide

Title compound was prepared following procedure and work up described for Intermediate 47 step 2 but starting from 3-(1,3-dioxolan-2-yl)benzonitrile obtained in step 1 (2000 mg; 11.42 mmol) (RT for 16 h). Title compound was obtained as an oil (2300 mg, 97%). $^1$H NMR: (DMSO-$d_6$, 300 MHz) δ 9.65 (s, 1H), 7.75 (m, 1H), 7.68 (m, 1H), 7.46-7.36 (m, 2H), 5.75 (s, 1H), 4.15-3.90 (m, 4H), 1.77 (s, 1H), 1.13 (s, 1H). LC/MS (Method B): 209.1 (M+H)$^+$.

Intermediate 69: (Tert-butyl {3-[amino(hydroxyimino)methyl]benzyl}(2-hydroxyethyl)carbamate

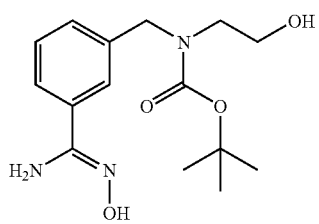

Step 1: 3-{[(2-Hydroxyethyl)amino]methyl}benzonitrile

To a stirred solution of ethanolamine (2.32 g, 0.0381 mol) in toluene (100 mL), was added 3-cyanobenzaldehyde (5 g, 0.0381 mol) under N$_2$ and refluxed at 140° C. After complete distilling out of toluene, the reaction mass was cooled to RT and dissolved in dry methanol (100 mL). To this solution was added in portions sodium borohydride (2.17 g, 0.0571 mol) at 0° C. The reaction mass was evaporated under pressure, washed with water (100 mL), extracted in DCM (100 mL), dried using sodium sulphate and concentrated under reduced pressure. The obtained crude was purified using column chromatography on silica and chloroform/methanol as eluent to afford the title compound as a white solid. $^1$H NMR (DMSO-$d_6$, 400 MHz) δ 7.76 (s, 1H), 7.65-7.69 (m, 2H), 7.49-7.52 (m, 1H), 4.45-4.48 (m, 1H), 3.74 (s, 2H), 3.42-3.46 (m, 2H), 2.51-2.54 (m, 2H).

Step 2: tert-Butyl 3-cyanobenzyl(2-hydroxyethyl)carbamate

To a stirred solution of 3-{[(2-Hydroxyethyl)amino]methyl}benzonitrile (4 g, 0.0227 mol) in dry THF (100 mL), was added di-tert-butyl dicarbonate (5.44 mL, 0.0249 mol) and refluxed at 70° C. for a period of 6 hours. The reaction mixture was then concentrated under reduced pressure to afford the title compound as a pale yellow liquid (6 g, 96%). $^1$H NMR (DMSO-$d_6$, 400 MHz) δ 7.71-7.73 (m, 1H), 7.64 (s, 1H), 7.54-7.55 (d, 2H), 4.68 (bs, 1H), 4.45 (s, 2H), 3.46 (s, 2H), 3.27-3.30 (m, 2H), 1.41-1.45 (d, 9H).

Step 3: tert-Butyl 3-[(Z)-amino(hydroxyimino)methyl]benzyl(2-hydroxyethyl)carbamate Title compound was prepared following procedure described for Intermediate 1 step 2 but starting from tert-Butyl 3-cyanobenzyl(2-hydroxyethyl)carbamate obtained from step 2 (6 g, 0.0217 mol) (RT for 12 h). Reaction mixture was concentrated under reduced pressure and purified by column chromatography using silica gel and chloroform/methanol as a eluent to afford the title compound as a white solid. $^1$H NMR (DMSO-$d_6$, 400 MHz) δ 9.60 (s, 1H), 7.52-7.53 (m, 2H), 7.31-7.34 (m, 1H), 7.19-7.20 (m, 1H), 5.76 (s, 1H), 4.65-4.68 (m, 1H), 4.42 (s, 2H), 3.42-3.47 (m, 2H), 3.13-3.16 (m, 2H), 1.33-1.41 (m, 9H). LC/MS (Method A): 310.0 (M+H)+. HPLC (Method B) Rt 4.57 min (Purity: 94.1%).

Intermediate 70: (Tert-butyl {3-[amino(hydroxy-imino)methyl]benzyl}(2-methoxyethyl)carbamate

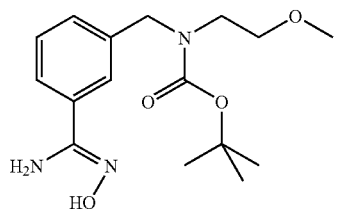

Step 1: 3-{[(2-Methoxyethyl)amino]methyl}benzonitrile

To a stirred solution of 2-methoxyethylamine (5.73 mL, 0.0612 mol) and triethylamine (4.05 mL, 0.0306 mol) in dry DCM (100 mL), was added 3-(bromomethyl)benzonitrile (6 g, 0.0306 mol) in portions over a period of 10 min at 0° C. After being stirred at RT for 5 h, the reaction mixture washed with water (2×100 mL), dried using sodium sulphate and concentrated under reduced pressure. The obtained crude was purified using column chromatography on silica gel (chloroform/methanol) to afford the title compound as a pale yellow liquid (5 g, 86%). $^1$H NMR (DMSO-$d_6$, 400 MHz) δ 7.75 (s, 1H), 7.64-7.68 (m, 2H), 7.48-7.52 (m, 1H), 3.73 (s, 2H), 3.35-3.38 (m, 2H), 3.21 (s, 3H), 2.59-2.61 (m, 2H).

Step 2: Tert-butyl 3-cyanobenzyl(2-methoxyethyl)carbamate

To a stirred solution of 3-{[(2-methoxyethyl)amino]methyl}benzonitrile (5.8 g, 0.0304 mol) in dry THF (100 mL), was added di-tert-butyl dicarbonate (6.62 mL, 0.0335 mol) and refluxed at 70° C. for a period of 6 hours. The reaction mixture was then concentrated under reduced pressure to afford the title compound (7.4 g, 84%) as a pale yellow liquid. 1H NMR (DMSO-d6, 400 MHz) δ 7.71-7.72 (t, 1H), 7.63 (s, 1H), 7.54-7.55 (d, 2H), 4.43 (s, 2H), 3.29-3.38 (m, 4H), 3.19 (s, 3H), 1.27-1.37 (d, 9H).

Step 3: tert-Butyl 3-[amino(hydroxyimino)methyl]benzyl(2-methoxyethyl)carbamate

Title compound was prepared following procedure and work up described for Intermediate 47 step 2 but starting from tert-Butyl 3-cyanobenzyl(2-methoxyethyl)carbamate obtained in step 2 (7.4 g, 0.0254 mol) (RT for 12 h). Title compound was obtained as a pale yellow gummy liquid (7.1 g, 86%). $^1$H NMR (DMSO-$d_6$, 400 MHz) δ 9.59 (s, 1H), 7.52-7.54 (m, 2H), 7.30-7.34 (m, 1H), 7.19-7.21 (m, 1H), 5.75 (s, 2H), 4.40 (s, 2H), 3.37-3.40 (m, 2H), 3.21-3.30 (m, 5H), 1.32-1.41 (m, 9H). LC/MS (Method A): 324.0 (M+H)+. HPLC (Method B) Rt 5.23 min (Purity: 96.2%).

Intermediate 71: 4-[Amino(hydroxyimino)methyl]benzamide

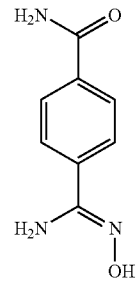

The title compound was obtained following procedure described for Intermediate 1 step 2 but starting from 4-cyanobenzamide (396.1 mg, 2.71 mmol) (60° C. for 24 h). Solvents were removed under vacuum, solid residue was triturated in water, filtered and dried under vacuum to give the title compound as a white solid (460 mg, 94%). $^1$H NMR (DMSO-$d_6$, 300 MHz) δ 9.78 (bs, 1H), 7.98 (bs, 1H), 7.87-7.84 (m, 2H), 7.74-7.72 (m, 2H), 7.38 (bs, 1H), 5.88 (bs, 2H).

Intermediate 72: N'-hydroxy-3-(hydroxymethyl)benzenecarboximidamide

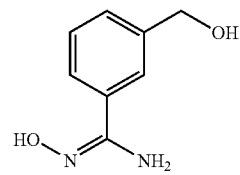

The title compound was obtained following procedure and work up described for Intermediate 47 step 2 but starting from 3-cyanobenzyl alcohol (360.8 mg, 2.71 mmol). It was obtained as a white powder (419 mg, 92%). $^1$H NMR (DMSO-$d_6$, 300 MHz) δ 9.57 (s, 1H), 7.63 (m, 1H), 7.53-7.50 (m, 1H), 7.32-7.30 (m, 2H), 5.75 (bs, 2H), 5.20 (t, J=5.7 Hz, 1H), 4.49 (t, J=5.7 Hz, 2H).

Intermediate 73: N'-hydroxy-3-(2-hydroxyethyl)benzenecarboximidamide

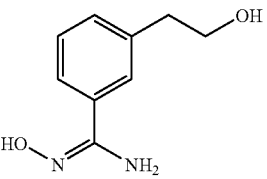

The title compound was obtained following procedure and work up described for Intermediate 47 step 2 but starting from 3-(2-hydroxy-ethyl)-benzonitrile (2 g, 13.59 mmol). Lyophilization of the reaction mixture gave the title compound as a white powder. ¹H NMR (DMSO-d₆, 300 MHz) δ 9.56 (s, 1H), 7.51-7.46 (m, 2H), 7.28-7.19 (m, 2H), 5.75 (bs, 2H), 4.64 (t, J=5.2 Hz, 1H), 3.63-3.57 (m, 2H), 2.71 (t, J=7.1 Hz, 2H). LC/MS (Method B): 181.1 (M+H)⁺.

Intermediate 74: N'-hydroxy-4-(hydroxymethyl)benzenecarboximidamide

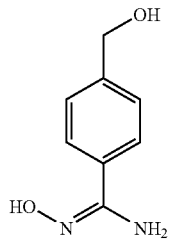

The title compound was obtained following procedure and work up described for Intermediate 47 step 2 but starting from 4-(hydroxymethyl)benzonitrile (500.00 mg; 3.76 mmol). It was isolated as a colorless oil that crystallized upon standing (649 mg, quantitative). ¹H NMR (DMSO-d₆, 300 MHz) δ 9.55 (s, 1H), 7.62 (d, J=8.2 Hz, 2H), 7.29 (d, J=8.2 Hz, 2H), 5.76 (bs, 2H), 5.19 (t, J=5.7 Hz, 1H), 4.49 (d, J=5.7 Hz, 2H). LC/MS (Method B): 167.0 (M+H)⁺

Intermediate 75: N'-hydroxy-3-[(2-methoxyethoxy)methyl]benzenecarboximidamide

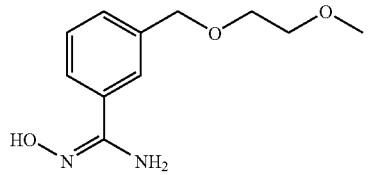

Step 1: 3-[(2-methoxyethoxy)methyl]benzonitrile

A solution of 3-(bromomethyl)benzonitrile (1 g, 5.1 mmol) in 2-methoxyethanol (10 mL) and n-ethyldiisopropylamine (0.89 mL, 5.1 mmol) was heated under microwave irradiations for 2 hours at 150° C. After this time, reaction mixture was diluted with EtOAc (200 mL), washed with water and brine to give the title compound as a colorless oil (800 mg, 81%). ¹H NMR (DMSO-d₆, 300 MHz) δ 7.76-7.74 (m, 2H), 7.68-7.65 (m, 1H), 7.59-7.54 (m, 1H), 4.54 (s, 2H), 3.59-3.56 (m, 2H), 3.51-3.47 (m, 2H), 3.25 (s, 3H). HPLC (Method A) Rt 3.09 min (Purity: 82.9%).

Step 2: N'-hydroxy-3-[(2-methoxyethoxy)methyl]benzenecarboximidamide

The title compound was obtained following procedure and work up described for Intermediate 47 step 2 but starting from 3-[(2-methoxyethoxy)methyl]benzonitrile obtained in step 1 (0.80 g; 4.18 mmol) as a yellowish oil (0.99 g, quantitative). ¹H NMR (DMSO-d₆, 300 MHz) δ 9.61 (bs, 1H), 7.63 (bs, 1H), 7.59-7.55 (m, 1H), 7.37-7.32 (m, 2H), 5.79 (bs, 2H), 4.49 (s, 2H), 3.57-3.54 (m, 2H), 3.50-3.46 (m, 2H), 3.25 (s, 3H). LC/MS (Method B): 225.1 (M+H)⁺.

Intermediate 76: N'-hydroxy-3-[(2-hydroxyethoxy)methyl]benzenecarboximidamide

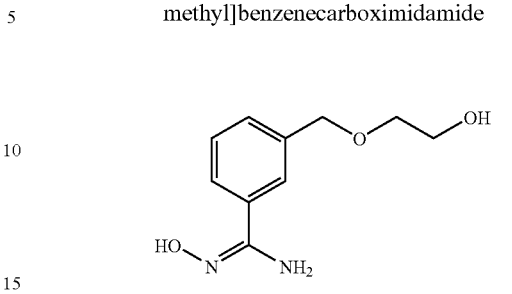

Step 1: 3-[(2-hydroxyethoxy)methyl]benzonitrile

The title compound was obtained following procedure described for Intermediate 75 but starting from 3-(bromomethyl)benzonitrile (1 g, 5.1 mmol) and ethylene glycol (10 mL) to give the title compound as a yellowish oil. ¹H NMR (DMSO-d₆, 300 MHz) δ 7.80 (bs, 1H), 7.76-7.74 (m, 2H), 7.69-7.67 (m, 1H), 7.59-7.53 (m, 1H), 4.68 (t, J=5.4 Hz, 1H), 4.55 (s, 2H), 3.58-3.53 (m, 2H), 3.50-3.46 (m, 2H). HPLC (Method A) Rt 2.31 min (Purity: 83.5%).

Step 2: N'-hydroxy-3-[(2-hydroxyethoxy)methyl]benzenecarboximidamide

The title compound was obtained following procedure and work up described for Intermediate 47 step 2 but starting from 3-[(2-hydroxyethoxy)methyl]benzonitrile obtained in step 1 (0.90 g; 5.08 mmol) to give the title compound as a yellowish oil (1.26 g, quantitative). ¹H NMR (DMSO-d₆, 300 MHz) δ 9.61 (s, 1H), 7.64 (bs, 1H), 7.60-7.55 (m, 1H), 7.37-7.31 (m, 2H), 5.75 (bs, 2H), 4.66-4.62 (m, 1H), 4.50 (s, 2H), 3.56-3.51 (m, 2H), 3.48-3.44 (m, 2H). LC/MS (Method B): 211.1 (M+H)⁺.

Intermediate 77: N-Hydroxy-3-{[(2-methoxy-ethyl)-methyl-amino]-methyl}-benzamidine

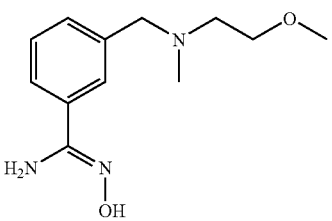

Step 1: 3-{[(2-Methoxy-ethyl)-methyl-amino]methyl}-methyl)

To a solution of N-(2-methoxyethyl)-N-methylamine (3.8 g, 42.8 mmol) and TEA (4.68 mL, 46.4 mmol) in ACN (75 mL) under N2, was added 3-(bromomethyl)benzonitrile (7 g, 35.7 mmol) at 0° C. After being stirred at RT for 5 h, the reaction mass was concentrated under reduced pressure and the resulting pale yellow liquid diluted with DCM and washed water with to afford the title compound as a pale yellow liquid (6.4 g, 87%). ¹H NMR (DMSO-d₆, 400 MHz) δ

7.69-7.71 (m, 2H), 7.62-7.64 (m, 1H), 7.50-7.54 (m, 1H), 3.54 (s, 2H), 3.41-3.44 (m, 2H), 3.21 (s, 3H), 2.48-2.52 (m, 2H), 2.14 (s, 3H).

Step 2: N-Hydroxy-3-{[(2-methoxy-ethyl)-methyl-amino]-methyl}-benzamidine

The title compound was obtained following procedure and work up described for Intermediate 47 step 2 but starting from 3-{[(2-Methoxy-ethyl)-methyl-amino]-methyl}-benzonitrile obtained in step 1 (6.4 g, 31.3 mmol) to give the title compound as yellow viscous liquid (6.9 g, 93%). $^1$H NMR (DMSO-d$_6$, 400 MHz) δ 9.57 (s, 1H), 7.59 (s, 1H), 7.50-7.53 (m, 1H), 7.28-7.29 (m, 2H), 5.75 (s, 2H), 3.48 (s, 2H), 3.41-3.44 (m, 2H), 3.21 (s, 3H), 2.48-2.52 (m, 2H), 2.13 (s, 3H). LC/MS (Method A): 238.1 (M+H)$^+$.

Intermediate 78: N-Hydroxy-3-{[2-methoxy-ethyl)-methyl-amino]-methyl}-benzamidine

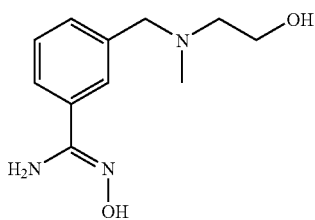

Step 1: 3-{[(2-Hydroxy-ethyl)-methyl-amino]methyl}-benzonitrile

To a solution of 2-(methylamino)ethanol (4 mL, 51 mmol) and TEA (4 mL, 28.05 mmol) in DCM (75 mL) under N$_2$, was added 3-(bromomethyl)benzonitrile (5 g, 25.50 mmol) at 0° C. and the mixture was stirred at RT for 30 min. After this time, reaction mixture was concentrated under reduced pressure and the remaining residue was dissolved in DCM and washed with water to give the title compound as a colorless liquid (4.9 g, 100%). $^1$H NMR (DMSO-d$_6$, 400 MHz) δ 7.76 (s, 1H), 7.69-7.71 (m, 2H), 7.63-7.65 (m, 1H), 7.49-7.53 (m, 1H), 4.41-4.43 (m, 1H), 3.47-3.51 (m, 2H), 3.32 (m, 2H), 2.40-2.43 (m, 2H), 2.13 (s, 3H).

Step 2: N-Hydroxy-3-{[(2-hydroxy-ethyl)-methyl-amino]-methyl}-benzamidine

The title compound was obtained following procedure and work up described for Intermediate 47 step 2 but starting from 3-{[(2-Hydroxy-ethyl)-methyl-amino]-methyl}-benzonitrile obtained in step 1 (4.9 g, 26.28 mmol) to give the title compound as white gummy solid (5.7 g, 99%). $^1$H NMR (DMSO-d$_6$, 400 MHz) δ 9.58 (s, 1H), 7.60 (s, 1H), 7.51-7.54 (m, 1H), 7.28-7.31 (m, 2H), 5.76-7.83 (s, 2H), 4.38 (bs, 1H), 3.48-3.51 (m, 4H), 2.40-2.43 (m, 2H), 2.13 (m, 3H). LC/MS (Method A): 224.1 (M+H)$^+$. HPLC (Method B): Rt 0.7 min, (Purity 91.1%).

Example 1

2-fluoro-4-{5-[2'-(trifluoromethyl)biphenyl-4-yl]-1,2,4-oxadiazol-3-yl}benzoic acid

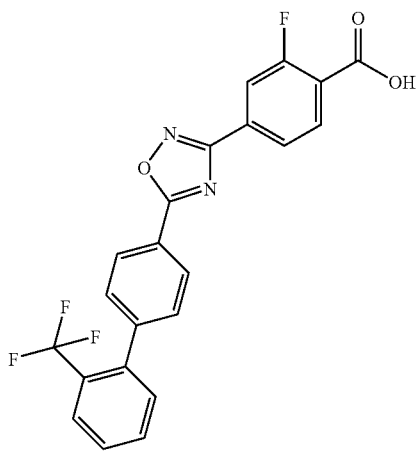

Step 1: methyl 2-fluoro-4-{5-[2'-(trifluoromethyl)biphenyl-4-yl]-1,2,4-oxadiazol-3-yl}benzoate In a microwave vial were added 4-(2-trifluoromethylphenyl)benzoic acid (Fluorochem, 53.2 mg; 0.20 mmol; 1 eq.), triphenylphosphine polymer bound (375 mg; 0.60 mmol; 3 eq.) and trichloroacetonitrile (30 μl; 0.30 mmol; 1.50 eq.). Anhydrous THF (2 mL) was added and the reaction vessel was sealed and heated to 100° C. for 5 min in the microwave. After cooling, the reaction vessel was uncapped and without filtering, Intermediate 1 (46.7 mg; 0.22 mmol; 1.10 eq.) in anhydrous THF (2 mL) was added to the solution along with DIEA (69 μl; 0.40 mmol; 2 eq.). The reaction was capped and heated at 150° C. for 15 min. After cooling, the reaction vessel was uncapped again and the resin was filtered, the filtrate passed through an NH2 SPE column (2 g) and washed by additional THF (2×2 mL). Solvents were evaporated, affording the title compound as a brown solid (61.9 mg; 70%). It was used in the next step without further purification. LC/MS (Method A): 443.3 (M+H)$^+$. HPLC (Method A), Rt 5.98 min (Purity: 87.9%).

Step 2: 2-fluoro-4-{5-[2'-(trifluoromethyl)biphenyl-4-yl]-1,2,4-oxadiazol-3-yl}benzoic acid Methyl 2-fluoro-4-{5-[2'-(trifluoromethyl)biphenyl-4-yl]-1,2,4-oxadiazol-3-yl}benzoate, obtained in step 1 (56 mg; 0.13 mmol; 1 eq.) was dissolved in a mixture of MeOH (2 mL) and THF (2 mL). Aqueous solution of sodium hydroxide (127 μl; 5 M; 0.63 mmol; 5 eq.) was added and the mixture was stirred overnight at RT. Solvents were concentrated. EtOAc (15 mL) and 0.1N NaOH (10 mL) were added. The two phases were separated and the aqueous phase was acidified with 1 N HCl until pH 2, then extracted with EtOAc (2×10 mL). Combined organic phases were washed with brine and dried over MgSO$_4$, affording the title compound as an off-white solid. LC/MS (Method A): 429.1 (M+H)⁺; 427.1 (M−H)⁻. HPLC (Method A) Rt 5.21 min (Purity: 86.7%).

Example 2

4-[5-(2'-chlorobiphenyl-4-yl)-1,2,4-oxadiazol-3-yl]-2-fluorobenzoic acid

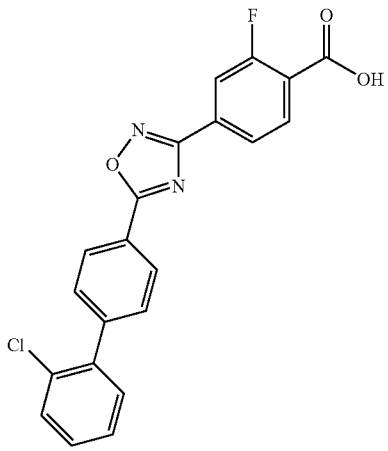

Step 1: methyl 4-[5-(2'-chlorobiphenyl-4-yl)-1,2,4-oxadiazol-3-yl]-2-fluorobenzoate The title compound was prepared following procedure described for example 1, step 1, but starting from 4-(2-chlorophenyl)benzoic acid, (Flrochem, 46.5 mg; 0.20 mmol; 1 eq.) and was isolated as a white solid. It was used in the next step without further purification. LC/MS (Method A): 409.3 (M+H)⁺. HPLC (Method A) Rt 5.92 min (Purity: 100%).

Step 2: 4-[5-(2'-chlorobiphenyl-4-yl)-1,2,4-oxadiazol-3-yl]-2-fluorobenzoic acid The title compound was prepared following procedure described for example 1, step 2, but starting from methyl methyl 4-[5-(2'-chlorobiphenyl-4-yl)-1,2,4-oxadiazol-3-yl]-2-fluorobenzoate, obtained in Step 1 (38 mg; 0.09 mmol; 1 eq.). Solvents were concentrated and EtOAc (20 mL) was added. Then it was washed with 10% citric acid (15 mL), brine (3×15 mL), and dried over MgSO₄, affording the title compound as an off-white solid. LC/MS (Method A): 393.2 (M−H)⁻; 395.1 (M+H)⁺. HPLC (Method A), Rt 5.32 min (Purity: 100%)

Example 3

4-[5-(2',6'-dimethylbiphenyl-4-yl)-1,2,4-oxadiazol-3-yl]-2-fluorobenzoic acid

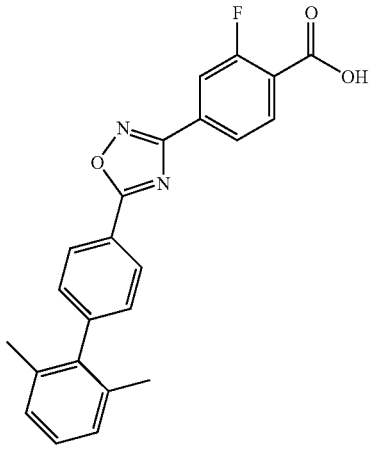

Step 1: methyl 4-[3-(2',6'-dimethylbiphenyl-4-yl)-1,2,4-oxadiazol-3-yl]-2-fluorobenzoate The title compound was prepared following procedure described for example 1, step 1, but starting from Intermediate 16 (46.5 mg; 0.20 mmol; 1 eq.) and was isolated as a brown semi-solid. It was used in the next step without further purification. LC/MS (Method A): 403.3 (M+H)⁺. HPLC (Method A), Rt 6.21 min.

Step 2: 4-[5-(2',6'-dimethylbiphenyl-4-yl)-1,2,4-oxadiazol-3-yl]-2-fluorobenzoic acid The title compound was prepared following procedure described for example 1, step 2, but starting from methyl 4-[5-(2',6'-dimethylbiphenyl-4-yl)-1,2,4-oxadiazol-3-yl]-2-fluorobenzoate, obtained in Step 1 (38 mg; 0.09 mmol; 1 eq.). Solvents were concentrated and EtOAc (20 mL) was added. It was washed with 10% citric acid (15 mL), brine (3×15 mL), and dried over MgSO₄, affording the title compound as a yellow solid (27 mg, 74%). LC/MS (Method A): 387.2 (M−H)⁻; 389.2 (M+H)⁺. HPLC (Method A) Rt 5.36 min (Purity: 90.7%).

Example 4

4-[5-(2,2'-dimethylbiphenyl-4-yl)-1,2,4-oxadiazol-3-yl]-2-fluorobenzoic acid

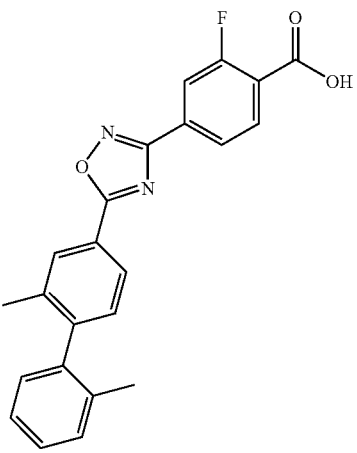

Step 1: methyl 4-[3-(2,2'-dimethylbiphenyl-4-yl)-1,2,4-oxadiazol-3-yl]-2-fluorobenzoate Intermediate 3 (814 mg; 3.60 mmol; 1.20 eq.), Intermediate 1 (637 mg; 3 mmol; 1 eq.) and 1-ethyl-3-(3-dimethylaminopropyl)carbodiimide hydrochloride (690 mg; 3.60 mmol; 1.20 eq.) were dissolved in THF (10 mL) and CH₃CN (10 mL) in a 20 mL microwave vial under N₂. The reaction mixture was stirred overnight at RT. Then n-ethyldiisopropylamine (DIEA) (1.22 mL; 7.20 mmol; 2.40 eq.) was added and the mixture was heated in the microwave at 150° C. for 30 min. The reaction mixture was evaporated to dryness. EtOAc (50 mL) was added and the mixture was washed with HCl 0.1 N (2×25 mL), a saturated aqueous solution of NaHCO₃ (25 mL) and dried over MgSO₄. After evaporation of the solvents, the resulting crude product was purified by flash chromatography (c-hex/EtOAc: 9.5/0.5), affording the title compound as a white powder. $^1$H NMR (DMSO-$d_6$, 300 MHz) δ 8.17-8.16 (m, 1H), 8.12 (d, J=7.2 Hz, 1H), 8.29-8.04 (m, 2H), 7.98 (dd, J=11.1, 2.5 Hz, 1H), 7.39-7.27 (m, 4H), 7.14-7.11 (m, 1H), 3.91 (s, 3H), 2.13 (s, 3H), 2.03 (s, 3H). LC/MS (Method A): 403.0 (M+H)$^+$. HPLC (Method A) Rt 6.23 min (Purity: 93.5%).

Step 2: 4-[5-(2,2'-dimethylbiphenyl-4-yl)-1,2,4-oxadiazol-3-yl]-2-fluorobenzoic acid Methyl 4-[5-(2,2'-dimethylbiphenyl-4-yl)-1,2,4-oxadiazol-3-yl]-2-fluorobenzoate, obtained in step 1 (495 mg; 1.23 mmol; 1 eq.) was dissolved in THF (10 mL) and MeOH (10 mL). Sodium hydroxide (1.23 mL; 5 M; 6.15 mmol; 5 eq.) was added and the mixture was stirred at RT overnight. Aqueous hydrogen chloride (1.23 mL; 5 M; 6.15 mmol; 5 eq.) was added and the mixture was evaporated to dryness. The resulting solid was dissolved in DCM (250 mL) and was washed with water (2×75 mL). The organic layer was dried over MgSO$_4$, filtered and concentrated, affording the title compound as a light yellow solid (457 mg; 95%). $^1$H NMR (DMSO-$d_6$, 300 MHz) δ 8.16-8.01 (m, 4H), 7.94 (dd, J=11.1, 1.4 Hz, 1H), 7.38-7.26 (m, 4H), 7.13-7.11 (m, 1H), 2.13 (s, 3H), 2.03 (s, 3H). LC/MS (Method A): 386.9 (M–H)$^-$; 388.7 (M+H)$^+$. HPLC (Method A) Rt 5.38 min (Purity: 98.0%). CHN analysis: [$C_{23}H_{17}N_2O_3F$] Calculated: C, 71.13%; H, 4.41%; N, 7.21%. Found: C, 71.26%; H, 4.75%; N, 6.83%.

Example 5

2-fluoro-4-[5-(2'-methylbiphenyl-4-yl)-1,2,4-oxadiazol-3-yl]benzoic acid

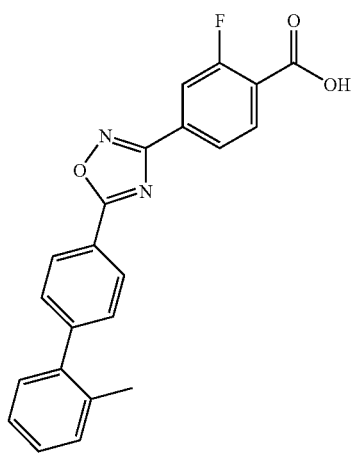

Step 1: methyl 2-fluoro-4-[5-(2'-methylbiphenyl-4-yl)-1,2,4-oxadiazol-3-yl]benzoate The title compound was prepared following procedure described for example 4, step 1, but starting from 4-(2-methylphenyl)benzoic acid (Chemcollect, 106.1 mg; 0.50 mmol; 1 eq.). The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as a off-white solid. LC/MS (Method A): 388.9 (M+H)$^+$. HPLC (Method A) 98.7%; Rt 5.99 min.

Step 2: 2-fluoro-4-[5-(2'-methylbiphenyl-4-yl)-1,2,4-oxadiazol-3-yl]benzoic acid The title compound was prepared following procedure described for example 4, step 2, but starting from methyl 2-fluoro-4-[5-(2'-methylbiphenyl-4-yl)-1,2,4-oxadiazol-3-yl]benzoate, obtained in step 1 (38 mg; 0.10 mmol; 1 eq.). Solvents were concentrated and DCM (50 mL) was added. It was washed with HCl 1N (30 mL). The aqueous phase was extracted with DMC (2×20 mL). Combined organic phases were dried over MgSO$_4$, affording the title compound as a off-white solid (36.8 mg; quantitative). LC/MS (Method A): 373.0 (M–H)$^-$; 375.0 (M+H)$^+$. HPLC (Method A), Rt 5.17 min (Purity: 97.6%).

Example 6

2-fluoro-4-[5-(2-methylbiphenyl-4-yl)-1,2,4-oxadiazol-3-yl]benzoic acid

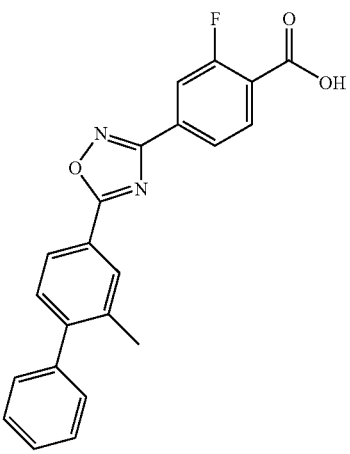

Step 1: methyl 2-fluoro-4-[5-(2-methylbiphenyl-4-yl)-1,2,4-oxadiazol-3-yl]benzoate The title compound was prepared following procedure described for example 4, step 1, but starting from 3-methyl-4-phenylbenzoic acid (106 mg; 0.50 mmol; 1 eq.). The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as a off-white solid. LC/MS (Method A): 389.0 (M+H)$^+$. HPLC (Method A) Rt 6.02 min (Purity: 99.1%).

Step 2: 2-fluoro-4-[5-(2-methylbiphenyl-4-yl)-1,2,4-oxadiazol-3-yl]benzoic acid

The title compound was prepared following procedure described for example 4, step 2, but starting from methyl 2-fluoro-4-[5-(2-methylbiphenyl-4-yl)-1,2,4-oxadiazol-3-yl]benzoate, obtained in Step 1 (75 mg; 0.19 mmol; 1 eq.). Solvents were concentrated and DCM (50 mL) was added. It was washed with HCl 1N (30 mL). The aqueous phase was extracted with DMC (2×20 mL). Combined organic phases were dried over MgSO$_4$, affording the title compound as a off-white solid (64 mg, 88%). LC/MS (Method A): 373.0 (M−H)$^−$; 375.0 (M+H)$^+$. HPLC (Method A), Rt 5.19 min (Purity: 99.3%).

Example 7

2-fluoro-4-[5-(2'-methoxy-2-methylbiphenyl-4-yl)-1,2,4-oxadiazol-3-yl]benzoic acid

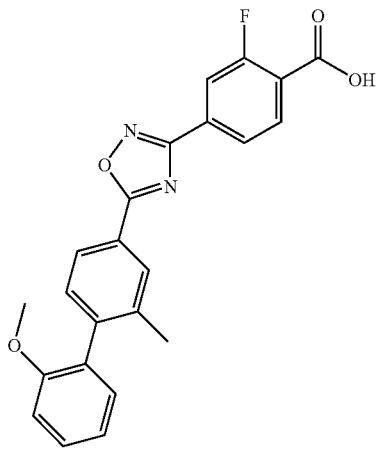

Step 1: methyl 2-fluoro-4-[5-(2'-methoxy-2-methyl-biphenyl-4-yl)-1,2,4-oxadiazol-3-yl]benzoate The title compound was prepared following procedure described for example 4, step 1, but starting from Intermediate 4 (121.1 mg; 0.50 mmol; 1 eq.). The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as a off-white solid (50 mg; 23%). LC/MS (Method A): 419.0 (M+H)$^+$. HPLC (Method A), Rt 6.01 min (Purity: 96.0%).

Step 2: 2-fluoro-4-[5-(2'-methoxy-2-methylbiphenyl-4-yl)-1,2,4-oxadiazol-3-yl]benzoic acid The title compound was prepared following procedure described for example 4, step 2, but starting from methyl 2-fluoro-4-[5-(2'-methoxy-2-methylbiphenyl-4-yl)-1,2,4-oxadiazol-3-yl]benzoate, obtained in Step 1 (45 mg; 0.11 mmol; 1 eq.). Solvents were concentrated and EtOAc (20 mL) was added. It was washed with 10% of AcOH (15 mL), water (15 mL) and was dried over MgSO$_4$, affording the title compound as a off-white solid (45 mg, quantitative). LC/MS (Method A): 403 (M−H)$^−$; 405.0 (M+H)$^+$. HPLC (Method A), Rt 5.11 min (Purity: 97.1%)

Example 8

2-fluoro-4-{5-[2-methyl-2'-(trifluoromethyl)biphenyl-4-yl]-1,2,4-oxadiazol-3-yl}benzoic acid

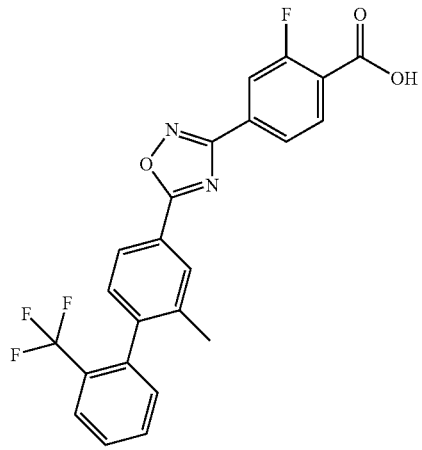

Step 1: methyl 2-fluoro-4-{5-[2-methyl-2'-(trifluoromethyl)biphenyl-4-yl]-1,2,4-oxadiazol-3-yl}benzoate The title compound was prepared following procedure described for example 4, step 1, but starting from Intermediate 5 (140.1 mg; 0.50 mmol; 1 eq.). The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as a off-white solid. LC/MS (Method A): 457.0 (M+H)+. HPLC (Method A), Rt 6.28 min (Purity: 98.8%).

Step 2: 2-fluoro-4-{5-[2-methyl-2'-(trifluoromethyl)biphenyl-4-yl]-1,2,4-oxadiazol-3-yl}benzoic acid The title compound was prepared following procedure described for example 4, step 2, but starting from methyl 2-fluoro-4-{5-[2-methyl-2'-(trifluoromethyl)biphenyl-4-yl]-1,2,4-oxadiazol-3-yl}benzoate, obtained in Step 1 (88 mg; 0.19 mmol; 1 eq.). Solvents were concentrated and EtOAc (20 mL) was added. It was washed with 10% of AcOH (15 mL), water (15 mL) and was dried over MgSO$_4$, affording the title compound as a off-white solid (75.9 mg, 89%). LC/MS (Method A): 441.0 (M−H)⁻; 443.4 (M+H)⁺. HPLC (Method A), Rt 5.40 min (Purity: 98.2%).

Example 9

2-fluoro-4-{5-[3-methyl-4-(4-methyl-3-thienyl)phenyl}-1,2,4-oxadiazol-3-yl]benzoic acid

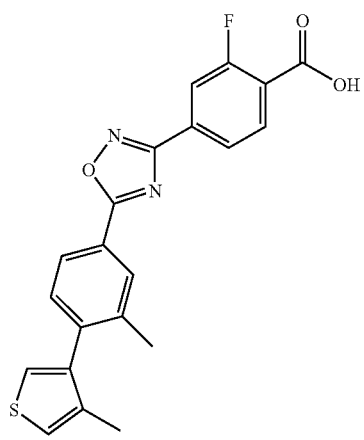

Step 1: methyl 2-fluoro-4-{5-[3-methyl-4-(4-methyl-3-thienyl)phenyl]-1,2,4-oxadiazol-3-yl}benzoate The title compound was prepared following procedure described for example 4, step 1, but starting from Intermediate 6 (121.14 mg; 0.50 mmol; 1 eq.). The reaction mixture was filtered through a SPE NH₂ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as a off-white solid. LC/MS (Method A): 409.1 (M+H)⁺. HPLC (Method A) Rt 6.23 min (Purity: 98.2%).

Step 2: 2-fluoro-4-{5-[3-methyl-4-(4-methyl-3-thienyl)phenyl]-1,2,4-oxadiazol-3-yl}benzoic acid The title compound was prepared following procedure described for example 4, step 2, but starting from methyl 2-fluoro-4-{5-[3-methyl-4-(4-methyl-3-thienyl)phenyl]-1,2,4-oxadiazol-3-yl}benzoate, obtained in Step 1 (66 mg; 0.16 mmol; 1 eq.). Solvents were concentrated and EtOAc (20 mL) was added. It was washed with 10% of AcOH (15 mL), water (15 mL) and was dried over MgSO₄, affording the title compound as a off-white solid (57.6 mg, 90%). LC/MS (Method A): 392.9 (M−H)⁻; 394.9 (M+H)⁺. HPLC (Method A) Rt 5.34 min (Purity: 98.9%).

Example 10

4-[5-(2,2'-dimethylbiphenyl-4-yl)-1,2,4-oxadiazol-3-yl]-3-fluorobenzoic acid

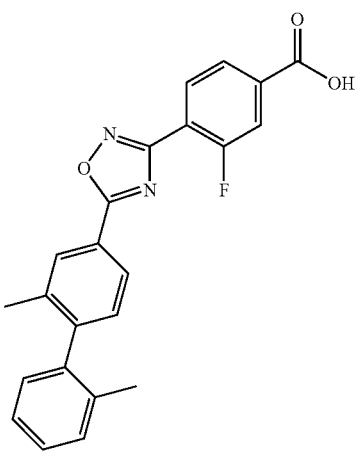

Step 1: methyl 4-[5-(2,2'-dimethylbiphenyl-4-yl)-1,2,4-oxadiazol-3-yl]-3-fluorobenzoate The title compound was prepared following procedure described for example 4, step 1, but starting from Intermediate 3 (113.1 mg; 0.50 mmol; 1 eq.) and Intermediate 2 (106.1 mg; 0.50 mmol; 1 eq.). The reaction mixture was filtered through a SPE NH₂ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as a off-white solid. LC/MS (Method A): 403.0 (M+H)⁺. HPLC (Method A) Rt 6.20 min (Purity: 96.8%).

Step 2: 4-[5-(2,2'-dimethylbiphenyl-4-yl)-1,2,4-oxadiazol-3-yl]-3-fluorobenzoic acid The title compound was prepared following procedure described for example 4, step 2, but starting from methyl 4-[5-(2,2'-dimethylbiphenyl-4-yl)-1,2,4-oxadiazol-3-yl]-3-fluorobenzoate, obtained in step 1 (69 mg; 0.17 mmol; 1 eq.). Solvents were concentrated and EtOAc (20 mL) was added. It was washed with HCl 1N (15 mL), water (15 mL) and was dried over MgSO₄, affording the title compound as a off-white solid (55.1 mg, 83%). LC/MS (Method A): 387.0 (M–H)⁻; 389.0 (M+H)⁺. HPLC (Method A) Rt 5.38 min (Purity: 98.8%).

Example 11

2-fluoro-4-[5-(2'-methyl-2-nitrobiphenyl-4-yl)-1,2,4-oxadiazol-3-yl]benzoic acid

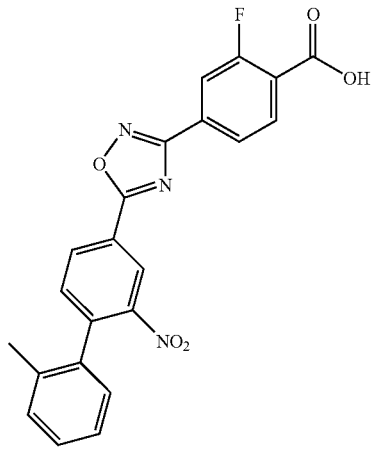

Step 1: methyl 2-fluoro-4-[5-(2'-methyl-2-nitrobiphenyl-4-yl)-1,2,4-oxadiazol-3-yl]benzoate The title compound was prepared following procedure described for example 4, step 1, but starting from Intermediate 7 (132.7 mg; 0.60 mmol; 1 eq.). The reaction mixture was filtered through a SPE NH₂ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as a yellow solid (19.6 mg, 9%). HPLC (Method A) Rt 5.67 min (Purity: 98.4%).

Step 2: 2-fluoro-4-[5-(2'-methyl-2-nitrobiphenyl-4-yl)-1,2,4-oxadiazol-3-yl]benzoic acid The title compound was prepared following procedure described for example 4, step 2, but starting from methyl 2-fluoro-4-[5-(2'-methyl-2-nitrobiphenyl-4-yl)-1,2,4-oxadiazol-3-yl]benzoate, obtained in step 1 (19.6 mg; 0.045 mmol; 1 eq.). Solvents were concentrated and EtOAc (15 mL) was added. It was washed with HCl 1N (10 mL), water (10 mL) and was dried over MgSO₄. The resulting solid was suspended in DCM/MeOH and filtrated, affording the title compound as a yellow solid (18.5 mg, quantitative). LC/MS (Method A): 417.9 (M–H)⁻. HPLC (Method A), Rt 5 min (purity: 90.7%).

Example 12

2-fluoro-4-{5-[3-methoxy-4-(4-methyl-3-thienyl)phenyl]-1,2,4-oxadiazol-3-yl}benzoic acid

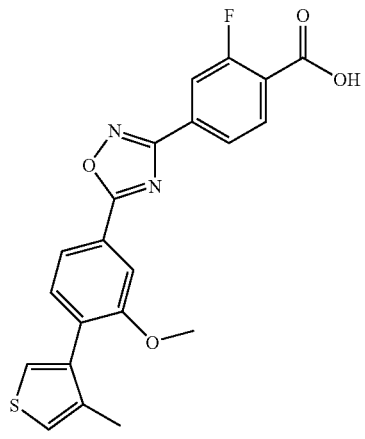

Step 1: methyl 2-fluoro-4-{5-[3-methoxy-4-(4-methyl-3-thienyl)phenyl]-1,2,4-oxadiazol-3-yl}benzoate The title compound was prepared following procedure described for example 4, step 1, but starting from Intermediate 8 (145.4 mg; 0.60 mmol; 1.20 eq.). The reaction mixture was filtered through a SPE NH₂ column (2 g) and rinsed with ACN. The filtrate was passed through a SPE SCX column (2 g) and rinsed with ACN. After evaporation of the solvents, the crude product was suspended in ACN, filtrated and dried under vacuo, affording the title compound as a off-white solid. LC/MS (Method A): 424.8 (M+H)⁺. HPLC (Method A) Rt 5.92 min (Purity: 98.6%).

Step 2: 2-fluoro-4-{5-[3-methoxy-4-(4-methyl-3-thienyl)phenyl]-1,2,4-oxadiazol-3-yl}benzoic acid The title compound was prepared following procedure described for example 4, step 2, but starting from methyl 2-fluoro-4-{5-[3-methoxy-4-(4-methyl-3-thienyl)phenyl]-1,2,4-oxadiazol-3-yl}benzoate obtained in Step 1 (64.3 mg; 0.15 mmol; 1 eq.). Solvents were concentrated and EtOAc (20 mL) was added. It was washed with HCl 1N (15 mL), water (15 mL) and was dried over MgSO₄, affording the title compound as a off-white solid (56 mg, 90%). LC/MS (Method A): 408.9 (M−H)⁻; 410.9 (M+H)⁺. HPLC (Method A) Rt 5.03 min (Purity: 93.8%).

Example 13

2-fluoro-4-[5-(2-methoxy-2'-methylbiphenyl-4-yl)-1,2,4-oxadiazol-3-yl]benzoic acid

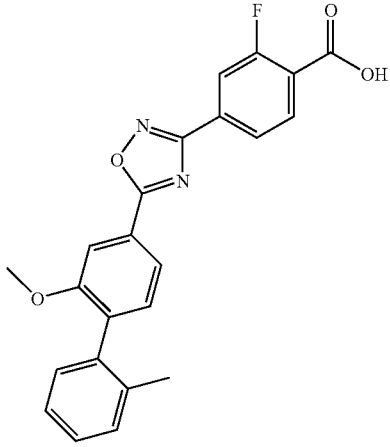

Step 1: methyl 2-fluoro-4-[5-(2-methoxy-2'-methyl-biphenyl-4-yl)-1,2,4-oxadiazol-3-yl]benzoate The title compound was prepared following procedure described for example 4, step 1, but starting from Intermediate 9 (150.2 mg; 0.60 mmol; 1.20 eq.). The reaction mixture was filtered through a SPE $NH_2$ column (2 g) and rinsed with ACN. The filtrate was passed through a SPE SCX column (2 g) and rinsed with ACN. After evaporation of the solvents, the crude product was suspended in ACN, filtrated and dried under vacuo, affording the title compound as a off-white solid. LC/MS (Method A): 419.0 (M+H)⁺. HPLC (Method A) Rt 5.98 min (Purity: 97.8%).

Step 2: 2-fluoro-4-[5-(2-methoxy-2'-methylbiphenyl-4-yl)-1,2,4-oxadiazol-3-yl]benzoic acid The title compound was prepared following procedure described for example 4, step 2, but starting from methyl 2-fluoro-4-[5-(2-methoxy-2'-methylbiphenyl-4-yl)-1,2,4-oxadiazol-3-yl]benzoate obtained in step 1 (74.4 mg; 0.18 mmol; 1 eq.). Solvents were concentrated and EtOAc (20 mL) was added. It was washed with HCl 1N (15 mL), water (15 mL) and was dried over $MgSO_4$, affording the title compound as a off-white solid (56 mg, 79%). LC/MS (Method A): 403.0 (M−H)⁻; 405.0 (M+H)⁺. HPLC (Method A) Rt 5.14 min (Purity: 96.5%).

Example 14

2-fluoro-4-[5-(3-nitro-4-piperidin-1-ylphenyl)-1,2,4-oxadiazol-3-yl]benzoic acid

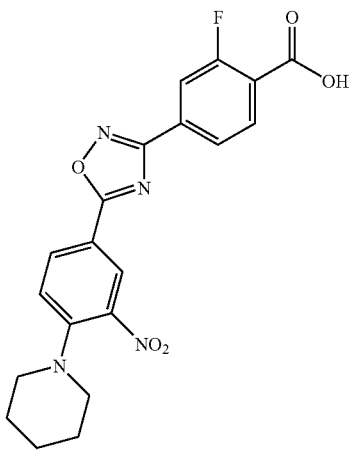

Step 1: methyl 2-fluoro-4-[5-(3-nitro-4-piperidin-1-ylphenyl)-1,2,4-oxadiazol-3-yl]benzoate The title compound was prepared following procedure described for example 4, step 1, but starting from Intermediate 10 (75 mg; 0.30 mmol; 1 eq.). The reaction mixture was filtered through a SPE $NH_2$ column (2 g) and rinsed with ACN. After evaporation of the solvents, the crude product was purified by flash chromatography (c-hex/EtOAc gradient: from 9.5/0.5 to 5/5), affording the title compound as a yellow solid. HPLC (Method A) Rt 5.67 min (Purity: 99.2%).

Step 2: 2-fluoro-4-[5-(3-nitro-4-piperidin-1-ylphenyl)-1,2,4-oxadiazol-3-yl]benzoic acid The title compound was prepared following procedure described for example 4, step 2, but starting from methyl 2-fluoro-4-[5-(3-nitro-4-piperidin-1-ylphenyl)-1,2,4-oxadiazol-3-yl]benzoate, obtained in step 1 (41 mg; 0.10 mmol; 1 eq.). Solvents were concentrated and EtOAc (20 mL) was added. It was washed with 5% AcOH (15 mL), water (15 mL) and was dried over $MgSO_4$, affording the title compound as a yellow solid (29.6 mg; 74%). LC/MS (Method A): 411.0 (M−H)⁻; 413.0 (M+H)⁺. HPLC (Method A) Rt 4.85 min (Purity: 99.3%).

Example 15

2-fluoro-4-{5-[4-(2-methylpiperidin-1-yl)-3-nitrophenyl]-1,2,4-oxadiazol-3-yl}benzoic acid

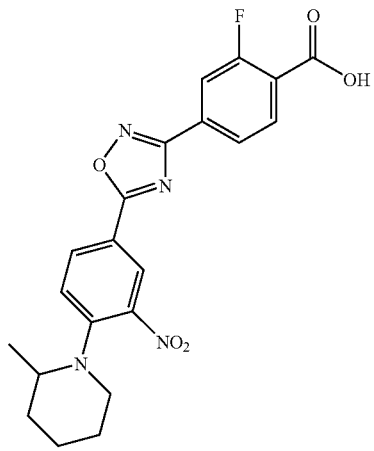

Step 1: methyl 2-fluoro-4-{5-[4-(2-methylpiperidin-1-yl)-3-nitrophenyl]-1,2,4-oxadiazol-3-yl}benzoate The title compound was prepared following procedure described for example 4, step 1, but starting from Intermediate 11 (79.3 mg; 0.30 mmol; 1 eq.). The reaction mixture was filtered through a SPE NH₂ column (2 g) and rinsed with ACN. After evaporation of the solvents, the crude product was purified by flash chromatography (c-hex/EtOAc gradient: from 9.5/0.5 to 5/5), affording the title compound as a yellow solid. M⁺ (ESI): 441.04. HPLC (Method A) Rt 5.91 min (Purity: 94.4%).

Step 2: 2-fluoro-4-{5-[4-(2-methylpiperidin-1-yl)-3-nitrophenyl]-1,2,4-oxadiazol-3-yl}benzoic acid The title compound was prepared following procedure described for example 4, step 2, but starting from methyl 2-fluoro-4-{5-[4-(2-methylpiperidin-1-yl)-3-nitrophenyl]-1,2,4-oxadiazol-3-yl}benzoate, obtained in step 1 (20 mg; 0.05 mmol; 1 eq.). Solvents were concentrated and EtOAc (20 mL) was added. It was washed with 10% AcOH (15 mL), water (15 mL) and was dried over MgSO₄, affording the title compound as a yellow solid (20 mg; quantitative). LC/MS (Method A): 425.0 (M−H)⁻; 427.0 (M+H)⁺. HPLC (Method A) Rt 5.13 min (Purity: 94.5%).

Example 16

2-fluoro-4-[5-(3-methyl-4-piperidin-1-ylphenyl)-1,2,4-oxadiazol-3-yl]benzoic acid

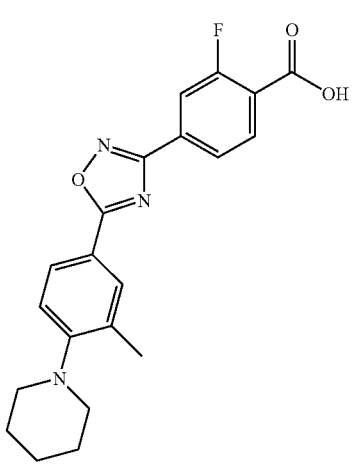

Step 1: methyl 2-fluoro-4-[5-(3-methyl-4-piperidin-1-ylphenyl)-1,2,4-oxadiazol-3-yl]benzoate The title compound was prepared following procedure described for example 4, step 1, but starting from Intermediate 12 (165.13 mg; 0.60 mmol; 1 eq.). The reaction mixture was filtered through a SPE NH₂ column (2 g) and rinsed with ACN. The filtrate was passed through a SPE SCX column (2 g) and rinsed with ACN. The filtrate was evaporated. After evaporation of the solvents, the title compound was isolated and used in the next step without further purification. LC/MS (Method A): 395.9 (M+H)⁺. HPLC (Method A) Rt 4.85 min (Purity: 56.1%).

Step 2: 2-fluoro-4-[5-(3-methyl-4-piperidin-1-ylphenyl)-1,2,4-oxadiazol-3-yl]benzoic acid The title compound was prepared following procedure described for example 4, step 2, but starting from methyl 2-fluoro-4-[5-(3-methyl-4-piperidin-1-ylphenyl)-1,2,4-oxadiazol-3-yl]benzoate, prepared in step 1 (98.9 mg; 0.25 mmol; 1 eq.). Solvents were concentrated and EtOAc (20 mL) was added. It was washed with 10% AcOH (15 mL), water (15 mL) and was dried over MgSO₄, affording the title compound as a off-white solid. LC/MS (Method A): 379.9 (M−H)⁻; 381.9 (M+H)⁺. HPLC (Method A) Rt 4.23 min (Purity: 97.9%).

Example 17

2-fluoro-4-{5-[4-morpholin-4-yl-3-(trifluoromethyl)phenyl]-1,2,4-oxadiazol-3-yl}benzoic acid

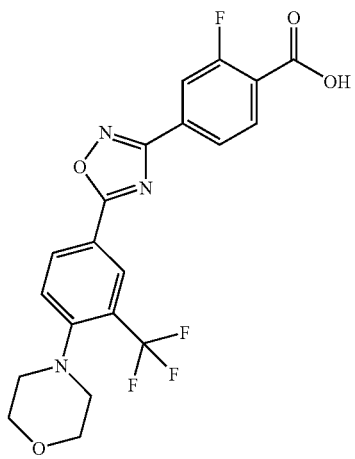

Step 1: methyl 2-fluoro-4-{5-[4-morpholin-4-yl-3-(trifluoromethyl)phenyl]-1,2,4-oxadiazol-3-yl}benzoate The title compound was prepared following procedure described for example 4, step 1, but starting from Intermediate 13 (165.1 mg; 0.60 mmol; 1 eq.). The reaction mixture was filtered through a SPE NH₂ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as a off-white solid. LC/MS (Method A): 451.6 (M+H)⁺. HPLC (Method A) Rt 5.41 min (Purity: 94.5%).

Step 2: 2-fluoro-4-{5-[4-morpholin-4-yl-3-(trifluoromethyl)phenyl]-1,2,4-oxadiazol-3-yl}benzoic acid The title compound was prepared following procedure described for example 4, step 2, but starting from methyl 2-fluoro-4-{5-[4-morpholin-4-yl-3-(trifluoromethyl)phenyl]-1,2,4-oxadiazol-3-yl}benzoate, obtained in step 1 (110 mg; 0.24 mmol; 1 eq.). Solvents were concentrated and EtOAc (20 mL) was added. It was washed with HCl 1N (15 mL), water (15 mL) and was dried over MgSO₄, affording the title compound as a off-white solid (88.3 mg, 83%). LC/MS (Method A): 435.8 (M−H)⁻; 437.5 (M+H)⁺. HPLC (Method A) Rt 4.58 min (Purity: 91.2%).

Example 18

2-fluoro-4-[5-(3-methyl-4-morpholin-4-ylphenyl)-1,2,4-oxadiazol-3-yl]benzoic acid

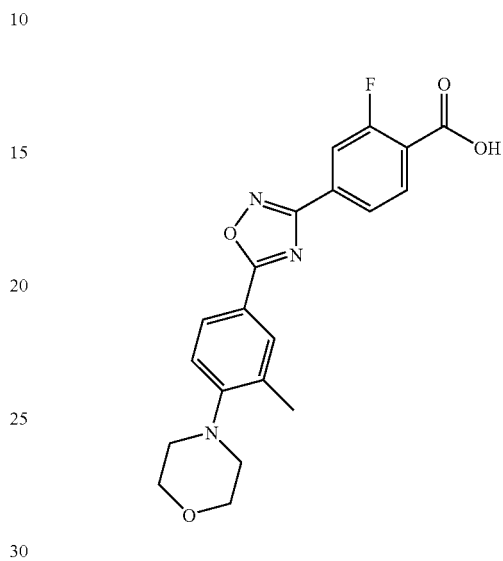

Step 1: methyl 2-fluoro-4-[5-(3-methyl-4-morpholin-4-ylphenyl)-1,2,4-oxadiazol-3-yl]benzoate The title compound was prepared following procedure described for example 4, step 1, but starting from Intermediate 14 (132.7 mg; 0.60 mmol; 1 eq.). The reaction mixture was filtered through a SPE NH₂ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as a off-white solid. LC/MS (Method A): 411.9 (M+H)⁺. HPLC (Method A) Rt 5.07 min (Purity: 100%).

Step 2: 2-fluoro-4-[5-(3-methyl-4-morpholin-4-ylphenyl)-1,2,4-oxadiazol-3-yl]benzoic acid The title compound was prepared following procedure described for example 4, step 2, but starting from methyl 2-fluoro-4-[5-(3-methyl-4-morpholin-4-ylphenyl)-1,2,4-oxadiazol-3-yl]benzoate, obtained in step 1 (37.6 mg; 0.09 mmol; 1 eq.). Solvents were concentrated and EtOAc (20 mL) was added. It was washed with HCl 1N (15 mL), water (15 mL) and was dried over MgSO₄, affording example 18 as a light orange solid (32.2 mg, 89%). LC/MS (Method A): 381.90 (M−H)⁻; 383.8 (M+H)⁺. HPLC (Method A) Rt 4.18 min (Purity: 98.6%).

Example 19

2-fluoro-4-{5-[4-(2-methylpiperidin-1-yl)-3-(trifluoromethyl)phenyl]-1,2,4-oxadiazol-3-yl}benzoic acid

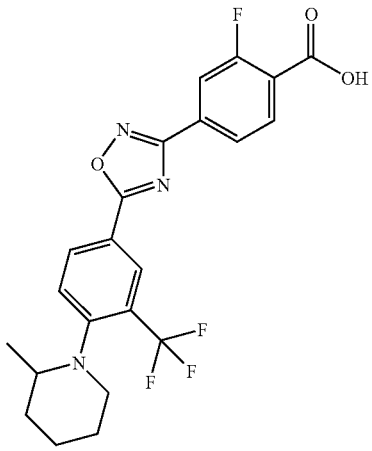

Step 1: methyl 2-fluoro-4-{5-[4-(2-methylpiperidin-1-yl)-3-(trifluoromethyl)phenyl]-1,2,4-oxadiazol-3-yl}benzoate The title compound was prepared following procedure described for example 4, step 1, but starting from Intermediate 15 (172.4 mg; 0.60 mmol; 1 eq.). The reaction mixture was filtered through a SPE NH₂ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as a off-white solid. LC/MS (Method A): 461.7 (M−H)⁻; 464.0 (M+H)⁺. HPLC (Method A) Rt 6.68 min (Purity: 98.9%).

Step 2: 2-fluoro-4-{5-[4-(2-methylpiperidin-1-yl)-3-(trifluoromethyl)phenyl]-1,2,4-oxadiazol-3-yl}benzoic acid The title compound was prepared following procedure described for example 4, step 2, but starting from methyl 2-fluoro-4-{5-[4-(2-methylpiperidin-1-yl)-3-(trifluoromethyl)phenyl]-1,2,4-oxadiazol-3-yl}benzoate, obtained in step 1 (100.8 mg; 0.22 mmol; 1 eq.). Solvents were concentrated and EtOAc (20 mL) was added. It was washed with HCl 1N (15 mL), water (15 mL) and was dried over MgSO₄, affording the title compound as a light yellow solid (80 mg, 82%). LC/MS (Method A): 447.9 (M−H)⁻; 449.6 (M+H)⁺. HPLC (Method A) Rt 5.91 min (Purity: 98.6%).

Example 20

4-[3-(2',4'-dimethoxy-2-methylbiphenyl-4-yl)-1,2,4-oxadiazol-3-yl]-2-fluorobenzoic acid

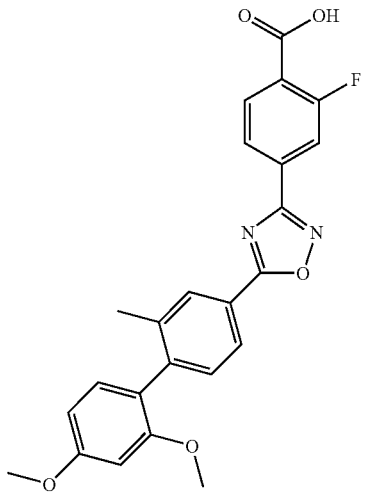

Step 1: methyl 4-[5-(2',4'-dimethoxy-2-methylbiphenyl-4-yl)-1,2,4-oxadiazol-3-yl]-2-fluorobenzoate The title compound was prepared following procedure described for example 4, step 1, but starting from Intermediate 17 (163.38 mg; 0.60 mmol). The reaction mixture was filtered through a SPE NH₂ column (2 g) and rinsed with ACN. The filtrate was passed through a SPE SCX column (2 g) and rinsed with ACN. After evaporation of the solvents, the crude product was suspended in MeCN, cooled down to 4° C. for 30 min, filtrated and rinsed with MeCN, affording the title compound as a off-white solid. LC/MS (Method A): 448.9 (M+H)⁺. HPLC (Method A) Rt 5.88 min (Purity: 99.0%).

Step 2: 4-[5-(2',4'-dimethoxy-2-methylbiphenyl-4-yl)-1,2,4-oxadiazol-3-yl]-2-fluorobenzoic acid The title compound was prepared following procedure described for example 4, step 2, but starting from methyl 4-[5-(2',4'-dimethoxy-2-methylbiphenyl-4-yl)-1,2,4-oxadiazol-3-yl]-2-fluorobenzoate, obtained in step 1 (40 mg; 0.09 mmol). Solvents were concentrated and EtOAc (20 mL) was added. It was washed with HCl 1N (15 mL), water (15 mL) and was dried over MgSO₄, affording the title compound as a off-white solid (31 mg, 80%). LC/MS (Method A): 432.9 (M−H)⁻; 434.6 (M+H)⁺. HPLC (Method A) Rt 5.08 min (Purity: 96.0%).

Example 21

2-fluoro-4-[5-(4-nitro-3-piperidin-1-ylphenyl)-1,2,4-oxadiazol-3-yl]benzoic acid

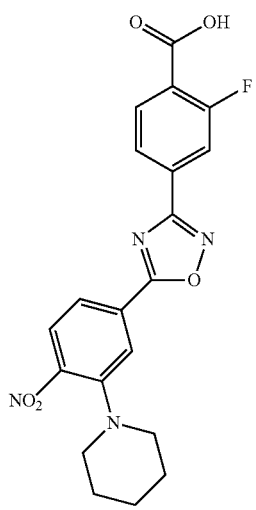

Step 1: methyl 2-fluoro-4-[5-(4-nitro-3-piperidin-1-ylphenyl)-1,2,4-oxadiazol-3-yl]benzoate The title compound was prepared following procedure described for example 4, step 1, but starting from Intermediate 18 (150.15 mg; 0.60 mmol). The reaction mixture was filtered through a SPE $NH_2$ column (2 g) and rinsed with ACN. The filtrate was passed through a SPE SCX column (2 g) and rinsed with ACN. After evaporation of the solvents, the crude product was suspended in MeCN/EtOH mixture (1:1), cooled down to 4° C. for 30 min, filtrated and rinsed with the same solvent mixture, affording the title compound as an orange solid. LC/MS (Method A): 426.9 (M+H)⁺. HPLC (Method A) Rt 5.85 min (Purity: 95.4%).

Step 2: 2-fluoro-4-[5-(4-nitro-3-piperidin-1-ylphenyl)-1,2,4-oxadiazol-3-yl]benzoic acid The title compound was prepared following procedure described for example 4, step 2, but starting from methyl 2-fluoro-4-[5-(4-nitro-3-piperidin-1-ylphenyl)-1,2,4-oxadiazol-3-yl]benzoate obtained in step 1 (66 mg; 0.15 mmol). Solvents were concentrated and EtOAc (20 mL) was added. It was washed with HCl 1N (15 mL), water (15 mL) and was dried over $MgSO_4$, affording the title compound as an orange solid (53 mg, 83%). LC/MS (Method A): 410.9 (M−H)⁻; 412.6 (M+H)⁺. HPLC (Method A) Rt 4.96 min (Purity: 97.8%).

Example 22

2-fluoro-4-{5-[2'-methyl-2-(trifluoromethyl)biphenyl-4-yl]-1,2,4-oxadiazol-3-yl}benzoic acid

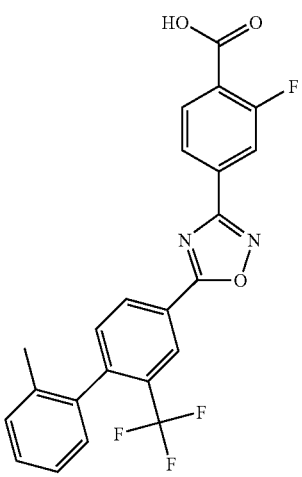

Step 1: methyl 2-fluoro-4-{5-[2'-methyl-2-(trifluoromethyl)biphenyl-4-yl]-1,2,4-oxadiazol-3-yl}benzoate The title compound was prepared following procedure described for example 4, step 1, but starting from Intermediate 19 (168.15 mg; 0.60 mmol). The reaction mixture was filtered through a SPE $NH_2$ column (2 g) and rinsed with ACN. The filtrate was passed through a SPE SCX column (2 g) and rinsed with ACN. After evaporation of the solvents, the crude product was suspended in ACN, filtrated and dried under vacuo, affording the title compound as a white solid. ¹H NMR (DMSO-$d_6$, 300 MHz) δ 8.56 (d, J=1.7 Hz, 1H), 8.51 (dd, J=8.1, 1.4 Hz, 1H), 8.17-8.01 (m, 3H), 7.68 (d, J=8.0 Hz, 1H), 7.39-7.26 (m, 3H), 7.17 (d, J=7.3 Hz, 1H), 3.92 (s, 3H), 2.02 (s, 3H). LC/MS (Method A): 497.9 (M+H)⁺. HPLC (Method A) Rt 6.31 min (Purity: 99.7%).

Step 2: 2-fluoro-4-{5-[2'-methyl-2-(trifluoromethyl)biphenyl-4-yl]-1,2,4-oxadiazol-3-yl}benzoic acid The title compound was prepared following procedure described for example 4, step 2, but starting from methyl 2-fluoro-4-{5-[2'-methyl-2-(trifluoromethyl)biphenyl-4-yl]-1,2,4-oxadiazol-3-yl}benzoate, obtained in step 1. Solvents were concentrated and EtOAc (20 mL) was added. It was washed with water. The organic layer was then dried over magnesium sulfate, filtered and concentrated to afford the title compound as a white solid (109 mg; 85%). ¹H NMR (DMSO-$d_6$, 300 MHz) δ 13.6 (br s, 1H), 8.56-8.49 (m, 2H), 8.14-7.97 (m, 3H), 7.67 (d, J=8.0 Hz, 1H), 7.41-7.26 (m, 3H), 7.17 (d, J=7.4 Hz, 1H), 2.02 (s, 3H). LC/MS (Method A): 440.9 (M−H)⁻. HPLC (Method A) Rt 5.51 min (Purity: 99.0%).

Example 23

2-fluoro-4-{5-[4-(4-methyl-3-thienyl)-3-(trifluoromethyl)phenyl]-1,2,4-oxadiazol-3-yl}benzoic acid

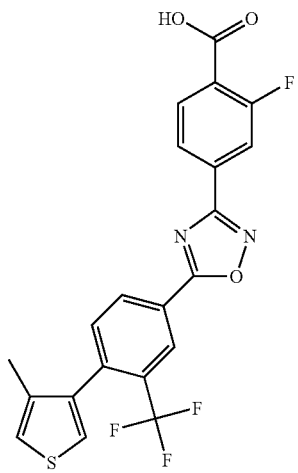

Step 1: methyl 2-fluoro-4-{5-[4-(4-methyl-3-thienyl)-3-(trifluoromethyl)phenyl]-1,2,4-oxadiazol-3-yl}benzoate The title compound was prepared following procedure described for example 4, step 1, but starting from Intermediate 20 (171.76 mg; 0.60 mmol). The reaction mixture was filtered through a SPE NH₂ column (2 g) and rinsed with ACN. The filtrate was passed through a SPE SCX column (2 g) and rinsed with ACN. After evaporation of the solvents, the crude product was suspended in ACN, filtrated and dried under vacuo, affording the title compound as an orange solid. ¹H NMR (DMSO-d₆, 300 MHz) δ 8.54 (d, J=1.6 Hz, 1H), 8.50 (dd, J=7.9, 1.6 Hz, 1H), 8.17-8.01 (m, 3H), 7.71 (d, J=7.9 Hz, 1H), 7.50 (d, J=3.1 Hz, 1H), 7.34 (dd, J=3.2, 1.1 Hz, 1H), 3.91 (s, 3H), 1.99 (s, 3H). LC/MS (Method A): 462.7 (M+H)⁺. HPLC (Method A) Rt 6.22 min (Purity: 97.2%).

Step 2: 2-fluoro-4-{5-[4-(4-methyl-3-thienyl)-3-(trifluoromethyl)phenyl]-1,2,4-oxadiazol-3-yl}benzoic acid The title compound was prepared following procedure described for example 4, step 2, but starting from methyl 2-fluoro-4-{5-[4-(4-methyl-3-thienyl)-3-(trifluoromethyl)phenyl]-1,2,4-oxadiazol-3-yl}benzoate, obtained in step 1. Solvents were concentrated and EtOAc (20 mL) was added. It was washed with water. The organic layer was then dried over magnesium sulfate, filtered and concentrated to afford the title compound (37 mg; 94%) as a white solid. ¹H NMR (DMSO-d₆, 300 MHz) δ 13.6 (br s, 1H), 8.54-8.48 (m, 2H), 8.13-7.96 (m, 3H), 7.71 (d, J=8.2 Hz, 1H), 7.50 (d, J=3.1 Hz, 1H), 7.34 (dd, J=3.1, 1.1 Hz, 1H), 1.99 (s, 3H). LC/MS (Method A): 446.9 (M−H)⁻. HPLC (Method A) Rt 5.43 min (Purity: 94.1%).

Example 24

4-[3-(2',5'-dimethoxy-2-methylbiphenyl-4-yl)-1,2,4-oxadiazol-3-yl]-2-fluorobenzoic acid

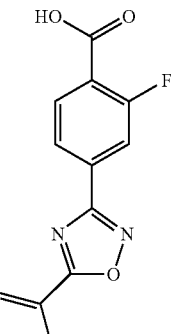

Step 1: methyl 4-[5-(2',5'-dimethoxy-2-methylbiphenyl-4-yl)-1,2,4-oxadiazol-3-yl]-2-fluorobenzoate The title compound was prepared following procedure described for example 4, step 1, but starting Intermediate 21 (163.38 mg; 0.60 mmol). The reaction mixture was filtered through a SPE NH₂ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as an off-white powder. ¹H NMR (DMSO-d₆, 300 MHz) δ 8.16-7.97 (m, 5H), 7.42 (d, J=7.9 Hz, 1H), 7.08 (d, J=9.0 Hz, 1H), 6.99 (dd, J=9.0, 3.2 Hz, 1H), 6.75 (d, J=2.8 Hz, 1H), 3.91 (s, 3H), 3.75 (s, 3H), 3.68 (s, 3H), 2.21 (s, 3H). LC/MS (Method A): 449.0 (M+H)⁺. HPLC (Method A) Rt 5.82 min (Purity: 97.9%).

Step 2: 4-[5-(2',5'-dimethoxy-2-methylbiphenyl-4-yl)-1,2,4-oxadiazol-3-yl]-2-fluorobenzoic acid The title compound was prepared following procedure described for example 4, step 2, but starting from methyl 4-[5-(2',5'-dimethoxy-2-methylbiphenyl-4-yl)-1,2,4-oxadiazol-3-yl]-2-fluorobenzoate, obtained in step 1. Solvents were concentrated and EtOAc (20 mL) was added. It was washed with water. The organic layer was then dried over magnesium sulfate, filtered and concentrated to afford the title compound as a white powder (69 mg; 85%). ¹H NMR (DMSO-d₆, 300 MHz) δ 13.6 (br s, 1H), 8.12-8.02 (m, 4H), 7.95 (dd, J=11.1, 1.5 Hz, 1H), 7.42 (d, J=8.1 Hz, 1H), 7.08 (d, J=9.1 Hz, 1H), 6.98 (dd, J=9.0, 3.1 Hz, 1H), 6.75 (d, J=3.1 Hz, 1H), 3.74 (s, 3H), 3.68 (s, 3H), 2.21 (s, 3H). LC/MS (Method A): 432.9 (M−H)⁻, 435.2 (M+H)⁺. HPLC (Method A) Rt 4.99 min (Purity: 98.3%).

Example 25

4-{5-[4-(3,5-dimethylisoxazol-4-yl)-3-methylphenyl]-1,2,4-oxadiazol-3-yl}-2-fluorobenzoic acid

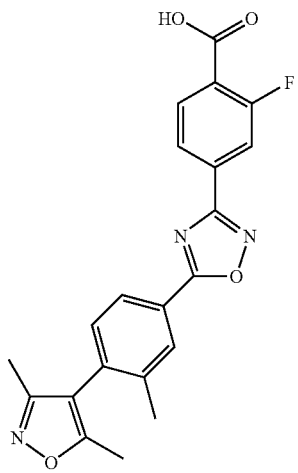

Step 1: methyl 4-{5-[4-(3,5-dimethylisoxazol-4-yl)-3-methylphenyl]-1,2,4-oxadiazol-3-yl}-2-fluorobenzoate The title compound was prepared following procedure described for example 4, step 1, but starting from Intermediate 22 (138.75 mg; 0.60 mmol). The reaction mixture was filtered through a SPE NH$_2$ column (2 g) and rinsed with ACN. The filtrate was passed through a SPE SCX column (2 g) and rinsed with ACN. After evaporation of the solvents, the crude product was suspended in ACN, filtrated and dried under vacuo, affording the title compound. $^1$H NMR (DMSO-d$_6$, 300 MHz) δ 8.22 (d, J=1.6 Hz, 1H), 8.16-8.05 (m, 3H), 7.99 (dd, J=11.2, 1.4 Hz, 1H), 7.50 (d, J=8.0 Hz, 1H), 3.91 (s, 3H), 2.25-2.26 (m, 6H), 2.07 (s, 3H). LC/MS (Method A): 408.0 (M+H)⁺. HPLC (Method A) Rt 5.31 min (Purity: 98.5%).

Step 2: 4-{5-[4-(3,5-dimethylisoxazol-4-yl)-3-methylphenyl]-1,2,4-oxadiazol-3-yl}-2-fluorobenzoic acid The title compound was prepared following procedure described for example 4, step 2, but starting from methyl 4-{5-[4-(3,5-dimethylisoxazol-4-yl)-3-methylphenyl]-1,2,4-oxadiazol-3-yl}-2-fluorobenzoate, obtained in step 1. Solvents were concentrated and EtOAc (20 mL) was added. It was washed with water. The organic layer was then dried over magnesium sulfate, filtered and concentrated to afford the title compound as a white solid (48 mg; 88%). $^1$H NMR (DMSO-d$_6$, 300 MHz) δ 13.6 (br s, 1H), 8.22 (d, J=1.8 Hz, 1H), 8.13-8.02 (m, 3H), 7.95 (dd, J=11.1, 1.4 Hz, 1H), 7.50 (d, J=7.9 Hz, 1H), 2.26 (s, 3H), 2.25 (s, 3H), 2.07 (s, 3H). LC/MS (Method A): 391.9 (M−H)⁻. HPLC (Method A) Rt 4.44 min (Purity: 99.3%).

Example 26

3-fluoro-4-{5-[3-methyl-4-(4-methyl-3-thienyl)phenyl]-1,2,4-oxadiazol-3-yl}benzoic acid

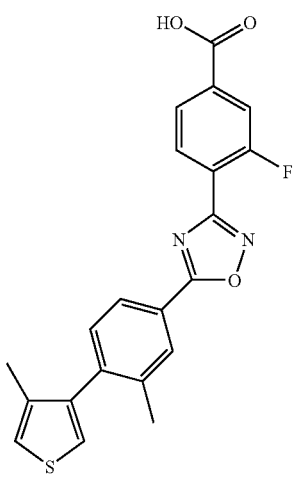

Step 1: methyl 3-fluoro-4-{5-[3-methyl-4-(4-methyl-3-thienyl)phenyl]-1,2,4-oxadiazol-3-yl}benzoate The title compound was prepared following procedure described for example 4, step 1, but starting from Intermediate 6 (116.2 mg; 0.50 mmol) and Intermediate 2 (106.1 mg; 0.50 mmol). The reaction mixture was filtered through a SPE NH$_2$ column (2 g) and rinsed with ACN. The filtrate was passed through a SPE SCX column (2 g) and rinsed with ACN. After evaporation of the solvents, the crude product was suspended in ACN, filtrated and washed with cHex dried under vacuo, affording the title compound. $^1$H NMR (DMSO-d$_6$, 300 MHz) δ 8.35-8.30 (m, 1H), 8.17 (d, J=1.3 Hz, 1H), 8.08-8.01 (m, 2H), 7.95 (dd, J=11.0, 1.3 Hz, 1H), 7.46-7.42 (m, 2H), 7.35 (dd, J=3.2, 1.1 Hz, 1H), 3.93 (s, 3H), 2.24 (s, 3H), 2.01 (s, 3H). LC/MS (Method B): 409.1 (M+H)⁺. HPLC (Method A) Rt 6.06 min (Purity: 93.6%).

Step 2: 3-fluoro-4-{5-[3-methyl-4-(4-methyl-3-thienyl)phenyl]-1,2,4-oxadiazol-3-yl}benzoic acid The title compound was prepared following procedure described for example 4, step 2, but starting from methyl 3-fluoro-4-{5-[3-methyl-4-(4-methyl-3-thienyl)phenyl]-1,2,4-oxadiazol-3-yl}benzoate, obtained in step 1. Solvents were concentrated and water (5 mL) was added. It was filtrated to afford the title compound as a white solid (39 mg; 84%). $^1$H NMR (DMSO-d$_6$, 300 MHz) δ 13.65 (br s, 1H), 8.29 (t, J=7.5 Hz, 1H), 8.16 (s, 1H), 8.06 (dd, J=7.8, 1.6 Hz, 1H), 8.01 (dd, J=8.1, 1.4 Hz, 1H), 7.91 (dd, J=10.8, 1.1 Hz, 1H), 7.46-4.42 (m, 2H), 7.36-7.34 (m, 1H), 2.24 (s, 3H), 2.01 (s, 3H). LC/MS (Method B): 393.2 (M−H)⁻, 395.1 (M+H)⁺. HPLC (Method A) Rt 5.31 min (Purity: 98.5%).

Example 27

3-fluoro-4-{5-[4-(2-methylpiperidin-1-yl)-3-(trifluoromethyl)phenyl]-1,2,4-oxadiazol-3-yl}benzoic acid

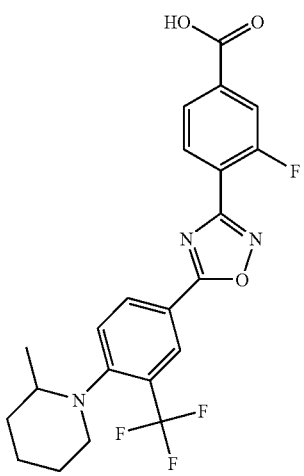

Step 1: methyl 3-fluoro-4-{5-[4-(2-methylpiperidin-1-yl)-3-(trifluoromethyl)phenyl]-1,2,4-oxadiazol-3-yl}benzoate The title compound was prepared following procedure described for example 4, step 1, but starting from Intermediate 2 (106.09 mg; 0.50 mmol) and Intermediate 15 (143.64 mg; 0.50 mmol). The reaction mixture was filtered through a SPE NH₂ column (2 g) and rinsed with ACN. The filtrate was passed through a SPE SCX column (2 g) and rinsed with ACN. After evaporation of the solvents, the crude product was suspended in ACN, filtrated and dried under vacuo, affording the title compound as a yellow solid. ¹H NMR (DMSO-d₆, 300 MHz) δ 8.45 (dd, J=8.5, 1.9 Hz, 1H), 8.38 (d, J=2.0 Hz, 1H), 8.34-8.29 (m, 1H), 8.01 (dd, J=8.1, 1.6 Hz, 1H), 7.94 (dd, J=10.9, 1.4 Hz, 1H), 7.87 (d, J=8.5 Hz, 1H), 3.92 (s, 3H), 3.20-3.13 (m, 1H), 2.98-2.94 (m, 1H), 2.66-2.58 (m, 1H), 1.81-1.76 (m, 2H), 1.63-1.27 (m, 4H), 0.79 (d, J=6.0 Hz, 3H). HPLC (Method A) Rt 6.60 min (Purity: 70.1%).

Step 2: 3-fluoro-4-{5-[4-(2-methylpiperidin-1-yl)-3-(trifluoromethyl)phenyl]-1,2,4-oxadiazol-3-yl}benzoic acid The title compound was prepared following procedure described for example 4, step 2, but starting from methyl 3-fluoro-4-{5-[4-(2-methylpiperidin-1-yl)-3-(trifluoromethyl)phenyl]-1,2,4-oxadiazol-3-yl}benzoate, obtained in step 1. Solvents were concentrated and EtOAc (20 mL) was added. It was washed with water. The organic layer was then dried over magnesium sulfate, filtered and concentrated to afford the title compound as a yellow solid (725 mg; 96%). ¹H NMR (DMSO-d₆, 300 MHz) δ 13.65 (br s, 1H), 8.46 (dd, J=8.4, 1.9 Hz, 1H), 8.39 (d, J=2.4 Hz, 1H), 8.32-8.27 (m, 1H), 7.99 (dd, J=8.1, 1.4 Hz, 1H), 7.92-7.85 (m, 2H), 3.20-3.15 (m, 1H), 2.98-2.94 (m, 1H), 2.66-2.58 (m, 1H), 1.80-1.77 (m, 2H), 1.63-1.22 (m, 4H), 0.78 (d, J=5.9 Hz, 3H). LC/MS (Method B): 448.3 (M−H)⁻, 450.2 (M+H)⁺. HPLC (Method A) Rt 5.94 min (Purity: 98.6%).

Example 28

2-fluoro-4-{5-[4-(2-methoxypyridin-3-yl)-3-methylphenyl]-1,2,4-oxadiazol-3-yl}benzoic acid

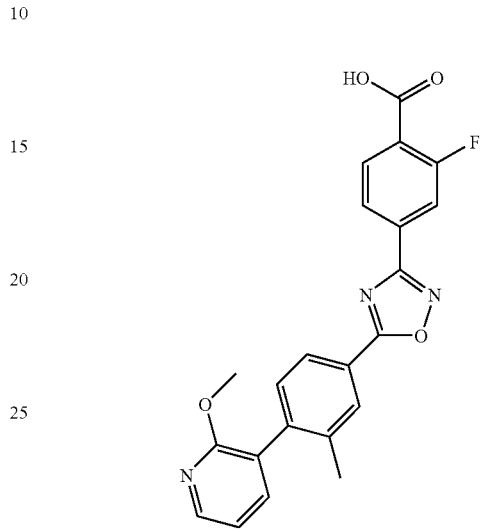

Step 1: methyl 2-fluoro-4-{5-[4-(2-methoxypyridin-3-yl)-3-methylphenyl]-1,2,4-oxadiazol-3-yl}benzoate The title compound was prepared following procedure described for example 4, step 1, but starting from Intermediate 23 (145.96 mg; 0.60 mmol). The reaction mixture was filtered through a SPE NH₂ column (2 g) and rinsed with ACN. The filtrate was passed through a SPE SCX column (2 g) and rinsed with ACN. After evaporation of the solvents, the crude product was suspended in ACN, filtrated and dried under vacuo, affording the title compound as a white solid. ¹H NMR (DMSO-d₆, 300 MHz) δ 8.28 (dd, J=5.0, 1.8 Hz, 1H), 8.16-8.05 (m, 4H), 8 (dd, J=11.3, 1.4 Hz, 1H), 7.66 (dd, J=7.1, 1.9 Hz, 1H), 7.46 (d, J=8.0 Hz, 1H), 7.14 (dd, J=7.2, 5.0 Hz, 1H), 3.91 (s, 3H), 3.85 (s, 3H), 2.21 (s, 3H). LC/MS (Method B): 420.3 (M+H)⁺. HPLC (Method A) Rt 5.53 min (Purity: 98.5%).

Step 2: 2-fluoro-4-{5-[4-(2-methoxypyridin-3-yl)-3-methylphenyl]-1,2,4-oxadiazol-3-yl}benzoic acid The title compound was prepared following procedure described for example 4, step 2, but starting from methyl 2-fluoro-4-{5-[4-(2-methoxypyridin-3-yl)-3-methylphenyl]-1,2,4-oxadiazol-3-yl}benzoate, obtained in step 1. Solvents were concentrated and water (5 mL) was added. It was filtrated to afford the title compound as a white powder (75 mg; 90%). ¹H NMR (DMSO-d₆, 300 MHz) δ 13.62 (br s, 1H), 8.28 (dd, J=4.9, 2.1 Hz, 1H), 8.15-8.02 (m, 4H), 7.96 (dd, J=11.1, 1.3 Hz, 1H), 7.67 (dd, J=7.1, 1.9 Hz, 1H), 7.46 (d, J=7.9 Hz, 1H), 7.14 (dd, J=7.3, 4.9 Hz, 1H), 3.85 (s, 3H), 2.21 (s, 3H). LC/MS (Method B): 404.3 (M−H)⁻, 406.2 (M+H)⁺.

Example 29

4-{5-[3-cyano-4-(2-methylpiperidin-1-yl)phenyl]-1,2,4-oxadiazol-3-yl}-2-fluorobenzoic acid

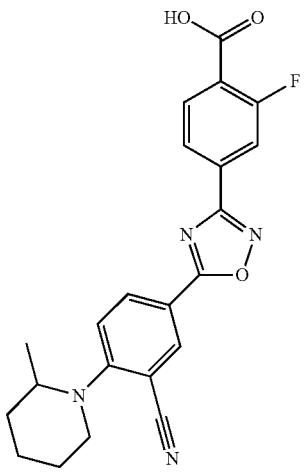

Step 1: methyl 4-{5-[3-cyano-4-(2-methylpiperidin-1-yl)phenyl]-1,2,4-oxadiazol-3-yl}-2-fluorobenzoate The title compound was prepared following procedure described for example 4, step 1, but starting from Intermediate 24 (146.58 mg; 0.60 mmol). The reaction mixture was filtered through a SPE NH₂ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as a white solid. ¹H NMR (DMSO-d₆, 300 MHz) δ 8.38 (d, J=2.2 Hz, 1H), 8.22 (dd, J=8.9, 2.2 Hz, 1H), 8.11 (t, J=7.7 Hz, 1H), 8.03 (dd, J=8.1, 1.5 Hz, 1H), 7.96 (dd, J=11.2, 1.4 Hz, 1H), 7.33 (d, J=9.1 Hz, 1H), 4.29-4.21 (m, 1H), 3.90 (s, 3H), 3.48-3.30 (m, 2H), 1.86-1.56 (m, 6H), 1.19 (d, J=6.6 Hz, 3H). LC/MS (Method B): 421.3 (M+H)⁺. HPLC (Method A) Rt 5.87 min (Purity: 96.3%).

Step 2: 4-{5-[3-cyano-4-(2-methylpiperidin-1-yl)phenyl]-1,2,4-oxadiazol-3-yl}-2-fluorobenzoic acid The title compound was prepared following procedure described for example 4, step 2, but starting from methyl 4-{5-[3-cyano-4-(2-methylpiperidin-1-yl)phenyl]-1,2,4-oxadiazol-3-yl}-2-fluorobenzoate, obtained in step 1. Solvents were concentrated and water (5 mL) was added. It was filtrated to afford the title compound as a beige powder (56 mg, 95%). ¹H NMR (DMSO-d₆, 300 MHz) δ 13.61 (br s, 1H), 8.38 (d, J=2.2 Hz, 1H), 8.23 (dd, J=9.0, 2.1 Hz, 1H), 8.08 (t, J=7.7 Hz, 1H), 8 (dd, J=8.1, 1.5 Hz, 1H), 7.92 (dd, J=11.1, 1.3 Hz, 1H), 7.33 (d, J=9.1 Hz, 1H), 4.29-4.21 (m, 1H), 3.46-3.30 (m, 2H), 1.86-1.57 (m, 6H), 1.19 (d, J=6.5 Hz, 3H). LC/MS (Method B): 405.3 (M−H)⁻, 407.2 (M+H)⁺. HPLC (Method A) Rt 5.11 min (Purity: 95.0%).

Example 30

2-fluoro-4-(5-{4-(2-methylpiperidin-1-yl)-3-[(methylsulfonyl)amino]phenyl}-1,2,4-oxadiazol-3-yl)benzoic acid

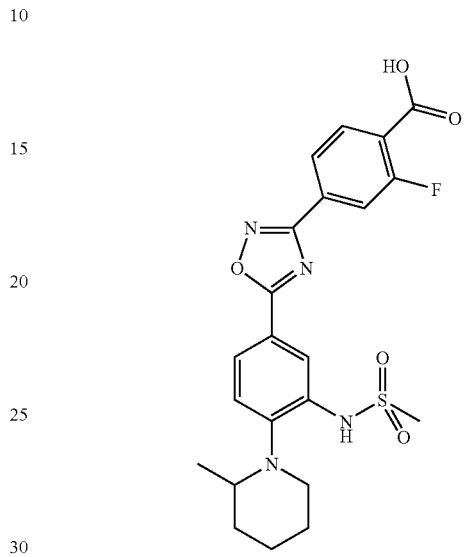

Step 1: methyl 2-fluoro-4-(5-{4-(2-methylpiperidin-1-yl)-3-[(methylsulfonyl)amino]phenyl}-1,2,4-oxadiazol-3-yl)benzoate The title compound was prepared following procedure described for example 4, step 1, but starting from Intermediate 25 (187.43 mg; 0.60 mmol). The reaction mixture was filtered through a SPE NH₂ column (2 g) and rinsed with ACN. The filtrate was passed through a SPE SCX column (2 g) and rinsed with ACN. The filtrate was evaporated to afford a yellow solid, which was triturated with ACN, filtered to give the title compound as a white solid. ¹H NMR (DMSO-d₆, 300 MHz) δ 8.68 (bs, 1H), 8.21 (d, J=1.8 Hz, 1H), 8.13 (t, J=7.3 Hz, 1H), 8.05 (dd, J=8.1, 1.6 Hz, 1H), 7.99-7.93 (m, 2H), 7.56 (d, J=8.5 Hz, 1H), 3.91 (s, 3H), 3.23 (s, 3H), 3.21-3.14 (m, 1H), 2.94-2.88 (m, 1H), 2.66-2.57 (m, 1H), 1.84-1.66 (m, 4H), 1.53-1.44 (m, 2H), 0.81 (d, J=6 Hz, 3H). LC/MS (Method B): 489.3 (M+H)⁺. HPLC (Method A) Rt 5.47 min (purity: 95.4%).

Step 2: 2-fluoro-4-(5-{4-(2-methylpiperidin-1-yl)-3-[(methylsulfonyl)amino]phenyl}-1,2,4-oxadiazol-3-yl)benzoic acid The title compound was prepared following procedure described for example 4, step 2, but starting from methyl 2-fluoro-4-(5-{4-(2-methylpiperidin-1-yl)-3-[(methylsulfonyl)amino]phenyl}-1,2,4-oxadiazol-3-yl)benzoate, obtained in step 1 (280 mg; 0.57 mmol). After 18 h, HCl (573.14 μL; 5 M; 2.87 mmol) was added and the mixture was evaporated to dryness. The solid was triturated in water and filtered to afford the title compound as a light yellow powder (220 mg; 80%). ¹H NMR (DMSO-d₆, 300 MHz) δ 13.6 (bs, 1H), 8.67, (bs, 1H), 8.20 (d, 2.1 Hz, 1H), 8.08, (t, J=7.9 Hz, 1H), 8 (dd, J=8.1, 1.6 Hz, 1H), 7.95-7.90 (m, 2H), 7.55 (d, J=8.4 Hz, 1H), 3.22

(s, 3H), 3.18-3.12 (m, 1H), 2.92-2.88 (m, 1H), 2.65-2.57 (m, 1H), 1.82-1.68 (m, 4H), 1.53-1.44 (m, 2H), 0.81 (d, J=6 Hz, 3H). LC/MS (Method B): 475.3 (M+H)⁺. HPLC (Method A) Rt 4.68 min (purity: 97.0%). CHN analysis: [C22H23N4O5SF] Calculated: C, 55.69%; H, 4.89%; N, 11.81%. Found: C, 55.41%; H, 4.76%; N, 11.70%.

Example 31

2-fluoro-4-[5-(2-methyl-1,1':2',1''-terphenyl-4-yl)-1,2,4-oxadiazol-3-yl]benzoic acid

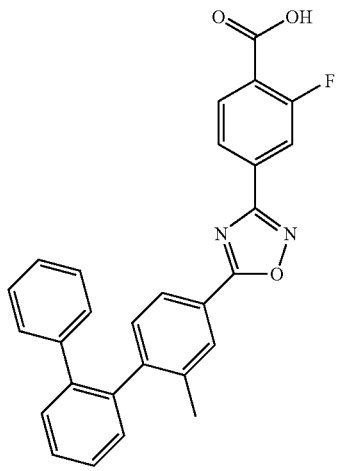

Step 1: methyl 2-fluoro-4-[5-(2-methyl-1,1':2',1''-terphenyl-4-yl)-1,2,4-oxadiazol-3-yl]benzoate The title compound was prepared following procedure described for example 4, step 1, but starting from Intermediate 26 (173.01 mg; 0.60 mmol). The reaction mixture was filtered through a SPE NH₂ column (2 g) and rinsed with ACN. The filtrate was passed through a SPE SCX column (2 g) and rinsed with ACN. After evaporation of the solvents, the crude product was purified by FC (c-hex/EtOAc: 9.5/0.5 to 5/5), affording the title compound as an off-white solid. LC/MS (Method A): 464.7 (M+H)⁺. HPLC (Method A) Rt 6.45 min (Purity: 98.7%).

Step 2: 2-fluoro-4-[5-(2-methyl-1,1':2',1''-terphenyl-4-yl)-1,2,4-oxadiazol-3-yl]benzoic acid The title compound was prepared following procedure described for example 4, step 2, but starting from methyl 2-fluoro-4-[5-(2-methyl-1,1':2',1''-terphenyl-4-yl)-1,2,4-oxadiazol-3-yl]benzoate, obtained in step 1, (86 mg; 0.19 mmol). Solvents were concentrated and EtOAc (20 mL) was added. It was washed with HCl 1N (15 mL), water (15 mL) and was dried over MgSO₄, affording the title compound as a off-white solid (75.4 mg, 90%). ¹H NMR (DMSO-d₆, 300 MHz) δ 13.59 (br s, 1H), 8.10-7.89 (m, 5H), 7.57-7.46 (m, 3H), 7.38-7.31 (m, 2H), 7.24-7.08 (m, 5H), 1.98 (s, 3H). LC/MS (Method B): 449.4 (M−H)⁻. HPLC (Method A) Rt 5.66 min (Purity: 95.3%).

Example 32

2-fluoro-4-[5-(2'-hydroxy-2-methylbiphenyl-4-yl)-1,2,4-oxadiazol-3-yl]benzoic acid

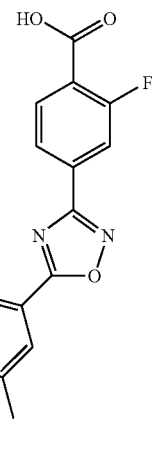

Step 1: methyl 2-fluoro-4-[5-(2'-hydroxy-2-methyl-biphenyl-4-yl)-1,2,4-oxadiazol-3-yl]benzoate The title compound was prepared following procedure described for example 4, step 1, but starting from Intermediate 27 (136.95 mg; 0.60 mmol). The reaction mixture was filtered through a SPE NH₂ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound. ¹H NMR (DMSO-d₆, 300 MHz) δ 9.61 (br s, 1H), 8.16-7.97 (m, 5H), 7.41 (d, J=7.8 Hz, 1H), 7.27-7.22 (m, 1H), 7.10 (dd, J=7.4, 1.7 Hz, 1H), 6.98-6.90 (m, 2H), 3.91 (s, 3H), 2.26 (s, 3H). LC/MS (Method B): 403.3 (M−H)⁻, 405.2 (M+H)⁺. HPLC (Method A) Rt 5.47 min (Purity: 95.4%).

Step 2: 2-fluoro-4-[5-(2'-hydroxy-2-methylbiphenyl-4-yl)-1,2,4-oxadiazol-3-yl]benzoic acid The title compound was prepared following procedure described for example 4, step 2, but starting from methyl 2-fluoro-4-[5-(2'-hydroxy-2-methylbiphenyl-4-yl)-1,2,4-oxadiazol-3-yl]benzoate, obtained in step 1. Solvents were concentrated and water (5 mL) was added. It was filtrated to afford the title compound as a white solid (30 mg; 78%). ¹H NMR (DMSO-d₆, 300 MHz) δ 13.60 (br s, 1H), 9.59 (br s, 1H), 8.13-8.02 (m, 4H), 7.96 (dd, J=11.2, 1.5 Hz, 1H), 7.41 (d, J=8.0 Hz, 1H), 7.28-7.22 (m, 1H), 7.10 (dd, J=7.4, 1.7 Hz, 1H), 6.98-6.88 (m, 2H), 2.26 (s, 3H). LC/MS (Method B): 389.3 (M−H)⁻, 391.2 (M+H)⁺. HPLC (Method A) Rt 4.67 min (Purity: 99.4%).

Example 33

2-fluoro-5-{5-[4-(2-methylpiperidin-1-yl)-3-(trifluoromethyl)phenyl]-1,2,4-oxadiazol-3-yl}benzoic acid

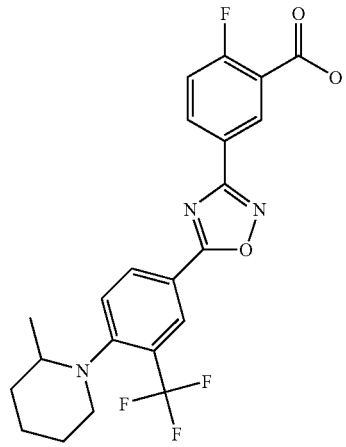

Step 1: methyl 2-fluoro-5-{5-[4-(2-methylpiperidin-1-yl)-3-(trifluoromethyl)phenyl]-1,2,4-oxadiazol-3-yl}benzoate The title compound was prepared following procedure described for example 4, step 1, but starting from Intermediate 15 (106.09 mg; 0.50 mmol) and Intermediate 45 (106.09 mg; 0.50 mmol). The reaction mixture was filtered through a SPE NH₂ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound. ¹H NMR (DMSO-d₆, 300 MHz) δ 8.58 (dd, J=7.0, 2.3 Hz, 1H), 8.46 (dd, J=8.3, 2.1 Hz, 1H), 8.41-8.36 (m, 2H), 7.87 (d, J=8.4 Hz, 1H), 7.62 (dd, 1H), 3.93 (s, 3H), 3.23-3.14 (m, 1H), 2.99-2.92 (m, 1H), 2.66-2.58 (m, 1H), 1.82-1.75 (m, 2H), 1.67-1.30 (m, 4H), 0.79 (d, J=6.1 Hz, 3H). LC/MS (Method B): 464.3 (M+H)⁺. HPLC (Method A) Rt 3.82 min (Purity: 99.9%).

Step 2: 2-fluoro-5-{5-[4-(2-methylpiperidin-1-yl)-3-(trifluoromethyl)phenyl]-1,2,4-oxadiazol-3-yl}benzoic acid The title compound was prepared following procedure described for example 4, step 2, but starting from methyl 2-fluoro-5-{5-[4-(2-methylpiperidin-1-yl)-3-(trifluoromethyl)phenyl]-1,2,4-oxadiazol-3-yl}benzoate, obtained in step 1. Solvents were concentrated and EtOAc (20 mL) was added. It was washed with water. The organic layer was then dried over magnesium sulfate, filtered and concentrated. Purification with MD-Autoprep afforded the title compound as a white powder. ¹H NMR (DMSO-d₆, 300 MHz) δ 13.71 (br s, 1H), 8.57 (dd, J=7.0, 2.3 Hz, 1H), 8.46 (dd, J=8.3, 2.0 Hz, 1H), 8.38 (d, J=2.0 Hz, 1H), 8.36-8.31 (m, 1H), 7.86 (d, J=8.6 Hz, 1H), 7.57 (dd, J=10.5, 8.7 Hz, 1H), 3.22-3.13 (m, 1H), 2.99-2.92 (m, 1H), 2.66-2.58 (m, 1H), 1.82-1.76 (m, 2H), 1.67-1.23 (m, 4H), 0.78 (d, J=6.1 Hz, 3H). LC/MS (Method B): 448.4 (M−H)⁻, 450.3 (M+H)⁺. HPLC (Method A) Rt 6.03 min (Purity: 99.8%).

Example 34

4-[5-(5-chloro-6-isobutoxypyridin-3-yl)-1,2,4-oxadiazol-3-yl]-2-fluorobenzoic acid

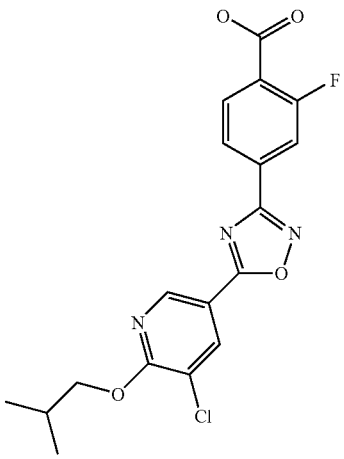

Step 1: methyl 4-[5-(5,6-dichloropyridin-3-yl)-1,2,4-oxadiazol-3-yl]-2-fluorobenzoate Oxalyl chloride (507.70 μL; 6 mmol) was added to suspension of 5,6-dichloronicotinic acid (FLUKA; 36000-10G; 384 mg; 2 mmol) and DMF (15.40 μL; 0.20 mmol) in DCM (30 mL) and the resulting mixture was stirred at RT for 1 hour. The solution was then evaporated to dryness. The residue was dissolved in THF (5 mL) and added dropwise to a mixture of Intermediate 1 (424.36 mg; 2 mmol), DIEA (1.03 mL; 6 mmol) in THF (5 mL). The reaction mixture was heated in the microwave at 150° C. for 30 min. When cool to RT the solid was filtered, rinsed with ACN, dissolved in DCM and washed with water. The organic layer was then dried over magnesium sulfate, filtered and concentrated to afford the title compound as a slightly yellow solid. ¹H NMR (DMSO-d₆, 300 MHz) δ 9.18-9.17 (m, 1H), 8.90-8.89 (m, 1H), 8.17-8 (m, 3H), 3.91 (s, 3H). ¹⁹F NMR (DMSO-d₆, 300 MHz) δ-108.7 ppm. HPLC (Method A) Rt 5.19 min (Purity: 98.0%).

Step 2: 4-[5-(5-chloro-6-isobutoxypyridin-3-yl)-1,2,4-oxadiazol-3-yl]-2-fluorobenzoic acid Lithium bis(trimethylsilyl)amide (700 μL; 1 M; 0.70 mmol) was added to a solution of methyl 4-[5-(5,6-dichloropyridin-3-yl)-1,2,4-oxadiazol-3-yl]-2-fluorobenzoate, obtained in step 1 (73.63 mg; 0.20 mmol) in 2-methyl-1-propanol (3 mL) and THF (2 mL). The resulting mixture was stirred at RT for 1 h. Water (500 uL) was added and the mixture was stirred at RT for 3 h, saponification was complete. The reaction mixture was then diluted with EtOAc and washed with HCl 1N, NaCl sat. solution and dried over magnesium sulfate. After evaporation of the solvents, the crude was purified by HPLC prep to afford the title compound as a slightly yellow powder. ¹H NMR (DMSO-d₆, 300 MHz) δ 8.94 (d, J=2.2 Hz, 1H), 8.60 (d, J=2.2 Hz, 1H), 8.08 (t, J=7.7

Hz, 1H), 8.01 (dd, J=8.1, 1.5 Hz, 1H), 7.94 (dd, J=11.1, 1.5 Hz, 1H), 4.27 (d, J=6.5 Hz, 2H), 2.16-2.07 (m, 1H), 1.01 (d, J=6.6 Hz, 6H). LC/MS (Method B): 390.3 (M−H)⁻, 392.2 (M+H)⁺. HPLC (Method A) Rt 5.49 min (Purity: 98.6%).

Example 35

2-fluoro-4-{5-[2-(methoxymethyl)-2'-methylbiphenyl-4-yl]-1,2,4-oxadiazol-3-yl}benzoic acid

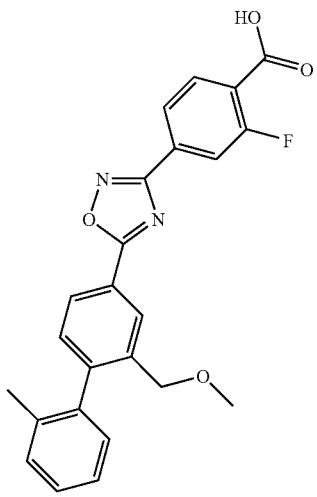

Step 1: Methyl 2-fluoro-4-{5-[2-(methoxymethyl)-2'-methylbiphenyl-4-yl]-1,2,4-oxadiazol-3-yl}benzoate Intermediate 28 (4 g; 15.61 mmol) was dissolved in dry Toluene (60 mL) under N₂ at RT, then oxalyl chloride (1.98 mL; 23.41 mmol) was added in one portion and then DMF (24.02 µl) was added. The reaction mixture was stirred at RT for 3 hours. The reaction mixture was concentrated to afford a yellow liquid. To a flask containing Intermediate 1 (3.31 g; 15.61 mmol) in Py (20 mL; 5 V) and toluene (20 mL) at RT and under N₂ was added dropwise the yellow liquid obtained previously in toluene (40 mL), the addition took 15 min. The reaction mixture was stirred at RT for 12 hours. Then the mixture was refluxed for 24 hours. The reaction mixture was cooled to RT and concentrated affording a beige solid which was washed with MeOH (40 mL). The suspension was filtered affording the title compound as a beige solid (5.58 g, 82%). ¹H NMR (DMSO-d₆, 300 MHz) δ 8.33 (m, 1H), 8.19-7.98 (m, 4H), 7.44-7.28 (m, 4H), 7.16-7.13 (m, 1H), 4.24-4.14 (m, 2H), 3.91 (s, 3H), 3.25 (s, 3H), 2.03 (s, 3H). LC/MS (Method B): 433.1 (M+H)⁺ HPLC: Rt 5.94 min (Purity: 94.9%).

Step 2: 2-fluoro-4-{5-[2-(methoxymethyl)-2'-methylbiphenyl-4-yl]-1,2,4-oxadiazol-3-yl}benzoic acid A solution of methyl 2-fluoro-4-{5-[2-(methoxymethyl)-2'-methylbiphenyl-4-yl]-1,2,4-oxadiazol-3-yl}benzoate (16 g; 37 mmol) in THF (400 mL) and MeOH (400 mL) at RT was treated with NaOH (37 mL; 5 M; 184.99 mmol). The reaction mixture was stirred at RT for 12 hours. The reaction mixture was concentrated to give a yellow solid. Water (600 mL) was added and the aqueous phase was washed with EtOAc (250 mL). Then the aqueous phase was acidified with HCl cc until pH 2 and extracted with EtOAc (2×300 mL). Organics were washed with brine, dried over MgSO4 and concentrated affording the title compound as a beige solid (11.66 g, 75%). ¹H NMR (DMSO, 400 MHz) δ 13.64 (br s, 1H), 8.33 (d, J=1.41 Hz, 1H), 8.17 (dd, J=7.92 Hz, 1.4 Hz, 1H), 8.13-8.03 (m, 2H), 7.96 (dd, J=11.10 Hz, 1.17 HZ, 1H), 7.43 (d, J=7.91 Hz, 1H), 7.37-7.27 (m, 3H), 7.15 (d, J=7.03 Hz, 1H), 4.25-4.14 (m, 2H), 3.25 (s, 3H), 2.04 (s, 3H). LC/MS (Method B): 419.1 (M+H)⁺; 417.2 (M−H)⁻. HPLC: Rt 5.19 min (Purity: 99.2%).

Example 36

4-[5-(5-chloro-6-isopropoxypyridin-3-yl)-1,2,4-oxadiazol-3-yl]-2-fluorobenzoic acid

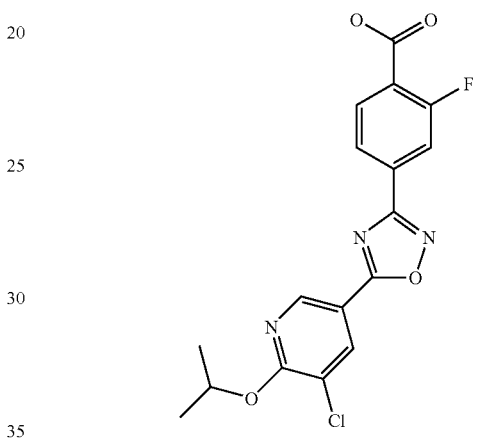

Sodium hydride (55% in oil) (21 mg; 0.48 mmol) was added to isopropanol (4 mL). After 30 min at rt, methyl 4-[5-(5,6-dichloropyridin-3-yl)-1,2,4-oxadiazol-3-yl]-2-fluorobenzoate, obtained in example 33 step 1 (60 mg; 0.16 mmol) was added and the mixture was heated in the microwave at 150° C. for 15 min. Water (2 mL) was added and the mixture was then diluted with EtOAc and washed with HCl 1N, NaCl sat. solution and dried over magnesium sulfate. After evaporation of the solvents, the crude was purified by flash chromatography (c-hex/EtOAc: 9.5/0.5), affording the mixture of methyl ester and isopropyl ester derivatives. The crude mixture was dissolved in THF (5 mL) and MeOH (5 mL), NaOH 5N (200 uL) was added and the mixture was stirred at RT for 1 hour. Solvents were concentrated and EtOAc (20 mL) was added. Then it was washed with HCl 1M (15 mL), NaCl sat. solution and dried over magnesium sulfate. The oily residue was purified by preparative HPLC to obtain the title compound as a white powder. ¹H NMR (DMSO-d₆, 300 MHz) δ 13.63 (br s, 1H), 8.92 (d, J=1.8 Hz, 1H), 8.55 (d, J=1.9 Hz, 1H), 8.08 (t, J=7.6 Hz, 1H), 7.99 (d, J=8.3 Hz, 1H), 7.91 (d, J=11.1 Hz, 1H), 5.44 (sept., J=5.9 Hz, 1H), 1.39 (d, J=6.2 Hz, 6H). LC/MS (Method B): 376.2 (M−H)⁻, 378.2 (M+H)⁺. HPLC (Method A) Rt 5.14 min (Purity: 99.7%).

Example 37

4-(5-{4-(2-methylpiperidin-1-yl)-3-[(methylsulfonyl)amino]phenyl}-1,2,4-oxadiazol-3-yl)benzenesulfonamide

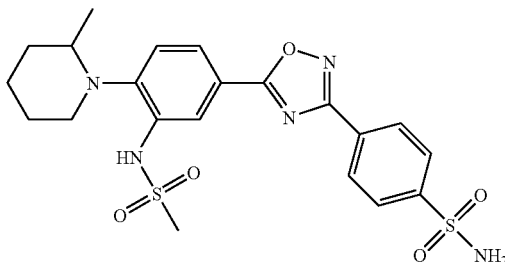

The title compound was prepared following procedure described for example 4, step 1, but starting from 4-(aminosulfonyl)-N'-hydroxybenzenecarboximidamide, prepared as described in WO 2006/013104 A1 from 4-cyanobenzene-1-sulfonamide (ABCR; CD10716), (322.85 mg; 1.50 mmol) and Intermediate 25 (562.30 mg; 1.80 mmol). The reaction mixture was evaporated under reduce pressure and was purified by flash chromatography (c-hex/EtOAc: 9.5/0.5), affording the title compound as a pale yellow solid. ¹H NMR (DMSO-d₆, 300 MHz) δ 8.68 (br s, 1H), 8.31-8.27 (m, 2H), 8.22 (d, J=2.0 Hz, 1H), 8.06-8.03 (m, 2H), 7.94 (dd, J=8.2, 1.8 Hz, 1H), 7.57 (br s, 2H), 7.55 (s, 1H), 3.23 (s, 3H), 3.20-3.13 (m, 1H), 2.94-2.87 (m, 1H), 2.66-2.57 (m, 1H), 1.84-1.66 (m, 4H), 1.50-1.44 (m, 2H), 0.82 (d, J=6.1 Hz, 3H). LC/MS (Method B): 490.4 (M−H)⁻, 492.4 (M+H)⁺. HPLC (Method A) Rt 4.34 min (Purity: 97.9%).

Example 38

4-{5-[4-(2-methylpiperidin-1-yl)-3-(trifluoromethyl)phenyl]-1,2,4-oxadiazol-3-yl}benzenesulfonamide

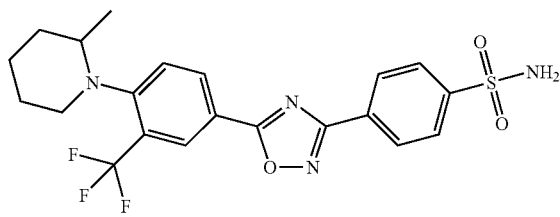

Oxalyl chloride (190 mg; 1.5 mmol) was added to a suspension of Intermediate 15 (144 mg; 0.5 mmol) and DMF (catalytic amount) in DCM (2 mL) and the reaction mixture was stirred at RT for 1 hour. After concentration to dryness, the residue was taken up in THF (2 mL) and added to a solution of 4-(aminosulfonyl)-N'-hydroxybenzenecarboximidamide, prepared as described in WO 2006/013104 A1 from 4-cyanobenzene-1-sulfonamide (ABCR; CD10716), (108 mg; 05 mmol, 1 eq.) and DIEA (194 mg; 1.5 mmol) in THF (1 mL). The reaction mixture was then stirred at 150° C. for 30 minutes in the microwave. After cooling, the mixture was filtered through a SPE-NH₂ column, which was further washed with THF. After concentration in vacuo, the residue was purified by recrystallisation from DCM/n-pentane, affording the title compound as a white solid. LC/MS (Method A): 467.3 (M+H)+. HPLC (Method A) Rt 5.59 min (purity 99.3%).

Example 39

4-{5-[3-methoxy-4-(4-methyl-3-thienyl)phenyl]-1,2,4-oxadiazol-3-yl}benzenesulfonamide

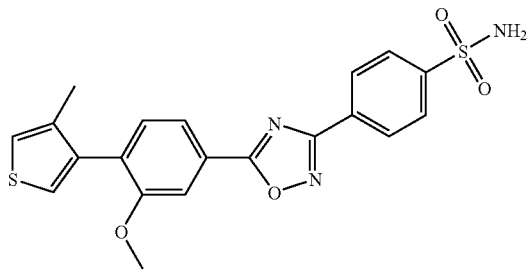

Oxalyl chloride (123 mL; 1.45 mmol), Intermediate 8 (120 mg; 0.48 mmol), 4-(aminosulfonyl)-N'-hydroxybenzenecarboximidamide, prepared as described in WO 2006/013104 A1 from 4-cyanobenzene-1-sulfonamide (ABCR; CD10716), (104 mg; 05 mmol, 1 eq.) and DIEA (250 mL; 1.45 mmol) were reacted according to the procedure described for Example 38. Purification by recrystallisation from DCM/n-pentane afforded the title compound as a white solid. LC/MS (Method A): 426.3 (M−H)⁻. HPLC (Method A) Rt 4.93 min (purity 89.2%).

Example 40

4-[5-(2,2'-dimethylbiphenyl-4-yl)-1,2,4-oxadiazol-3-yl]benzenesulfonamide

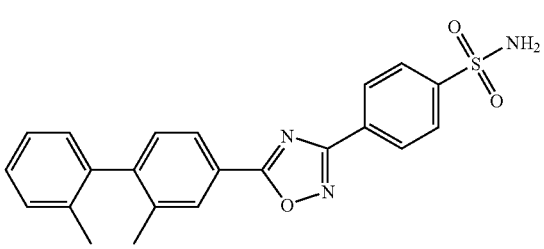

Oxalyl chloride (134 mL; 1.59 mmol), Intermediate 3 (120 mg; 0.53 mmol), 4-(aminosulfonyl)-N'-hydroxybenzenecarboximidamide, prepared as described in WO 2006/013104 A1 from 4-cyanobenzene-1-sulfonamide (ABCR; CD10716), (114 mg; 0.53 mmol, 1 eq.) and DIEA (274 mL; 1.59 mmol) were reacted according to the procedure described for Example 38. Purification by recrystallisation

Example 41

4-(5-{6-[2-(methoxymethyl)pyrrolidin-1-yl]-5-methylpyridin-3-yl}-1,2,4-oxadiazol-3-yl)benzenesulfonamide

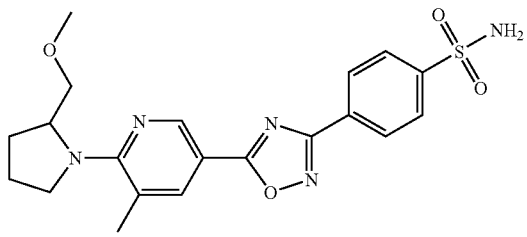

Oxalyl chloride (122 mL; 1.44 mmol), Intermediate 29 (120 mg; 0.48 mmol), 4-(aminosulfonyl)-N'-hydroxybenzenecarboximidamide, prepared as described in WO 2006/013104 A1 from 4-cyanobenzene-1-sulfonamide (ABCR; CD10716), (103 mg; 0.48 mmol, 1 eq.) and DIEA (248 mL; 1.44 mmol) were reacted according to the procedure described for Example 38. Purification by column chromatography (from cHex/EtOAc, 50/50 to EtOAc) followed by recrystallisation from DCM/n-pentane afforded the title compound as a yellow solid. LC/MS (Method A): 430.3 (M+H)$^+$. HPLC (Method A) Rt 2.80 min (purity 93.1%).

Example 42

4-[5-(2,2'-dimethylbiphenyl-4-yl)-1,2,4-oxadiazol-3-yl]benzoic acid

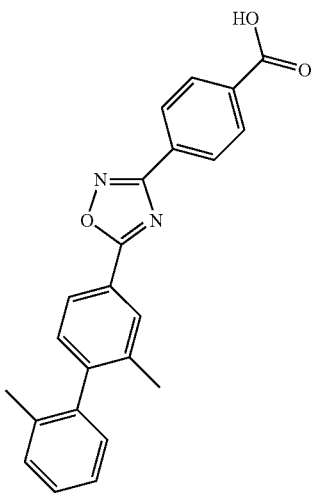

Step 1: methyl 4-[5-(2,2'-dimethylbiphenyl-4-yl)-1,2,4-oxadiazol-3-yl]benzoate

The title compound was prepared following procedure described for example 4, step 1, but starting from Intermediate 3 (113.14 mg; 0.50 mmol) and methyl 4-[amino(hydroxyimino)methyl]benzoate (Maybridge; 97.10 mg; 0.50 mmol). The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as a colorless oil. LC/MS (Method A): 385.0 (M+H)$^+$. HPLC (Method A) Rt 6.16 min (Purity: 98.5%).

Step 2: 4-[5-(2,2'-dimethylbiphenyl-4-yl)-1,2,4-oxadiazol-3-yl]benzoic acid

The title compound was prepared following procedure described for example 4, step 2, but starting from methyl 4-[5-(2,2'-dimethylbiphenyl-4-yl)-1,2,4-oxadiazol-3-yl]benzoate, obtained in step 1 (60 mg; 0.16 mmol). Solvents were concentrated and EtOAc (20 mL) was added. It was washed with HCl 1N (15 mL), water (15 mL) and was dried over MgSO$_4$, affording the title compound as a off-white solid (31 mg, 80%). LC/MS (Method A): 369.0 (M−H)$^−$; 371.1 (M+H)$^+$. HPLC (Method A) Rt 5.40 min (Purity: 100%).

Example 43

5-[5-(2,2'-dimethylbiphenyl-4-yl)-1,2,4-oxadiazol-3-yl]-2-hydroxybenzoic acid

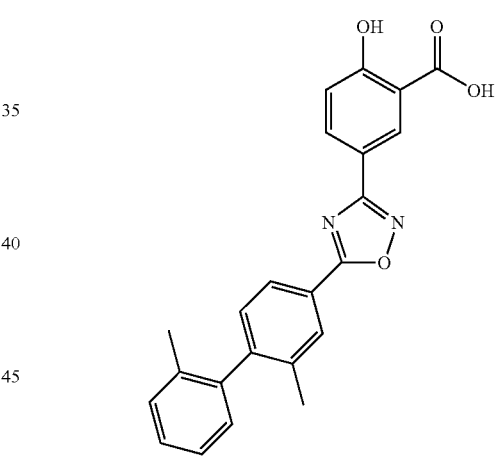

Step 1: methyl 5-[5-(2,2'-dimethylbiphenyl-4-yl)-1,2,4-oxadiazol-3-yl]-2-hydroxybenzoate Under Argon atmosphere, Intermediate 3 (147.08 mg; 0.65 mmol) was stirred in anhydrous DCM (5 mL). Oxalyl chloride (57.75 μL; 0.68 mmol) was added followed by DMF (0.50 μL; 0.01 mmol). The reaction mixture was stirred 3 hours at RT. Solvents were evaporated to give 2,2'-dimethylbiphenyl-4-carbonyl chloride as a yellow oil. The latter was dissolved in anhydrous THF (3 mL), Intermediate 46 (136.62 mg; 0.65 mmol) and DIEA (221.08 μL; 1.30 mmol) were added under argon. The mixture was heated in the microwave at 150° C. for 15 min. The reaction mixture was diluted in water and extracted with EtOAc, the organic phase was then washed with NH$_4$Cl, NaHCO$_3$ and NaCl sat. solution. The organic layer was then dried over magnesium sulfate, filtered and concentrated, the crude product was purified by flash

Step 2: 5-[5-(2,2'-dimethylbiphenyl-4-yl)-1,2,4-oxadiazol-3-yl]-2-hydroxybenzoic acid The title compound was prepared following procedure described for example 4, step 2, but starting from methyl 5-[5-(2,2'-dimethylbiphenyl-4-yl)-1,2,4-oxadiazol-3-yl]-2-hydroxybenzoate, obtained in step 1, and using 25 eq. of NaOH at 60° C. for 6 h. Solvents were concentrated and DCM (20 mL) was added. It was washed with HCl 1M. The organic layer was then dried over magnesium sulfate, filtered and concentrated to afford the title compound as a pale orange solid (18 mg; 90%). $^1$H NMR (DMSO-$d_6$, 300 MHz) δ 8.54 (d, J=2.1 Hz, 1H), 8.22-8.17 (m, 2H), 8.08-8.05 (m, 1H), 7.38-7.28 (m, 4H), 7.19-7.12 (m, 2H), 2.14 (s, 3H), 2.04 (s, 3H). LC/MS (Method A): 385.0 (M−H)$^-$. HPLC (Method A) Rt 5.49 min (Purity: 97.2%).

Example 44

2-hydroxy-5-{5-[3-methyl-4-(4-methyl-3-thienyl)phenyl]-1,2,4-oxadiazol-3-yl}benzoic acid

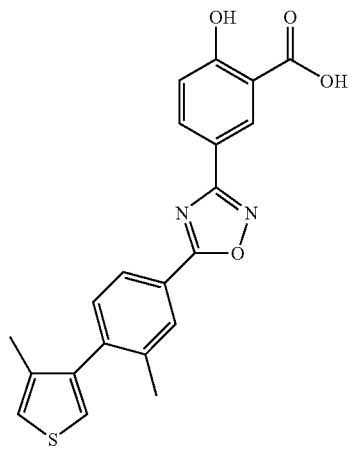

Step 1: methyl 2-hydroxy-5-{5-[3-methyl-4-(4-methyl-3-thienyl)phenyl]-1,2,4-oxadiazol-3-yl}benzoate The title compound was prepared following procedure described for example 43, step 1, but starting from Intermediate 6 (92 mg; 0.40 mmol) to give 3-methyl-4-(4-methyl-3-thienyl)benzoyl chloride as a brownish oil. The latter was dissolved in anhydrous THF (2 mL), Intermediate 46 (84.08 mg; 0.40 mmol) and DIEA (136.05 μL; 0.80 mmol) were added under argon. The mixture was heated in the microwave at 150° C. for 15 min. The reaction mixture was diluted in water and extracted with EtOAc, the organic phase was then washed with NH$_4$Cl, NaHCO$_3$ and NaCl sat. solution. The organic layer was then dried over magnesium sulfate, filtered and concentrated, the crude product was purified by flash chromatography (c-hex/EtOAc: 9.5/0.5), affording the title compound. HPLC (Method A) Rt 6.23 min (Purity: 100.0%).

Step 2: 2-hydroxy-5-{5-[3-methyl-4-(4-methyl-3-thienyl)phenyl]-1,2,4-oxadiazol-3-yl}benzoic acid The title compound was prepared following procedure described for example 4, step 2, but starting from methyl 2-hydroxy-5-{5-[3-methyl-4-(4-methyl-3-thienyl)phenyl]-1,2,4-oxadiazol-3-yl}benzoate, obtained in step 1 and using 25 eq. of NaOH at 60° C. for 6 h. Solvents were concentrated and DCM (20 mL) was added. It was washed with HCl 1M. The organic layer was then dried over magnesium sulfate, filtered and concentrated to afford the title compound as a slightly orange solid. $^1$H NMR (DMSO-$d_6$, 300 MHz) δ 8.52 (d, J=2.0 Hz, 1H), 8.15-8.12 (m, 2H), 8.06-8.03 (m, 1H), 7.46-7.39 (m, 2H), 7.35-7.34 (m, 1H), 7.10 (d, J=8.6 Hz, 1H), 2.24 (s, 3H), 2.01 (s, 3H). LC/MS (Method A): 390.9 (M−H)$^-$. HPLC (Method A) Rt 5.39 min (Purity: 97.1%).

Example 45

4-[5-(2,2'-dimethylbiphenyl-4-yl)-1,2,4-oxadiazol-3-yl]-3-methoxybenzoic acid

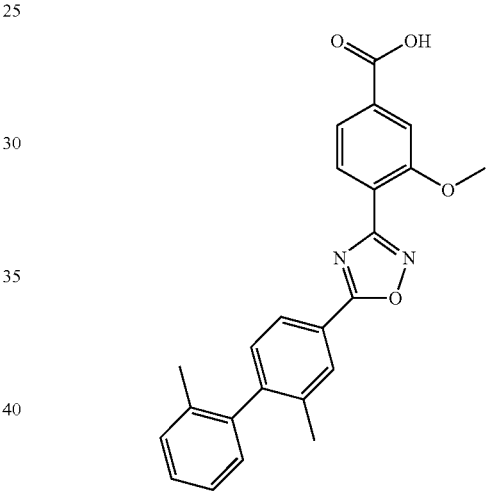

Step 1: methyl 4-[5-(2,2'-dimethylbiphenyl-4-yl)-1,2,4-oxadiazol-3-yl]-3-methoxybenzoate The title compound was prepared following procedure described for example 43, step 1 to give 2,2'-dimethylbiphenyl-4-carbonyl chloride (0.50 mmol) as a yellow oil. The latter was dissolved in anhydrous THF (3 mL), Intermediate 47 (112.11 mg; 0.50 mmol) and DIEA (170.06 μL; 1 mmol) were added under argon. The mixture was heated in the microwave at 150° C. for 15 min. The reaction mixture was diluted in water and extracted with EtOAc, the organic phase was then washed with NH$_4$Cl, NaHCO$_3$ and NaCl sat. solution. The organic layer was then dried over magnesium sulfate, filtered and concentrated, the crude product was suspended in ACN, filtrated, recristalized in EtOAC and dried under vacuo, affording the title compound as a white solid. $^1$H NMR (DMSO-$d_6$, 300 MHz) δ 8.15-8.12 (m, 2H), 8.06 (dd, J=7.6, 1.5 Hz, 1H), 7.77-7.72 (m, 2H), 7.38-7.27 (m, 4H), 7.14-7.11 (m, 1H), 4 (s, 3H), 3.92 (s, 3H), 2.13 (s, 3H), 2.03 (s, 3H). LC/MS (Method A): 415.3 (M+H)$^+$. HPLC (Method A) Rt 6 min (Purity: 98.1%).

Example 45

Step 2: 4-[5-(2,2'-dimethylbiphenyl-4-yl)-1,2,4-oxadiazol-3-yl]-3-methoxybenzoic acid The title compound was prepared following procedure described for example 4, step 2, but starting from methyl 4-[5-(2,2'-dimethylbiphenyl-4-yl)-1,2,4-oxadiazol-3-yl]-3-methoxybenzoate, obtained in step 1. Solvents were concentrated and water (5 mL) was added. It was filtrated to afford the title compound as a white solid (49 mg; 78%). $^1$H NMR (DMSO-d$_6$, 300 MHz) δ 13.98 (br s, 1H), 8.15-8.04 (m, 3H), 7.74-7.72 (m, 2H), 7.38-7.27 (m, 4H), 7.14-7.12 (m, 1H), 3.98 (s, 3H), 2.14 (s, 3H), 2.04 (s, 3H). LC/MS (Method A): 399.0 (M−H)$^-$, 400.9 (M+H)$^+$. HPLC (Method A) Rt 5.05 min (Purity: 98.4%).

Example 46

4-[5-(2,2'-dimethylbiphenyl-4-yl)-1,2,4-oxadiazol-3-yl]-2-methoxybenzoic acid

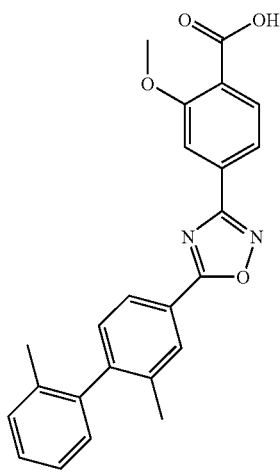

Step 1: methyl 4-[5-(2,2'-dimethylbiphenyl-4-yl)-1,2,4-oxadiazol-3-yl]-2-methoxybenzoate The title compound was prepared following procedure described for example 43, step 1 to give 2,2'-dimethylbiphenyl-4-carbonyl chloride (0.50 mmol) as a yellow oil. The latter was dissolved in anhydrous THF (3 mL), Intermediate 48 (112.11 mg; 0.50 mmol) and DIEA (170.06 μL; 1 mmol) were added under argon. The mixture was heated in the microwave at 150° C. for 15 min. The reaction mixture was diluted in water and extracted with EtOAc, the organic phase was then washed with NH$_4$Cl, NaHCO$_3$ and NaCl sat. solution. The organic phase was then dried over magnesium sulfate, filtered and concentrated, the crude product was purified by flash chromatography (c-hex/EtOAc: 9.5/0.5). The pure fractions were evaporated then washed with cHex affording the title compound as a beige solid. LC/MS (Method A): 415.0 (M+H)$^+$. HPLC (Method A) Rt 5.99 min (Purity: 95.9%).

Step 2: 4-[5-(2,2'-dimethylbiphenyl-4-yl)-1,2,4-oxadiazol-3-yl]-2-methoxybenzoic acid The title compound was prepared following procedure described for example 4, step 2, but starting from methyl 4-[5-(2,2'-dimethylbiphenyl-4-yl)-1,2,4-oxadiazol-3-yl]-2-methoxybenzoate, obtained in step 1. Solvents were concentrated and EtOAc (20 mL) was added. It was washed with water. The organic layer was then dried over magnesium sulfate, filtered and concentrated to afford the title compound as an orange solid (17 mg; 89%). $^1$H NMR (DMSO-d$_6$, 300 MHz) δ 12.97 (br s, 1H), 8.18 (d, J=1.9 Hz, 1H), 8.09 (dd, J=7.8, 1.5 Hz, 1H), 7.84 (d, J=8.2 Hz, 1H), 7.77-7.74 (m, 2H), 7.39-7.27 (m, 4H), 7.14-7.12 (m, 1H), 3.96 (s, 3H), 2.14 (s, 3H), 2.04 (s, 3H). LC/MS (Method A): 399.0 (M−H)$^-$, 400.9 (M+H)$^+$. HPLC (Method A) Rt 5.35 min (Purity: 90.4%).

Example 47

(2-fluoro-4-{5-[4-(2-methylpiperidin-1-yl)-3-(trifluoromethyl)phenyl]-1,2,4-oxadiazol-3-yl}phenoxy)acetic acid

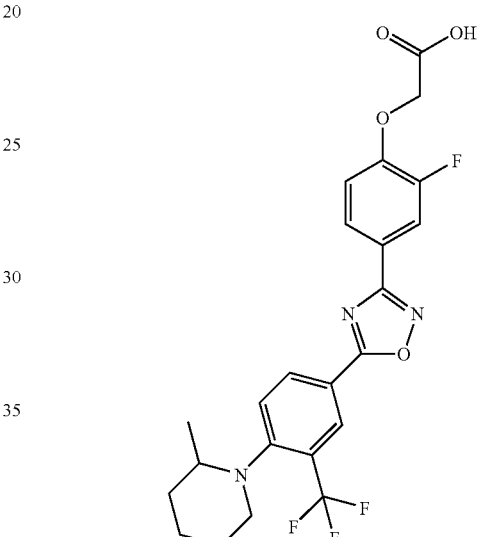

Step 1: tert-butyl (2-fluoro-4-{5-[4-(2-methylpiperidin-1-yl)-3-(trifluoromethyl)phenyl]-1,2,4-oxadiazol-3-yl}phenoxy)acetate The title compound was prepared following procedure described for example 4, step 1, but starting from Intermediate 49 (142.14 mg; 0.50 mmol) and Intermediate 15 (172.37 mg; 0.60 mmol). The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as a white solid. LC/MS (Method B): 536.4 (M+H)$^+$. HPLC (Method A) Rt 7.2 min (Purity: 99.4%).

Step 2: (2-fluoro-4-{5-[4-(2-methylpiperidin-1-0)-3-(trifluoromethyl)phenyl]-1,2,4-oxadiazol-3-yl}phenoxy)acetic acid Tert-butyl (2-fluoro-4-{5-[4-(2-methylpiperidin-1-yl)-3-(trifluoromethyl)phenyl]-1,2,4-oxadiazol-3-yl}phenoxy)acetate, obtained in Step 1 (80 mg; 0.15 mmol) was dissolved in DCM (3 mL) and cooled down to 0° C. Trifluoroacetic acid (0.3 mL) was added and the resulting mixture was stirred at RT overnight. As the reaction was not complete, trifluoroacetic acid (0.3 mL) was added and the mixture was stirred one more day. The solvents were evaporated and the crude product was dissolved in EtOAc, washed with HCl 1N, dried over $MgSO_4$ and evaporated, affording the title product as a beige-yellow solid (71 mg; 99%). $^1H$ NMR (DMSO-$d_6$, 300 MHz) δ 13.21 (br s, 1H), 8.45-8.37 (m, 2H), 7.91-7.81 (m, 3H), 7.32 (t, J=9 Hz, 1H), 4.92 (s, 2H), 3.25-3.1 (m, 1H), 2.98-2.89 (m, 1H), 2.72-2.58 (m, 1H), 1.85-1.70 (m, 2H), 1.70-1.20 (m, 4H), 0.78 (d, J=6 Hz, 3H). LC/MS (Method B): 478.4 (M–H)$^-$; 480.3 (M+H)$^+$. HPLC (Method A) Rt 5.88 min (Purity: 93.8%).

Example 48

{4-[5-(2,2'-dimethylbiphenyl-4-yl)-1,2,4-oxadiazol-3-yl]-2-fluorophenoxy}acetic acid

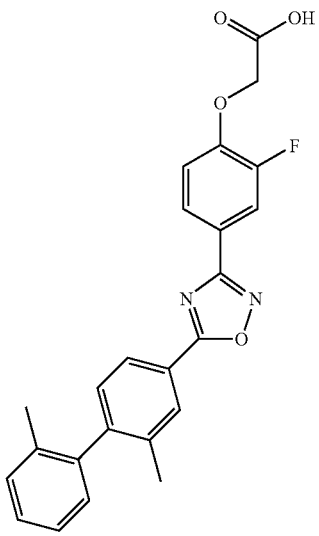

Step 1: tert-butyl {4-[5-(2,2'-dimethylbiphenyl-4-yl)-1,2,4-oxadiazol-3-yl]-2-fluorophenoxy}acetate The title compound was prepared following procedure described for example 4, step 1, but starting from Intermediate 49 (142.14 mg; 0.50 mmol) and Intermediate 3 (135.76 mg; 0.60 mmol). The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as a colorless oil. LC/MS (Method B): 475.4 (M+H)$^+$. HPLC (Method A) Rt 6.78 min (Purity: 99.3%).

Step 2: {4-[5-(2,2'-dimethylbiphenyl-4-yl)-1,2,4-oxadiazol-3-yl]-2-fluorophenoxy}acetic acid The title compound was prepared following procedure described for example 47, step 2, but starting from tert-butyl {4-[5-(2,2'-dimethylbiphenyl-4-yl)-1,2,4-oxadiazol-3-yl]-2-fluorophenoxy}acetate, obtained in step 1, (73 mg; 0.15 mmol). The title compound was isolated as a beige solid (64 mg; 99%). $^1H$ NMR (DMSO-$d_6$, 300 MHz) δ 13.26 (br s, 1H), 8.15 (d, J=1.5 Hz, 1H), 8.06 (dd, J=1.5, 7.5 Hz, 1H), 7.91-7.87 (m, 2H), 7.39-7.27 (m, 5H), 7.14-7.11 (m, 1H), 4.92 (s, 2H), 2.14 (s, 3H), 2.03 (s, 3H). LC/MS (Method B): 417.4 (M–H)$^-$; 419.3 (M+H)$^+$. HPLC (Method A) Rt 5.34 min (Purity: 98.7%).

Example 49

{4-[5-(5-chloro-6-isobutoxypyridin-3-yl)-1,2,4-oxadiazol-3-yl]-2-fluorophenoxy}acetic acid

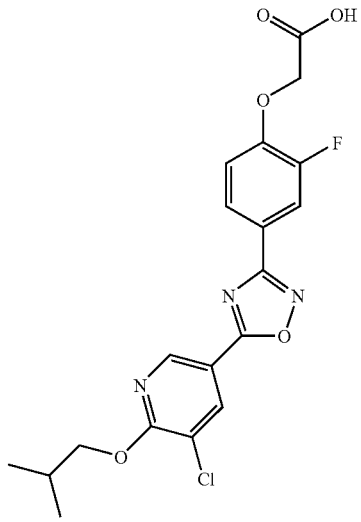

Step 1: tert-butyl {4-[5-(5,6-dichloropyridin-3-yl)-1,2,4-oxadiazol-3-yl]-2-fluorophenoxy}acetate The title compound was prepared following procedure described for example 4, step 1, but starting from Intermediate 49 (995.01 mg; 3.50 mmol) and 5,6-dichloronicotinic acid (806.4 mg; 4.2 mmol). The reaction mixture was evaporated. The crude product was dissolved in EtOAc and washed with $NH_4Cl$ sat, $NaHCO_3$ sat, brine and dried over $MgSO_4$. After evaporation of the solvents, the resulting solid was suspended in MeCN and filtrated, affording the title compound as an off-white solid. LC/MS (Method B): 420.3 (M–H)$^-$. HPLC (Method A) Rt 5.72 min (Purity: 99.4%).

Step 2: {4-[5-(5-chloro-6-isobutoxypyridin-3-yl)-1,2,4-oxadiazol-3-yl]-2-fluorophenoxy}acetic acid Lithium bis(trimethylsilyl)amide (225 µl; 1 M; 0.22 mmol) was added to a solution of tert-butyl {4-[5-(5,6-dichloropyridin-3-yl)-1,2,4-oxadiazol-3-yl]-2-fluorophenoxy}acetate (66.04 mg; 0.15 mmol) in 2-methyl-1-propanol (1.50 mL) and THF (2 mL). The resulting mixture was heated at 130° C. for 10 min in the microwave. A mixture of the desired product and the isopropyl ester was isolated. NaOH (5N solution; 5 eq; 0.15 mL) was added and the mixture was stirred at RT for 2 hours. The reaction mixture was diluted with EtOAc and washed with HCl 1N, brine and dried over $MgSO_4$. After evaporation of the solvents, the title product was isolated as white solid (51 mg; 81%). $^1H$ NMR (DMSO-$d_6$, 300 MHz) δ 13.25 (br s, 1H), 8.91 (d, J=2 Hz, 1H), 8.57 (d, J=2 Hz, 1H), 7.90-7.86 (m, 2H), 7.32 (t, J=9 Hz, 1H), 4.91 (s, 2H), 4.27 (d, J=6 Hz, 2H), 2.12 (m, 1H), 1.02 (d, J=6 Hz, 6H). LC/MS (Method B): 420.3 (M−H)⁻. HPLC (Method A) Rt 5.29 min (Purity: 100%).

Example 50

{4-[5-(6-sec-butoxy-5-chloropyridin-3-yl)-1,2,4-oxadiazol-3-yl]-2-fluorophenoxy}acetic acid

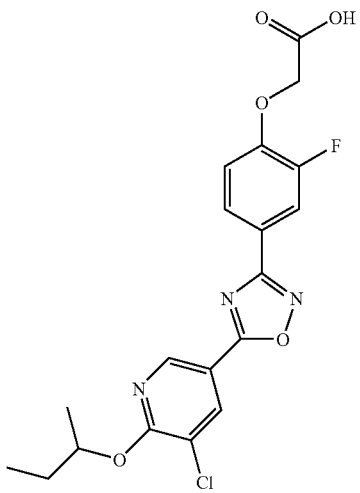

The title compound was prepared following procedure described for example 49, step 2, but using a mixture of THF (2 mL) and (rac)-2-butanol (2 mL; 26.14 mmol) as solvent. The resulting mixture was heated at 130° C. for 20 min in the microwave, affording directly the desired product. After evaporation of the solvents, it was diluted with EtOAc and washed with HCl 1N, brine and dried over MgSO₄. It was finally suspended in MeOH and filtrated affording the title compound as a white solid. ¹H NMR (DMSO-d₆, 300 MHz) δ 13.26 (br s, 1H), 8.91 (d, J=2 Hz, 1H), 8.55 (d, J=2 Hz, 1H), 7.89-7.85 (m, 2H), 7.31 (t, J=9 Hz, 1H), 5.30 (m, 1H), 4.91 (s, 2H), 1.75 (m, 2H), 1.36 (d, J=6 Hz, 3H), 0.95 (t, J=7.5 Hz, 3H). LC/MS (Method B): 420.3 (M−H)⁻; 422.2 (M+H)⁺. HPLC (Method A) Rt 5.39 min (Purity: 94.5%).

Example 51

(4-{5-[5-chloro-6-(prop-2-yn-1-yloxy)pyridin-3-yl]-1,2,4-oxadiazol-3-yl}-2-fluorophenoxy)acetic acid

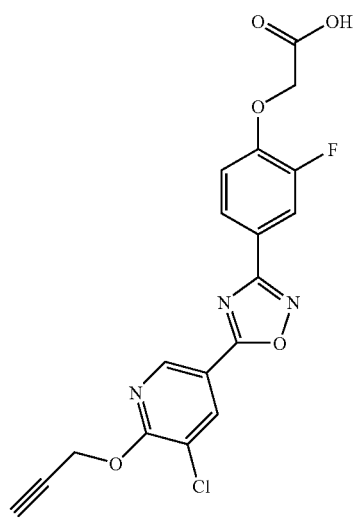

The title compound was prepared following procedure described for example 50, but using a mixture of THF (2 mL) and propargyl alcohol (2 mL) as solvent. It was suspended in MeOH and filtrated affording the title compound as a white solid. ¹H NMR (DMSO-d₆, 300 MHz) δ 13.25 (br s, 1H), 8.95 (d, J=2 Hz, 1H), 8.62 (d, J=2 Hz, 1H), 7.90-7.82 (m, 2H), 7.35 (t, J=9 Hz, 1H), 5.20 (d, J=3 Hz, 2H), 4.92 (s, 2H), 3.65 (t, J=3 Hz, 1H). LC/MS (Method B): 402.3 (M−H)⁻. HPLC (Method A) Rt 4.53 min (Purity: 92.4%).

Example 52

(4-{5-[5-chloro-6-(cyclopropylmethoxy)pyridin-3-yl]-1,2,4-oxadiazol-3-yl}-2-fluorophenoxy)acetic acid

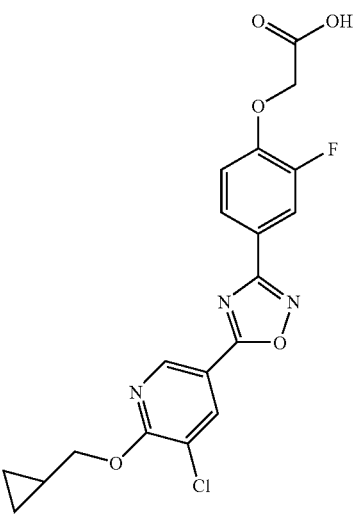

The title compound was prepared following procedure described for example 49, step 2, but using a mixture of THF (2 mL) and cyclopropylmethanol (2 mL) as solvent. Trituration in MeOH and filtration in MeOH afforded the title compound as a white solid. ¹H NMR (DMSO-d₆, 300 MHz) δ 13.2 (br s, 1H), 8.91 (d, J=2.1 Hz, 1H), 8.57 (d, J=2.1 Hz, 1H), 7.93-7.82 (m, 2H), 7.35-7.26 (m, 1H), 4.90 (s, 2H), 4.34 (m, 2H), 1.42-1.21 (m, 1H), 0.66-0.56 (m, 2H), 0.45-0.37 (m, 2H). LC/MS (Method B): 418.4 (M−H)⁻. HPLC (Method A) Rt 5.05 min (Purity: 97.0%).

Example 53

{4-[5-(5-chloro-6-isopropoxypyridin-3-yl)-1,2,4-oxadiazol-3-yl]-2-fluorophenoxy}acetic acid

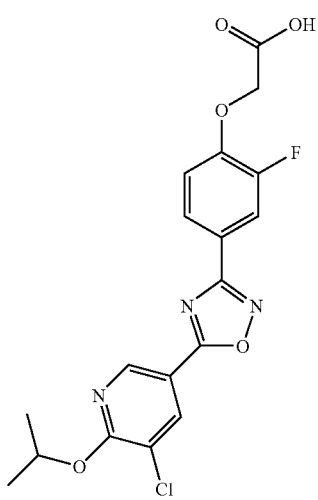

The title compound was prepared following procedure described for example 49, step 2, but using a mixture of THF (2 mL) and propan-2-ol (2 mL) as solvent. It was suspended in MeOH and filtrated affording a white solid. ¹H NMR (DMSO-d₆, 300 MHz) δ 8.90 (d, J=3 Hz, 1H), 8.53 (d, J=3 Hz, 1H), 7.87-7.82 (m, 2H), 7.28 (t, J=9 Hz, 1H), 5.44 (sept, J=6 Hz, 1H), 4.87 (s, 2H), 1.39 (d, J=6 Hz, 6H). LC/MS (Method B): 406.3 (M−H)⁻; 408.3 (M+H)⁺. HPLC (Method A) Rt 5.08 min (Purity: 100%).

Example 54

N-{4-[5-(2,2'-dimethylbiphenyl-4-yl)-1,2,4-oxadiazol-3-yl]-2-fluorobenzoyl}glycine

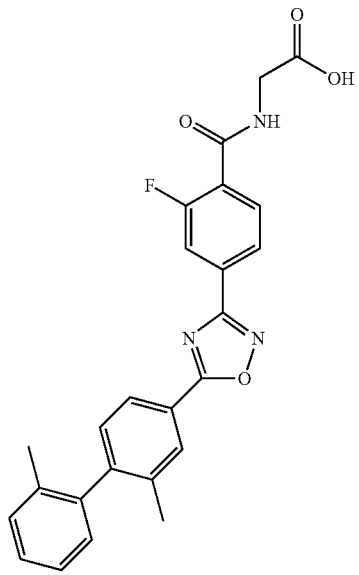

Step 1: methyl N-{4-[5-(2,2'-dimethylbiphenyl-4-yl)-1,2,4-oxadiazol-3-yl]-2-fluorobenzoyl}glycinate Oxalyl chloride (63.46 µL; 0.75 mmol) was added to suspension of example 4 (97.10 mg; 0.25 mmol) and DMF (0.50 µL; 0.01 mmol) in DCM (10 mL) and the resulting mixture was stirred at RT for 1 hour. The solution was then evaporated to dryness, the residue taken up in THF (3 mL) and then added to a mixture of glycine methyl ester hydrochloride salt (FLUKA; 50110; 31.39 mg; 0.25 mmol) and DIEA (189.56 µL; 1.10 mmol) in THF (2 mL). The reaction mixture was stirred at RT for 2 hours, filtered through a SPE NH₂ column (2 g) and rinsed with ACN. After evaporation of the solvents, the crude product was purified by flash chromatography (c-hex/EtOAc: 9.5/0.5), affording the title compound as a yellow oil (99 mg; 86%). ¹H NMR (DMSO-d₆, 300 MHz) δ 8.95-8.90 (m, 1H), 8.18 (br s, 1H), 8.10-8.04 (m, 2H), 7.98 (dd, J=10.8, 1.3 Hz, 1H), 7.93-7.88 (m, 1H), 7.40-7.27 (m, 4H), 7.15-7.12 (m, 1H), 4.07 (d, J=5.5 Hz, 2H), 3.69 (s, 3H), 2.14 (s, 3H), 2.04 (s, 3H). LC/MS (Method B): 458.5 (M−H)⁻, 460.3 (M+H)⁺. HPLC (Method A) Rt 5.57 min (Purity: 99.2%).

Step 2: N-{4-[3-(2,2'-dimethylbiphenyl-4-yl)-1,2,4-oxadiazol-3-yl]-2-fluorobenzoyl}glycine The title compound was prepared following procedure described for example 4, step 2, but starting from methyl N-{4-[5-(2,2'-dimethylbiphenyl-4-yl)-1,2,4-oxadiazol-3-yl]-2-fluorobenzoyl}glycinate, obtained in step 1. Solvents were concentrated and EtOAc (20 mL) was added. It was washed with water. The organic layer was then dried over magnesium sulfate, filtered and concentrated to afford the title compound as a white solid. ¹H NMR (DMSO-d₆, 300 MHz) δ 12.72 (br s, 1H), 8.81-8.77 (m, 1H), 8.19 (d, J=1.4 Hz, 1H), 8.10-8.04 (m, 2H), 7.97 (dd, J=10.9, 1.4 Hz, 1H), 7.93-7.88 (m, 1H), 7.40-7.27 (m, 4H), 7.14-7.12 (m, 1H), 3.97 (d, J=5.8 Hz, 2H), 2.14 (s, 3H), 2.04 (s, 3H). LC/MS (Method B): 444.4 (M−H)⁻, 446.3 (M+H)⁺. HPLC (Method A) Rt 5.09 min (Purity: 96.8%).

Example 55

N-{4-[5-(2,2'-dimethylbiphenyl-4-yl)-1,2,4-oxadiazol-3-yl]-2-fluorobenzoyl}-beta-alanine

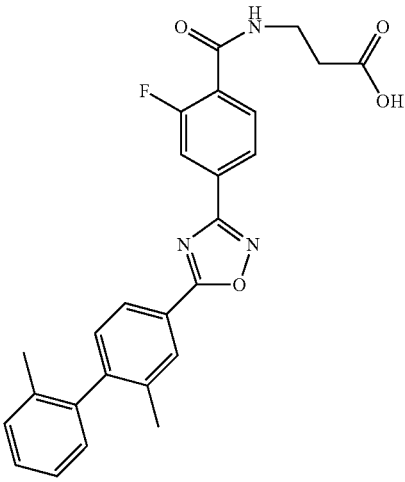

Step 1: methyl N-{4-[5-(2,2'-dimethylbiphenyl-4-yl)-1,2,4-oxadiazol-3-yl]-2-fluorobenzoyl}-beta-alaninate The title compound was prepared following procedure described for example 54, step 1, but starting from beta-alanine methyl ester hydrochloride (FLUKA; 05210-10G; 34.90 mg; 0.25 mmol). The reaction mixture was filtered through a SPE NH₂ column (2 g) and rinsed with ACN. Evaporation of the solvents afforded the title compound as a pale yellow solid (105 mg; 89%). ¹H NMR (DMSO-d₆, 300 MHz) δ 8.64-8.60 (m, 1H), 8.18 (d, J=1.8 Hz, 1H), 8.08 (dd, J=7.9, 1.4 Hz, 1H), 8.02 (dd, J=8.0, 1.5 Hz, 1H), 7.94 (dd, J=10.6, 1.5 Hz, 1H), 7.83 (t, J=7.6 Hz, 1H), 7.40-7.27 (m, 4H), 7.14-7.11 (m, 1H), 3.63 (s, 3H), 3.52 (q, J=6.5 Hz, 2H), 2.62 (t, J=6.9 Hz, 2H), 2.14 (s, 3H), 2.03 (s, 3H). LC/MS (Method B): 472.4 (M−H)⁻, 474.3 (M+H)⁺. HPLC (Method A) Rt 5.62 min (Purity: 97.8%).

Step 2: N-{4-[5-(2,2'-dimethylbiphenyl-4-yl)-1,2,4-oxadiazol-3-yl]-2-fluorobenzoyl}-beta-alanine The title compound was prepared following procedure described for example 4, step 2, but starting from methyl N-{4-[5-(2,2'-dimethylbiphenyl-4-yl)-1,2,4-oxadiazol-3-yl]-2-fluorobenzoyl}-beta-alaninate, obtained in step 1. Solvents were concentrated and DCM (20 mL) was added. The resulting solution was washed with water. The organic layer was then dried over magnesium sulfate, filtered, concentrated and dry freezed to afford the title compound as a white solid. $^1$H NMR (DMSO-$d_6$, 300 MHz) δ 12.31 (br s, 1H), 8.60-8.55 (m, 1H), 8.17 (d, J=1.3 Hz, 1H), 8.08 (dd, J=7.9, 1.3 Hz, 1H), 8.01 (dd, J=7.9, 1.5 Hz, 1H), 7.93 (dd, J=10.8, 1.3 Hz, 1H), 7.86-7.81 (m, 1H), 7.39-7.27 (m, 4H), 7.14-7.11 (m, 1H), 3.49 (q, J=6.5 Hz, 2H), 2.56-2.51 (m, 2H), 2.13 (s, 3H), 2.03 (s, 3H). LC/MS (Method B): 458.4 (M−H)$^-$, 460.3 (M+H)$^+$. HPLC (Method A) Rt 5.07 min (Purity: 97.3%).

Example 56

N-{4-[5-(2,2'-dimethylbiphenyl-4-yl)-1,2,4-oxadiazol-3-yl]-2-fluorophenyl}glycine

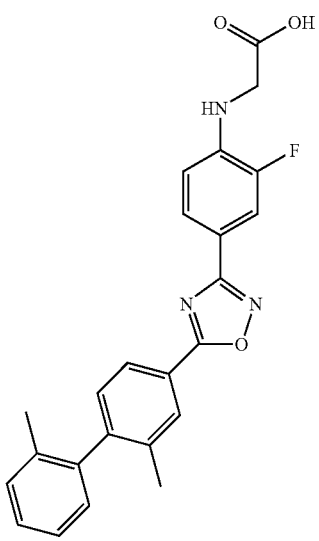

Step 1: tert-butyl N-{4-[5-(2,2'-dimethylbiphenyl-4-yl)-1,2,4-oxadiazol-3-yl]-2-fluorophenyl}glycinate The title compound was prepared following procedure described for example 4, step 1, but starting from Intermediate 50 (141.65 mg; 0.50 mmol) and Intermediate 3 (135.76 mg; 0.60 mmol). The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as a colorless oil. LC/MS (Method B): 474.4 (M+H)$^+$. HPLC (Method A) Rt 6.70 min (Purity: 84.4%).

Step 2: N-{4-[5-(2,2'-dimethylbiphenyl-4-yl)-1,2,4-oxadiazol-3-yl]-2-fluorophenyl}glycine Tert-butyl N-{4-[5-(2,2'-dimethylbiphenyl-4-yl)-1,2,4-oxadiazol-3-yl]-2-fluorophenyl}glycinate, obtained in step 1, (85 g; 0.18 mmol) was dissolved in DCM (4 mL) and the resulting solution was cooled down to 0° C. Trifluoroacetic acid (0.4 mL; 1.79 mmol) was added dropwise. The resulting mixture was stirred at RT overnight. The solvents were evaporated and the resulting crude product was purified by MD Autoprep, affording the title compound as a light yellow solid. $^1$H NMR (DMSO-$d_6$, 300 MHz) δ 12.75 (br s, 1H), 8.13 (br s, 1H), 8.07-8 (m, 1H), 7.79-7.64 (m, 2H), 7.40-7.24 (m, 4H), 7.16-7.09 (m, 1H), 6.79 (t, J=9.07 Hz, 1H), 6.46-6.36 (br m, 1H), 3.97 (m, 2H), 2.13 (s, 3H), 2.03 (s, 3H). LC/MS (Method B): 416.2 (M−H)$^-$; 418.1 (M+H)$^+$. HPLC (Method A) Rt 5.27 min (Purity: 96.7%).

Example 57

N-methyl-N-[3-(5-{4-(2-methylpiperidin-1-yl)-3-[(methylsulfonyl)amino]phenyl}-1,2,4-oxadiazol-3-yl)benzyl]glycine, Hydrochloride salt

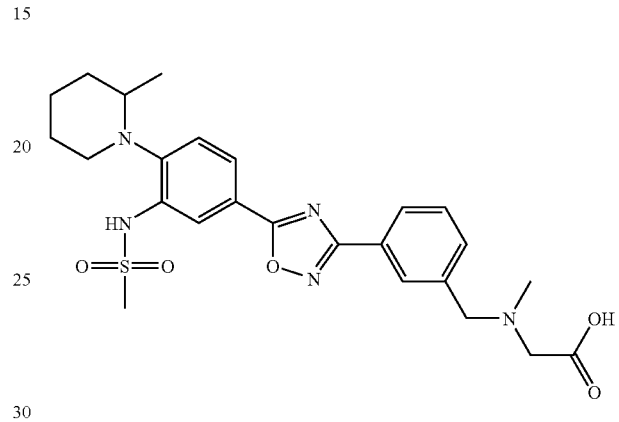

Step 1: tert-butyl N-methyl-N-[3-(5-{4-(2-methylpiperidin-1-yl)-3-[(methylsulfonyl)amino]phenyl}-1,2,4-oxadiazol-3-yl)benzyl]glycinate The title compound was prepared following procedure described for example 4, step 1, but starting from Intermediate 51 (440.05 mg; 1.50 mmol), and Intermediate 25 (562.30 mg; 1.80 mmol). The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography over Alumina column (c-hex/EtOAc: 9.5/0.5), affording the title compound as an off-white powder. HPLC (Method A) Rt 4.76 min (Purity: 96.7%).

Step 2: N-methyl-N-[3-(5-{4-(2-methylpiperidin-1-yl)-3-[(methylsulfonyl)amino]phenyl}-1,2,4-oxadiazol-3-yl)benzyl]glycine, Hydrochloride salt To tert-butyl N-methyl-N-[3-(5-{4-(2-methylpiperidin-1-yl)-3-[(methylsulfonyl)amino]phenyl}-1,2,4-oxadiazol-3-yl)benzyl]glycinate, obtained in step 1 (279.20 mg; 0.49 mmol) was added HCl 4M in dioxane (6 mL; 4 M; 24 mmol). The mixture was stirred at RT for 24 h. Solvents were concentrated to dryness. ACN and water were added it was dried freezed to afford the title compound as a beige solid. $^1$H NMR (DMSO-$d_6$, 300 MHz) δ 10.48 (br s, 1H), 8.71 (br s, 1H), 8.31 (s, 1H), 8.22-8.18 (m, 2H), 7.94 (dd, J=8.1, 1.5 Hz, 1H), 7.80 (d, J=7.9 Hz, 1H), 7.71 (t, J=7.7 Hz, 1H), 7.57 (d, J=8.2 Hz, 1H), 4.51 (br s, 2H), 4.14 (s, 2H), 3.23 (s, 3H), 3.19-3.12 (m, 1H), 2.93-2.89 (m, 1H), 2.82 (s, 3H), 2.66-2.56 (m, 1H), 1.85-1.66 (m, 4H), 1.51-1.43 (m, 2H), 0.82 (d, J=6.0 Hz, 3H).

LC/MS (Method B): 512.4 (M−H)⁻, 514.3 (M+H)⁺. HPLC (Method A) Rt 3.45 min (Purity: 96.0%).

Example 58

2-fluoro-4-{5-[2-(hydroxymethyl)-2'-methylbiphenyl-4-yl]-1,2,4-oxadiazol-3-yl}benzoic acid

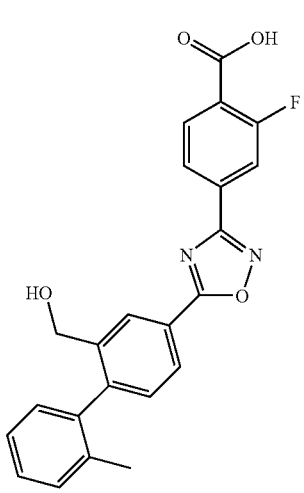

Step 1: methyl 2-fluoro-4-{5-[2-(hydroxymethyl)-2'-methylbiphenyl-4-yl]-1,2,4-oxadiazol-3-yl}benzoate The title compound was prepared following procedure described for example 4, step 1, but starting from Intermediate 30 (145.36 mg; 0.60 mmol). The reaction mixture was filtered through a SPE NH₂ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5 to 5/5), affording the title compound as an off-white solid. ¹H NMR (DMSO-d₆, 300 MHz) δ 8.44 (d, J=1.5 Hz, 1H), 8.17-8.07 (m, 3H), 8.01 (dd, J=11.2, 1.3 Hz, 1H), 7.39-7.26 (m, 4H), 7.13 (d, J=7.2 Hz, 1H), 5.44 (br s, 1H), 4.34-4.17 (m, 2H), 3.92 (s, 3H), 2.03 (s, 3H). LC/MS (Method B): 419.3 (M+H)⁺. HPLC (Method A) Rt 5.29 min (Purity: 98.5%).

Step 2: 2-fluoro-4-{5-[2-(hydroxymethyl)-2'-methylbiphenyl-4-yl]-1,2,4-oxadiazol-3-yl}benzoic acid The title compound was prepared following procedure described for example 4, step 2, but starting from methyl 2-fluoro-4-{5-[2-(hydroxymethyl)-2'-methylbiphenyl-4-yl]-1,2,4-oxadiazol-3-yl}benzoate, obtained in step 1, (44.30 mg; 0.11 mmol). Solvents were concentrated and EtOAc (20 mL) was added. It was washed with HCl 1N (15 mL), water (15 mL) and was dried over MgSO₄, affording the title compound as a off-white solid (40 mg, 93%). ¹H NMR (DMSO-d₆, 300 MHz) δ 13.61 (br s, 1H), 8.47-8.42 (m, 1H), 8.18-7.92 (m, 4H), 7.43-7.24 (m, 4H), 7.13 (d, J=6.9 Hz, 1H), 5.43 (br s, 1H), 4.31 (d, J=14.1 Hz, 1H), 4.19 (d, J=14.1 Hz, 1H), 2.03 (s, 3H). LC/MS (Method B): 403.4 (M−H)⁻; 405.4 (M+H)⁺. HPLC (Method A) Rt 4.37 min (Purity: 95.1%).

Example 59

2-fluoro-4-{5-[2-(isopropoxymethyl)-2'-methylbiphenyl-4-yl]-1,2,4-oxadiazol-3-yl}benzoic acid

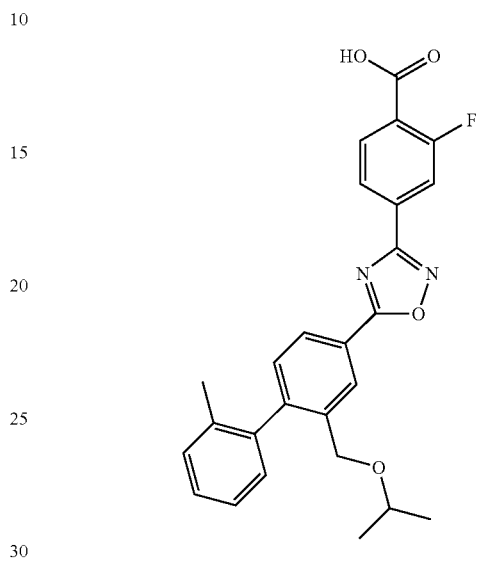

Step 1: methyl 2-fluoro-4-[5-(2'-methyl-2-{[(methylsulfonyl)oxy]methyl}biphenyl-4-yl)-1,2,4-oxadiazol-3-yl]benzoate At 0° C., into a solution of methyl 2-fluoro-4-{5-[2-(hydroxymethyl)-2'-methylbiphenyl-4-yl]-1,2,4-oxadiazol-3-yl}benzoate, prepared as in example 58, step 1, (500 mg; 1.19 mmol) in DCM (15 mL) was added DIEA (610 μL; 3.58 mmol) and methanesulfonyl chloride (139 μL; 1.79 mmol). The reaction was allowed to warm to RT for 2 h30. Water (5 mL) was added and the DCM extract was rapidly washed twice more with water. The organic layer was then dried over magnesium sulfate, filtered and concentrated to afford the title compound as a yellow foam (573 mg; 97%). ¹H NMR (DMSO-d₆, 300 MHz) δ 8.47 (d, J=1.8 Hz, 1H), 8.30 (dd, J=8.0, 1.8 Hz, 1H), 8.18-8.13 (m, 1H), 8.09 (dd, J=8.1, 1.5 Hz, 1H), 8.02 (dd, J=11.2, 1.4 Hz, 1H), 7.54 (d, J=8.0 Hz, 1H), 7.40-7.29 (m, 3H), 7.19 (d, J=7.0 Hz, 1H), 5.11 (d, J=11.4 Hz, 1H), 5.05 (d, J=11.4 Hz, 1H), 3.92 (s, 3H), 3.04 (s, 3H), 2.05 (s, 3H). LC/MS (Method B): 497.3 (M+H)⁺. HPLC (Method A) Rt 5.52 min (Purity: 96.7%).

Step 2: 2-fluoro-4-{5-[2-(isopropoxymethyl)-2'-methylbiphenyl-4-yl]-1,2,4-oxadiazol-3-yl}benzoic acid Methyl 2-fluoro-4-[5-(2'-methyl-2-{[(methylsulfonyl)oxy]methyl}biphenyl-4-yl)-1,2,4-oxadiazol-3-yl]benzoate, obtained in step 1 (50 mg; 0.10 mmol) was dissolved in 2-propanol (4 mL). The solution was then heated under microwave irradiation at 130° C. for 10 min. Sodium hydroxide (5 M; 5 eq.) was added and the mixture was heated at 60° C. for 10 min in the microwave. Hydrogen chloride (5 M; 5 eq.) was added and the mixture was evaporated to dryness. The crude was purified with MD Autoprep, to afford the title compound as a white powder. ¹H NMR (DMSO-d₆, 300 MHz) δ 13.64 (br s, 1H), 8.32 (d, J=1.6 Hz, 1H), 8.16 (dd, J=7.9, 1.8 Hz, 1H), 8.13-8.08 (m, 1H), 8.05 (dd, J=8.2, 1.6 Hz, 1H), 7.96 (dd, J=11.0, 1.3 Hz, 1H), 7.43 (d, J=8.0 Hz, 1H), 7.36-7.26 (m, 3H), 7.15 (d, J=7.2 Hz, 1H), 4.22 (s, 2H), 3.44 (sept., J=6.1 Hz, 1H), 2.04 (s, 3H), 1.03 (d, J=6.1 Hz, 3H), 1 (d, J=6.2 Hz, 3H). LC/MS (Method B): 445.3 (M−H)⁻, 447.3 (M+H)⁺. HPLC (Method A) Rt 5.79 min (Purity: 99.9%).

Example 60

2-fluoro-4-{5-[2-(isobutoxymethyl)-2'-methylbiphenyl-4-yl]-1,2,4-oxadiazol-3-yl}benzoic acid

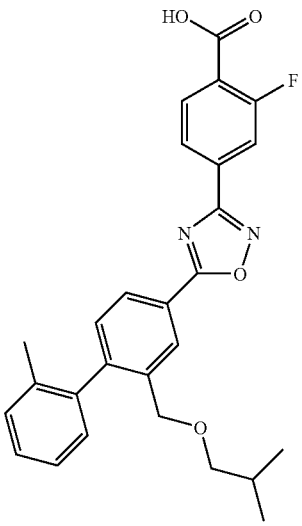

Methyl 2-fluoro-4-[5-(2'-methyl-2-{[(methylsulfonyl)oxy]methyl}biphenyl-4-yl)-1,2,4-oxadiazol-3-yl]benzoate, prepared as in example 58, step 1, (75 mg; 0.15 mmol) was dissolved in 2-methyl-1-propanol (5 mL). The solution was then heated in the microwave at 130° C. for 10 min. Sodium hydroxide (151.05 μL; 5 M; 0.76 mmol) was added and the mixture was heated at 60° C. for 10 min in the microwave. Hydrogen chloride (151.05 μL; 5 M; 0.76 mmol) was added and the mixture was evaporated to dryness. The crude was purified with MD Autoprep, to afford the title compound as a white powder. ¹H NMR (DMSO-d₆, 300 MHz) δ 13.63 (br s, 1H), 8.34 (d, J=1.5 Hz, 1H), 8.18 (dd, J=8.0, 1.8 Hz, 1H), 8.13-8.08 (m, 1H), 8.03 (dd, J=8.1, 1.4 Hz, 1H), 7.95 (dd, J=11.0, 1.2 Hz, 1H), 7.43 (d, J=7.9 Hz, 1H), 7.36-7.25 (m, 3H), 7.15 (d, J=7.0 Hz, 1H), 4.23 (s, 2H), 3.10 (d, J=6.4 Hz, 2H), 2.04 (s, 3H), 1.77 (sept, J=6.6 Hz, 1H), 0.84 (d, J=6.6 Hz, 6H). LC/MS (Method B): 459.4 (M−H)⁻, 461.3 (M+H)⁺. HPLC (Method A) Rt 6.04 min (Purity: 99.3%).

Example 61

4-(5-{2-[(cyclopropylmethoxy)methyl]-2'-methylbiphenyl-4-yl}-1,2,4-oxadiazol-3-yl)-2-fluorobenzoic acid

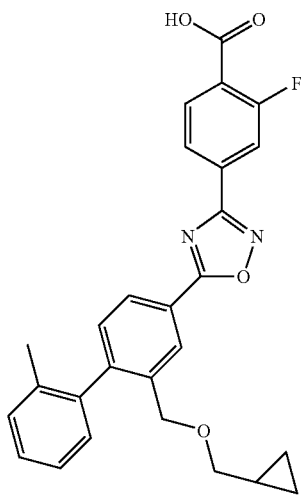

Methyl 2-fluoro-4-[5-(2'-methyl-2-{[(methylsulfonyl)oxy]methyl}biphenyl-4-yl)-1,2,4-oxadiazol-3-yl]benzoate, prepared as in example 58, step 1, (75 mg; 0.15 mmol) was dissolved in cyclopropylmethanol (5 mL). The solution was then heated in the microwave at 130° C. for 10 min. Sodium hydroxide (151.05 μL; 5 M; 0.76 mmol) was added and the mixture was heated at 60° C. for 10 min in the microwave. Hydrogen chloride (151.05 μL; 5 M; 0.76 mmol) was added and the mixture was evaporated to dryness. The crude was purified with MD Autoprep, to afford the title compound as a white powder. ¹H NMR (DMSO-d₆, 300 MHz) 13.63 (br s, 1H), 8.35 (d, J=1.5 Hz, 1H), 8.18 (dd, J=7.8, 1.9 Hz, 1H), 8.13-8.08 (m, 1H), 8.04 (dd, J=8.0, 1.4 Hz, 1H), 7.96 (dd, J=11.1, 1.2 Hz, 1H), 7.43 (d, J=7.9 Hz, 1H), 7.36-7.26 (m, 3H), 7.15 (d, J=7.2 Hz, 1H), 4.30-4.20 (m, 2H), 3.20-3.17 (m, 2H), 2.04 (s, 3H), 1-0.91 (m, 1H), 0.46-40 (m, 2H), 0.14-0.09 (m, 2H). LC/MS (Method B): 457.3 (M−H)⁻, 459.2 (M+H)⁺. HPLC (Method A) Rt 5.67 min (Purity: 98.5%).

Example 62

4-(5-{2-[(dimethylamino)methyl]-2'-methylbiphenyl-4-yl}-1,2,4-oxadiazol-3-yl)-2-fluorobenzoic acid, Hydrochloride salt

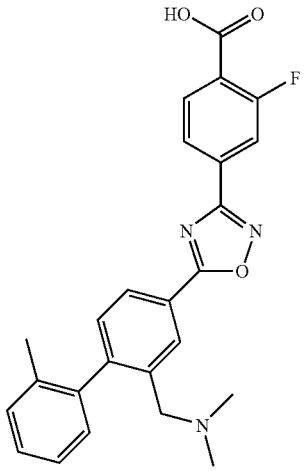

To a solution of methyl 2-fluoro-4-[5-(2'-methyl-2-{[(methylsulfonyl)oxy]methyl}biphenyl-4-yl)-1,2,4-oxadiazol-3-yl], prepared as in example 58, step 1, (75 mg; 0.15 mmol) in THF (750 μL) was added dimethylamine (2M in THF, 225 μL; 0.45 mmol). The reaction was stirred overnight at RT. Sodium hydroxide (151.05 μL; 5 M; 0.76 mmol) was added and the mixture was heated at 60° C. for 10 min under microwave irradiation. Hydrogen chloride (302.11 μL; 5 M; 1.51 mmol) was added and the mixture was evaporated to dryness. The crude was purified with MD Autoprep, to afford the title compound as a white solid. ¹H NMR (DMSO-d₆, 300 MHz) δ 8.63 (s, 1H), 8.25 (dd, J=8.0, 1.5 Hz, 1H), 8.15-8.10 (m, 1H), 8.04 (dd, J=8.1, 1.5 Hz, 1H), 7.96 (dd, J=11.1, 1.4 Hz, 1H), 7.50 (d, J=8.0 Hz, 1H), 7.40-7.30 (m, 3H), 7.19 (d, J=7.2 Hz, 1H), 3.97 (br s, 1H), 3.68 (d, J=12.4 Hz, 1H), 2.42 (br s, 6H), 2.02 (s, 3H). LC/MS (Method B): 430.2 (M−H)⁻, 432.2 (M+H)⁺. HPLC (Method A) Rt 3.41 min (Purity: 99.6%).

Example 63

4-{5-[2-(ethoxymethyl)-2'-methylbiphenyl-4-yl]-1,2,4-oxadiazol-3-yl}-2-fluorobenzoic acid

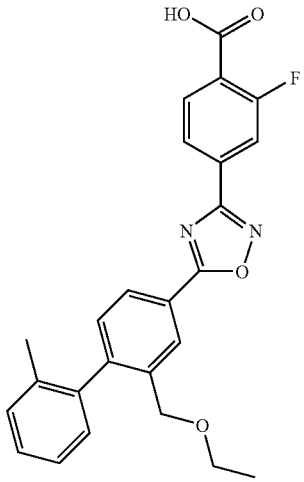

Step 1: methyl 4-{5-[2-(ethoxymethyl)-2'-methylbiphenyl-4-yl]-1,2,4-oxadiazol-3-yl}-2-fluorobenzoate The title compound was prepared following procedure described for example 4, step 1, but starting from Intermediate 42 (247.80 mg; 0.50 mmol). The reaction mixture was filtered through a SPE NH₂ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), then by preparative HPLC affording the title compound as a colorless oil. ¹H NMR (CDCl₃) δ 8.43 (d, J=1.4 Hz, 1H), 8.17 (dd, J=7.9, 1.8 Hz, 1H), 8.13-7.98 (m, 3H), 7.36-7.23 (m, 4H), 7.13 (d, J=7.4 Hz, 1H), 4.27 (s, 2H), 3.98 (s, 3H), 3.44 (q, J=7.0 Hz, 2H), 2.08 (s, 3H), 1.20 (t, J=7.0 Hz, 3H). LC/MS (Method B): 447.3 (M+H)⁺. HPLC (Method A) Rt 6.29 min (Purity: 99.8%).

Step 2: 4-{5-[2-(ethoxymethyl)-2'-methylbiphenyl-4-yl]-1,2,4-oxadiazol-3-yl}-2-fluorobenzoic acid The title compound was prepared following procedure described for example 4, step 2, but starting from methyl 4-{5-[2-(ethoxymethyl)-2'-methylbiphenyl-4-yl]-1,2,4-oxadiazol-3-yl}-2-fluorobenzoate, obtained in step 1. Solvents were concentrated and water (5 mL) was added. It was filtrated to afford the title compound as a white solid (55 mg, quantitative). ¹H NMR (DMSO-d₆, 300 MHz) δ 13.63 (br s, 1H), 8.33 (d, J=1.4 Hz, 1H), 8.18 (dd, J=8.1, 1.8 Hz, 1H), 8.13-8.03 (m, 2H), 7.96 (dd, J=11.2, 1.1 Hz, 1H), 7.43 (d, J=8.1 Hz, 1H), 7.37-7.26 (m, 3H), 7.15 (d, J=7.2 Hz, 1H), 4.26 (d, J=12.4 Hz, 1H), 4.20 (d, J=12.5 Hz, 1H), 3.38 (q, J=7.1 Hz, 2H), 2.04 (s, 3H), 1.09 (t, J=7.0 Hz, 3H). LC/MS (Method B): 431.4 (M−H)⁻, 433.3 (M+H)⁺. HPLC (Method A) Rt 5.54 min (Purity: 99.6%).

Example 64

2-fluoro-4-(5-{4-isobutoxy-3-[(methylsulfonyl)amino]phenyl}-1,2,4-oxadiazol-3-yl)benzoic acid

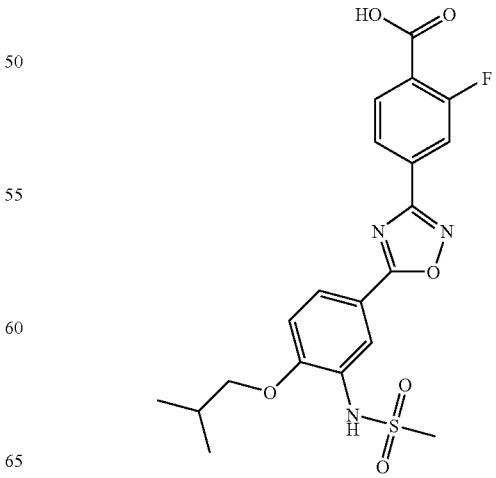

Step 1: methyl 2-fluoro-4-(5-{4-isobutoxy-3-[(methylsulfonyl)amino]phenyl}-1,2,4-oxadiazol-3-yl)benzoate The title compound was prepared following procedure described for example 4, step 1, but starting from Intermediate 31 (172.40 mg; 0.60 mmol). The reaction mixture was filtered through a SPE NH$_2$ column (2 g) and rinsed with ACN. The filtrate was passed through a SPE SCX column (2 g) and rinsed with ACN. After evaporation of the solvents, the crude product was suspended in ACN, filtrated and dried under vacuo, affording the title compound as a white powder. $^1$H NMR (DMSO-d$_6$, 300 MHz) δ 9.29 (br s, 1H), 8.14-8.01 (m, 4H), 7.97 (dd, J=11.2, 1.3 Hz, 1H), 7.34 (d, J=8.6 Hz, 1H), 3.93 (d, J=6.6 Hz, 2H), 3.91 (s, 3H), 3.04 (s, 3H), 2.14 (sept., J=6.7 Hz, 1H), 1.04 (d, J=6.6 Hz, 6H). LC/MS (Method B): 462.3 (M−H)$^−$, 505.3 (M+ACN)$^+$. HPLC (Method A) Rt 5.14 min (Purity: 98.6%).

Step 2: 2-fluoro-4-(5-{4-isobutoxy-3-[(methylsulfonyl)amino]phenyl}-1,2,4-oxadiazol-3-yl)benzoic acid The title compound was prepared following procedure described for example 4, step 2, but starting from methyl 2-fluoro-4-(5-{4-isobutoxy-3-[(methylsulfonyl)amino]phenyl}-1,2,4-oxadiazol-3-yl)benzoate, obtained in step 1. Solvents were concentrated and water (5 mL) was added. It was filtrated to afford the title compound as a white powder (72 mg; 93%). $^1$H NMR (DMSO-d$_6$, 300 MHz) δ 13.61 (br s, 1H), 9.29 (br s, 1H), 8.11-7.99 (m, 4H), 7.92 (dd, J=11.1, 1.4 Hz, 1H), 7.34 (d, J=8.7 Hz, 1H), 3.93 (d, J=6.6 Hz, 2H), 3.04 (s, 3H), 2.14 (sept., J=6.7 Hz, 1H), 1.04 (d, J=6.8 Hz, 6H). LC/MS (Method B): 448.3 (M−H)$^−$, 450.2 (M+H)$^+$. HPLC (Method A) Rt 4.44 min (Purity: 98.6%).

Example 65

4-{5-[3-(acetylamino)-4-(2-methylpiperidin-1-yl)phenyl]-1,2,4-oxadiazol-3-yl}-2-fluorobenzoic acid

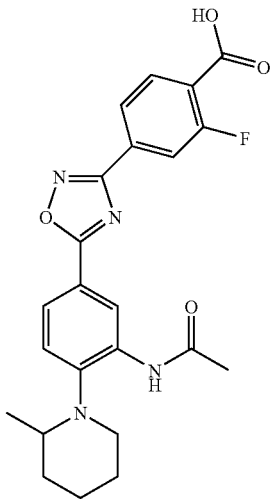

Step 1: methyl 4-{5-[3-(acetylamino)-4-(2-methylpiperidin-1-yl)phenyl]-1,2,4-oxadiazol-3-yl}-2-fluorobenzoate The title compound was obtained following procedure described for example 4, step 1, but starting from Intermediate 1 (70 mg; 0.33 mmol) and Intermediate 32 (91.17 mg; 0.33 mmol). Title compound was isolated after trituration with MeOH as an off-white powder. $^1$H NMR (DMSO-d$_6$, 300 MHz) δ 9.10 (bs, 1H), 8.88, (bs, 1H), 8.11 (t, J=7.6 Hz, 1H), 8.03 (dd, J=8.1, 1.5 Hz, 1H), 7.97-7.87 (m, 2H), 7.45 (d, 8.4 Hz, 1H), 3.90 (s, 3H), 3.19-3.12 (m, 1H), 2.96-2.89 (m, 1H), 2.65-2.57 (m, 1H), 2.19 (s, 3H), 1.87-1.66 (m, 4H), 1.53-1.44 (m, 2H), 0.84 (d, J=6 Hz, 3H). LC/MS (Method B): 453.3 (M+H)$^+$. HPLC (Method A) Rt 5.16 min (purity: 97.5%).

Step 2: 4-{5-[3-(acetylamino)-4-(2-methylpiperidin-1-yl)phenyl]-1,2,4-oxadiazol-3-yl}-2-fluorobenzoic acid The title compound was obtained following procedure and work up described for example 4, step 2, but starting from methyl 4-{5-[3-(acetylamino)-4-(2-methylpiperidin-1-yl)phenyl]-1,2,4-oxadiazol-3-yl}-2-fluorobenzoate, obtained in step 1 (27 mg; 0.06 mmol). It was isolated as a white powder (22 mg; 84%). $^1$H NMR (DMSO-d$_6$, 300 MHz) δ 13.58 (bs, 1H), 9.10 (bs, 1H), 8.89 (bs, 1H), 8-7.88 (m, 4H), 7.46 (d, J=8.4 Hz, 1H), 3.17-3.15 (m, 1H), 2.95-2.89 (m, 1H), 2.65-2.58 (m, 1H), 2.19 (s, 3H), 1.80-1.66 (m, 4H), 1.53-1.44 (m, 2H), 0.85 (d, J=6 Hz, 3H). LC/MS (Method B): 439.3 (M+H)$^+$. HPLC (Method A) Rt 3.97 min (purity: 97.5%).

Example 66

2-fluoro-4-(5-{4-[isobutyl(propyl)amino]-3-[(methylsulfonyl)amino]phenyl}-1,2,4-oxadiazol-3-yl)benzoic acid

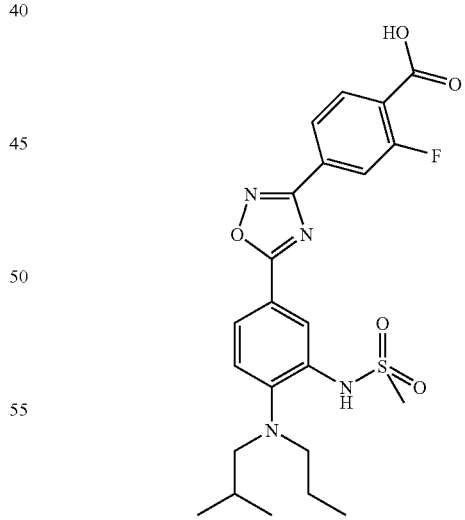

Step 1: methyl 2-fluoro-4-(5-{4-[isobutyl(propyl)amino]-3-[(methylsulfonyl)amino]phenyl}-1,2,4-oxadiazol-3-yl)benzoate The title compound was obtained following procedure described for example 4, step 1, but starting from Intermediate 1 (300 mg; 1.41 mmol) and Intermediate 33 (464.37 mg; 1.41 mmol). It was isolated after trituration with ACN as an off-white powder. LC/MS (Method B): 505.3 (M+H)⁺. HPLC (Method A) Rt 6.42 min (purity: 67.9%).

Step 2: 2-fluoro-4-(5-{4-[isobutyl(propyl)amino]-3-[(methylsulfonyl)amino]phenyl}-1,2,4-oxadiazol-3-yl)benzoic acid The title compound was obtained following procedure and work up described for example 4, step 2, but starting from methyl 2-fluoro-4-(5-{4-[isobutyl(propyl)amino]-3-[(methylsulfonyl)amino]phenyl}-1,2,4-oxadiazol-3-yl)benzoate, obtained in step 1. It was isolated as a light yellow powder. ¹H NMR (DMSO-d₆, 300 MHz) δ 13.60 (bs, 1H), 8.69 (bs, 1H), 8.11-7.98 (m, 3H), 7.92-7.89 (m, 2H), 7.37 (d, J=8.6 Hz, 1H), 3.16-3.11 (m, 5H), 3.01 (d, J=7.2 Hz, 2H), 1.78-1.69 (m, 1H), 1.49-1.42 (m, 1H), 0.86-0.80 (m, 9H). LC/MS (Method B): 491.3 (M+H)⁺. HPLC (Method A) Rt 5.71 min (purity: 94.7%).

Example 67

4-{5-[3-[(ethylsulfonyl)amino]-4-(2-methylpiperidin-1-yl)phenyl]-1,2,4-oxadiazol-3-yl}-2-fluorobenzoic acid

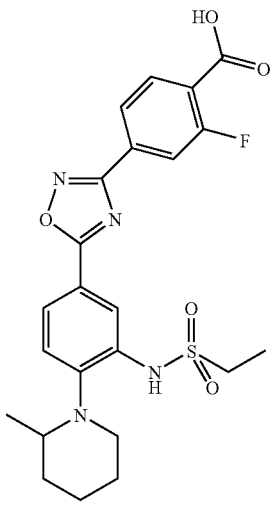

Step 1: Methyl 2-fluoro-4-{5-[4-(2-methylpiperidin-1-yl)-3-nitrophenyl]-1,2,4-oxadiazol-3-yl}benzoate Intermediate 11 (12.46 g; 47.13 mmol) was dissolved in DCM (200 mL) and n,n'-dicyclohexylcarbodiimide (11.67 g; 56.56 mmol) was added. Then Intermediate 1 was added (10 g; 47.13 mmol) and the suspension was stirred at RT for 12 hours. The precipitate was filtered off and the solvent evaporated to give a yellow solid. The residue was dissolved in Toluene (300 mL) and Py (150 mL) and the solution was heated to 130° C. for 12 hours. The reaction mixture was concentrated to afford a yellow sticky oil which was precipitated from ACN affording the title compound as a yellow solid. LC/MS (Method B): 441.3 (M+H)⁺ HPLC: Rt 5.86 min (Purity: 95.1%).

Step 2: Methyl 4-{5-[3-amino-4-(2-methylpiperidin-1-yl)phenyl]-1,2,4-oxadiazol-3-yl}-2-fluorobenzoate Stannous chloride dihydrate (20.49 g; 90.82 mmol) was added to a suspension of methyl 2-fluoro-4-{5-[4-(2-methylpiperidin-1-yl)-3-nitrophenyl]-1,2,4-oxadiazol-3-yl}benzoate, obtained in step 1, (8 g; 18.16 mmol) in EtOH (80 mL) and the resulting mixture was stirred at reflux for 3 hours. The solution was diluted with a saturated aqueous solution of NaHCO₃ and extracted with EtOAc (2×). The combined organic layers were washed with brine, dried over MgSO₄ and concentrated affording the title compound as a yellow solid. ¹H NMR (DMSO, 400 MHz) δ 8.18-7.95 (m, 3H), 7.56-7.55 (d, J=1.77 Hz, 1H), 7.44-7.41 (m, 1H), 7.21-7.19 (d, J=8.38 Hz, 1H), 5.32 (br s, 2H), 3.94 (s, 3H), 3.21-2.92 (m, 2H), 1.88-1.22 (m, 7H), 0.88 (d, J=6 Hz, 3H). LC/MS (Method B): 411.4 (M+H)⁺; 417.2 (M–H)⁻. HPLC: Rt 4.47 min (Purity: 95.6%).

Step 3: methyl 4-{5-[3-[(ethylsulfonyl)amino]-4-(2-methylpiperidin-1-yl)phenyl]-1,2,4-oxadiazol-3-yl}-2-fluorobenzoate Methyl 4-{5-[3-amino-4-(2-methylpiperidin-1-yl)phenyl]-1,2,4-oxadiazol-3-yl}-2-fluorobenzoate, obtained in Step 2, (100 mg, 0.24 mmol) was suspended in a DCM/Pyridine mixture (4 mL, 1:1) to which was added ethanesulfonyl chloride (30 μL, 0.4 mmol) and heated at 40° C. for 48 h. After this time, reaction mixture was concentrated under vacuum, then partitioned between EtOAc (25 mL) and water (25 mL). Organic phases were then washed with an aqueous solution of HCl (0.1 M, 25 mL), dried over MgSO₄, filtered, evaporated and purified by flash chromatography (EtOAc:c-hex, from 0:100 to 100:0). Title compound was obtained as a white powder. LC/MS (Method B): 504.3 (M+H)⁺. HPLC (Method A) Rt 6.21 min (purity: 99.4%).

Step 4: 4-{5-[3-[(ethylsulfonyl)amino]-4-(2-methylpiperidin-1-yl)phenyl]-1,2,4-oxadiazol-3-yl}-2-fluorobenzoic acid The title compound was obtained following procedure and work up described for example 4, step 2, but starting methyl 4-{5-[3-[(ethylsulfonyl)amino]-4-(2-methylpiperidin-1-yl)phenyl]-1,2,4-oxadiazol-3-yl}-2-fluorobenzoate, obtained in step 3. It was isolated as a light yellow powder (47 mg; 96%). ¹H NMR (DMSO-d₆, 300 MHz) δ 13.63 (bs, 1H), 8.62 (bs, 1H), 8.20 (d, J=2 Hz, 1H), 8.08 (t, J=7.7 Hz, 1H), 8 (dd, J=8.0, 1.5 Hz, 1H), 7.95-7.89 (m, 2H), 3.35 (q, J=7.3 Hz, 2H), 3.16-3.09 (m, 1H), 2.90-2.87 (m, 1H), 2.65-2.57 (m, 1H), 1.82-1.64 (m, 4H), 1.49-1.43 (m, 2H), 1.27 (t, J=7.2 Hz, 3H), 0.81 (d, J=6 Hz, 3H). LC/MS (Method B): 489.3 (M+H)+. HPLC (Method A) Rt 4.95 min (purity: 95.6%).

Example 68

2-chloro-4-[5-(2,2'-dimethylbiphenyl-4-yl)-1,2,4-oxadiazol-3-yl]benzoic acid

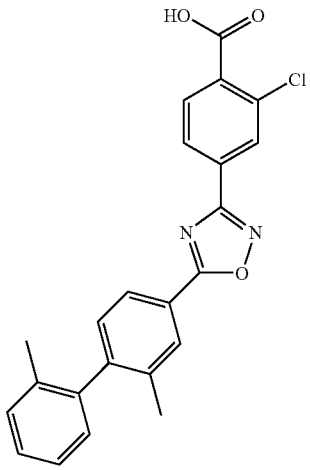

Step 1: methyl 2-chloro-4-[5-(2,2'-dimethylbiphenyl-4-yl)-1,2,4-oxadiazol-3-yl]benzoate The title compound was prepared following procedure described for example 4, step 1, but starting from Intermediate 3 (113.14 mg; 0.50 mmol) and Intermediate 34 (114.32 mg; 0.50 mmol). The reaction mixture was filtered through a SPE NH₂ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as an off-white solid. LC/MS (Method B): 419.3 (M–H)⁻, 460.3 (M+ACN)⁺. HPLC (Method A) Rt 6.51 min (Purity: 99.8%).

Step 2: 2-chloro-4-[5-(2,2'-dimethylbiphenyl-4-yl)-1,2,4-oxadiazol-3-yl]benzoic acid The title compound was prepared following procedure described for example 4, step 2, but starting from methyl 2-chloro-4-[5-(2,2'-dimethylbiphenyl-4-yl)-1,2,4-oxadiazol-3-yl]benzoate, obtained in step 1. Solvents were concentrated and water (5 mL) was added. It was filtrated to afford the title compound as a white powder. ¹H NMR (DMSO-d₆, 300 MHz) δ 13.77 (br s, 1H), 8.18-8.19 (m, 2H), 8.15 (dd, J=8.0, 1.5 Hz, 1H), 8.08 (dd, J=7.9, 1.4 Hz, 1H), 8.02 (d, J=8.1 Hz, 1H), 7.39-7.27 (m, 4H), 7.14-7.11 (m, 1H), 2.14 (s, 3H), 2.03 (s, 3H). LC/MS (Method B): 403.3 (M–H)⁻, 405.2 (M+H)⁺. HPLC (Method A) Rt 5.68 min (Purity: 99.8%).

Example 69

2-chloro-4-{5-[2-(methoxymethyl)-2'-methylbiphenyl-4-yl]-1,2,4-oxadiazol-3-yl}benzoic acid

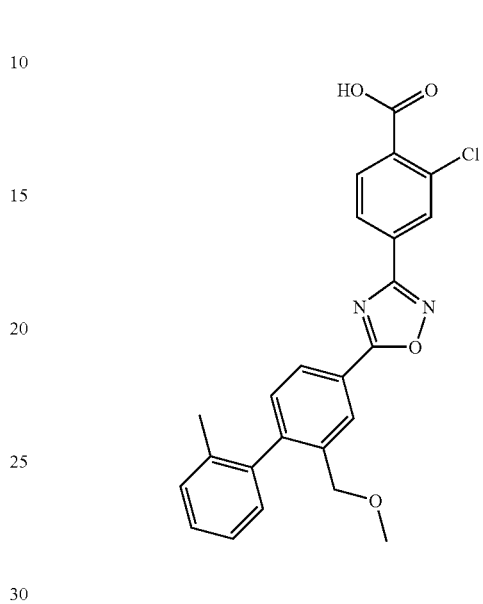

Step 1: methyl 2-chloro-4-{5-[2-(methoxymethyl)-2'-methylbiphenyl-4-yl]-1,2,4-oxadiazol-3-yl}benzoate The title compound was prepared following procedure described for example 35, step 1, but starting from Intermediate 28 (1 076.46 mg; 4.20 mmol) and Intermediate 34 (960.27 mg; 4.20 mmol). The reaction mixture was cooled to RT and concentrated affording a brownish oil which was washed with MeOH (20 mL) affording a suspension that was filtered affording the title compound as a beige solid (1.5 g; 82%). ¹H NMR (DMSO-d₆, 300 MHz) δ 8.34 (d, J=1.5 Hz, 1H), 8.23 (d, J=1.3 Hz, 1H), 8.21 (dd, J=3.6, 1.7 Hz, 1H), 8.18 (dd, J=3.5, 1.8 Hz, 1H), 8.06 (d, J=8.0 Hz, 1H), 7.44 (d, J=7.9 Hz, 1H), 7.37-7.27 (m, 3H), 7.15 (d, J=7.0 Hz, 1H), 4.23 (d, J=12.8 Hz, 1H), 4.16 (d, J=12.8 Hz, 1H), 3.92 (s, 3H), 3.25 (s, 3H), 2.04 (s, 3H). LC/MS (Method B): 449.1 (M+H)⁺. HPLC (Method A) Rt 6.14 min (Purity: 97.6%).

Step 2: 2-chloro-4-{5-[2-(methoxymethyl)-2'-methylbiphenyl-4-yl]-1,2,4-oxadiazol-3-yl}benzoic acid The title compound was prepared following procedure described for example 4, step 2, but starting from methyl 2-chloro-4-{5-[2-(methoxymethyl)-2'-methylbiphenyl-4-yl]-1,2,4-oxadiazol-3-yl}benzoate, obtained in step 1. Solvents were concentrated and EtOAc (200 mL) was added. It was washed with water. The organic layer was then dried over magnesium sulfate, filtered and concentrated, washed with ACN to afford the title compound as a white powder. ¹H NMR (DMSO-d₆, 300 MHz) δ 13.77 (br s, 1H), 8.34 (d, J=1.5 Hz, 1H), 8.20-8.15 (m, 3H), 8.02 (d, J=7.9 Hz, 1H), 7.43 (d, J=7.9 Hz, 1H), 7.37-7.27 (m, 3H), 7.15 (d, J=7.2 Hz, 1H), 4.25-4.14 (m, 2H), 3.25 (s, 3H), 2.04 (s, 3H). LC/MS (Method B): 433.2 (M–H)⁻, 435.2 (M+H)⁺. HPLC (Method A) Rt 5.35 min (Purity: 98.5%). CHN analysis: [C₂₄H₁₉N₂O₄Cl] Calculated:

C, 66.29%; H, 4.40%; N, 6.44%; Cl, 8.15%. Found: C, 66.04%; H, 4.52%; N, 6.49%; Cl, 8.23%.

Example 70

2-chloro-4-(5-{4-(2-methylpiperidin-1-yl)-3-[(methylsulfonyl)amino]phenyl}-1,2,4-oxadiazol-3-yl)benzoic acid

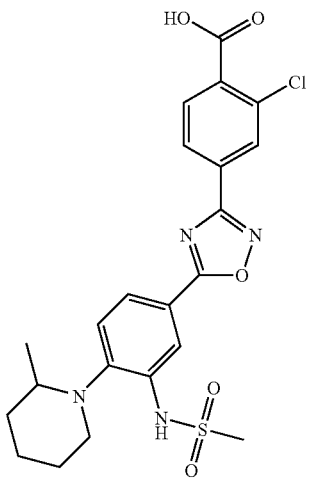

Step 1: methyl 2-chloro-4-(5-{4-(2-methylpiperidin-1-yl)-3-[(methylsulfonyl)amino]phenyl}-1,2,4-oxadiazol-3-yl)benzoate In a 2-5 microwave vial, placed in a dry-ice acetone bath, was added THF (2 mL) and CH$_3$CN (2 mL) to a mixture of Intermediate 25 (156.19 mg; 0.50 mmol), Intermediate 34 (114.32 mg; 0.50 mmol) and 1-ethyl-3-(3-dimethylaminopropyl)carbodiimide hydrochloride (115.02 mg; 0.60 mmol). The reaction mixture was allowed to warm to RT for half a hour then DIEA (204.07 µL; 1.20 mmol) was added and the mixture was heated by microwave irradiation at 150° C. for 30 min. The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound. LC/MS (Method B): 503.4 (M−H)$^−$, 505.3 (M+H)$^+$. HPLC (Method A) Rt 5.64 min (Purity: 100.0%).

Step 2: 2-chloro-4-(5-{4-(2-methylpiperidin-1-yl)-3-[(methylsulfonyl)amino]phenyl}-1,2,4-oxadiazol-3-yl)benzoic acid The title compound was prepared following procedure described for example 4, step 2, but starting from methyl 2-chloro-4-(5-{4-(2-methylpiperidin-1-yl)-3-[(methylsulfonyl)amino]phenyl}-1,2,4-oxadiazol-3-yl)benzoate, obtained in step 1. Solvents were concentrated and water (5 mL) was added. It was filtrated to afford the title compound as a slightly yellow powder. $^1$H NMR (DMSO-d$_5$, 300 MHz) δ 13.74 (br s, 1H), 8.68 (br s, 1H), 8.21 (d, J=2.0 Hz, 1H), 8.16-8.11 (m, 2H), 8.01 (d, J=8.1 Hz, 1H), 7.95 (dd, J=8.4, 1.9 Hz, 1H), 7.56 (d, J=8.4 Hz, 1H), 3.23 (s, 3H), 3.18-3.12 (m, 1H), 2.93-2.89 (m, 1H), 2.66-2.57 (m, 1H), 1.83-1.65 (m, 1H), 1.50-1.44 (m, 2H), 0.82 (d, J=6.2 Hz, 3H). LC/MS (Method B): 489.3 (M−H)$^−$, 491.3 (M+H)$^+$. HPLC (Method A) Rt 4.80 min (Purity: 99.1%).

Example 71 methyl 4-(5-{4-(dimethylamino)-3-[(methylsulfonyl)amino]phenyl}-1,2,4-oxadiazol-3-yl)-2-fluorobenzoate

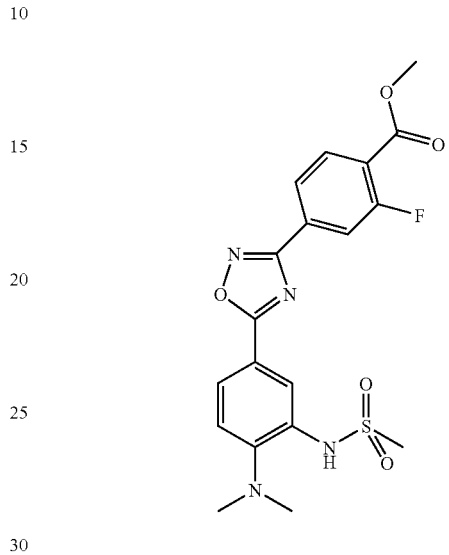

Step 1: methyl 4-{5-[4-(dimethylamino)-3-nitrophenyl]-1,2,4-oxadiazol-3-yl}-2-fluorobenzoate The title compound was obtained following procedure described for example 4, step 1, but starting from Intermediate 1 (300 mg; 1.41 mmol) and Intermediate 35 (326.90 mg; 1.56 mmol). Title compound was isolated after trituration with MeOH as a brown powder. $^1$H NMR (DMSO-d$_6$, 300 MHz) δ 8.50 (d, J=2.1 Hz, 1H), 8.16 (dd, J=9.1, 2.2 Hz, 1H), 8.09 (d, J=7.2 Hz, 1H), 8.03 (dd, J=8.2, 1.5 Hz, 1H), 7.98-7.94 (m, 1H), 7.38 (d, J=9 Hz, 1H), 3.90 (s, 3H), 2.99 (s, 6H). LC/MS (Method B): 387.2 (M+H)$^+$. HPLC (Method A) Rt. 5.07 min (purity: 98%).

Step 2: methyl 4-{5-[3-amino-4-(dimethylamino)phenyl]-1,2,4-oxadiazol-3-yl}-2-fluorobenzoate To a suspension of methyl 4-{5-[4-(dimethylamino)-3-nitrophenyl]-1,2,4-oxadiazol-3-yl}-2-fluorobenzoate obtained in step 1 (150 mg; 0.39 mmol) in EtOH (15 mL) was added stannous chloride dihydrate (438.05 mg; 1.94 mmol) and stirred at 70° C. for 3 h, then at RT for 16 h. After this time, the solution was diluted with a saturated aqueous solution of NaHCO$_3$ (75 mL) and extracted with EtOAc (100 mL). The combined organic layers were washed with brine (50 mL), dried over magnesium sulfate and concentrated under vacuum to give the title compound. LC/MS (Method B): 357.3 (M+H)$^+$. HPLC (Method A) Rt. 3.75 min (purity: 95.4%).

Step 3: methyl 4-(5-{4-(dimethylamino)-3-[(methylsulfonyl)amino]phenyl}-1,2,4-oxadiazol-3-yl)-2-fluorobenzoate Methyl 4-{5-[3-amino-4-(dimethylamino)phenyl]-1,2,4-oxadiazol-3-yl}-2-fluorobenzoate was taken up in Pyridine (750 μL) and mesylchloride (40 μL; 0.46 mmol) was added and stirred at RT for 72 h. After the time, the reaction mixture was concentrated in vacuo and the residue was purified by flash chromatography (DCM:MeOH from 100:0 to 90:10) to give the title compound as a yellow powder (150 mg; 88%, 2 steps). $^1$H NMR (DMSO-$d_6$, 300 MHz) δ 9.07 (bs, 1H), 8.13-8.08 (m, 1H), 8.04-7.91 (m, 4H), 7.23 (d, J=8.7 Hz, 1H), 3.90 (s, 3H), 3.14 (s, 3H), 2.88 (s, 6H). LC/MS (Method B): 435.3 (M+H)$^+$. HPLC (Method A) Rt 4.33 min (purity: 94.4%).

Example 72

2-fluoro-4-{5-[4-(2-methylpiperidin-1-yl)-3-(propionylamino)phenyl]-1,2,4-oxadiazol-3-yl}benzoic acid

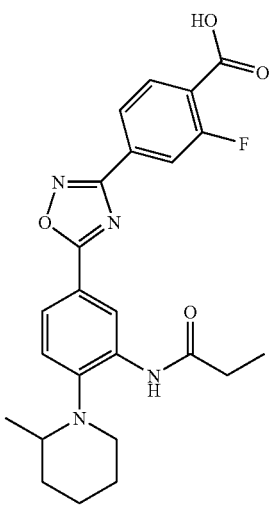

Step 1: methyl 4-{5-[3-(propionylamino)-4-(2-methylpiperidin-1-yl)phenyl]-1,2,4-oxadiazol-3-yl}-2-fluorobenzoate Methyl 4-{5-[3-amino-4-(2-methylpiperidin-1-yl)phenyl]-1,2,4-oxadiazol-3-yl}-2-fluorobenzoate, prepared as in example 67, Steps 1 and 2, (100 mg; 0.24 mmol) was suspended in a DCM/Pyridine mixture (4 mL, 1:1). Propionyl chloride (25 μL, 0.29 mmol) was added and the mixture was heated to 40° C. for 18 h. After this time, solvents were removed under vacuum and title compound was obtained as an off-white powder after trituration with MeOH (96 mg; 83%). LC/MS (Method B): 467.4 (M+H)$^+$. HPLC (Method A) Rt. 5.69 min (purity: 93.6%).

Step 2: 2-fluoro-4-{5-[4-(2-methylpiperidin-1-yl)-3-(propionylamino)phenyl]-1,2,4-oxadiazol-3-yl}benzoic acid The title compound was obtained following procedure and work up described for example 4, step 2, but starting from methyl 4-{5-[3-(propionylamino)-4-(2-methylpiperidin-1-yl)phenyl]-1,2,4-oxadiazol-3-yl}-2-fluorobenzoate (80 mg; 0.17 mmol), obtained in step 1. It was isolated as a white powder (68.60 mg; 88%). $^1$H NMR (DMSO-$d_6$, 300 MHz) δ 13.59 (bs, 1H), 9.10 (bs, 1H), 8.95 (d, J=1.8 Hz, 1H), 8.11-8.06 (m, 1H), 8.03-8 (m, 1H), 7.94-7.88 (m, 2H), 7.48 (d, J=8.4 Hz, 1H), 3.17-3.11 (m, 1H), 2.93-2.90 (m, 1H), 2.64-2.60 (m, 1H), 2.51-2.48 (m, 2H), 1.84-1.46 (m, 6H), 1.15 (t, J=7.6 Hz, 3H), 0.83 (d, J=6 Hz, 3H). LC/MS (Method B): 453.4 (M+H)$^+$. HPLC (Method A) Rt 4.46 min (purity: 100.0%).

Example 73

4-{5-[3-{[(dimethylamino)sulfonyl]amino}-4-(2-methylpiperidin-1-yl)phenyl]-1,2,4-oxadiazol-3-yl}-2-fluorobenzoic acid

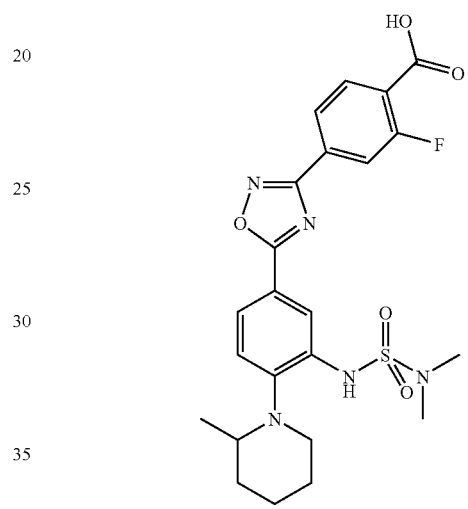

Step 1: methyl 2-fluoro-4-{5-[4-(2-methylpiperidin-1-yl)-3-nitrophenyl]-1,2,4-oxadiazol-3-yl}benzoate The title compound was obtained following procedure and work up described for example 67, step 1, but starting from methyl 4-{5-[3-amino-4-(2-methylpiperidin-1-yl)phenyl]-1,2,4-oxadiazol-3-yl}-2-fluorobenzoate, prepared as in example 67, Steps 1 and 2, (100 mg; 0.24 mmol) and dimethylsulfamoyl chloride (63 μL; 0.6 mmol). Title compound was isolated after trituration with MeOH as a brown powder. LC/MS (Method B): 518.3 (M+H)$^+$. HPLC (Method A) Rt. 6.21 min (purity: 99.3%).

Step 2: 4-{5-[3-{[(dimethylamino)sulfonyl]amino}-4-(2-methylpiperidin-1-yl)phenyl]-1,2,4-oxadiazol-3-yl}-2-fluorobenzoic acid The title compound was obtained following procedure and work up described for example 4, step 2, but starting from methyl 2-fluoro-4-{5-[4-(2-methylpiperidin-1-yl)-3-nitro phenyl]-1,2,4-oxadiazol-3-yl}benzoate obtained in step 1 (10 mg; 0.02 mmol). It was isolated as an off-white powder. LC/MS (Method B): 504.3 (M+H)⁺. HPLC (Method A) Rt 5.41 min (purity: 95.3%).

Example 74

2-fluoro-4-(5-{4-(2-methylpiperidin-1-yl)-3-[(propylsulfonyl)amino]phenyl}-1,2,4-oxadiazol-3-yl)benzoic acid

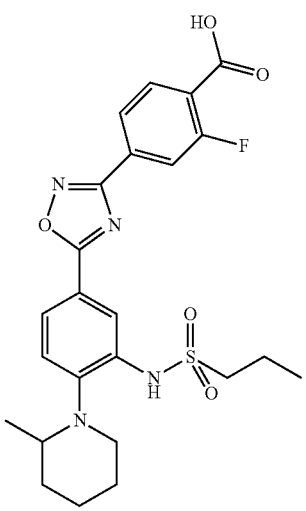

Step 1: methyl 4-{5-[3-[(propylsulfonyl)amino]-4-(2-methylpiperidin-1-yl)phenyl]-1,2,4-oxadiazol-3-yl}-2-fluorobenzoate The title compound was obtained following procedure and work up described for example 67, step 1, but starting from methyl 4-{5-[3-amino-4-(2-methylpiperidin-1-yl)phenyl]-1,2,4-oxadiazol-3-yl}-2-fluorobenzoate, prepared as in example 67, Steps 1 and 2, (200 mg; 0.49 mmol) and 1-propanesulfonyl chloride (280 mg; 2 mmol). The title compound was obtained as a yellow powder after column chromatography (EtOAc:cHex from 10:90 to 100:0). LC/MS (Method B): 517.4 (M+H)⁺. HPLC (Method A) Rt. 6.37 min (purity: 96.5%).

Step 2: 2-fluoro-4-(5-{4-(2-methylpiperidin-1-yl)-3-[(propylsulfonyl)amino]phenyl}-1,2,4-oxadiazol-3-yl)benzoic acid The title compound was obtained following procedure and work up described for example 4, step 2, but starting from methyl 2-fluoro-4-{5-[4-(2-methylpiperidin-1-yl)-3-nitrophenyl]-1,2,4-oxadiazol-3-yl}benzoate obtained in step 1 (10 mg; 0.02 mmol). It was isolated as an off-white powder. ¹H NMR (DMSO-d₆, 300 MHz) δ 13.60 (bs, 1H), 8.62 (bs, 1H), 8.21 (d, J=2 Hz, 1H), 8.12-8.07 (m, 1H), 8.01 (dd, J=8.1, 1.5 Hz, 1H), 7.95-7.90 (m, 2H), 3.35-3.30 (m, 2H), 3.15-3.10 (m, 1H), 2.89-2.84 (m, 1H), 2.65-2.57 (m, 1H), 1.82-1.65 (m, 6H), 1.52-1.40 (m, 2H), 0.98 (t, J=7.4 Hz, 3H), 0.80 (d, J=6 Hz, 3H). LC/MS (Method B): 503.3 (M+H)⁺. HPLC (Method A) Rt 5.57 min (purity: 94.1%).

Example 75

2-fluoro-4-{5-[2'-methyl-2-(morpholin-4-ylmethyl)biphenyl-4-yl]-1,2,4-oxadiazol-3-yl}benzoic acid, Trifluoroacetic acid salt

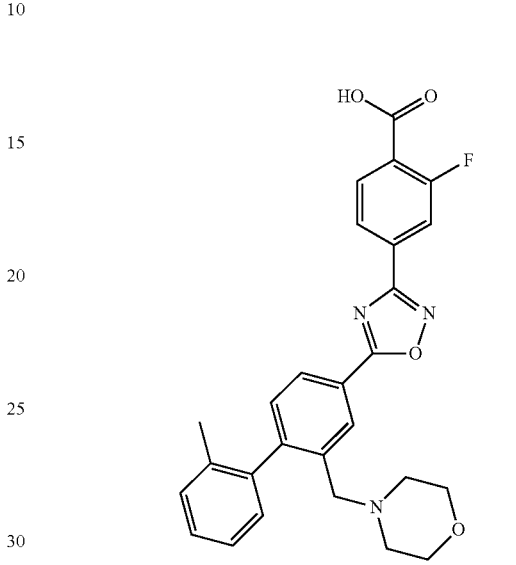

Step 1: methyl 2-fluoro-4-{5-[2'-methyl-2-(morpholin-4-ylmethyl)biphenyl-4-yl]-1,2,4-oxadiazol-3-yl}benzoate To a solution of methyl 2-fluoro-4-[5-(2'-methyl-2-{[(methylsulfonyl)oxy]methyl}biphenyl-4-yl)-1,2,4-oxadiazol-3-yl]benzoate, obtained example 59 step 1 (100 mg; 0.2 mmol) in THF (750 µL) was added morpholine (90 µL; 2 mmol). The reaction was heated at 130° C. for 20 min under microwave irradiation. Solvents were concentrated and DCM (20 mL) was added. It was washed with HCl 0.1 M. The organic layer was then dried over magnesium sulfate, filtered and concentrated, the crude product was purified by flash chromatography (c-hex/EtOAc: 9.5/0.5), affording the title compound as a colorless oil. ¹H NMR (CDCl₃) δ 8.41 (br s, 1H), 8.16-8.04 (m, 3H), 8.01 (dd, J=11.2, 1.1 Hz, 1H), 7.36-7.23 (m, 4H), 7.11 (d, J=7.4 Hz, 1H), 3.98 (s, 3H), 3.66-3.63 (m, 4H), 3.35 (d, J=13.9 Hz, 1H), 3.24 (d, J=13.6 Hz, 1H), 2.32 (br s, 4H), 2.07 (s, 3H). LC/MS (Method B): 488.4 (M+H)⁺. HPLC (Method A) Rt 4.02 min (Purity: 99.0%).

Step 2: 2-fluoro-4-{5-[2'-methyl-2-(morpholin-4-ylmethyl)biphenyl-4-yl]-1,2,4-oxadiazol-3-yl}benzoic acid, Trifluoroacetic acid salt The title compound was prepared following procedure described for example 4, step 2, but starting from methyl 2-fluoro-4-{5-[2'-methyl-2-(morpholin-4-ylmethyl)biphenyl-4-yl]-1,2,4-oxadiazol-3-yl}benzoate, obtained in step 1. Solvents were concentrated and the crude mixture was purified by preparative HPLC to afford the title compound as a white solid. ¹⁹F NMR (DMSO-d₆, 300 MHz) δ-75.75 ppm.

LC/MS (Method B): 472.3 (M−H)⁻, 474.3 (M+H)⁺. HPLC (Method A) Rt 3.87 min (Purity: 98.1%).

Example 76
2-fluoro-4-{5-[2'-methyl-2-(pyrrolidin-1-ylmethyl)biphenyl-4-yl]-1,2,4-oxadiazol-3-yl}benzoic acid, Hydrochloride salt

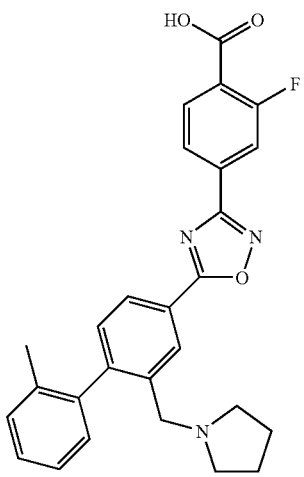

To a solution of methyl 2-fluoro-4-[5-(2'-methyl-2-{[(methylsulfonyl)oxy]methyl}biphenyl-4-yl)-1,2,4-oxadiazol-3-yl]benzoate, obtained example 59 step 1 (75 mg; 0.15 mmol) in THF (750 μL) was added pyrrolidine (37.83 μL; 0.45 mmol). The reaction was heated at 130° C. for 10 min under microwave irradiation. Sodium hydroxide (241.68 μL; 5 M; 1.21 mmol) was added and the mixture was heated at 60° C. for 10 min in the microwave. Hydrogen chloride (241.68 μL; 5 M; 1.21 mmol) was added and the mixture was evaporated to dryness. The crude was purified with MD Autoprep, to afford the title compound as a white powder. ¹H NMR (DMSO-d₆, 300 MHz) δ 8.73 (s, 1H), 8.29 (dd, J=8.0, 1.6 Hz, 1H), 8.16-8.11 (m, 1H), 8.05 (dd, J=8.1, 1.5 Hz, 1H), 7.97 (dd, J=11.1, 1.4 Hz, 1H), 7.54 (d, J=8.0 Hz, 1H), 7.42-7.32 (m, 3H), 7.25 (d, J=7.2 Hz, 1H), 4.37 (br s, 1H), 3.97 (d, J=12.6 Hz, 1H), 3.10-2.87 (m, 4H), 2.04 (s, 3H), 1.85-1.77 (m, 4H). ¹⁹F NMR (DMSO-d₆, 300 MHz) δ-109.03 ppm. LC/MS (Method B): 456.3 (M−H)⁻, 458.3 (M+H)⁺. HPLC (Method A) Rt 3.72 min (Purity: 98.7%).

Example 77
2-fluoro-4-(5-{2'-methyl-2-[(methylamino)methyl]biphenyl-4-yl}-1,2,4-oxadiazol-3-yl)benzoic acid, Hydrochloride salt

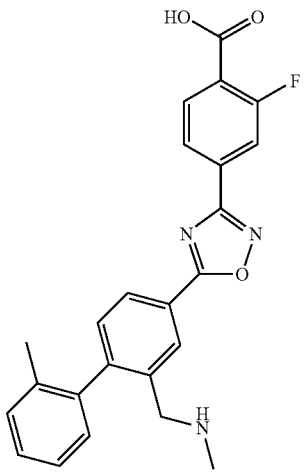

To a solution of methyl 2-fluoro-4-[5-(2'-methyl-2-{[(methylsulfonyl)oxy]methyl}biphenyl-4-yl)-1,2,4-oxadiazol-3-yl]benzoate, obtained example 59 step 1 (75 mg; 0.15 mmol) in THF (750 μL) was added methylamine (41% in water) (39.01 μL; 0.45 mmol). The reaction was stirred overnight at RT. Sodium hydroxide (151.05 μL; 5 M; 0.76 mmol) was added and the mixture was heated at 60° C. for 10 min under microwave irradiation. Hydrogen chloride (302.11 μL; 5 M; 1.51 mmol) was added and the mixture was evaporated to dryness. The crude was purified with MD Autoprep, to afford the title compound as a white powder. ¹H NMR (DMSO-d₆, 300 MHz) δ 8.61 (d, J=1.4 Hz, 1H), 8.28 (dd, J=7.9, 1.7 Hz, 1H), 8.16-8.11 (m, 1H), 8.04 (dd, J=8.1, 1.5 Hz, 1H), 7.96 (dd, J=11.0, 1.3 Hz, 1H), 7.54 (d, J=8.0 Hz, 1H), 7.41-7.32 (m, 3H), 7.24 (d, J=7.2 Hz, 1H), 4.07 (d, J=14.1 Hz, 1H), 3.83 (d, J=14.3 Hz, 1H), 2.49 (s, 3H), 2.05 (s, 3H). LC/MS (Method B): 416.3 (M−H)⁻, 418.2 (M+H)⁺. HPLC (Method A) Rt 3.36 min (Purity: 98.4%).

Example 78

4-{5-[2'-ethyl-2-(methoxymethyl)biphenyl-4-yl]-1,2,4-oxadiazol-3-yl}-2-fluorobenzoic acid

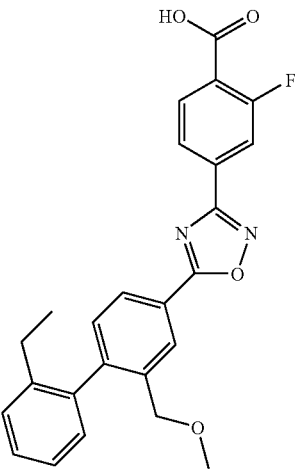

The title compound was prepared following procedure described for example 4, step 2, but starting from example 80. Solvents were concentrated and EtOAc (150 mL) was added. It was washed with water. Then the aqueous was acidified with HCl 5M until pH 2 and extracted with EtOAc. Organics were washed with NaCl sat. solution, dried over magnesium sulfate, filtered and concentrated to afford the title compound as a white powder (920 mg; 79%). ¹H NMR (DMSO-d₆, 300 MHz) δ 13.62 (br s, 1H), 8.33 (d, J=1.5 Hz, 1H), 8.17 (dd, J=7.8, 1.9 Hz, 1H), 8.13-8.08 (m, 1H), 8.05 (dd, J=8.1, 1.4 Hz, 1H), 7.97 (dd, J=11.1, 1.3 Hz, 1H), 7.45 (d, J=8.0 Hz, 1H), 7.41-7.40 (m, 2H), 7.32-7.27 (m, 1H), 7.12 (d, J=7.3 Hz, 1H), 4.23 (d, J=12.8 Hz, 1H), 4.14 (d, J=12.8 Hz, 1H), 3.26 (s, 3H), 2.47-2.22 (m, 2H), 0.99 (t, J=7.5 Hz, 3H). LC/MS (Method B): 431.2 (M−H)⁻, 433.1 (M+H)⁺. HPLC (Method A) Rt 5.39 min (Purity: 99.2%). CHN analysis: [C$_{26}$H$_{21}$N$_2$O$_4$F] Calculated: C, 69.44%; H, 4.89%; N, 6.48%. Found: C, 69.09%; H, 4.96%; N, 6.45%.

Example 79

2-fluoro-4-{5-[2'-methoxy-2-(methoxymethyl)biphenyl-4-yl]-1,2,4-oxadiazol-3-yl}benzoic acid

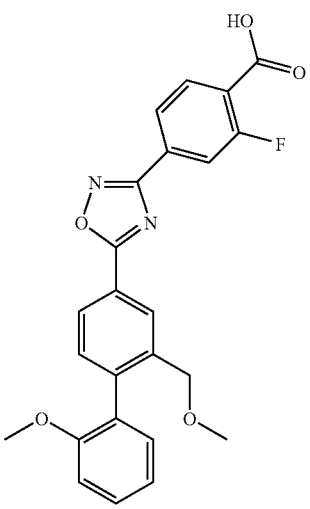

Step 1: methyl 4-{5-[4-bromo-3-(methoxymethyl)phenyl]-1,2,4-oxadiazol-3-yl}-2-fluorobenzoate The title compound was obtained following procedure described for example 4, step 1, but starting from Intermediate 1 (0.50 g; 2.36 mmol) and Intermediate 37 (0.64 g; 2.59 mmol). Title compound was isolated after trituration with ACN as a white powder. $^1$H NMR (DMSO-d$_6$, 300 MHz) δ 8.23 (d, J=2 Hz, 1H), 8.14-8.09 (m, 1H), 8.06-8.02 (m, 1H), 8-7.92 (m, 3H), 4.57 (s, 2H), 3.90 (s, 3H), 3.46 (s, 3H). LC/MS (Method B): 423.1 (M+H)$^+$. HPLC (Method A) Rt 5.91 min (purity: 98.5%).

Step 2: methyl 2-fluoro-4-{5-[2'-methoxy-2-(methoxymethyl)biphenyl-4-yl]-1,2,4-oxadiazol-3-yl}benzoate Title compound was prepared following procedure and work up described for Intermediate 5 step 2 but starting from methyl 4-{5-[4-bromo-3-(methoxymethyl)phenyl]-1,2,4-oxadiazol-3-yl}-2-fluorobenzoate obtained from step 1 (50 mg, 0.12 mmol) and 2-(2-methoxy-phenyl)-4,4,5,5-tetramethyl-1,3,2-dioxaborolane (30.5 mg, 0.13 mmol) (130° C. for 10 min under microwave irradiation). Purification by flash chromatography (cHex:EtOAc, from 100:0 to 20:80) gave the title compound as a yellow powder. LC/MS (Method B): 449.2 (M+H)$^+$.

Step 3: 2-fluoro-4-{5-[2'-methoxy-2-(methoxymethyl)biphenyl-4-yl]-1,2,4-oxadiazol-3-yl}benzoic acid The title compound was obtained following procedure and work up described for example 4, step 2, but starting from methyl 2-fluoro-4-{5-[2'-methoxy-2-(methoxymethyl)biphenyl-4-yl]-1,2,4-oxadiazol-3-yl}benzoate, obtained in step 2. It was isolated as an off-white powder. $^1$H NMR (DMSO-d$_6$, 300 MHz) δ 13.6 (bs, 1H), 8.29 (m, 1H), 8.15-8.12 (m, 1H), 8.09-8.02 (m, 2H), 7.98-7.94 (m, 1H), 7.48-7.42 (m, 2H), 7.21-7.14 (m, 2H), 7.09-7.04 (m, 1H), 4.32-4.24 (m, 2H), 3.74 (s, 3H), 3.25 (s, 3H). LC/MS (Method B): 435.1 (M+H)$^+$. HPLC (Method A) Rt 4.9 min (purity: 92.4%).

Example 80 methyl 4-{5-[2'-ethyl-2-(methoxymethyl)biphenyl-4-yl]-1,2,4-oxadiazol-3-yl}-2-fluorobenzoate

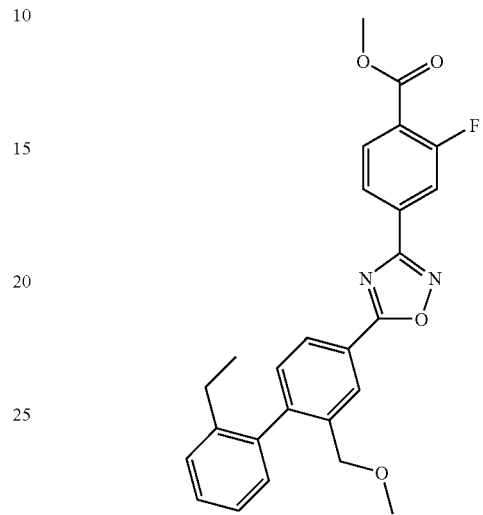

The title compound was prepared following procedure described for example 35, step 1, but starting from Intermediate 36 (1 135.37 mg; 4.20 mmol) and Intermediate 1 (891.15 mg; 4.20 mmol). The reaction mixture was cooled to RT and concentrated affording yellow oil. It was precipitating in ACN. Solvent were removed and the solid was washed with MeOH, filtered off and dried under vacuum to afford the title compound as a white powder. $^1$H NMR (CDCl$_3$) δ 8.43 (s, 1H), 8.18-7.99 (m, 4H), 7.41-7.35 (m, 3H), 7.29-7.24 (m, 1H), 7.11 (d, J=7.2 Hz, 1H), 4.27-4.17 (m, 2H), 3.98 (s, 3H), 3.34 (s, 3H), 2.50-2.28 (m, 2H), 1.05 (t, J=7.5 Hz, 3H). LC/MS (Method B): 447.2 (M+H)$^+$. HPLC (Method A) Rt 6.14 min (Purity: 99.5%).

Example 81

2-fluoro-4-{5-[2'-fluoro-2-(methoxymethyl)biphenyl-4-yl]-1,2,4-oxadiazol-3-yl}benzoic acid

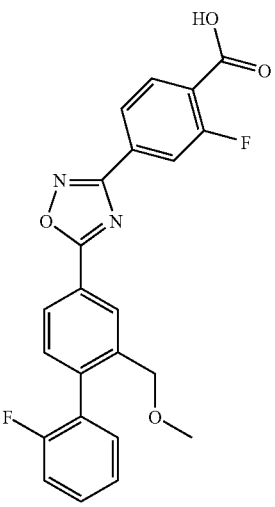

Step 1: methyl 2-fluoro-4-{5-[2'-fluoro-2-(methoxymethyl)biphenyl-4-yl]-1,2,4-oxadiazol-3-yl}benzoate The title compound was obtained following procedure and work up described for example 79, step 2, but starting from methyl 4-{5-[4-bromo-3-(methoxymethyl)phenyl]-1,2,4-oxadiazol-3-yl}-2-fluorobenzoate obtained in example 79, step 1 (100 mg, 0.24 mmol) and 2-fluorophenylboronic acid (66 mg, 0.47 mmol). It was isolated as an off-white powder. LC/MS (Method B): 437.2 (M+H)+. HPLC (Method A) Rt 5.70 min (purity: 97.9%).

Step 2: 2-fluoro-4-{5-[2'-fluoro-2-(methoxymethyl)biphenyl-4-yl]-1,2,4-oxadiazol-3-yl}benzoic acid The title compound was obtained following procedure and work up described for example 4, step 2, but starting from methyl 2-fluoro-4-{5-[2'-fluoro-2-(methoxymethyl)biphenyl-4-yl]-1,2,4-oxadiazol-3-yl}benzoate obtained in step 1. It was isolated as an off-white powder. $^1$H NMR (DMSO-$d_6$, 300 MHz) δ 8.48 (m, 1H), 8.28-8.10 (m, 4H), 7.51-7.45 (m, 2H), 7.35-7.18 (m, 3H), 4.43 (s, 2H), 3.39 (s, 3H). LC/MS (Method B): 421.2 (M−H)−. HPLC (Method A) Rt 4.97 min (purity: 99.5%).

Example 82

4-{5-[2',3'-dimethoxy-2-(methoxymethyl)biphenyl-4-yl]-1,2,4-oxadiazol-3-yl}-2-fluorobenzoic acid

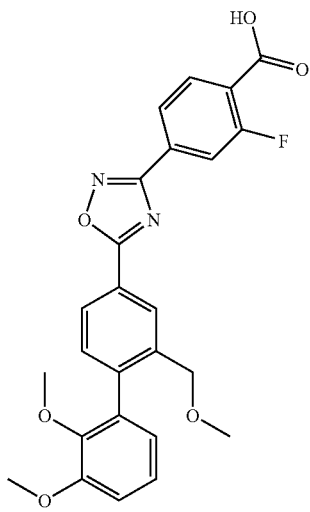

Step 1: methyl 4-{5-[2',3'-dimethoxy-2-(methoxymethyl)biphenyl-4-yl]-1,2,4-oxadiazol-3-yl}-2-fluorobenzoate The title compound was obtained following procedure and work up described for example 79, step 2, but starting from methyl 4-{5-[4-bromo-3-(methoxymethyl)phenyl]-1,2,4-oxadiazol-3-yl}-2-fluorobenzoate obtained in example 79, step 1 (100 mg, 0.24 mmol) and 2,3-dimethoxybenzeneboronic acid (86 mg, 0.47 mmol). It was isolated as an off-white powder. LC/MS (Method B): 479.2 (M+H)+. HPLC (Method A) Rt 6.12 min (purity: 94.2%).

Step 2: 4-{5-[2',3'-dimethoxy-2-(methoxymethyl)biphenyl-4-yl]-1,2,4-oxadiazol-3-yl}-2-fluorobenzoic acid The title compound was obtained following procedure and work up described for example 4, step 2, but starting Methyl 4-{5-[2',3'-dimethoxy-2-(methoxymethyl)biphenyl-4-yl]-1,2,4-oxadiazol-3-yl}-2-fluorobenzoate obtained in step 1. It was isolated as an off-white powder. $^1$H NMR (DMSO-$d_6$, 300 MHz) δ 13.63 (bs, 1H), 8.31-8.30 (m, 1H), 8.17-8.14 (m, 1H), 8.09-8.02 (m, 2H), 7.98-7.94 (m, 1H), 7.49 (d, J=8 Hz, 1H), 7.18-7.15 (m, 2H), 6.81-6.78 (m, 1H), 4.32 (m, 2H), 3.87 (s, 3H), 3.47 (s, 3H), 3.27 (s, 3H). LC/MS (Method B): 465.1 (M+H)+. HPLC (Method A) Rt 4.85 min (purity: 95.1%).

Example 83

2-fluoro-4-{5-[2'-methyl-2-(methylsulfonyl)biphenyl-4-yl]-1,2,4-oxadiazol-3-yl}benzoic acid

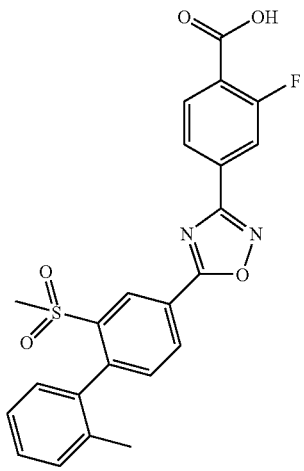

Step 1: methyl 2-fluoro-4-{5-[2'-methyl-2-(methylsulfonyl)biphenyl-4-yl]-1,2,4-oxadiazol-3-yl}benzoate The title compound was prepared following procedure described for example 4, step 1, but starting from Intermediate 38 (159.69 mg; 0.55 mmol). The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5 to 5/5). It was then suspended in MeCN and filtrated, affording the title compound as a white solid. LC/MS (Method B): 467.2 (M+H)+. HPLC (Method A) Rt 5.24 min (Purity: 99.7%).

Step 2: 2-fluoro-4-{5-[2'-methyl-2-(methylsulfonyl)biphenyl-4-yl]-1,2,4-oxadiazol-3-yl}benzoic acid The title compound was prepared following procedure described for example 4, step 2, but starting from methyl 2-fluoro-4-{5-[2'-methyl-2-(methylsulfonyl)biphenyl-4-yl]-1,2,4-oxadiazol-3-yl}benzoate obtained in step 1, (110 mg; 0.24 mmol). Solvents were concentrated and EtOAc (20 mL) was added. It was washed with HCl 1N (15 mL), water (15 mL) and was dried over MgSO$_4$, affording the title compound as a white solid (90.6 mg; 85%). $^1$H NMR (DMSO-d$_6$, 300 MHz) δ 13.64 (br s, 1H), 8.84 (d, J=1.8 Hz, 1H), 8.54 (dd, J=1.8, 7.8 Hz, 1H), 8.17-7.96 (m, 3H), 7.66 (d, J=7.8 Hz, 1H), 7.45-7.27 (m, 4H), 2.97 (s, 3H), 2.05 (s, 3H). LC/MS (Method B): 451.2 (M−H)$^−$; 453.2 (M+H)$^+$. HPLC (Method A) Rt 4.96 min (Purity: 97.8%).

Example 84

2-fluoro-4-{5-[5'-fluoro-2-(methoxymethyl)-2'-methylbiphenyl-4-yl]-1,2,4-oxadiazol-3-yl}benzoic acid

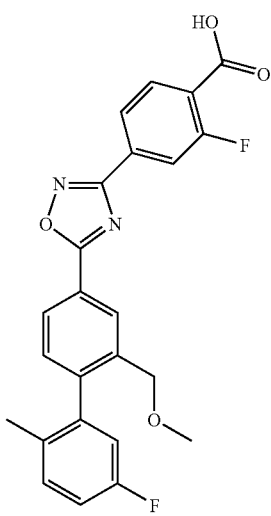

Step 1: methyl 2-fluoro-4-{5-[5'-fluoro-2-(methoxymethyl)-2'-methylbiphenyl-4-yl]-1,2,4-oxadiazol-3-yl}benzoate The title compound was obtained following procedure and work up described for example 79, step 2, but starting from methyl 4-{5-[4-bromo-3-(methoxymethyl)phenyl]-1,2,4-oxadiazol-3-yl}-2-fluorobenzoate obtained in example 79, step 1 (100 mg, 0.24 mmol) and 5-fluoro-2-methylphenylboronic acid (73 mg, 0.47 mmol). It was isolated as an off-white powder. HPLC (Method A) Rt 6.49 min (purity: 96.9%).

Step 2: 2-fluoro-4-{5-[5'-fluoro-2-(methoxymethyl)-2'-methylbiphenyl-4-yl]-1,2,4-oxadiazol-3-yl}benzoic acid The title compound was obtained following procedure and work up described for example 4, step 2, but starting methyl 4-{5-[2',3'-dimethoxy-2-(methoxymethyl)biphenyl-4-yl]-1,2,4-oxadiazol-3-yl}-2-fluorobenzoate obtained in step 1. It was isolated as an off-white powder. $^1$H NMR (DMSO-d$_6$, 300 MHz) δ 13.61 (bs, 1H), 8.34-8.33 (m, 1H), 8.20-8.17 (m, 1H), 8.10-8.03 (m, 2H), 7.98-7.94 (m, 1H), 7.46-7.37 (m, 1H), 7.23-7.16 (m, 1H), 7.06-7.02 (m, 1H), 4.25 (d, J=12.6 Hz, 1H), 4.17 (d, J=12.6 Hz, 1H), 3.26 (s, 3H), 1.99 (s, 3H). LC/MS (Method B): 437.1 (M+H)$^+$. HPLC (Method A) Rt 5.71 min (purity: 95.9%).

Example 85

4-{5-[2,2'-bis(methoxymethyl)biphenyl-4-yl]-1,2,4-oxadiazol-3-yl}-2-fluorobenzoic acid

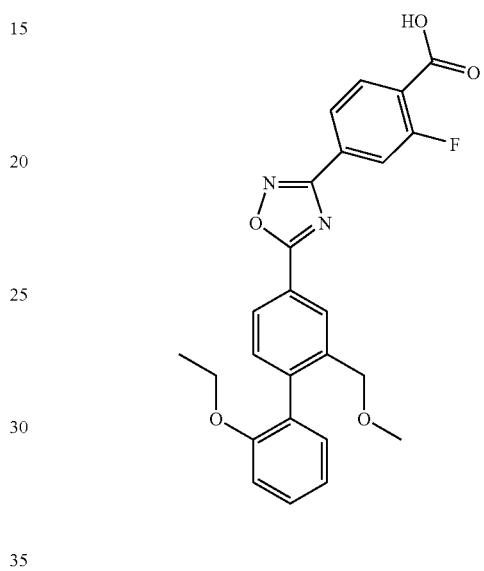

Step 1: methyl 4-{5-[2,2'-bis(methoxymethyl)biphenyl-4-yl]-1,2,4-oxadiazol-3-yl}-2-fluorobenzoate The title compound was obtained following procedure and work up described for example 79, step 2, but starting from methyl 4-{5-[4-bromo-3-(methoxymethyl)phenyl]-1,2,4-oxadiazol-3-yl}-2-fluorobenzoate obtained in example 79, step 1 (100 mg, 0.24 mmol) and (2-methoxymethylphenyl)boronic acid (78 mg, 0.47 mmol). It was isolated as an off-white powder. LC/MS (Method B): 463.2 (M+H)$^+$. HPLC (Method A) Rt 6.15 min (purity: 97.1%).

Step 2: 4-{5-[2,2'-bis(methoxymethyl)biphenyl-4-yl]-1,2,4-oxadiazol-3-yl}-2-fluorobenzoic acid The title compound was obtained following procedure and work up described for example 4, step 2, but starting methyl 4-{5-[2,2'-bis(methoxymethyl)biphenyl-4-yl]-1,2,4-oxadiazol-3-yl}-2-fluorobenzoate obtained in step 1. It was isolated as an off-white powder. $^1$H NMR (DMSO-d$_6$, 300 MHz) δ 13.61 (bs, 1H), 8.32 (m, 1H), 8.18-8.15 (m, 1H), 8.12-8.03 (m, 2H), 7.98-7.94 (m, 1H), 7.54-7.52 (m, 1H), 7.49-7.40 (m, 3H), 7.21-7.16 (m, 1H), 7.07-7.03 (m, 1H), 4.23 (d, J=12.5 Hz, 1H), 4.15 (d, J=12.5 Hz, 1H), 4.11 (s, 2H), 3.24 (s, 3H),

Example 86

2-fluoro-4-{5-[2-(methoxymethyl)-2'-(trifluoromethyl)biphenyl-4-yl]-1,2,4-oxadiazol-3-yl}benzoic acid

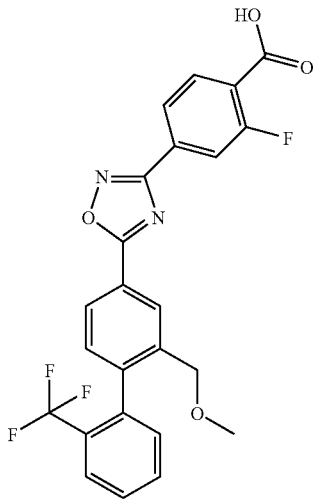

Step 1: methyl 2-fluoro-4-{5-[2-(methoxymethyl)-2'-(trifluoromethyl)biphenyl-4-yl]-1,2,4-oxadiazol-3-yl}benzoate The title compound was obtained following procedure and work up described for example 79, step 2, but starting from methyl 4-{5-[4-bromo-3-(methoxymethyl)phenyl]-1,2,4-oxadiazol-3-yl}-2-fluorobenzoate obtained in example 79, step 1 (25 mg, 0.06 mmol) and 2-(trifluoromethyl)phenylboronic acid (22 mg, 0.12 mmol). It was isolated as a beige powder. LC/MS (Method B): 487.1 (M+H)$^+$. HPLC (Method A) Rt 6.44 min (purity: 82.4%).

Step 2: 2-fluoro-4-{5-[2-(methoxymethyl)-2'-(trifluoromethyl)biphenyl-4-yl]-1,2,4-oxadiazol-3-yl}benzoic acid The title compound was obtained following procedure and work up described for example 4, step 2, but starting methyl 2-fluoro-4-{5-[2-(methoxymethyl)-2'-(trifluoromethyl)biphenyl-4-yl]-1,2,4-oxadiazol-3-yl}benzoate obtained in step 1. It was isolated as a beige powder. $^1$H NMR (DMSO-d$_6$, 300 MHz) δ 13.59 (bs, 1H), 8.32 (m, 1H), 8.19-8.16 (m, 1H), 8.13-8.03 (m, 2H), 7.99-7.90 (m, 2H), 7.80-7.70 (m, 2H), 7.49-7.38 (m, 2H), 4.21 (d, J=13 Hz, 1H), 4.13 (d, J=13 Hz, 1H), 3.12 (s, 3H). LC/MS (Method B): 449.3 (M+H)$^+$. HPLC (Method A) Rt 5.34 min (purity: 100.0%).

Example 87

2-fluoro-4-{5-[2'-(methoxymethyl)-2-methylbiphenyl-4-yl]-1,2,4-oxadiazol-3-yl}benzoic acid

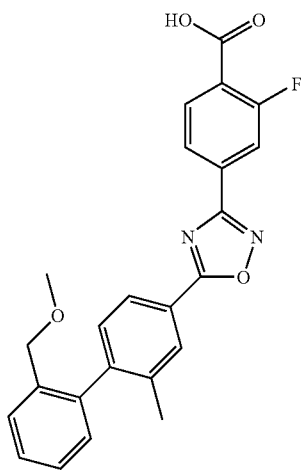

Step 1: methyl 2-fluoro-4-{5-[2'-(methoxymethyl)-2-methylbiphenyl-4-yl]-1,2,4-oxadiazol-3-yl}benzoate The title compound was prepared following procedure described for example 4, step 1, but starting from Intermediate 39 (153.78 mg; 0.60 mmol). The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording the title compound as an off-white powder. $^1$H NMR (CDCl$_3$) δ 8.14 (br s, 1H), 8.10-8.03 (m, 3H), 8 (dd, J=11.1, 1.3 Hz, 1H), 7.58-7.55 (m, 1H), 7.46-7.34 (m, 3H), 7.15 (dd, J=7.3, 1.5 Hz, 1H), 4.20-4.11 (m, 2H), 3.98 (s, 3H), 3.24 (s, 3H), 2.18 (s, 3H). LC/MS (Method B): 433.2 (M+H)$^+$. HPLC (Method A) Rt 6.08 min (Purity: 98.3%).

Step 2: 2-fluoro-4-{5-[2'-(methoxymethyl)-2-methylbiphenyl-4-yl]-1,2,4-oxadiazol-3-yl}benzoic acid The title compound was prepared following procedure described for example 4, step 2, but starting from methyl 2-fluoro-4-{5-[2'-(methoxymethyl)-2-methylbiphenyl-4-yl]-1,2,4-oxadiazol-3-yl}benzoate, obtained in step 1. Solvents were concentrated and water (5 mL) was added. The resulting precipitate was filtrated to afford the title compound as a white powder (88 mg; 84%). $^1$H NMR (DMSO-d$_6$, 300 MHz) δ 13.61 (br s, 1H), 8.17 (d, J=1.0 Hz, 1H), 8.13-8.02 (m, 3H), 7.96 (dd, J=11.1, 1.3 Hz, 1H), 7.56-7.53 (m, 1H), 7.48-7.39 (m, 3H), 7.20-7.17 (m, 1H), 4.14 (d, J=12.0 Hz, 1H), 4.09 (d, J=11.9 Hz, 1H), 3.13 (s, 3H), 2.14 (s, 3H). LC/MS (Method B): 473.1 (M+H)$^+$. HPLC (Method A) Rt 5.69 min (purity: 86.5%).

Example 88

2-chloro-4-(5-{2'-methyl-2-[(methylsulfonyl)methyl]biphenyl-4-yl}-1,2,4-oxadiazol-3-yl)benzoic acid

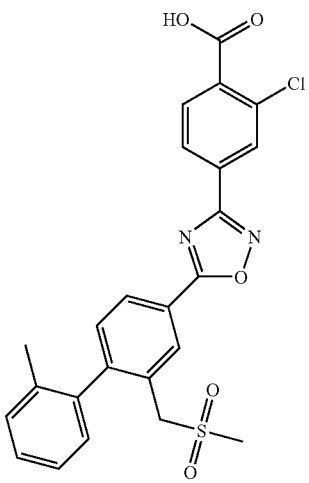

Step 1: methyl 2-chloro-4-(5-{2'-methyl-2-[(methylsulfonyl)methyl]biphenyl-4-yl}-1,2,4-oxadiazol-3-yl)benzoate The title compound was prepared following procedure described for example 4, step 1, but starting from Intermediate 40 (182.62 mg; 0.60 mmol) and Intermediate 34 (114.32 mg; 0.50 mmol). The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/EtOAc: 1/1), affording the title compound. $^1$H NMR (CDCl$_3$) δ 8.58 (d, J=1.7 Hz, 1H), 8.32 (d, J=1.5 Hz, 1H), 8.28 (dd, J=8.0, 1.8 Hz, 1H), 8.15 (dd, J=8.1, 1.6 Hz, 1H), 7.98 (d, J=8.1 Hz, 1H), 7.48 (d, J=7.9 Hz, 1H), 7.41-7.29 (m, 3H), 7.20 (d, J=7.3 Hz, 1H), 4.33 (d, J=13.9 Hz, 1H), 4.19 (d, J=14.0 Hz, 1H), 3.98 (s, 3H), 2.64 (s, 3H), 2.09 (s, 3H). LC/MS (Method B): 495.2 (M−H)$^−$, 497.1 (M+H)$^+$. HPLC (Method A) Rt 5.51 min (Purity: 99.6%).

Step 2: 2-chloro-4-(5-{2'-methyl-2-[(methylsulfonyl)methyl]biphenyl-4-yl}-1,2,4-oxadiazol-3-yl)benzoic acid The title compound was prepared following procedure described for example 4, step 2, but starting from methyl 2-chloro-4-(5-{2'-methyl-2-[(methylsulfonyl)methyl]biphenyl-4-yl}-1,2,4-oxadiazol-3-yl)benzoate, obtained in step 1. Solvents were concentrated and water (5 mL) was added. It was filtrated to afford the title compound as a white powder (119 mg; 97%). $^1$H NMR (DMSO-d$_6$, 300 MHz) δ 13.78 (br s, 1H), 8.48 (d, J=1.7 Hz, 1H), 8.26 (dd, J=7.9, 1.9 Hz, 1H), 8.19 (d, J=1.4 Hz, 1H), 8.16 (d, J=8.0, 1.6 Hz, 1H), 8.03 (d, J=8.0 Hz, 1H), 7.53 (d, J=8.1 Hz, 1H), 7.38-7.28 (m, 3H), 7.23 (d, J=7.3 Hz, 1H), 4.60 (d, J=13.8 Hz, 1H), 4.27 (d, J=13.6 Hz, 1H), 2.91 (s, 3H), 2.05 (s, 3H). LC/MS (Method B): 481.2 (M−H)$^−$, 483.1 (M+H)$^+$. HPLC (Method A) Rt 4.80 min (Purity: 99.4%).

Example 89

2-fluoro-4-{5-[5'-fluoro-2'-methoxy-2-(methoxymethyl)biphenyl-4-yl]-1,2,4-oxadiazol-3-yl}benzoic acid

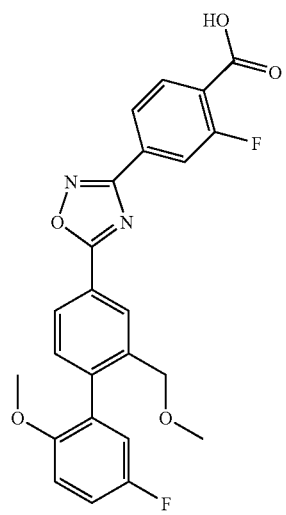

Step 1: methyl 2-fluoro-4-{5-[5'-fluoro-2'-methoxy-2-(methoxymethyl)biphenyl-4-yl]-1,2,4-oxadiazol-3-yl}benzoate The title compound was obtained following procedure and work up described for example 79, step 2, but starting from methyl 4-{5-[4-bromo-3-(methoxymethyl)phenyl]-1,2,4-oxadiazol-3-yl}-2-fluorobenzoate obtained in example 79, step 1 (150 mg, 0.35 mmol) and 5-fluoro-2-methoxyphenylboronic acid (91 mg, 0.53 mmol). It was isolated as a yellow powder. LC/MS (Method B): 467.1 (M+H)$^+$. HPLC (Method A) Rt 6.18 min (purity: 76.1%).

Step 2: 2-fluoro-4-{5-[5'-fluoro-2'-methoxy-2-(methoxymethyl)biphenyl-4-yl]-1,2,4-oxadiazol-3-yl}benzoic acid The title compound was obtained following procedure and work up described for example 4, step 2, but starting from methyl 2-fluoro-4-{5-[5'-fluoro-2'-methoxy-2-(methoxymethyl)biphenyl-4-yl]-1,2,4-oxadiazol-3-yl}benzoate obtained in step 1. It was isolated as a yellow powder. $^1$H NMR (DMSO-d$_6$, 300 MHz) δ 13.60 (bs, 1H), 8.29 (m, 1H), 8.16-8.13 (m, 1H), 8.10-8.03 (m, 2H), 7.98-7.94 (m, 1H), 7.47 (d, J=8 Hz, 2H), 7.32-7.25 (m, 1H), 7.18-7.09 (m, 2H), 4.29 (bs, 2H), 3.72 (s, 3H), 3.26 (s, 3H). LC/MS (Method B): 453.1 (M+H)⁺. HPLC (Method A) Rt 5.41 min (purity: 90.7%).

Example 90

4-{5-[2'-ethoxy-2-(methoxymethyl)biphenyl-4-yl]-1,2,4-oxadiazol-3-yl}-2-fluorobenzoic acid

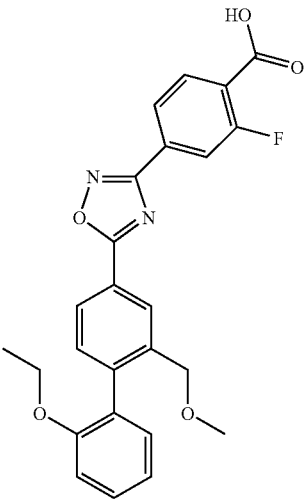

Step 1: methyl 4-{5-[2'-ethoxy-2-(methoxymethyl)biphenyl-4-yl]-1,2,4-oxadiazol-3-yl}-2-fluorobenzoate The title compound was obtained following procedure and work up described for example 79, step 2, but starting from methyl 4-{5-[4-bromo-3-(methoxymethyl)phenyl]-1,2,4-oxadiazol-3-yl}-2-fluorobenzoate obtained in example 79, step 1 (150 mg, 0.35 mmol) and 2-ethoxyphenylboronic acid (88 mg, 0.53 mmol). It was isolated as a yellow powder. LC/MS (Method B): 463.2 (M+H)⁺. HPLC (Method A) Rt 6.41 min (purity: 98.5%).

Step 2: 4-{5-[2'-ethoxy-2-(methoxymethyl)biphenyl-4-yl]-1,2,4-oxadiazol-3-yl}-2-fluorobenzoic acid The title compound was obtained following procedure and work up described for example 4, step 2, but starting from methyl 4-{5-[2'-ethoxy-2-(methoxymethyl)biphenyl-4-yl]-1,2,4-oxadiazol-3-yl}-2-fluorobenzoate obtained in step 1. It was isolated as a yellow powder. ¹H NMR (DMSO-d₆, 300 MHz) δ 13.60 (bs, 1H), 8.29 (m, 1H), 8.15-8.12 (m, 1H), 8.10-8.03 (m, 2H), 7.98-7.94 (m, 1H), 7.47-7.39 (m, 2H), 7.21-7.18 (m, 1H), 7.15-7.12 (m, 1H), 7.08-7.03 (m, 1H), 4.35-4.25 (m, 2H), 4.04 (q, J=7 Hz, 2H), 3.26 (s, 3H), 1.17 (t, J=7 Hz, 3H). LC/MS (Method B): 449.2 (M+H)⁺. HPLC (Method A) Rt 5.64 min (purity: 97.1%).

Example 91

4-{5-[2',5'-difluoro-2-(methoxymethyl)biphenyl-4-yl]-1,2,4-oxadiazol-3-yl}-2-fluorobenzoic acid

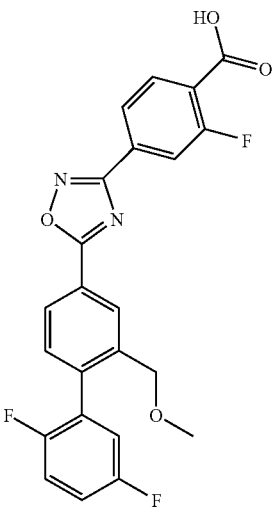

Step 1: methyl 4-{5-[2',5'-difluoro-2-(methoxymethyl)biphenyl-4-yl]-1,2,4-oxadiazol-3-yl}-2-fluorobenzoate The title compound was obtained following procedure and work up described for example 79, step 2, but starting from methyl 4-{5-[4-bromo-3-(methoxymethyl)phenyl]-1,2,4-oxadiazol-3-yl}-2-fluorobenzoate obtained in example 79, step 1 (150 mg, 0.35 mmol) and 2,5-difluorophenylboronic acid (84 mg, 0.53 mmol). It was isolated as a yellow powder. LC/MS (Method B): 455.1 (M+H)⁺. HPLC (Method A) Rt 6.21 min (purity: 100.0%).

Step 2: 4-{5-[2',5'-difluoro-2-(methoxymethyl)biphenyl-4-yl]-1,2,4-oxadiazol-3-yl}-2-fluorobenzoic acid The title compound was obtained following procedure and work up described for example 4, step 2, but starting from methyl 4-{5-[2'-ethoxy-2-(methoxymethyl)biphenyl-4-yl]-1,2,4-oxadiazol-3-yl}-2-fluorobenzoate obtained in step 1. It was isolated as a yellow powder. ¹H NMR (DMSO-d₆, 300 MHz) δ 8.34 (m, 1H), 8.22-8.19 (m, 1H), 7.81-7.78 (m, 1H), 7.68-7.57 (m, 3H), 7.44-7.34 (m, 3H), 4.38 (s, 2H), 3.27 (s, 3H). LC/MS (Method B): 441.2 (M+H)⁺. HPLC (Method A) Rt 5.46 min (purity: 94.3%).

Example 92

3-{5-[2-(methoxymethyl)-2'-methylbiphenyl-4-yl]-1,2,4-oxadiazol-3-yl}benzoic acid

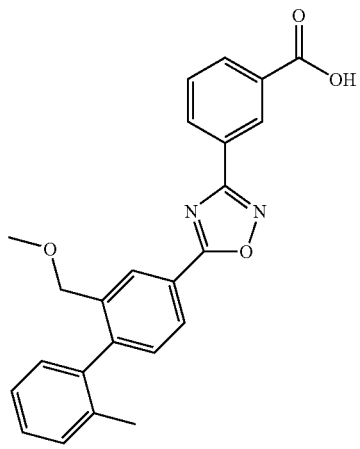

Step 1: methyl 3-{5-[2-(methoxymethyl)-2'-methyl-biphenyl-4-yl]-1,2,4-oxadiazol-3-yl}benzoate The title compound was prepared following procedure described for example 4, step 1, but starting from Intermediate 28 (128.15 mg; 0.5 mmol) and methyl 3-[(E)-amino(hydroxyimino)methyl]benzoate, prepared as described in US2004/204461 from methyl 3-cynaobenzoate (Maybridge; RJC00610EA), (97 mg; 0.5 mmol). The reaction mixture was filtered through a SPE NH₂ column (2 g) and rinsed with ACN. The filtrate was passed through a SPE SCX column (2 g) and rinsed with ACN. After evaporation of the solvents, the crude product was purified by FC (c-hex/EtOAc: 9.5/0.5 to 5/5). It was then suspended in MeCN and filtrated, affording the title compound as a white solid. LC/MS (Method B): 415.2 (M+H)⁺. HPLC (Method A) Rt 6.48 min (Purity: 96.2%).

Step 2: 3-{5-[2-(methoxymethyl)-2'-methylbiphenyl-4-yl]-1,2,4-oxadiazol-3-yl}benzoic acid The title compound was prepared following procedure described for example 4, step 2, but starting from methyl 3-{5-[2-(methoxymethyl)-2'-methylbiphenyl-4-yl]-1,2,4-oxadiazol-3-yl}benzoate obtained in step 1, (110 mg; 0.24 mmol). Solvents were concentrated and EtOAc (20 mL) was added. It was washed with HCl 1N (15 mL), water (15 mL) and was dried over MgSO₄, affording the title compound as a white solid. ¹H NMR (DMSO-d₅, 300 MHz) δ 13.39 (br s, 1H), 8.67 (m, 1H), 8.40-8.32 (m, 2H), 8.23-8.16 (m, 2H), 7.77 (t, J=8.1 Hz, 1H), 7.47-7.25 (m, 4H), 7.19-7.13 (m, 1H), 4.22 (d, J=12.2 Hz, 1H), 4.18 (d, J=12.2 Hz, 1H), 3.26 (s, 3H), 2.04 (s, 3H). LC/MS (Method B): 399.2 (M–H)⁻; 401.2 (M+H)⁺. HPLC (Method A) Rt 5.19 min (Purity: 100%).

Example 93

2-fluoro-4-{5-[3-(methoxymethyl)-4-(4-methyl-3-thienyl)phenyl]-1,2,4-oxadiazol-3-yl}benzoic acid

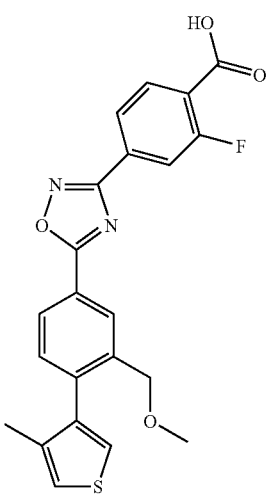

Step 1: methyl 2-fluoro-4-{5-[3-(methoxymethyl)-4-(4-methyl-3-thienyl)phenyl]-1,2,4-oxadiazol-3-yl}benzoate The title compound was obtained following procedure and work up described for example 79, step 2, but starting from methyl 4-{5-[4-bromo-3-(methoxymethyl)phenyl]-1,2,4-oxadiazol-3-yl}-2-fluorobenzoate obtained in example 79, step 1 (150 mg, 0.35 mmol) and 4-methyl-3-thiopheneboronic acid (55.62 mg; 0.39 mmol;). It was isolated as a yellow powder. LC/MS (Method B): 439.1 (M+H)⁺.

Step 2: 2-fluoro-4-{5-[3-(methoxymethyl)-4-(4-methyl-3-thienyl)phenyl]-1,2,4-oxadiazol-3-yl}benzoic acid The title compound was obtained following procedure and work up described for example 4, step 2, but starting from methyl 2-fluoro-4-{5-[3-(methoxymethyl)-4-(4-methyl-3-thienyl)phenyl]-1,2,4-oxadiazol-3-yl}benzoate obtained in step 1. It was isolated as a yellow powder. ¹H NMR (DMSO-d₆, 300 MHz) δ 13.61 (bs, 1H), 8.32 (m, 1H), 8.17-8.14 (m, 1H), 8.12-8.02 (m, 2H), 7.98-7.93 (m, 1H), 7.50-7.47 (m, 2H), 7.36-7.35 (m, 1H), 4.31 (s, 2H), 3.30 (s, 3H), 2.02 (s, 3H). LC/MS (Method B): 425.1 (M+H)+. HPLC (Method A) Rt 5.60 min (purity: 95.4%).

Example 94

2-fluoro-4-{5-[4'-fluoro-2-(methoxymethyl)-2'-methylbiphenyl-4-yl]-1,2,4-oxadiazol-3-yl}benzoic acid

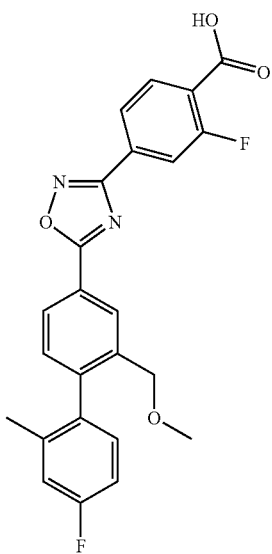

Step 1: methyl 2-fluoro-4-{5-[4'-fluoro-2-(methoxymethyl)-2'-methylbiphenyl-4-yl]-1,2,4-oxadiazol-3-yl}benzoate The title compound was obtained following procedure and work up described for example 79, step 2, but starting from methyl 4-{5-[4-bromo-3-(methoxymethyl)phenyl]-1,2,4-oxadiazol-3-yl}-2-fluorobenzoate obtained in example 79, step 1 (150 mg, 0.35 mmol) and 4-fluoro-2-methylbenzeneboronic acid (82 mg; 0.53 mmol;). It was isolated as a yellow powder. LC/MS (Method B): 451.2 (M+H)+.

Step 2: 2-fluoro-4-{5-[4'-fluoro-2-(methoxymethyl)-2'-methylbiphenyl-4-yl]-1,2,4-oxadiazol-3-yl}benzoic acid The title compound was obtained following procedure and work up described for example 4, step 2, but starting from methyl 2-fluoro-4-{5-[4'-fluoro-2-(methoxymethyl)-2'-methylbiphenyl-4-yl]-1,2,4-oxadiazol-3-yl}benzoate obtained in step 1. It was isolated as a yellow powder. ¹H NMR (DMSO-d₆, 300 MHz) δ 13.62 (bs, 1H), 8.32 (m, 1H), 8.19-8.16 (m, 1H), 8.13-8.03 (m, 2H), 7.98-7.94 (m, 1H), 7.43 (d, J=8 Hz, 1H), 7.26-7.09 (m, 3H), 4.23-4.13 (m, 2H), 3.25 (s, 3H), 2.04 (s, 3H). LC/MS (Method B): 437.1 (M+H)+. HPLC (Method A) Rt 5.74 min (purity: 94.1%).

Example 95

2-fluoro-4-{5-[2-(methoxymethyl)-2',3'-dimethylbiphenyl-4-yl]-1,2,4-oxadiazol-3-yl}benzoic acid

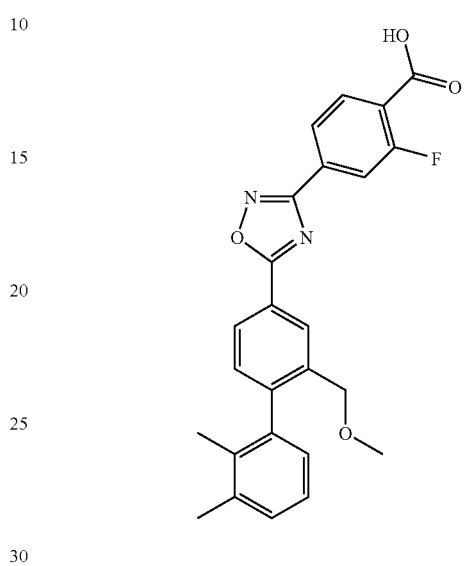

Step 1: methyl 2-fluoro-4-{5-[2-(methoxymethyl)-2',3'-dimethylbiphenyl-4-yl]-1,2,4-oxadiazol-3-yl}benzoate The title compound was obtained following procedure and work up described for example 79, step 2, but starting from methyl 4-{5-[4-bromo-3-(methoxymethyl)phenyl]-1,2,4-oxadiazol-3-yl}-2-fluorobenzoate obtained in example 79, step 1 (300 mg, 0.71 mmol) and 2,3-dimethylbenzeneboronic acid (117 mg; 0.78 mmol). It was isolated as a white powder. LC/MS (Method B): 447.1 (M+H)+.

Step 2: 2-fluoro-4-{5-[2-(methoxymethyl)-2',3'-dimethylbiphenyl-4-yl]-1,2,4-oxadiazol-3-yl}benzoic acid The title compound was obtained following procedure and work up described for example 4, step 2, but starting from methyl 2-fluoro-4-{5-[4'-fluoro-2-(methoxymethyl)-2'-methylbiphenyl-4-yl]-1,2,4-oxadiazol-3-yl}benzoate obtained in step 1. It was isolated as a yellow powder. ¹H NMR (DMSO-d₆, 300 MHz) δ 13.62 (bs, 1H), 8.32 (m, 1H), 8.18-8.15 (m, 1H), 8.13-8.03 (m, 2H), 7.98-7.94 (m, 1H), 7.39 (d, J=8 Hz, 1H), 7.26-7.18 (m, 2H), 6.98-6.96 (m, 1H), 4.23-4.13 (m, 2H), 3.26 (s, 3H), 2.31 (s, 3H), 1.92 (s, 3H). LC/MS (Method B): 433.2 (M+H)+. HPLC (Method A) Rt 5.74 min (purity: 98.8%).

Example 96

2-fluoro-4-{5-[2-(3-methoxyprop-1-yn-1-yl)-2'-methylbiphenyl-4-yl]-1,2,4-oxadiazol-3-yl}benzoic acid

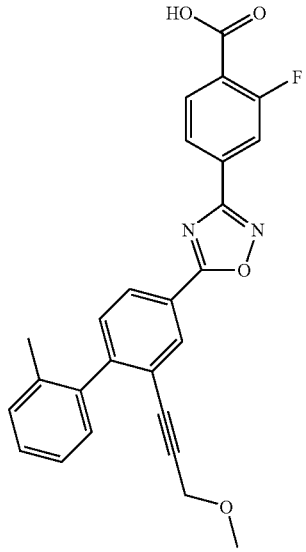

The title compound was prepared following procedure described for example 4, step 1, but starting from Intermediate 41 (134.56 mg; 0.48 mmol; 1.20 eq.). The reaction mixture was filtered through a SPE NH₂ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5), affording a yellow oil. It was dissolved in MeOH (1 mL) and THF (1 mL) and NaOH (50 μL; 0.25 mmol; 5 M solution) was added. After one night stirring at RT, solvents were concentrated and the crude was purified by MD Autoprep to afford the title compound as a white powder (10 mg; 6%). ¹H NMR (DMSO-d₆, 300 MHz) δ 13.63 (br s, 1H), 8.32 (d, J=1.7 Hz, 1H), 8.26 (dd, J=8.0, 1.9 Hz, 1H), 8.13-8.08 (m, 1H), 8.05 (dd, J=8.0, 1.6 Hz, 1H), 7.98 (dd, J=11.1, 1.2 Hz, 1H), 7.60 (d, J=8.0 Hz, 1H), 7.36-7.27 (m, 3H), 7.23 (d, J=6.8 Hz, 1H), 4.16 (s, 2H), 3.02 (s, 3H), 2.16 (s, 3H). LC/MS (Method B): 441.2 (M−H)⁻, 443.2 (M+H)⁺. HPLC (Method A) Rt 5.21 min (Purity: 99.1%).

Example 97

2,5-difluoro-4-{5-[2-(methoxymethyl)-2'-methylbiphenyl-4-yl]-1,2,4-oxadiazol-3-yl}benzoic acid

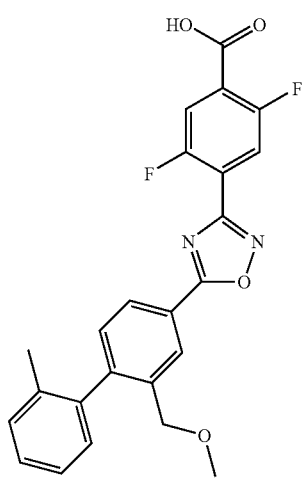

Step 1: methyl 2,5-difluoro-4-{5-[2-(methoxymethyl)-2'-methylbiphenyl-4-yl]-1,2,4-oxadiazol-3-yl}benzoate Oxalyl chloride (190.39 mg; 1.50 mmol; 3 eq.) was added to a suspension of Intermediate 28 (143.64 mg; 0.50 mmol; 1 eq.) and DMF (cat.) in DCM (2 mL) and the resulting mixture was stirred at RT for 1 hour. After evaporation to dryness, the residue was taken up in THF (2 mL) and added to solution of Intermediate 52 (108.62 mg; 0.50 mmol; 1 eq.) and DIEA (193.87 mg; 1.50 mmol; 3 eq.) in THF (1 mL). The resulting mixture was heated to 150° C. for 30 minutes in the microwave. It was then filtered through a SPE-NH₂ column, which was further washed with THF. After evaporation, the residue was purified by FC(C-Hex/EtOAc 9:1 until 5:5), affording the title product as a off-white solid. LC/MS (Method B): 451.2 (M+H)⁺. HPLC (Method A) Rt 6.0 min (Purity: 89.6%).

Step 2: 2,5-di fluoro-4-{5-[2-(methoxymethyl)-2'-methylbiphenyl-4-yl]-1,2,4-oxadiazol-3-yl}benzoic acid The title compound was obtained following procedure and work up described for example 4, step 2, but starting from methyl 2,5-difluoro-4-{5-[2-(methoxymethyl)-2'-methylbiphenyl-4-yl]-1,2,4-oxadiazol-3-yl}benzoate obtained in step 1 (40 mg; 0.09 mmol; 1 eq.). It was isolated as a yellow beige solid. ¹H NMR (DMSO-d₆, 300 MHz) δ 13.92 (bs, 1H), 8.34 (m, 1H), 8.17 (d, J=1.8 Hz, 1H), 8.05 (dd, J=5.3, 10.3 Hz, 1H), 7.90 (dd, J=5.8, 10.3 Hz, 1H), 7.44 (d, J=8.0 Hz, 1H), 7.40-7.11 (m, 4H), 4.22 (d, J=12.8 Hz, 1H), 4.17 (d, J=12.8 Hz, 1H), 3.25 (s, 3H), 2.04 (s, 3H). LC/MS (Method B): 435.2 (M−H)⁻; 437.1 (M+H)⁺. HPLC (Method A) Rt 5.05 min (purity: 99.8%).

Example 98

4-{5-[7-chloro-2-(methoxymethyl)biphenyl-4-yl]-1,2,4-oxadiazol-3-yl}-2-fluorobenzoic acid

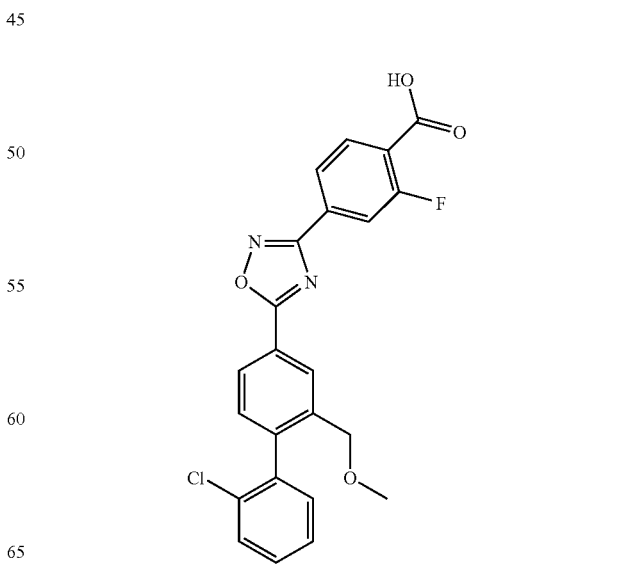

Step 1: methyl 4-{5-[2'-chloro-2-(methoxymethyl) biphenyl-4-yl]-1,2,4-oxadiazol-3-yl}-2-fluorobenzoate The title compound was obtained following procedure and work up described for example 79, step 2, but starting from methyl 4-{5-[4-bromo-3-(methoxymethyl)phenyl]-1,2,4-oxadiazol-3-yl}-2-fluorobenzoate obtained in example 79, step 1 (300 mg, 0.71 mmol) and 2-chlorobenzeneboronic acid (122 mg; 0.78 mmol). It was isolated as a white powder. LC/MS (Method B): 453.1 (M+H)+.

Step 2: 4-{5-[2'-chloro-2-(methoxymethyl)biphenyl-4-yl]-1,2,4-oxadiazol-3-yl}-2-fluorobenzoic acid The title compound was obtained following procedure and work up described for example 4, step 2, but starting from methyl 4-{5-[2'-chloro-2-(methoxymethyl)biphenyl-4-yl]-1,2,4-oxadiazol-3-yl}-2-fluorobenzoate obtained in step 1. It was isolated as a yellow powder. $^1$H NMR (DMSO-$d_6$, 300 MHz) δ 13.64 (bs, 1H), 8.34-8.33 (m, 1H), 8.22-8.19 (m, 1H), 8.12-7.94 (m, 3H), 7.65-7.62 (m, 1H), 7.51-7.47 (m, 3H), 7.41-7.37 (m, 1H), 4.30 (d, J=13 Hz, 1H), 4.22 (d, J=13 Hz, 1H), 3.25 (s, 3H). LC/MS (Method B): 439.2 (M+H)+. HPLC (Method A) Rt 5.11 min (purity: 97.8%).

Example 99

2-fluoro-4-[5-(2-hydroxy-2'-methylbiphenyl-4-yl)-1,2,4-oxadiazol-3-yl]benzoic acid

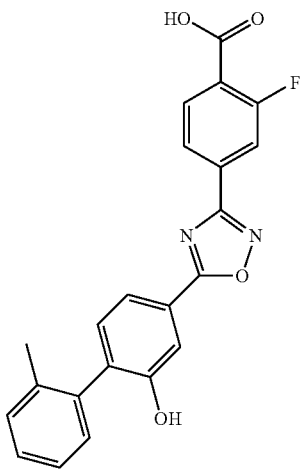

Step 1: methyl 2-fluoro-4-[5-(2-hydroxy-2'-methylbiphenyl-4-yl)-1,2,4-oxadiazol-3-yl]benzoate The title compound was prepared following procedure described for example 4, step 1, but starting from Intermediate 43 (456.49 mg; 2 mmol). After evaporation of the solvents, the crude product was purified by flash chromatography (c-hex/EtOAc: 9.5/0.5), affording the title compound. LC/MS (Method B): 403.2 (M−H)−, 405.2 (M+H)+. HPLC (Method A) Rt 5.34 min (Purity: 82.6%).

Step 2: 2-fluoro-4-[5-(2-hydroxy-2'-methylbiphenyl-4-yl)-1,2,4-oxadiazol-3-yl]benzoic acid The title compound was prepared following procedure described for example 4, step 2, but starting from methyl 2-fluoro-4-[5-(2-hydroxy-2'-methylbiphenyl-4-yl)-1,2,4-oxadiazol-3-yl]benzoate, obtained in step 1. Solvents were concentrated and the crude was purified by MD Autoprep. to afford the title compound as a white powder. $^1$H NMR (DMSO-$d_6$, 300 MHz) δ 13.61 (br s, 1H), 10.20 (br s, 1H), 8.14-8.08 (m, 1H), 8.02 (dd, J=7.9, 1.4 Hz, 1H), 7.93 (d, J=10.9 Hz, 1H), 7.76 (d, J=1.4 Hz, 1H), 7.71 (dd, J=7.7, 1.6 Hz, 1H), 7.34 (d, J=7.9 Hz, 1H), 7.29-7.22 (m, 3H), 7.17 (d, J=6.8 Hz, 1H), 2.15 (s, 3H). LC/MS (Method B): 389.2 (M−H)−, 391.2 (M+H)+. HPLC (Method A) Rt 4.67 min (Purity: 99.5%).

Example 100

2-fluoro-4-{5-[2-(3-methoxypropyl)-2'-methylbiphenyl-4-yl]-1,2,4-oxadiazol-3-yl}benzoic acid

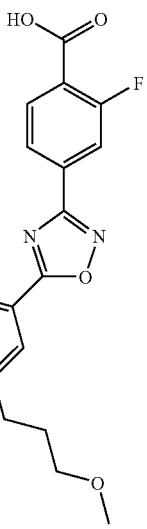

The title compound was prepared following procedure described for example 4, step 1, but starting from Intermediate 44 (156.40 mg; 0.55 mmol). The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/EtOAc: 9.5/0.5). The latter was saponified following the procedure described for example 4, step 2, but starting from methyl 2-fluoro-4-{5-[2-(3-methoxypropyl)-2'-methylbiphenyl-4-yl]-1,2,4-oxadiazol-3-yl}benzoate, not isolated. Solvents were concentrated and the crude was purified by MD Autoprep to afford the title compound as a beige powder. $^1$H NMR (DMSO-$d_6$, 300 MHz) δ 13.62 (br s, 1H), 8.18 (s, 1H), 8.13-8.04 (m, 3H), 7.97 (d, J=11.2 Hz, 1H), 7.39-7.30 (m, 4H), 7.15 (d, J=7.0 Hz, 1H), 3.18 (t, 2H), 3.10 (s, 3H), 2.62-

2.55 (m, 1H), 2.44-2.39 (m, 1H), 2.03 (s, 3H), 1.66-1.61 (m, 2H). LC/MS (Method B): 445.3 (M−H)⁻, 447.2 (M+H)⁺.

Example 101

2-fluoro-4-[5-(2-isopropoxy-2'-methylbiphenyl-4-yl)-1,2,4-oxadiazol-3-yl]benzoic acid

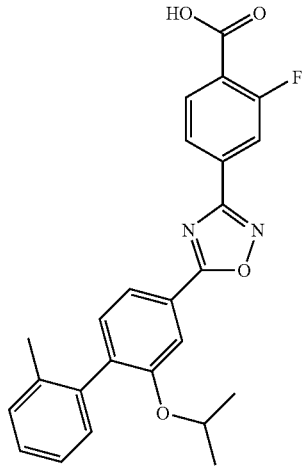

To a solution example 99 (75 mg; 0.19 mmol) in DMF (1.12 mL), potassium carbonate (56.39 mg; 0.41 mmol) and 2-bromopropane (38.31 μL; 0.41 mmol) were added. The reaction mixture was heated under microwave irradiation at 130° C. for 30 min. Sodium hydroxide (185.46 μL; 5 M; 0.93 mmol) was added and the mixture was heated at 100° C. for 2 min. Hydrochloric acid (315.28 μL; 5 M; 1.58 mmol) was added. EtOAc was added (3×2 mL) and the combined organic layers were dried over magnesium sulfate. After evaporation of the solvent, the crude was injected in MD Autoprep to afford the title compound as a beige powder. ¹H NMR (DMSO-d₆, 300 MHz) δ 13.63 (br s, 1H), 8.13-8.07 (m, 1H), 8.04 (dd, J=8.0, 1.5 Hz, 1H), 7.96 (dd, J=11.1, 1.3 Hz, 1H), 7.84 (d, J=7.8, 1.6 Hz, 1H), 7.80 (d, J=1.3 Hz, 1H), 7.40 (d, J=7.9 Hz, 1H), 7.30-7.23 (m, 3H), 7.15 (d, J=6.8 Hz, 1H), 4.73 (sept., J=5.9 Hz, 1H), 2.12 (s, 3H), 1.19 (s, 6H). LC/MS (Method B): 431.3 (M−H)⁻, 433.1 (M+H)⁺. HPLC (Method A) Rt 5.59 min (Purity: 98.1%).

Example 102

4-[5-(2-ethoxy-2'-methylbiphenyl-4-yl)-1,2,4-oxadiazol-3-yl]-2-fluorobenzoic acid

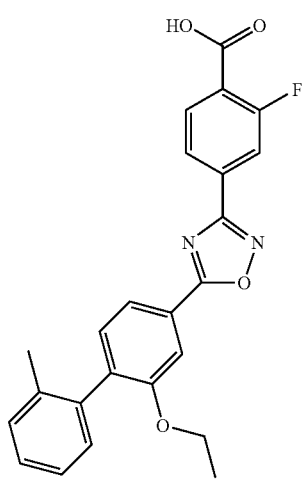

To a solution example 99 (75 mg; 0.19 mmol) in DMF (1.12 mL), potassium carbonate (56.39 mg; 0.41 mmol) and bromoethane (55.37 μL; 0.74 mmol) were added. The reaction mixture was heated under microwave irradiation at 120° C. for 20 min. Sodium hydroxide (185.46 μL; 5 M; 0.93 mmol) was added and the mixture was heated at 100° C. for 2 min under microwave irradiation. Hydrochloric acid (315.28 μL; 5 M; 1.58 mmol) was added. EtOAc was added (3×2 mL) and the combined organic layers were dried over magnesium sulfate. After evaporation of the solvent, the crude was injected in MD Autoprep to afford the title compound as a white powder. ¹H NMR (DMSO-d₆, 300 MHz) δ 13.63 (br s, 1H), 8.13-8.02 (m, 2H), 7.96 (d, J=11.1 Hz, 1H), 7.86 (d, J=7.8 Hz, 1H), 7.79 (s, 1H), 7.41 (d, J=7.7 Hz, 1H), 7.31-7.23 (m, 3H), 7.17 (d, J=6.7 Hz, 1H), 4.19 (q, J=6.8 Hz, 2H), 2.12 (s, 3H), 1.24 (t, J=6.9 Hz, 3H). LC/MS (Method B): 417.3 (M−H)⁻, 419.1 (M+H)⁺. HPLC (Method A) Rt 5.38 min (Purity: 99.3%).

Example 103

2-fluoro-4-{5-[2-(2-methoxyethoxy)-2'-methylbiphenyl-4-yl]-1,2,4-oxadiazol-3-yl}benzoic acid

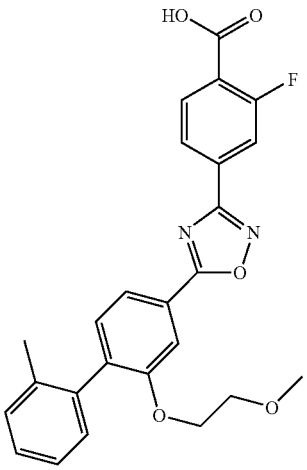

To a solution example 99 (100 mg; 0.25 mmol) in DMF (1.5 mL), potassium carbonate (136.70 mg; 0.99 mmol) and 2-bromoethyl methyl ether (92.95 μL; 0.99 mmol) were added. The reaction mixture was heated under microwave irradiation at 120° C. for 20 min. Sodium hydroxide (247.28 μL; 5 M; 1.24 mmol) was added and the mixture was heated at 100° C. for 2 min under microwave irradiation. Hydrochloric acid (544.02 μL; 5 M; 2.72 mmol) was added. EtOAc was added (3×2 mL) and the combined organic layers were dried over magnesium sulfate. After evaporation of the solvent, the crude was injected in MD Autoprep to afford the title compound as a white solid. ¹H NMR (DMSO-d₆, 300 MHz) δ 13.62 (br s, 1H), 8.13-8.03 (m, 2H), 7.97 (d, J=11.3 Hz, 1H), 7.88 (d, J=6.9 Hz, 1H), 7.84 (s, 1H), 7.42 (d, J=7.9 Hz, 1H), 7.29-7.22 (m, 3H), 7.18 (d, J=6.9 Hz, 1H), 4.26-4.25 (m, 2H), 3.60-3.57 (m, 2H), 3.18 (s, 3H), 2.13 (s, 3H). LC/MS (Method B): 447.2 (M−H)⁻, 449.2 (M+H)⁺. HPLC (Method A) Rt 5.10 min (Purity: 98.8%).

Example 104

2-fluoro-4-[5-(2-isobutoxy-2'-methylbiphenyl-4-yl)-1,2,4-oxadiazol-3-yl]benzoic acid

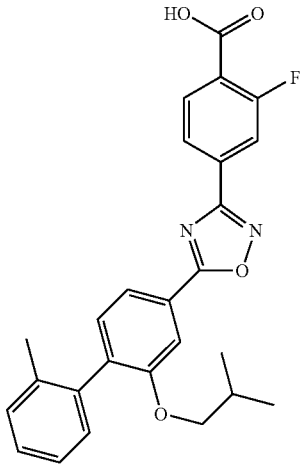

To a solution example 99 (100 mg; 0.25 mmol) in DMF (1.5 mL), potassium carbonate (136.70 mg; 0.99 mmol) and 1-bromo-2-methylpropane (107.56 μL; 0.99 mmol) were added. The reaction mixture was heated in the microwave at 120° C. for 20 min. Sodium hydroxide (247.28 μL; 5 M; 1.24 mmol) was added and the mixture was heated at 100° C. for 2 min. Hydrochloric acid (544.02 μL; 5 M; 2.72 mmol) was added. EtOAc was added (3×2 mL) and the combined organic layers were dried over magnesium sulfate. After evaporation of the solvent, the crude was injected in MD Autoprep to afford the title compound as a white powder. $^1$H NMR (DMSO-$d_6$, 300 MHz) δ 13.62 (br s, 1H), 8.14-8.03 (m, 2H), 7.98 (d, J=10.9 Hz, 1H), 7.87 (d, J=7.8 Hz, 1H), 7.79 (s, 1H), 7.42 (d, J=7.7 Hz, 1H), 7.31-7.25 (m, 3H), 7.16 (d, J=6.6 Hz, 1H), 3.89 (d, J=6.4 Hz, 2H), 2.11 (s, 3H), 1.91-1.83 (m, 1H), 0.82 (d, J=6.6 Hz, 6H). LC/MS (Method B): 445.3 (M−H)$^−$, 447.2 (M+H)$^+$. HPLC (Method A) Rt 5.91 min (Purity: 98.0%).

Example 105

4-{5-[2-(cyclopropylmethoxy)-2'-methylbiphenyl-4-yl]-1,2,4-oxadiazol-3-yl}-2-fluorobenzoic acid

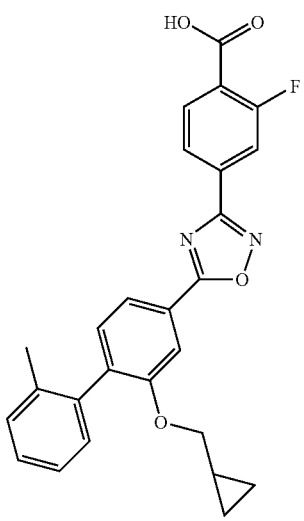

To a solution example 99 (100 mg; 0.25 mmol) in DMF (1.5 mL), potassium carbonate (136.70 mg; 0.99 mmol) and (bromomethyl)cyclopropane (96.07 μL; 0.99 mmol) were added. The reaction mixture was heated in the microwave at 120° C. for 20 min. Sodium hydroxide (247.28 μL; 5 M; 1.24 mmol) was added and the mixture was heated at 100° C. for 2 min. Hydrochloric acid (544.02 μL; 5 M; 2.72 mmol) was added. EtOAc was added (3×2 mL) and the combined organic layers were dried over magnesium sulfate. After evaporation of the solvent, the crude was injected in MD Autoprep to afford the title compound as a white powder. $^1$H NMR (DMSO-$d_6$, 300 MHz) δ 13.62 (br s, 1H), 8.13-8.03 (m, 2H), 7.97 (d, J=11.1 Hz, 1H), 7.86 (d, J=7.8 Hz, 1H), 7.79 (s, 1H), 7.41 (d, J=7.8 Hz, 1H), 7.31-7.26 (m, 3H), 7.18 (d, J=6.2 Hz, 1H), 4 (d, J=6.2 Hz, 2H), 2.15 (s, 3H), 1.16-1.06 (m, 1H), 0.49 (d, J=7.0 Hz, 2H), 0.27 (d, J=4.1 Hz, 2H). LC/MS (Method B): 443.3 (M−H)$^−$, 445.2 (M+H)$^+$. HPLC (Method A) Rt 5.58 min (Purity: 98.8%).

Example 106 methyl 4-methoxy-3-{5-[2-(methoxymethyl)-2'-methylbiphenyl-4-yl]-1,2,4-oxadiazol-3-yl}benzoate

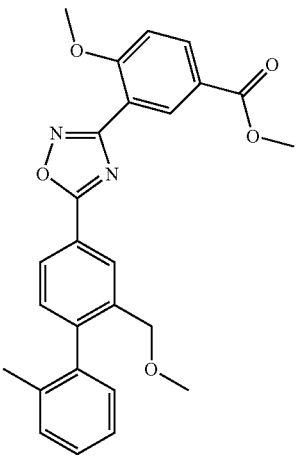

To a solution of Intermediate 28 (149.42 mg; 0.58 mmol) and n-ethyldiisopropylamine (198.29 μL; 1.17 mmol) in anhydrous DMF (2 mL) and cooled at 0° C., HATU (221.67 mg; 0.58 mmol) was added and the mixture stirred at RT for 10 min. After this time, Intermediate 53 (100 mg; 0.60 mmol) and DIEA (0.10 mL) in anhydrous DMF (1 mL) were added and the mixture was heated at 80° C. for 18 h. The reaction mixture was cooled to RT, partitioned between water and Et$_2$O, dried over MgSO$_4$, filtered and evaporated under vacuum. Product was adsorbed on silica and purified by flash chromatography (cHex/EtOAc from 9:1 to 8:2), which gave the title compound as a colorless oil. LC/MS (Method B): 445.2 (M+H)$^+$. HPLC (Method A) Rt 6.01 min (purity: 96.5%).

Example 107

4-methoxy-3-{5-[2-(methoxymethyl)-2'-methylbiphenyl-4-yl]-1,2,4-oxadiazol-3-yl}benzoic acid

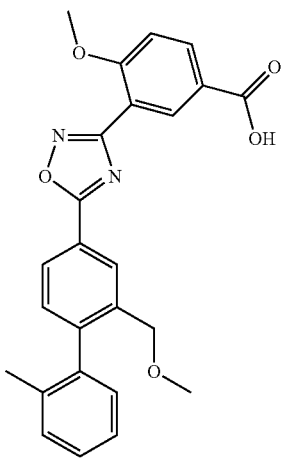

The title compound was obtained following procedure and work up described for example 4, step 2, but starting from methyl 4-methoxy-3-{5-[2-(methoxymethyl)-2'-methylbiphenyl-4-yl]-1,2,4-oxadiazol-3-yl}benzoate, obtained in example 106 (77 mg; 0.17 mmol). It was isolated as a white powder. $^1$H NMR (DMSO-$d_6$, 300 MHz) δ 13.02 (bs, 1H), 8.60 (m, 1H), 8.31 (m, 1H), 8.18-8.14 (m, 2H), 7.42-7.26 (m, 5H), 7.16-7.13 (m, 1H), 4.24-4.14 (m, 2H), 4.01 (s, 3H), 3.21 (s, 3H), 2.03 (s, 3H). LC/MS (Method B): 431.2 (M+H)$^+$. HPLC (Method A) Rt 4.80 min (purity: 97.2%).

Example 108

2-chloro-5-{5-[2-(methoxymethyl)-2'-methylbiphenyl-4-yl]-1,2,4-oxadiazol-3-yl}benzoic acid

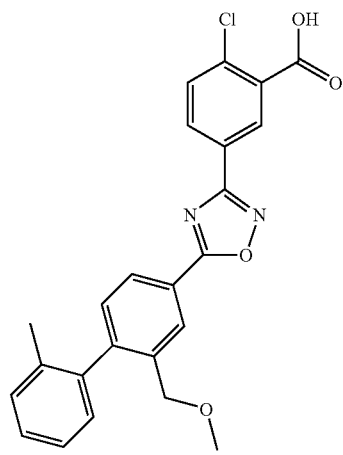

Step 1: methyl 2-chloro-5-{5-[2-(methoxymethyl)-2'-methylbiphenyl-4-yl]-1,2,4-oxadiazol-3-yl}benzoate The title compound was prepared following procedure described for example 4, step 1, but starting from Intermediate 28 (461.34 mg; 1.80 mmol) and Intermediate 54 (342.95 mg; 1.50 mmol). The reaction mixture was filtered through a SPE NH$_2$ column (10 g) and rinsed with ACN. The filtrate was passed through a SPE SCX column (10 g) and rinsed with ACN. After evaporation of the solvents, the crude product was purified by flash chromatography (c-hex/(DCM/EtOAc 1:1) gradient from 1:0 to 1:1), affording the title compound as a colorless oil. $^1$H NMR (CDCl$_3$, 300 MHz) δ 8.68 (d, J=2.1 Hz, 1H), 8.43 (d, J=1.1 Hz, 1H), 8.25 (dd, J=8.3, 2.1 Hz, 1H), 8.17 (dd, J=7.9, 1.7 Hz, 1H), 7.62 (d, J=8.4 Hz, 1H), 7.36-7.24 (m, 4H), 7.13 (d, J=7.2 Hz, 1H), 4.28-4.19 (m, 2H), 4 (s, 3H), 3.34 (s, 3H), 2.08 (s, 3H). LC/MS (Method B): 449.1 (M+H)$^+$. HPLC (Method A) Rt 6.10 min (Purity: 96.0%).

Step 2: 2-chloro-5-{5-[2-(methoxymethyl)-2'-methylbiphenyl-4-yl]-1,2,4-oxadiazol-3-yl}benzoic acid The title compound was prepared following procedure described for example 4, step 2, but starting from methyl 2-chloro-5-{5-[2-(methoxymethyl)-2'-methylbiphenyl-4-yl]-1,2,4-oxadiazol-3-yl}benzoate, obtained in step 1. Solvents were concentrated and water (15 mL) was added. It was filtrated to afford the title compound as a white solid (198 mg; 84%). $^1$H NMR (DMSO-$d_6$, 300 MHz) δ 13.81 (br s, 1H), 8.50 (s, 1H), 8.33 (s, 1H), 8.24 (d, J=8.3 Hz, 1H), 8.18 (d, J=7.6 Hz, 1H), 7.81 (d, J=7.7 Hz, 1H), 7.43 (d, J=7.6 Hz, 1H), 7.37-7.28 (m, 3H), 7.15 (d, J=7.2 Hz, 1H), 4.25-4.14 (m, 2H), 3.25 (s, 3H), 2.04 (s, 3H). LC/MS (Method B): 433.2 (M−H)$^−$, 435.1 (M+H)$^+$. HPLC (Method A) Rt 5.34 min (Purity: 97.4%).

Example 109

2-chloro-5-fluoro-4-{5-[2-(methoxymethyl)-2'-methylbiphenyl-4-yl]-1,2,4-oxadiazol-3-yl}benzoic acid

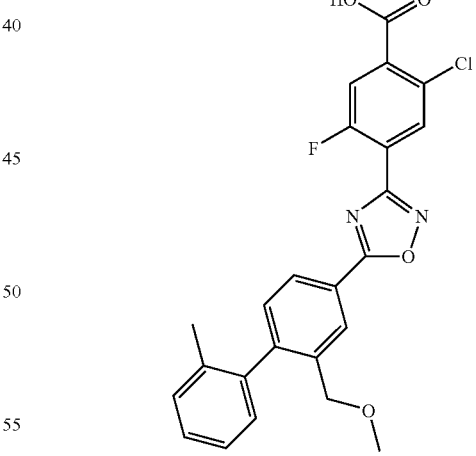

Step 1: methyl 2-chloro-5-fluoro-4-{5-[2-(methoxymethyl)-2'-methylbiphenyl-4-yl]-1,2,4-oxadiazol-3-yl}benzoate The title compound was prepared following procedure described for example 4, step 1, but starting from Intermediate 28 (230.67 mg; 0.90 mmol) and Intermediate 55 (184.97 mg; 0.75 mmol). The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/(DCM/EtOAc 1:1) gradient from 1:0 to 1:1). The white solid was washed with MeOH affording the title compound as a white powder. $^1$H NMR (CDCl$_3$, 300 MHz) δ 8.44-8.43 (m, 1H), 8.35 (d, J=6.1 Hz, 1H), 8.18 (dd, J=7.9, 1.8 Hz, 1H), 7.77 (d, J=10.1 Hz, 1H), 7.35 (d, J=7.9 Hz, 1H), 7.32-7.24 (m, 3H), 7.13 (d, J=7.2 Hz, 1H), 4.27-4.18 (m, 2H), 3.99 (s, 3H), 3.34 (s, 3H), 2.08 (s, 3H). LC/MS (Method B): 467.1 (M+H)$^+$. HPLC (Method A) Rt 6.09 min (Purity: 98.8%).

Step 2: 2-chloro-5-fluoro-4-{5-[2-(methoxymethyl)-2'-methylbiphenyl-4-yl]-1,2,4-oxadiazol-3-yl}benzoic acid The title compound was prepared following procedure described for example 4, step 2, but starting from methyl 2-fluoro-4-{5-[2'-methyl-2-(trifluoromethyl)biphenyl-4-yl]-1,2,4-oxadiazol-3-yl}benzoate, obtained in step 1. Solvents were concentrated and EtOAc (20 mL) was added. It was washed with HCl 1M and NaCl sat. solution. The organic extract was dried over magnesium sulfate, filtered and concentrated under vacuum to afford the title compound as a white powder (32 mg; 94%). $^1$H NMR (DMSO-d$_6$, 300 MHz) δ 14.05 (br s, 1H), 8.34 (s, 1H), 8.25 (d, J=6.1 Hz, 1H), 8.20 (d, J=8.0 Hz, 1H), 7.92 (d, J=10.2 Hz, 1H), 7.44 (d, J=7.9 Hz, 1H), 7.37-7.28 (m, 3H), 7.15 (d, J=7.0 Hz, 1H), 4.25-4.15 (m, 2H), 3.25 (s, 3H), 2.04 (s, 3H). LC/MS (Method B): 451.2 (M−H)$^-$, 453.1 (M+H)$^+$. HPLC (Method A) Rt 5.34 min (Purity: 97.9%).

Example 110 methyl 2-fluoro-4-{5-[4-isopropoxy-3-(methoxymethyl)phenyl]-1,2,4-oxadiazol-3-yl}benzoate

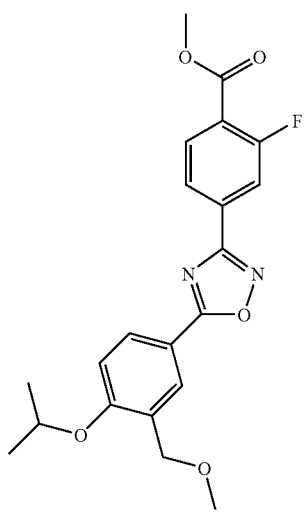

The title compound was prepared following procedure described for example 4, step 1, but starting from Intermediate 56 (201.83 mg; 0.90 mmol). The reaction mixture was filtrated through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/(DCM/EtOAc 1:1) gradient from 1:0 to 1:1) affording the title compound as a white powder. $^1$H NMR (CDCl$_3$) δ 8.25 (d, J=1.7 Hz, 1H), 8.11-7.95 (m, 4H), 6.99 (d, J=8.9 Hz, 1H), 4.71 (sept., J=6.0 Hz, 1H), 4.54 (s, 2H), 3.97 (s, 3H), 3.51 (s, 3H), 1.40 (d, J=6.0 Hz, 6H). LC/MS (Method B): 401.1 (M+H)$^+$. HPLC (Method A) Rt 5.53 min (Purity: 99.7%).

Example 111

2-fluoro-4-{5-[4-isopropoxy-3-(methoxymethyl)phenyl]-1,2,4-oxadiazol-3-yl}benzoic acid

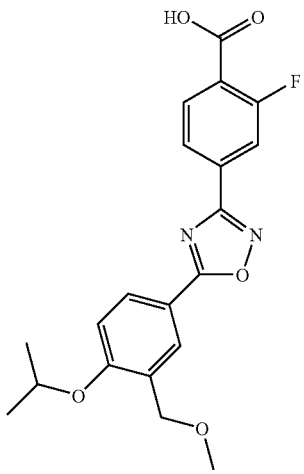

The title compound was prepared following procedure described for example 4, step 2, but starting from example 110. Solvents were concentrated and water (5 mL) was added. It was filtrated to afford the title compound as a white powder (84 mg; 88%). $^1$H NMR (DMSO-d$_6$, 300 MHz) δ 13.59 (br s, 1H), 8.12-8.06 (m, 3H), 8.01 (d, J=8.1 Hz, 1H), 7.92 (d, J=11.1 Hz, 1H), 7.29 (d, J=8.5 Hz, 1H), 4.87-4.79 (m, 1H), 4.47 (s, 2H), 3.42 (s, 3H), 1.34 (d, J=5.8 Hz, 6H). LC/MS (Method B): 385.2 (M−H)$^-$, 387.2 (M+H)$^+$. HPLC (Method A) Rt 4.76 min (Purity: 100.0%).

Example 112

2-fluoro-5-methoxy-4-{5-[2-(methoxymethyl)-2'-methylbiphenyl-4-yl]-1,2,4-oxadiazol-3-yl}benzoic acid

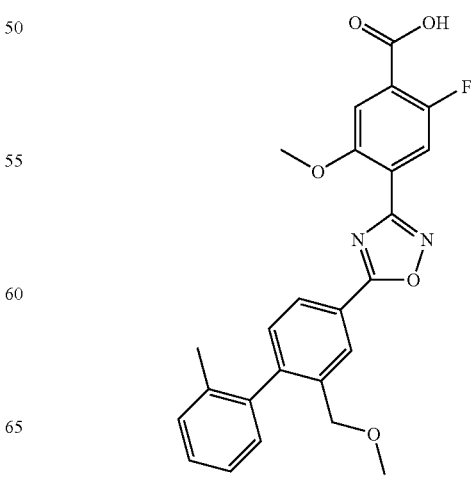

Step 1: methyl 2-fluoro-5-methoxy-4-{5-[2-(methoxymethyl)-2'-methylbiphenyl-4-yl]-1,2,4-oxadiazol-3-yl}benzoate The title compound was prepared following procedure described for example 4, step 1, but starting from Intermediate 28 (78.31 mg; 0.31 mmol) and Intermediate 57 (74 mg; 0.31 mmol). The reaction mixture was filtered through a SPE $NH_2$ column (2 g) and rinsed with ACN. The filtrate was passed through a SPE SCX column (2 g) and rinsed with ACN. After evaporation of the solvents, the crude product was purified by flash chromatography (c-hex/(DCM/EtOAc 1:1) gradient from 1:0 to 1:1). The white solid was washed with MeOH affording the title compound as an off-white powder. LC/MS (Method B): 463.2 $(M+H)^+$. HPLC (Method A) Rt 6.16 min (Purity: 97.9%).

Step 2: 2-fluoro-5-methoxy-4-{5-[2-(methoxymethyl)-2'-methylbiphenyl-4-yl]-1,2,4-oxadiazol-3-yl}benzoic acid The title compound was prepared following procedure described for example 4, step 2, but starting from methyl 2-fluoro-5-methoxy-4-{5-[2-(methoxymethyl)-2'-methylbiphenyl-4-yl]-1,2,4-oxadiazol-3-yl}benzoate, obtained in step 1. Solvents were concentrated and EtOAc (20 mL) was added. It was washed with HCl 1M and NaCl sat. solution. The organic extract was dried over magnesium sulfate, filtered and concentrated under vacuum to afford the title compound as a yellow solid. $^1$H NMR (DMSO-$d_6$, 300 MHz) δ 13.70 (br s, 1H), 8.31 (br s, 1H), 8.17 (dd, J=1.5, 8.0 Hz, 1H), 7.90 (d, J=10.6 Hz, 1H), 7.60 (d, J=6.1 Hz, 1H), 7.42 (d, J=8.0 Hz, 1H), 7.39-7.10 (m, 4H), 4.21 (d, J=12.8 Hz, 1H), 4.17 (d, J=12.8 Hz, 1H), 3.97 (s, 3H), 3.25 (s, 3H), 2.04 (s, 3H). LC/MS (Method B): 447.2 $(M-H)^-$, 449.2 $(M+H)^+$. HPLC (Method A) Rt 5.44 min (Purity: 97.5%).

Example 113 methyl 2-fluoro-4-{5-[3-(methoxymethyl)-4-(2-methylpiperidin-1-yl)phenyl]-1,2,4-oxadiazol-3-yl}benzoate

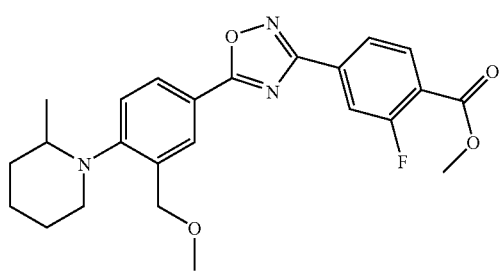

A solution of Intermediate 58 (325 mg, 1.24 mmol) and DIEA (0.42 mL, 2.48 mmol) was prepared in anhydrous DMF (5 mL) and cooled at 0° C. HATU (470 mg, 1.24 mmol) was added at once and the resulting mixture was stirred at 0° C. for 15 minutes. Intermediate 1 (250 mg, 1.18 mmol) was added at once. The resulting mixture was stirred at 0° C. for 1 hour, then at RT for 2 hours. The reaction mixture was diluted with $Et_2O$ (50 mL) and washed with water (2×30 mL) and brine (30 mL). The aqueous layers were extracted with $Et_2O$ (30 mL). The organic layers were combined, dried (MgSO$_4$) and the solvents were removed under reduced pressure. The residue was taken up with toluene (7.5 mL) and pyridine (2.5 mL). The resulting mixture was heated at 100° C. for 36 hours. The reaction mixture was cooled at RT, then diluted with $Et_2O$ (50 mL) and washed with water (2×25 mL) and brine (25 mL). The aqueous layers were extracted with $Et_2O$ (25 mL). The organic layers were combined, dried (MgSO$_4$) and the solvents were removed under reduced pressure. The residue was purified by flash chromatography on silica (heptane/EtOAc) to give the title compound as an off-white powder. $^1$H NMR (CDCl$_3$, 300 MHz): d=8.33 (d, J=2.1 Hz, 1H), 8.11-7.97 (m, 4H), 7.27 (d, J=8.4 Hz, 1H), 4.66 (d, J=12.5 Hz, 1H), 4.58 (d, J=12.5 Hz, 1H), 3.98 (s, 3H), 3.50 (s, 3H), 3.18 (m, 1H), 3.05 (m, 1H), 2.66 (m, 1H), 1.90-1.67 (m, 1H), 1.50 (m, 2H), 0.91 (d, J=6.3 Hz, 3H). LC/MS (Method A): 440.2 $(M+H)^+$. HPLC (Method A) Rt: 4.12 min (purity: 99.1%).

Example 114

2-fluoro-4-{5-[3-(methoxymethyl)-4-(2-methylpiperidin-1-yl)phenyl]-1,2,4-oxadiazol-3-yl}benzoic acid

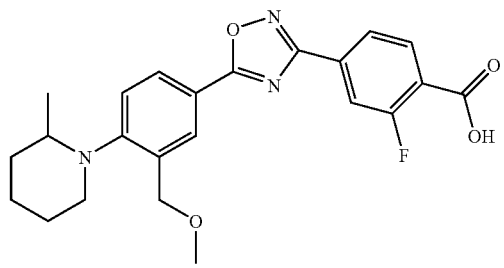

A 5N aqueous solution of NaOH (0.52 mL, 2.62 mmol) was added to a suspension of methyl 2-fluoro-4-{5-[3-(methoxymethyl)-4-(2-methylpiperidin-1-yl)phenyl]-1,2,4-oxadiazol-3-yl}benzoate (230 mg, 0.52 mmol, obtained in Example 113) in MeOH (5 mL). The resulting mixture was stirred at RT for 30 minutes. The reaction mixture was acidified with a 1N aqueous solution of HCl until pH=4 and diluted with water. The precipitate was filtered off, washed with water (3×) and dried under reduced pressure to give the title compound as a white powder. HPLC (Method A), Rt: 3.79 min (purity: 99.5%). LC/MS, M+(ESI): 426.2, M−(ESI): 424.3.

1HNMR (CDCl$_3$): d=8.34 (d, J=1.8 Hz, 1H), 8.19 (dd, J=7.8, 7.5 Hz, 1H), 8.11-8.01 (m, 3H), 7.27 (d, J=8.4 Hz, 1H), 4.68 (d, J=12.4 Hz, 1H), 4.60 (d, J=12.4 Hz, 1H), 3.51 (s, 3H), 3.19 (m, 1H), 3.05 (m, 1H), 2.66 (m, 1H), 1.89-1.71 (m, 4H), 1.50 (m, 2H), 0.91 (d, J=6.2 Hz, 3H).

Example 115

2-chloro-5-methoxy-4-{5-[2-(methoxymethyl)-2'-methylbiphenyl-4-yl]-1,2,4-oxadiazol-3-yl}benzoic acid

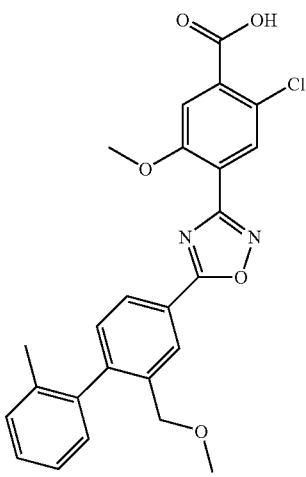

Step 1: methyl 2-chloro-5-methoxy-4-{5-[2-(methoxymethyl)-2'-methylbiphenyl-4-yl]-1,2,4-oxadiazol-3-yl}benzoate The title compound was prepared following procedure described for example 4, step 1, but starting from Intermediate 28 (99.09 mg; 0.39 mmol) and Intermediate 59 (100 mg; 0.39 mmol). The reaction mixture was filtered through a SPE NH$_2$ column (2 g) and rinsed with ACN. The filtrate was passed through a SPE SCX column (2 g) and rinsed with ACN. After evaporation of the solvents, the crude product was purified by flash chromatography (c-hex/(DCM/EtOAc 1:1) gradient from 1:0 to 1:1). The white solid was washed with MeOH affording the title compound as an off-white powder. LC/MS (Method B): 479.2 (M+H)$^+$. HPLC (Method A) Rt 5.86 min (Purity: 98.1%).

Step 2: 2-chloro-5-methoxy-4-{5-[2-(methoxymethyl)-2'-methylbiphenyl-4-yl]-1,2,4-oxadiazol-3-yl}benzoic acid The title compound was prepared following procedure described for example 4, step 2, but starting from methyl 2-chloro-5-methoxy-4-{5-[2-(methoxymethyl)-2'-methylbiphenyl-4-yl]-1,2,4-oxadiazol-3-yl}benzoate, obtained in step 1, (64 mg; 0.13 mmol). Solvents were concentrated and EtOAc (20 mL) was added. It was washed with HCl 1M and NaCl sat. solution. The organic extract was dried over magnesium sulfate, filtered and concentrated under vacuum to afford the title compound as an off-white solid (45.1 mg; 75%). $^1$H NMR (DMSO-d$_6$, 300 MHz) δ 13.82 (br s, 1H), 8.31 (m, 1H), 8.21-8.14 (m, 1H), 8.10 (s, 1H), 7.60 (s, 1H), 7.42 (d, J=8.0 Hz, 1H), 7.40-7.11 (m, 4H), 4.21 (d, J=12.7 Hz, 1H), 4.17 (d, J=12.7 Hz, 1H), 3.98 (s, 3H), 3.25 (s, 3H), 2.03 (s, 3H). LC/MS (Method B): 463.2 (M–H)$^-$, 465.2 (M+H)$^+$. HPLC (Method A) Rt 5.6 min (Purity: 96.6%).

Example 116 methyl N-(2-fluoro-4-{5-[2-(methoxymethyl)-2'-methylbiphenyl-4-yl]-1,2,4-oxadiazol-3-yl}benzoyl)-N-methylglycinate

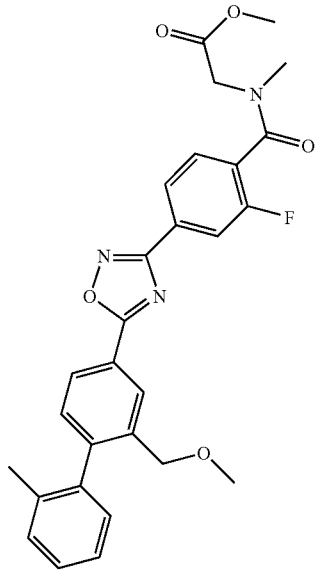

To a solution of example 35 (2 170 mg; 5.2 mmol) in dry DCM (40 mL), oxalyl chloride (1 316 μl; 15.6 mmol) was added followed by dry DMF (40 μl). The reaction mixture was stirred at RT for 2 h and concentrated to afford 2-fluoro-4-{5-[2-(methoxymethyl)-2'-methylbiphenyl-4-yl]-1,2,4-oxadiazol-3-yl}benzoyl chloride as a white powder (2300 mg, 100%). In dry THF (1 mL) with a catalytic amount of DMF was swelled morpholinomethyl polystyrene high loading resin (NovaBiochem; 35.77 mg; 0.14 mmol), 3.9 mmol/g). 2-Fluoro-4-{5-[2-(methoxymethyl)-2'-methylbiphenyl-4-yl]-1,2,4-oxadiazol-3-yl}benzoyl chloride (25 mg; 0.06 mmol) was added followed by sarcosine methyl ester hydrochloride (15.98 mg; 0.11 mmol). The mixture was stirred overnight at rt. Isocyanate resin Si—NCO (Argonaut, 97 mg; 1.5 eq; 1.7 mmol/g) was added and the mixture stirred for 2 h. It was filtered through a SAX column (2 g) to obtain the title compound as a colorless oil. LC/MS (Method B): 504.2 (M+H)+ HPLC (Method A) Rt: 5.39 min (purity: 97%).

Example 117

Methyl N-(2-fluoro-4-{5-[2-(methoxymethyl)-2'-methylbiphenyl-4-yl]-1,2,4-oxadiazol-3-yl}benzoyl)-beta-alaninate

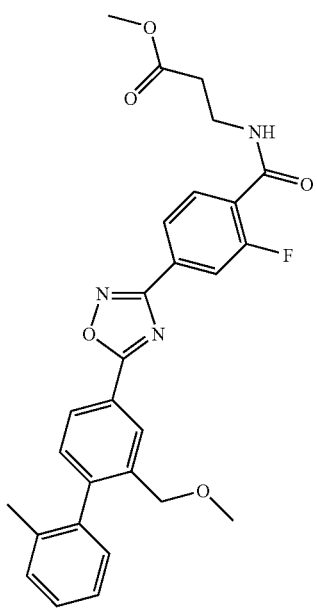

The title compound was prepared following procedure described in example 116, starting from beta-alanine methyl ester hydrochloride. The title compound was obtained as a yellow oil. LC/MS (Method B): 504.2 (M+H)+ 502.3 (M–H)–. HPLC (Method A) Rt: 5.14 min (purity: 85.4%).

Example 118

Ethyl 1-[(2-fluoro-4-{5-[2-(methoxymethyl)-2'-methylbiphenyl-4-yl]-1,2,4-oxadiazol-3-yl}benzoyl)amino]cyclopropanecarboxylate

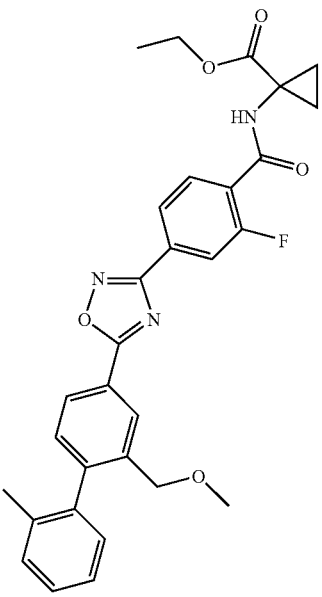

The title compound was prepared following procedure described in example 116, starting from 1-aminocyclopropane-1-carboxylic acid ethyl ester hydrochloride and the compound was purified by flash chromatography (EtOAc/cHex). The title compound was obtained as a white foam. ¹H NMR: (CDCl₃, 300 MHz) δ 8.42 (m, 1H), 8.25 (t, 1H, J=7.9 Hz), 8.16 (dd, J=1.9, 7.9 Hz, 1H), 8.10 (dd, J=1.5, 8.2 Hz, 1H), 7.98 (dd, J=1.4, 12.5 Hz, 1H), 7.38-7.22 (m, 5H), 7.12 (d, J=7.3 Hz, 1H), 4.22 (m, 2H), 4.18 (q, J=7.1 Hz, 2H), 3.33 (s, 3H), 2.04 (s, 3H), 1.70 (m, 2H), 1.31 (m, 2H), 1.24 (t, J=7.1 Hz, 3H). LC/MS (Method B): 530.2 (M+H)+ 528.3 (M–H)– HPLC (Method A) Rt: 5.37 min (purity: 95.9%).

Example 119

N-(2-fluoro-4-{5-[2-(methoxymethyl)-2'-methylbiphenyl-4-yl]-1,2,4-oxadiazol-3-yl}benzoyl)-beta-alanine

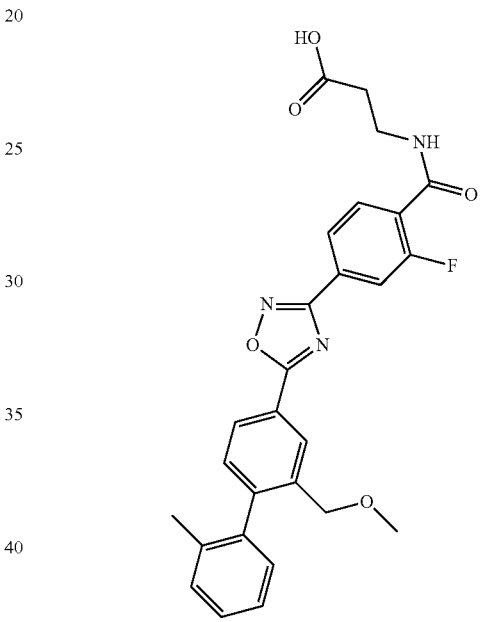

To a solution of example 117 (1 860 mg; 3.69 mmol) in MeOH (40 mL), sodium hydroxide (3.69 mL; 5 M; 18.5 mmol) in H₂O was added. The reaction was stirred at RT for 1 h. EtOAc was added and the organic phase washed 3 times with HCl 1M. The organic phase was dried over MgSO₄, filtered off and concentrated to afford the title compound as a white powder (1490.0 mg, 82%). ¹H NMR: (DMSO-d₆, 300 MHz) δ 8.58 (m, 1H), 8.33 (brs, 1H), 8.18 (dd, J=1.7 Hz, 8 Hz, 1H), 8.03 (dd, J=1.7 Hz, 8 Hz, 1H), 7.95 (d, J=10.6 Hz, 1H), 7.84 (t, J=7.6 Hz, 1H), 7.44 (d, J=7.9 Hz, 1H), 7.40-7.22 (m, 3H), 7.15 (m, 1H), 4.23 (d, J=12.9 Hz, 1H), 4.17 (d, J=12.9 Hz, 1H), 3.49 (m, 2H), 3.25 (s, 3H), 2.53 (m, 2H), 2.04 (s, 3H). LC/MS (Method B): 490.3 (M+H)+ 488.4 (M–H)–. HPLC (Method A) Rt: 4.83 min (purity: 99.7%).

Example 120

1-[(2-fluoro-4-{5-[2-(methoxymethyl)-2'-methylbiphenyl-4-yl]-1,2,4-oxadiazol-3-yl}benzoyl)amino]cyclopropanecarboxylic acid

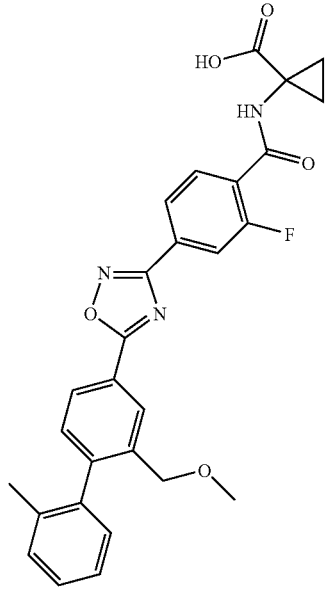

The title compound was prepared following procedure described in example 119 starting from example 118. The title compound was obtained as a white powder (16 mg, 70%). $^1$H NMR: (DMSO-d$_6$, 300 MHz) δ 12.50 (brs, 1H), 9.06 (brs, 1H), 8.33 (m, 1H), 8.18 (dd, J=1.9, 8 Hz, 1H), 8.04 (dd, J=1.5, 8 Hz, 1H), 7.95 (dd, J=1.5, 10.4 Hz, 1H), 7.82 (t, J=7.8 Hz, 1H), 7.43 (d, J=8 Hz, 1H), 7.38-7.25 (m, 3H), 7.15 (m, 1H), 4.23 (d, J=12.9 Hz, 1H), 4.17 (d, J=12.9 Hz, 1H), 3.25 (s, 3H), 2.04 (s, 3H), 1.43 (m, 2H), 1.14 (m, 2H). LC/MS (Method B): 502.2 (M+H)$^+$ 500.3 (M−H)$^-$. HPLC (Method A) Rt: 4.74 min (purity: 93.2%).

Example 121

Ethyl 3-[(2-fluoro-4-{5-[2-(methoxymethyl)-2'-methylbiphenyl-4-yl]-1,2,4-oxadiazol-3-yl}benzoyl)amino]butanoate

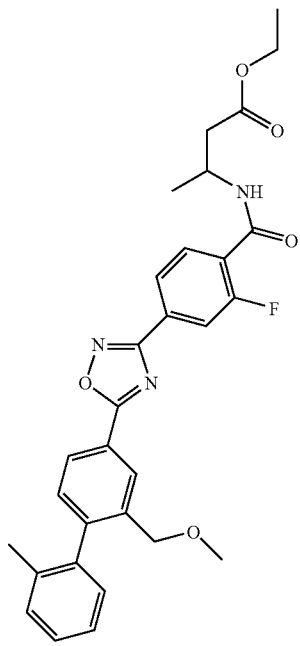

To a solution of 2-fluoro-4-{5-[2-(methoxymethyl)-2'-methylbiphenyl-4-yl]-1,2,4-oxadiazol-3-yl}benzoyl chloride, prepared as in example 116 (75 mg; 0.17 mmol) in dry THF, DIEA (103 µl; 0.60 mmol) was added followed by ethyl-3-aminobutyrate (45 mg; 0.34 mmol) and the reaction mixture stirred for 2 h30 at RT. The solvent was then removed under vacuum and the crude material purified by flash chromatography (EtOAc/cHex) to afford the title compound as a colorless oil (82 mg, 89%). $^1$H NMR: (CDCl$_3$, 300 MHz) δ 8.42 (m, 1H), 8.23 (t, J=8 Hz, 1H), 8.16 (dd, J=1.9, 8 Hz. 1H), 8.09 (dd, J=1.5, 8.1 Hz, 1H), 7.96 (dd, J=1.3, 12.4 Hz, 1H), 7.47 (m, 1H), 7.38-7.22 (m, 5H), 7.12 (m, 1H), 4.62 (m, 1H), 4.21 (m, 2H), 4.19 (q, J=7.1 Hz, 2H), 3.33 (s, 3H), 2.65 (m, 2H), 2.07 (s, 3H), 1.37 (d, J=6.8 Hz, 3H), 1.28 (t, J=7.1 Hz, 3H). UPLC/MS: 532.3 (M+H)$^+$ 530.3 (M−H)$^-$. HPLC (Method A) Rt: 5.52 min (purity: 98.5%).

Example 122

Methyl N-(2-fluoro-4-{5-[2-(methoxymethyl)-2'-methylbiphenyl-4-yl]-1,2,4-oxadiazol-3-yl}benzoyl)glycinate

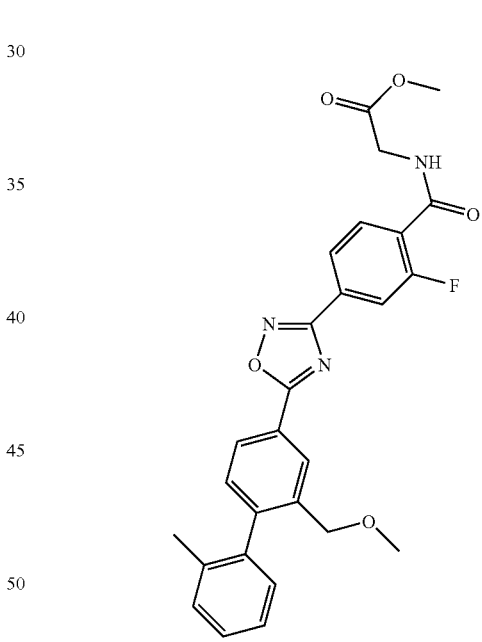

The title compound was prepared following procedure described in example 121 starting from glycine methyl ester hydrochloride. The title compound was obtained as an orange solid. $^1$H NMR: (CDCl$_3$, 300 MHz) δ 8.42 (m, 1H), 8.25 (t, J=8 Hz, 1H), 8.16 (dd, J=1.9 Hz, 7.9 Hz, 1H), 8.11 (dd, J=1.5, 7.9 Hz, 1H), 8.01 (dd, J=1.4, 12.4 Hz, 1H), 7.39-7.22 (m, 5H), 7.12 (m, 1H), 4.30 (d, J=4.8 Hz, 2H), 4.22 (d, J=2 Hz, 2H), 3.81 (s, 3H), 3.33 (s, 3H), 2.07 (s, 3H), 1.37 (d, J=6.8 Hz, 3H), 1.28 (t, J=7.1 Hz, 3H). LC/MS (Method B): 490.2 (M+H)$^+$ 488.3 (M−H)$^-$. HPLC (Method A) Rt: 5.22 min (purity: 100%).

Example 123

3-[(2-fluoro-4-{5-[2-(methoxymethyl)-2'-methylbiphenyl-4-yl]-1,2,4-oxadiazol-3-yl}benzoyl)amino]butanoic acid

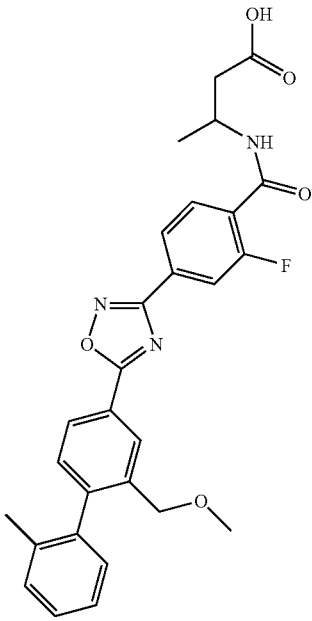

The title compound was prepared following procedure described in example 119 starting from example 121. The title compound was obtained as a white powder. $^1$H NMR: (CDCl$_3$, 300 MHz) δ 8.42 (m, 1H), 8.24 (t, J=8 Hz, 1H), 8.16 (dd, J=1.6, 7.9 Hz, 1H), 8.10 (dd, J=1.5 Hz, 8.2 Hz, 1H), 7.99 (m, 1H), 7.42-7.22 (m, 5H), 7.13 (m, 1H), 4.65 (m, 1H), 4.22 (m, 2H), 3.33 (s, 3H), 2.76 (d, J=5.1 Hz, 2H), 2.07 (s, 3H), 1.43 (d, J=7 Hz, 3H). LC/MS (Method B): 504.2 (M+H)$^+$ 502.3 (M−H)$^−$. HPLC (Method A) Rt: 4.77 min (purity: 97.4%).

Example 124

N-(2-fluoro-4-{5-[2-(methoxymethyl)-2'-methylbiphenyl-4-yl]-1,2,4-oxadiazol-3-yl}benzoyl)glycine

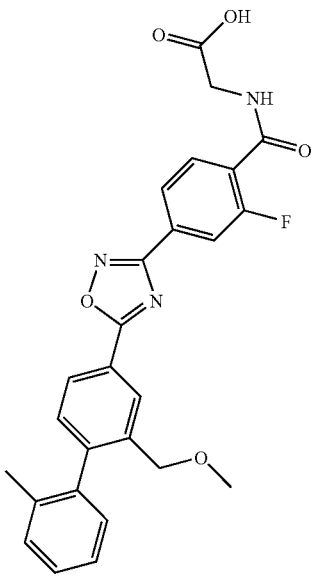

The title compound was prepared following procedure described in example 119 starting from example 122. The title compound was obtained as a white solid. $^1$H NMR: (DMSO-d$_6$, 300 MHz) δ (m, 1H), 8.34 (m, 1H), 8.19 (dd, J=1.9 Hz, 8 Hz, 1H), 8.07 (dd, J=1.5 Hz, 8 Hz, 1H), 7.98 (dd, J=1.5 Hz, 11 Hz, 1H), 7.91 (t, J=7.7 Hz, 1H), 7.44 (d, J=8 Hz, 1H), 7.39-7.24 (m, 3H), 7.15 (m, 1H), 4.23 (d, J=12.9 Hz, 1H), 4.17 (d, J=12.9 Hz, 1H), 3.96 (d, J=6 Hz, 2H), 3.26 (s, 3H), 2.04 (s, 3H). LC/MS (Method B): 476.1 (M+H)$^+$ 474.3 (M−H)$^−$. HPLC (Method A) Rt: 4.63 min (purity: 99.9%).

Example 125

N-(2-fluoro-4-{5-[2-(methoxymethyl)-2'-methylbiphenyl-4-yl]-1,2,4-oxadiazol-3-yl}benzoyl)-N-methylglycine

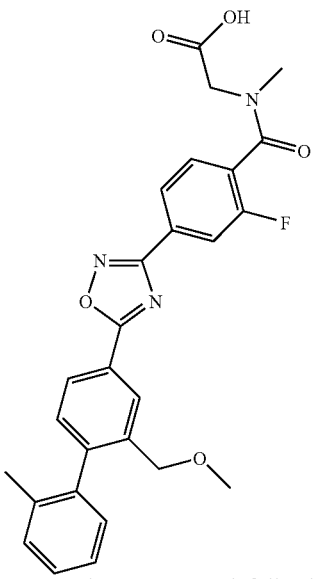

The title compound was prepared following procedure described in example 119 starting from example 116. The title compound was obtained as a white foam. $^1$H NMR: (DMSO-d$_6$, 300 MHz) δ 8.33 (m, 1H), 8.19 (m, 1H), 8.10-7.92 (m, 2H), 7.68-7.50 (m, 1H), 7.43 (d, J=8 Hz, 1H), 7.39-7.24 (m, 3H), 7.15 (m, 1H), 4.26-3.95 (m, 4H), 3.25 (s, 3H), 3.06 (s, 1H), 2.90 (s, 2H), 2.04 (s, 3H). LC/MS (Method B): 490.2 (M+H)$^+$ 488.2 (M−H)$^−$. HPLC (Method A) Rt: 4.69 min (purity: 96.8%).

Example 126

Methyl 4-[(2-fluoro-4-{5-[2-(methoxymethyl)-2'-methylbiphenyl-4-yl]-1,2,4-oxadiazol-3-yl}benzoyl)amino]butanoate

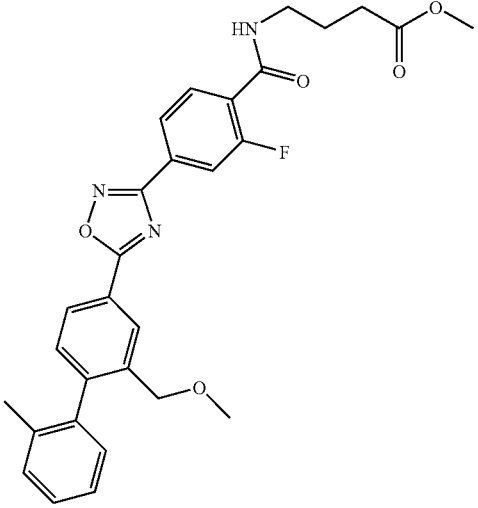

The title compound was prepared following procedure described in example 121 starting from methyl 4-aminobutyrate hydrochloride. The title compound was obtained as a colorless oil. $^1$H NMR: (CDCl$_3$, 300 MHz) δ 8.42 (brs, 1H), 8.23 (t, J=7.9 Hz, 1H), 8.16 (dd, J=1.7, 7.9 Hz, 1H), 8.09 (dd, J=1.3 Hz, 8.1 Hz, 1H), 7.98 (dd, J=1.30 Hz, 12.4 Hz, 1H), 7.36-7.22 (m, 5H), 7.12 (m, 1H), 6.92 (m, 1H), 4.22 (m, 2H), 3.68 (s, 3H), 3.56 (m, 2H), 3.33 (s, 3H), 2.45 (t, 2H, J=7.1 Hz), 2.07 (s, 3H), 1.99 (m, 2H). LC/MS (Method B): 518.2 (M+H)$^+$ 516.2 (M−H)$^−$. HPLC (Method A) Rt: 5.2 min (purity: 99.1%).

Example 127

4-[(2-fluoro-4-{5-[2-(methoxymethyl)-2'-methylbiphenyl-4-yl]-1,2,4-oxadiazol-3-yl}benzoyl)amino]butanoic acid

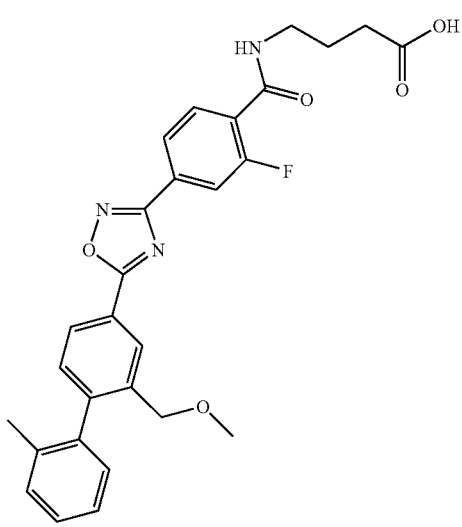

The title compound was prepared following procedure described in example 119 starting from example 126. The title compound was obtained as a white solid. $^1$H NMR: (DMSO-d$_6$, 300 MHz) δ 12.10 (brs, 1H), 8.57 (m, 1H), 8.33 (brs, 1H), 8.19 (dd, J=1.8 Hz, 7.9 Hz, 1H), 8.03 (dd, J=1.5 Hz, 7.9 Hz, 1H), 7.95 (dd, J=1.3 Hz, 10.5 Hz, 1H), 7.82 (t, J=7.5 Hz, 1H), 7.43 (d, J=7.9 Hz, 1H), 7.39-7.24 (m, 3H), 7.15 (m, 1H), 4.23 (d, J=12.9 Hz, 1H), 4.17 (d, J=12.9 Hz, 1J), 3.30 (m, 2H), 3.25 (s, 3H), 3.21 (m, 2H), 2.31 (t, J=7.3 Hz, 2H), 2.04 (s, 3H), 1.77 (q, J=7.3 Hz, 2H). LC/MS (Method B): 504.2 (M+H)$^+$ 502.3 (M−H)$^−$. HPLC (Method A) Rt: 4.8 min (purity: 99%).

Example 128

Methyl N-(2-fluoro-4-{5-[2-(methoxymethyl)-2'-methylbiphenyl-4-yl]-1,2,4-oxadiazol-3-yl}benzoyl)-2-methylalaninate

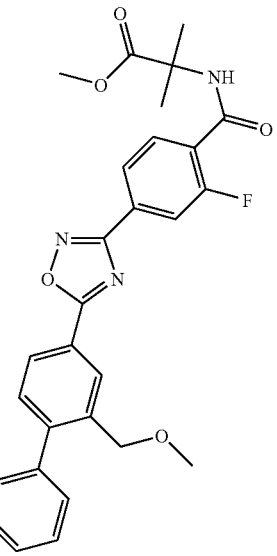

The title compound was prepared following procedure described in example 121 starting from alpha-aminoisobutyric acid methyl ester hydrochloride. The title compound was obtained as a white foam (97 mg, 81%). $^1$H NMR: (DMSO-d$_6$, 300 MHz) δ 8.89 (brs, 1H), 8.33 (brs, 1H), 8.18 (dd, J=1.8 Hz, 7.9 Hz, 1H), 8.04 (dd, J=1.5 Hz, 7.9 Hz, 1H), 7.95 (dd, J=1.5 Hz, 10.3 Hz, 1H), 7.70 (t, J=7.6 Hz, 1H), 7.44 (d, J=7.9 Hz, 1H), 7.38-7.26 (m, 3H), 7.15 (m, 1H), 4.23 (d, J=12.9 Hz, 1H), 4.17 (d, J=12.9 Hz, 1H), 3.65 (s, 3H), 3.25 (s, 3H), 2.04 (s, 3H), 1.48 (s, 6H). LC/MS (Method B): 518.2 (M+H)$^+$ 516.3 (M−H)$^−$. HPLC (Method A) Rt: 5.64 min (purity: 99.7%).

Example 129

N-(2-fluoro-4-{5-[2-(methoxymethyl)-2'-methylbiphenyl-4-yl]-1,2,4-oxadiazol-3-yl}benzoyl)-2-methylalanine

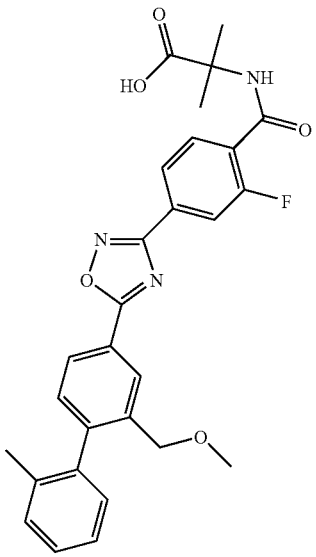

The title compound was prepared following procedure described in example 119 starting from example 128. The title compound was obtained as a white powder (22 mg, 70%). ¹H NMR: (DMSO-d₆, 300 MHz) δ 12.43 (brs, 1H), 8.34 (brs, 1H), 8.19 (m, 1H), 8.03 (m, 1H), 7.94 (m, 1H), 7.79 (m, 1H), 7.44 (m, 1H), 7.39-7.24 (m, 3H), 7.15 (m, 1H), 4.23 (d, J=12.9 Hz, 1H), 4.17 (d, J=12.9 Hz, 1H), 3.26 (s, 3H), 2.04 (s, 3H), 1.48 (s, 6H). LC/MS (Method B): 504.2 (M+H)⁺ 502.3 (M−H)⁻. HPLC (Method A) Rt: 5.08 min (purity: 98.4%).

Example 130

Methyl N-(3-{5-[2-(methoxymethyl)-2'-methylbiphenyl-4-yl]-1,2,4-oxadiazol-3-yl}benzoyl)glycinate

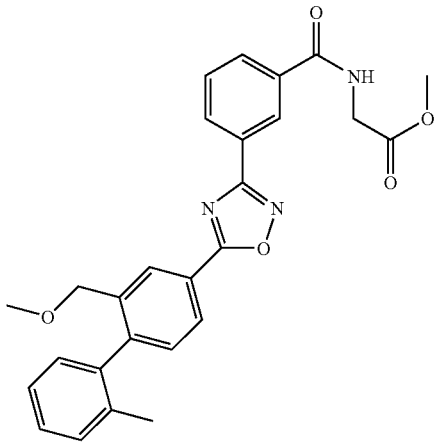

3-{5-[2-(methoxymethyl)-2'-methylbiphenyl-4-yl]-1,2,4-oxadiazol-3-yl}benzoyl chloride was prepared following procedure described in example 116 starting from example 92. It was obtained as an oil (1070 mg, 96%). The title compound was prepared following procedure described in example 121 starting from 3-{5-[2-(methoxymethyl)-2'-methylbiphenyl-4-yl]-1,2,4-oxadiazol-3-yl}benzoyl chloride and glycine methyl ester hydrochloride. The title compound was obtained as a pale yellow powder (97 mg, 86%). ¹H NMR: (DMSO-d₆, 300 MHz) δ 9.27 (m, 1H), 8.63 (m, 1H), 8.35 (m, 1H), 8.31 (m, 1H), 8.19 (dd, J=1.8 Hz, 7.9 Hz, 1H), 8.12 (m, 1H), 7.76 (t, J=7.9 Hz, 1H), 7.43 (d, J=7.9 Hz, 1H), 7.39-7.26 (m, 3H), 7.15 (m, 1H), 4.23 (d, J=12.9 Hz, 1H), 4.17 (d, J=12.9 Hz, 1H), 4.07 (d, J=5.8 Hz, 1H), 3.68 (s, 3H), 3.25 (s, 3H), 2.04 (s, 3H). LC/MS (Method B): 472.2 (M+H)⁺ 470.2 (M−H)⁻. HPLC (Method A) Rt: 4.92 min (purity: 99.2%).

Example 131

Ethyl 1-[(3-{5-[2-(methoxymethyl)-2'-methylbiphenyl-4-yl]-1,2,4-oxadiazol-3-yl}benzoyl)amino]cyclopropanecarboxylate

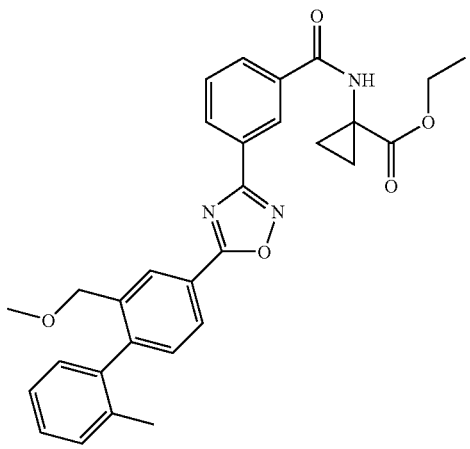

The title compound was prepared following procedure described in Example 121 starting from 3-{5-[2-(methoxymethyl)-2'-methylbiphenyl-4-yl]-1,2,4-oxadiazol-3-yl}benzoyl chloride, prepared as in example 130, and 1-aminocyclopropane-1-carboxylic acid ethyl ester hydrochloride. The title compound was obtained as a white foam (120 mg, 98%). ¹H NMR: (DMSO-d₆, 300 MHz) δ 9.35 (m, 1H), 8.60 (m, 1H), 8.35 (m, 1H), 8.29 (m, 1H), 8.19 (m, 1H), 8.09 (m, 1H), 7.77 (t, J=7.8 Hz, 1H), 7.43 (d, J=7.9 Hz, 1H), 7.39-7.26 (m, 3H), 7.15 (m, 1H), 4.23 (d, J=12.9 Hz, 1H), 4.17 (d, J=12.9 Hz, 1H), 4.08 (q, J=7.1 Hz, 2H), 3.25 (s, 3H), 2.04 (s, 3H), 1.47 (m, 2H), 1.21 (m, 1H), 1.15 (t, J=7.1 Hz, 3H). LC/MS (Method B): 512.2 (M+H)⁺ 510.3 (M−H)⁻. HPLC (Method A) Rt: 5.27 min (purity: 99%).

Example 132

Methyl N-(3-{5-[2-(methoxymethyl)-2'-methylbiphenyl-4-yl]-1,2,4-oxadiazol-3-yl}benzoyl)-beta-alaninate

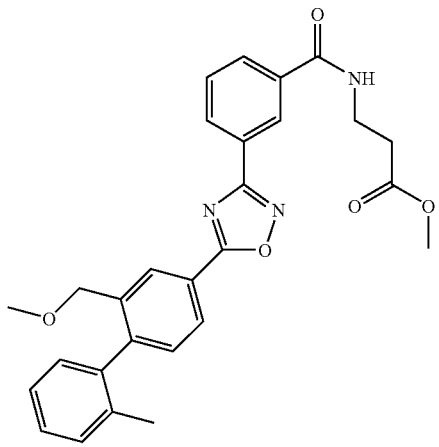

The title compound was prepared following procedure described in example 121 starting from 3-{5-[2-(methoxymethyl)-2'-methylbiphenyl-4-yl]-1,2,4-oxadiazol-3-yl}benzoyl chloride, prepared as in example 130, and beta-alanine methyl ester hydrochloride. The title compound was obtained as a white foam. ¹H NMR: (DMSO-d₆, 300 MHz) δ 8.87 (m, 1H), 8.58 (m, 1H), 8.35 (m, 1H), 8.27 (m, 1H), 8.19 (dd, J=1.9 Hz, 7.9 Hz, 1H), 8.07 (m, 1H), 7.72 (t, J=7.9 Hz, 1H), 7.43 (d, J=7.9 Hz, 1H), 7.38-7.25 (m, 3H), 7.15 (m, 1H), 4.23 (d, J=12.9 Hz, 1H), 4.17 (d, J=12.9 Hz, 1H), 3.63 (s, 3H), 3.54 (m, 1H), 3.25 (s, 3H), 3.64 (t, J=6.9 Hz, 2H), 2.04 (s, 3H).

LC/MS (Method B): 486.2 (M+H)+ 484.2 (M–H)−. HPLC (Method A) Rt: 5 min (purity: 99.3%).

Example 133

1-[(3-{5-[2-(methoxymethyl)-2'-methylbiphenyl-4-yl]-1,2,4-oxadiazol-3-yl}benzoyl)amino]cyclopropanecarboxylic acid

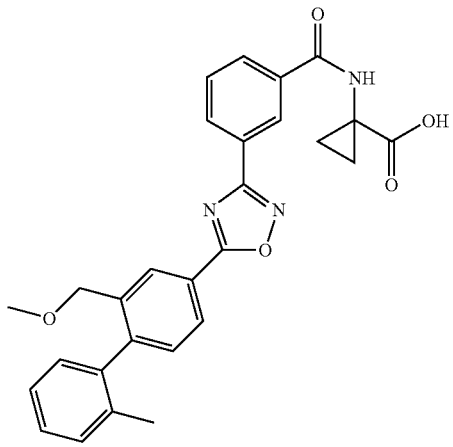

The title compound was prepared following procedure described in example 119 starting from example 131. The title compound was obtained as a white foam (56 mg, 89%). 1H NMR: (DMSO-d6, 300 MHz) δ 9.28 (brs, 1H), 8.60 (m, 1H), 8.35 (m, 1H), 8.28 (dd, J=1.3 Hz, 7.9 Hz, 1H), 8.19 (dd, J=1.8 Hz, 7.9 Hz, 1H), 8.09 (dd, J=1.2 Hz, 7.9 Hz, 1H), 7.72 (t, J=7.9 Hz, 1H), 7.43 (d, J=7.9 Hz, 1H), 7.38-7.25 (m, 3H), 7.15 (m, 1H), 4.23 (d, J=12.9 Hz, 1H), 4.17 (d, J=12.9 Hz, 1H), 3.26 (s, 3H), 2.04 (s, 3H), 1.99 (s, 1H), 1.91 (s, 1H), 1.44 (m, 2H), 1.17 (m, 2H). LC/MS (Method B): 484.2 (M+H)+ 482.2 (M–H)−. HPLC (Method A) Rt: 4.36 min (purity: 94.3%).

Example 134

N-(3-{5-[2-(methoxymethyl)-2'-methylbiphenyl-4-yl]-1,2,4-oxadiazol-3-yl}benzoyl)glycine

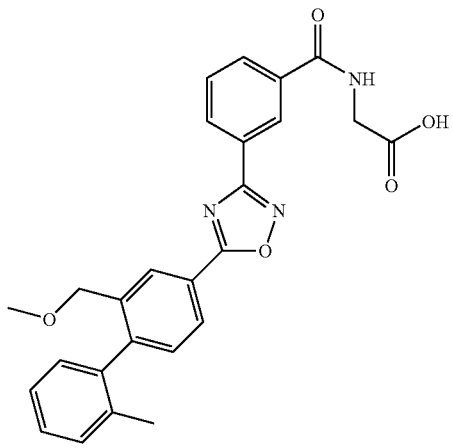

The title compound was prepared following procedure described in example 119 starting from example 130. The title compound was obtained as a white foam. 1H NMR: (DMSO-d6, 300 MHz) δ 12.68 (brs, 1H), 9.15 (m, 1H), 8.63 (brs, 1H), 8.35 (brs, 1H), 8.30 (d, J=7.8 Hz, 1H), 8.19 (d, J=7.8 Hz, 1H), 8.12 (d, J=7.8 Hz, 1H), 7.75 (t, J=7.8 Hz, 1H), 7.43 (d, J=7.8 Hz, 1H), 7.38-7.25 (m, 3H), 7.15 (m, 1H), 4.23 (d, J=12.9 Hz, 1H), 4.17 (d, J=12.9 Hz, 1H), 3.98 (m, 2H), 3.26 (s, 3H), 2.04 (s, 3H). LC/MS (Method B): 458.2 (M+H)+ 456.2 (M–H)−. HPLC (Method A) Rt: 5.08 min (purity: 95.3%).

Example 135

N-(3-{5-[2-(methoxymethyl)-2'-methylbiphenyl-4-yl]-1,2,4-oxadiazol-3-yl}benzoyl)-beta-alanine

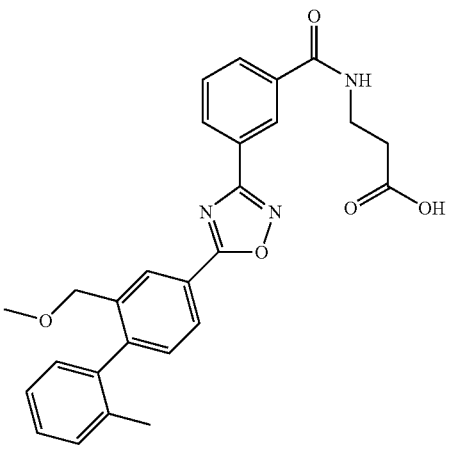

The title compound was prepared following procedure described in example 119 starting from example 132. The title compound was obtained as a white powder. 1H NMR: (DMSO-d6, 300 MHz) δ 12.28 (brs, 1H), 8.86 (m, 1H), 8.59 (brs, 1H), 8.36 (brs, 1H), 8.27 (d, J=7.9 Hz, 1H), 8.19 (d, J=7.9 Hz, 1H), 8.09 (d, J=7.9 Hz, 1H), 7.72 (t, J=7.9 Hz, 1H), 7.44 (d, J=7.9 Hz, 1H), 7.40-7.25 (m, 3H), 7.15 (m, 1H), 4.23 (d, J=12.9 Hz, 1H), 4.17 (d, J=12.9 Hz, 1H), 3.52 (m, 2H), 3.20 (s, 3H), 2.56 (t, J=7.5 Hz, 1H), 2.04 (s, 3H). LC/MS (Method B): 472.2 (M+H)+ 470.3 (M–H)−. HPLC (Method A) Rt: 5.09 min (purity: 97.4%).

Example 136

Methyl N-(3-{5-[2-(methoxymethyl)-2'-methylbiphenyl-4-yl]-1,2,4-oxadiazol-3-yl}benzoyl)-N-methylglycinate

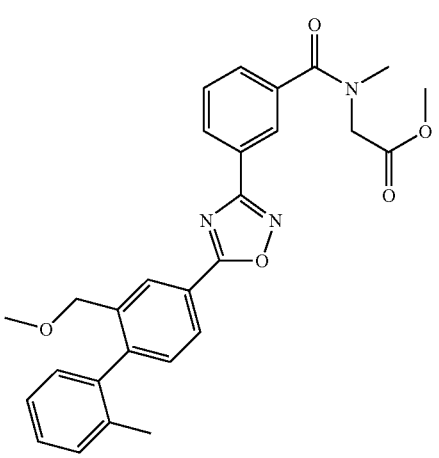

The title compound was prepared following procedure described in example 121 starting from 3-{5-[2-(methoxymethyl)-2'-methylbiphenyl-4-yl]-1,2,4-oxadiazol-3-yl}benzoyl chloride, prepared as in example 130, and sarcosine methyl ester hydrochloride. The title compound was obtained as a sticky solid. $^1$H NMR: (DMSO-d$_6$, 300 MHz) δ 8.42 (brs, 1H), 8.28 (m, 2H), 8.17 (m, 1H), 7.61 (m, 2H), 7.34-7.22 (m, 4H), 7.12 (m, 1H), 4.32 (s, 1H), 4.22 (s, 1H), 3.80 (m, 3H), 3.32 (s, 3H), 3.1 (m, 3H). LC/MS (Method B): 486.2 (M+H)$^+$ no (M−H)$^−$. HPLC (Method A) Rt: 5.66 min (purity: 98.5%).

Example 137

Methyl 4-[(3-{5-[2-(methoxymethyl)-2'-methylbiphenyl-4-yl]-1,2,4-oxadiazol-3-yl}benzoyl)amino]butanoate

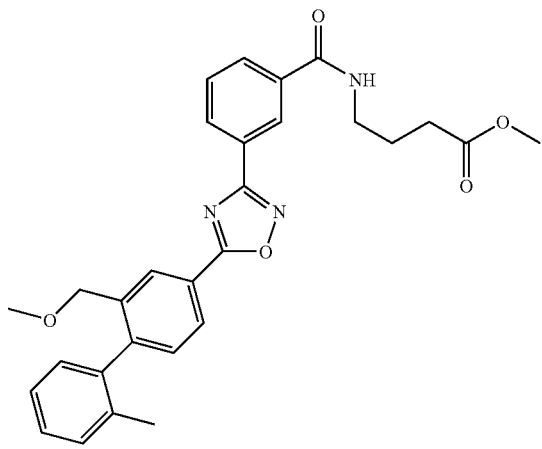

The title compound was prepared following procedure described in example 121 starting from 3-{5-[2-(methoxymethyl)-2'-methylbiphenyl-4-yl]-1,2,4-oxadiazol-3-yl}benzoyl chloride and methyl 4-aminobutyrate hydrochloride (55.01 mg; 0.36 mmol) The title compound was obtained as a sticky foam (85 mg, 71%). $^1$H NMR: (DMSO-d$_6$, 300 MHz) δ 8.53 (brs, 1H), 8.43 (brs, 1H), 8.32 (m, 1H), 8.17 (m, 1H), 8 (m, 1H), 7.60 (t, J=7.8 Hz, 1H), 7.34-7.22 (m, 4H), 7.12 (m, 1H), 6.65 (m, 1H), 4.22 (s, 2H), 3.69 (s, 3H), 3.56 (m, 2H), 3.32 (s, 3H), 2.48 (t, J=7 Hz, 1H), 2.07 (s, 3H), 2.01 (m, 2H). LC/MS (Method B): 500.2 (M+H)$^+$ 498.3 (M−H)$^−$. HPLC (Method A) Rt: 5.68 min (purity: 99.2%).

Example 138

N-(3-{5-[2-(methoxymethyl)-2'-methylbiphenyl-4-yl]-1,2,4-oxadiazol-3-yl}benzoyl)-N-methylglycine

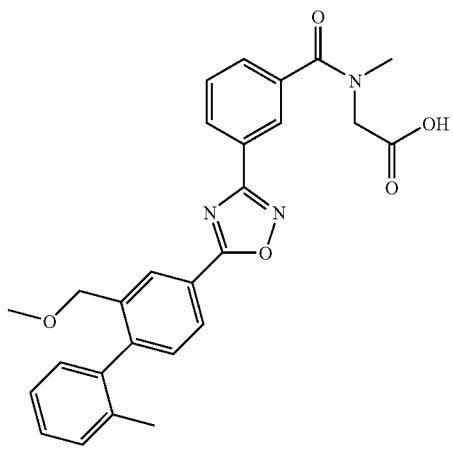

The title compound was prepared following procedure described in example 119 starting from example 136. The title compound was obtained as a white foam. $^1$H NMR: (DMSO-d$_6$, 300 MHz) δ 12.91 (brs, 1H), 8.33 (brs, 1H), 8.19 (m, 2H), 8.08 (m, 1H), 7.78-7.55 (m, 2H), 7.43 (m, 1H), 7.38-7.25 (m, 3H), 7.15 (m, 1H), 4.19 (m, 1.2H), 4 (m, 0.8H), 3.25 (s, 3H), 3.02 (m, 3H), 2.04 (s, 3H). LC/MS (Method B): 472.2 (M+H)$^+$ 470.2 (M−H)$^−$. HPLC (Method A) Rt: 4.54 min (purity: 99.3%).

Example 139

4-[(3-{5-[2-(methoxymethyl)-2'-methylbiphenyl-4-yl]-1,2,4-oxadiazol-3-yl}benzoyl)amino]butanoic acid

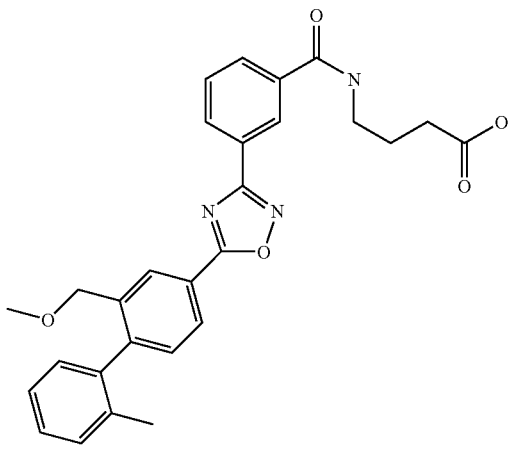

The title compound was prepared following procedure described in example 119 starting from example 137. The title compound was obtained as a white powder (45 mg, 71%). $^1$H NMR: (DMSO-d$_5$, 300 MHz) δ 12.07 (brs, 1H), 8.80 (m, 1H), 8.60 (brs, 1H), 8.35 (brs, 1H), 8.27 (d, J=7.9 Hz, 1H), 8.20 (d, J=1.7 Hz, 7.9 Hz, 1H), 8.10 (d, J=7.9 Hz, 1H), 7.72 (t, J=7.9 Hz, 1H), 7.43 (d, J=7.9 Hz, 1H), 7.38-7.25 (m, 3H), 7.16 (m, 1H), 4.23 (d, J=12.9 Hz, 1H), 4.17 (d, J=12.9 Hz, 1H), 3.30 (m, 2H), 3.26 (s, 3H), 2.31 (t, J=7.4 Hz, 2H), 2.04 (s, 3H), 1.80 (q, J=7.4 Hz, 1H). LC/MS (Method B): 485.9 (M+H)$^+$ 484 (M−H)$^−$. HPLC (Method A) Rt: 4.58 min (purity: 97.6%).

Example 140

Ethyl 1-[(3-{5-[2-(methoxymethyl)-2'-methylbiphenyl-4-yl]-1,2,4-oxadiazol-3-yl}benzyl)amino]cyclopropanecarboxylate

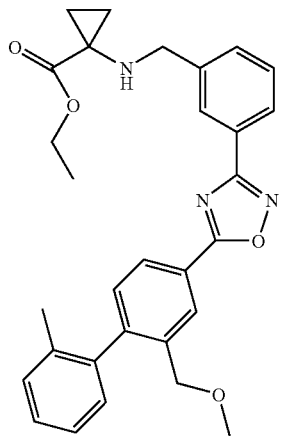

Step 1: 3-[3-(1,3-dioxolan-2-yl)phenyl]-5-[2-(methoxymethyl)-2'-methylbiphenyl-4-yl]-1,2,4-oxadiazole To a solution of Intermediate 28 (2 973 mg; 11.60 mmol) and DIEA (3.94 mL; 23.2 mmol) in anhydrous DMF (10 mL) at 0° C. was added HATU (4 410 mg; 11.60 mmol). The reaction mixture was stirred at 0° C. for 10 min. Intermediate 68 (2 300 mg; 11.05 mmol) was added at once. The reaction mixture was stirred at 0° C. for 15 min and RT for 2 h. EtOAc was added and the organic layer was washed with water and brine (50 mL), dried (MgSO$_4$) and the solvents were removed under reduced pressure to give an oil. The oil was taken up with toluene (70 mL) and pyridine (10 mL). The resulting mixture was heated at 110° C. overnight. EtOAc was added and the organic layer was washed with water and brine (50 mL), dried (MgSO$_4$) and the solvents were removed under reduced pressure to give a yellow oil. The crude material was purified by flash chromatography (EtOAc/cHex) to afford the title compound as an oil. $^1$H NMR: (DMSO-d$_6$, 300 MHz) δ 8.33 (m, 1H), 8.17 (m, 3H), 7.76 (m, 2H), 7.43 (d, J=7.9 Hz, 1H), 7.38-7.25 (m, 3H), 7.16 (m, 1H), 5.90 (s, 1H), 4.23 (d, J=12.9 Hz, 1H), 4.17 (d, J=12.9 Hz, 1H), 4.15-3.98 (m, 4H), 3.25 (s, 3H), 2.31 (t, J=7.40 Hz, 2H), 2.04 (s, 3H). LC/MS (Method B): 429.2 (M+H)$^+$ no (M−H)$^−$. HPLC (Method A) Rt: 5.53 min (purity: 89.8%).

Step 2: 3-{5-[2-(methoxymethyl)-2'-methylbiphenyl-4-yl]-1,2,4-oxadiazol-3-yl}benzaldehyde To a solution of 3-[3-(1,3-dioxolan-2-yl)phenyl]-5-[2-(methoxymethyl)-2'-methylbiphenyl-4-yl]-1,2,4-oxadiazole, obtained in step 1, (1 000 mg; 2.33 mmol) in dry THF (10 mL), hydrogen chloride solution in dioxane (1 750 μl; 4 M; 7 mmol) was added and the reaction mixture stirred overnight at 80° C. The solvents were removed under reduced pressure, EtOAc was added and the organic layers were washed with NaHCO$_3$ sat solution, dried over MgSO$_4$, filtered off and concentrated to afford the title compound as an oil (850 mg, 94%). $^1$H NMR: (DMSO-d$_6$, 300 MHz) δ 10.18 (s, 1H), 8.64 (m, 1H), 8.44 (m, 1H), 8.35 (m, 1H), 8.18 (m, 2H), 7.87 (t, J=7.9 Hz, 1H), 7.44 (m, 1H), 7.38-7.25 (m, 3H), 7.15 (m, 1H), 4.20 (m, 2H), 3.26 (s, 3H), 2.04 (s, 3H). LC/MS (Method B): 385.2 (M+H)$^+$. HPLC (Method A) Rt: 5.57 min (purity: 82.2%).

Step 3: E4thyl 1-[(3-{5-[2-(methoxymethyl)-2'-methylbiphenyl-4-yl]-1,2,4-oxadiazol-3-yl}benzyl)amino]cyclopropanecarboxylate To a solution of 3-{5-[2-(methoxymethyl)-2'-methylbiphenyl-4-yl]-1,2,4-oxadiazol-3-yl}benzaldehyde, obtained in step 2, (125 mg; 0.33 mmol) in 1,2 DCE (1.25 mL) was added 1-aminocyclopropane-1-carboxylic acid ethyl ester hydrochloride (70 mg; 0.42 mmol) followed by sodium triacetoxyborohydride (110 mg; 0.52 mmol). The reaction was heated at 80° C. for 1 h 30. The reaction was cooled down; DCM was added, the organic phase were washed with NaHCO$_3$ sat.sol, dried on MgSO$_4$, filtered off and concentrated. The crude material was purified by flash chromatography (EtOAc/cHex) to afford the title compound as a colorless oil. $^1$H NMR: (DMSO-d$_6$, 300 MHz) δ 8.32 (m, 1H), 8.17 (dd, J=1.9 Hz, 7.9 Hz, 1H), 8.07 (brs, 1H), 7.98 (m, 1H), 7.54 (m, 2H), 7.42 (d, J=7.9 Hz, 1H), 7.38-7.25 (m, 3H), 7.15 (m, 1H), 4.23 (d, J=12.7 Hz, 1H), 4.17 (d, J=12.7 Hz, 1H), 4.09 (q, J=7.2 Hz, 2H), 3.94 (d, J=6.6 Hz, 2H), 3.25 (s, 3H), 2.04 (s, 3H), 1.22 (t, J=7.2 Hz, 3H), 1.15 (m, 2H), 0.96 (m, 2H). LC/MS (Method B): 498.3 (M+H)$^+$ no (M−H)$^−$. HPLC (Method A) Rt: 4.55 min (purity: 93.4%).

Example 141

N-(3-{5-[2-(methoxymethyl)-2'-methylbiphenyl-4-yl]-1,2,4-oxadiazol-3-yl}benzyl)-N-methylglycine, Hydrochloride salt

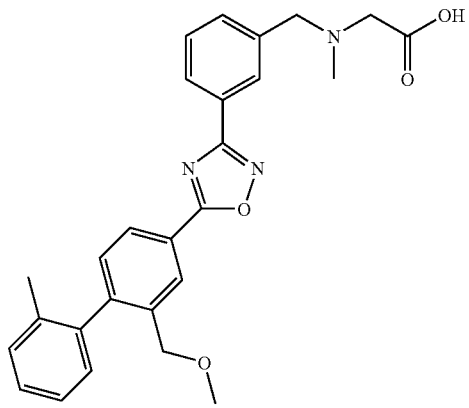

Step 1: tert-butyl N-(3-{5-[2-(methoxymethyl)-2'-methylbiphenyl-4-yl]-1,2,4-oxadiazol-3-yl}benzyl)-N-methylglycinate To a solution of Intermediate 28 (1.03 g; 4 mmol), DIEA (1.43 mL; 8.40 mmol) was added at once. The reaction mixture was stirred at 0° C. for 2 h. The reaction mixture was diluted with EtOAc (30 mL), washed with water (2×10 mL) and NaCl sat. solution (5×10 mL). The organic layer was dried over magnesium sulfate. After evaporation of the solvents, the crude product was dissolved in toluene (22.50 mL) and pyridine (7.50 mL; 30.97 mmol). The resulting mixture was heated at 90° C. for 24 h. After removal of pyridine and toluene, the crude mixture was purified by flash chromatography (c-hex/(DCM/EtOAc 1:1) gradient from 1:0 to 1:1) to afford the title compound as a colorless oil (1.7 g; 83%). $^1$H NMR (CDCl$_3$) δ 8.43 (d, J=1.4 Hz, 1H), 8.20-8.16 (m, 2H), 8.11 (d, J=7.6 Hz, 1H), 7.58 (d, J=7.7 Hz, 1H), 7.49 (t, J=7.6 Hz, 1H), 7.36-7.24 (m, 4H), 7.13 (d, J=7.3 Hz, 1H), 4.23 (s, 2H), 3.80 (s, 2H), 3.33 (s, 3H), 3.24 (s, 2H), 2.43 (s, 3H), 2.08 (s, 3H), 1.50 (s, 9H). LC/MS (Method B): 514.5 (M+H)$^+$. HPLC (Method A) Rt 4.80 min (Purity: 98.1%).

Step 2: N-(3-{5-[2-(methoxymethyl)-2'-methylbiphenyl-4-yl]-1,2,4-oxadiazol-3-yl}benzyl)-N-methylglycine, Hydrochloride salt To tert-butyl N-(3-{5-[2-(methoxymethyl)-2'-methylbiphenyl-4-yl]-1,2,4-oxadiazol-3-yl}benzyl)-N-methylglycinate, obtained in step 1 was added HCl 4M in dioxane (16.45 mL; 4 M; 65.81 mmol). The mixture was stirred at RT for 16 h. Solvents were concentrated to dryness to afford the title compound as a white powder (1.4 g; 85%). $^1$H NMR (DMSO-d$_6$, 300 MHz) δ 8.35-8.34 (m, 2H), 8.22 (d, J=1.8 Hz, 1H), 8.17 (dd, J=7.9, 1.8 Hz, 1H), 7.83 (d, J=7.8 Hz, 1H), 7.72 (t, J=7.7 Hz, 1H), 7.44 (d, J=8.0 Hz, 1H), 7.37-7.27 (m, 3H), 7.15 (d, J=7.2 Hz, 1H), 4.52 (s, 2H), 4.25-4.13 (m, 4H), 3.26 (s, 3H), 2.82 (s, 3H), 2.04 (s, 3H). LC/MS (Method B): 456.4 (M−H)$^−$, 458.4 (M+H)$^+$. HPLC (Method A) Rt 4.45 min (Purity: 98.6%). CHN analysis: [C$_{27}$H$_{28}$O$_4$N$_3$Cl] Calculated: C, 65.65%; H, 5.71%; N, 8.51%; Cl, 7.18%. Found: C, 65.36%; H, 5.65%; N, 8.49%; Cl, 7.08%.

Example 142

Tert-butyl N-(3-{5-[3-(methoxymethyl)-4-(2-methylpiperidin-1-yl)phenyl]-1,2,4-oxadiazol-3-yl}benzyl)-N-methylglycinate

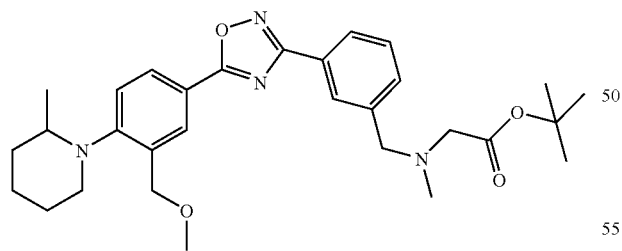

The title compound was prepared following procedure described in Example 113 starting from Intermediate 51. The title compound was obtained as colorless oil. $^1$HNMR (CDCl$_3$, 300 MHz): d=8.33 (d, J=2.1 Hz, 1H), 8.13-8.08 (m, 3H), 7.57 (d, J=7.5 Hz, 1H), 7.48 (dd, J=7.6, 7.5 Hz, 1H), 7.26 (d, J=8.3 Hz, 1H), 4.66 (d, J=12.3 Hz, 1H), 4.58 (d, J=12.3 Hz, 1H), 3.79 (s, 3H), 3.50 (s, 2H), 3.24 (s, 2H), 3.16 (m, 1H), 3.04 (m, 1H), 2.64 (m, 1H), 2.42 (s, 3H), 1.90-166 (m, 4H), 1.51 (m, 11H), 0.90 (d, J=6.2 Hz, 3H). LC/MS, M+(ESI): 521.3. HPLC (Method A), Rt: 3.41 min (purity: 99.5%).

LC/MS (Method A): 521.3 (M+H)$^+$. HPLC (Method A) Rt: 3.41 min (purity: 99.5%).

Example 143

N-(3-{5-[2'-ethyl-2-(methoxymethyl)biphenyl-4-yl]-1,2,4-oxadiazol-3-yl}benzyl)-N-methylglycine, hydrochloride salt

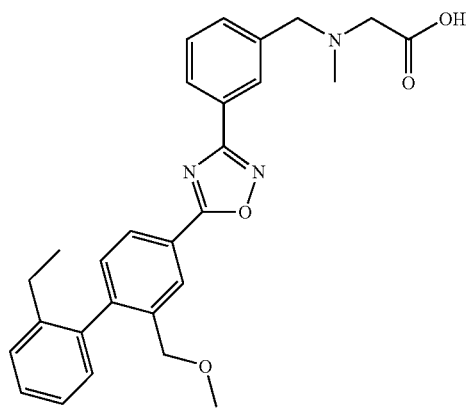

Step 1: tert-butyl N-(3-{5-[2'-ethyl-2-(methoxymethyl)biphenyl-4-yl]-1,2,4-oxadiazol-3-yl}benzyl)-N-methylglycinate The title compound was prepared following procedure described for example 4, step 1, but starting from Intermediate 36 and Intermediate 51. The reaction mixture was filtered through a SPE NH$_2$ column (10 g) and rinsed with ACN. After evaporation of the solvents, the crude product was purified by flash chromatography (c-hex/(DCM/EtOAc 1:1) gradient from 1:0 to 1:1), affording the title compound as a pale yellow oil. $^1$H NMR (CDCl$_3$) δ 8.43 (d, J=1.3 Hz, 1H), 8.19-8.16 (m, 2H), 8.11 (d, J=7.5 Hz, 1H), 7.61-7.47 (m, 2H), 7.41-7.34 (m, 3H), 7.29-7.23 (m, 1H), 7.13-7.10 (m, 1H), 4.27-4.18 (m, 2H), 3.80 (s, 2H), 3.33 (s, 3H), 3.24 (s, 2H), 2.48-2.29 (m, 5H), 1.50 (s, 9H), 1.05 (t, J=7.6 Hz, 3H). LC/MS (Method B): 528.3 (M+H)$^+$. HPLC (Method A) Rt 5.05 min (Purity: 98.4%).

Step 2: N-(3-{5-[2'-ethyl-2-(methoxymethyl)biphenyl-4-yl]-1,2,4-oxadiazol-3-yl}benzyl)-N-methylglycine, hydrochloride salt To, tert-butyl N-(3-{5-[2'-ethyl-2-(methoxymethyl)biphenyl-4-yl]-1,2,4-oxadiazol-3-yl}benzyl)-N-methylglycinate obtained in step 1 was added HCl 4M in dioxane (5.92 mL; 4 M; 23.69 mmol). The mixture was stirred at RT for 16 h. Solvents were concentrated to dryness to afford the title compound as a white powder (189 mg; 78%). $^1$H NMR (DMSO-d$_6$, 300 MHz) δ 8.34 (t, J=1.7 Hz, 2H), 8.23 (d, J=7.6 Hz, 1H), 8.17 (dd, J=7.9, 1.8 Hz, 1H), 7.8 (d, J=7.6 Hz, 1H), 7.72 (t, J=7.5 Hz, 1H), 7.46 (d, J=7.9 Hz, 1H), 7.42-7.40 (m, 2H), 7.34-7.26 (m, 1H), 7.12 (d, J=7.3 Hz, 1H), 4.50 (s, 2H), 4.26-4.12 (m, 4H), 3.27 (s, 3H), 2.82 (s, 3H), 2.46-2.23 (m, 2H), 1 (t, J=7.5 Hz, 3H). LC/MS (Method B): 470.3 (M−H)$^−$, 472.3 (M+H)$^+$. HPLC (Method A) Rt 4.28 min (Purity: 98.9%). CHN analysis: [C$_{28}$H$_{29}$N$_3$O$_4$.HCl.0.04

Example 144

N-(3-{5-[3-(methoxymethyl)-4-(2-methylpiperidin-1-yl)phenyl]-1,2,4-oxadiazol-3-yl}benzyl)-N-methylglycine, dihydrochloride salt

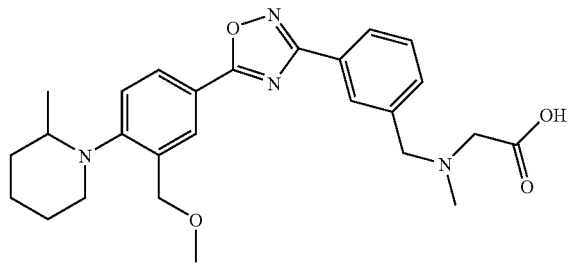

Example 142 was dissolved in a solution of HCl in dioxane (4 M, 4 mL). The resulting mixture was stirred at RT for 15 hours. The reaction mixture was evaporated under reduced pressure to give an oil that was taken up with EtOH (2 mL) and added dropwise into Et$_2$O (100 mL). The precipitate was filtered off, washed with Et$_2$O (2×) and pentane (2×). To remove solvent residues, the precipitate was taken up with water (10 mL) and lyophilized to give the title compound as a pale yellow powder. $^1$H NMR (DMSO-d$_6$, 300 MHz): δ 10.55 (bs, 1H), 8.22 (brs, 1H), 8.19 (m, 2H), 8.09 (d, J=8.2 Hz, 1H), 7.80 (d, J=7.8 Hz, 1H), 7.70 (dd, J=7.8, 7.7 Hz, 1H), 7.41 (brs, 1H), 4.57 (m, 4H), 4.14 (s, 2H), 3.41 (s, 3H), 3.24 (m, 1H), 3.03 (m, 1H), 2.82 (s, 3H), 2.63 (m, 1H), 1.84-1.64 (m, 4H), 1.46 (m, 2H), 0.86 (d, J=6.1 Hz, 3H). LC/MS (Method A): 465.3 (M+H)$^+$ . 463.4 (M−H)$^-$. HPLC (Method A) Rt: 2.41 min (Purity: 98.9%).

Example 145

Methyl N-(3-{5-[2-(methoxymethyl)-2'-methylbiphenyl-4-yl]-1,2,4-oxadiazol-3-yl}benzyl)-beta-alaninate

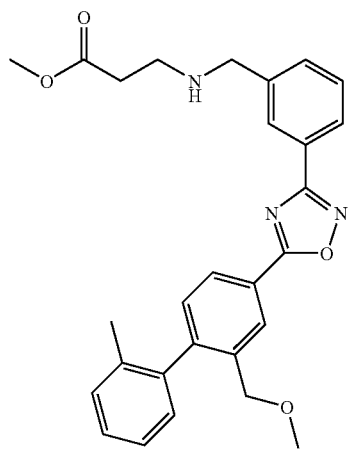

The title compound was prepared following procedure described in example 140, step 3, starting from beta-alanine methyl ester hydrochloride. The title compound was obtained as a colorless oil. $^1$H NMR: (DMSO-d$_6$, 300 MHz) δ 8.33 (m, 1H), 8.17 (dd, J=1.9 Hz, 7.9 Hz, 1H), 8.09 (brs, 1H), 7.98 (m, 1H), 7.55 (m, 2H), 7.42 (d, J=7.9 Hz, 1H), 7.38-7.25 (m, 3H), 7.15 (m, 1H), 4.23 (d, J=12.9 Hz, 1H), 4.17 (d, J=12.9 Hz, 1H), 3.81 (s, 2H), 3.59 (s, 3H), 3.25 (s, 3H), 2.76 (t, J=6.9 Hz, 2H), 2.04 (s, 3H). LC/MS (Method B): 472.3 (M+H)$^+$ 470.4 (M−H)$^-$. HPLC (Method A) Rt: 4.1 min (purity: 96.5%).

Example 146

N-(2-fluoro-5-{5-[2-(methoxymethyl)-2'-methylbiphenyl-4-yl]-1,2,4-oxadiazol-3-yl}benzyl)-N-methylglycine, Hydrochloride salt

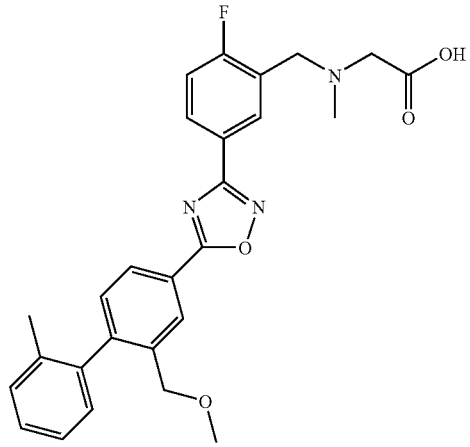

Step 1: tert-butyl N-(2-fluoro-5-{5-[2-(methoxymethyl)-2'-methylbiphenyl-4-yl]-1,2,4-oxadiazol-3-yl}benzyl)-N-methylglycinate The title compound was prepared following procedure described for example 4, step 1, but starting from Intermediate 60 (256.87 mg; 0.83 mmol) and Intermediate 28 (192.22 mg; 0.75 mmol). The reaction mixture was filtered through a SPE NH$_2$ column (2 g) and rinsed with ACN. After evaporation of the solvents, the crude product was purified by flash chromatography (c-hex/(DCM/EtOAc 1:1) gradient from 1:0 to 1:1), affording the title compound as a slightly yellow oil. $^1$H NMR (CDCl$_3$) δ 8.42 (d, J=1.4 Hz, 1H), 8.27 (d, J=5.8 Hz, 1H), 8.19-8.09 (m, 2H), 7.36-7.12 (m, 6H), 4.23 (s, 2H), 3.92 (s, 2H), 3.33 (s, 3H), 3.29 (s, 2H), 2.48 (s, 3H), 2.08 (s, 3H), 1.51 (s, 9H). LC/MS (Method B): 532.3 (M+H)$^+$. HPLC (Method A) Rt 4.85 min (Purity: 98.6%).

Step 2: N-(2-fluoro-5-{5-[2-(methoxymethyl)-2'-methylbiphenyl-4-yl]-1,2,4-oxadiazol-3-yl}benzyl)-N-methylglycine, Hydrochloride salt To tert-butyl N-(2-fluoro-5-{5-[2-(methoxymethyl)-2'-methylbiphenyl-4-yl]-1,2,4-oxadiazol-3-yl}benzyl)-N-methylglycinate, obtained in step 1 was added HCl in dioxane (5.06 mL; 4 M; 20.22 mmol). The mixture was stirred at RT for 16 h. Solvents were concentrated to dryness to afford the title compound as a white powder. $^1$H NMR (DMSO-d$_6$, 300 MHz) δ 8.46 (dd, J=7.0, 2.1 Hz, 1H), 8.33 (d, J=1.5 Hz, 1H), 8.30-8.26 (m, 1H), 8.17 (dd, J=7.9, 1.9 Hz, 1H), 7.59 (t, J=9.2 Hz, 1H), 7.45 (d, J=8.0 Hz, 1H), 7.38-7.27 (m, 3H), 7.15 (d, J=7.0 Hz, 1H), 4.53 (d, 2H), 4.26-4.16 (m, 4H), 3.26 (s, 3H), 2.83 (s, 3H), 2.04 (s, 3H). LC/MS (Method B): 474.3 (M−H)⁻, 476.2 (M+H)⁺. HPLC (Method A) Rt 4.54 min (Purity: 98.4%).

Example 147

N-(5-{5-[2'-ethyl-2-(methoxymethyl)biphenyl-4-yl]-1,2,4-oxadiazol-3-yl}-2-fluorobenzyl)-N-methylglycine, Hydrochloride salt

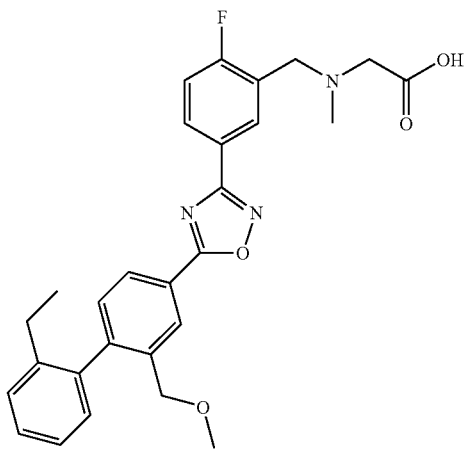

Step 1: tert-butyl N-(5-{5-[2'-ethyl-2-(methoxymethyl)biphenyl-4-yl]-1,2,4-oxadiazol-3-yl}-2-fluorobenzyl)-N-methylglycinate The title compound was prepared following procedure described for example 4, step 1, but starting from Intermediate 60 (256.87 mg; 0.83 mmol) and Intermediate 36 (202.74 mg; 0.75 mmol). The reaction mixture was filtered through a SPE NH₂ column (2 g) and rinsed with ACN. After evaporation of the solvents, the crude product was purified by flash chromatography (c-hex/(DCM/EtOAc 1:1) gradient from 1:0 to 1:1), affording the title compound as a pale yellow oil. ¹H NMR (CDCl₃) δ 8.42 (d, J=1.4 Hz, 1H), 8.26 (dd, J=7.0, 2.1 Hz, 1H), 8.18-8.09 (m, 2H), 7.41-7.34 (m, 3H), 7.29-7.23 (m, 1H), 7.19 (t, J=9.0 Hz, 1H), 7.12-7.10 (m, 1H), 4.27-4.17 (m, 2H), 3.90 (s, 2H), 3.38 (s, 3H), 3.28 (s, 2H), 2.47-2.29 (m, 5H), 1.51 (s, 9H), 1.05 (t, J=7.5 Hz, 3H). LC/MS (Method B): 546.3 (M+H)⁺. HPLC (Method A) Rt 5.04 min (Purity: 99.5%).

Step 2: N-(5-{5-[2'-ethyl-2-(methoxymethyl)biphenyl-4-yl]-1,2,4-oxadiazol-3-yl}-2-fluorobenzyl)-N-methylglycine, Hydrochloride salt To tert-butyl N-(5-{5-[2'-ethyl-2-(methoxymethyl)biphenyl-4-yl]-1,2,4-oxadiazol-3-yl}-2-fluorobenzyl)-N-methylglycinate, obtained in step 1 was added HCl 4M in dioxane (4.12 mL; 4 M; 16.49 mmol). The mixture was stirred at RT for 16 h. Solvents were concentrated to dryness to afford the title compound as a white powder (125 mg; 72%). ¹H NMR (DMSO-d₆, 300 MHz) δ 8.46 (dd, J=6.9, 2.1 Hz, 1H), 8.34 (d, J=1.5 Hz, 1H), 8.31-8.26 (m, 1H), 8.17 (dd, J=7.9, 1.9 Hz, 1H), 7.59 (t, J=9.2 Hz, 1H), 7.47 (d, J=8.0 Hz, 1H), 7.42-7.40 (m, 2H), 7.34-7.26 (m, 1H), 7.12 (d, J=7.3 Hz, 1H), 4.52 (s, 2H), 4.26-4.12 (m, 4H), 3.27 (s, 3H), 2.82 (s, 3H), 2.45-2.23 (m, 2H), 0.99 (t, J=7.5 Hz, 3H). LC/MS (Method B): 488.3 (M−H)⁻, 490.3 (M+H)⁺. HPLC (Method A) Rt 4.76 min (Purity: 99.7%).

Example 148

N-(3-{5-[4-isopropoxy-3-(methoxymethyl)phenyl]-1,2,4-oxadiazol-3-yl}benzyl)-N-methylglycine, Hydrochloride salt

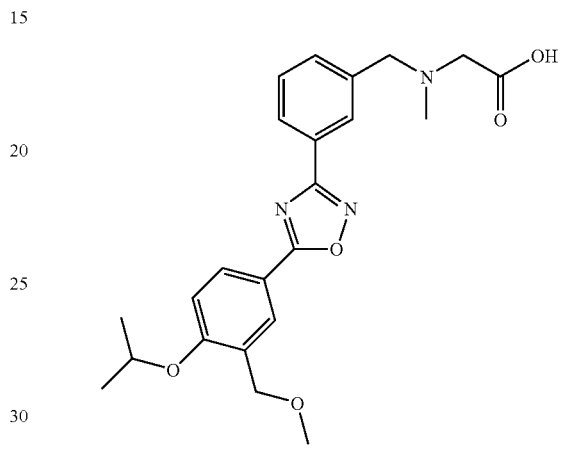

Step 1: tert-butyl N-(3-{5-[4-isopropoxy-3-(methoxymethyl)phenyl]-1,2,4-oxadiazol-3-yl}benzyl)-N-methylglycinate The title compound was prepared following procedure described for example 4, step 1, but starting from Intermediate 56 (201.83 mg; 0.90 mmol) and Intermediate 51 (220 mg; 0.75 mmol). The reaction mixture was filtered through a SPE NH₂ column (2 g) and rinsed with ACN. After evaporation of the solvents, the crude product was purified by flash chromatography (c-hex/(DCM/EtOAc 1:1) gradient from 1:0 to 1:1), affording the title compound as a slightly yellow solid. ¹H NMR (CDCl₃) δ 8.25 (d, J=2.2 Hz, 1H), 8.12 (d, J=1.7 Hz, 1H), 8.09 (d, J=2.2 Hz, 1H), 8.06 (br s, 1H), 7.57-7.55 (m, 1H), 7.47 (t, J=7.5 Hz, 1H), 6.98 (d, J=8.9 Hz, 1H), 4.70 (quint., J=6.1 Hz, 1H), 4.54 (s, 2H), 3.78 (s, 2H), 3.50 (s, 3H), 3.23 (s, 2H), 2.41 (s, 3H), 1.50 (s, 9H), 1.40 (d, J=6.0 Hz, 6H). HPLC (Method A) Rt 4.96 min (Purity: 100.0%).

Step 2: N-(3-{5-[4-isopropoxy-3-(methoxymethyl)phenyl]-1,2,4-oxadiazol-3-yl}benzyl)-N-methylglycine, Hydrochloride salt To tert-butyl N-(3-{5-[4-isopropoxy-3-(methoxymethyl)phenyl]-1,2,4-oxadiazol-3-yl}benzyl)-N-methylglycinate, obtained in step 1 was added HCl 4M in dioxane (4.12 mL; 4 M; 16.49 mmol). The mixture was stirred at RT for 16 h. Solvents were concentrated to dryness to afford the title compound as a white powder (87 mg; 87%). ¹H NMR (DMSO-d₆, 300 MHz) δ 8.31 (s, 1H), 8.20-8.08 (m, 3H), 7.78-7.67 (m, 2H), 7.30 (d, J=8.9 Hz, 1H), 4.83 (sept., J=6.0 Hz, 1H), 4.48

(s, 4H), 4.09 (s, 2H), 3.43 (s, 3H), 2.79 (s, 3H), 1.34 (d, J=5.8 Hz, 6H). LC/MS (Method B): 424.3 (M−H)⁻, 426.2 (M+H)⁺. HPLC (Method A) Rt 4.06 min (Purity: 98.3%).

Example 149

Tert-butyl N-(tert-butoxycarbonyl)-N-(3-{5-[2-(methoxymethyl)-2'-methylbiphenyl-4-yl]-1,2,4-oxadiazol-3-yl}benzyl)glycinate

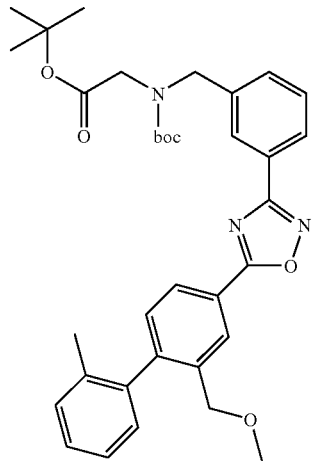

The title compound was prepared following procedure described in example 140, step 1, starting from Intermediate 61. The title compound was obtained as a colorless oil. ¹H NMR: (DMSO-d₆, 300 MHz) δ 8.33 (brs, 1H), 8.16 (m, 1H), 8.03 (m, 1H), 7.55 (m, 2H), 7.42 (d, J=7.9 Hz, 1H), 7.38-7.25 (m, 3H), 7.15 (m, 1H), 4.52 (d, J=10.5 Hz, 2H), 4.23 (d, J=12.9 Hz, 1H), 4.17 (d, J=12.9 Hz, 1H), 3.88 (d, J=18 Hz, 2H), 3.25 (s, 3H), 2.04 (s, 3H), 1.43 (m, 9H), 1.36 (m, 9H). LC/MS (Method B): no (M+H)⁺ no (M−H)⁻. HPLC (Method A) Rt: 6.98 min (purity: 97.6%).

Example 150

N-(3-{5-[2-(methoxymethyl)-2'-methylbiphenyl-4-yl]-1,2,4-oxadiazol-3-yl}benzyl)-N-methyl-beta-alanine

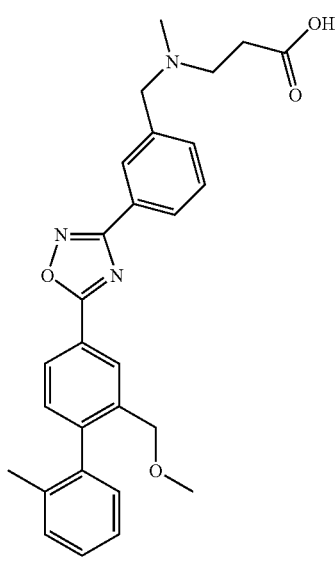

Step 1: tert-butyl N-(2-fluoro-5-{5-[2-(methoxymethyl)-2'-methylbiphenyl-4-yl]-1,2,4-oxadiazol-3-yl}benzyl)-N-methyl-beta-alaninate To a solution of Intermediate 28 (2 g; 7.80 mmol) in DCM (40 mL) was added oxalyl chloride (1.98 mL; 23.41 mmol) followed by DMF (60 µL) under vigorous stirring at RT. After 2 h, solvents were removed under vacuum to give 2-(methoxymethyl)-2'-methylbiphenyl-4-carbonyl chloride as a yellow oil that was dried under vacuum. To a solution of Intermediate 62 (150 mg; 0.49 mmol) in CH₃CN (1.50 mL) and DIEA (0.33 mL) was added a solution of 2-(methoxymethyl)-2'-methylbiphenyl-4-carbonyl chloride (134.07 mg; 0.49 mmol) in CH3CN (1.50 mL). Reaction mixture was stirred at RT for 1 h 30 after which it was heated to 150° C., 30 min under microwave irradiations. Reaction mixture was concentrated under vacuum, dissolved in DCM and purified by column chromatography (EtOAc:cHex from 10:90 to 80:20) to give the title compound as a colorless oil. LC/MS (Method B): 528.5 (M+H)⁺.

Step 2: N-(3-{5-[2-(methoxymethyl)-2'-methylbiphenyl-4-yl]-1,2,4-oxadiazol-3-yl}benzyl)-N-methyl-beta-alanine tert-butyl N-(2-fluoro-5-{5-[2-(methoxymethyl)-2'-methylbiphenyl-4-yl]-1,2,4-oxadiazol-3-yl}benzyl)-N-methyl-beta-alaninate obtained in step 1 was dissolved in HCl in dioxane (4M, 10 mL), stirred at RT for 30 h. After this time, solvents were removed under vacuum, residue was triturated with Et₂O and filtered to give the title compound as an off-white powder. ¹H NMR (DMSO-d₆, 300 MHz) δ 12.74 (bs, 1H), 10.38 (bs, 1H), 8.36-8.33 (m, 1H), 8.23-8.20 (m, 1H), 8.18-8.15 (m, 1H), 7.87-7.84 (m, 1H), 7.72 (t, J=7.8 Hz, 1H), 7.44 (d, J=7.9 Hz, 1H), 7.37-7.28 (m, 3H), 7.15-7.13 (m, 1H), 4.48 (bs, 2H), 4.23 (d, J=12.7 Hz, 1H), 4.16 (d, J=12.7 Hz, 1H), 3.25 (s, 3H), 2.89-2.84 (m, 2H), 2.70 (s, 3H), 2.03 (s, 3H). LC/MS (Method B): 472.4 (M+H)⁺. HPLC (Method A) Rt 4.53 min (purity: 97.4%).

Example 151

1-[(3-{5-[2-(methoxymethyl)-2'-methylbiphenyl-4-yl]-1,2,4-oxadiazol-3-yl}benzyl)amino]cyclopropanecarboxylic acid

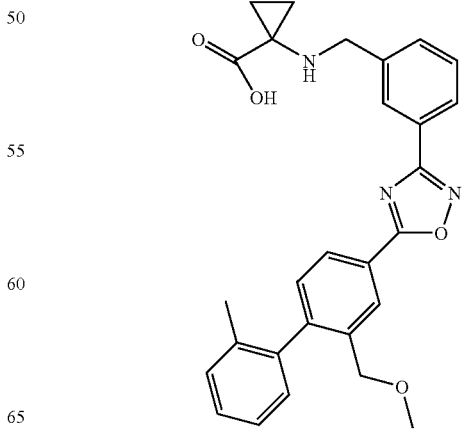

The title compound was prepared following procedure described in example 119 starting from example 140. The title compound was obtained as a white powder. ¹H NMR: (DMSO-d₆, 300 MHz) δ 8.33 (m, 1H), 8.17 (dd, J=1.9 Hz, 7.9 Hz 1H), 8.07 (brs, 1H), 7.99 (m, 1H), 7.55 (m, 2H), 7.42 (d, J=7.9 Hz, 1H), 7.38-7.25 (m, 3H), 7.15 (m, 1H), 4.23 (d, J=12.7 Hz, 1H), 4.17 (d, J=12.7 Hz, 1H), 3.97 (s, 2H), 3.25 (s, 3H), 2.31 (t, J=7.40 Hz, 2H), 2.04 (s, 3H), 1.15 (m, 2H), 0.96 (m, 2H). LC/MS (Method B): 470.3 (M+H)⁺ 468.3 (M−H)⁻. HPLC (Method A) Rt: 4.19 min (purity: 100%).

Example 152

N-(2-fluoro-5-{5-[3-(methoxymethyl)-4-(2-methylpiperidin-1-yl)phenyl]-1,2,4-oxadiazol-3-yl}benzyl)-N-methylglycine, Dihydrochloride salt

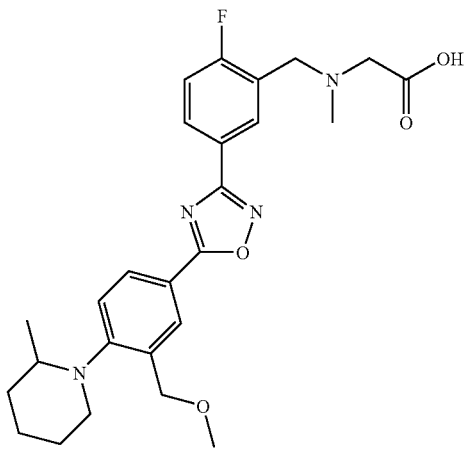

Step 1: tert-butyl N-(2-fluoro-5-{5-[3-(methoxymethyl)-4-(2-methylpiperidin-1-yl)phenyl]-1,2,4-oxadiazol-3-yl}benzyl)-N-methylglycinate The title compound was prepared following procedure described for example 4, step 1, but starting from Intermediate 60 (256.87 mg; 0.83 mmol) and Intermediate 58 (197.50 mg; 0.75 mmol). The reaction mixture was filtered through a SPE NH₂ column (10 g) and rinsed with ACN. After evaporation of the solvents, the crude product was purified by flash chromatography (c-hex/(DCM/EtOAc 1:1) gradient from 1:0 to 1:1), affording the title compound as a colorless oil. ¹H NMR (CDCl₃) δ 8.31 (d, J=2.1 Hz, 1H), 8.22 (dd, J=7.0, 2.2 Hz, 1H), 8.11-8.06 (m, 2H), 7.23-7.14 (m, 2H), 4.67-4.55 (m, 2H), 4.16-4.08 (m, 2H), 3.89 (s, 2H), 3.49 (s, 3H), 3.27 (s, 2H), 3.18-3.12 (m, 1H), 3.06-2.99 (m, 1H), 2.67-2.59 (m, 1H), 2.46 (s, 3H), 1.89-1.76 (m, 2H), 1.73-1.65 (m, 2H), 1.51 (s, 9H), 0.89 (d, J=6.3 Hz, 3H). LC/MS (Method B): 539.4 (M+H)⁺. HPLC (Method A) Rt 3.84 min (Purity: 99.1%).

Step 2: N-(2-fluoro-5-{5-[3-(methoxymethyl)-4-(2-methylpiperidin-1-yl)phenyl]-1,2,4-oxadiazol-3-yl}benzyl)-N-methylglycine, dihydrochloride salt To tert-butyl N-(2-fluoro-5-{5-[3-(methoxymethyl)-4-(2-methylpiperidin-1-yl)phenyl]-1,2,4-oxadiazol-3-yl}benzyl)-N-methylglycinate, obtained in step 1 was added HCl 4M in dioxane (2.78 mL; 4 M; 11.14 mmol). The mixture was stirred at RT for 16 h. Solvents were concentrated to dryness to afford the title compound as a pale orange solid (95 mg; 76%). ¹H NMR (DMSO-d₆, 300 MHz) δ 10.53 (br s, 1H), 8.44 (dd, J=6.9, 2.0 Hz, 1H), 8.29-8.24 (m, 1H), 8.20 (d, J=1.8 Hz, 1H), 8.08 (dd, J=8.2, 2.1 Hz, 1H), 7.58 (t, J=9.1 Hz, 1H), 7.40 (d, J=8.1 Hz, 1H), 4.61-4.51 (m, 4H), 4.21 (s, 2H), 3.42 (s, 3H), 3.24 (br s, 1H), 3.06-3.02 (m, 1H), 2.85 (s, 3H), 2.63-2.62 (m, 1H), 1.84-1.64 (m, 4H), 1.49-1.40 (m, 2H), 0.86 (d, J=6.2 Hz, 3H). LC/MS (Method B): 481.4 (M−H)⁻, 483.3 (M+H)⁺. HPLC (Method A) Rt 2.43 min (Purity: 98.7%).

Example 153 tert-butyl N-(3-{5-[2-(methoxymethyl)-2'-methylbiphenyl-4-yl]-1,2,4-oxadiazol-3-yl}benzyl)-beta-alaninate

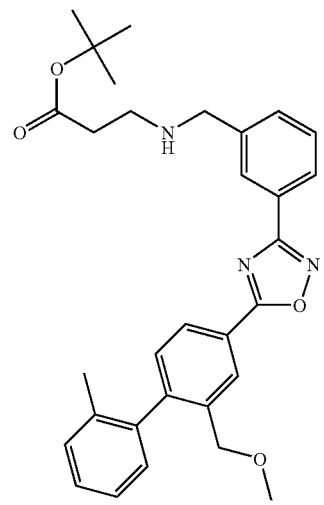

The title compound was prepared following procedure described in example 140, Step 3, starting from beta-alanine t-butyl ester hydrochloride (Bachem). The title compound was obtained as a colorless oil. ¹H NMR: (DMSO-d₆, 300 MHz) δ 8.33 (brs, 2H), 8.17 (m, 1H), 8.10 (brs, 1H), 7.99 (m, 1H), 7.55 (m, 2H), 7.42 (d, J=7.9 Hz, 1H), 7.38-7.25 (m, 3H), 7.15 (m, 1H), 4.23 (d, J=12.7 Hz, 1H), 4.17 (d, J=12.7 Hz, 1H), 3.80 (s, 2H), 3.25 (s, 3H), 2.72 (t, J=6.80 Hz, 2H), 2.37 (t, J=6.80 Hz, 2H), 2.04 (s, 3H), 1.40 (s, 9H). LC/MS (Method B): 514.3 (M+H)⁺ no (M−H)⁻. HPLC (Method A) Rt: 4.92 min (purity: 99.4%).

Example 154

N-(2-fluoro-5-{5-[2-(methoxymethyl)-2'-methylbiphenyl-4-yl]-1,2,4-oxadiazol-3-yl}benzyl)-N-methyl-beta-alanine, Hydrochloride salt

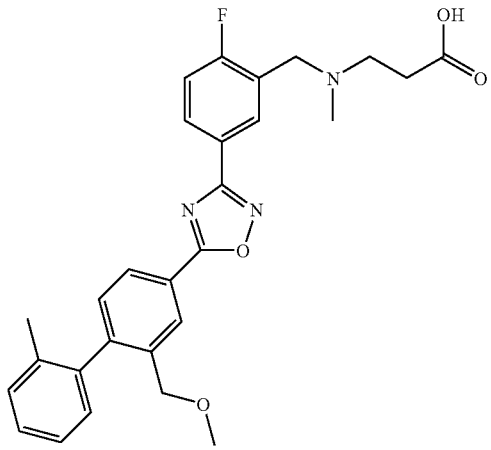

Step 1: tert-butyl N-(2-fluoro-5-{5-[2-(methoxymethyl)-2'-methylbiphenyl-4-yl]-1,2,4-oxadiazol-3-yl}benzyl)-N-methyl-beta-alaninate The title compound was prepared following procedure described for example 4, step 1, but starting from Intermediate 63 (268.44 mg; 0.83 mmol) and Intermediate 28 (192.22 mg; 0.75 mmol). The reaction mixture was filtered through a SPE $NH_2$ column (2 g) and rinsed with ACN. After evaporation of the solvents, the crude product was purified by flash chromatography (c-hex/(DCM/EtOAc 1:1) gradient from 1:0 to 1:1), affording the title compound as a colorless oil. $^1$H NMR (CDCl$_3$) δ 8.42 (d, J=1.4 Hz, 1H), 8.25-8.22 (m, 1H), 8.17 (dd, J=7.8, 1.9 Hz, 1H), 8.12-8.07 (m, 1H), 7.36-7.23 (m, 4H), 7.20-7.12 (m, 2H), 4.23 (s, 2H), 3.65 (s, 2H), 3.33 (s, 3H), 2.80 (t, J=7.3 Hz, 2H), 2.49 (t, J=7.2 Hz, 2H), 2.27 (s, 3H), 2.08 (s, 3H), 1.45 (s, 9H). $^{19}$F NMR (CDCl$_3$) δ-113.6 ppm. LC/MS (Method B): 546.4 (M+H)$^+$. HPLC (Method A) Rt 5 min (Purity: 97.8%).

Step 2: N-(2-fluoro-5-{5-[2-(methoxymethyl)-2'-methylbiphenyl-4-yl]-1,2,4-oxadiazol-3-yl}benzyl)-N-methyl-beta-alanine, Hydrochloride salt To tert-butyl N-(2-fluoro-5-{5-[2-(methoxymethyl)-2'-methylbiphenyl-4-yl]-1,2,4-oxadiazol-3-yl}benzyl)-N-methyl-beta-alaninate, obtained in step 1 was added HCl 4M in dioxane (2.29 mL; 4 M; 9.16 mmol). The mixture was stirred at RT for 16 h. Solvents were concentrated to dryness to afford the title compound as a white powder. $^1$H NMR (DMSO-d$_6$, 300 MHz) δ 12.77 (brs, 1H), 10.15 (br s, 1H), 8.50 (dd, J=6.9, 2.2 Hz, 1H), 8.34 (d, J=1.5 Hz, 1H), 8.32-8.27 (m, 1H), 8.17 (dd, J=7.9, 1.9 Hz, 1H), 7.61 (t, J=9.2 Hz, 1H), 7.44 (d, J=7.9 Hz, 1H), 7.38-7.27 (m, 3H), 7.15 (d, J=7.0 Hz, 1H), 4.54 (brs, 2H), 4.26-4.14 (m, 2H), 3.40-3.36 (m, 2H), 3.26 (s, 3H), 2.85 (t, J=7.4 Hz, 2H), 2.77 (s, 3H), 2.04 (s, 3H). $^{19}$F NMR (DMSO-d$_6$, 300 MHz) δ-109.8 ppm. LC/MS (Method B): 488.3 (M-H)$^-$, 490.3 (m+H)$^+$. HPLC (Method A) Rt 4.16 min (Purity: 97.8%).

Example 155

N-(3-{5-[2-(methoxymethyl)-2'-methylbiphenyl-4-yl]-1,2,4-oxadiazol-3-yl}benzyl)-beta-alanine, Hydrochloride salt

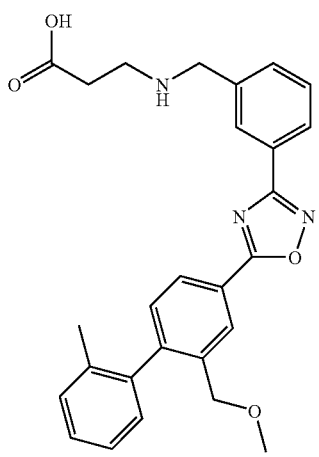

The title compound was prepared following procedure described in example 119 starting from example 153. The title compound was obtained as a sticky oil (21 mg, 84%). $^1$H NMR: (DMSO-d$_6$, 300 MHz) δ 8.34 (brs, 2H), 8.18 (m, 2H), 7.79 (m, 1H), 7.70 (m, 1H), 7.45 (d, J=7.9 Hz, 1H), 7.38-7.25 (m, 3H), 7.15 (m, 1H), 4.33 (brs, 2H), 4.23 (d, J=12.7 Hz, 1H), 4.17 (d, J=12.7 Hz, 1H), 3.25 (s, 3H), 3.19 (m, 2H), 2.72 (m, 2H), 2.04 (s, 3H) LC/MS (Method B): 458.3 (M+H)$^+$ 456.4 (M−H)$^-$. HPLC (Method A) Rt: 4.13 min (purity: 98.3%).

Example 156

N-(5-{5-[2'-ethyl-2-(methoxymethyl)biphenyl-4-yl]-1,2,4-oxadiazol-3-yl}-2-fluorobenzyl)-N-methyl-beta-alanine, Hydrochloride salt

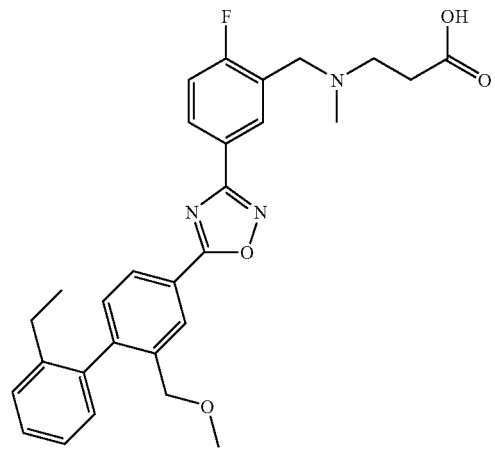

Step 1: tert-butyl N-(5-{5-[2'-ethyl-2-(methoxymethyl)biphenyl-4-yl]-1,2,4-oxadiazol-3-yl}-2-fluorobenzyl)-N-methyl-beta-alaninate The title compound was prepared following procedure described for example 141, step 1, but starting from Intermediate 36 (162.20 mg; 0.60 mmol) and Intermediate 63 (185.47 mg; 0.57 mmol), the crude mixture was purified by flash chromatography (c-hex/(DCM/EtOAc 1:1) gradient from 1:0 to 1:1) to afford the title compound as a colorless oil. $^1$H NMR (CDCl$_3$) δ 8.42 (d, J=1.4 Hz, 1H), 8.23 (dd, J=7.1, 1.4 Hz, 1H), 8.17 (dd, J=7.9, 1.8 Hz, 1H), 8.12-8.08 (m, 1H), 7.41-7.10 (m, 6H), 4.27-4.17 (m, 2H), 3.66 (br s, 2H), 3.33 (s, 3H), 2.08 (t, J=7.0 Hz, 2H), 2.52-2.31 (m, 4H), 2.28 (s, 3H), 1.45 (s, 9H), 1.05 (t, J=7.5 Hz, 3H). LC/MS (Method B): 560.5 (M+H)$^+$. HPLC (Method A) Rt 5.14 min (Purity: 94.0%).

Step 2: N-(5-{5-[2'-ethyl-2-(methoxymethyl)biphenyl-4-yl]-1,2,4-oxadiazol-3-yl}-2-fluorobenzyl)-N-methyl-beta-alanine, Hydrochloride salt To tert-butyl N-(5-{5-[2'-ethyl-2-(methoxymethyl)biphenyl-4-yl]-1,2,4-oxadiazol-3-yl}-2-fluorobenzyl)-N-methyl-beta-alaninate, obtained in step 1 was added HCl 4M in dioxane (3.02 mL; 4 M; 12.06 mmol). The mixture was stirred at RT for 16 h. Solvents were concentrated to dryness to afford the title compound as a white powder. $^1$H NMR (DMSO-d$_6$, 300 MHz) δ 12.77 (br s, 1H), 10.22 (br s, 1H), 8.51 (dd, J=7.0, 2.2 Hz, 1H), 8.34-8.27 (m, 2H), 8.17 (dd, J=8.0, 1.9 Hz, 1H), 7.62 (t, J=9.1 Hz, 1H), 7.46 (d, J=7.9 Hz, 1H), 7.42-7.40 (m, 2H), 7.34-7.26 (m, 1H), 7.12 (d, J=7.3 Hz, 1H), 4.54 (br s, 2H), 4.24 (d, J=12.8 Hz, 1H), 4.14 (d, J=12.8 Hz, 1H), 3.27 (s, 3H), 2.87 (t, J=7.4 Hz, 2H), 2.77 (s, 3H), 2.45-2.23 (m, 2H), 1 (t, J=7.5 Hz, 3H). LC/MS (Method B): 502.4 (M−H)⁻, 504.4 (M+H)⁺. HPLC (Method A) Rt 4.31 min (Purity: 98.8%).

Example 157

N-(2-fluoro-5-{5-[4-isopropoxy-3-(methoxymethyl)phenyl]-1,2,4-oxadiazol-3-yl}benzyl)-N-methyl-beta-alanine, Hydrochloride salt

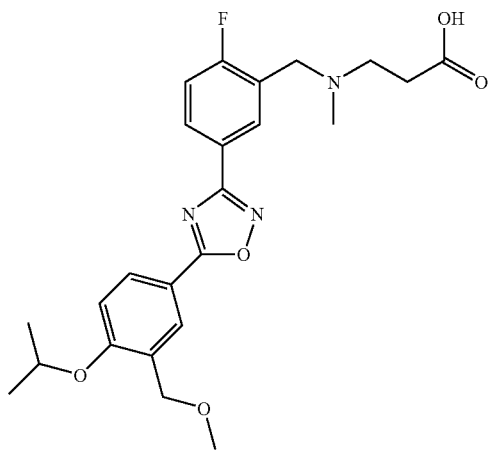

Step 1: tert-butyl N-(2-fluoro-5-{5-[4-isopropoxy-3-(methoxymethyl)phenyl]-1,2,4-oxadiazol-3-yl}benzyl)-N-methyl-beta-alaninate The title compound was prepared following procedure described for example 141, step 1, but starting from Intermediate 56 (134.55 mg; 0.60 mmol), the crude mixture was purified by flash chromatography (c-hex/(DCM/EtOAc 1:1) gradient from 1:0 to 1:1) to afford the title compound as a colorless oil. ¹H NMR (CDCl₃) δ 8.24 (d, J=2.3 Hz, 1H), 8.19 (dd, J=7.0, 1.9 Hz, 1H), 8.11-8.04 (m, 2H), 7.15 (t, J=9.0 Hz, 1H), 6.98 (d, J=8.9 Hz, 1H), 4.70 (quint., J=6.1 Hz, 1H), 4.54 (s, 2H), 3.64 (s, 2H), 3.50 (s, 3H), 2.79 (t, J=7.3 Hz, 2H), 2.48 (t, J=7.1 Hz, 2H), 2.26 (s, 3H), 1.45 (s, 9H), 1.40 (d, J=6.0 Hz, 6H). LC/MS (Method B): 514.5 (M+H)⁺. HPLC (Method A) Rt 4.56 min (Purity: 90.3%).

Step 2: N-(2-fluoro-5-{5-[4-isopropoxy-3-(methoxymethyl)phenyl]-1,2,4-oxadiazol-3-yl}benzyl)-N-methyl-beta-alanine, Hydrochloride salt To tert-butyl N-(2-fluoro-5-{5-[4-isopropoxy-3-(methoxymethyl)phenyl]-1,2,4-oxadiazol-3-yl}benzyl)-N-methyl-beta-alaninate, obtained in step 1 was added HCl 4M in dioxane (4.02 mL; 4 M; 16.06 mmol). The mixture was stirred at RT for 16 h. Solvents were concentrated to dryness to afford the title compound as a white powder. ¹H NMR (DMSO-d₆, 300 MHz) δ 12.77 (br s, 1H), 10.16 (br s, 1H), 8.46 (dd, J=7.0, 2.0 Hz, 1H), 8.28-8.23 (m, 1H), 8.13 (d, J=2.2 Hz, 1H), 8.09 (dd, J=8.6, 2.3 Hz, 1H), 7.59 (t, J=9.1 Hz, 1H), 7.30 (d, J=8.9 Hz, 1H), 4.83 (sept, J=6.2 Hz, 1H), 4.52 (br s, 2H), 4.48 (s, 2H), 3.43 (s, 3H), 3.40 (br s, 2H), 2.85 (t, J=7.3 Hz, 2H), 2.76 (s, 3H), 1.34 (d, J=6.0 Hz, 6H). LC/MS (Method B): 456.4 (M−H)⁻, 458.3 (M+H)⁺. HPLC (Method A) Rt 3.68 min (Purity: 94.9%).

Example 158

N-(2-fluoro-5-{5-[4-isopropoxy-3-(methoxymethyl)phenyl]-1,2,4-oxadiazol-3-yl}benzyl)-N-methylglycine, Hydrochloride salt

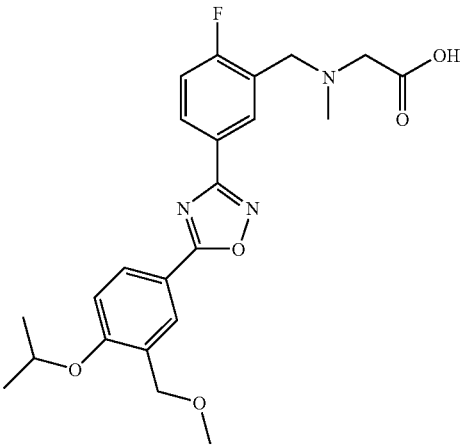

Step 1: tert-butyl N-(2-fluoro-5-{5-[4-isopropoxy-3-(methoxymethyl)phenyl]-1,2,4-oxadiazol-3-yl}benzyl)-N-methylglycinate The title compound was prepared following procedure described for example 141, step 1, but starting from Intermediate 56 (134.55 mg; 0.60 mmol) and Intermediate 60 (177.47 mg; 0.57 mmol), the crude mixture was purified by flash chromatography (c-hex/(DCM/EtOAc 1:1) gradient from 1:0 to 1:1) to afford the title compound as a colorless oil. ¹H NMR (CDCl₃) δ 8.24-8.20 (m, 2H), 8.11-8.04 (m, 2H), 7.17 (t, J=9.0 Hz, 1H), 6.98 (d, J=8.8 Hz, 1H), 4.70 (quint., J=6.1 Hz, 1H), 4.54 (s, 2H), 3.89 (s, 2H), 3.50 (s, 3H), 3.27 (s, 2H), 2.46 (s, 3H), 1.51 (s, 9H), 1.40 (d, J=6.0 Hz, 6H). LC/MS (Method B): 500.4 (M+H)⁺. HPLC (Method A) Rt 4.44 min (Purity: 97.6%).

Step 2: N-(2-fluoro-5-{5-[4-isopropoxy-3-(methoxymethyl)phenyl]-1,2,4-oxadiazol-3-yl}benzyl)-N-methylglycine, Hydrochloride salt To tert-butyl N-(2-fluoro-5-{5-[4-isopropoxy-3-(methoxymethyl)phenyl]-1,2,4-oxadiazol-3-yl}benzyl)-N-methylglycinate, obtained in step 1 was added HCl 4M in dioxane (5 mL; 4 M; 20.02 mmol). The mixture was stirred at RT for 16 h. Solvents were concentrated to dryness to afford the title compound as a white powder (137 mg; 71%). ¹H NMR (DMSO-d₆, 300 MHz) δ 8.42 (dd, J=6.9, 2.1 Hz, 1H), 8.27-8.22 (m, 1H), 8.13 (d, J=2.1 Hz, 1H), 8.09 (dd, J=8.5, 2.3 Hz, 1H), 7.57 (t, J=9.1 Hz, 1H), 7.30 (d, J=8.9 Hz, 1H), 4.83 (sept., J=5.9 Hz, 1H), 4.51 (s, 2H), 4.48 (s, 2H), 4.14 (s, 2H), 3.43 (s, 3H), 2.81 (s, 3H), 1.34 (d, J=6.0 Hz, 6H). LC/MS (Method B): 442.3 (M−H)⁻, 444.3 (M+H)⁺. HPLC (Method A) Rt 3.62 min (Purity: 98.6%).

Example 159

Methyl [(3-{5-[2-(methoxymethyl)-2'-methylbiphenyl-4-yl]-1,2,4-oxadiazol-3-yl}benzyl)oxy]acetate

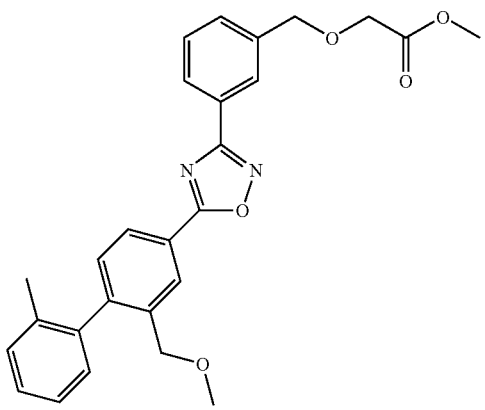

Step 1: (3-{5-[2-(methoxymethyl)-2'-methylbiphenyl-4-yl]-1,2,4-oxadiazol-3-yl}phenyl)methanol The title compound was prepared following procedure described in example 140, step 1, starting from Intermediate 72. The title compound was obtained as colorless oil. $^1$H NMR: (DMSO-$d_6$, 300 MHz) δ 8.33 (brs, 2H), 8.14 (m, 2H), 8 (m, 1H), 7.70 (m, 1H), 7.56 (m, 2H), 7.42 (m, 1H), 7.38-7.25 (m, 3H), 7.15 (m, 1H), 5.42 (m, 1H), 4.63 (m, 2H), 4.23 (d, J=12.7 Hz, 1H), 4.17 (d, J=12.7 Hz, 1H), 3.25 (s, 3H), 2.04 (s, 3H). LC/MS (Method B): 387.2 (M+H)⁺.

Step 2: Methyl [(3-{5-[2-(methoxymethyl)-2'-methylbiphenyl-4-yl]-1,2,4-oxadiazol-3-yl}benzyl)oxy]acetate To a solution of (3-{5-[2-(methoxymethyl)-2'-methylbiphenyl-4-yl]-1,2,4-oxadiazol-3-yl}phenyl)methanol, obtained in step 1, (400 mg; 1.04 mmol) in dry DMF (8 000 µl) at 0° C., sodium hydride (53.82 mg; 1.35 mmol) was added and the reaction stirred at 0° C. for 10 min. Methyl bromoacetate (143.08 µl; 1.55 mmol) was then added and the reaction mixture stirred 1 h at 0° C. and at RT overnight. EtOAc was added and the organic phase was washed with H₂O, dried over MgSO₄, filtered off and concentrated. The crude material was purified by flash chromatography (EtOAc/CHex) to afford the title compound as a colorless oil. $^1$H NMR: (DMSO-$d_6$, 300 MHz) δ 8.33 (brs, 2H), 8.18 (dd, J=1.8 Hz, 7.9 Hz, 1H), 8.13 (brs, 1H), 8.07 (m, 1H), 7.61 (m, 2H), 7.43 (d, J=7.9 Hz, 1H), 7.38-7.25 (m, 3H), 7.15 (m, 1H), 4.70 (s, 2H), 4.27 (s, 2H), 4.23 (d, J=12.7 Hz, 1H), 4.17 (d, J=12.7 Hz, 1H), 3.70 (s, 3H), 3.25 (s, 3H), 2.04 (s, 3H). LC/MS (Method B): 459.2 (M+H)⁺. HPLC (Method A) Rt: 5.82 min (purity: 97%).

Example 160

[(3-{5-[2-(methoxymethyl)-2'-methylbiphenyl-4-yl]-1,2,4-oxadiazol-3-yl}benzyl)oxy]acetic acid

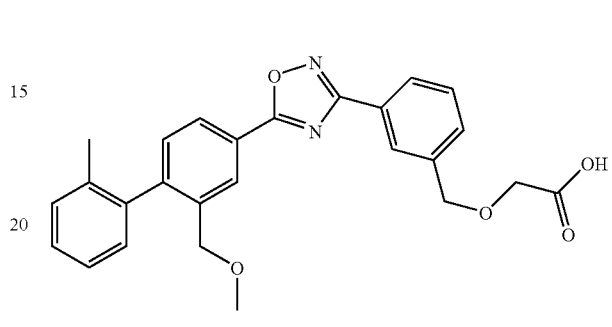

Step 1: tert-butyl [(3-{5-[2-(methoxymethyl)-2'-methylbiphenyl-4-yl]-1,2,4-oxadiazol-3-yl}benzyl)oxy]acetate To a solution of (3-{5-[2-(methoxymethyl)-2'-methylbiphenyl-4-yl]-1,2,4-oxadiazol-3-yl}phenyl)methanol, prepared as in example 159, step 1, (500 mg, 1.29 mmol) in toluene (10 mL) were added tert-butyl bromoacetate (215 µl, 1.45 mmol) and tetrabutylammonium hydrogen sulfate (45 mg, 0.13 mmol), followed by a 33% aqueous solution of sodium hydroxide (10 mL). The biphasic mixture was stirred strongly at RT for 45 minutes. The aqueous layer was removed. The organic layer was diluted with Et₂O (20 mL) and washed with water (10 mL), then brine (10 mL). The organic layer was dried (MgSO₄) and the solvents were removed under reduced pressure to give a yellow oil. This oil was purified by flash chromatography on silica (cHex/EtOAc) to give the title compound as a colorless oil. LC/MS (Method A): 501.4 (M+H)⁺. HPLC (Method A) Rt: 6.52 min (purity: 99.5%).

Step 2: [(3-{5-[2-(methoxymethyl)-2'-methylbiphenyl-4-yl]-1,2,4-oxadiazol-3-yl}benzyl)oxy]acetic acid

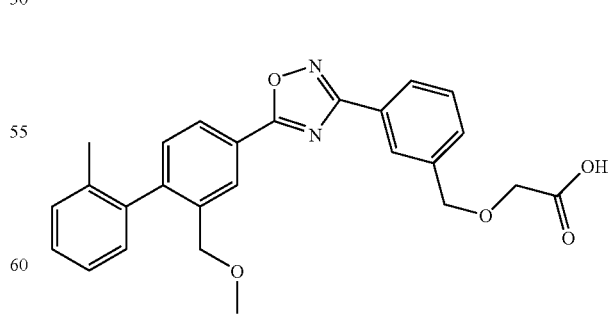

Tert-butyl [(3-{5-[2-(methoxymethyl)-2'-methylbiphenyl-4-yl]-1,2,4-oxadiazol-3-yl}benzyl)oxy]acetate (411 mg, 0.82 mmol) was dissolved in a 4M solution of HCl in dioxane (5 mL). The resulting mixture was stirred at RT for 5 hours.

The reaction mixture was concentrated under reduced pressure to give the title compound as a colorless oil (298 mg, 82%). $^1$H NMR (DMSO-$d_6$, 300 MHz): d=12.75 (brs, 1H), 8.33 (d, J=1.5 Hz, 1H), 8.18 (dd, J=7.9, 1.8 Hz, 1H), 8.13 (brs, 1H), 8.06 (m, 1H), 7.61 (m, 2H), 7.43 (d, J=8.0H, 1H), 7.37-7.26 (m, 3H), 7.15 (d, J=7.0 Hz, 1H), 4.68 (s, 2H), 4.23 (d, 2H), 4.17 (d, J=12.7 Hz, 1H), 4.17 (d, J=12.7 Hz, 1H), 4.16 (s, 2H), 3.25 (s, 3H), 2.04 (s, 3H). LC/MS (Method A): 445.3 (M+H)$^+$. 443.4 (M−H)$^−$. HPLC (Method A) Rt: 5.18 min (purity: 97.5%).

Example 161

[2-(3-{5-[2-(methoxymethyl)-2'-methylbiphenyl-4-yl]-1,2,4-oxadiazol-3-yl}phenyl)ethoxy]acetic acid

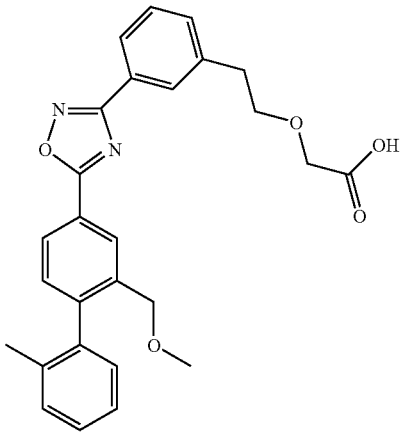

Step 1: tert-butyl [2-(3-{5-[2-(methoxymethyl)-2'-methylbiphenyl-4-yl]-1,2,4-oxadiazol-3-yl}phenyl)ethoxy]acetate The title compound was obtained following procedure and work up described for example 150, step 1, but starting from 2-(methoxymethyl)-2'-methylbiphenyl-4-carbonyl chloride obtained in example 150, step 1 (300 mg; 1.09 mmol) and Intermediate 65 (353 mg, 1.2 mmol). It was isolated as a colorless oil.

Step 2: [2-(3-{5-[2-(methoxymethyl)-2'-methylbiphenyl-4-yl]-1,2,4-oxadiazol-3-yl}phenyl)ethoxy]acetic acid The title compound was obtained following procedure and work up described for example 150, step 2, but starting from tert-butyl [2-(3-{5-[2-(methoxymethyl)-2'-methylbiphenyl-4-yl]-1,2,4-oxadiazol-3-yl}phenyl)ethoxy]acetate, obtained in step 1. It was isolated as a colorless sticky oil. $^1$H NMR (DMSO-$d_6$, 300 MHz) δ 12.6 (bs, 1H), 8.33-8.32 (m, 1H), 8.19-8.16 (m, 1H), 8.01-7.94 (m, 2H), 7.54-7.53 (m, 2H), 7.42 (d, J=8 Hz, 1H), 7.37-7.25 (m, 3H), 7.16-7.14 (m, 1H), 4.25-4.14 (m, 2H), 4.08-4.08 (m, 2H), 3.76 (m, 3H), 3.52 (s, 3H), 3-2.95 (m, 2H), 2.04 (s, 3H). LC/MS (Method B): 459.3 (M+H)$^+$. HPLC (Method A) Rt 4.53 min (purity: 97.4%).

Example 162

4-(4-{5-[2'-ethyl-2-(methoxymethyl)biphenyl-4-yl]-1,2,4-oxadiazol-3-yl}-2-fluorophenoxy)butanoic acid

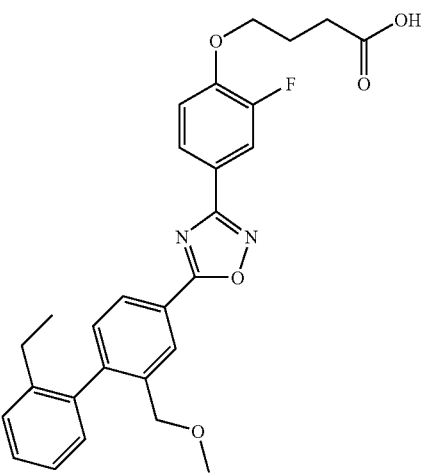

Step 1: ethyl 4-(4-{5-[2'-ethyl-2-(methoxymethyl)biphenyl-4-yl]-1,2,4-oxadiazol-3-yl}-2-fluorophenoxy)butanoate The title compound was prepared following procedure described for example 4, step 1, but starting from Intermediate 36 (202.74 mg; 0.75 mmol) and Intermediate 66 (234.54 mg; 0.83 mmol). The reaction mixture was filtered through a SPE NH$_2$ column (10 g) and rinsed with ACN. The filtrate was passed through a SPE SCX column (10 g) and rinsed with ACN. After evaporation of the solvents, the crude product was purified by flash chromatography (c-hex/(DCM/EtOAc 1:1) gradient from 1:0 to 1:1), affording the title compound as a colorless oil. $^1$H NMR (CDCl$_3$) δ 8.41 (d, J=1.3 Hz, 1H), 8.15 (dd, J=7.9, 1.8 Hz, 1H), 7.95-7.90 (m, 2H), 7.41-7.34 (m, 3H), 7.29-7.23 (m, 1H), 7.12-7.05 (m, 2H), 4.22-4.13 (m, 6H), 3.33 (s, 3H), 2.57 (t, J=7.2 Hz, 2H), 2.50-2.28 (m, 2H), 2.24-2.17 (m, 2H), 1.27 (t, J=7.2 Hz, 3H), 1.05 (t, J=7.5 Hz, 3H). LC/MS (Method B): 519.4 (M+H)$^+$. HPLC (Method A) Rt 6.62 min (Purity: 99.9%).

Step 2: 4-(4-{5-[2'-ethyl-2-(methoxymethyl)biphenyl-4-yl]-1,2,4-oxadiazol-3-yl}-2-fluorophenoxy)butanoic acid The title compound was prepared following procedure described for example 4, step 2, but starting from ethyl 4-(4-{5-[2'-ethyl-2-(methoxymethyl)biphenyl-4-yl]-1,2,4-oxadiazol-3-yl}-2-fluorophenoxy)butanoate, obtained in step 1. Solvents were concentrated and EtOAc (20 mL) was added. It was washed with water. The organic extract was dried over magnesium sulfate, filtered and concentrated under vacuum to afford the title compound as a slightly yellow solid. $^1$H NMR (DMSO-$d_6$, 300 MHz) δ 12.28 (br s, 1H), 8.28 (s, 1H), 8.13 (d, J=5.6 Hz, 1H), 7.91-7.83 (m, 2H), 7.43-7.39 (m, 4H), 7.31-7.26 (m, 1H), 7.11 (d, J=7.4 Hz, 1H), 4.23-4.10 (m, 4H), 3.24 (s, 3H), 2.44-2.21 (m, 4H), 2.04-1.95 (m, 2H), 0.98 (t, J=7.5 Hz, 3H). LC/MS (Method B): 491.3 (M+H)⁺. HPLC (Method A) Rt 5.74 min (Purity: 100.0%).

Example 163
ethyl 4-(2-fluoro-4-{5-[3-(methoxymethyl)-4-(2-methylpiperidin-1-yl)phenyl]-1,2,4-oxadiazol-3-yl}phenoxy)butanoate

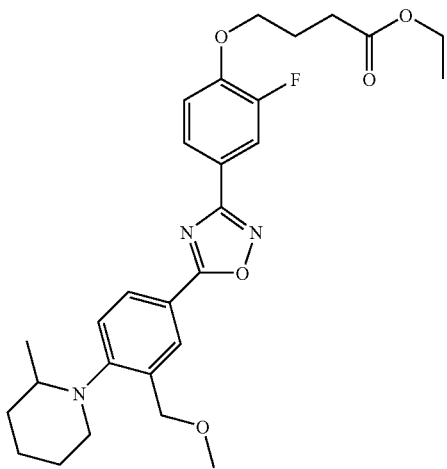

The title compound was prepared following procedure described for example 141, step 1, but starting from Intermediate 58 (158 mg; 0.60 mmol) and Intermediate 66 (162.04 mg; 0.57 mmol), the crude mixture was purified by flash chromatography (c-hex/(DCM/EtOAc 1:1) gradient from 1:0 to 1:1) to afford the title compound as a colorless oil. ¹H NMR (CDCl₃) δ 8.30 (d, J=2.1 Hz, 1H), 8.07 (dd, J=8.2, 2.0 Hz, 1H), 7.92-7.87 (m, 2H), 7.26 (d, J=8.4 Hz, 1H), 7.06 (t, J=8.5 Hz, 1H), 4.67-4.61 (m, 2H), 4.20-4.13 (m, 4H), 3.49 (s, 3H), 3.17 (br s, 1H), 3.06-3.03 (m, 1H), 2.65 (br s, 1H), 2.57 (t, J=7.3 Hz, 2H), 2.19 (quint, J=6.6 Hz, 2H), 1.86-1.70 (m, 4H), 1.51-1.48 (m, 2H), 1.27 (t, J=7.1 Hz, 3H), 0.90 (d, J=6.0 Hz, 3H). LC/MS (Method B): 512.4 (M+H)⁺. HPLC (Method A) Rt 4.62 min (Purity: 100.0%).

Example 164
4-(3-{5-[3-(methoxymethyl)-4-(2-methylpiperidin-1-yl)phenyl]-1,2,4-oxadiazol-3-yl}phenoxy)butanoic acid

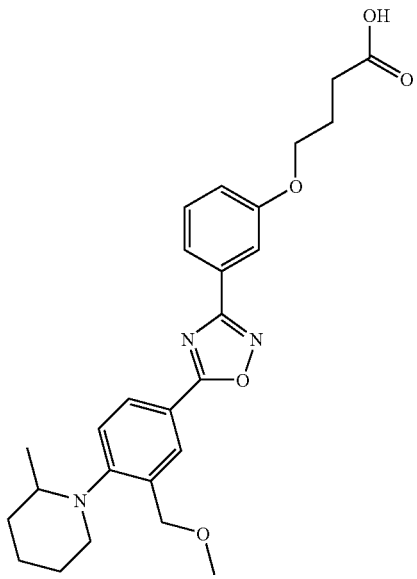

Step 1: ethyl 4-(3-{5-[3-(methoxymethyl)-4-(2-methylpiperidin-1-yl)phenyl]-1,2,4-oxadiazol-3-yl}phenoxy)butanoate The title compound was prepared following procedure described for example 141, step 1, but starting from Intermediate 58 (158 mg; 0.60 mmol) and Intermediate 67 (151.79 mg; 0.57 mmol), the crude mixture was purified by flash chromatography (c-hex/(DCM/EtOAc 1:1) gradient from 1:0 to 1:1) to afford the title compound as a colorless oil. ¹H NMR (CDCl₃) δ 8.32 (d, J=2.1 Hz, 1H), 8.09 (dd, J=8.2, 2.1 Hz, 1H), 7.77 (dd, J=7.7, 1.2 Hz, 1H), 7.69 (dd, J=2.5, 1.4 Hz, 1H), 7.40 (t, J=8.0 Hz, 1H), 7.26 (d, J=8.3 Hz, 1H), 7.04 (ddd, J=8.3, 2.6, 0.9 Hz, 1H), 4.68-4.57 (m, 2H), 4.20-4.09 (m, 4H), 3.49 (s, 3H), 3.16 (br s, 1H), 3.06-3.02 (m, 1H), 2.65-2.62 (m, 1H), 2.56 (t, J=7.3 Hz, 2H), 2.20-2.11 (m, 2H), 1.86-1.69 (m, 4H), 1.49-1.45 (m, 2H), 1.27 (t, J=7.2 Hz, 3H), 0.89 (d, J=6.2 Hz, 3H). LC/MS (Method B): 494.5 (M+H)⁺. HPLC (Method A) Rt 4.59 min (Purity: 98.9%).

Step 2: 4-(3-{5-[3-(methoxymethyl)-4-(2-methylpiperidin-1-yl)phenyl]-1,2,4-oxadiazol-3-yl}phenoxy)butanoic acid The title compound was prepared following procedure described for example 4, step 2, but starting from ethyl 4-(3-{5-[3-(methoxymethyl)-4-(2-methylpiperidin-1-yl)phenyl]-1,2,4-oxadiazol-3-yl}phenoxy)butanoate, obtained in step 1. Solvents were concentrated and EtOAc (20 mL) was added. It was washed with 1M citric acid solution. The organic extract was dried over magnesium sulfate, filtered and concentrated under vacuum to afford the title compound as a yellow oil (128 mg; 82%). ¹H NMR (DMSO-d₆, 300 MHz) δ 12.17 (br s, 1H), 8.18 (d, J=2.1 Hz, 1H), 8.07 (dd, J=8.3, 2.2 Hz, 1H), 7.69-7.66 (m, 1H), 7.58-7.57 (m, 1H), 7.51 (t, J=8.0 Hz, 1H), 7.38 (d, J=8.5 Hz, 1H), 7.19 (ddd, J=8.4, 2.6, 0.8 Hz, 1H), 4.61-4.51 (m, 2H), 4.10 (t, J=6.3 Hz, 2H), 3.41 (s, 3H), 3.25-3.18 (m, 1H), 3.07-3 (m, 1H), 2.66-2.59 (m, 1H), 2.43 (t, J=7.3 Hz, 2H), 2.04-1.94 (m, 2H), 1.87-1.60 (m, 4H), 1.53-1.35 (m, 2H), 0.86 (d, J=6.2 Hz, 3H). LC/MS (Method B): 464.4 (M−H)⁻, 466.3 (M+H)⁺. HPLC (Method A) Rt 3.67 min (Purity: 97.4%).

Example 165
4-(2-fluoro-4-{5-[3-(methoxymethyl)-4-(2-methylpiperidin-1-yl)phenyl]-1,2,4-oxadiazol-3-yl}phenoxy)butanoic acid

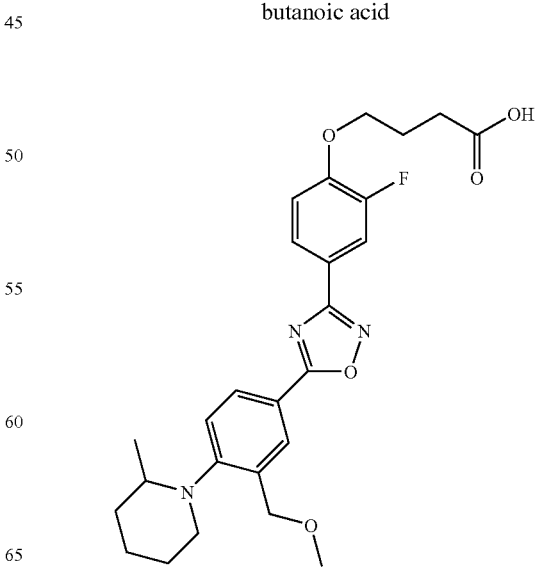

The title compound was prepared following procedure described for example 4, step 2, but starting from example 163. Solvents were concentrated and EtOAc (20 mL) was added. It was washed with 1M citric acid solution. The organic extract was dried over magnesium sulfate, filtered and concentrated under vacuum to afford the title compound as a yellow oil (128 mg, quantitative). $^1$H NMR (DMSO-$d_6$, 300 MHz) δ 12.19 (br s, 1H), 8.17 (d, J=2.1 Hz, 1H), 8.06 (dd, J=8.4, 2.2 Hz, 1H), 7.90-7.82 (m, 2H), 7.42-7.36 (m, 2H), 4.60-4.50 (m, 2H), 4.18 (t, J=6.4 Hz, 2H), 3.41 (s, 3H), 3.27-3.18 (m, 1H), 3.07-3 (m, 1H), 2.66-2.58 (m, 1H), 2.42 (t, J=7.3 Hz, 2H), 2.05-1.96 (m, 2H), 1.88-1.62 (m, 4H), 1.55-1.34 (m, 2H), 0.86 (d, J=6.2 Hz, 3H). LC/MS (Method B): 484.3 (M+H)$^+$. HPLC (Method A) Rt 3.71 min (Purity: 99.5%).

Example 166

(2-fluoro-{5-[2-(methoxymethyl)-2'-methylbiphenyl-4-yl]-1,2,4-oxadiazol-3-yl}phenoxy)acetic acid

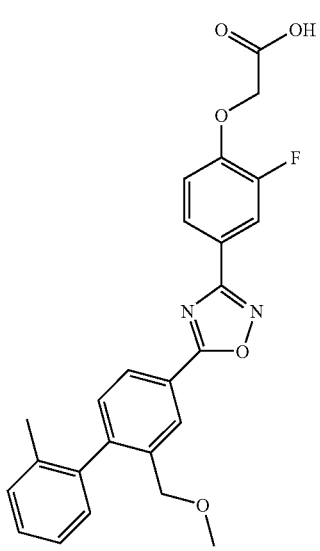

Step 1: tert-butyl (2-fluoro-4-{5-[2-(methoxymethyl)-2'-methylbiphenyl-4-yl]-1,2,4-oxadiazol-3-yl}phenoxy)acetate The title compound was prepared following procedure described for example 4, step 1, but starting from Intermediate 28 (1 281.50 mg; 5 mmol) and Intermediate 49 (1 421.44 mg; 5 mmol). The reaction mixture was filtered through a SPE NH$_2$ column (10 g) and rinsed with ACN. The filtrate was passed through a SPE SCX column (10 g) and rinsed with ACN. After evaporation of the solvents, the crude product was purified by flash chromatography (c-hex/(DCM/EtOAc 1:1) gradient from 1:0 to 1:1), affording the title compound as a white powder. $^1$H NMR (CDCl$_3$) δ 8.41 (d, J=1.3 Hz, 1H), 8.15 (dd, J=7.8, 1.8 Hz, 1H), 7.98-7.91 (m, 2H), 7.36-7.23 (m, 4H), 7.13 (d, J=7.1 Hz, 1H), 7.03-6.97 (m, 1H), 4.68 (s, 2H), 4.22 (s, 2H), 3.33 (s, 3H), 2.07 (s, 3H), 1.49 (s, 9H). LC/MS (Method B): 505.2 (M+H)$^+$. HPLC (Method A) Rt 6.36 min (Purity: 98.6%).

Step 2: (2-fluoro-4-{5-[2-(methoxymethyl)-2'-methylbiphenyl-4-yl]-1,2,4-oxadiazol-3-yl}phenoxy)acetic acid To tert-butyl (2-fluoro-4-{5-[2-(methoxymethyl)-2'-methylbiphenyl-4-yl]-1,2,4-oxadiazol-3-yl}phenoxy)acetate, obtained in step 1 was added HCl 4M in dioxane (40 mL; 4 M; 160 mmol). The mixture was stirred at RT for 16 h. Solvents were concentrated to dryness to afford the title compound as a white powder. $^1$H NMR (DMSO-$d_6$, 300 MHz) δ 13.24 (br s, 1H), 8.31 (s, 1H), 8.16 (d, J=8.2 Hz, 1H), 7.92 (s, 1H), 7.89 (s, 1H), 7.42 (d, J=8.0 Hz, 1H), 7.35-7.30 (m, 4H), 7.15 (d, J=7.1 Hz, 1H), 4.93 (s, 2H), 4.25-4.14 (m, 2H), 3.25 (s, 3H), 2.04 (s, 3H). LC/MS (Method B): 447.2 (M−H)$^−$, 449.1 (M+H)$^+$. HPLC (Method A) Rt 5.18 min (Purity: 100.0%). CHN analysis: [$C_{25}H_{21}N_2O_5F$-$0.1H_2O$] Calculated: C, 66.69%; H, 4.75%; N, 6.22%. Found: C, 66.53%; H, 4.71%; N, 6.18%.

Example 167

(3-{5-[2-(methoxymethyl)-2'-methylbiphenyl-4-yl]-1,2,4-oxadiazol-3-yl}phenoxy)acetic acid

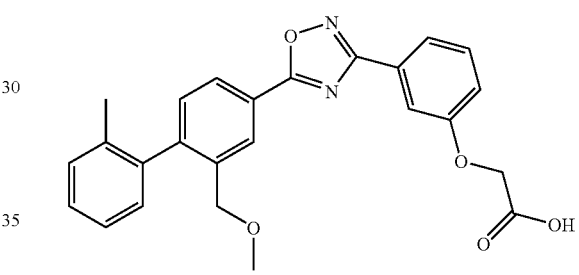

A solution of Intermediate 28 (141 mg, 0.55 mmol) and DIEA (0.2 mL, 1.1 mmol) was prepared in anhydrous DMF (2 mL) and cooled at 0° C. HATU (210 mg, 1.1 mmol) was added at once and the resulting mixture was stirred at RT for 15 minutes. A solution of [3-(n-hydroxycarbamimidoyl)-phenoxy]-acetic acid, obtained according the procedure described for Intermediate 49, starting from 4-hydroxybenzonitrile (Aldrich), (105 mg, 0.5 mmol) and DIEA (0.1 mL, 0.5 mmol) in anhydrous DMF (1 mL) was added. The resulting mixture was stirred at RT for 30 minutes, then at 100° C. for 36 hours. The reaction mixture was cooled at RT, then diluted with Et$_2$O and washed with a 1N aqueous solution of HCl and brine. The aqueous layers were extracted with Et$_2$O. The organic layers were combined, dried (MgSO$_4$) and the solvents were removed under reduced pressure. The residue was purified by flash chromatography on silica (DCM/MeOH) to give the title compound as pale yellow foam. $^1$HNMR (CDCl$_3$; 300 MHz): d=8.43 (brs, 1H), 8.17 (dd, J=7.9, 1.6 Hz, 1H), 7.88 (d, J=7.7 Hz, 1H), 7.76 (m, 1H), 7.47 (dd, J=8.0, 7.9 Hz, 1H), 7.35-7.24 (m, 4H), 7.13 (m, 2H), 4.81 (s, 2H), 4.23 (s, 2H), 3.33 (s, 3H), 2.06 (s, 3H). LC/MS (Method A): 431.1 (M+H)⁺; 429.2 (M–H)⁻. HPLC (Method A), Rt: 5.07 min (purity: 97.2%).

Example 168

4-(2-fluoro-4-{5-[2-(methoxymethyl)-2'-methylbiphenyl-4-yl]-1,2,4-oxadiazol-3-yl}phenoxy)butanoic acid

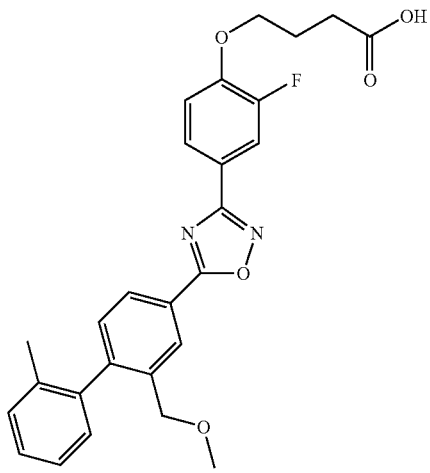

Step 1: ethyl 4-(2-fluoro-4-{5-[2-(methoxymethyl)-2'-methylbiphenyl-4-yl]-1,2,4-oxadiazol-3-yl}phenoxy)butanoate The title compound was prepared following procedure described for example 4, step 1, but starting from Intermediate 28 (192.22 mg; 0.75 mmol) and Intermediate 66 (234.54 mg; 0.83 mmol). The reaction mixture was filtered through a SPE NH₂ column (2×2 g) and rinsed with ACN. The filtrate was passed through a SPE SCX column (2×2 g) and rinsed with ACN. After evaporation of the solvents, the crude product was purified by flash chromatography (c-hex/(DCM/EtOAc 1:1) gradient from 1:0 to 1:1), affording the title compound as a colorless oil. ¹H NMR (CDCl₃) δ 8.41 (d, J=1.4 Hz, 1H), 8.15 (dd, J=7.8, 1.9 Hz, 1H), 7.95-7.90 (m, 2H), 7.36-7.23 (m, 4H), 7.14-7.05 (m, 2H), 4.27-4.13 (m, 6H), 3.33 (s, 3H), 2.57 (t, J=7.2 Hz, 2H), 2.19 (quint., J=6.6 Hz, 2H), 2.08 (s, 3H), 1.27 (t, J=7.2 Hz, 3H). LC/MS (Method B): 505.3 (M+H)⁺. HPLC (Method A) Rt 6.24 min (Purity: 98.9%).

Step 2: 4-(2-fluoro-4-{5-[2-(methoxymethyl)-2'-methylbiphenyl-4-yl]-1,2,4-oxadiazol-3-yl}phenoxy)butanoic acid The title compound was prepared following procedure described for example 4, step 2, but starting from ethyl 4-(2-fluoro-4-{5-[2-(methoxymethyl)-2'-methylbiphenyl-4-yl]-1,2,4-oxadiazol-3-yl}phenoxy)butanoate, obtained in step 1. Solvents were concentrated and EtOAc (20 mL) was added. It was washed with water and NaCl sat. solution. The organic extract was dried over magnesium sulfate, filtered and concentrated under vacuum to afford the title compound as a white powder (125 mg; 92%). ¹H NMR (DMSO-d₆, 300 MHz) δ 12.21 (br s, 1H), 8.31 (d, J=1.5 Hz, 1H), 8.16 (dd, J=7.9, 1.9 Hz, 1H), 7.94-7.85 (m, 2H), 7.42 (d, J=8.1 Hz, 1H), 7.38-7.27 (m, 4H), 7.15 (d, J=7.2 Hz, 1H), 4.25-4.14 (m, 4H), 3.25 (s, 3H), 2.43 (t, J=7.3 Hz, 2H), 2.06-1.99 (m, 5H). LC/MS (Method B): 477.2 (M+H)⁺. HPLC (Method A) Rt 5.40 min (Purity: 98.7%).

Example 169

(2-fluoro-4-{5-[3-(methoxymethyl)-4-(2-methylpiperidin-1-yl)phenyl]-1,2,4-oxadiazol-3-yl}phenoxy) acetic acid, hydrochloride salt

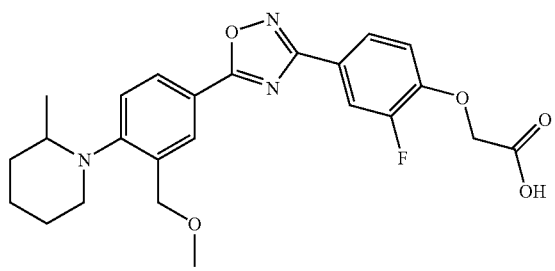

Step 1: tert-butyl (2-fluoro-4-{5-[3-(methoxymethyl)-4-(2-methylpiperidin-1-yl)phenyl]-1,2,4-oxadiazol-3-yl}phenoxy)acetate The title compound was prepared following procedure described in Example 113 starting from Intermediate 49. The title compound was obtained as a pale yellow oil. LC/MS (Method A): 512.4 (M+H)⁺. HPLC (Method A) Rt: 4.82 min (Purity: 99.9%).

Step 2: (2-fluoro-4-{5-[3-(methoxymethyl)-4-(2-methylpiperidin-1-yl)phenyl]-1,2,4-oxadiazol-3-yl}phenoxy)acetic acid, hydrochloride salt Tert-butyl (2-fluoro-4-{5-[3-(methoxymethyl)-4-(2-methylpiperidin-1-yl)phenyl]-1,2,4-oxadiazol-3-yl}phenoxy)acetate (340 mg, 0.66 mmol) was dissolved in a 4M solution of HCl in dioxane (4 mL). The resulting mixture was stirred at RT for 15 hours. The precipitate was filtered off, washed with Et₂O (3×) and pentane (3×), then dried under reduced pressure to give the title compound an as white powder (287 mg, 88%). ¹HNMR (DMSO-d₆, 300 MHz): 8.18 (brs, 1H), 8.07 (brs, 1H), 7.86 (m, 2H), 7.40 (brs, 1H), 7.30 (dd, J=8.6, 8.5 Hz, 1H), 4.91 (s, 2H), 4.58 (brs, 2H), 3.41 (s, 3H), 3.26 (m, 1H), 3.07 (m, 1H), 2.65 (m, 1H), 1.84-1.47 (m, 6H), 0.87 (brs, 3H). LC/MS (Method A): 456.3 (M+H)+; 454.4 (M–H)–. HPLC (Method A) Rt: 3.42 min (Purity: 99.7%).

Example 170
3-{5-[2-(methoxymethyl)-2'-methylbiphenyl-4-yl]-1,2,4-oxadiazol-3-yl}benzenesulfonamide

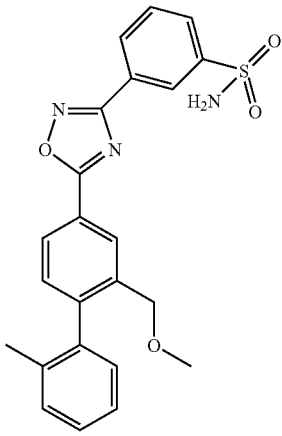

The title compound was obtained following procedure and work up described for example 107, step 1, but starting from 3-(aminosulfonyl)-N'-hydroxybenzenecarboximidamide, prepared as described in WO 2006/013104 A1 from 3-cyanobenzene-1-sulfonamide (Maybridge; GK 03054), (1.50 g; 6.97 mmol) and Intermediate 28 (1.79 g; 6.97 mmol), followed by a recrystallization from DCM gave the title compound as a white powder. $^{1}$H NMR (DMSO-$d_6$, 300 MHz) δ 8.58-8.57 (m, 1H), 8.35-8.32 (m, 2H), 8.20-8.17 (m, 1H), 8.08-8.05 (m, 1H), 7.83 (t, J=7.8 Hz, 1H), 7.59 (bs, 2H), 7.43 (d, J=8 Hz, 1H), 7.36-7.27 (m, 3H), 7.16-7.13 (m, 1H), 4.23 (d, J=12.6 Hz, 1H), 4.16 (d, J=12.6 Hz, 1H), 3.25 (s, 3H), 2.03 (s, 3H). LC/MS (Method B): 436.3 (M+H)+. HPLC (Method A) Rt 5.37 min (purity: 99.6%).

Example 171

4-[5-(2,2'-dimethylbiphenyl-4-yl)-1,2,4-oxadiazol-3-yl]-2-fluorobenzamide

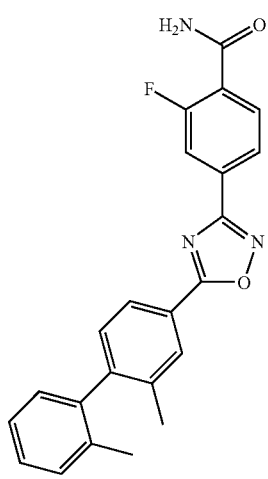

Step 1: N-(2,4-dimethoxybenzyl)-4-[5-(2,2'-dimethylbiphenyl-4-yl)-1,2,4-oxadiazol-3-yl]-2-fluorobenzamide The title compound was prepared following procedure described for example 54, step 1, but starting from 2,4-dimethoxybenzylamine (ALDRICH; 432725; 58.02 μl; 0.39 mmol). The reaction mixture was filtered through a SPE NH$_2$ column (2 g) and rinsed with ACN. Evaporation of the solvents afforded the title compound as a yellowish oil (201 mg; 97%). $^{1}$H NMR (DMSO-$d_6$, 300 MHz) δ 8.81-8.77 (m, 1H), 8.18 (d, J=1.3 Hz, 1H), 8.08 (dd, J=8.0, 1.4 Hz, 1H), 8.02 (dd, J=7.9, 1.6 Hz, 1H), 7.94 (dd, J=10.6, 1.4 Hz, 1H), 7.85 (t, J=7.6 Hz, 1H), 7.40-7.27 (m, 4H), 7.18 (d, J=8.3 Hz, 1H), 7.14-7.12 (m, 1H), 6.58 (d, J=2.4 Hz, 1H), 6.52 (dd, J=8.3, 2.3 Hz, 1H), 4.39 (d, J=5.6 Hz, 2H), 3.82 (s, 3H), 3.76 (s, 3H), 2.14 (s, 3H), 2.03 (s, 3H). LC/MS (Method B): 538.4 (M+H)+. HPLC (Method A) Rt 6.66 min (Purity: 95.4%).

Step 2: 4-[5-(2,2'-dimethylbiphenyl-4-yl)-1,2,4-oxadiazol-3-yl]-2-fluorobenzamide Toluene-4-sulfonic acid monohydrate (141.53 mg; 0.74 mmol) was added to a mixture of N-(2,4-dimethoxybenzyl)-4-[5-(2,2'-dimethylbiphenyl-4-yl)-1,2,4-oxadiazol-3-yl]-2-fluorobenzamide, obtained in step 1 and toluene (2 mL). The mixture was heated at 110° C. The reaction was quenched with water (3 mL) and extracted with EtOAc (3×5 mL). The organic layer was then dried over magnesium sulfate, filtered and concentrated. The crude was purified with MD Autoprep, to afford the title compound as a white solid. LC/MS (Method B): 388.3 (M+H)+. HPLC (Method A) Rt 5.20 min (Purity: 100.0%).

Example 172

2-fluoro-N-(2-methoxyethyl)-4-{5-[2-(methoxymethyl)-2'-methylbiphenyl-4-yl]-1,2,4-oxadiazol-3-yl}benzamide

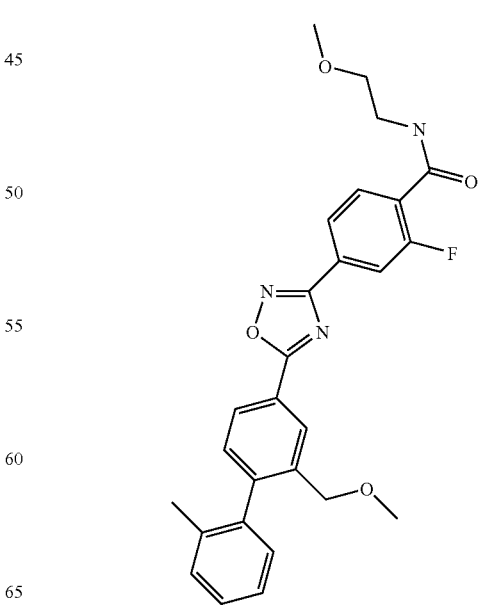

The title compound was prepared following procedure described in example 121 starting from 2-methoxyethylamine (59 µl; 0.69 mmol). The title compound was obtained as a sticky oil (170 mg, 78%). $^1$H NMR: (DMSO-d$_6$, 300 MHz) δ 8.55 (m, 1H), 8.33 (brs, 1H), 8.18 (m, 1H), 8.02 (m, 1H), 7.95 (m, 1H), 7.83 (m, 1H), 7.44 (m, 1H), 7.38-7.24 (m, 3H), 7.15 (m, 1H), 4.20 (m, 2H), 3.47 (m, 4H), 3.30 (s, 3H), 3.25 (s, 3H), 2.04 (s, 3H). LC/MS (Method B): 474.3 (M−H)$^−$; 476.2 (M+H)$^+$. HPLC (Method A), Rt: 5.23 min (purity: 100%).

Example 173

N-(2-cyanoethyl)-2-fluoro-{5-[2-(methoxymethyl)-2'-methylbiphenyl-4-yl]-1,2,4-oxadiazol-3-yl}benzamide

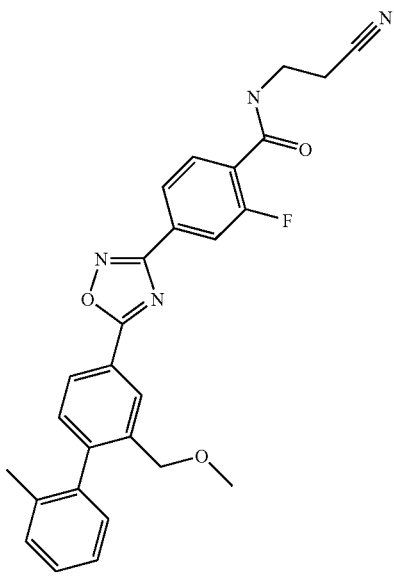

The title compound was prepared following procedure described in example 121 starting from N-(2-cyanoethyl)amine (48.13 mg; 0.69 mmol). The title compound was obtained as a white solid (160 mg, 74%). $^1$H NMR: (CDCl$_3$, 300 MHz) δ 8.42 (m, 1H), 8.24 (t, J=8 Hz 1H), 8.16 (dd, J=1.8 Hz, 8 Hz, 1H), 8.12 (dd, J=1.5 Hz, 8.2 Hz, 1H), 8.01 (dd, J=1.5 Hz, 12.6 Hz, 1H), 7.37-7.16 (m, 3H), 7.12 (m, 1H), 4.22 (m, 2H), 3.78 (m, 2H), 3.33 (s, 3H), 2.79 (t, J=6.5 Hz, 2H), 2.07 (s, 3H). LC/MS (Method B): 469.3 (M−H)$^−$; 471.2 (M+H)$^+$. HPLC (Method A), Rt: 5.13 min (purity: 99.7%).

Example 174

N-[2-(acetylamino)ethyl]-2-fluoro-4-{5-[2-(methoxymethyl)-2'-methylbiphenyl-4-yl]-1,2,4-oxadiazol-3-yl}benzamide

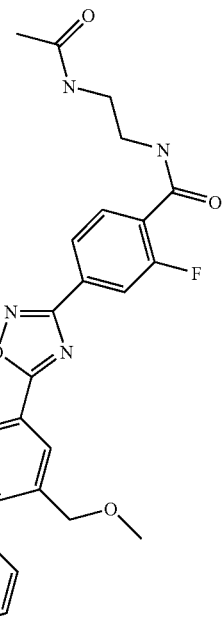

The title compound was prepared following procedure described in example 116, step 2, starting from methyl N-(2-amino-ethyl)-acetamide (16.01 mg; 0.12 mmol). The title compound was obtained as a white powder. $^1$H NMR: (CDCl$_3$, 300 MHz) δ 8.42 (m, 1H), 8.25-8.08 (m, 3H), 7.99 (dd, J=1.4 Hz, 12.4 Hz, 1H), 7.37-7.20 (m, 4H), 7.12 (m, 1H), 6.20 (m, 1H), 4.22 (m, 2H), 3.68 (m, 2H), 3.54 (m, 2H), 3.33 (s, 3H), 2.07 (s, 3H), 2.02 (s, 3H). LC/MS (Method B): 501.3 (M−H)$^−$; 503.2 (M+H)$^+$. HPLC (Method A), Rt: 4.6 min (purity: 98.7%).

Example 175

3-{4-[(3,3-difluoroazetidin-1-yl)carbonyl]-3-fluorophenyl}-5-[2-(methoxymethyl)-2'-methylbiphenyl-4-yl]-1,2,4-oxadiazole

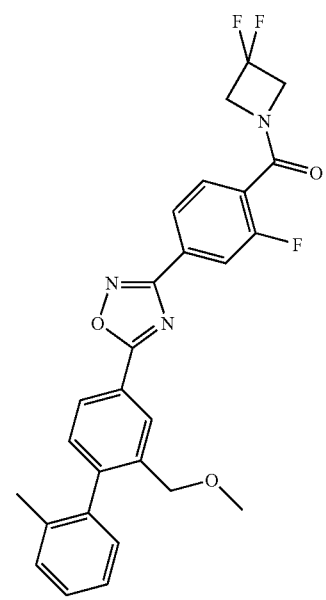

The title compound was prepared following procedure described in example 116, step 2, starting from ethyl 3,3-difluoroazetidine hydrochloride (16.01 mg; 0.12 mmol). The title compound was obtained as a white foam. ¹H NMR: (CDCl₃, 300 MHz) δ 8.42 (m, 1H), 8.16 (dd, J=1.7 Hz, 7.9 Hz, 1H), 8.09 (dd, J=1.3 Hz, 7.9 Hz, 1H), 7.98 (dd, J=1.3 Hz, 10.6 Hz, 1H), 7.77 (m, 1H), 7.36-7.23 (m, 4H), 7.12 (m, 1H), 4.50 (m, 4H), 4.22 (m, 2H), 3.33 (s, 3H), 2.07 (s, 3H). LC/MS (Method B): 494.2 (M+H)⁺. HPLC (Method A), Rt: 5.61 min (purity: 100%).

Example 176

N-[2-(5-ethyl-1,3-oxazol-2-yl)ethyl]-2-fluoro-4-{5-[2-(methoxymethyl)-2'-methylbiphenyl-4-yl]-1,2,4-oxadiazol-3-yl}benzamide

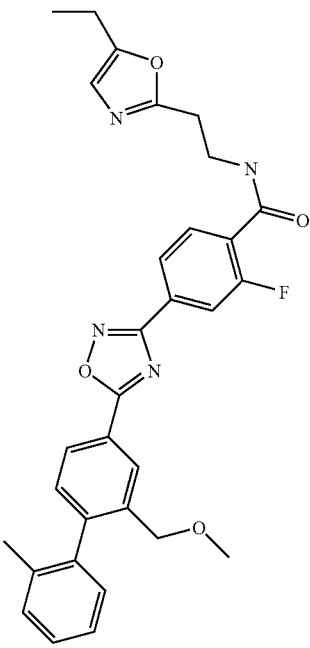

The title compound was prepared following procedure described in example 121 starting from 2-(5-ethyl-oxazol-2-yl)-ethylamine (36.10 mg; 0.26 mmol). The title compound was obtained as a colorless oil. ¹H NMR: (CD₃OD, 300 MHz) δ 8.41 (m, 1H), 8.21 (m, 1H), 8.08 (m, 1H), 7.98 (m, 1H), 7.87 (m, 1H), 7.41-7.23 (m, 4H), 7.12 (m, 1H), 6.72 (m, 1H), 4.22 (m, 2H), 3.79 (m, 2H), 3.33 (s, 3H), 3.08 (m, 2H), 2.69 (m, 2H), 2.07 (s, 3H), 1.24 (m, 3H). LC/MS (Method B): 539.3 (M−H)⁻; 541.2 (M+H)⁺. HPLC (Method A), Rt: 5.35 min (purity: 94.2%).

Example 177

2-fluoro-4-{5-[2-(methoxymethyl)-2'-methylbiphenyl-4-yl]-1,2,4-oxadiazol-3-yl}-N-[2-(1H-tetrazol-5-yl)ethyl]benzamide

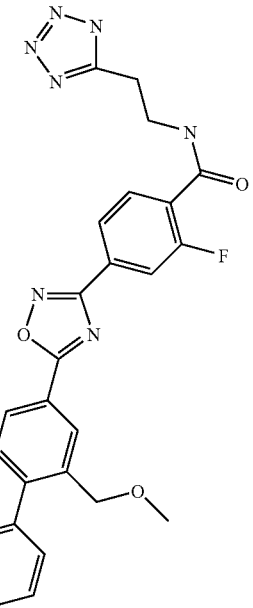

The title compound was prepared following procedure described in example 121 starting from 2-(1H-tetrazol-5-yl)-ethylamine.2HCl. The title compound was obtained as a white powder. ¹H NMR: (DMSO-d₆, 300 MHz) δ 8.71 (m, 1H), 8.33 (d, J=1.6 Hz, 1H), 8.18 (dd, J=1.8 Hz, 8 Hz, 1H), 8.03 (dd, J=1.5 Hz, 8 Hz, 1H), 7.95 (dd, J=1.5 Hz, 10.7 Hz, 1H), 7.83 (t, J=7.6 Hz, 1H), 7.44 (d, J=8 Hz, 1H), 7.39-7.26 (m, 3H), 7.15 (d, J=7 Hz, 1H), 4.21 (d, J=12.8 Hz, 1H), 4.18 (d, J=12.8 Hz, 1H), 3.67 (m, 2H), 3.25 (s, 3H), 3.18 (t, J=6.9 Hz, 2H), 2.04 (s, 3H). LC/MS (Method B): 512.3 (M−H)⁻; 514.2 (M+H)⁺. HPLC (Method A), Rt: 4.57 min (purity: 99.7%).

Example 178

4-{5-[2-(methoxymethyl)-2'-methylbiphenyl-4-yl]-1,2,4-oxadiazol-3-yl}benzamide

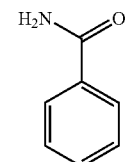
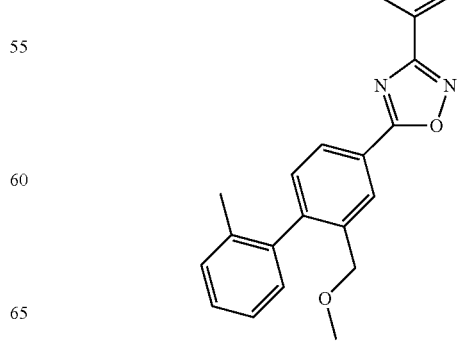

The title compound was obtained following procedure described for example 106 but starting from Intermediate 28 (149.42 mg; 0.58 mmol) and Intermediate 71 (94.96 mg; 0.53 mmol) as a light orange powder. $^1$H NMR (DMSO-d$_6$) δ 8.33 (bs, 1H), 8.21-8.16 (m, 4H), 8.10-8.08 (m, 2H), 7.56 (bs, 1H), 7.44-7.41 (m, 1H), 7.36-7.26 (m, 3H), 7.16-7.13 (m, 1H), 3.25 (s, 3H), 2.03 (s, 3H). LC/MS (Method B): 441.2 (M+H)$^+$. HPLC (Method A) Rt 5.16 min (Purity: 97.1%).

Example 179

2-fluoro-4-{5-[2-(methoxymethyl)-2'-methylbiphenyl-4-yl]-1,2,4-oxadiazol-3-yl}benzamide

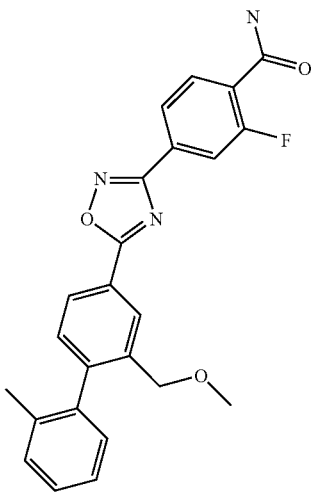

The title compound was prepared following procedure described for example 121 starting from ammonia in dioxane (2.3 mL; 0.50 M; 1.14 mmol). The title compound was obtained as a white powder. $^1$H NMR: (DMSO-d$_6$, 300 MHz) δ 8.33 (m, 1H), 8.18 (m, 1H), 8.02 (m, 1H), 7.97-7.77 (m, 4H), 7.44 (m, 1H), 7.38-7.24 (m, 4H), 7.15 (m, 2H), 4.20 (m, 2H), 3.25 (s, 3H), 2.04 (s, 3H). LC/MS 3 min: 417.9 (M+H)$^+$. HPLC (Method A), Rt: 4.79 min (purity: 97.1%).

Example 180

N-[2-(5-ethyl-2H-tetrazol-2-yl)ethyl]-2-fluoro-4-{5-[2-(methoxymethyl)-2'-methylbiphenyl-4-yl]-1,2,4-oxadiazol-3-yl}benzamide

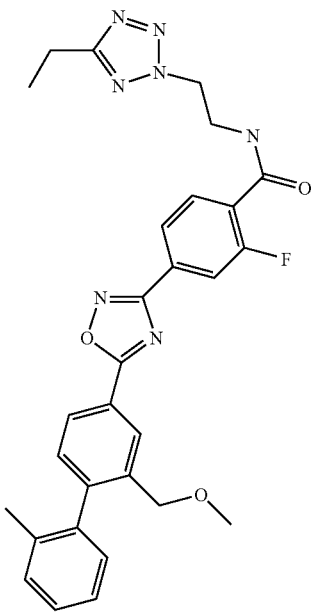

The title compound was prepared following procedure described in example 121 starting from 2-(5-ethyl-tetrazol-2-yl)-ethylamine. HCl (36.60 mg; 0.21 mmol). The title compound was obtained as an oil. $^1$H NMR: (DMSO-d$_6$, 300 MHz) δ 8.69 (m, 1H), 8.33 (brs, 1H), 8.18 (m, 1H), 8.03 (m, 1H), 7.95 (m, 1H), 7.78 (m, 1H), 7.43 (m, 1H), 7.40-7.22 (m, 3H), 7.15 (m, 1H), 4.82 (m, 2H), 4.20 (m, 2H), 3.79 (m, 2H), 3.25 (s, 3H), 2.86 (m, 2H), 2.04 (s, 3H). LC/MS (Method B): 539.6 (M−H)$^-$; 541.8 (M+H)$^+$. HPLC (Method A), Rt: 5.21 min (purity: 98.6%).

Example 181

N-(2-methoxyethyl)-3-{5-[2-(methoxymethyl)-2'-methylbiphenyl-4-yl]-1,2,4-oxadiazol-3-yl}benzamide

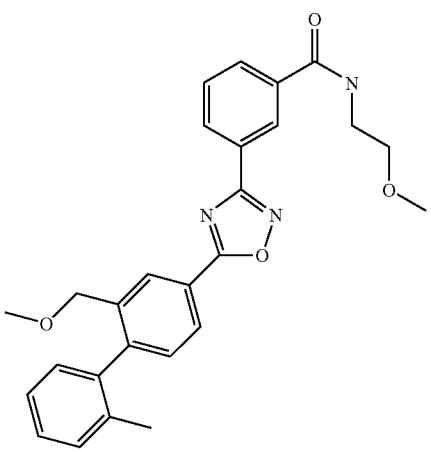

The title compound was prepared following procedure described example 121 starting from 2-methoxyethylamine (26.79 μl; 0.31 mmol). The title compound was obtained as a white foam. $^1$H NMR: (DMSO-d$_6$, 300 MHz) δ 8.84 (m, 1H), 8.35 (m, 1H), 8.27 (m, 1H), 8.19 (m, 1H), 8.10 (m, 1H), 7.72 (m, 1H), 7.43 (d, J=7.9 Hz, 1H), 7.39-7.25 (m, 3H), 7.15 (m, 1H), 4.23 (d, J=12.7 Hz, 1H), 4.17 (d, J=12.7 Hz, 1H), 3.49 (m, 4H), 3.29 (s, 3H), 3.26 (s, 3H), 2.04 (s, 3H). LC/MS (Method B): 456.3 (M−H)$^-$; 458.2 (M+H)$^+$. HPLC (Method A), Rt: 4.96 min (purity: 99%).

Example 182

3-{5-[2-(methoxymethyl)-2'-methylbiphenyl-4-yl]-1,2,4-oxadiazol-3-yl}benzamide

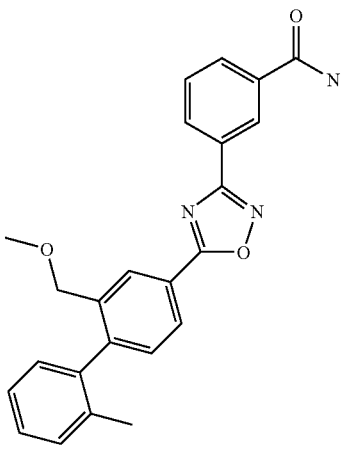

The title compound was prepared following procedure described example 121 starting from ammonia in dioxane (1.7 mL; 0.50 M; 0.84 mmol). The title compound was obtained as a white powder (50 mg, 100%). $^1$H NMR: (DMSO-d$_6$, 300 MHz) δ 8.63 (m, 1H), 8.34 (m, 1H), 8.26 (m, 2H), 8.20 (m, 1H), 8.13 (m, 1H), 7.71 (m, 1H), 7.59 (m, 1H), 7.43 (d, J=7.9 Hz, 1H), 7.38-7.20 (m, 3H), 7.15 (m, 1H), 4.23 (d, J=12.7 Hz, 1H), 4.17 (d, J=12.7 Hz, 1H), 3.26 (s, 3H), 2.04 (s, 3H). LC/MS (Method B): 398.4 (M−H)$^-$; 400.1 (M+H)$^+$. HPLC (Method A), Rt: 4.63 min (purity: 100%).

Example 183

N-(2-cyanoethyl)-3-{5-[2-(methoxymethyl)-2'-methylbiphenyl-4-yl]-1,2,4-oxadiazol-3-yl}benzamide

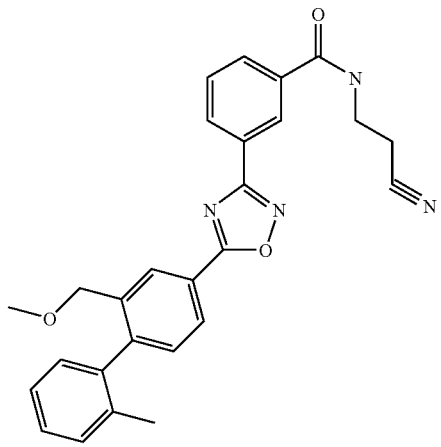

The title compound was prepared following procedure described example 121 starting from n-(2-cyanoethyl)amine (21.75 mg; 0.31 mmol). The title compound was obtained as a white foam (88 mg, 81%). $^1$H NMR: (DMSO-d$_6$, 300 MHz) δ 9.15 (m, 1H), 8.61 (m, 1H), 8.35 (m, 1H), 8.30 (m, 1H), 8.20 (m, 1H), 8.11 (m, 1H), 7.75 (t, J=7.9 Hz, 1H), 7.43 (d, J=7.9 Hz, 1H), 7.38-7.24 (m, 3H), 7.15 (m, 1H), 4.23 (d, J=12.7 Hz, 1H), 4.17 (d, J=12.7 Hz, 1H), 3.55 (m, 2H), 3.26 (s, 3H), 2.83 (m, 2H), 2.04 (s, 3H). LC/MS (Method B): 451.2 (M−H)$^-$; 453.2 (M+H)$^+$. HPLC (Method A), Rt: 4.92 min (purity: 99.5%).

Example 184

N-[2-(acetylamino)ethyl]-3-{5-[2-(methoxymethyl)-2'-methylbiphenyl-4-yl]-1,2,4-oxadiazol-3-yl}benzamide

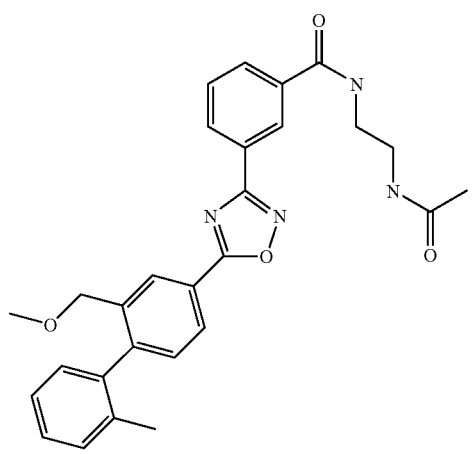

The title compound was prepared following procedure described in example 121 starting from n-acetylethylenediamine (27.43 mg; 0.27 mmol). The title compound was obtained as a white powder (70 mg, 81%). $^1$H NMR: (DMSO-d$_6$, 300 MHz) δ 8.18 (m, 1H), 8.60 (brs, 1H), 8.35 (brs, 1H), 8.28 (m, 1H), 8.19 (m, 1H), 8.09 (m, 1H), 8.02 (m, 1H), 7.72 (t, J=7.9 Hz, 1H), 7.43 (d, J=7.9 Hz, 1H), 7.38-7.24 (m, 3H), 7.15 (m, 1H), 4.23 (d, J=12.7 Hz, 1H), 4.17 (d, J=12.7 Hz, 1H), 3.36 (m, 2H), 3.26 (s, 3H), 3.23 (m, 2H), 2.04 (s, 3H), 1.83 (s, 3H). LC/MS (Method B): 483.3 (M−H)$^-$; 485.2 (M+H)$^+$. HPLC (Method A), Rt: 4.43 min (purity: 98.7%).

Example 185

2-methoxy-N-(3-{5-[2-(methoxymethyl)-2'-methylbiphenyl-4-yl]-1,2,4-oxadiazol-3-yl}benzyl)-N-methylethanamine, Hydrochloride salt

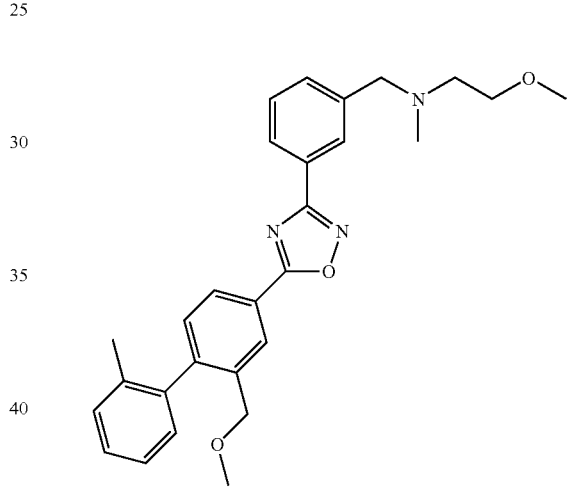

The title compound was obtained following procedure described for example 54 step 1 but starting from Intermediate 28 (161 mg, 0.63 mmol) and Intermediate 77 (150 mg; 0.63 mmol). Purification by column chromatography (EtOAc:cHex from 10:90 to 80:20) gave a colorless oil that was triturated in HCl/Dioxane (4M, 5 mL), evaporated under vacuum to give the title compound as a brown sticky oil. $^1$H NMR (DMSO-d$_6$, 300 MHz) δ 10.12 (bs, 1H), 8.36-8.33 (m, 2H), 8.23-8.20 (m, 1H), 8.18-8.15 (m, 1H), 7.83-7.81 (m, 1H), 7.74-7.69 (m, 1H), 7.44 (d, J=8 Hz, 1H), 7.37-7.26 (m, 3H), 7.15-7.13 (m, 1H), 4.57-4.39 (m, 2H), 4.25-4.14 (m, 2H), 3.72-3.66 (m, 2H), 3.31 (s, 3H), 3.25 (s, 3H), 2.76-2.75 (m, 3H), 2.03 (s, 3H). LC/MS (Method B): 458.3 (M+H)$^+$. HPLC (Method A) Rt 4.39 min (Purity: 97.6%).

Example 186

2-[(3-{5-[2-(methoxymethyl)-2'-methylbiphenyl-4-yl]-1,2,4-oxadiazol-3-yl}benzyl)(methyl)amino]ethanol, Hydrochloride salt

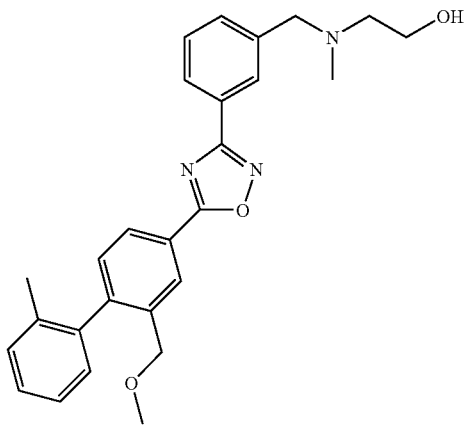

The title compound was obtained following procedure described for example 54 step 1 but starting from Intermediate 28 (161 mg, 0.63 mmol) and Intermediate 78 (121.90 mg; 0.55 mmol). Purification by Autoprep gave the desired compound to which was added HCl (1N, 20 mL) before lyophilization that gave the title compound as a brown oil. $^1$H NMR (CDCl$_3$, 300 MHz) δ 9.92 (bs, 1H), 8.36-8.33 (m, 2H), 8.23-8.20 (m, 1H), 8.17 (dd, J=8, 1.8 Hz, 1H), 7.83-7.81 (m, 1H), 7.72 (t, J=7.7 Hz, 1H), 7.44 (d, J=8 Hz, 1H), 7.37-7.26 (m, 3H), 7.15-7.13 (m, 1H), 5.36 (bs, 1H), 4.58-4.42 (m, 2H), 4.23 (d, J=12.8 Hz, 1H), 4.16 (d, J=12.8 Hz, 1H), 3.78 (m, 2H), 3.25 (s, 3H), 3.2-3.14 (m, 2H), 2.79 (m, 3H), 2.03 (s, 3H). LC/MS (Method B): 443.3 (M+H)$^+$. HPLC (Method A) Rt 4.54 min (Purity: 94.3%).

Example 187

2-[(3-{5-[2-(methoxymethyl)-2'-methylbiphenyl-4-yl]-1,2,4-oxadiazol-3-yl}benzyl)amino]ethanol, Hydrochloride salt

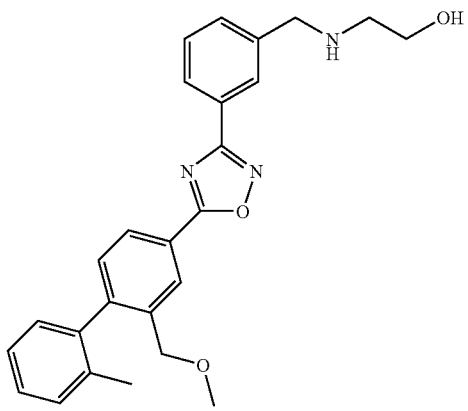

Step 1: tert-butyl (2-hydroxyethyl)(3-{5-[2-(methoxymethyl)-2'-methylbiphenyl-4-yl]-1,2,4-oxadiazol-3-yl}benzyl)carbamate The title compound was prepared following procedure described for example 141, step 1, but starting from Intermediate 69 (185.62 mg; 0.60 mmol) and Intermediate 28 (161.47 mg; 0.63 mmol), the crude mixture was purified by flash chromatography (cHex/(DCM/EtOAc 1:1) to afford the title compound as a colorless oil. $^1$H NMR (CDCl$_3$, 300 MHz) δ 8.43 (d, J=1.4 Hz, 1H), 8.17 (dd, J=7.9, 1.9 Hz, 1H), 8.13-8.11 (m, 2H), 7.50 (t, J=8.0 Hz, 1H), 7.43-7.41 (m, 1H), 7.36-7.24 (m, 4H), 7.13 (d, J=7.1 Hz, 1H), 4.58 (s, 2H), 4.23 (s, 2H), 3.73 (br s, 2H), 3.46 (br s, 2H), 3.33 (s, 3H), 2.08 (s, 3H), 1.52 (s, 9H). LC/MS (Method B): 530.4 (M+H)$^+$. HPLC (Method A) Rt 5.91 min (Purity: 96.0%).

Step 2: 2-[(3-{5-[2-(methoxymethyl)-2'-methylbiphenyl-4-yl]-1,2,4-oxadiazol-3-yl}benzyl)amino]ethanol, Hydrochloride salt To tert-butyl (2-hydroxyethyl)(3-{5-[2-(methoxymethyl)-2'-methylbiphenyl-4-yl]-1,2,4-oxadiazol-3-yl}benzyl)carbamate, obtained in step 1 was added HCl in dioxane (6.73 ml; 4.00 M; 26.91 mmol). The mixture was stirred at RT for 16 h. Solvents were concentrated to dryness to afford the title compound as a white powder. $^1$H NMR (DMSO-d$_6$, 300 MHz) δ 9.20 (br s, 2H), 8.36-8.34 (m, 2H), 8.19 (d, J=1.5 Hz, 1H), 8.16 (d, J=1.8 Hz, 1H), 7.82 (d, J=7.9 Hz, 1H), 7.69 (t, J=7.7 Hz, 1H), 7.44 (d, J=7.9 Hz, 1H), 7.38-7.27 (m, 3H), 7.15 (d, J=7.1 Hz, 1H), 5.28 (t, J=5.1 Hz, 1H), 4.32 (s, 2H), 4.26-4.15 (m, 2H), 3.74-3.68 (m, 2H), 3.26 (s, 3H), 3.03 (t, J=5.0 Hz, 2H), 2.04 (s, 3H). HPLC (Method A) Rt 4.03 min (Purity: 98.4%).

Example 188

2-methoxy-N-(3-{5-[2-(methoxymethyl)-2'-methylbiphenyl-4-yl]-1,2,4-oxadiazol-3-yl}benzyl)ethanamine, Hydrochloride salt

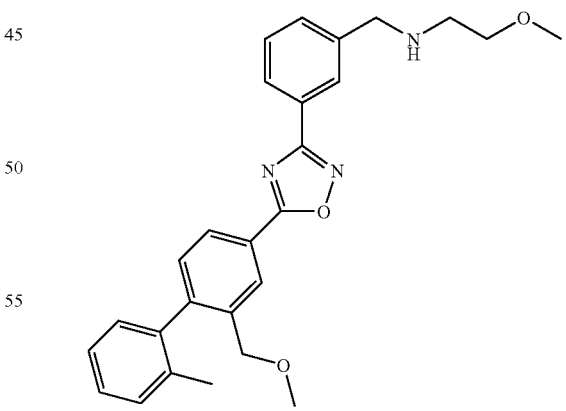

Step 1: tert-butyl (2-methoxyethyl)(3-{5-[2-(methoxymethyl)-2'-methylbiphenyl-4-yl]-1,2,4-oxadiazol-3-yl}benzyl)carbamate The title compound was prepared following procedure described for example 141, step 1, but starting from Intermediate 70 (194.03 mg; 0.60 mmol) and Intermediate 28 (161.47 mg; 0.63 mmol), the crude mixture was purified by flash chromatography (C-hex/(DCM/EtOAc 1:1) to afford the title compound as a colorless oil. $^1$H NMR (CDCl$_3$, 300 MHz) δ 8.45 (d, J=1.4 Hz, 1H), 8.17 (dd, J=7.8, 1.7 Hz, 1H), 8.11-8.08 (m, 2H), 7.48 (t, J=7.7 Hz, 1H), 7.41-7.23 (m, 5H), 7.13 (d, J=7.3 Hz, 1H), 4.63-4.60 (m, 2H), 4.23 (s, 2H), 3.54-3.33 (m, 10H), 2.08 (s, 3H), 1.49 (br s, 9H).). LC/MS (Method B): 544.5 (M+H)$^+$. HPLC (Method A) Rt 6.61 min (Purity: 99.5%).

Step 2: 2-[(3-{5-[2-(methoxymethyl)-2'-methylbiphenyl-4-yl]-1,2,4-oxadiazol-3-yl}benzyl)amino]ethanol, Hydrochloride salt To tert-butyl (2-methoxyethyl)(3-{5-[2-(methoxymethyl)-2'-methylbiphenyl-4-yl]-1,2,4-oxadiazol-3-yl}benzyl)carbamate, obtained in step 1 was added HCl in dioxane (4.94 ml; 4.00 M; 19.77 mmol). The mixture was stirred at RT for 16 h. Solvents were concentrated to dryness to afford the title compound as a white powder. $^1$H NMR (DMSO-d$_6$, 300 MHz) δ 9.25 (br s, 2H), 8.35 (s, 2H), 8.19 (d, J=1.6 Hz, 1H), 8.16 (d, J=1.6 Hz, 1H), 7.81 (d, J=7.9 Hz, 1H), 7.69 (t, J=7.7 Hz, 1H), 7.44 (d, J=7.9 Hz, 1H), 7.38-7.27 (m, 3H), 7.15 (d, J=7.0 Hz, 1H), 4.31 (s, 2H), 4.26-4.15 (m, 2H), 3.64 (t, J=5.2 Hz, 2H), 3.32 (s, 3H), 3.26 (s, 3H), 3.15 (t, J=5.0 Hz, 2H), 2.04 (s, 3H). HPLC (Method A) Rt 4.26 min (Purity: 99.3%).

Example 189

(3-{5-[2-(methoxymethyl)-2'-methylbiphenyl-4-yl]-1,2,4-oxadiazol-3-yl}phenyl)methanol

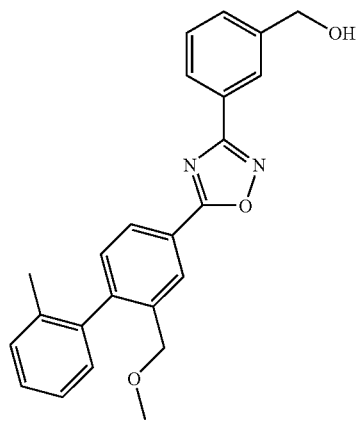

The title compound was obtained following procedure described for example 54 step 1 but starting from Intermediate 28 (149 mg; 0.58 mmol) and Intermediate 72 (88 mg; 0.53 mmol) as a gummy white solid. $^1$H NMR (DMSO-d$_6$, 300 MHz) δ 8.33 (d, J=1.5 Hz, 1H), 8.17 (dd, J=7.9, 1.9 Hz, 1H), 8.11 (bs, 1H), 8.01-7.97 (m, 1H), 7.57-7.55 (m, 1H), 7.42 (d, J=8 Hz, 1H), 7.36-7.27 (m, 3H), 7.16-7.13 (m, 1H), 5.40 (t, J=5.7 Hz, 1H), 4.63 (d, J=5.7 Hz, 2H), 4.23 (d, J=12.7 Hz, 1H), 4.16 (d, J=12.7 Hz, 1H), 3.28 (s, 3H), 3.25 (s, 3H), 2.03 (s, 3H). LC/MS (Method B): 387.2 (M+H)$^+$. HPLC (Method A) Rt 5.55 min (Purity: 94.5%).

Example 190

2-(3-{5-[2-(methoxymethyl)-2'-methylbiphenyl-4-yl]-1,2,4-oxadiazol-3-yl}phenyl)ethanol

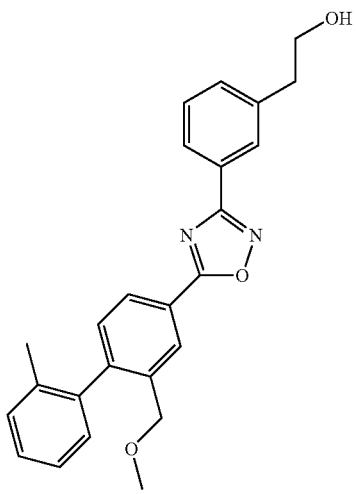

The title compound was obtained following procedure described for example 54 step 1 but starting from Intermediate 28 (149.42 mg; 0.58 mmol) and Intermediate 73 (100.00 mg; 0.60 mmol). Purification by column chromatography (cHex/EtOAc from 9:1 to 8:2) gave the title compound as a colorless oil. $^1$H NMR (DMSO-d$_6$, 300 MHz) δ 8.32 (d, J=1.5 Hz, 1H), 8.16 (dd, J=7.9, 1.8 Hz, 1H), 7.98-7.93 (m, 2H), 7.54-7.47 (m, 2H), 7.41 (d, J=7.9 Hz, 1H), 7.36-7.26 (m, 3H), 7.15-7.13 (m, 1H), 4.71 (t, J=5.2 Hz, 1H), 4.22 (d, J=12.7 Hz, 1H), 4.16 (d, J=12.7 Hz, 1H), 3.24 (s, 3H), 2.85 (t, J=6.7 Hz, 2H), 2.03 (s, 3H). LC/MS (Method B): 401.2 (M+H)$^+$. HPLC (Method A) Rt 5.17 min (Purity: 98.2%).

Example 191

(4-{5-[2-(methoxymethyl)-2'-methylbiphenyl-4-yl]-1,2,4-oxadiazol-3-yl}phenyl)methanol

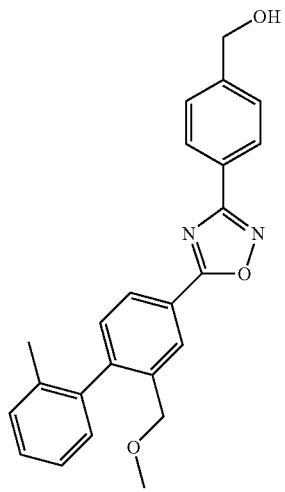

The title compound was obtained following procedure described for example 54 step 1 but starting from Intermediate 28 (248.00 mg; 0.90 mmol) and Intermediate 74 (150.00 mg; 0.90 mmol). Recrystallization from Et$_2$O/pentane gave the title compound as a white powder. $^1$H NMR (DMSO-d$_6$, 300 MHz) δ 8.32 (d, J=1.5 Hz, 1H), 8.16 (dd, J=7.9, 1.8 Hz, 1H), 8.10-8.07 (m, 2H), 7.55 (d, J=8.3 Hz, 2H), 7.41 (d, J=7.9 Hz, 1H), 7.36-7.26 (m, 3H), 7.15-7.13 (m, 1H), 5.38 (t, J=5.7 Hz, 1H), 4.61 (d, J=5.7 Hz, 1H), 4.22 (d, J=12.7 Hz, 1H), 4.15 (d, J=12.7 Hz, 1H), 3.25 (s, 3H), 2.03 (s, 3H). LC/MS (Method B): 387.2 (M+H)$^+$. HPLC (Method A) Rt 5.51 min (Purity: 97.0%).

Example 192

3-{3-[2-methoxyethoxy)methyl]phenyl}-5-[2-(methoxymethyl)-2'-methylbiphenyl-4-yl]-1,2,4-oxadiazole

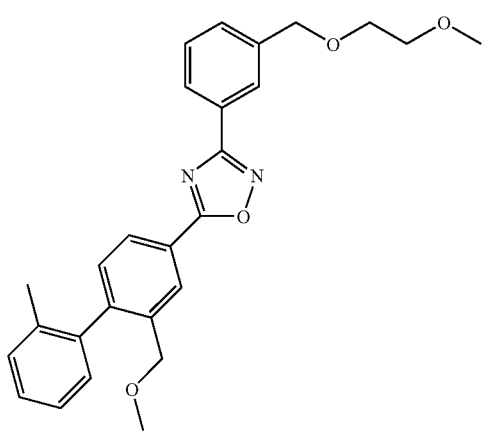

The title compound was obtained following procedure described for example 54 step 1 but starting from Intermediate 28 (200 mg; 0.73 mmol) and Intermediate 75 (163 mg; 0.73 mmol). Purification by column chromatography (EtOAc:cHex from 5:95 to 39:70) gave the title compound as a colorless oil. $^1$H NMR (DMSO-d$_6$, 300 MHz) δ 8.32 (d, J=1.5 Hz, 1H), 8.16 (dd, J=7.9, 1.8 Hz, 1H), 8.09 (bs, 1H), 8.06-8.02 (m, 1H), 7.60-7.57 (m, 1H), 7.41 (d, J=7.9 Hz, 1H), 7.36-7.27 (m, 3H), 7.15-7.13 (m, 1H), 4.62 (s, 2H), 4.22 (d, J=12.7 Hz, 1H), 4.15 (d, J=12.7 Hz, 1H), 3.64-3.61 (m, 2H), 3.54-3.51 (m, 2H), 3.25 (s, 3H), 2.03 (s, 3H). LC/MS (Method B): 445.3 (M+H)$^+$. HPLC (Method A) Rt 6.13 min (Purity: 97.9%).

Example 193

2-[(3-{5-[2-(methoxymethyl)-2'-methylbiphenyl-4-yl]-1,2,4-oxadiazol-3-yl}benzyl)oxy]ethanol

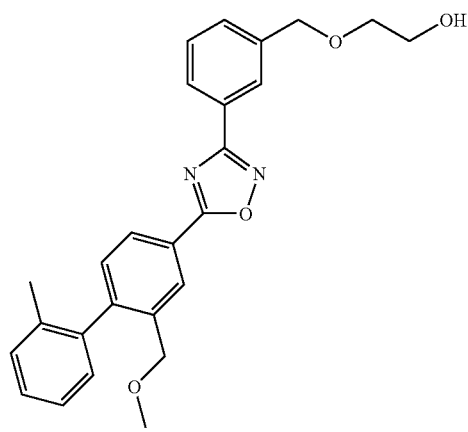

The title compound was obtained following procedure described for example 54 step 1 but starting from Intermediate 28 (200 mg; 0.73 mmol) and Intermediate 76 (153 mg; 0.73 mmol). Purification by column chromatography (EtOAc:cHex from 10:90 to 50:50) gave the title compound as a colorless oil. $^1$H NMR (DMSO-d$_6$, 300 MHz) δ 8.32 (d, J=1.5 Hz, 1H), 8.17 (dd, J=7.9, 1.8 Hz, 1H), 8.10 (bs, 1H), 8.06-8.02 (m, 1H), 7.60-7.59 (m, 1H), 7.42 (d, J=7.9 Hz, 1H), 7.36-7.26 (m, 3H), 7.15-7.13 (m, 1H), 4.69 (t, J=5.4 Hz, 1H), 4.22 (d, J=12.7 Hz, 1H), 4.16 (d, J=12.7 Hz, 1H), 3.61-3.51 (m, 4H), 3.25 (s, 3H), 2.03 (s, 3H). LC/MS (Method B): 431.3 (M+H)$^+$. HPLC (Method A) Rt 5.50 min (Purity: 96.9%).

Example 194

5-[2-(methoxymethyl)-2'-methylbiphenyl-4-yl]-3-[3-(methylsulfonyl)phenyl]-1,2,4-oxadiazole

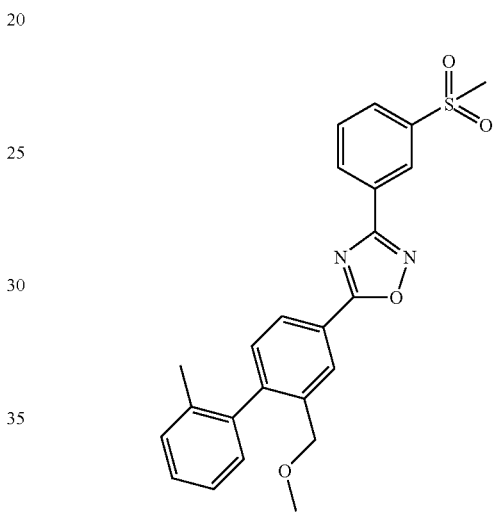

The title compound was obtained following procedure described for example 54 step 1 but starting from Intermediate 28 (112 mg; 0.44 mmol) and Intermediate 64 (197 mg; 0.44 mmol). Purification by column chromatography (EtOAc:cHex from 10:90 to 50:50) yielded to a colorless oil. Trituration in ACN/pentane followed by filtration gave the title compound as an off-white powder. $^1$H NMR (DMSO-d$_6$, 300 MHz) δ 8.59 (t, J=1.7 Hz, 1H), 8.47 (m, 1H), 8.35 (d, J=1.7 Hz, 1H), 8.21 (m, 2H), 7.93 (t, J=8.0 Hz, 1H), 7.44 (d, J=8.0 Hz, 1H), 7.33 (m, 3H), 7.15 (d, J=7.1 Hz, 1H), 4.23 (d, J=13.8 Hz, 1H), 4.17 (d, J=13.8 Hz, 1H), 3.35 (s, 3H), 3.26 (s, 3H), 2.04 (s, 3H). LC/MS (Method B): 435.3 (M+H)$^+$. HPLC (Method A) Rt 5.35 min (Purity: 97.6%).

Example 195

In Vitro Assays

Receptor binding assay: Membranes were prepared from CHO cells expressing S1P$_1$ or S1P$_3$ for use in ligand and 355-GTPγS binding studies. Cells were suspended in 50 mM TRIS, pH 7.4, 2 mM EDTA, 250 mM Sucrose (buffer A) and 1× Complete protease inhibitor cocktail (Roche), and disrupted at 4° C. by N$_2$ decompression using a cell disruption bomb (Parr Instrument). Following centrifugation at 1000 RPM for 10 min at 4° C., the supernatant was suspended in buffer A and centrifuged again at 19000 RPM for 60 min at 4° C. The pellet was then suspended in 10 mM HEPES, pH 7.4, 1 mM EDTA, 250 mM Sucrose (Buffer B), and 1× Complete EDTA-free protease inhibitor cocktail and homogenized using a potter. Membranes were flash frozen in liquid $N_2$ and stored at −80° C. [33P]sphingosine 1-phosphate (3000 Ci/mmol; American Radiolabeled Chemicals, Inc.) was added to test compounds in DMSO. Membranes and WGA SPA beads (GE Healthcare) were added to give a final volume of 100 μl in 96-well plates with assay concentrations of 25 pM or 10 pM [33P]sphingosine 1-phosphate (respectively for S1P1 or S1P3), 50 mM HEPES, pH 7.5, 5 mM $MgCl_2$, 100 mM NaCl, 0.4% fatty acid-free BSA, 1-5 μg/well of proteins and 100 μg/well of WGA SPA beads. Binding was performed for 60 min at RT on a shaker and bound radioactivity was measured on a PerkinElmer 1450 MicroBeta counter. Specific binding was calculated by subtracting remaining radioactivity in the presence of 1000-fold excess of unlabeled S1P. Binding data were analyzed using the GraphPad Prism program.

Measurements of $^{35}$S-GTPγS Binding: Membranes (1 to 10 μg protein) prepared as described above, were incubated in 96-well Scintiplates (PerkinElmer) with test compounds diluted in DMSO, in 180 μl of 20 mM HEPES, pH 7.4, 10 mM $MgCl_2$, 2 μg/well Saponin, 0.2% fatty acid free BSA (Assay buffer), 140 mM NaCl and 1.7 μM GDP. The assay was initiated with the addition of 20 μl of 1.5 nM [35S]-GTPγS (1100 Ci/mmol; GE Healthcare) in assay buffer. After 60 min incubation at 30° C. on a shaker, plates were centrifuged for 10 min at 2000 RPM. Supernatant was discarded and membrane bound radioactivity was measured on a PerkinElmer 1450 MicroBeta counter. Triplicate samples were averaged and expressed as % response relative to S1P activation in absence of compound (n=2).

The compounds of formula (I) have utility as immunoregulatory agents as demonstrated by their activity as potent agonists of the $S_1P_1$ receptor, as measured in the assays described above. $EC_{50}$ of the compounds of formula (I) and subformulae for $S_1P_1$ is below 0.1 μM. Preferred compounds of formula (I) exhibit an $EC_{50}$ for $S_1P_1$ receptor below 0.01 μM. More preferred compounds of Formula (I) exhibit $EC_{50}$ for $S_1P_1$ below 0.001 μM. Compounds of formula (I) exhibit a selectivity for the $S_1P_1$ receptor over the $S_1P_3$ receptor as measured by the ratio of $EC_{50}$ for the $S_1P_1$ receptor to the $EC_{50}$ for the $S_1P_3$ receptor as evaluated in the $^{35}$S-GTPγS binding assay described above. The ratio of EC50 $S_1P_1$ to EC50 $S_1P_3$ is more than 20, preferably more than 50, more preferably more than 100 and even more preferably more than 1000.

The following results have been obtained:

| | | | S1P1 | | S1P3 |
| --- | --- | --- | --- | --- | --- |
| Example Nb | structure | | Binding Ki (μM) | GTPγS EC50 (μM) | GTPγS EC50 (μM) |
| 1 | | | 2.47 | — | — |
| 2 | | | 1.5 | 4.72 | >30 |

-continued

| Example Nb | structure | S1P1 Binding Ki (μM) | S1P1 GTPγS EC50 (μM) | S1P3 GTPγs EC50 (μM) |
|---|---|---|---|---|
| 3 | 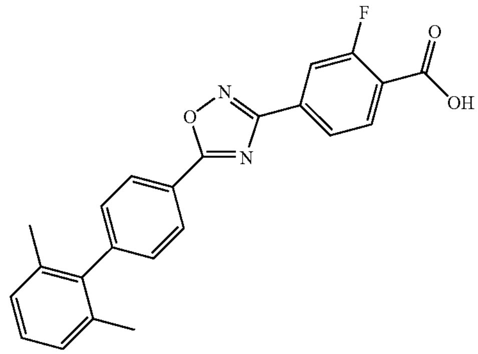 | 2.6 | — | — |
| 4 | 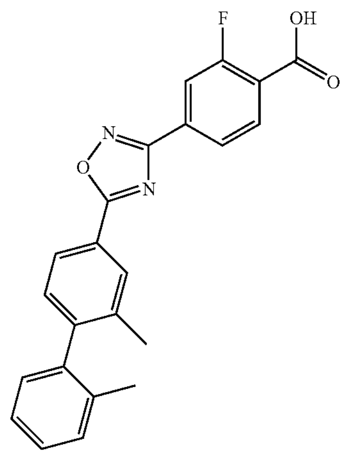 | 0.126 | 0.317 | >30 |
| 5 | 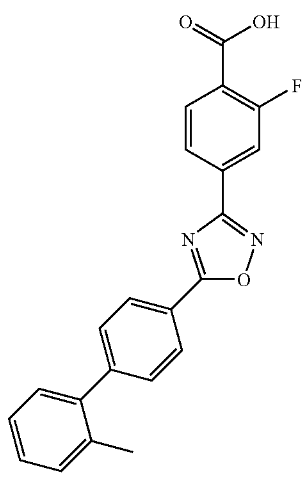 | — | 5.14 | — |

-continued

| Example Nb | structure | S1P1 Binding Ki (µM) | S1P1 GTPγS EC50 (µM) | S1P3 GTPγs EC50 (µM) |
|---|---|---|---|---|
| 6 | 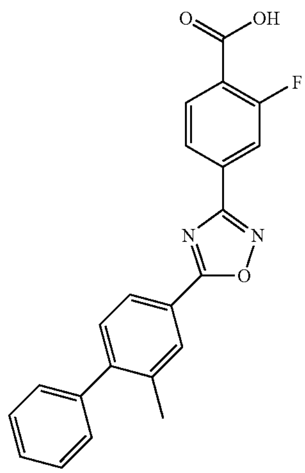 | — | 2.92 | — |
| 7 | 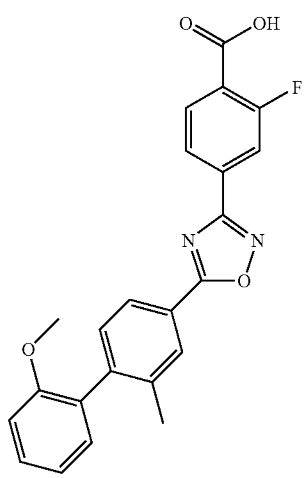 | — | 0.924 | >30 |
| 8 | 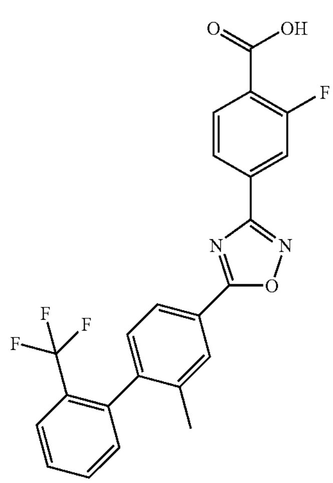 | — | 0.85 | — |

-continued

| Example Nb | structure | S1P1 Binding Ki (μM) | S1P1 GTPγS EC50 (μM) | S1P3 GTPγs EC50 (μM) |
|---|---|---|---|---|
| 9 | 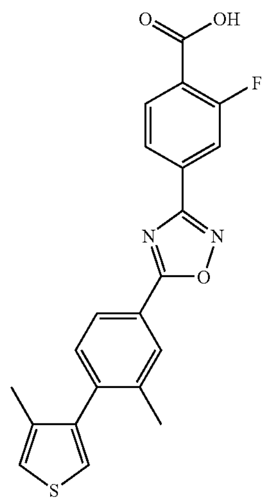 | 0.04 | 0.136 | >30 |
| 10 | 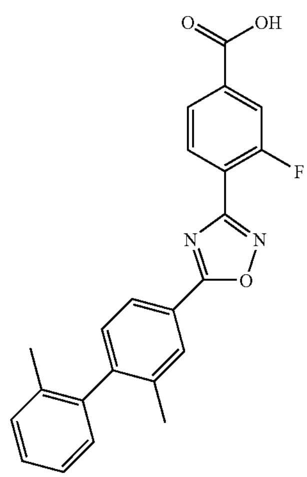 | 0.33 | 3.51 | >30 |
| 11 | 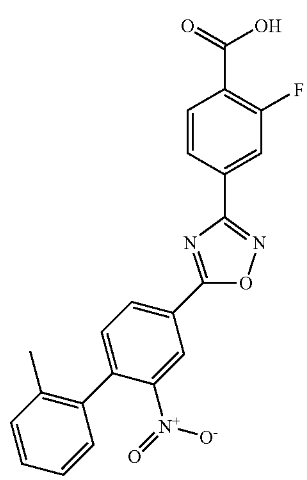 | — | 0.645 | >30 |

-continued

| Example Nb | structure | S1P1 Binding Ki (μM) | S1P1 GTPγS EC50 (μM) | S1P3 GTPγs EC50 (μM) |
|---|---|---|---|---|
| 12 | 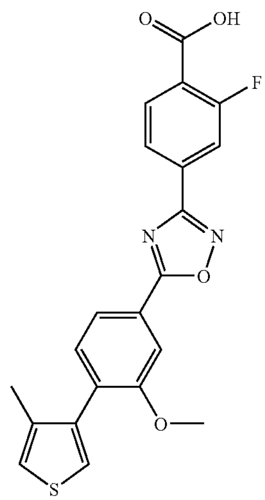 | 0.06 | 0.148 | >30 |
| 13 | 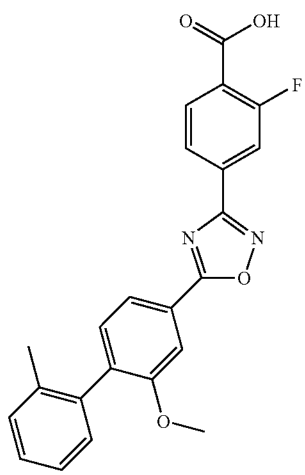 | 0.13 | 0.341 | >30 |
| 14 | 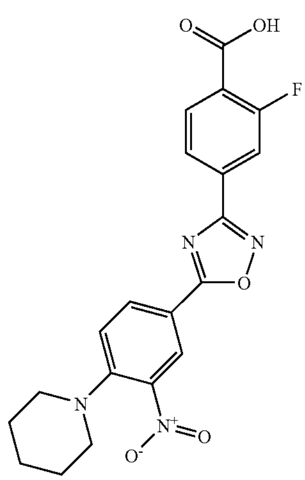 | — | 5.18 | — |

-continued

| Example Nb | structure | S1P1 Binding Ki (μM) | S1P1 GTPγS EC50 (μM) | S1P3 GTPγs EC50 (μM) |
|---|---|---|---|---|
| 15 | 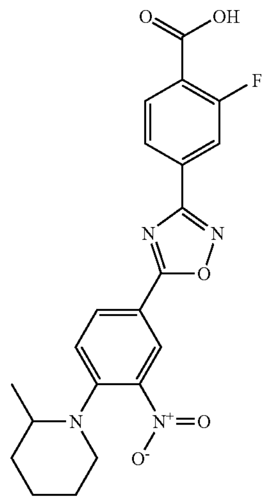 | — | 1.22 | >30 |
| 16 | 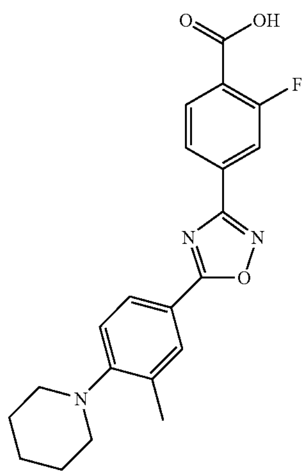 | — | 2.06 | — |
| 17 | 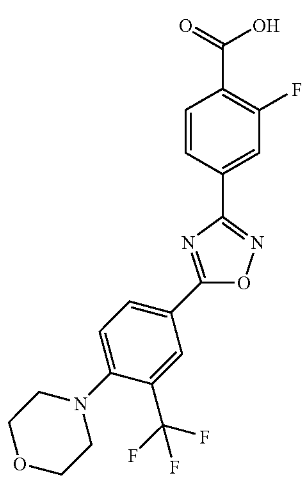 | — | 3.45 | — |

-continued

| Example Nb | structure | S1P1 Binding Ki (µM) | S1P1 GTPγS EC50 (µM) | S1P3 GTPγs EC50 (µM) |
|---|---|---|---|---|
| 18 | 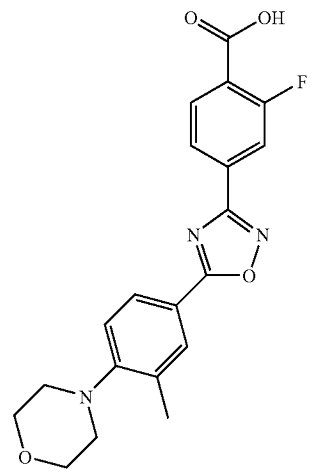 | — | 7.00 | — |
| 19 | 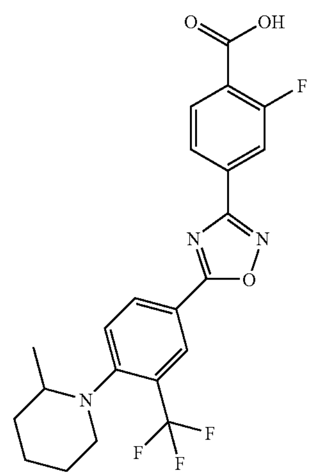 | 0.11 | 0.347 | >30 |
| 20 | 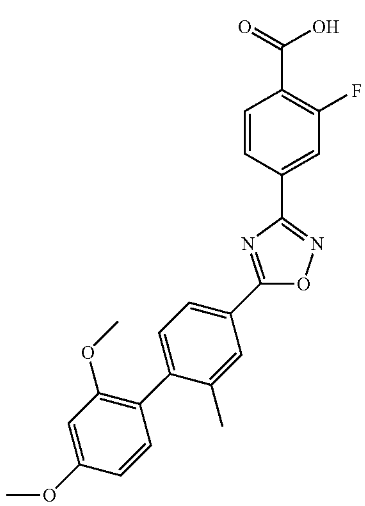 | — | 10.9 | — |

-continued

| Example Nb | structure | S1P1 Binding Ki (μM) | S1P1 GTPγS EC50 (μM) | S1P3 GTPγs EC50 (μM) |
|---|---|---|---|---|
| 21 | | — | 9.74 | — |
| 22 | | 0.524 | 0.417 | >20 |
| 23 | | 0.09 | 0.197 | 14.9 |

-continued

| Example Nb | structure | S1P1 Binding Ki (μM) | S1P1 GTPγS EC50 (μM) | S1P3 GTPγs EC50 (μM) |
|---|---|---|---|---|
| 24 | 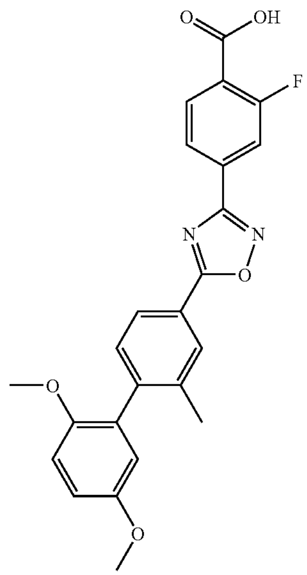 | — | 10.4 | — |
| 25 | 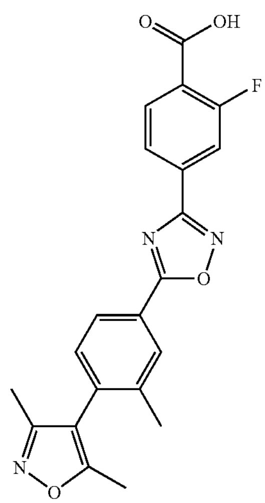 | — | 14.2 | — |
| 26 | 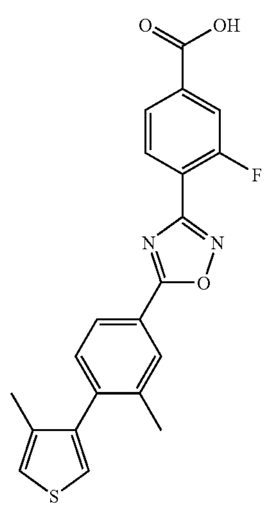 | 0.172 | 0.36 | >20 |

-continued
| Example Nb | structure | S1P1 Binding Ki (μM) | S1P1 GTPγS EC50 (μM) | S1P3 GTPγs EC50 (μM) |
|---|---|---|---|---|
| 27 | 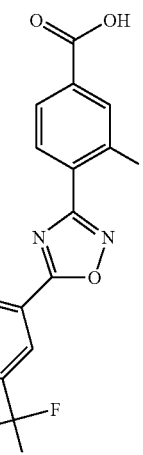 | 0.505 | 1.1 | >20 |
| 28 |  | 0.19 | 0.834 | >30 |
| 29 | 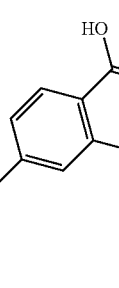 | 0.07 | 0.43 | >30 |

-continued

| Example Nb | structure | S1P1 Binding Ki (μM) | S1P1 GTPγS EC50 (μM) | S1P3 GTPγs EC50 (μM) |
| --- | --- | --- | --- | --- |
| 30 | 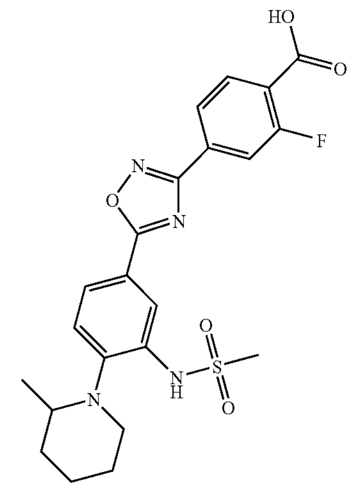 | 0.04 | 0.05 | 5.93 |
| 31 | 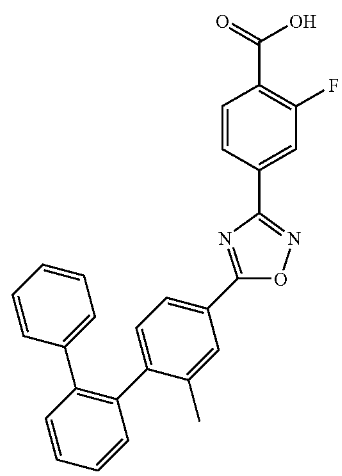 | — | 2.4 | — |
| 32 | 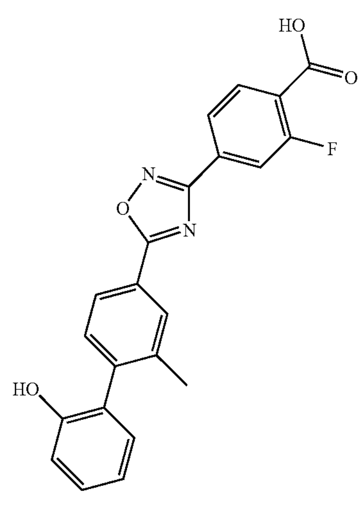 | — | 2.92 | — |

-continued

| Example Nb | structure | S1P1 Binding Ki (μM) | S1P1 GTPγS EC50 (μM) | S1P3 GTPγs EC50 (μM) |
|---|---|---|---|---|
| 33 | 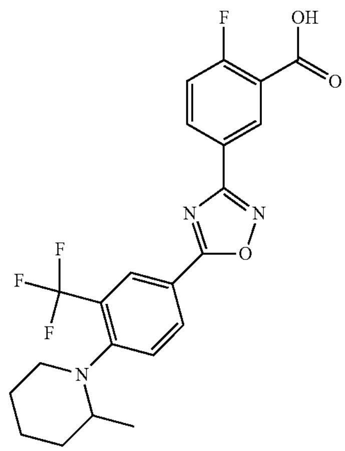 | — | 0.18 | — |
| 34 | 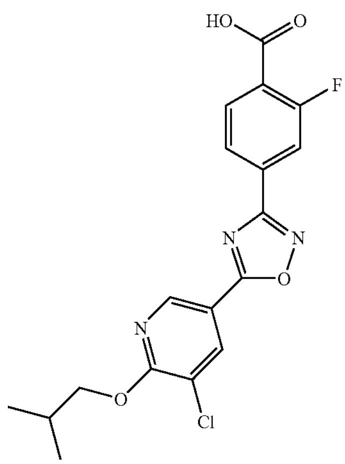 | 2.93 | 4.99 | — |
| 35 | 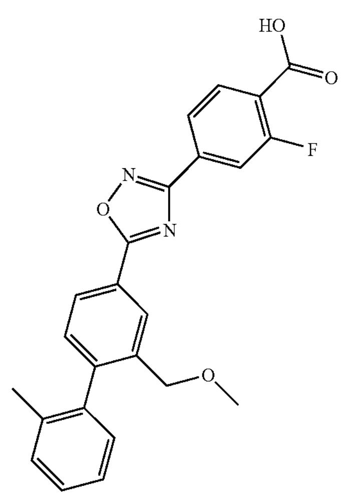 | 0.01 | 0.03 | — |

-continued

| Example Nb | structure | S1P1 Binding Ki (µM) | S1P1 GTPγS EC50 (µM) | S1P3 GTPγs EC50 (µM) |
|---|---|---|---|---|
| 36 | 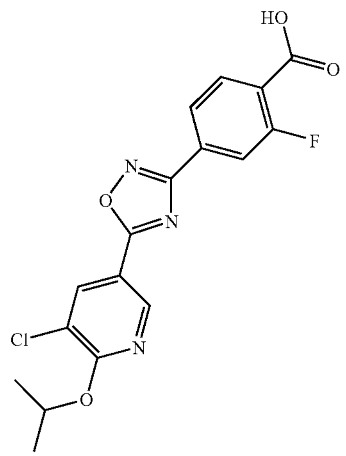 | 0.53 | — | — |
| 37 | 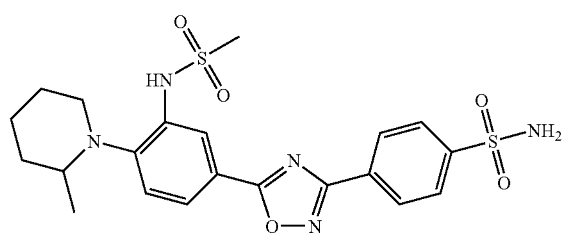 | 0.01 | 0.0016 | — |
| 38 | 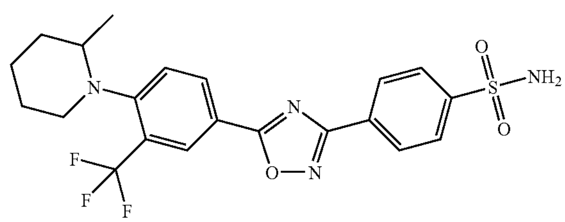 | — | 0.0015 | — |
| 39 | 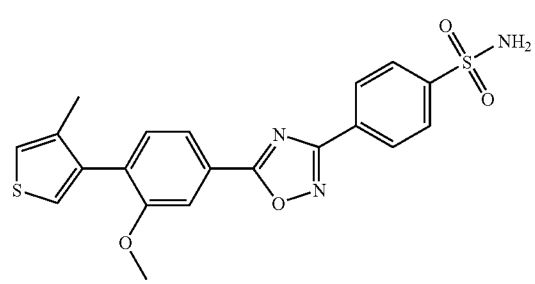 | — | 0.0029 | — |
| 40 | 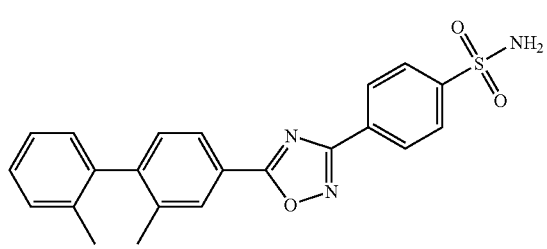 | — | 0.01 | — |

-continued

| Example Nb | structure | S1P1 Binding Ki (μM) | S1P1 GTPγS EC50 (μM) | S1P3 GTPγS EC50 (μM) |
|---|---|---|---|---|
| 41 | 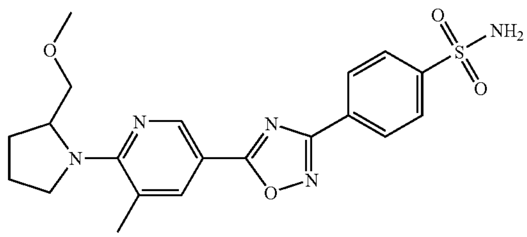 | — | 1.09 | — |
| 42 | 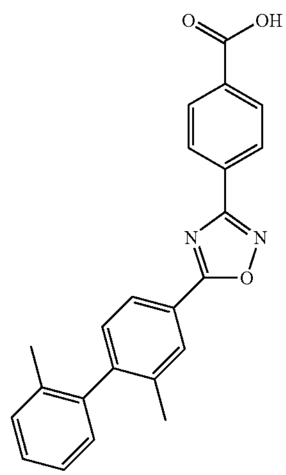 | — | 1.69 | — |
| 43 | 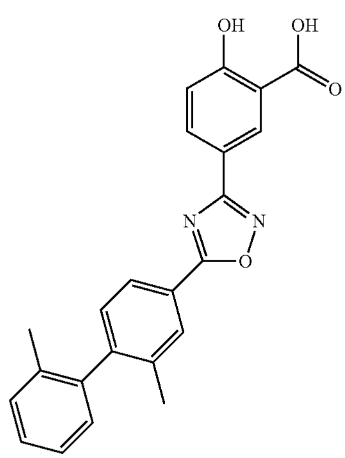 | — | 4.36 | — |

-continued

| Example Nb | structure | S1P1 Binding Ki (µM) | S1P1 GTPγS EC50 (µM) | S1P3 GTPγs EC50 (µM) |
|---|---|---|---|---|
| 44 | 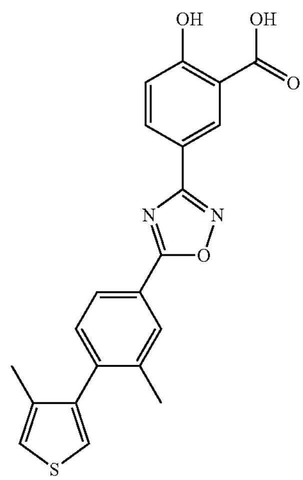 | — | 1.45 | — |
| 45 | 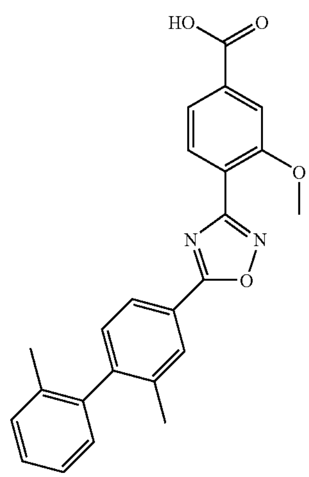 | — | 4.48 | — |
| 46 | 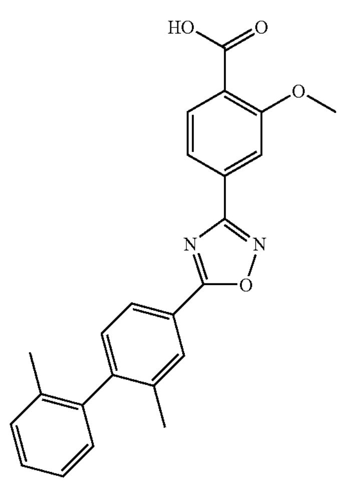 | — | 2.27 | — |

-continued
| Example Nb | structure | S1P1 Binding Ki (μM) | S1P1 GTPγS EC50 (μM) | S1P3 GTPγs EC50 (μM) |
|---|---|---|---|---|
| 47 | 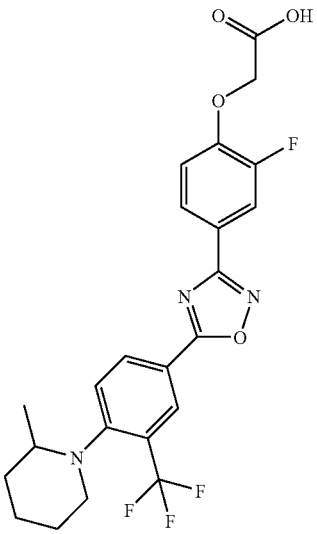 | 0.004 | 0.04 | 1 |
| 48 | 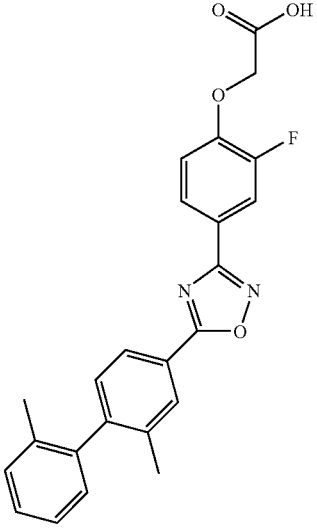 | 0.04 | 0.129 | 17 |

-continued

| Example Nb | structure | S1P1 Binding Ki (μM) | S1P1 GTPγS EC50 (μM) | S1P3 GTPγs EC50 (μM) |
|---|---|---|---|---|
| 49 | 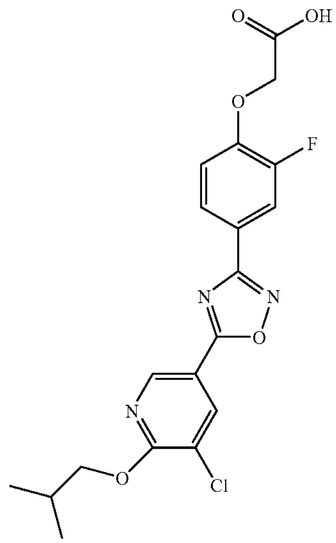 | — | 1.28 | — |
| 50 | 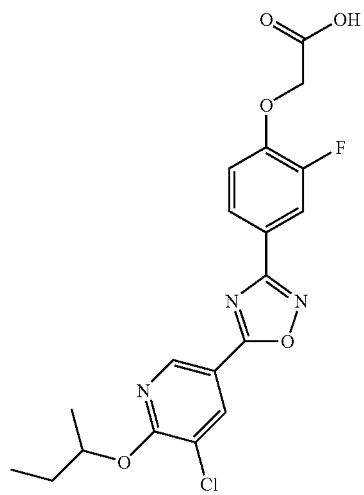 | 0.05 | 0.261 | — |
| 51 | 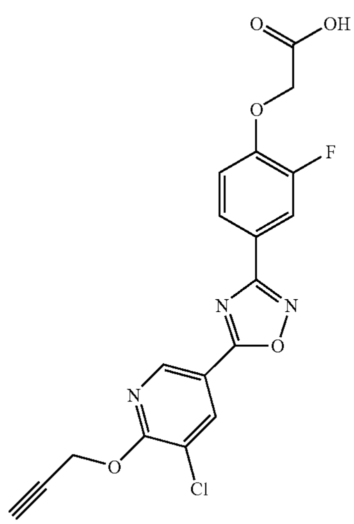 | — | 2.02 | — |

-continued

| Example Nb | structure | S1P1 Binding Ki (µM) | S1P1 GTPγS EC50 (µM) | S1P3 GTPγs EC50 (µM) |
|---|---|---|---|---|
| 52 | 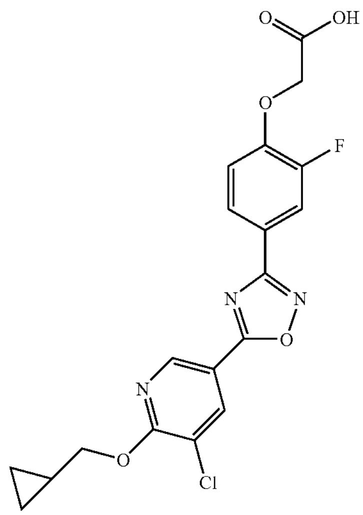 | — | 1.54 | — |
| 53 | 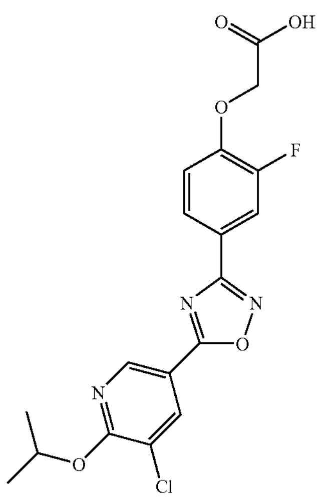 | — | 0.294(1) | >20 |
| 54 | 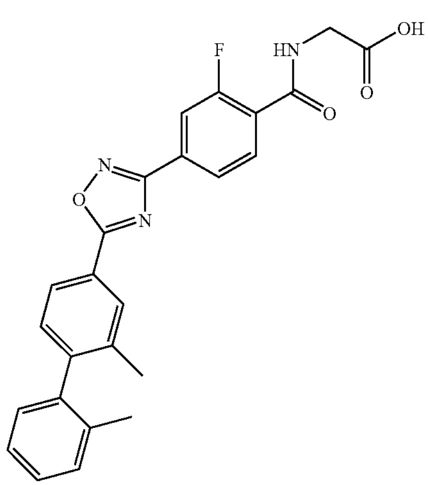 | — | 0.168 | 6.43 |

-continued

| Example Nb | structure | S1P1 Binding Ki (µM) | S1P1 GTPγS EC50 (µM) | S1P3 GTPγs EC50 (µM) |
|---|---|---|---|---|
| 55 | 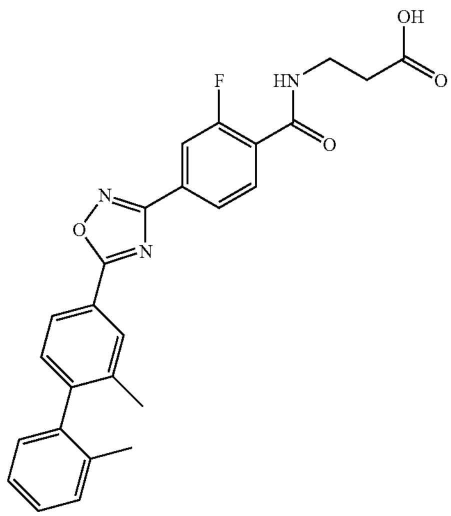 | — | 0.053 | 12.6 |
| 56 | 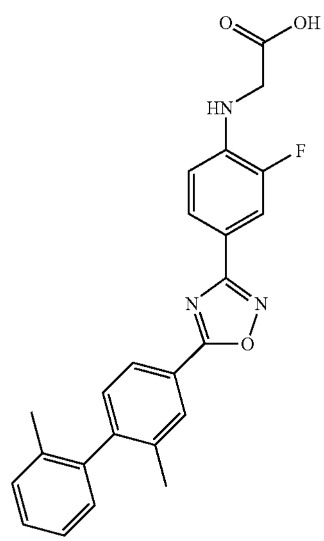 | 0.01 | 0.07 | 14.5 |
| 57 | 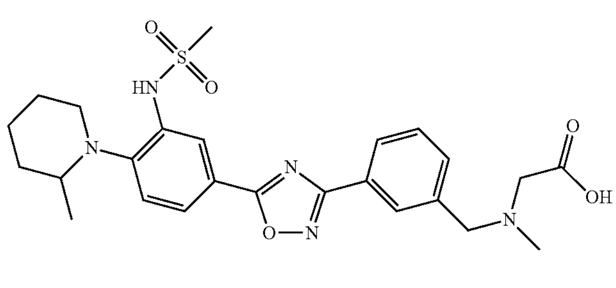 | 0.006 | 0.004 | — |

-continued

| Example Nb | structure | S1P1 Binding Ki (μM) | S1P1 GTPγS EC50 (μM) | S1P3 GTPγs EC50 (μM) |
| --- | --- | --- | --- | --- |
| 58 | 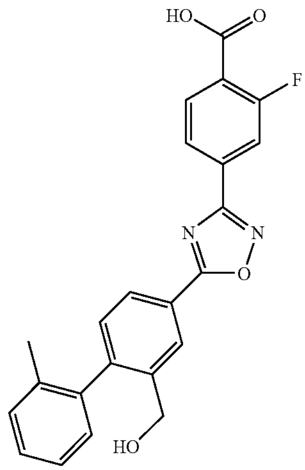 | — | 2.93 | — |
| 59 | 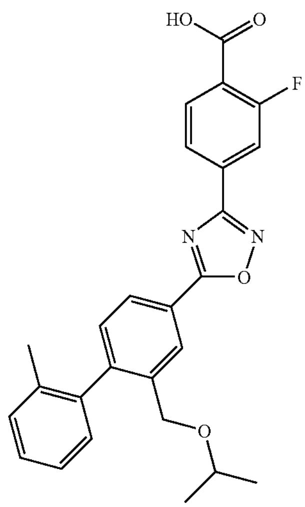 | 0.182 | 0.286 | 0.767 |
| 60 | 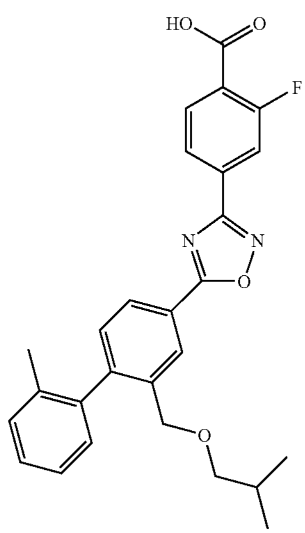 | — | 3.7 | — |

-continued

| Example Nb | structure | S1P1 Binding Ki (μM) | S1P1 GTPγS EC50 (μM) | S1P3 GTPγS EC50 (μM) |
|---|---|---|---|---|
| 61 | 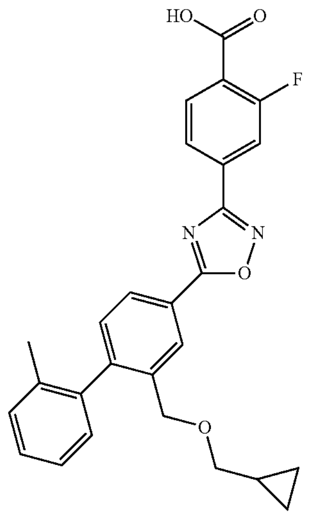 | — | 2.24 | — |
| 62 | 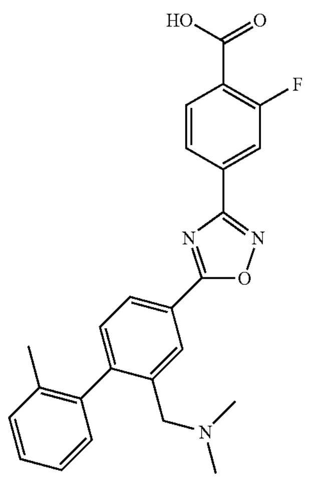 | 0.024 | 0.092 | 0.699 |
| 63 | 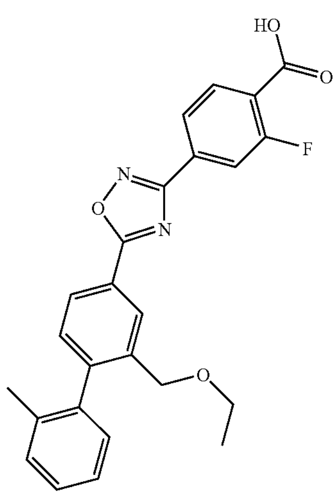 | 0.03 | 0.06 | 0.615 |

-continued

| Example Nb | structure | S1P1 Binding Ki (μM) | S1P1 GTPγS EC50 (μM) | S1P3 GTPγs EC50 (μM) |
|---|---|---|---|---|
| 64 | 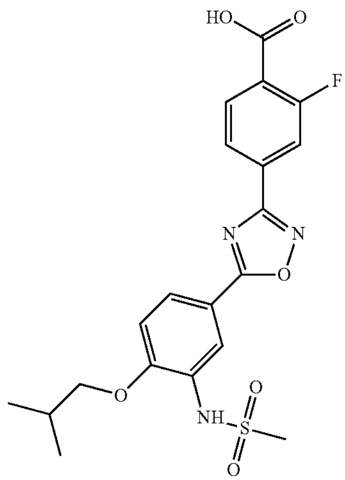 | — | 4.72 | — |
| 65 | 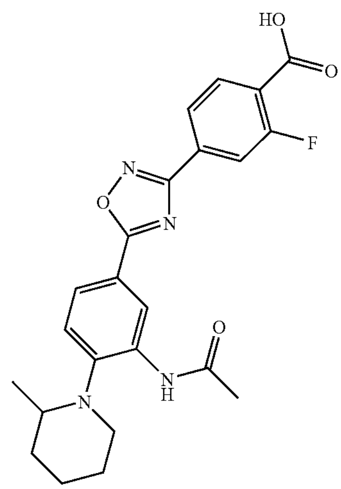 | — | 10.4 | — |
| 66 | 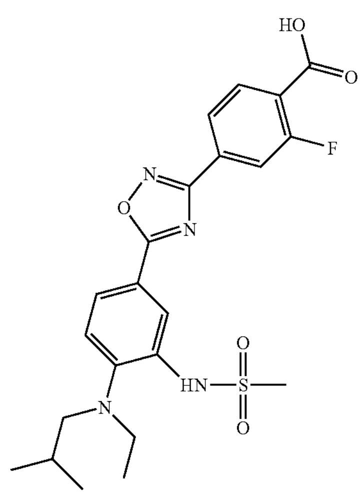 | — | 10 | — |

-continued
| Example Nb | structure | S1P1 Binding Ki (μM) | S1P1 GTPγS EC50 (μM) | S1P3 GTPγs EC50 (μM) |
|---|---|---|---|---|
| 67 | 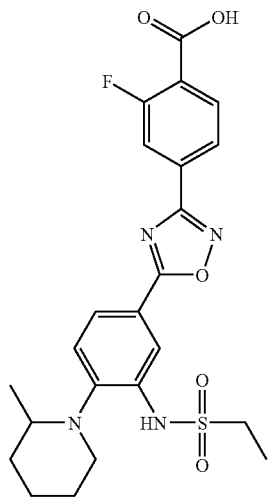 | 0.067 | 0.072 | 1.75 |
| 68 | 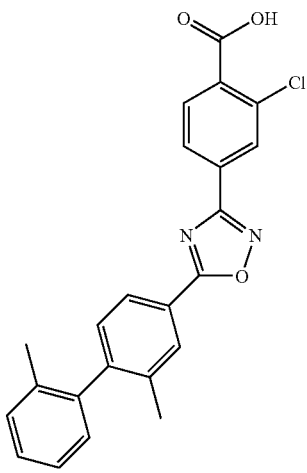 | 0.065 | 0.133 | >30 |
| 69 | 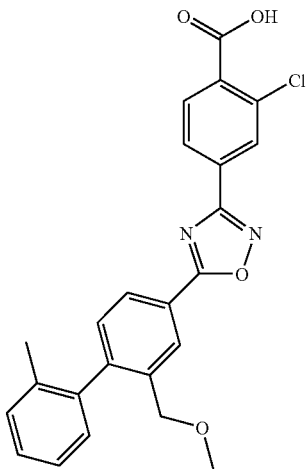 | 0.026 | 0.034 | 2.63 |

-continued
| Example Nb | structure | S1P1 Binding Ki (μM) | S1P1 GTPγS EC50 (μM) | S1P3 GTPγs EC50 (μM) |
|---|---|---|---|---|
| 70 | 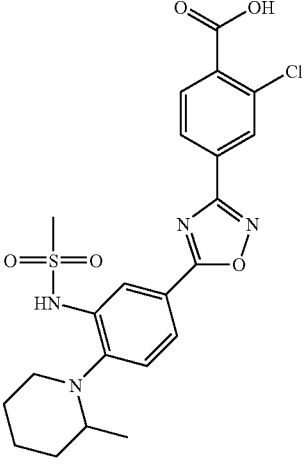 | 0.069 | 0.057 | 1.41 |
| 71 | 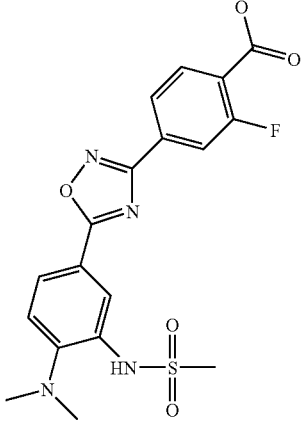 | — | 0.481 | — |
| 72 | 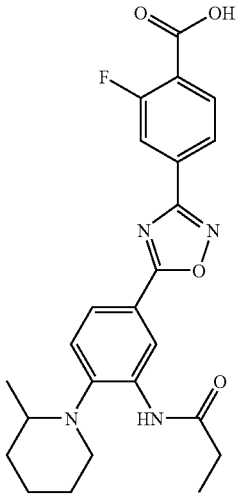 | — | 8.51 | — |

-continued

| Example Nb | structure | S1P1 Binding Ki (μM) | S1P1 GTPγS EC50 (μM) | S1P3 GTPγs EC50 (μM) |
|---|---|---|---|---|
| 73 | 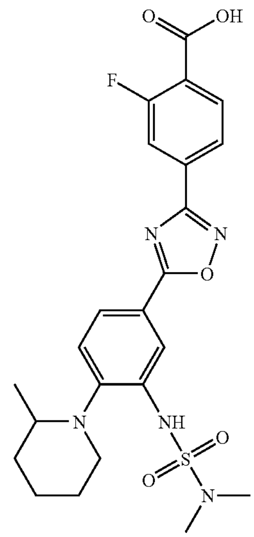 | 0.213 | 0.122 | 2 |
| 74 | 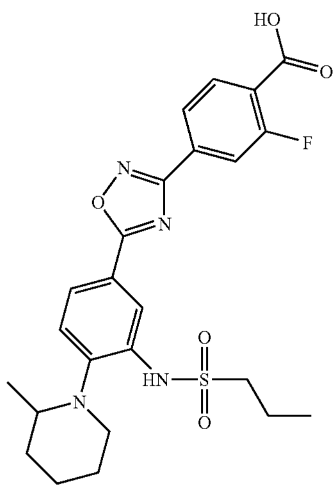 | 0.443 | 0.408 | 1.77 |
| 75 | 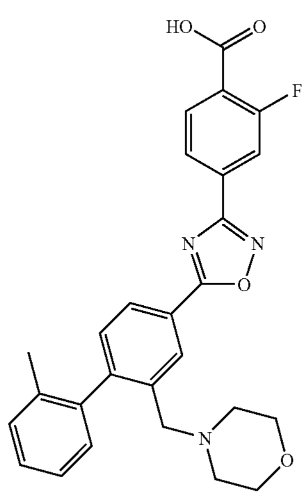 | 0.177 | 0.182 | 1.35 |

-continued

| Example Nb | structure | S1P1 Binding Ki (μM) | S1P1 GTPγS EC50 (μM) | S1P3 GTPγs EC50 (μM) |
|---|---|---|---|---|
| 76 | | — | 0.772 | — |
| 77 | | — | 2.9 | — |
| 78 | | 0.002 | 0.015 | 3.03 |

-continued

| Example Nb | structure | S1P1 Binding Ki (μM) | S1P1 GTPγS EC50 (μM) | S1P3 GTPγs EC50 (μM) |
| --- | --- | --- | --- | --- |
| 79 | 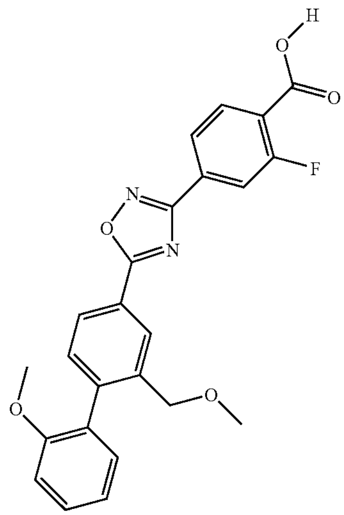 | 0.074 | 0.208 | >20 |
| 80 | 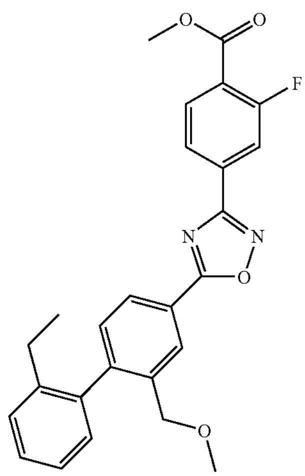 | — | 0.274 | — |
| 81 | 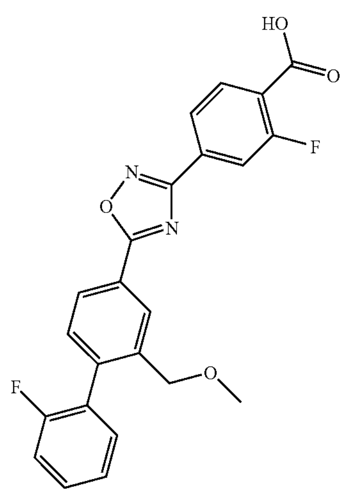 | 0.028 | 0.115 | 2.78 |

-continued

| Example Nb | structure | S1P1 Binding Ki (μM) | S1P1 GTPγS EC50 (μM) | S1P3 GTPγs EC50 (μM) |
| --- | --- | --- | --- | --- |
| 82 | 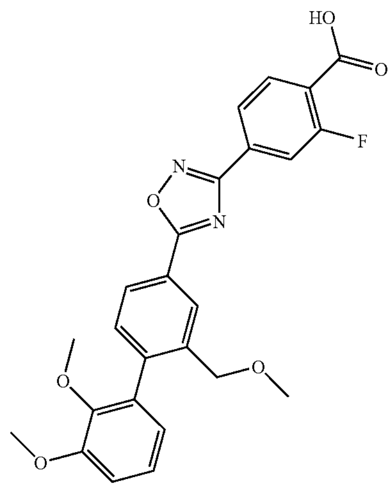 | — | 1.58 | — |
| 83 | 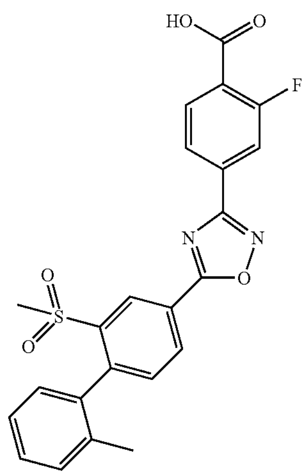 | — | 3.99 | — |
| 84 | 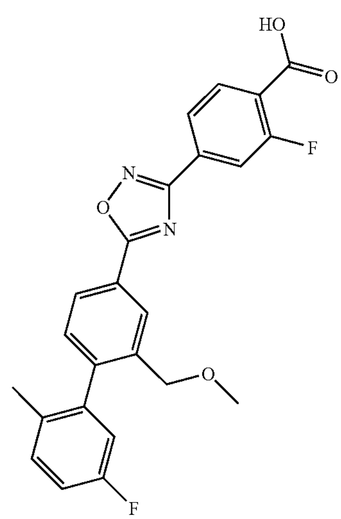 | 0.055 | 0.034 | 2.8 |

-continued

| Example Nb | structure | S1P1 Binding Ki (µM) | S1P1 GTPγS EC50 (µM) | S1P3 GTPγs EC50 (µM) |
|---|---|---|---|---|
| 85 | 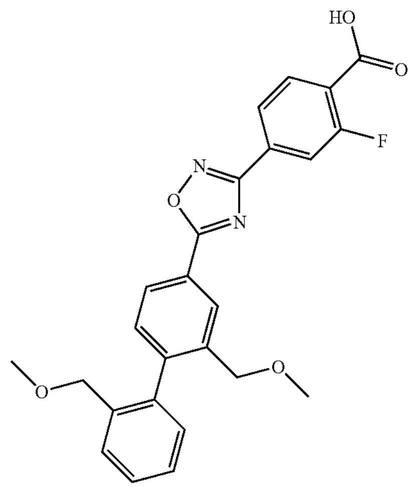 | — | 0.556 | 2.3 |
| 86 | 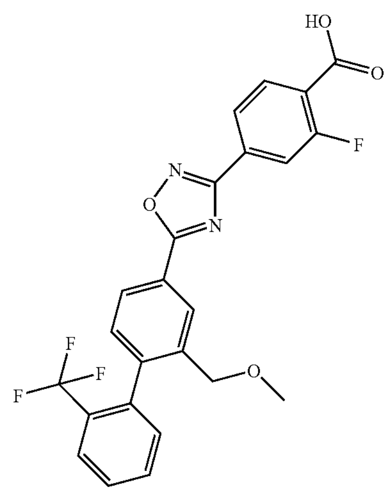 | 0.048 | 0.155 | >20 |
| 87 | 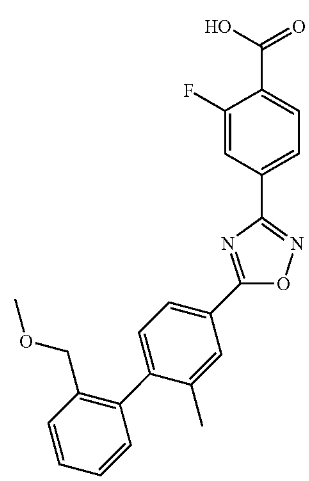 | — | 2.01 | — |

-continued

| Example Nb | structure | S1P1 Binding Ki (µM) | S1P1 GTPγS EC50 (µM) | S1P3 GTPγS EC50 (µM) |
|---|---|---|---|---|
| 88 | 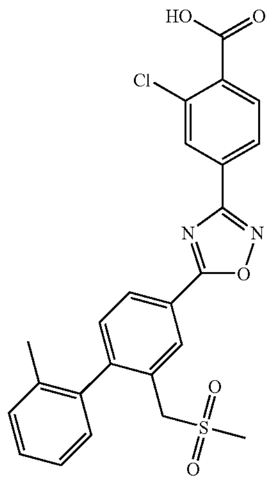 | — | 4.64 | — |
| 89 | 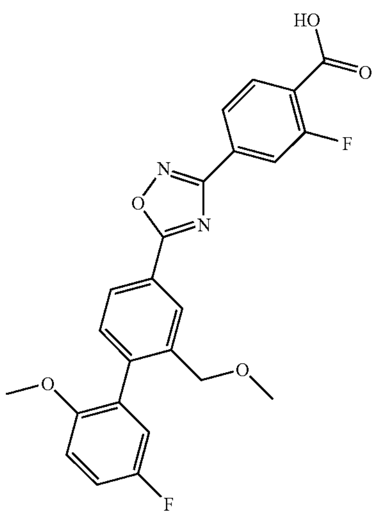 | — | 0.46 | — |
| 90 | 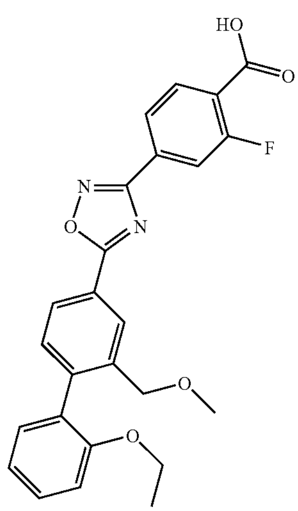 | — | 0.479 | — |

-continued

| Example Nb | structure | S1P1 Binding Ki (μM) | S1P1 GTPγS EC50 (μM) | S1P3 GTPγs EC50 (μM) |
|---|---|---|---|---|
| 91 | 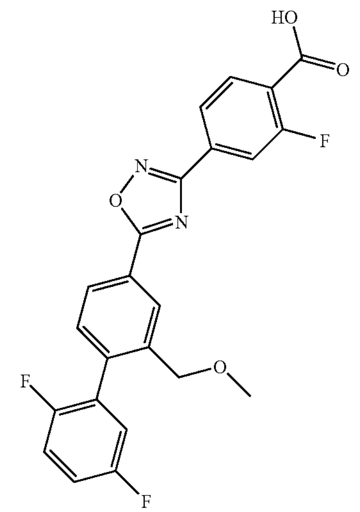 | — | 0.41 | — |
| 92 | 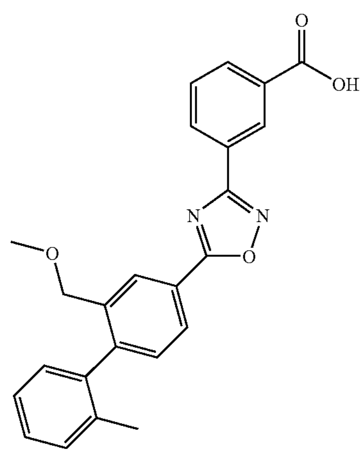 | 0.037 | 0.063 | 1.25 |
| 93 | 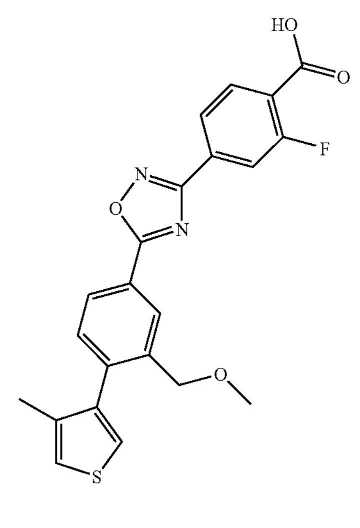 | 0.01 | 0.018 | 1.38 |

-continued

| Example Nb | structure | S1P1 Binding Ki (μM) | S1P1 GTPγS EC50 (μM) | S1P3 GTPγs EC50 (μM) |
|---|---|---|---|---|
| 94 | 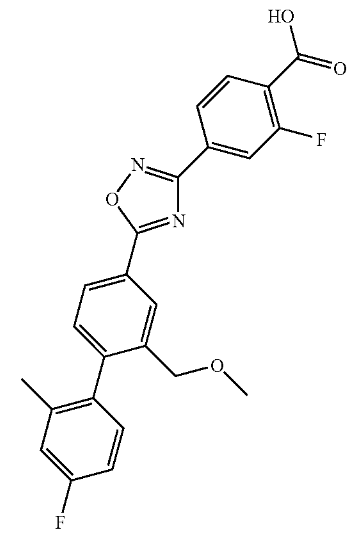 | — | 0.513 | — |
| 95 | 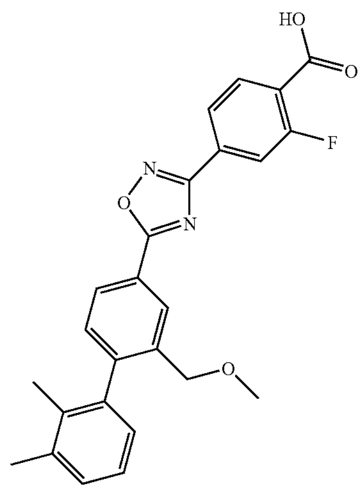 | 0.016 | 0.048 | 4.96 |
| 96 | 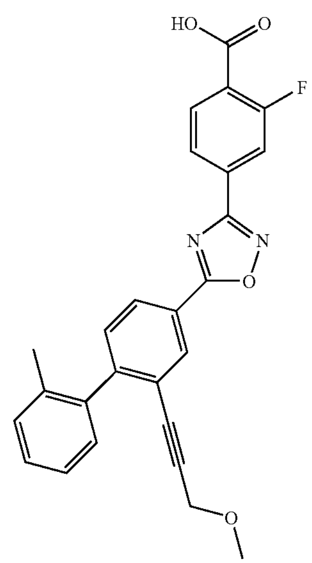 | — | 0.462 | — |

-continued

| Example Nb | structure | S1P1 Binding Ki (μM) | S1P1 GTPγS EC50 (μM) | S1P3 GTPγs EC50 (μM) |
|---|---|---|---|---|
| 97 | 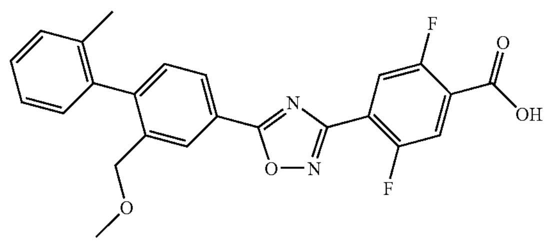 | 0.008 | 0.064 | 1.94 |
| 98 | 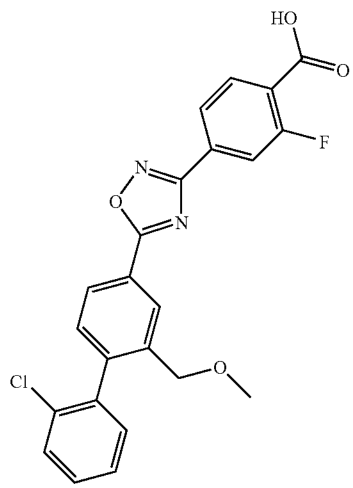 | — | 0.067 | — |
| 99 | 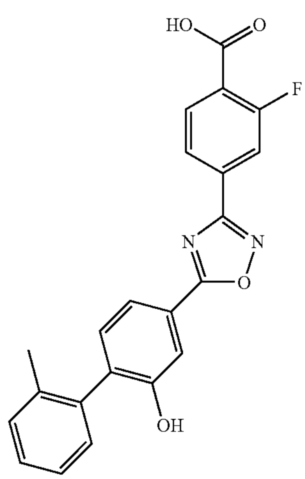 | — | 7.7 | — |

-continued
| Example Nb | structure | S1P1 Binding Ki (μM) | S1P1 GTPγS EC50 (μM) | S1P3 GTPγs EC50 (μM) |
|---|---|---|---|---|
| 100 | 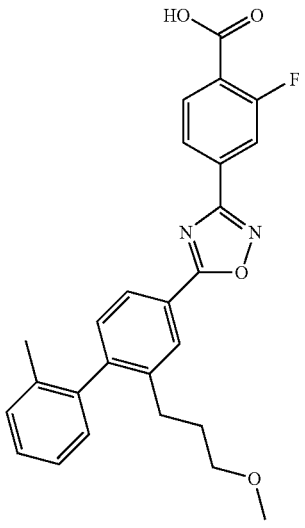 | — | 0.5385 | — |
| 101 | 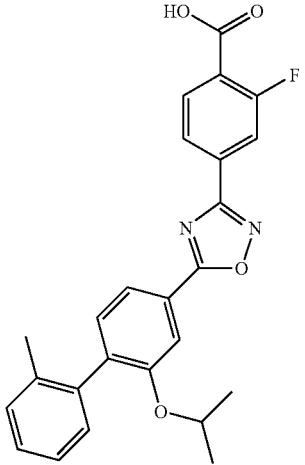 | — | 0.233 | — |
| 102 | 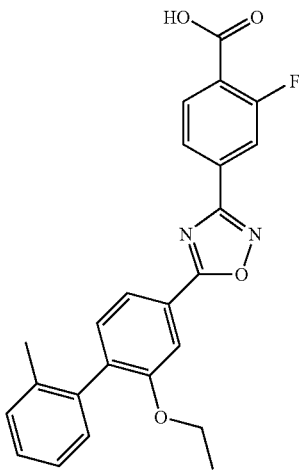 | 0.011 | 0.058 | 1.76 |

-continued

| Example Nb | structure | S1P1 Binding Ki (μM) | S1P1 GTPγS EC50 (μM) | S1P3 GTPγS EC50 (μM) |
|---|---|---|---|---|
| 103 | 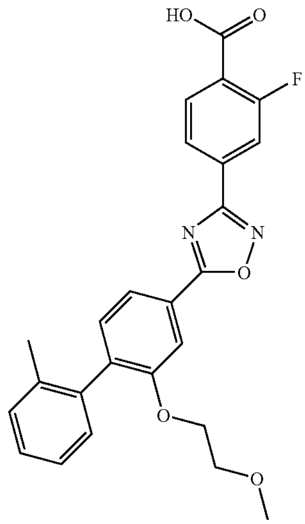 | — | 0.257 | — |
| 104 | 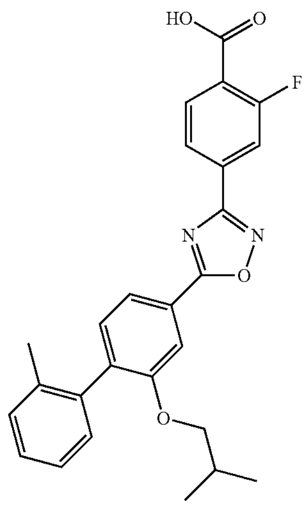 | — | 0.8 | — |
| 105 | 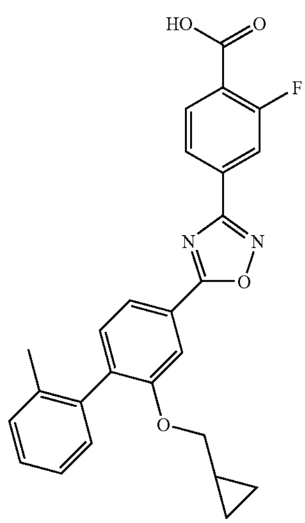 | — | 0.103 | — |

-continued
| Example Nb | structure | S1P1 Binding Ki (μM) | S1P1 GTPγS EC50 (μM) | S1P3 GTPγs EC50 (μM) |
|---|---|---|---|---|
| 106 | 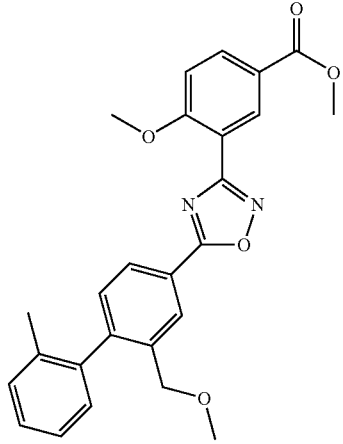 | — | 0.05 | — |
| 107 | 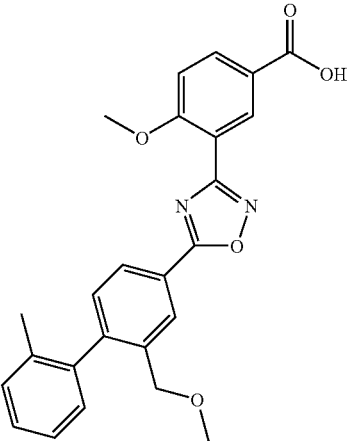 | — | 0.133 | — |
| 108 | 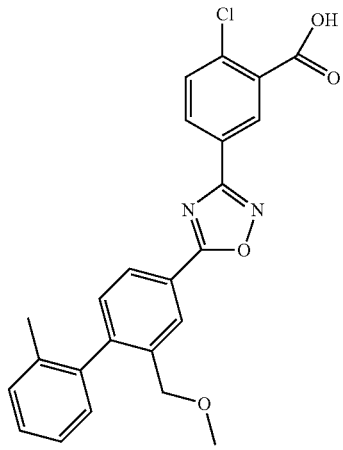 | — | 0.163 | — |

-continued
| Example Nb | structure | S1P1 Binding Ki (μM) | S1P1 GTPγS EC50 (μM) | S1P3 GTPγs EC50 (μM) |
|---|---|---|---|---|
| 109 | 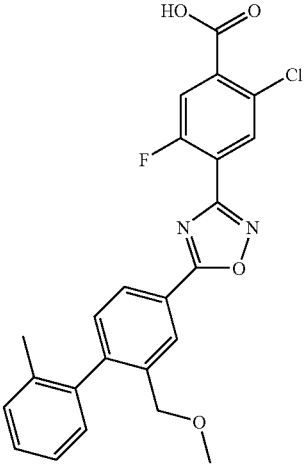 | — | 0.09 | — |
| 110 | 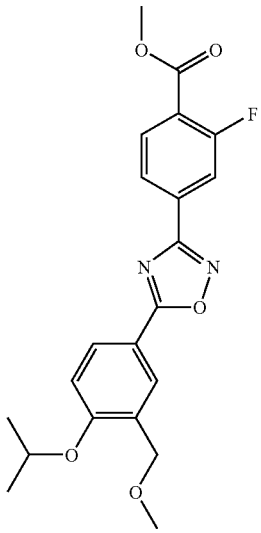 | — | 0.24 | — |
| 111 | 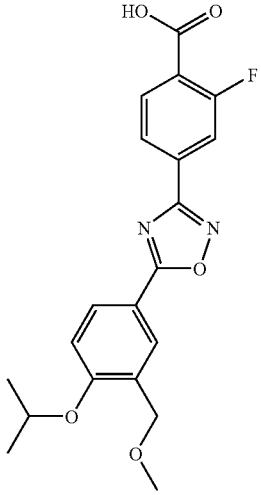 | — | 0.61 | — |

-continued

| Example Nb | structure | S1P1 Binding Ki (μM) | S1P1 GTPγS EC50 (μM) | S1P3 GTPγs EC50 (μM) |
|---|---|---|---|---|
| 112 | 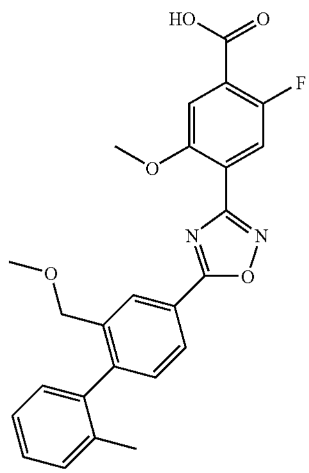 | — | 0.102 | — |
| 113 | 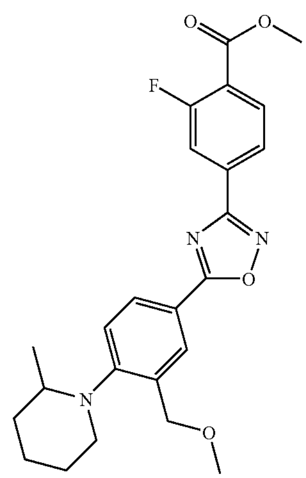 | — | 0.485 | — |
| 114 | 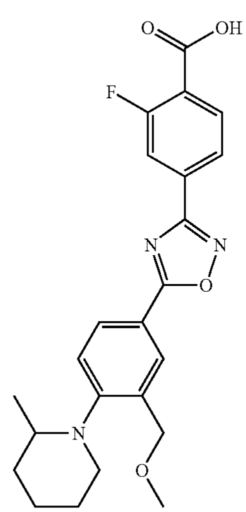 | 0.0027 | 0.013 | 2.81 |

-continued
| Example Nb | structure | S1P1 Binding Ki (μM) | S1P1 GTPγS EC50 (μM) | S1P3 GTPγS EC50 (μM) |
|---|---|---|---|---|
| 115 | 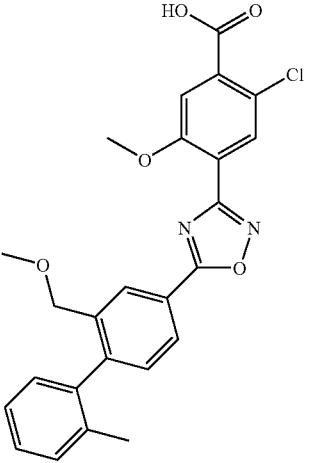 | — | 0.2455 | — |
| 116 | 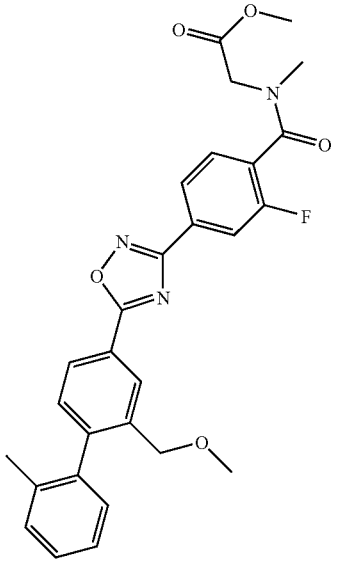 | — | 0.24 | — |

-continued
| Example Nb | structure | S1P1 Binding Ki (μM) | S1P1 GTPγS EC50 (μM) | S1P3 GTPγs EC50 (μM) |
|---|---|---|---|---|
| 117 | 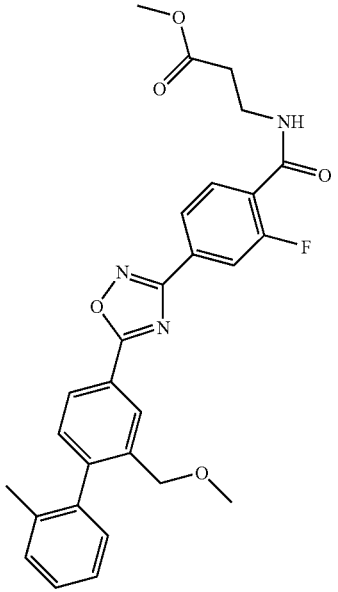 | — | 0.009 | — |
| 118 | 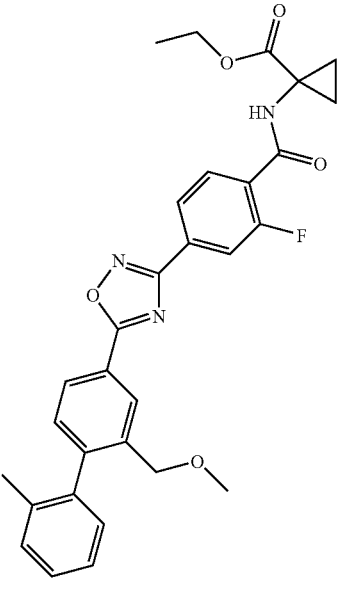 | 0.002 | 0.007 | 2.16 |

-continued

| Example Nb | structure | S1P1 Binding Ki (μM) | S1P1 GTPγS EC50 (μM) | S1P3 GTPγs EC50 (μM) |
|---|---|---|---|---|
| 119 | 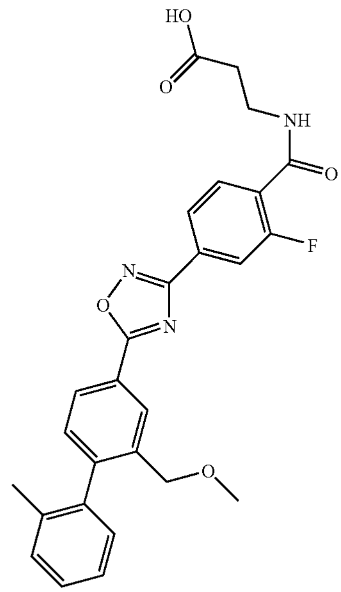 | 0.002 | 0.0073 | 0.502 |
| 120 | 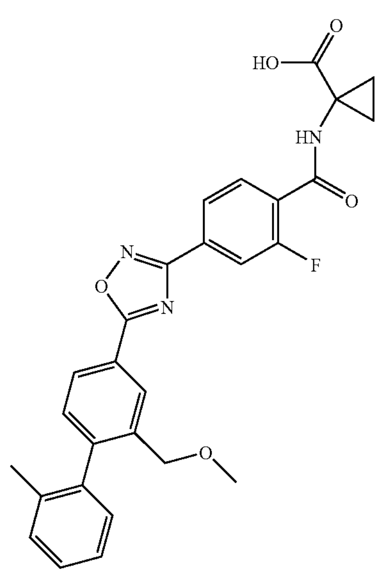 | — | 0.058 | — |

-continued

| Example Nb | structure | S1P1 Binding Ki (μM) | S1P1 GTPγS EC50 (μM) | S1P3 GTPγs EC50 (μM) |
|---|---|---|---|---|
| 121 | 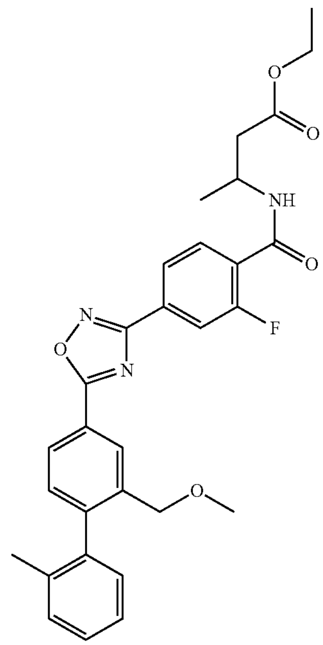 | — | 0.281 | — |
| 122 | 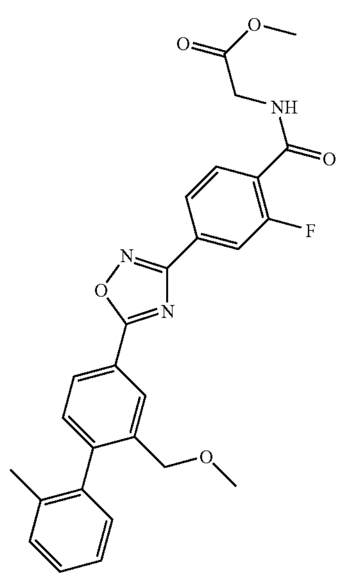 | 0.0009 | 0.0025 | — |

-continued

| Example Nb | structure | S1P1 Binding Ki (µM) | S1P1 GTPγS EC50 (µM) | S1P3 GTPγs EC50 (µM) |
|---|---|---|---|---|
| 123 | | 0.004 | 0.0373 | 1.21 |
| 124 | | 0.002 | 0.022 | 1 |

-continued

| Example Nb | structure | S1P1 Binding Ki (μM) | S1P1 GTPγS EC50 (μM) | S1P3 GTPγS EC50 (μM) |
|---|---|---|---|---|
| 125 | 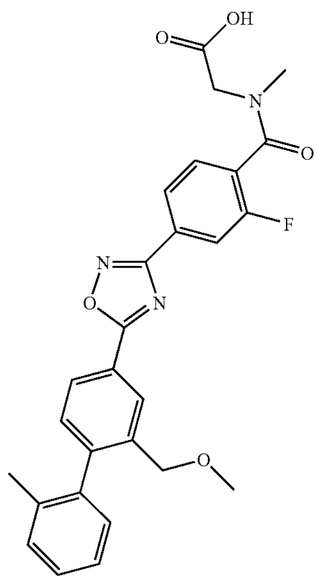 | — | 0.086 | — |
| 126 | 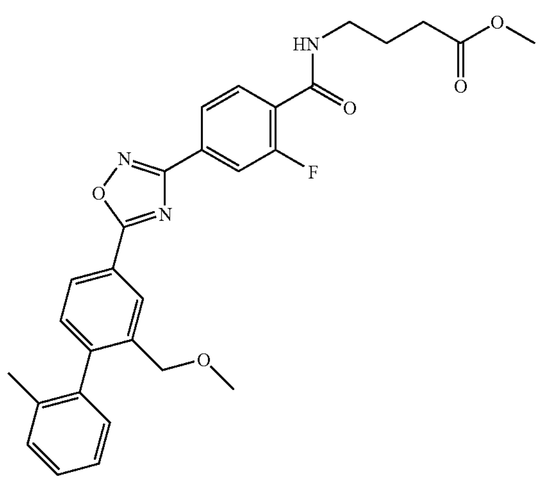 | — | 0.035 | — |
| 127 | 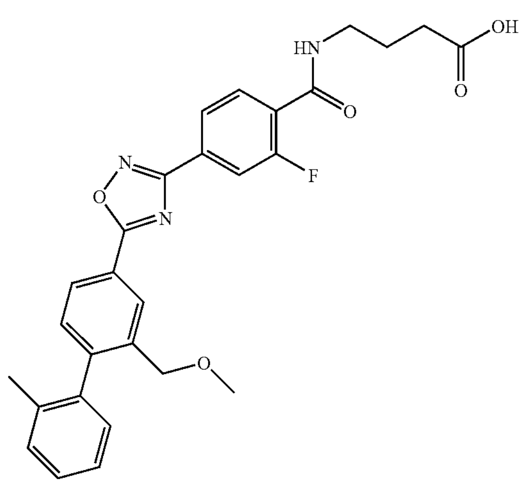 | 0.0021 | 0.006 | 1.22 |

-continued

| Example Nb | structure | S1P1 Binding Ki (μM) | S1P1 GTPγS EC50 (μM) | S1P3 GTPγs EC50 (μM) |
|---|---|---|---|---|
| 128 | 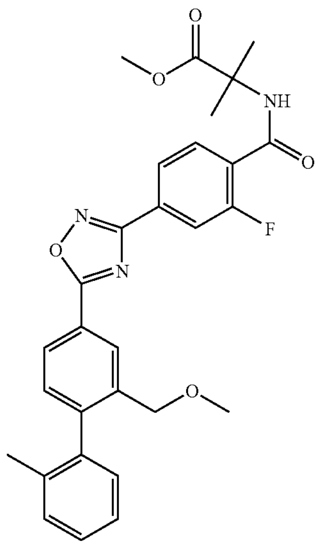 | — | 0.154 | — |
| 129 | 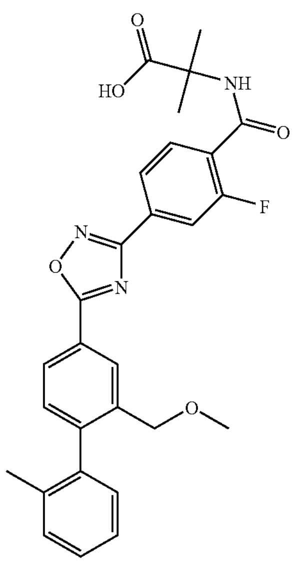 | — | 0.04 | — |
| 130 | 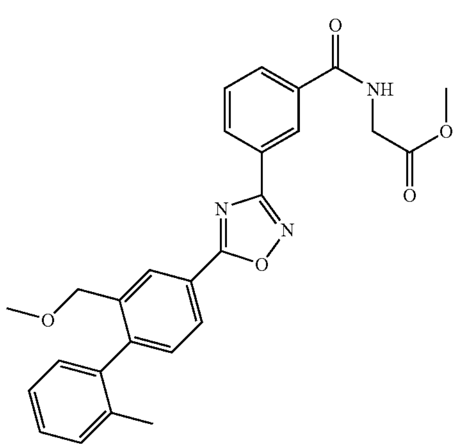 | — | 0.0086 | — |

-continued
| Example Nb | structure | S1P1 Binding Ki (μM) | S1P1 GTPγS EC50 (μM) | S1P3 GTPγs EC50 (μM) |
|---|---|---|---|---|
| 131 | 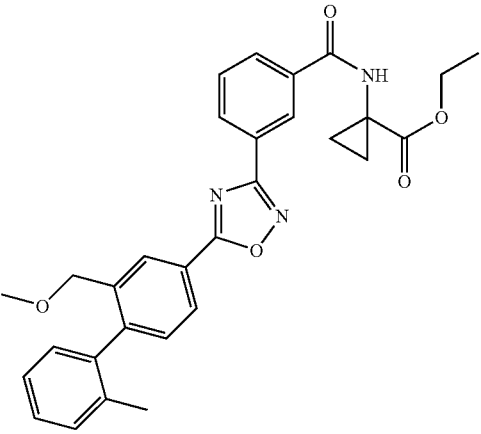 | — | 0.035 | — |
| 132 | 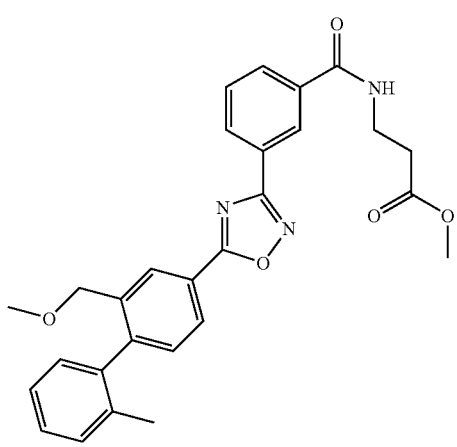 | — | 0.0029 | — |
| 133 | 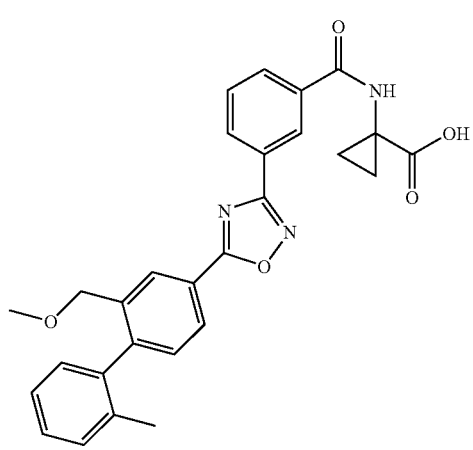 | — | 0.0216 | — |

-continued

| Example Nb | structure | S1P1 Binding Ki (μM) | S1P1 GTPγS EC50 (μM) | S1P3 GTPγs EC50 (μM) |
|---|---|---|---|---|
| 134 | 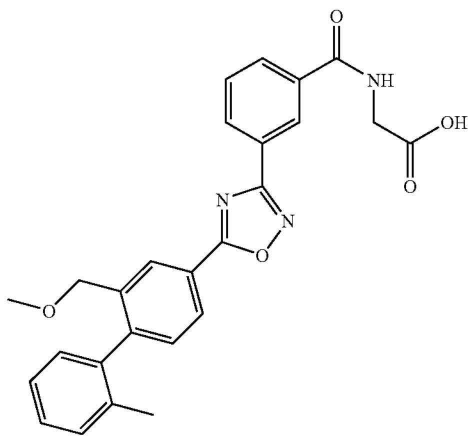 | — | 0.0051 | — |
| 135 | 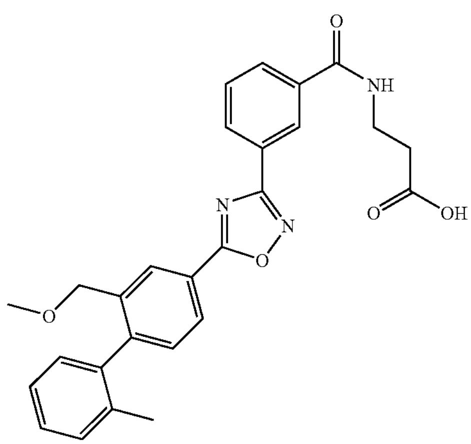 | — | 0.0078 | — |
| 136 | 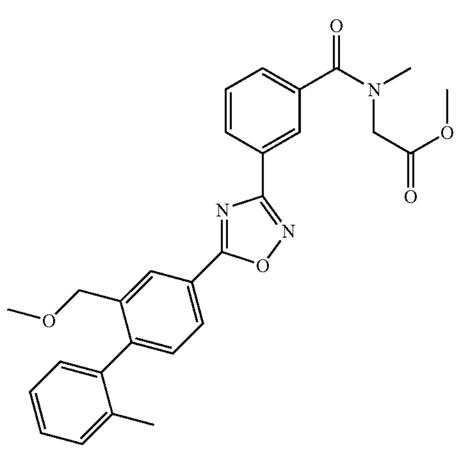 | — | 0.046 | — |

-continued

| Example Nb | structure | S1P1 Binding Ki (μM) | S1P1 GTPγS EC50 (μM) | S1P3 GTPγs EC50 (μM) |
| --- | --- | --- | --- | --- |
| 137 | 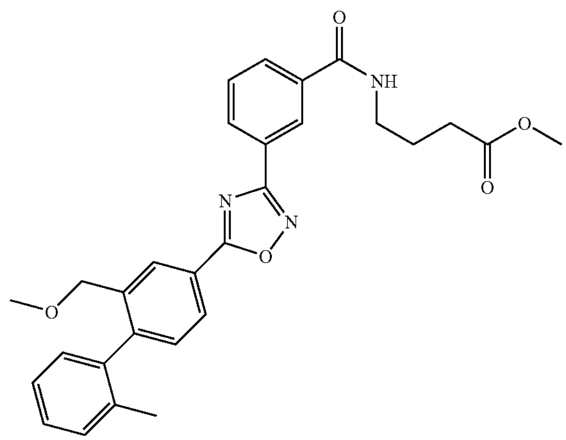 | — | 0.025 | — |
| 138 | 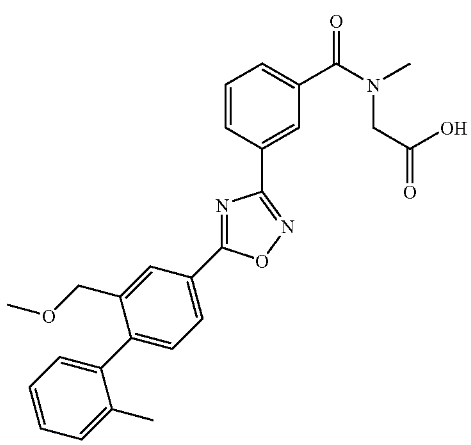 | — | 0.0486 | — |
| 139 | 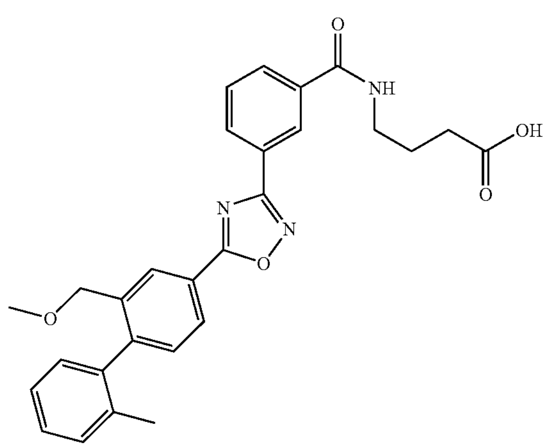 | — | 0.0096 | — |

| Example Nb | structure | S1P1 Binding Ki (μM) | S1P1 GTPγS EC50 (μM) | S1P3 GTPγs EC50 (μM) |
|---|---|---|---|---|
| 140 | 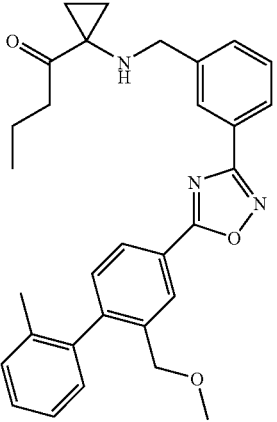 | — | 0.142 | — |
| 141 | 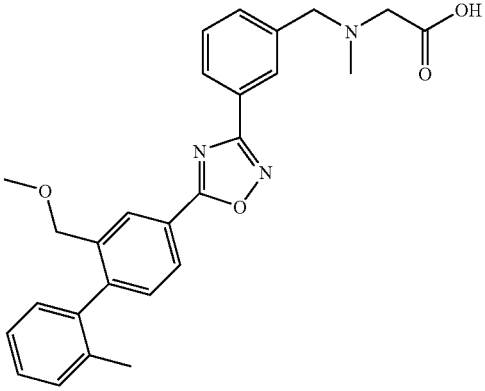 | 0.0014 | 0.00085 | 0.621 |
| 142 | 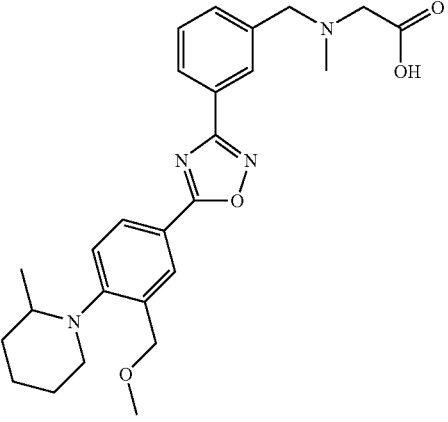 | 0.00014 | 0.00062 | 0.112 |

| Example Nb | structure | S1P1 Binding Ki (μM) | S1P1 GTPγS EC50 (μM) | S1P3 GTPγs EC50 (μM) |
|---|---|---|---|---|
| 143 | 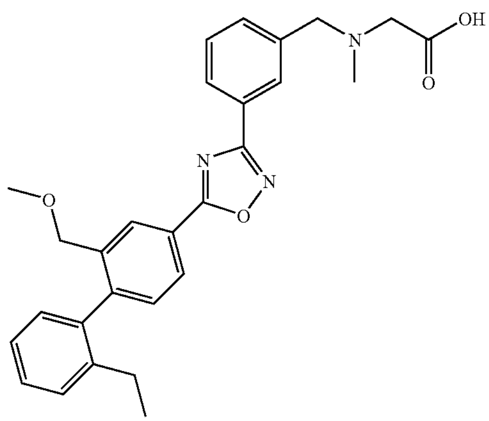 | 0.0008 | 0.0006 | 0.281 |
| 144 | 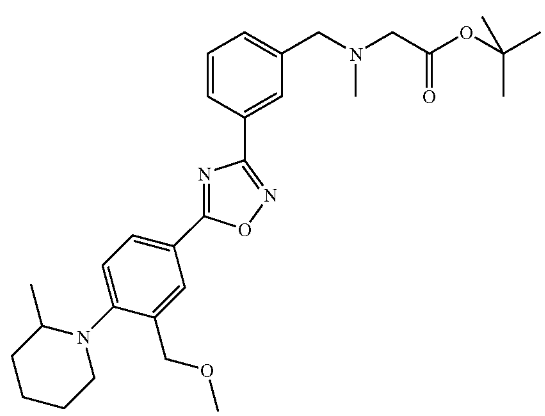 | — | 0.256 | — |
| 145 | 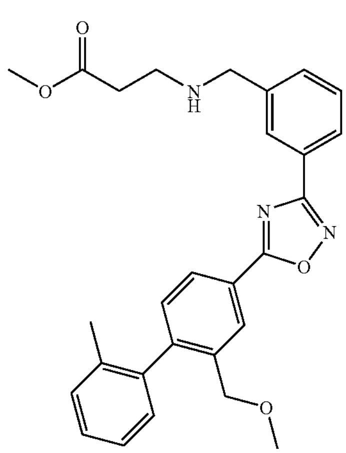 | — | 0.0023 | — |

-continued

| Example Nb | structure | S1P1 Binding Ki (μM) | S1P1 GTPγS EC50 (μM) | S1P3 GTPγS EC50 (μM) |
|---|---|---|---|---|
| 146 | 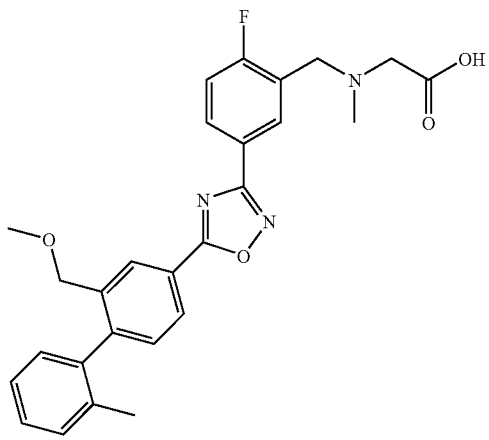 | 0.0008 | 0.0025 | 0.422 |
| 147 | 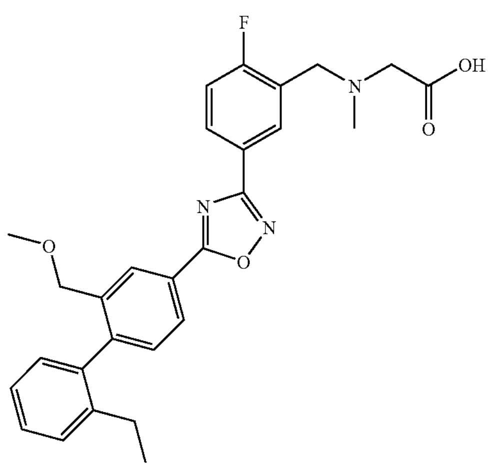 | 0.002 | 0.0015 | 0.754 |
| 148 | 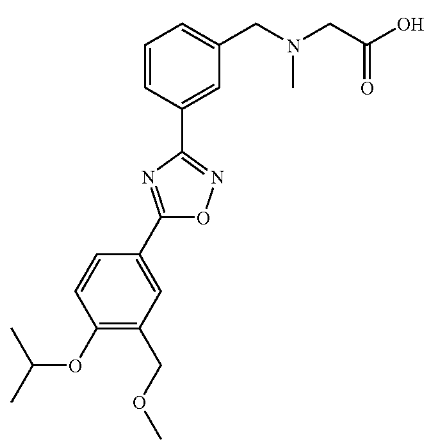 | 0.0007 | 0.0040 | 2.35 |

-continued
| Example Nb | structure | S1P1 Binding Ki (μM) | S1P1 GTPγS EC50 (μM) | S1P3 GTPγs EC50 (μM) |
|---|---|---|---|---|
| 149 | 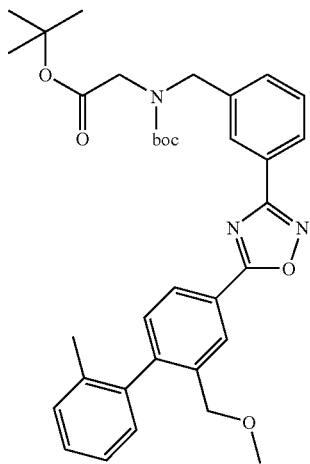 | — | 1.2450 | — |
| 150 | 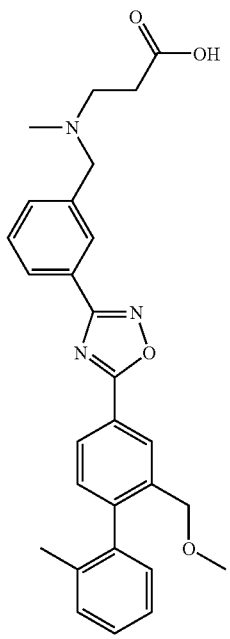 | 0.0003 | 0.0005 | 0.095 |
| 151 | 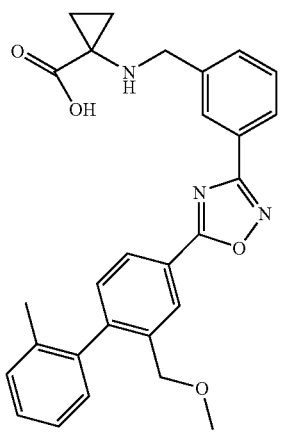 | 0.0065 | 0.0048 | 0.175 |

-continued

| Example Nb | structure | S1P1 Binding Ki (μM) | S1P1 GTPγS EC50 (μM) | S1P3 GTPγs EC50 (μM) |
|---|---|---|---|---|
| 152 | 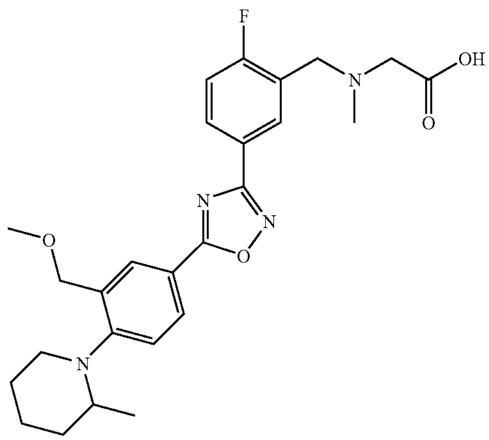 | — | 0.0006 | 0.223 |
| 153 | 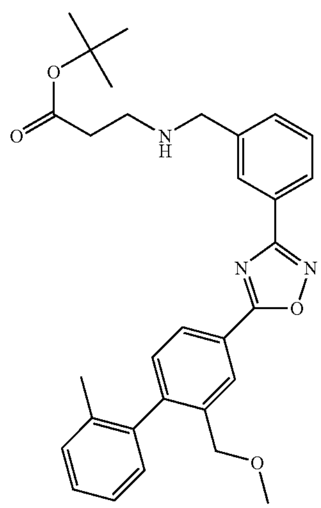 | — | 0.0252 | — |
| 154 | 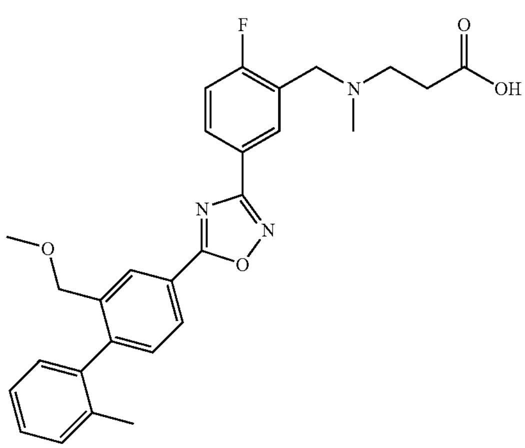 | — | 0.0012 | — |

-continued

| Example Nb | structure | S1P1 Binding Ki (μM) | S1P1 GTPγS EC50 (μM) | S1P3 GTPγs EC50 (μM) |
|---|---|---|---|---|
| 155 | 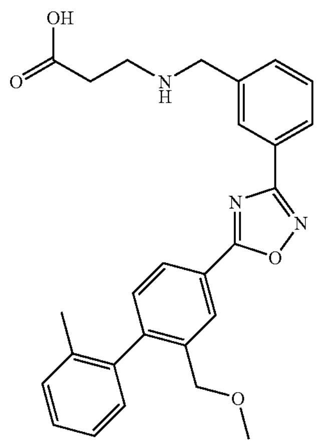 | — | 0.0004 | — |
| 156 | 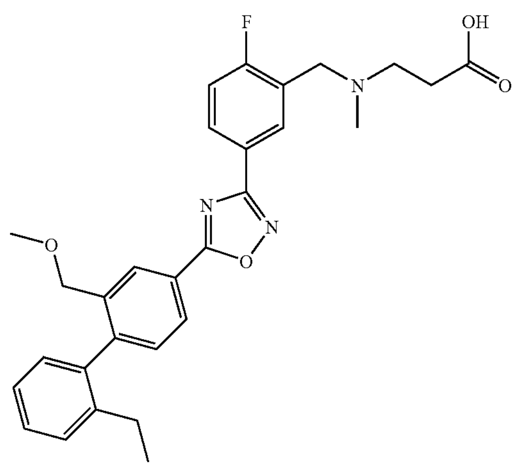 | — | 0.0025 | — |
| 157 | 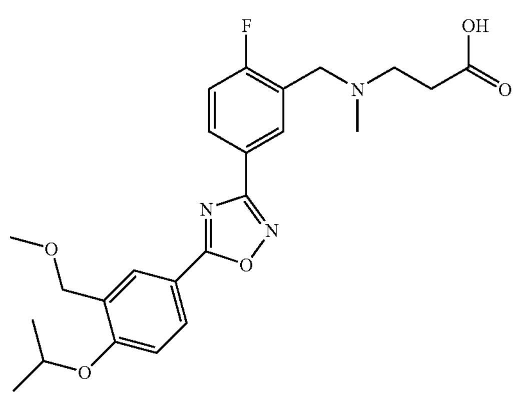 | — | 0.004 | — |

-continued
| Example Nb | structure | S1P1 Binding Ki (μM) | S1P1 GTPγS EC50 (μM) | S1P3 GTPγs EC50 (μM) |
|---|---|---|---|---|
| 158 | 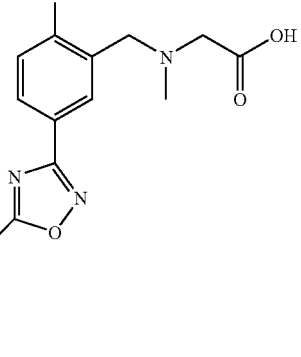 | — | 0.01 | — |
| 159 | 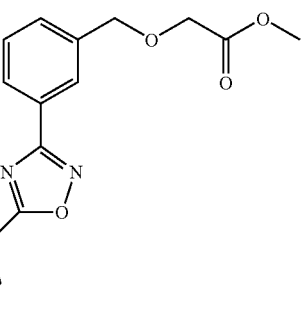 | — | 0.0029 | — |
| 160 | 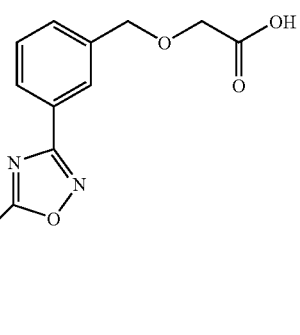 | — | 0.0006 | — |

-continued

| Example Nb | structure | S1P1 Binding Ki (μM) | S1P1 GTPγS EC50 (μM) | S1P3 GTPγs EC50 (μM) |
|---|---|---|---|---|
| 161 | 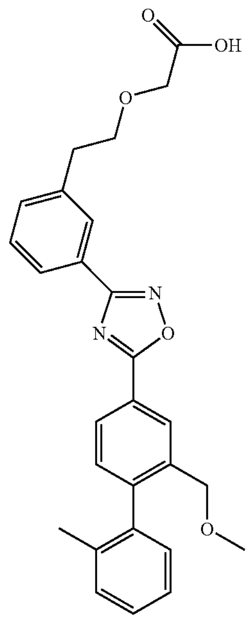 | — | 0.0021 | — |
| 162 | 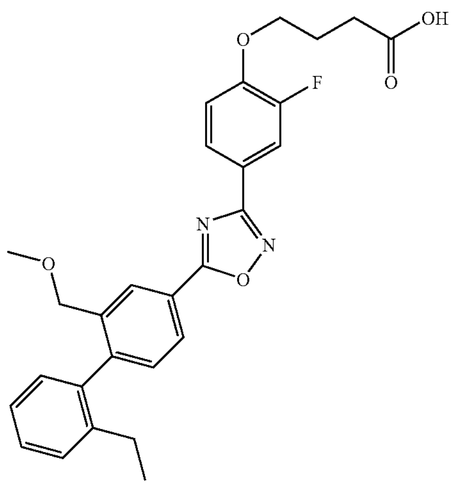 | — | 0.005 | — |
| 163 | 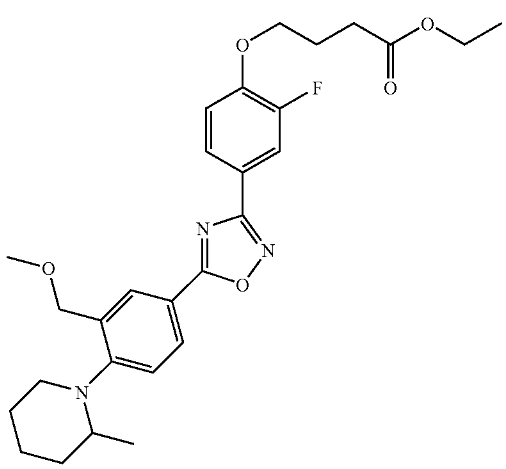 | — | 0.0055 | — |

-continued
| Example Nb | structure | S1P1 Binding Ki (μM) | S1P1 GTPγS EC50 (μM) | S1P3 GTPγs EC50 (μM) |
|---|---|---|---|---|
| 164 | 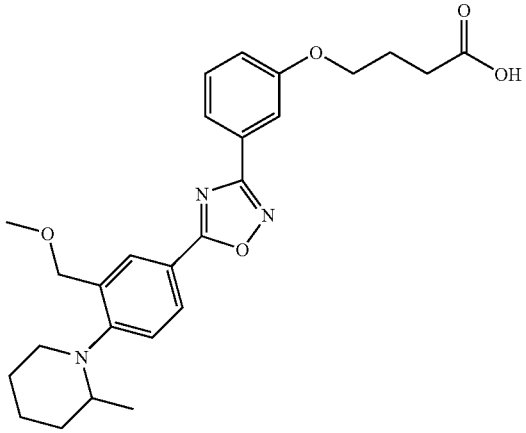 | — | 0.0015 | — |
| 165 | 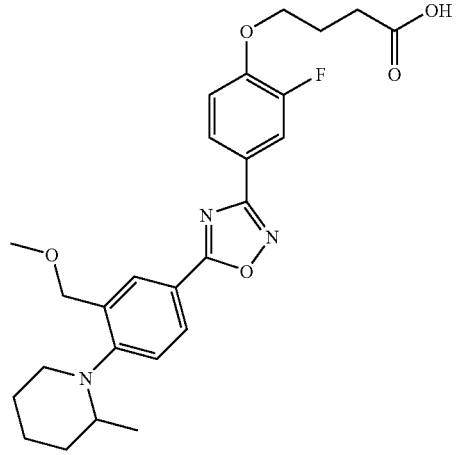 | — | 0.0016 | — |
| 166 | 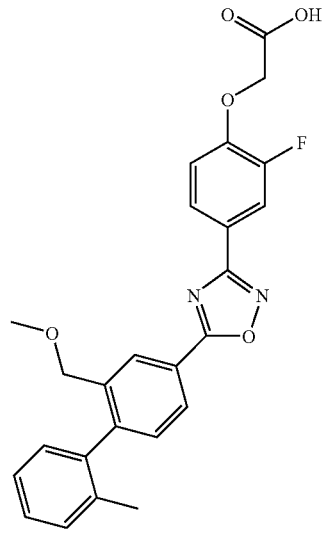 | 0.011 | 0.014 | 0.219 |

-continued

| Example Nb | structure | S1P1 Binding Ki (μM) | S1P1 GTPγS EC50 (μM) | S1P3 GTPγS EC50 (μM) |
|---|---|---|---|---|
| 167 | 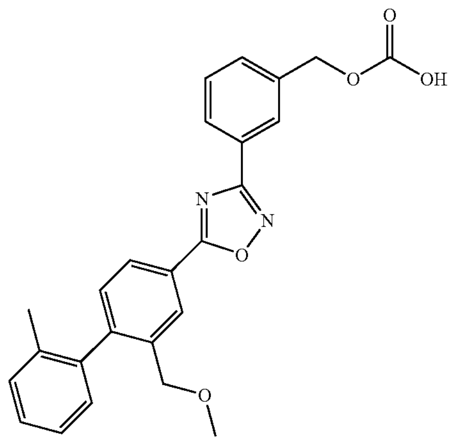 | 0.01 | 0.0224 | — |
| 168 | 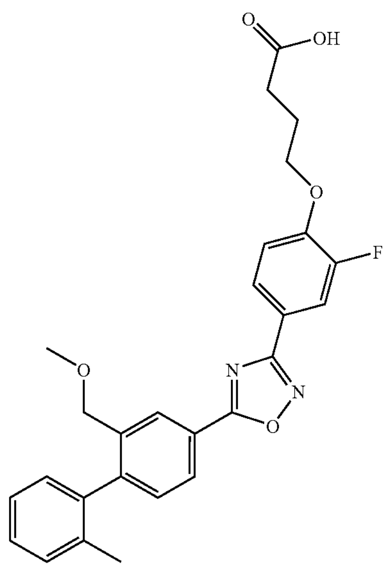 | — | 0.0078 | 0.219 |
| 169 | 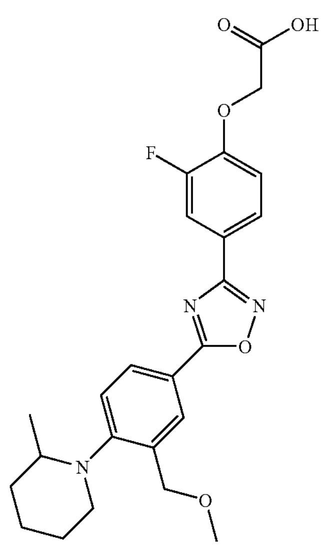 | — | 0.0052 | — |

-continued
| Example Nb | structure | S1P1 Binding Ki (µM) | S1P1 GTPγS EC50 (µM) | S1P3 GTPγs EC50 (µM) |
|---|---|---|---|---|
| 170 | 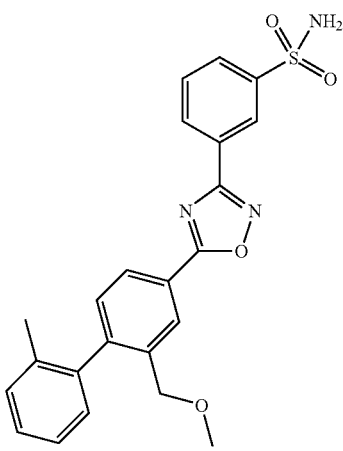 | 0.0008 | 0.0007 | 0.214 |
| 171 | 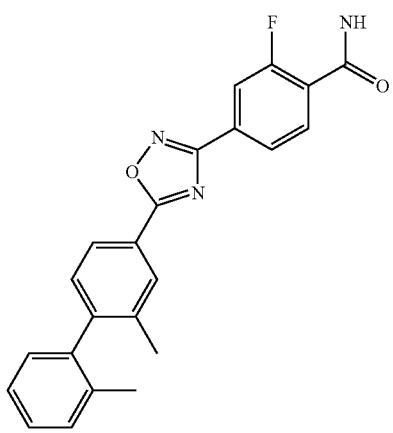 | 0.039 | 0.019 | >20 |
| 172 | 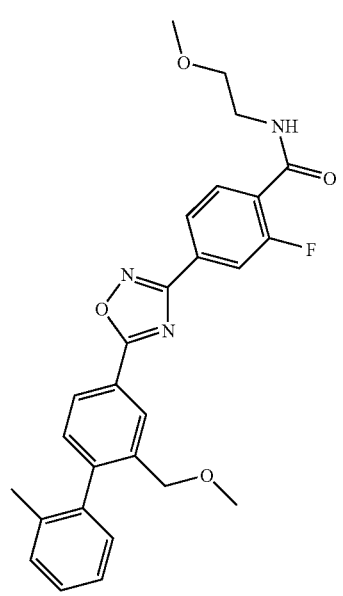 | — | 0.033 | — |

-continued
| Example Nb | structure | S1P1 Binding Ki (μM) | S1P1 GTPγS EC50 (μM) | S1P3 GTPγs EC50 (μM) |
|---|---|---|---|---|
| 173 | 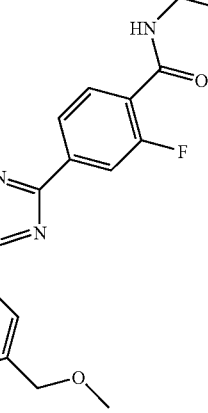 | 0.002 | 0.006 | — |
| 174 | 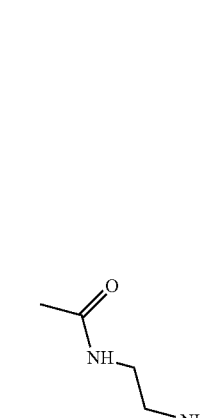 | 0.0034 | 0.017 | 1.42 |

-continued

| Example Nb | structure | S1P1 Binding Ki (μM) | S1P1 GTPγS EC50 (μM) | S1P3 GTPγS EC50 (μM) |
|---|---|---|---|---|
| 175 | 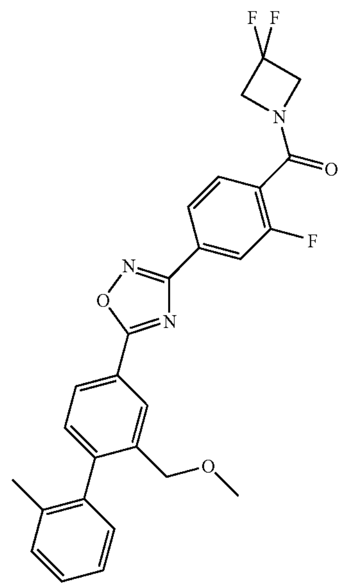 | — | 0.128 | — |
| 176 | 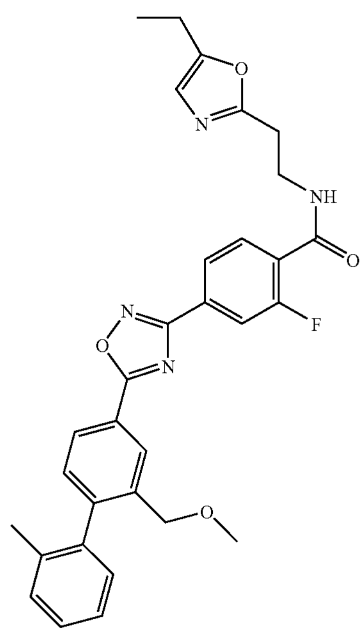 | — | 0.197 | — |

-continued
| Example Nb | structure | S1P1 Binding Ki (μM) | S1P1 GTPγS EC50 (μM) | S1P3 GTPγs EC50 (μM) |
|---|---|---|---|---|
| 177 | 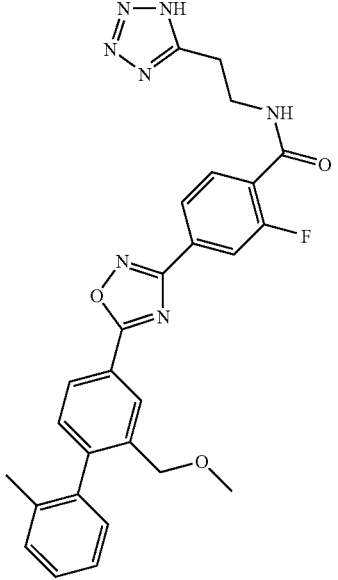 | 0.002 | 0.0013 | 1.15 |
| 178 | 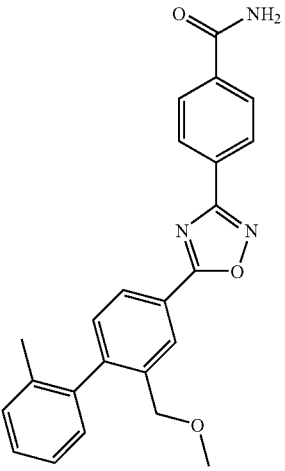 | 0.001 | 0.0048 | 0.141 |
| 179 | 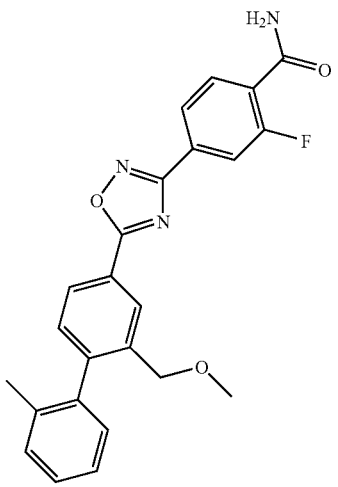 | 0.003 | 0.008 | 0.274 |

-continued

| Example Nb | structure | S1P1 Binding Ki (µM) | S1P1 GTPγS EC50 (µM) | S1P3 GTPγs EC50 (µM) |
|---|---|---|---|---|
| 180 | 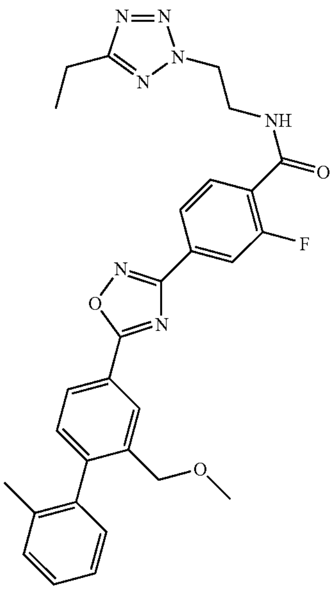 | — | 0.026 | — |
| 181 | 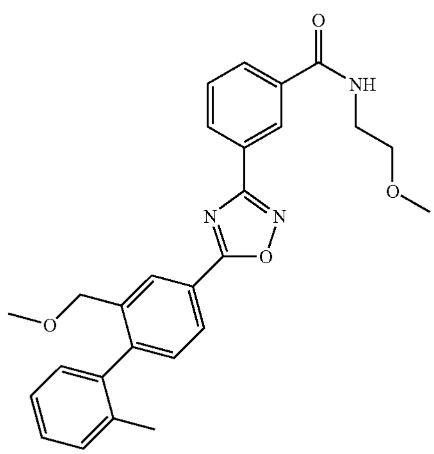 | — | 0.016 | — |
| 182 | 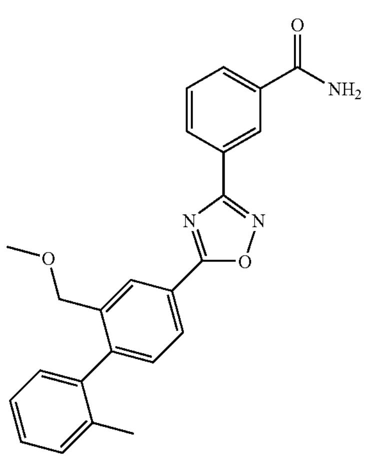 | — | 0.011 | — |

-continued

| Example Nb | structure | S1P1 Binding Ki (μM) | S1P1 GTPγS EC50 (μM) | S1P3 GTPγs EC50 (μM) |
|---|---|---|---|---|
| 183 | 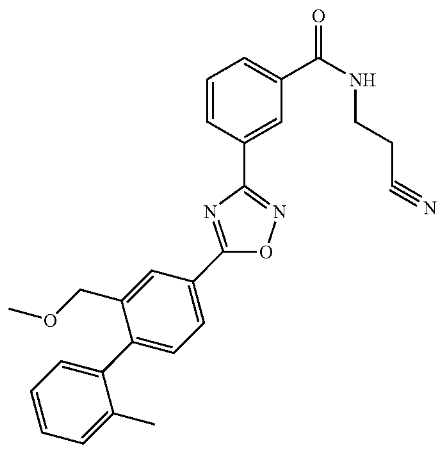 | 0.002 | 0.0024 | 5.6 |
| 184 | 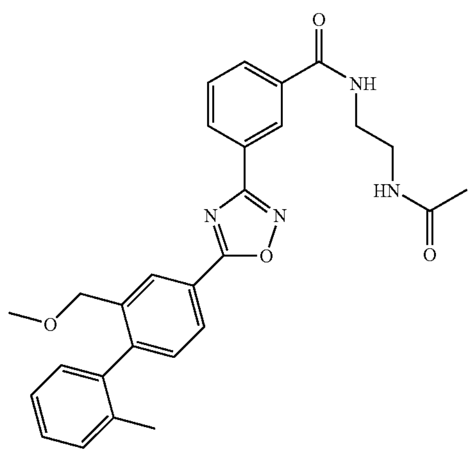 | 0.001 | 0.0033 | 4.49 |
| 185 | 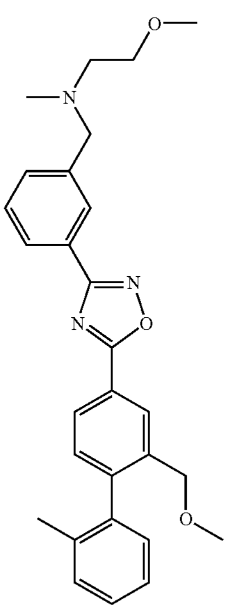 | 0.007 | 0.005 | — |

-continued
| Example Nb | structure | S1P1 Binding Ki (μM) | S1P1 GTPγS EC50 (μM) | S1P3 GTPγs EC50 (μM) |
|---|---|---|---|---|
| 186 | 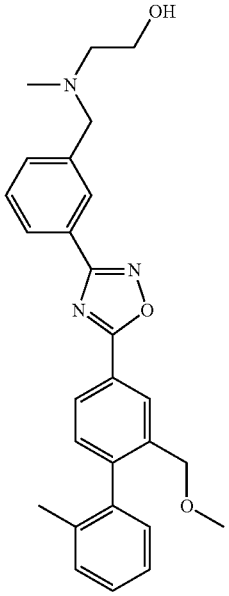 | 0.0008 | 0.0011 | 1.62 |
| 187 | 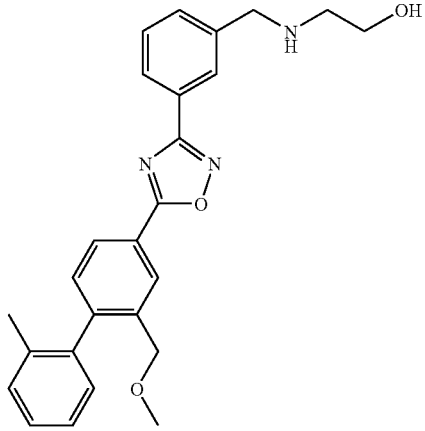 | — | 0.002 | — |
| 188 | 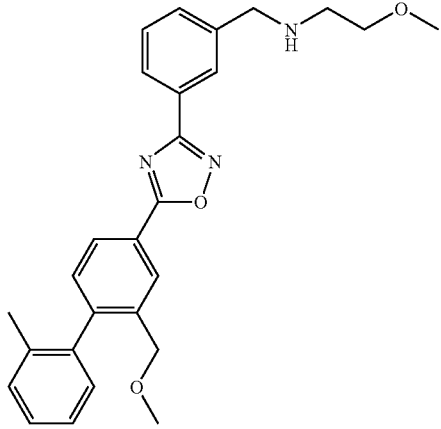 | — | 0.004 | — |

-continued

| Example Nb | structure | S1P1 Binding Ki (μM) | S1P1 GTPγS EC50 (μM) | S1P3 GTPγs EC50 (μM) |
|---|---|---|---|---|
| 189 | 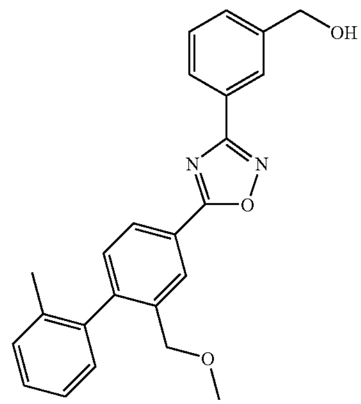 | 0.001 | 0.0021 | 0.574 |
| 190 | 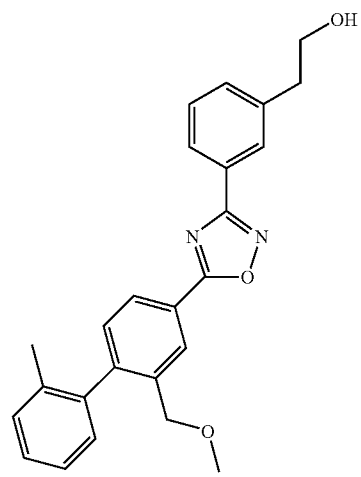 | 0.0043 | 0.0007 | — |
| 191 | 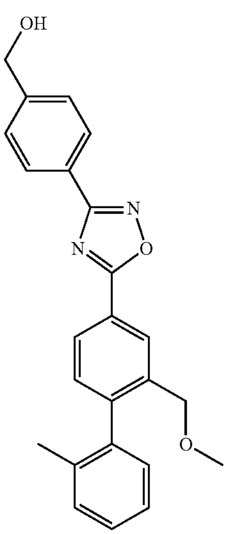 | 0.007 | 0.0021 | — |

-continued

| Example Nb | structure | S1P1 Binding Ki (μM) | S1P1 GTPγS EC50 (μM) | S1P3 GTPγs EC50 (μM) |
|---|---|---|---|---|
| 192 | 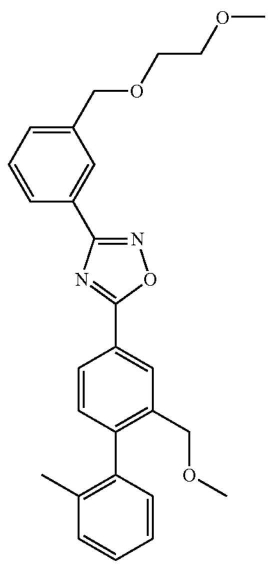 | — | 0.0061 | — |
| 193 | 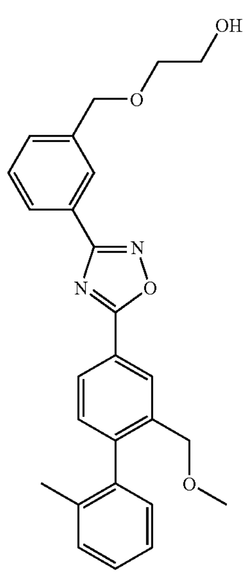 | — | 0.0018 | — |

| Example Nb | structure | S1P1 Binding Ki (μM) | S1P1 GTPγS EC50 (μM) | S1P3 GTPγS EC50 (μM) |
|---|---|---|---|---|
| 194 | 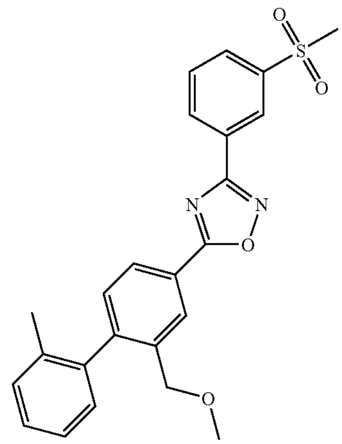 | 0.0016 | 0.001 | 1.715 |

Example 196

Animal Models Evaluating the In Vivo Efficacy of S1P Agonists Model of S1P Agonists-Induced Lymphopenia in Mice Female C57BL/6 mice (Elevage Janvier) (8 week old) receive S1P agonists by oral route. Blood is sampled in heparinized (100 IU/kg, ip) mice by intracardiac or retroorbital puncture under isoflurane anesthesia 2 to 120 hrs after drug treatment. The white blood cells (lymphocytes and neutrophils) are counted using a Beckman/Coulter counter. The quality of blood sampling is assessed by counting erythrocytes and platelets.

Model of MOG-Induced Experimental Autoimmune Encephalomyelytis (EAE) in Mice

EAE was induced in 9 weeks old female mice (C57BL/6, Elevage Janvier) by an immunization against MOG. The mice received Pertussis toxin (Alexis, 300 ng/mouse in 200 μl of PBS) by ip route and 100 μl of an emulsion containing MOG35-55 peptide (NeoMPS, 200 μg/mouse), *Mycobacterium Tuberculosis* (0.25 mg/mouse) in Complete Freund's Adjuvant (DIFCO) by subcutaneous injection into the back. Two days later an additional injection of Pertussis toxin (Alexis, 300 ng/mouse in 200 μl of PBS) was done by ip route. After EAE induction, mice were weighed daily and the neurological impairment was quantified using a 15-points clinical scale assessing the paralysis (tail, hind limbs and fore limbs), the incontinency and the death.

Clinical Score

1—Tail
 Score=0 A normal mouse holds its tail erect when moving.
 Score=1 If the extremity of the tail is flaccid with a tendency to fall.
 Score=2 If the tail is completely flaccid and drags on the table.

2—Hind limbs
 Score=0 A normal mouse has an energetic walk and doesn't drag his paws.
 Score=1 Either one of the following tests is positive:
  a—Flip test: while holding the tail between thumb and index finger, flip the animal on his back and observe the time it takes to right itself. A healthy mouse will turn itself immediately. A delay suggests hind-limb weakness.
  b—Place the mouse on the wire cage top and observe as it crosses from one side to the other. If one or both limbs frequently slip between the bars we consider that there is a partial paralysis.
 Score=2 Both previous tests are positive.
 Score=3 One or both hind limbs show signs of paralysis but some movements are preserved; for example: the animal can grasp and hold on to the underside of the wire cage top for a short moment before letting go
 Score=4 When both hind legs are paralyzed and the mouse drags them when moving.

3—Fore limbs:
 Score=0 A normal mouse uses his front paws actively for grasping and walking and holds his head erect.
 Score=1 Walking is possible but difficult due to a weakness in one or both of the paws, for example, the front paws are considered weak when the mouse has difficulty grasping the underside of the wire top cage. Another sign of weakness is head drooping.
 Score=2 When one forelimb is paralyzed (impossibility to grasp and the mouse turns around the paralyzed limb). At this time the head has also lost much of its muscle tone.
 Score=3 Mouse cannot move, and food and water are unattainable.

4—Bladder:
 Score=0 A normal mouse has full control of his bladder.
 Score=1 A mouse is considered incontinent when his lower body is soaked with urine.

5—Death:
 Score=15

The final score for each animal is determined by the addition of all the above-mentioned categories. The maximum score for live animals is 10.

At day 12 (first signs of paralysis) the mice were stratified in experimental groups (n=10) according to the clinical score and the body weight loss. The semi-curative treatment started at day 14.

Example 197

Preparation of a Pharmaceutical Formulation

Formulation 1—Tablets

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of formula (I) is dissolved in a buffered sterile saline injectable aqueous medium to a concentration of approximately 5 mg/mL.

The invention claimed is:
1. A compound of Formula (I)

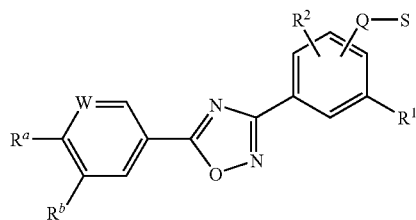

I wherein:
$R^1$, $R^2$ denote H, Hal, $CF_3$, $OCF_3$, CN, $NO_2$, OH, A, or OA,
S is $COOR^3$, or $CON(R^3)_2$,
Q denotes $X(CH_2)_m$, $(CH_2)_m X(CH_2)_m$ or a single bond,
X is —O—, —$NR^3$—, —COO— or —$CONR^3$—,
W denotes CH or N,
$R^a$ is Ar or Het,
$R^b$ is, A, $OR^3$, $NO_2$, $NH_3$, Hal, $CH_2OR^3$, or $(CH_2)_mOA$,
A is branched or linear alkyl having 1 to 12 C-atoms, wherein one or more H atoms may be replaced by Hal, $OR^3$, $COOR^3$, CN, $N(R^3)_2$ or Het and wherein one or more non-adjacent $CH_2$-groups may be replaced by O, $NR^3$, CO or S and/or by —CH=CH— or C≡C-groups or cycloalkylene groups having 3 to 7 carbon atoms, or denotes cycloalkyl or cycloalkylalkylene having 3-7 ring C atoms, Hal is F, Cl, Br or I, Ar denotes a monocyclic or bicyclic, saturated, unsaturated or aromatic carbocyclic ring having 6 to 14 carbon atoms, which may be monosubstituted, disubstituted or trisubstituted by Hal, A, $OR^3$, $N(R^3)_2$, $NO_2$, CN, $COOR^3$, $CF_3$, $OCF_3$, $CON(R^3)_2$, $NR^3COA$, $NR^3CON(R^3)_2$, $NR^3SO_2A$, $COR^3$, $SO_2N(R^3)_2$, SOA or $SO_2A$, phenyl, pyridyl-$[C(R^3)_2]_n$—$COOR^S$ and/or —$O[C(R^3)_2]_n$—$CON(R^3)_2$, such that at least one atom adjacent to the atom linking the group Ar to the rest of the molecule bears one of said substituents, Het denotes a monocyclic or bicyclic, saturated, unsaturated or aromatic heterocyclic ring having 1 to 4 N, O and/or S atoms which may be monosubstituted, disubstituted or trisubstituted by Hal, A, —$[C(R^3)_2]_n$—Ar, —$[C(R^3)_2]_n$-cycloalkyl, $OR^3$, $CF_3$, $OCF_3$, $N(R^3)_2$, $NR^3CON(R^3)_2$, $NO_2$, CN, —$[C(R^3)_2]_n$—$COOR^3$, —$[C(R^3)_2]_n$—$CON(R^3)_2$, $NR^3COA$, $NR^3SO_2A$, $COR^3$, $SO_2N(R^3)_2$, SOA, phenyl, pyridyl and/or $SO_2A$, such that at least one atom adjacent to the atom linking the group Het to the rest of the molecule bears one of said substituents, $R^3$ is H or A; 2 geminal groups $R^3$ together may form a ring with the atom they are attached to, n is 0, 1, 2, 3, 4, 5, 6, 7 or 8, and m is 1, 2, 3, 4, 5, 6, 7 or 8 and tautomers, salts and stereoisomers thereof, including mixtures thereof in all ratios.

2. The compound according to claim 1 having the structures IA, IB, ID, IE, IF, IG, IH, IJ, IK

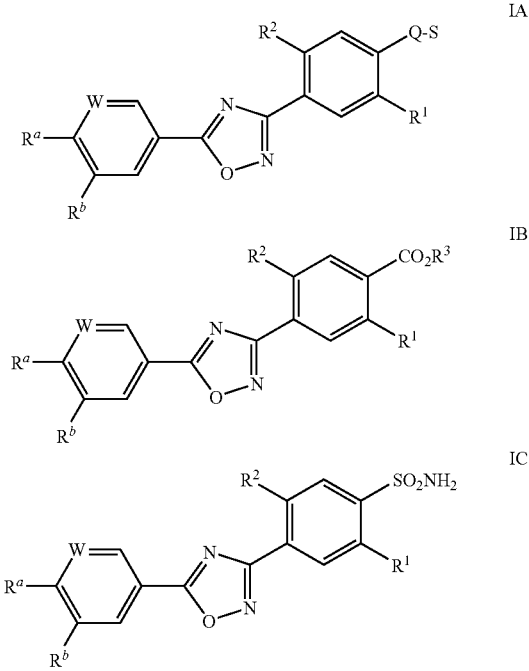

-continued

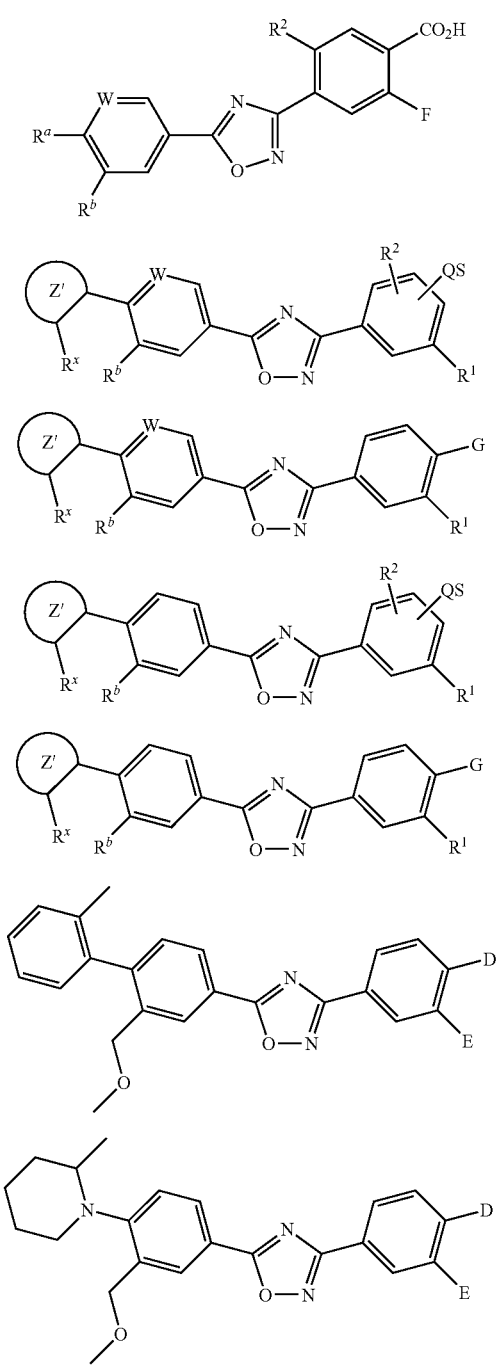

wherein $R^1, R^2, R^3, R^a, R^b, Q, S, W$ are as defined in claim 1,

D denotes $R^2$ or Q-S,

E denotes $R^1$,

G denotes a linear or branched carbon chain terminated with carboxylic acid, carboxylic ester, amide, amine cyano or alcohol function, and optionally containing 1 or 2 oxygen and/or nitrogen atoms, or 1 —$CONR^3$— group, or a $C_3$-$C_6$cycloalkyl, Z' denotes Ar or Het, $R^x$ denotes Hal, A, $OR^3$, $N(R^3)_2$, $NO_2$, CN, $COOR^3$, $CF_3$, $OCF_3$, $CON(R^3)_2$, $NR^3COA$, $NR^3CON(R^3)_2$, $NR^3SO_2A$, $COR^3$, $SO_2N(R^3)_2$, SOA or $SO_2A$, phenyl, pyridyl, —$[C(R^3)_2]_n$—$COOR^3$ or —$O[C(R^3)_2]_n$—$CON(R^3)_2$, wherein n is as defined in claim 1, or structure IL

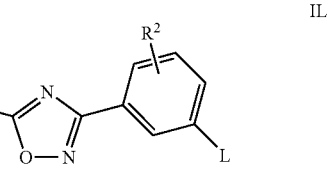

wherein $R^2$ is as defined in claim 1, K denotes A, and L denotes —$(CH_2)_mX(CH_2)_mS$ wherein m and S are as defined in claim 1 and X denotes —$NR^3$—, —COO— or —$CONR^3$, wherein $R^3$ is as defined in claim 1.

3. The compound according to claim 1, wherein Ar denotes one of the following groups:

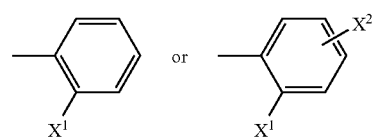

wherein $X^1$, and $X^2$ denote independently of one another F, Cl, —$OCH_3$, —$CH_3$, —$C_2H_5$, —$CF_3$, —$OCF_3$, —O-isoPropyl, —O-isobutyl, —$OCH_2CN$, —$OCH_2$cyclopropyl, —$CH_2OH$, —$CH_2$O-isoPropyl, —$CH_2$O-isobutyl, —$CH_2OCH_2$cyclopropyl, —$CH_2Nme_2$, —$CH_2OC_2H_5$, —NHCOMe, —NHCOEt, —NHS$O_2Nme_2$, —$NHSO_2$propyl, —$CH_2$morpholine, —$CH_2$pirolidine, —$CH_2NHMe$, —$SO_2Me$, —$CH_2SO_2Me$, —C≡C—$CH_2$Ome, —$(CH_2)_3$Ome, —$O(CH_2)_2$Ome, —$CO_2H$, —OH, —$NO_2$, —CN, —$NHSO_2CH_3$, and/or phenyl or pyridyl or piperidine, or morpholine.

4. The compound according to claim 1, wherein Het denotes one of the following groups:

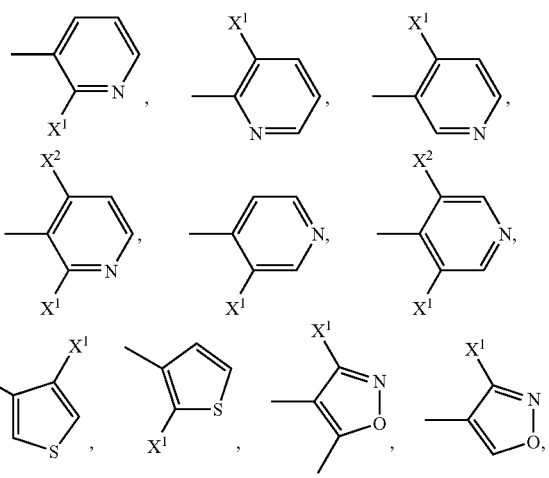

571

-continued

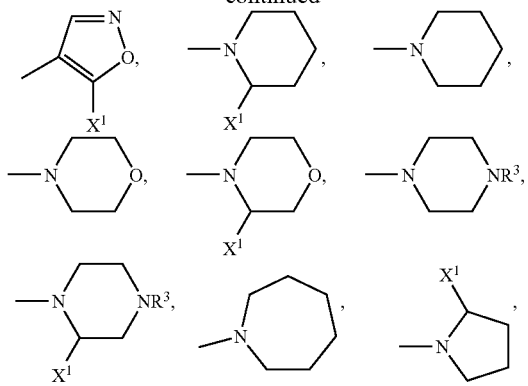

572

-continued

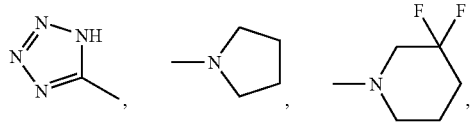

wherein $X^1$, $X^2$ and $R^3$ are defined in claim 1.

5. The compound according to claim 1, wherein QS denotes —COOR$^3$, —CON(R$^3$)(CH$_2$)$_n$CO$_2$R$^3$, —CONR$^3$(C$_3$-C$_6$cycloalkyl)CO$_2$R$^3$, —CH$_2$N(R$^3$)(CH$_2$)$_n$CO$_2$R$^3$, —CH$_2$NR$^3$(C$_3$-C$_6$cycloalkyl)CO$_2$R$^3$, —CH$_2$O(CH$_2$)$_n$CO$_2$R$^3$, —CH$_2$O(C$_3$-C$_6$cycloalkyl)CO$_2$R$^3$, —O(CH$_2$)$_n$CO$_2$R$^3$, —O(C$_3$-C$_6$cycloalkyl)CO$_2$R$^3$ wherein n and R$^3$ are as above defined.

6. The compound according to claim 1 selected from:

| Example Nb | Formula |
|---|---|
| 1 | |
| 2 | |
| 3 | |

-continued
| Example Nb | Formula |
|---|---|
| 4 | 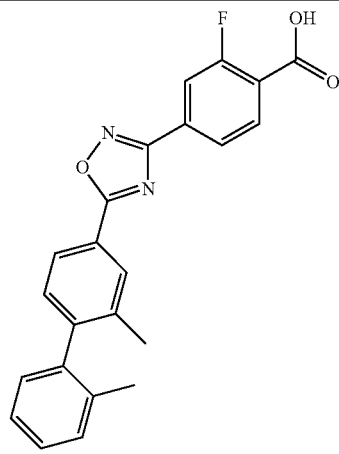 |
| 5 | 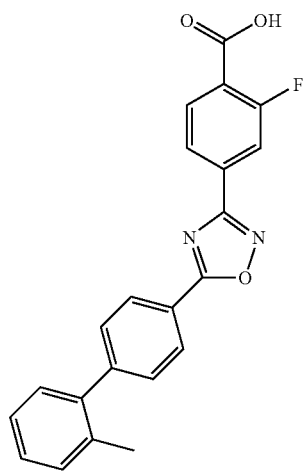 |
| 6 | 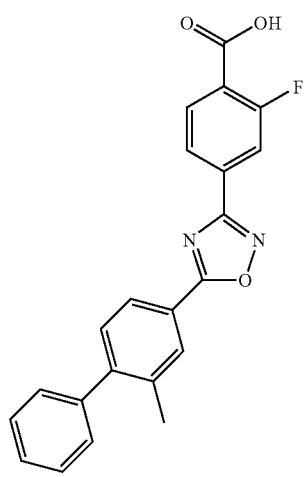 |

| Example Nb | Formula |
|---|---|
| 7 | 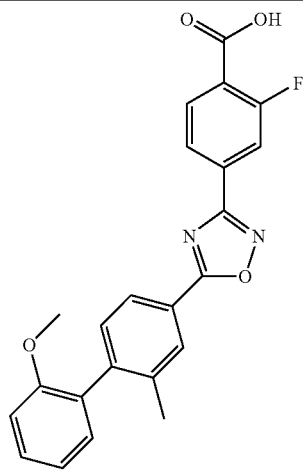 |
| 8 | 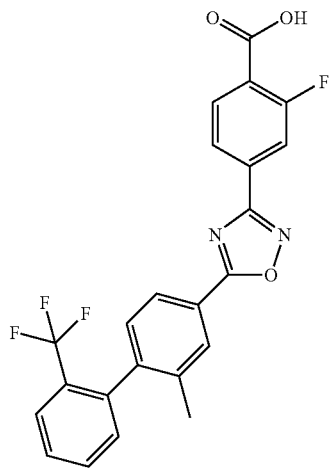 |
| 9 | 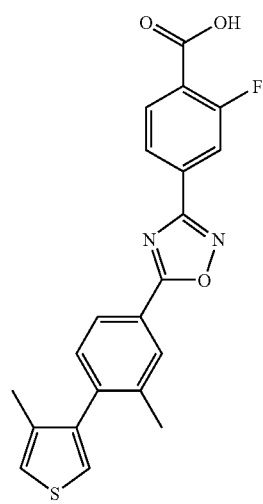 |

-continued
| Example Nb | Formula |
|---|---|
| 10 | 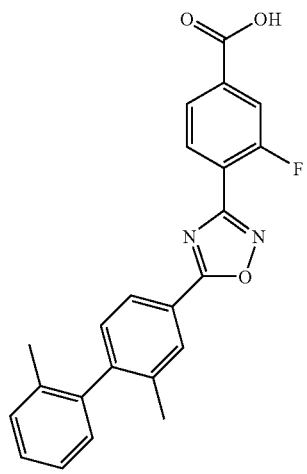 |
| 11 | 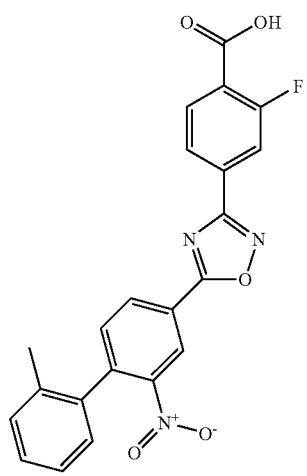 |
| 12 | 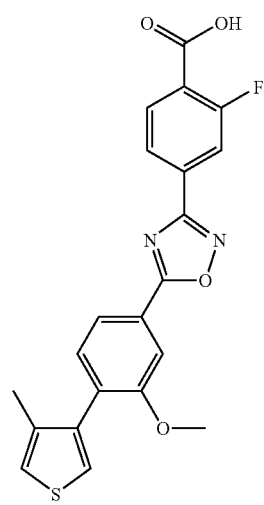 |

| Example Nb | Formula |
|---|---|
| 13 | 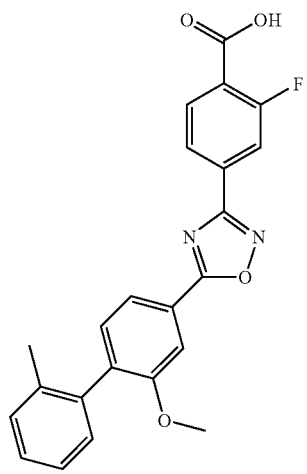 |
| 14 | 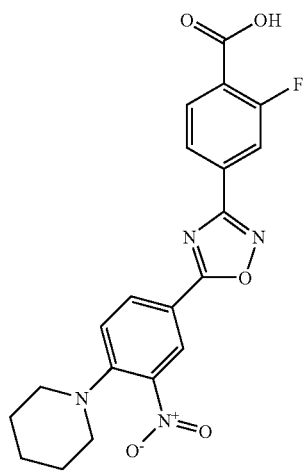 |
| 15 | 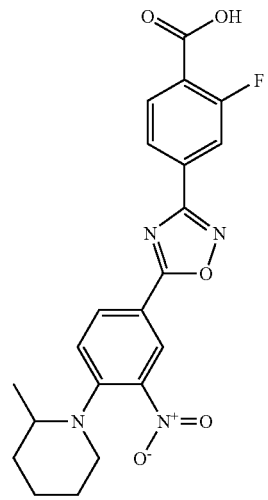 |

-continued
| Example Nb | Formula |
|---|---|
| 16 | 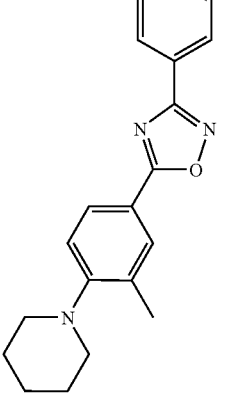 |
| 17 | 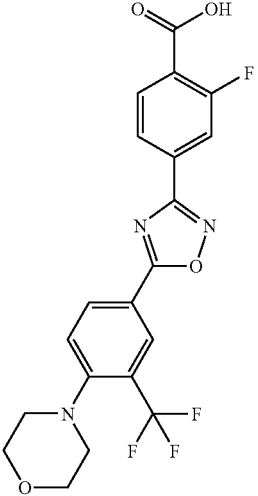 |
| 18 | 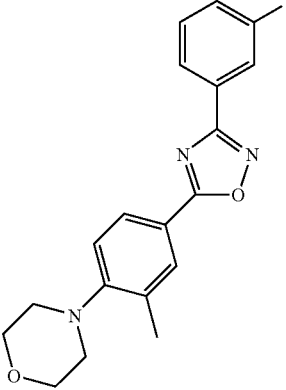 |

-continued
| Example Nb | Formula |
|---|---|
| 19 | 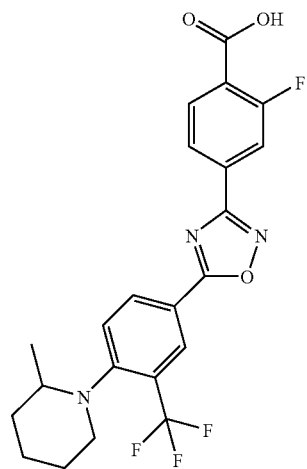 |
| 20 | 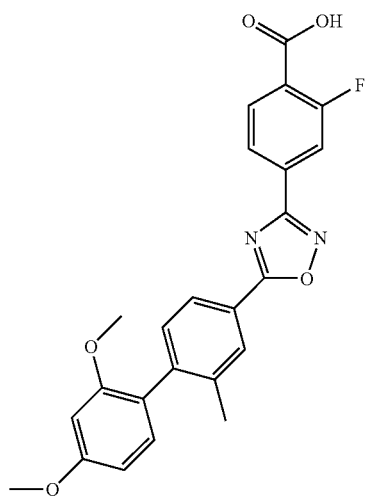 |
| 21 | 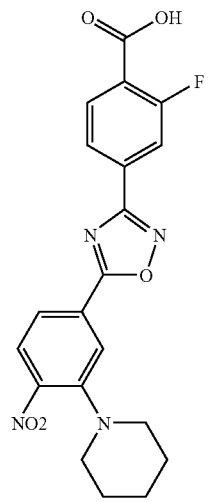 |

-continued
| Example Nb | Formula |
|---|---|
| 22 | 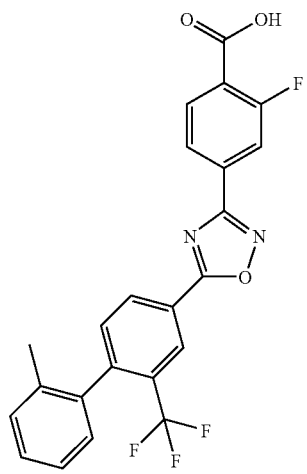 |
| 23 | 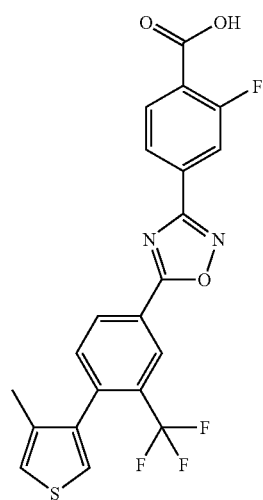 |
| 24 | 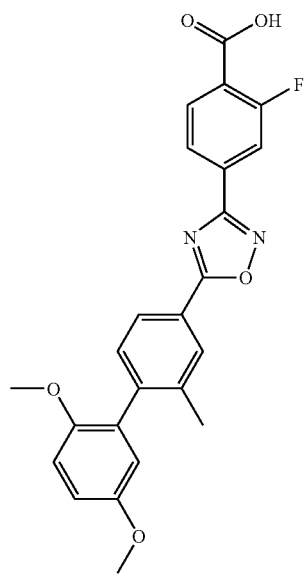 |

-continued
| Example Nb | Formula |
|---|---|
| 25 | 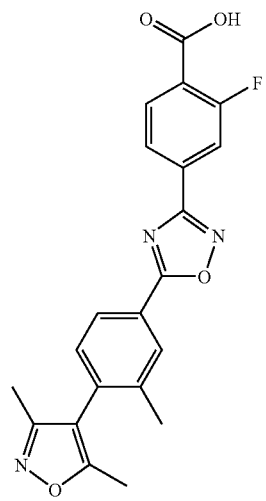 |
| 26 | 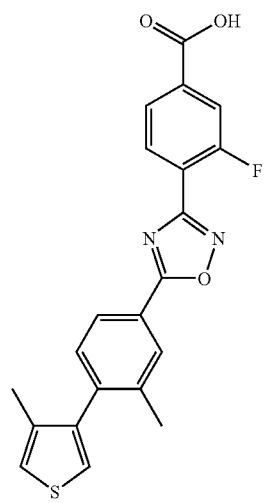 |
| 27 | 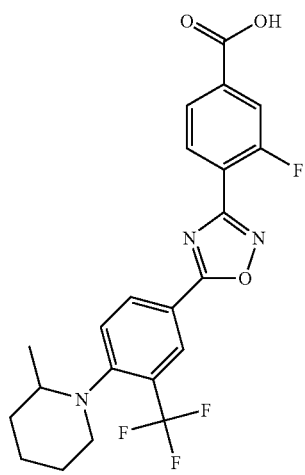 |

| Example Nb | Formula |
|---|---|
| 28 | 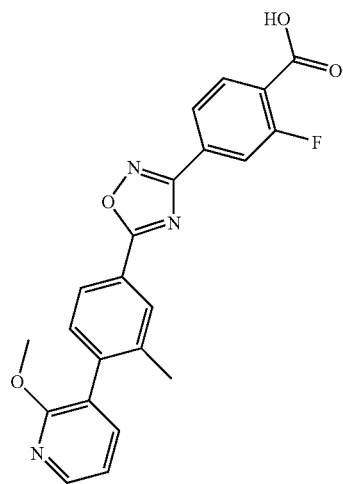 |
| 29 | 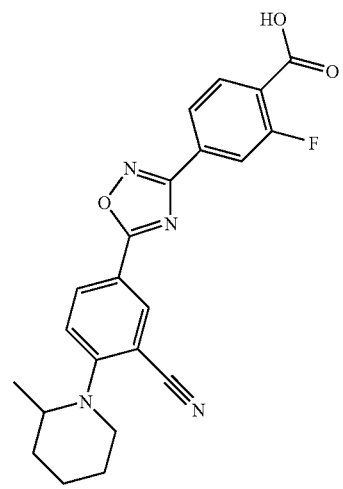 |
| 30 | 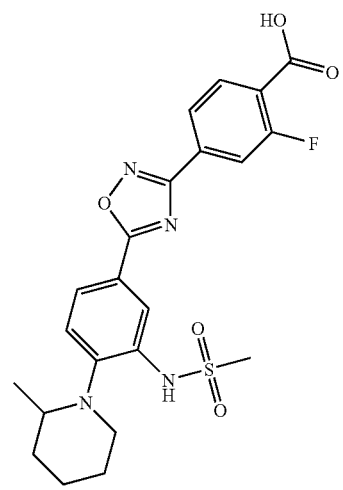 |

-continued
| Example Nb | Formula |
|---|---|
| 31 | 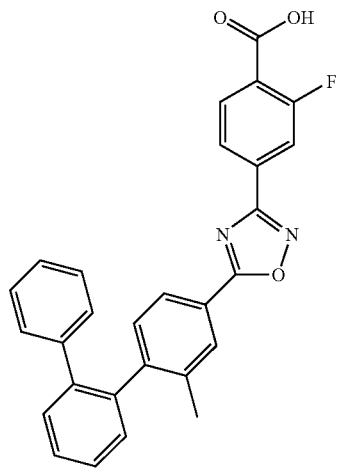 |
| 32 | 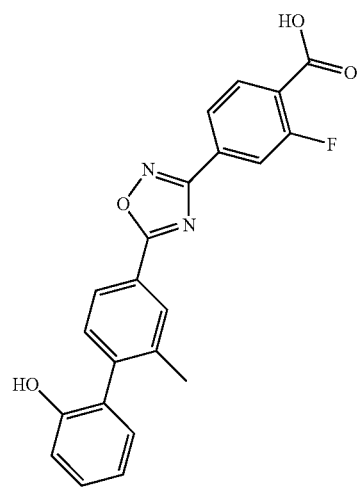 |
| 33 | 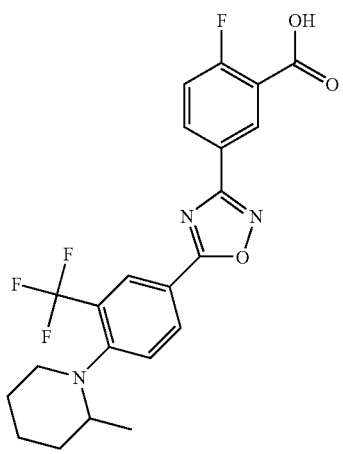 |

-continued
| Example Nb | Formula |
|---|---|
| 34 | 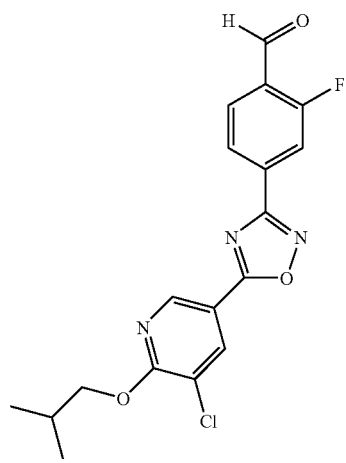 |
| 35 | 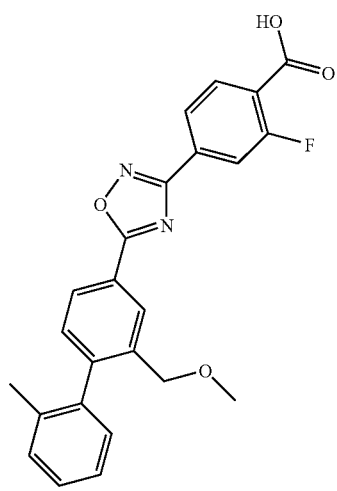 |
| 36 | 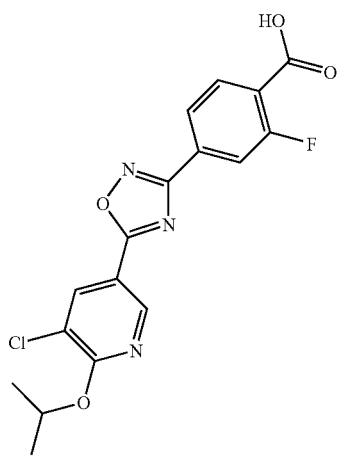 |

-continued
| Example Nb | Formula |
|---|---|
| 42 | 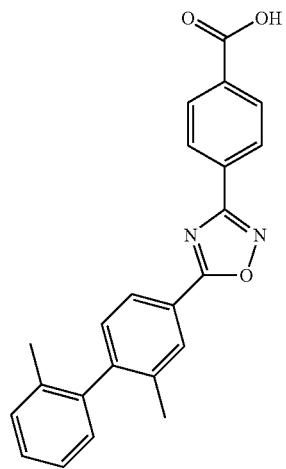 |
| 43 | 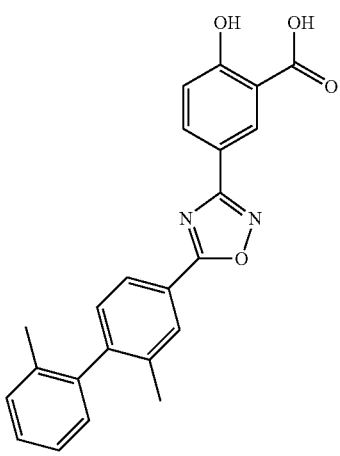 |
| 44 | 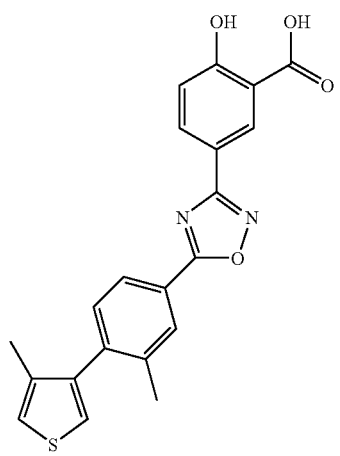 |

-continued
| Example Nb | Formula |
|---|---|
| 45 | 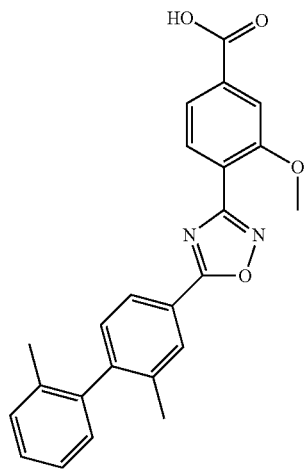 |
| 46 | 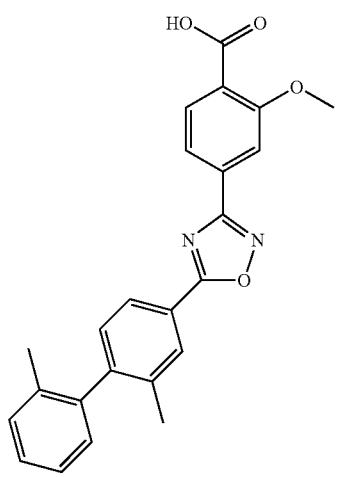 |
| 47 | 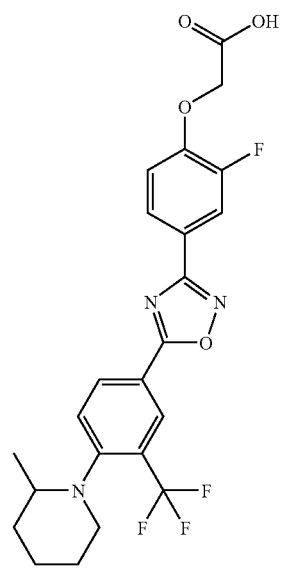 |

-continued
| Example Nb | Formula |
|---|---|
| 48 | 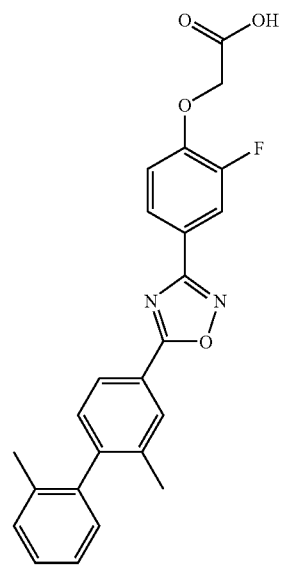 |
| 49 | 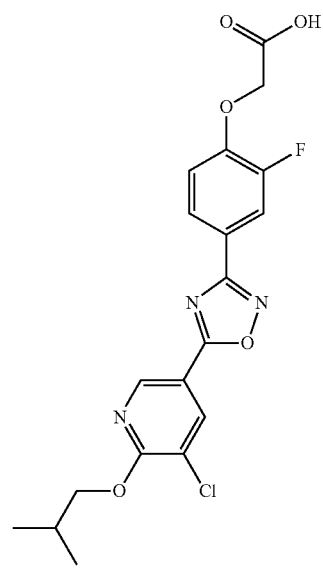 |
| 50 | 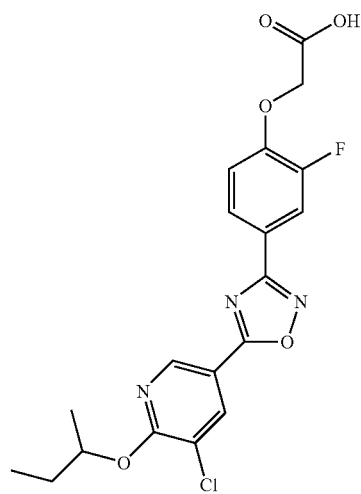 |

-continued
| Example Nb | Formula |
|---|---|
| 51 | 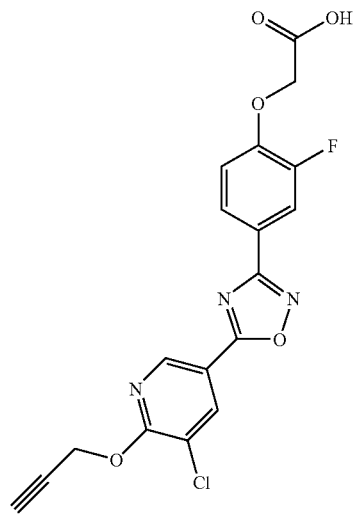 |
| 52 | 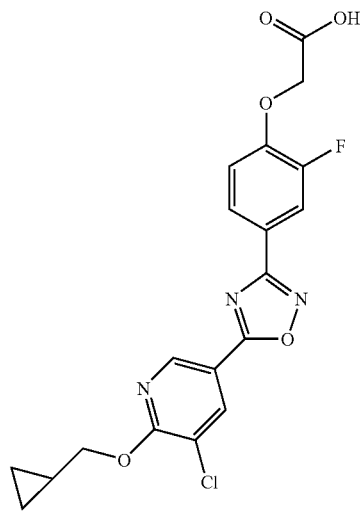 |
| 53 | 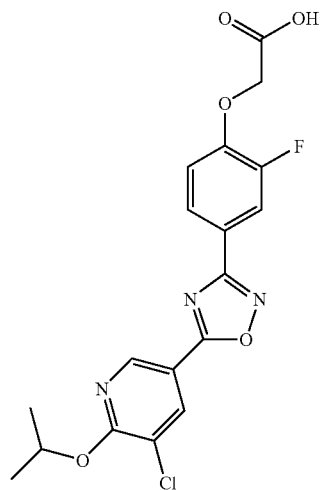 |

-continued

| Example Nb | Formula |
|---|---|
| 54 | |
| 55 | |
| 56 | |

| Example Nb | Formula |
|---|---|
| 57 | |
| 58 | |
| 59 | |

-continued
| Example Nb | Formula |
|---|---|
| 60 | 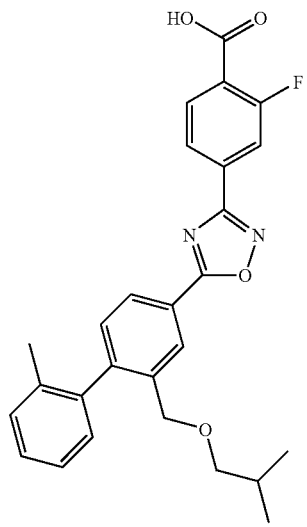 |
| 61 | 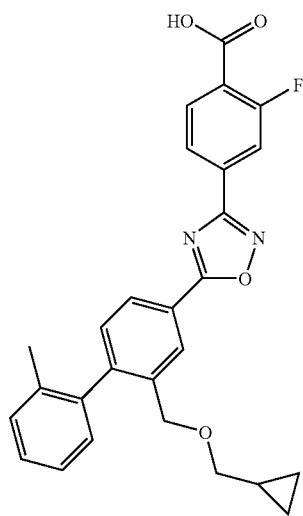 |
| 62 | 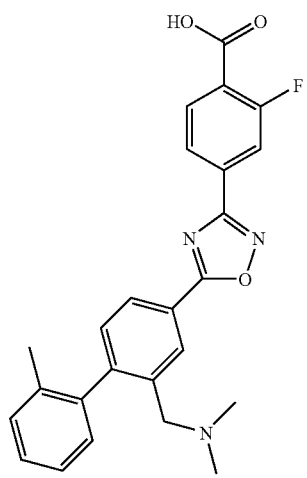 |

-continued
| Example Nb | Formula |
|---|---|
| 63 | 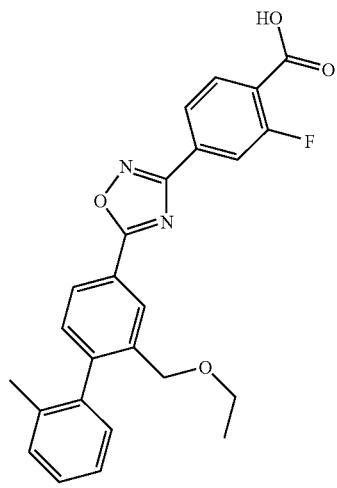 |
| 64 | 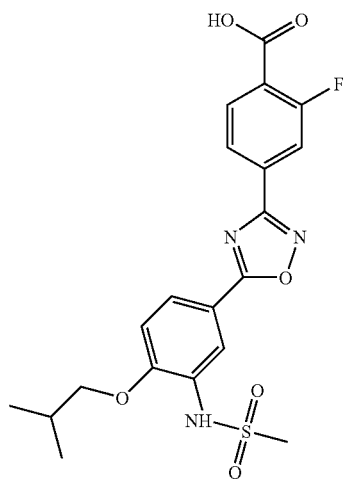 |
| 65 | 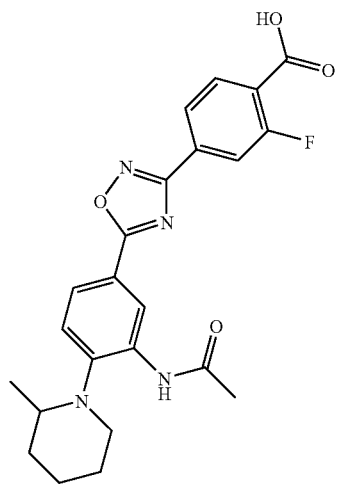 |

-continued
| Example Nb | Formula |
|---|---|
| 66 | 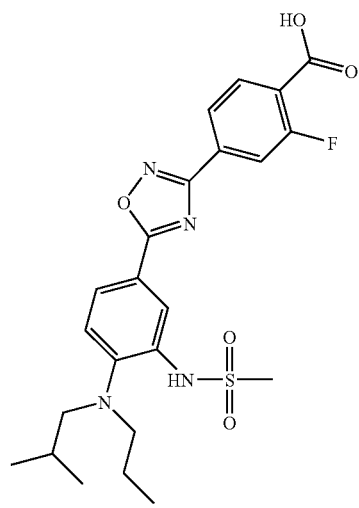 |
| 67 | 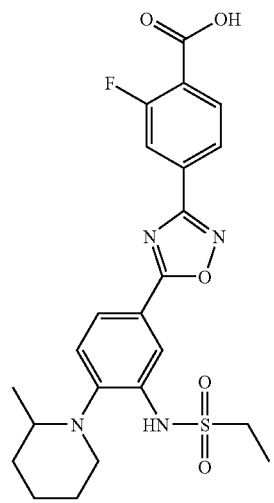 |
| 68 | 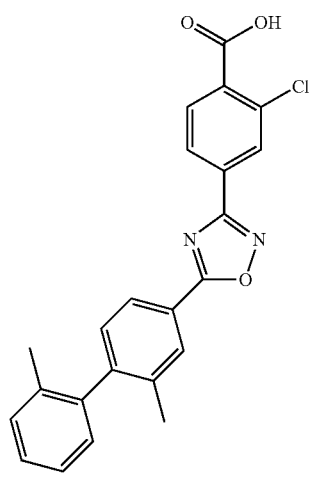 |

-continued
| Example Nb | Formula |
|---|---|
| 69 | 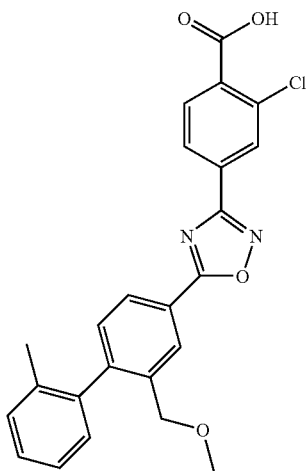 |
| 70 | 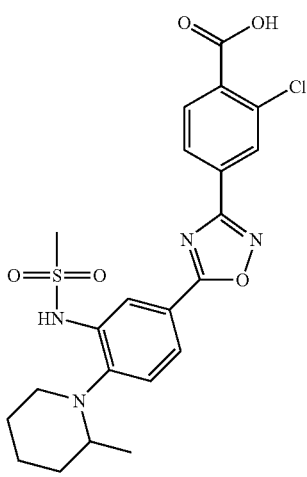 |
| 71 | 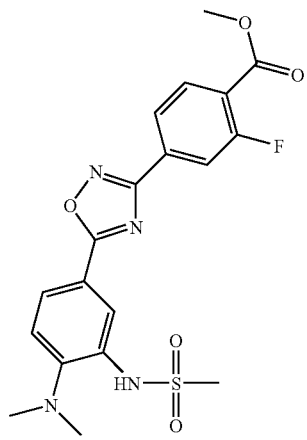 |

| Example Nb | Formula |
|---|---|
| 72 | 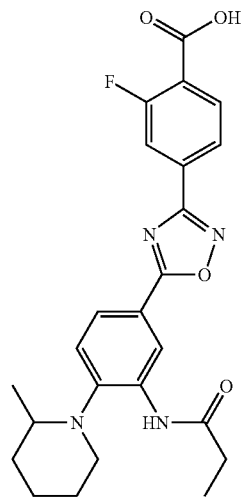 |
| 73 | 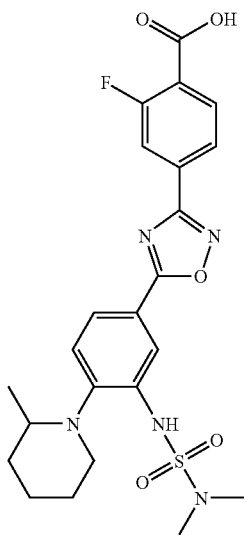 |
| 74 | 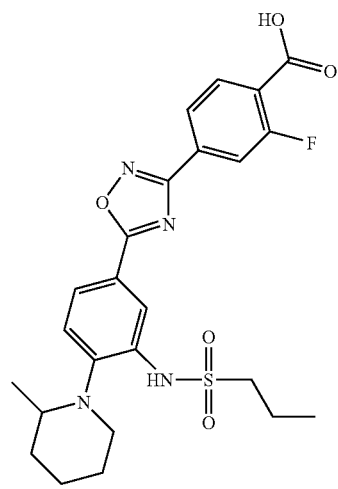 |

-continued
| Example Nb | Formula |
|---|---|
| 75 | 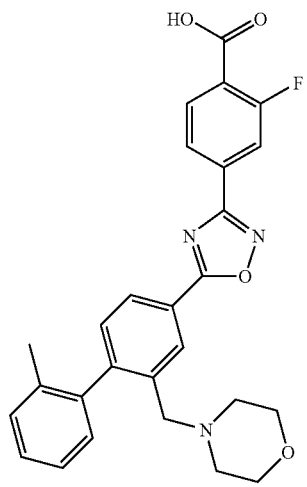 |
| 76 | 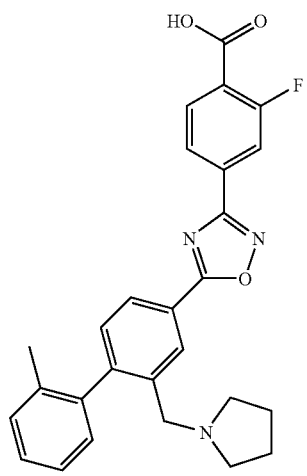 |
| 77 | 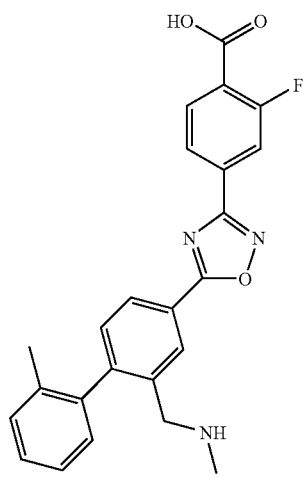 |

-continued
| Example Nb | Formula |
|---|---|
| 78 | 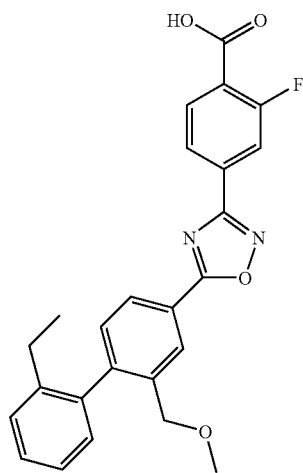 |
| 79 | 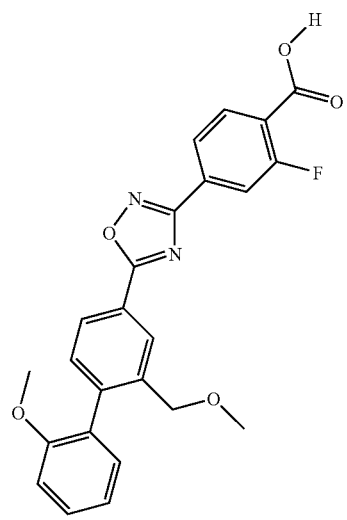 |
| 80 | 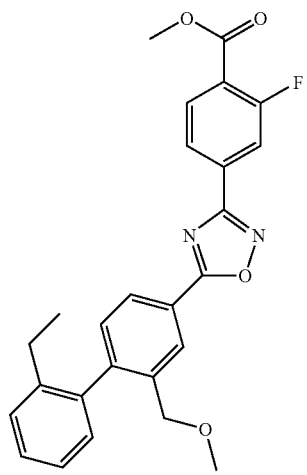 |

-continued
| Example Nb | Formula |
|---|---|
| 81 | 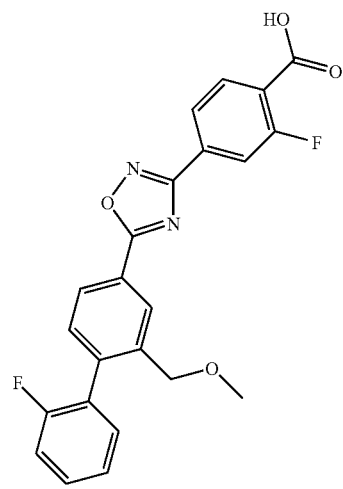 |
| 82 | 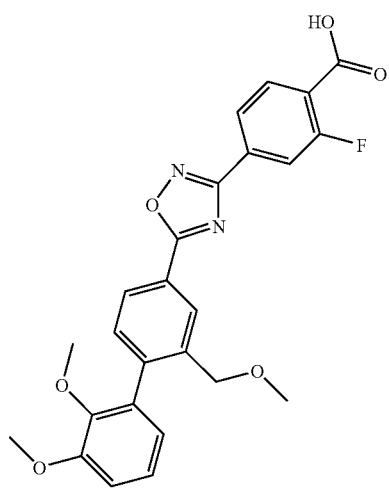 |
| 83 | 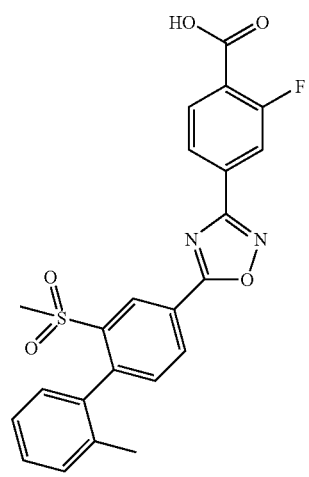 |

-continued
| Example Nb | Formula |
|---|---|
| 84 | 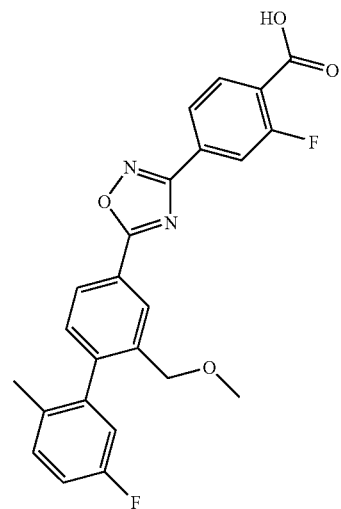 |
| 85 | 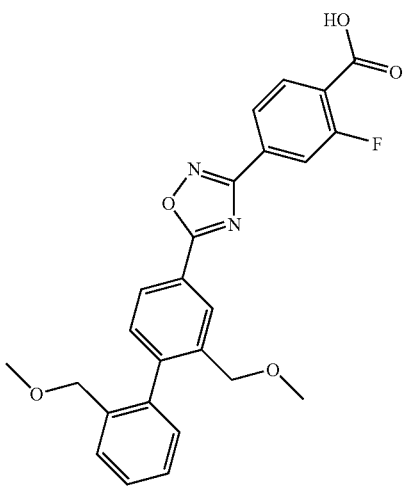 |
| 86 | 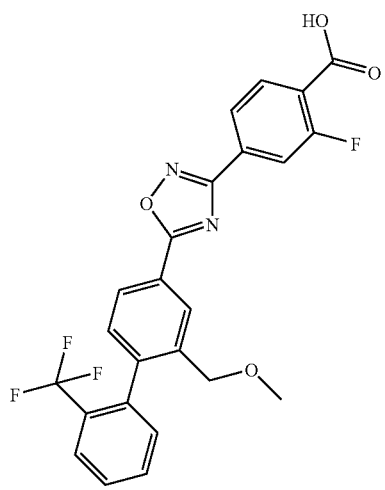 |

-continued
| Example Nb | Formula |
|---|---|
| 87 | 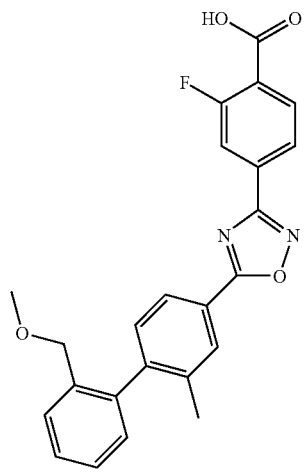 |
| 88 | 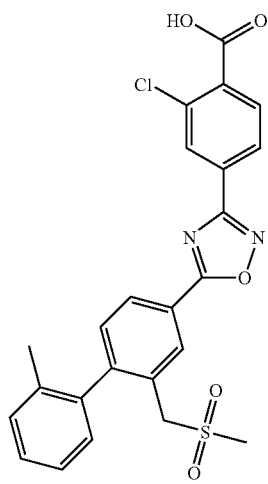 |
| 89 | 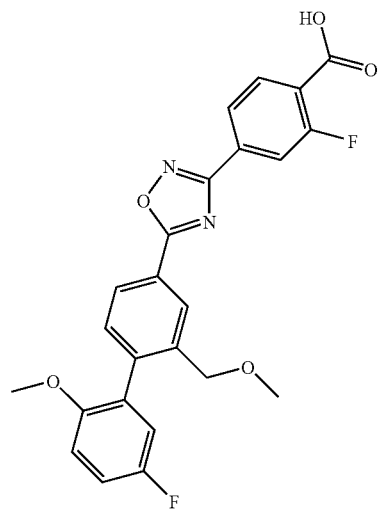 |

-continued
| Example Nb | Formula |
|---|---|
| 90 | 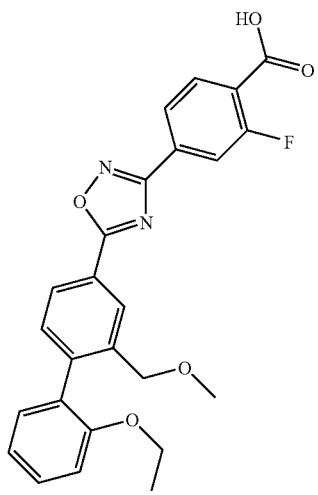 |
| 91 | 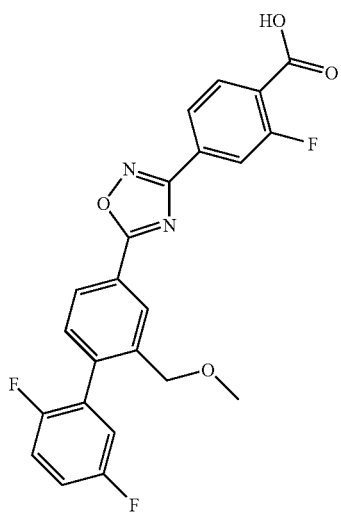 |
| 92 | 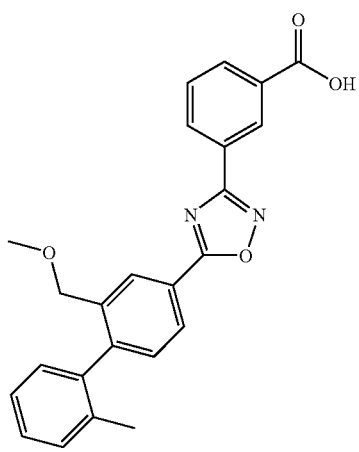 |

-continued
| Example Nb | Formula |
| --- | --- |
| 93 | 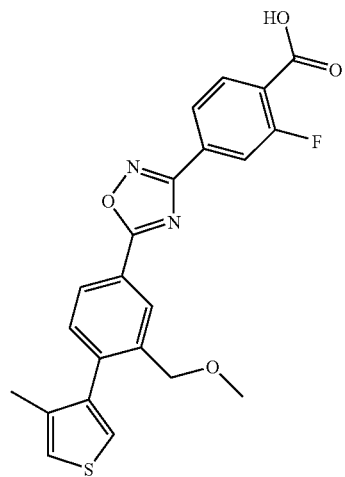 |
| 94 | 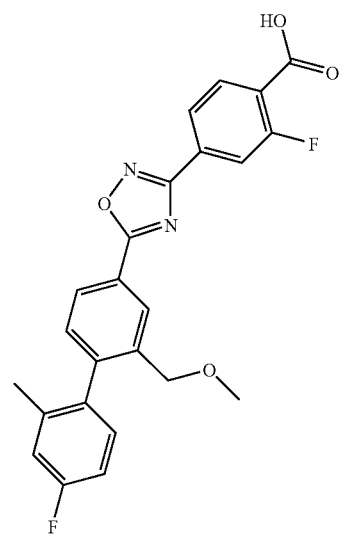 |
| 95 | 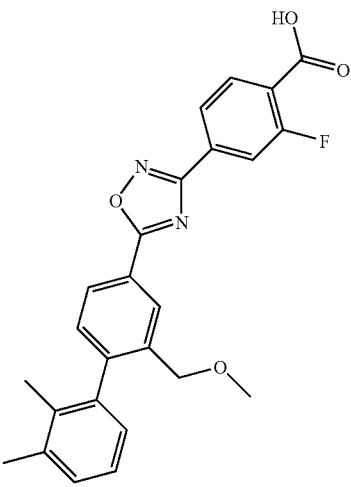 |

-continued
| Example Nb | Formula |
|---|---|
| 96 | 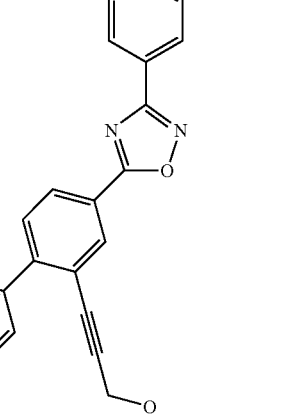 |
| 97 | 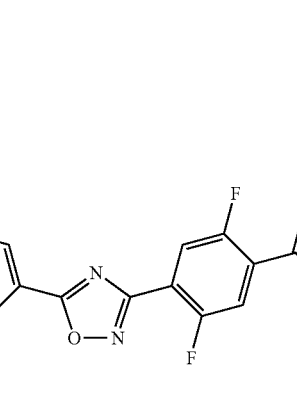 |
| 98 | 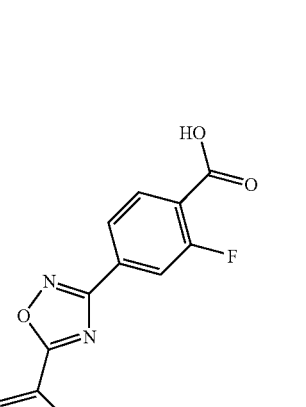 |

-continued
| Example Nb | Formula |
|---|---|
| 99 | 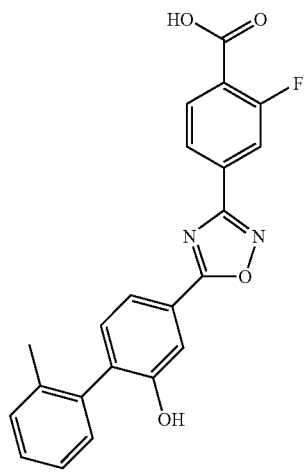 |
| 100 | 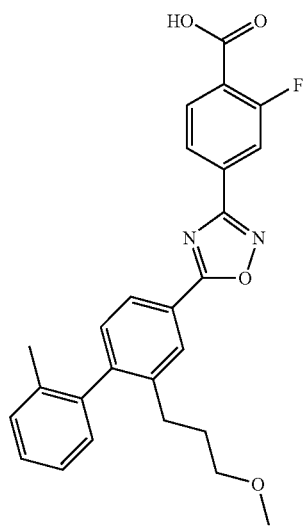 |
| 101 | 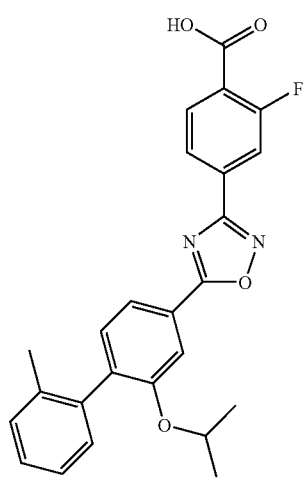 |

-continued
| Example Nb | Formula |
|---|---|
| 102 | 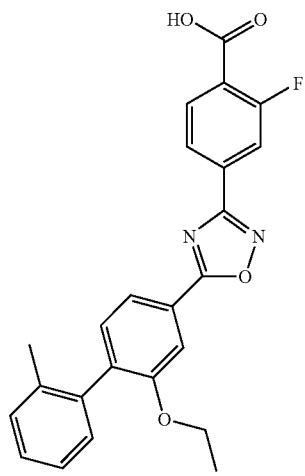 |
| 103 | 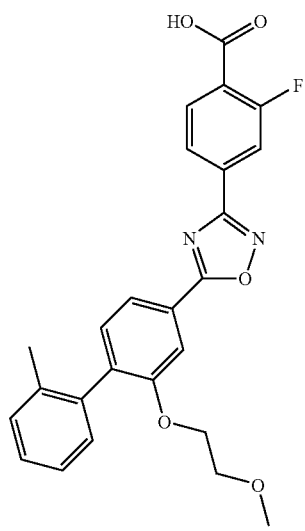 |
| 104 | 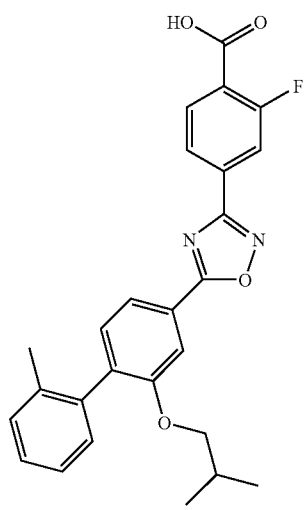 |

-continued
| Example Nb | Formula |
|---|---|
| 105 | 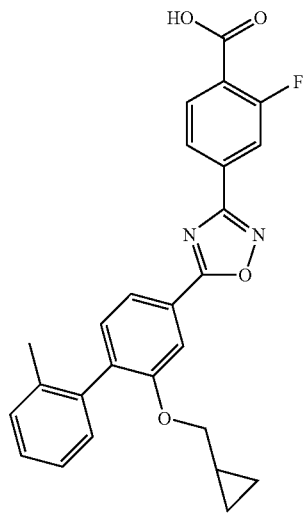 |
| 106 | 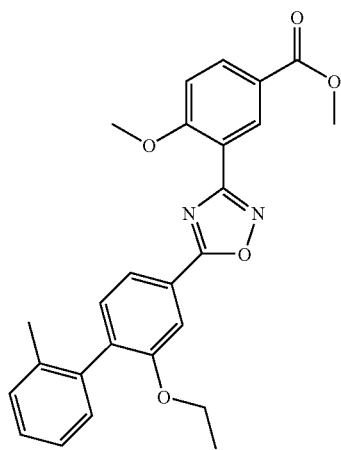 |
| 107 | 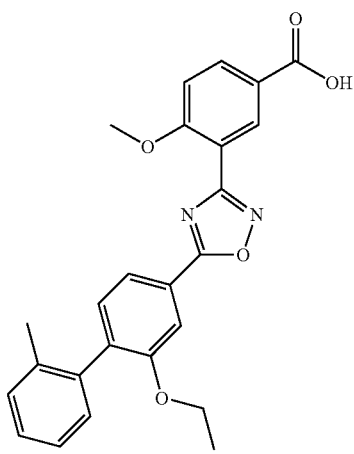 |

-continued
| Example Nb | Formula |
|---|---|
| 108 | 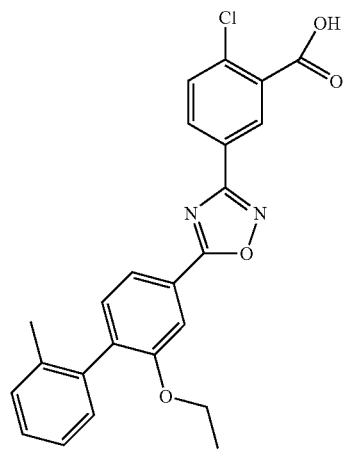 |
| 109 | 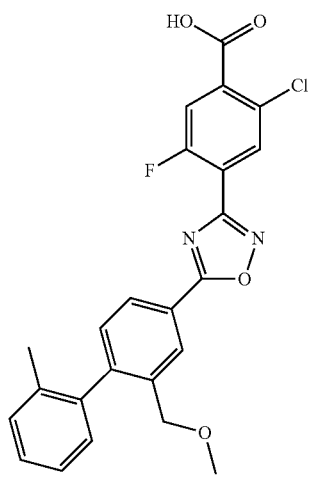 |
| 110 | 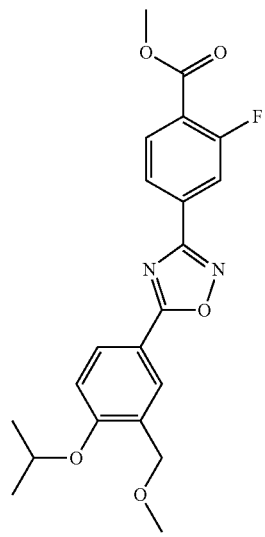 |

-continued
| Example Nb | Formula |
|---|---|
| 111 | 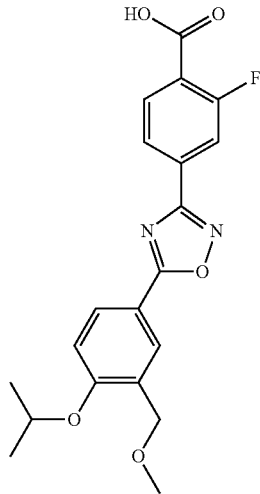 |
| 112 | 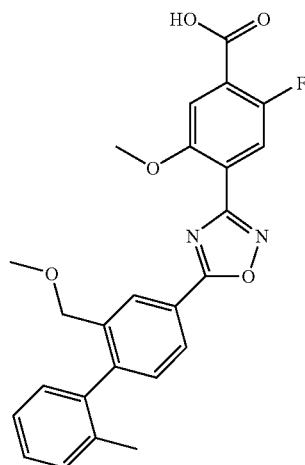 |
| 113 | 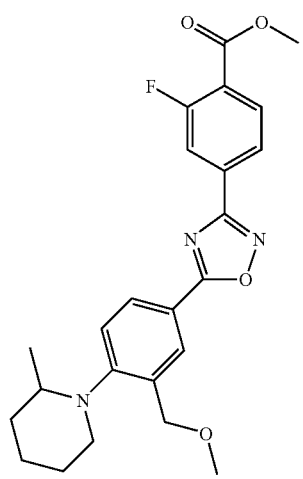 |

| Example Nb | Formula |
|---|---|
| 114 | 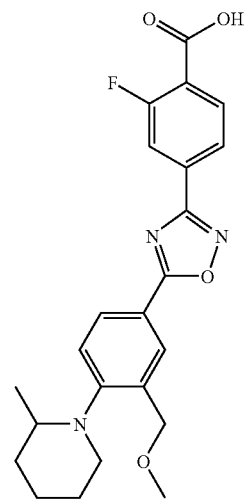 |
| 115 | 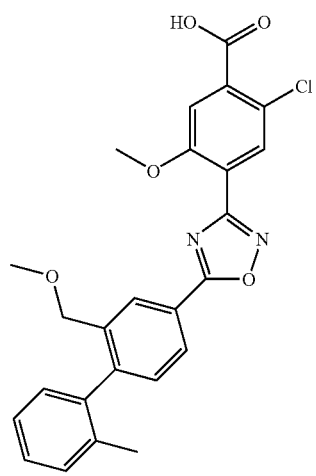 |
| 116 | 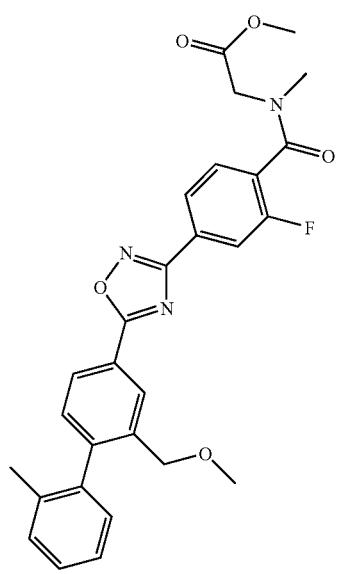 |

-continued
| Example Nb | Formula |
|---|---|
| 117 | 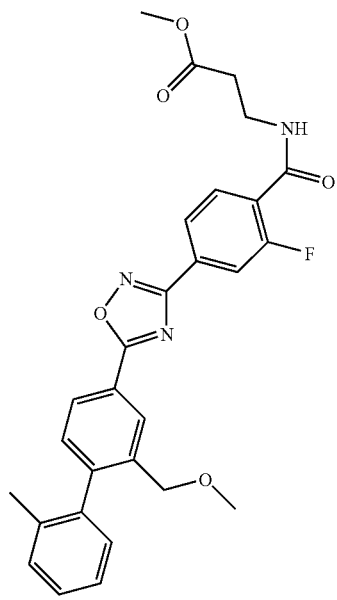 |
| 118 | 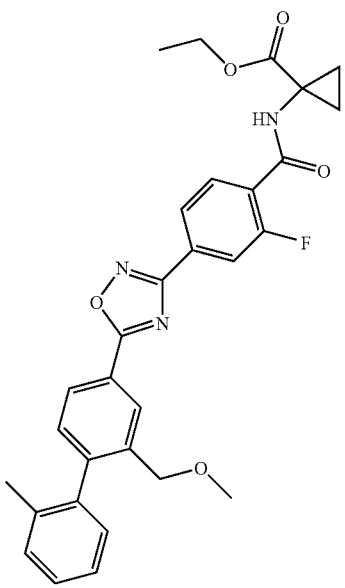 |

-continued
| Example Nb | Formula |
|---|---|
| 119 | 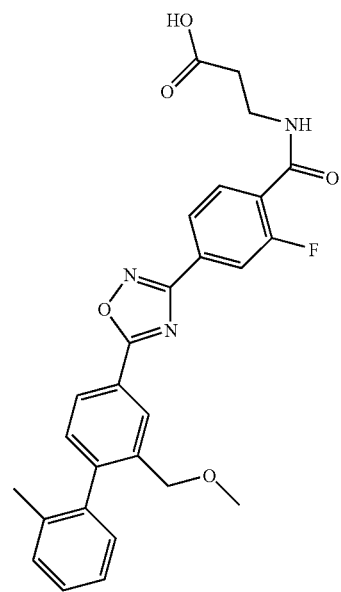 |
| 120 | 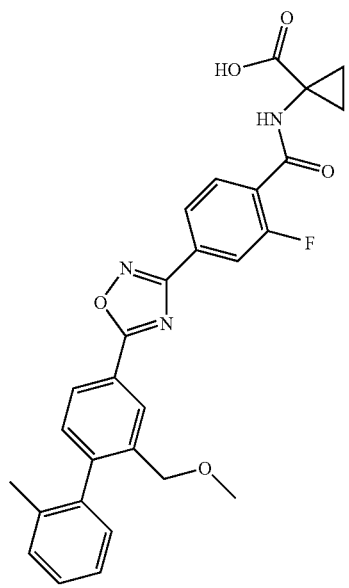 |

-continued
| Example Nb | Formula |
|---|---|
| 121 | 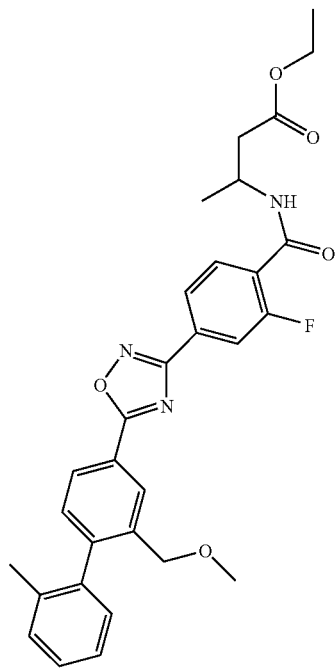 |
| 122 | 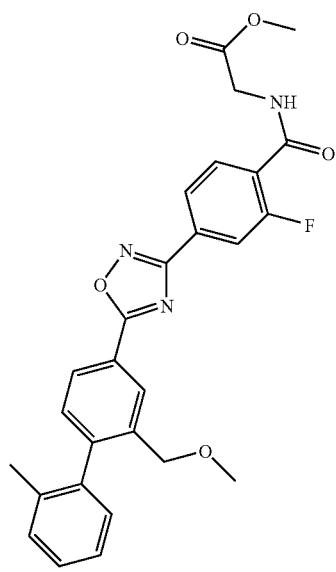 |

-continued
| Example Nb | Formula |
|---|---|
| 123 | 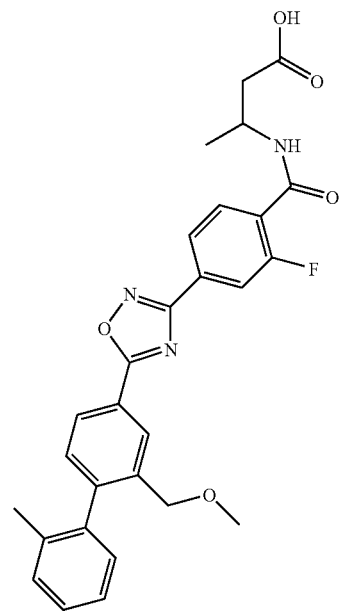 |
| 124 | 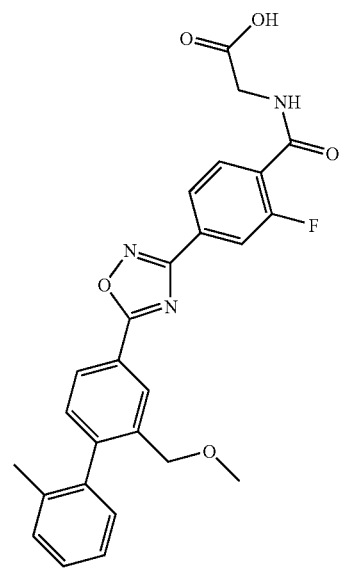 |

| Example Nb | Formula |
|---|---|
| 125 | 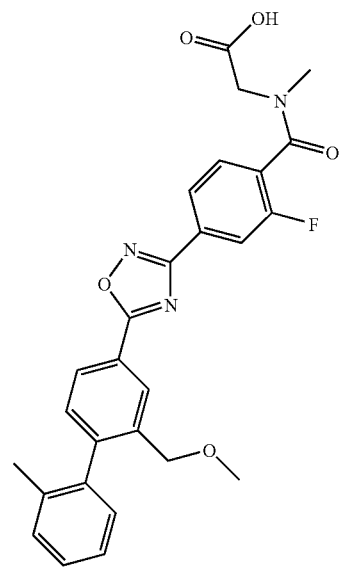 |
| 126 | 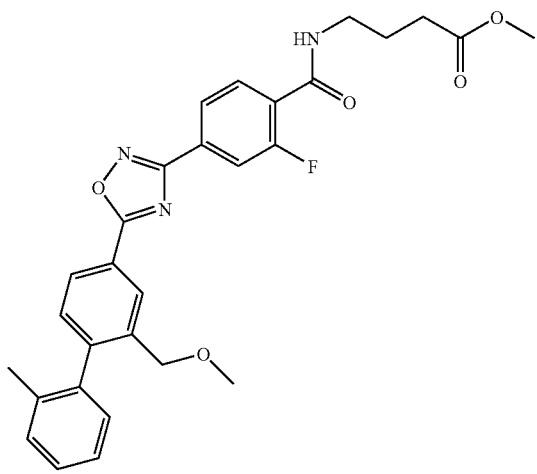 |
| 127 | 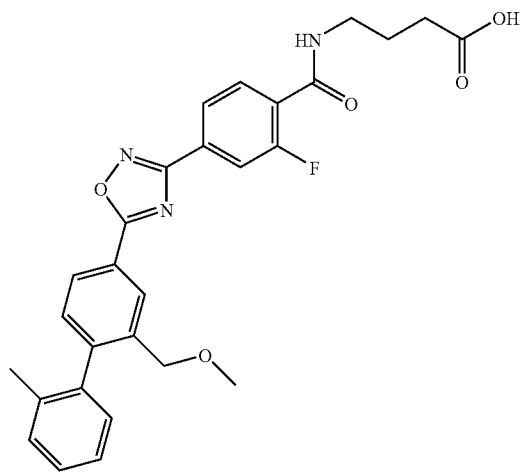 |

-continued
| Example Nb | Formula |
|---|---|
| 128 | 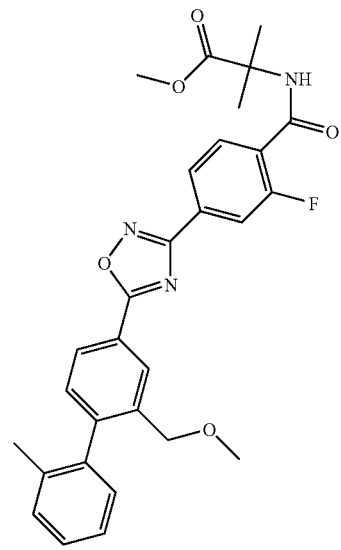 |
| 129 | 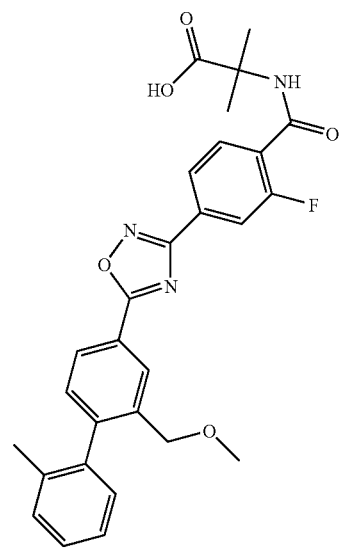 |
| 130 | 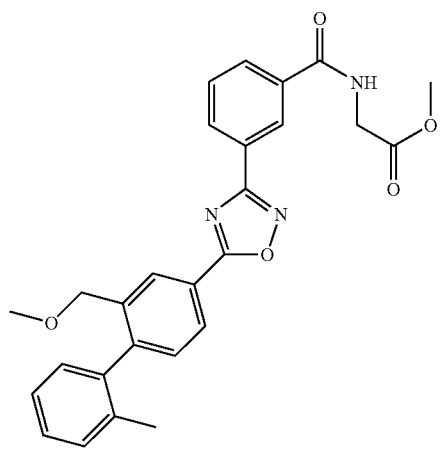 |

| Example Nb | Formula |
|---|---|
| 131 | 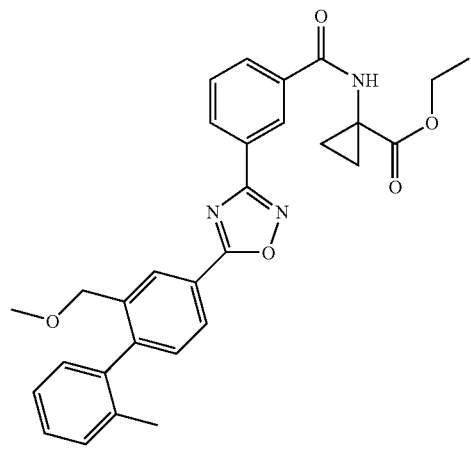 |
| 132 | 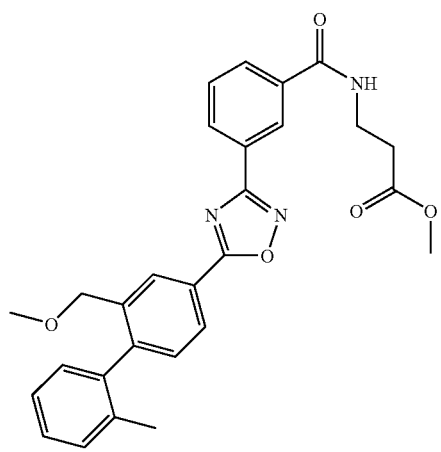 |
| 133 | 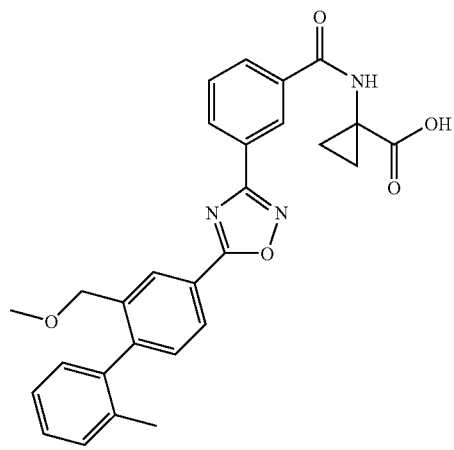 |

-continued
| Example Nb | Formula |
|---|---|
| 134 | 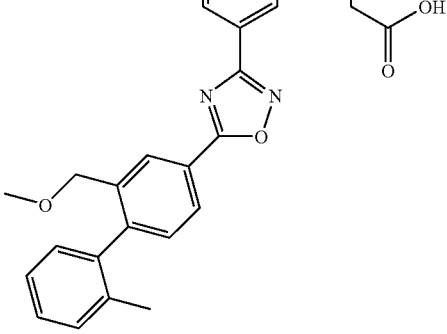 |
| 135 | 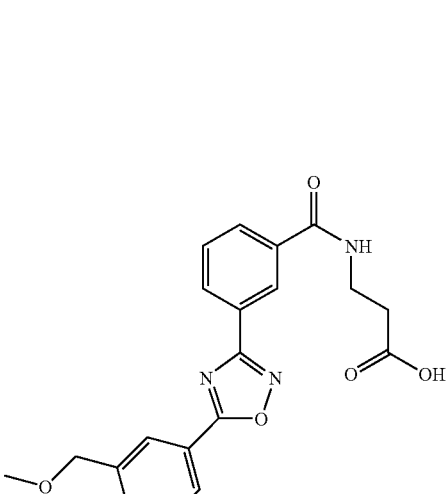 |
| 136 | 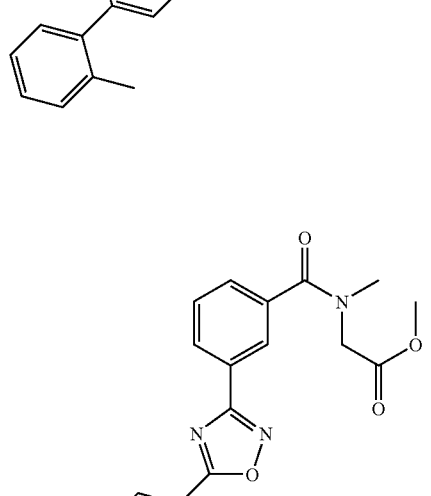 |

-continued
| Example Nb | Formula |
|---|---|
| 137 | 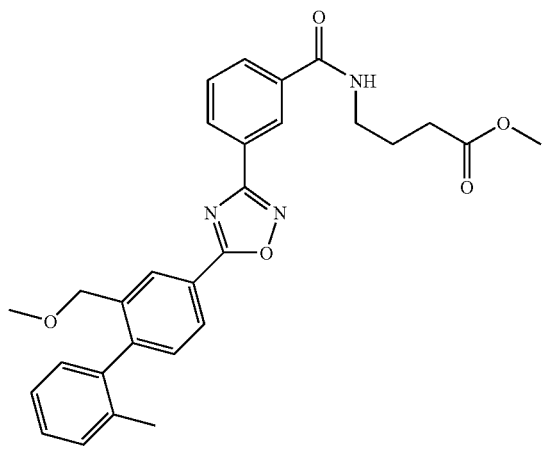 |
| 138 | 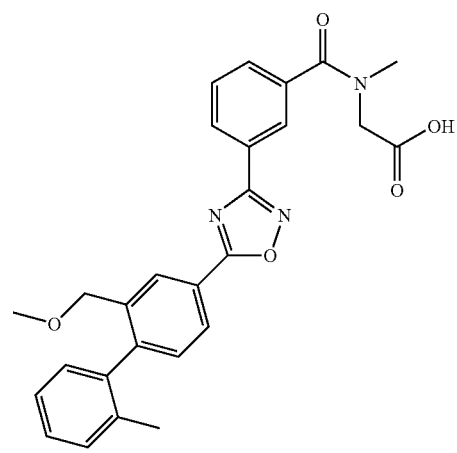 |
| 139 | 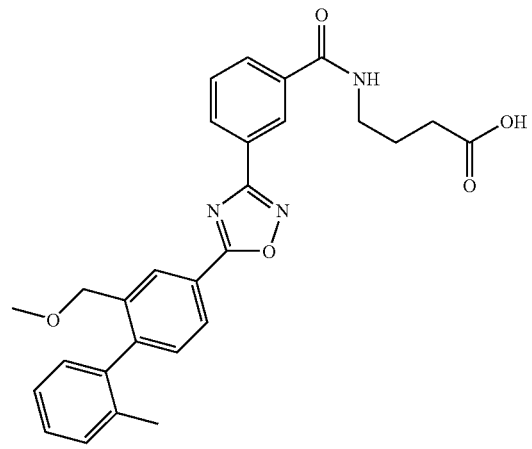 |

| Example Nb | Formula |
|---|---|
| 140 | 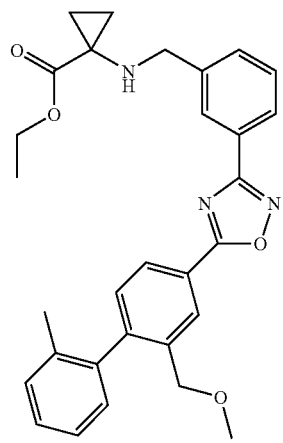 |
| 141 | 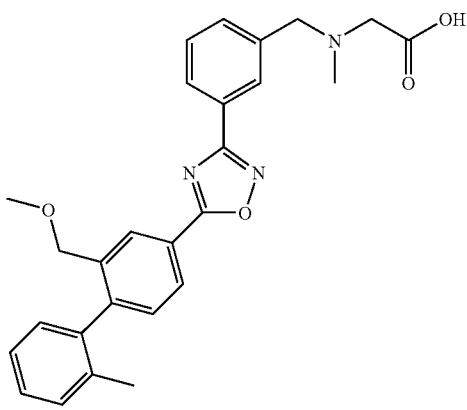 |
| 142 | 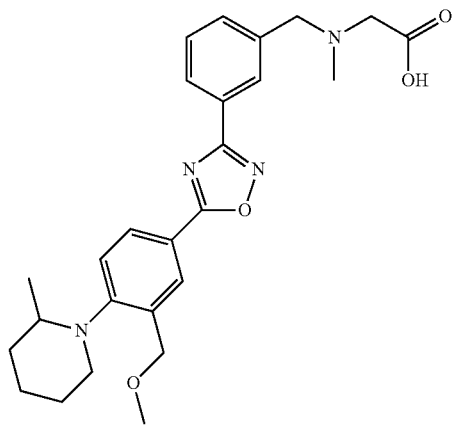 |

-continued
| Example Nb | Formula |
|---|---|
| 143 | 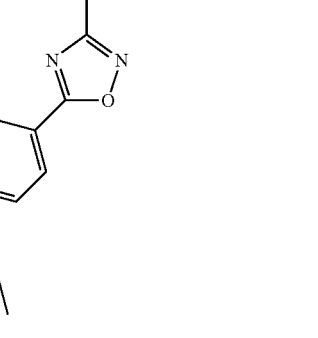 |
| 144 | 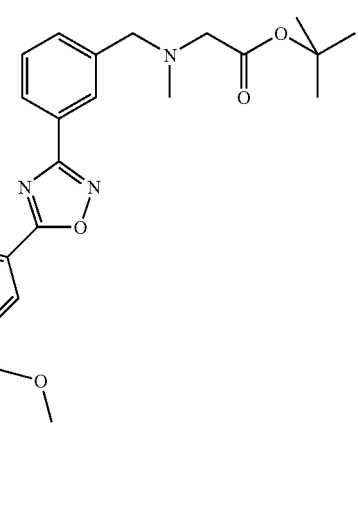 |
| 145 | 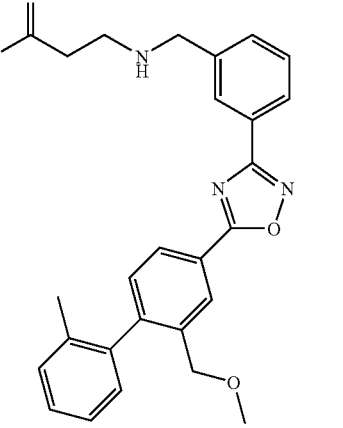 |

-continued
| Example Nb | Formula |
|---|---|
| 146 | 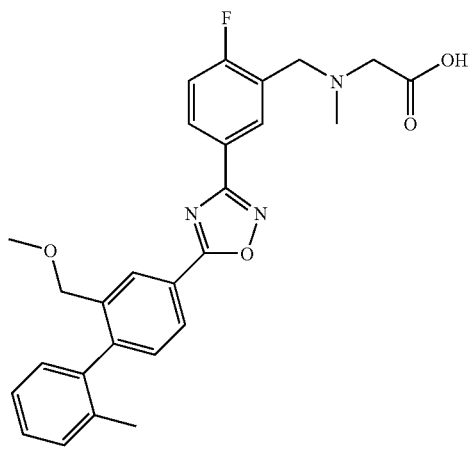 |
| 147 | 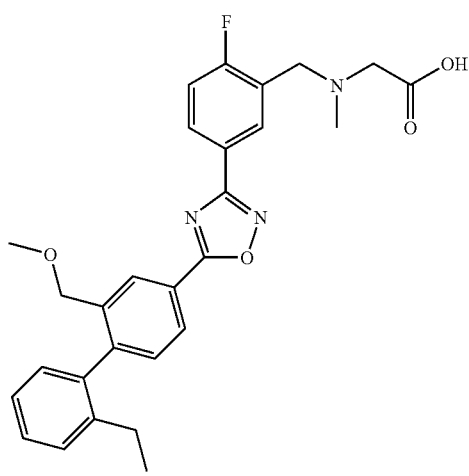 |
| 148 | 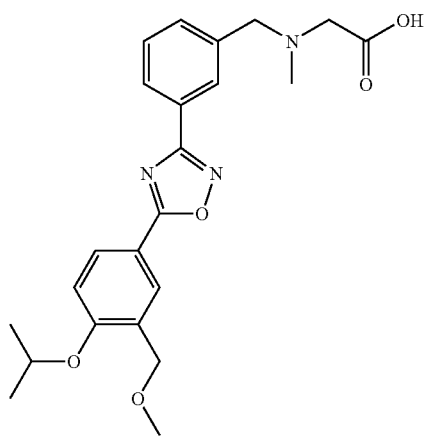 |

-continued
| Example Nb | Formula |
|---|---|
| 149 | 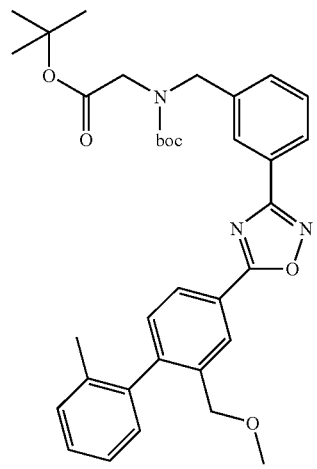 |
| 150 | 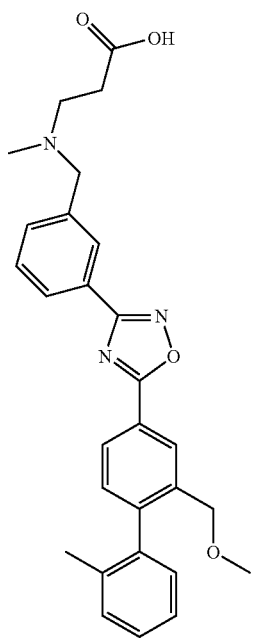 |
| 151 | 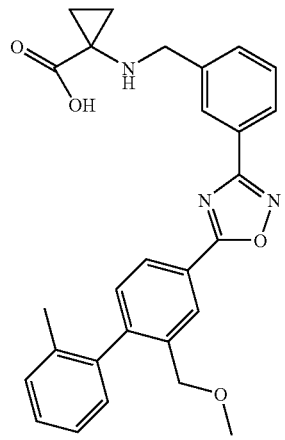 |

| Example Nb | Formula |
|---|---|
| 152 | 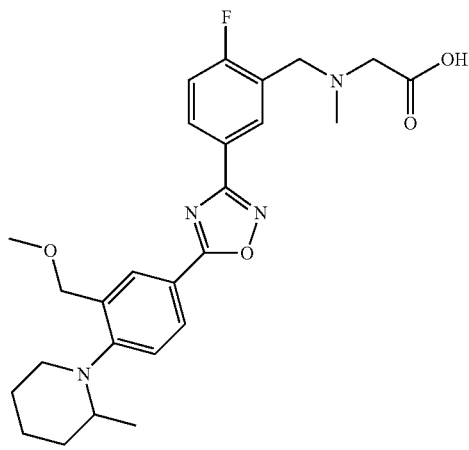 |
| 153 | 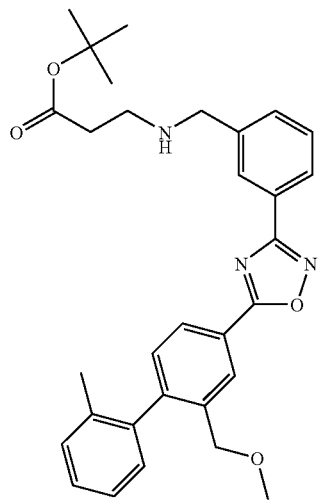 |
| 154 | 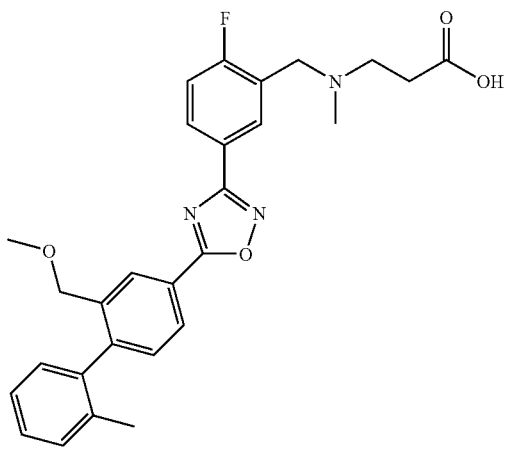 |

| Example Nb | Formula |
|---|---|
| 155 | 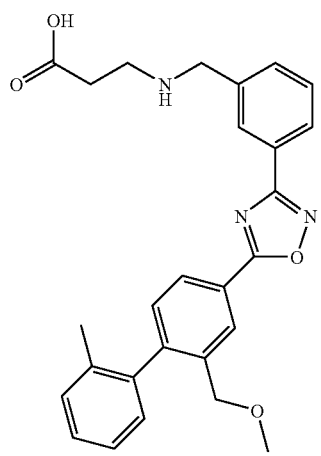 |
| 156 | 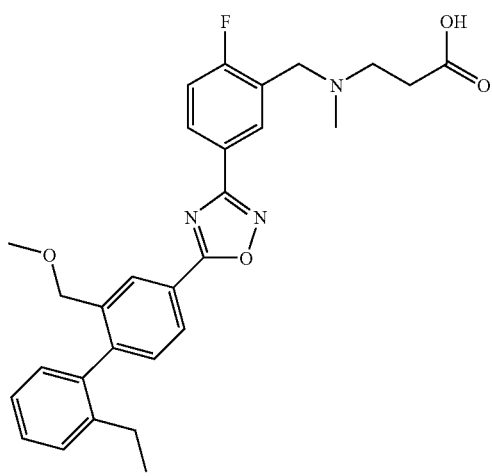 |
| 157 | 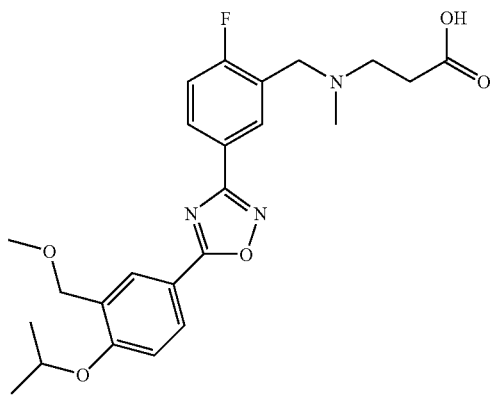 |

| Example Nb | Formula |
|---|---|
| 158 | 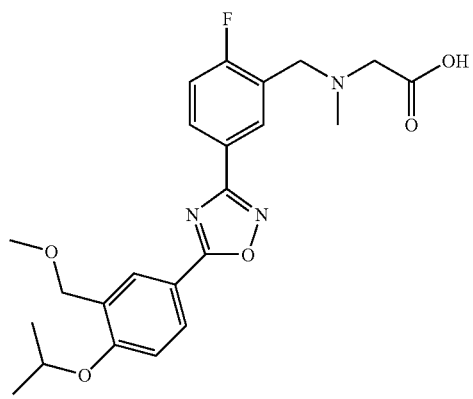 |
| 159 | 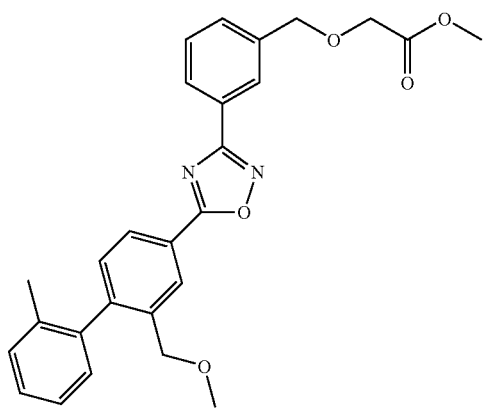 |
| 160 | 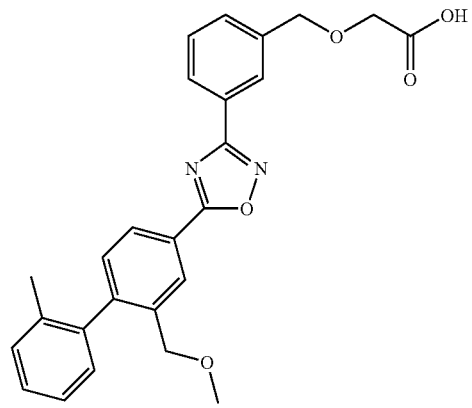 |

-continued
| Example Nb | Formula |
|---|---|
| 161 | 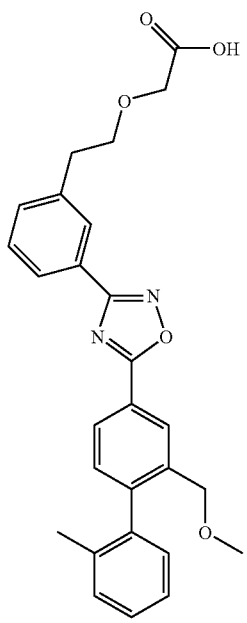 |
| 162 | 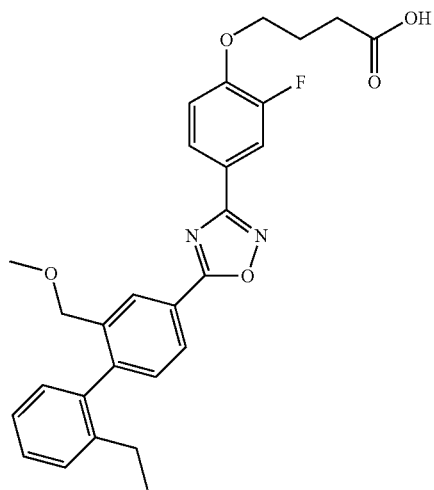 |
| 163 | 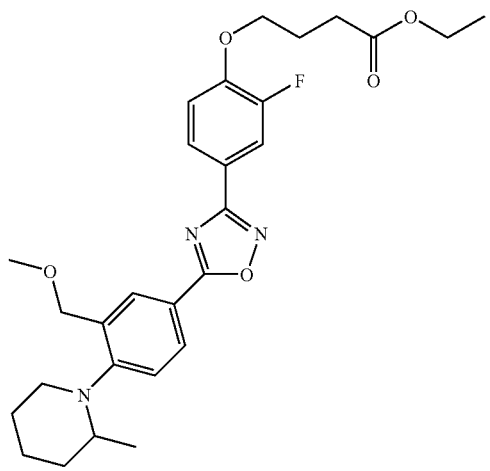 |

-continued
| Example Nb | Formula |
|---|---|
| 164 | 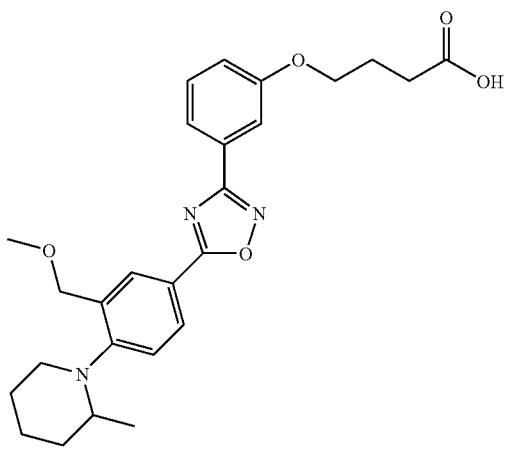 |
| 165 | 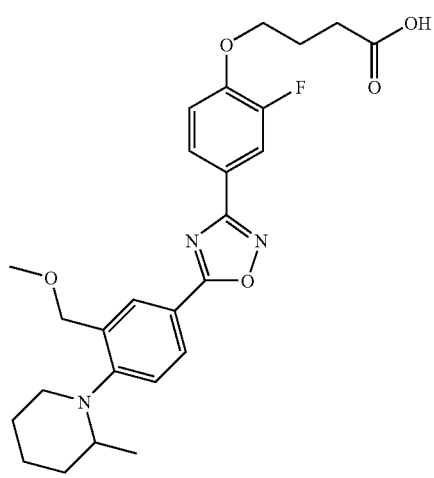 |
| 166 | 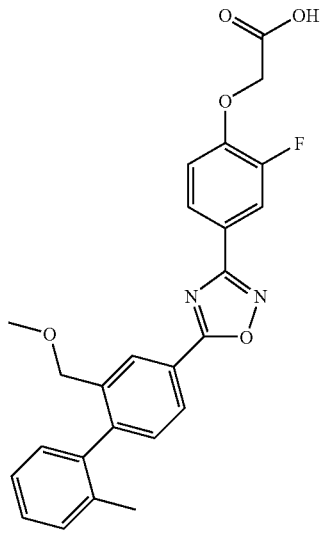 |

| Example Nb | Formula |
|---|---|
| 167 | 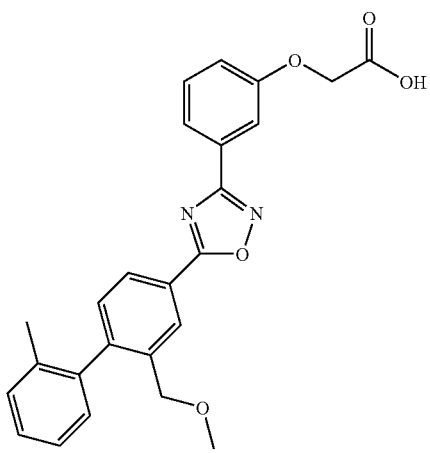 |
| 168 | 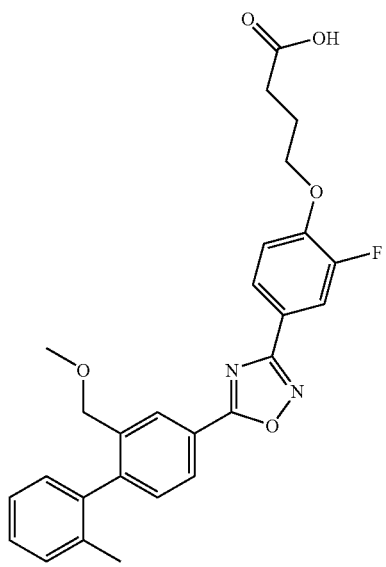 |
| 169 | 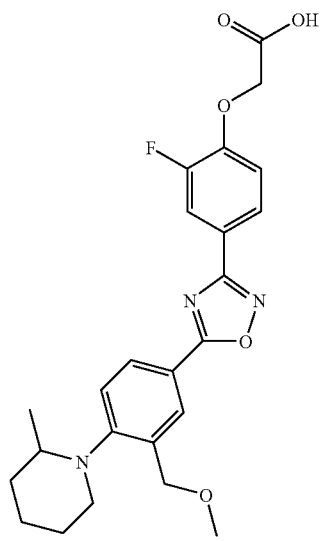 |

-continued

| Example Nb | Formula |
|---|---|
| 171 | |
| 172 | |
| 173 | |

-continued
| Example Nb | Formula |
|---|---|
| 175 | 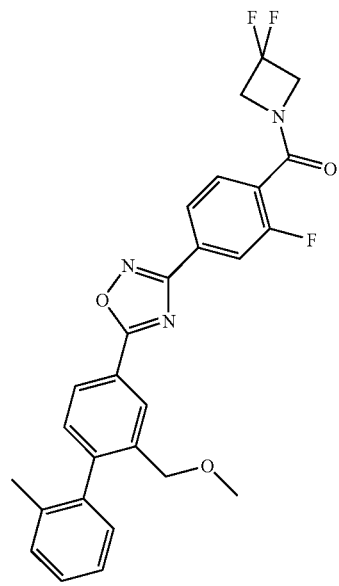 |
| 176 | 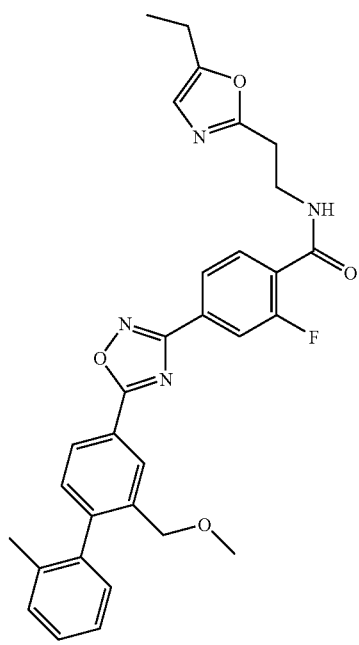 |

-continued
| Example Nb | Formula |
|---|---|
| 177 | 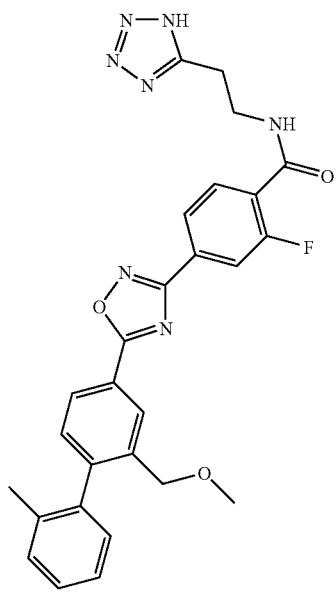 |
| 178 | 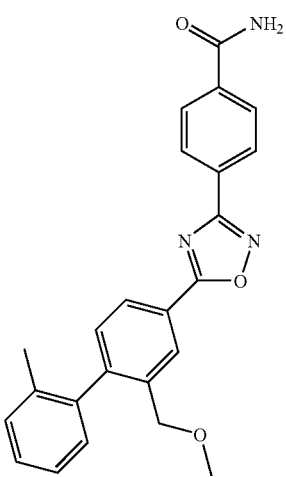 |
| 179 | 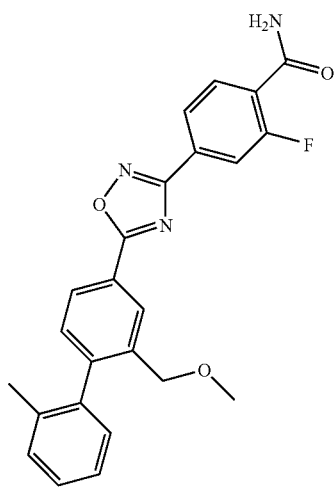 |

-continued

| Example Nb | Formula |
|---|---|
| 180 | |
| 181 | |
| 182 | |

| Example Nb | Formula |
|---|---|
| 183 | 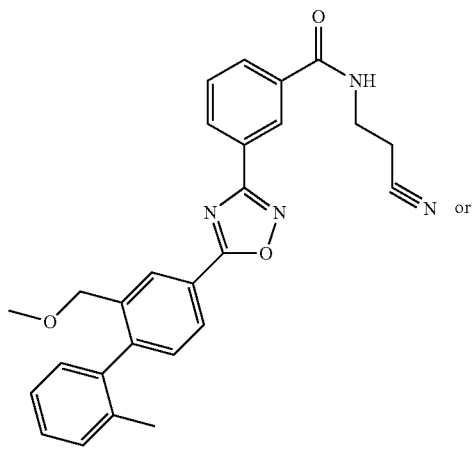 or |
| 195 | 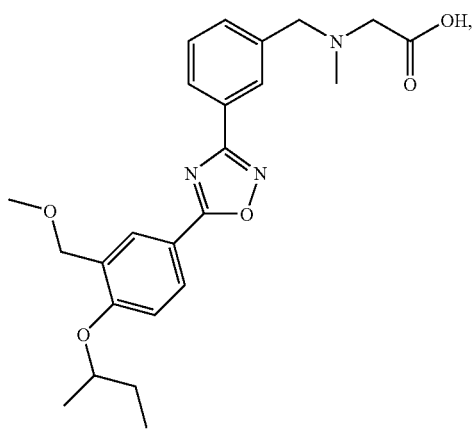 | and tautomers, salts and stereoisomers thereof, including mixtures thereof in all ratios.

7. The compound according to claim 1, said compound having an $EC_{50}$ in GTPγS for the binding to the $S_1P_1$ receptor of less than about 5 μM.

8. A process for the preparation of a compound according to claim 1 comprising reacting:

a) a compound of formula A

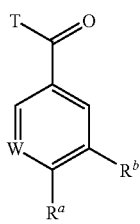

wherein W, $R^a$ and $R^b$ are defined according to claim 1, and T is OH, or a leaving group, or the product of the reaction of isobutyl chloroformate with formula A, wherein T is OH, with a compound of formula B

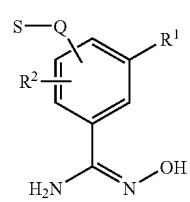

wherein $R^1$, $R^2$ Q and S have the meanings given in claim 1 in the presence of a base, or in case T is OH, in the presence of a suitable condensation reagent, and cyclizing the product,
and optionally converting the compound into a salt.

9. A pharmaceutical composition comprising at least one compound according to claim 1 and/or tautomers, salts, and stereoisomers thereof, and optionally excipients and/or adjuvants.

10. The pharmaceutical composition according to claim 9, further comprising at least one further active ingredient.

11. A kit comprising of separate packs of:
(a) an effective amount of a compound according to claim 1 and/or tautomers, salts, and stereoisomers thereof, and
(b) an effective amount of an active ingredient.

12. A method of treating an disease in a subject comprising administering a composition according to claim 9 to a subject having said disease, wherein the disease is selected from multiple sclerosis, systemic lupus erythematosus, chronic rheumatoid arthritis, rheumatoid arthritis, type I diabetes mellitus, inflammatory bowel disease, biliary cirrhosis, uveitis, Crohn's disease, ulcerative colitis, bullous pemphigoid, sarcoidosis, psoriasis, autoimmune myositis, Wegener's granulomatosis, ichthyosis, Graves ophthalmopathy, atopic dermatitis, asthma, organ transplant rejection, graft versus host disease, lymphoma or leukemia.

13. The compound according to claim 1, wherein $R^b$ is selected from —$CH_3$, —OH, $NO_2$, —$CH_2OH$, —$CH_2OCH_3$, —$CH_2OC_2H_5$, —$CH_2OCH(CH_3)_2$, —$CH_2NHCH_3$, —$CH_2N(CH_3)_2$, —$CH_2SO_2CH_3$, —$(CH_2)_3OCH_3$, —$OCH_3$, —O—$(CH_2)_2OCH_3$, —$OCH_2CH(CH_3)_2$, —$CF_3$, CN, —$NHCOCH_3$, —$NHCOC_2H_5$, —$NHSO_2CH_3$, —$NHSO_2C_2H_5$, —$NHSO_2C_3H_7$, —$NHSO_2N(CH_3)_2$, Cl,

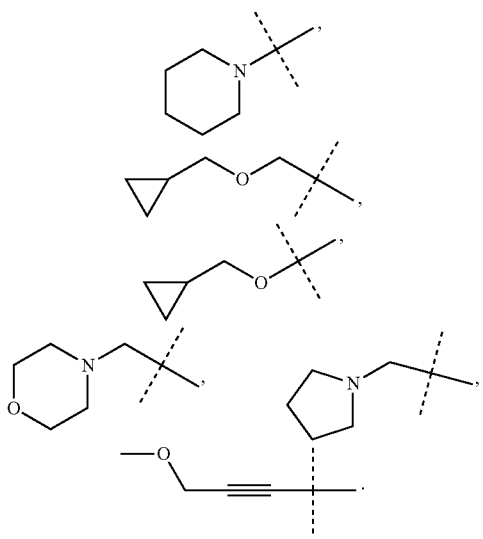

14. The method according to claim 12, wherein said disease is multiple sclerosis.

15. The method according to claim 12, wherein said disease is systemic lupus erythematosus.

16. The method according to claim 12, wherein said disease is chronic rheumatoid arthritis.

17. The method according to claim 12, wherein said disease is rheumatoid arthritis.

18. The method according to claim 12, wherein said disease is type I diabetes mellitus.

19. The method according to claim 12, wherein said disease is inflammatory bowel disease.

20. The method according to claim 12, wherein said disease is biliary cirrhosis.

21. The method according to claim 12, wherein said disease is uveitis.

22. The method according to claim 12, wherein said disease is Crohn's disease.

23. The method according to claim 12, wherein said disease is ulcerative colitis.

24. The method according to claim 12, wherein said disease is bullous pemphigoid.

25. The method according to claim 12, wherein said disease is sarcoidosis.

26. The method according to claim 12, wherein said disease is psoriasis.

27. The method according to claim 12, wherein said disease is autoimmune myositis.

28. The method according to claim 12, wherein said disease is Wegener's granulomatosis.

29. The method according to claim 12, wherein said disease is ichthyosis.

30. The method according to claim 12, wherein said disease is Graves ophthalmopathy.

31. The method according to claim 12, wherein said disease is atopic dermatitis.

32. The method according to claim 12, wherein said disease is asthma.

33. The method according to claim 12, wherein said disease is organ transplant rejection.

34. The method according to claim 12, wherein said disease is graft versus host disease.

35. The method according to claim 12, wherein said disease is lymphoma.

36. The method according to claim 12, wherein said disease is leukemia.

37. A method of suppressing the immune system of a subject comprising the administration of a composition according to claim 9 to a subject in an amount effective to suppress the immune system of said subject.

* * * * *

UNITED STATES PATENT AND TRADEMARK OFFICE
CERTIFICATE OF CORRECTION

PATENT NO. : 8,202,865 B2
APPLICATION NO. : 12/675235
DATED : June 19, 2012
INVENTOR(S) : Anna Quattropani et al.

It is certified that error appears in the above-identified patent and that said Letters Patent is hereby corrected as shown below:

Column 2,
Lines 2-3, "—O[C($R^3$)$_2$], —CON($R^3$)$_2$" should read -- —O[C($R^3$)$_2$]$_n$—CON($R^3$)$_2$--.
Lines 11-12, "—[C($R^3$)$_2$], —CON($R^3$)$_2$" should read -- —[C($R^3$)$_2$]$_n$—CON($R^3$)$_2$--.

Column 3,
Line 65, "PyBOPO" should read --PyBOP®--.

Column 4,
Line 64, "consists in" should read --consists of--.

Column 5,
Line 10, "chloride Vila" should read --chloride VIIa--.

Column 9,
Lines 31-32, "methyl 2-fluoro-4-{5-[2-methyl-2-(morpholin-4-ylmethyl)biphenyl-4-yl]-1,2,4-oxadiazol-3-yl}benzoate" should read
--methyl 2-fluoro-4-{5-[2'-methyl-2-(morpholin-4-ylmethyl)biphenyl-4-yl]-1,2,4-oxadiazol-3-yl}benzoate--.

Column 11,
Line 9, "(Miyaura, N." should read --(Miyura, N.--.
Lines 12-13, "temperature" should read --temperatures--.

Column 16,
Line 11, "temperature" should read --temperatures--.
Line 60, "(XI) or" should read --(Xi) or--.

Signed and Sealed this
Seventeenth Day of December, 2013

Margaret A. Focarino
*Commissioner for Patents of the United States Patent and Trademark Office*

Column 17,
Line 52, "2-methyl-1,1':2,1"-terphenyl-4-carboxylic acid" should read
--2-methyl-1,1':2',1"-terphenyl-4-carboxylic acid--.
Column 18,
Line 63, "as it" should read --as is--.
Column 19,
Scheme 9,
"
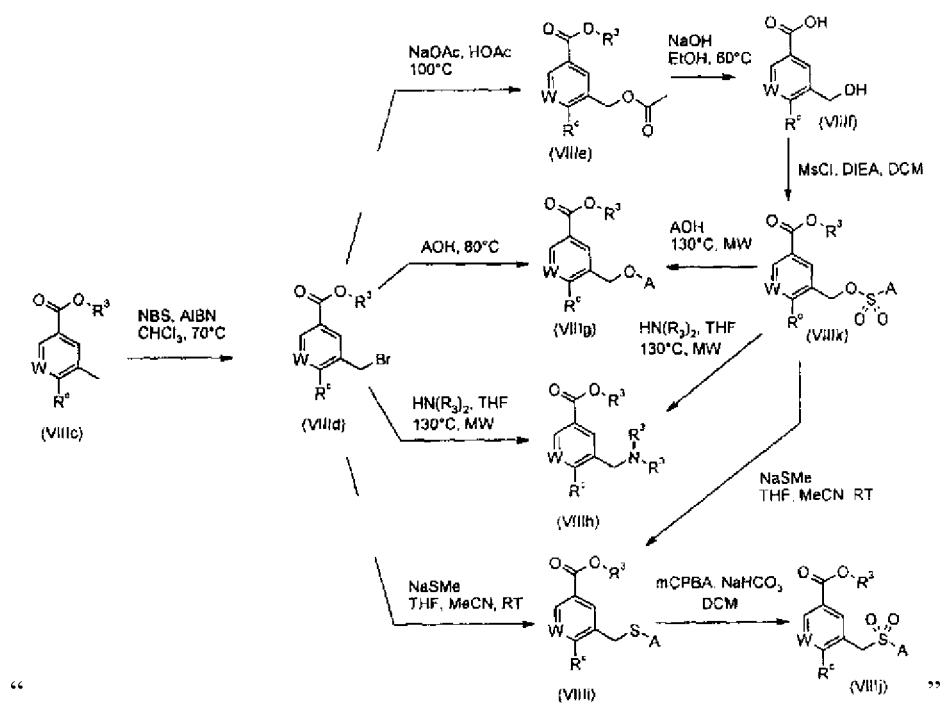
"
should read

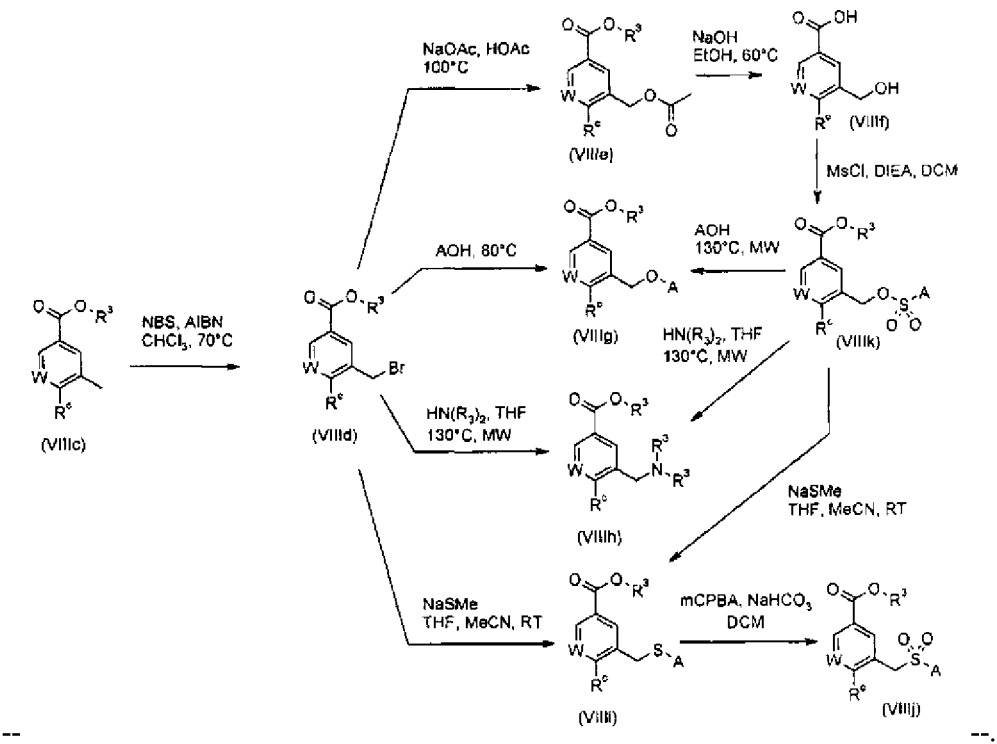

Column 23,
Line 62, "a two steps process" should read --a two-step process--.

Column 27,
Line 49, "temperature" should read --temperatures--.

Column 28,
Lines 4-5, "temperature" should read --temperatures--.
Line 64, "analine" should read --aniline--.

Column 32,
Line 22, "a compounds" should read --a compound--.
Line 40, "a compounds" should read --a compound--.

Column 35,
Lines 36-37, "-CH$_2$-O-(CH$_2$)$_n$CO$_2$H, -CH$_2$-O-(CH$_2$)$_n$CO$_2$CH$_3$" should read
-- -CH$_2$O(CH$_2$)$_n$CO$_2$H, -CH$_2$O(CH$_2$)$_n$CO$_2$CH$_3$--.

Column 35,
Lines 37-38, "-CH$_2$-O-(CH$_2$)$_n$CO$_2$C$_2$H$_5$, -CH$_2$-O-(CH$_2$)$_n$CO$_2$C(CH$_3$)$_3$" should read
-- -CH$_2$O(CH$_2$)$_n$CO$_2$C$_2$H$_5$, -CH$_2$O(CH$_2$)$_n$CO$_2$C(CH$_3$)$_3$--.
Line 55, "defined" should read --defined.--.

Column 36,
Line 1, "defined" should read --defined.--.

CERTIFICATE OF CORRECTION (continued)
U.S. Pat. No. 8,202,865 B2

Line 61, "-CH$_2$N(CH$_3$)-(CH$_2$)$_n$-CO$_2$CH$_3$" should read -- -CH$_2$N(CH$_3$)-(CH$_2$)$_n$CO$_2$CH$_3$--.
Line 67, "-CH$_2$-O-(CH$_2$)$_n$CO$_2$H" should read -- -CH$_2$O(CH$_2$)$_n$CO$_2$H--.

Column 37,
Line 1, "-CH$_2$-O-(CH$_2$)$_n$CO$_2$C$_2$H$_5$" should read -- -CH$_2$O(CH$_2$)$_n$CO$_2$C$_2$H$_5$--.
Line 2, "-O(CH$_2$)$_n$CO$_2$" should read -- -O(CH$_2$)$_n$CO$_2$H--.
Line 39, "-CH$_2$N(CH$_3$)-(CH$_2$)$_n$CO$_2$C(CF$_{13}$)$_3$" should read
    -- -CH$_2$N(CH$_3$)-(CH$_2$)$_n$CO$_2$C(CH$_3$)$_3$--.
Lines 44-46, "-CH$_2$-O-(CH$_2$)$_n$CO$_2$H, -CH$_2$-O-(CH$_2$)$_n$CO$_2$CH$_3$, -CH$_2$-O-(CH$_2$)$_n$CO$_2$C$_2$H$_5$,
    -CH$_2$-O-(CH$_2$)$_n$CO$_2$C(CH$_3$)$_3$" should read
    -- -CH$_2$O(CH$_2$)$_n$CO$_2$H, -CH$_2$O(CH$_2$)$_n$CO$_2$CH$_3$, -CH$_2$O(CH$_2$)$_n$CO$_2$C$_2$H$_5$,
       -CH$_2$O(CH$_2$)$_n$CO$_2$C(CH$_3$)$_3$--.
Lines 47-48, "-O(CH$_2$)$_n$CO$_2$C(CF$_{13}$)$_3$" should read -- -O(CH$_2$)$_n$CO$_2$C(CH$_3$)$_3$--.

Column 38,
Line 17, "denotes -COO- or" should read --denotes -NR$^3$-, -COO- or--.

Column 59,
Example Nb "32",

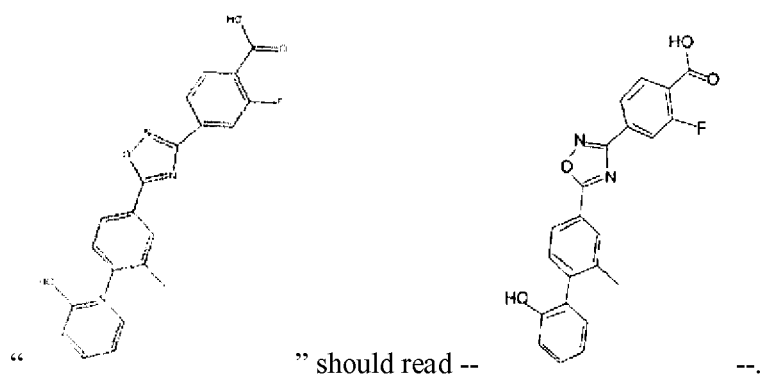

" should read --

Column 101.
Example Nb "97",

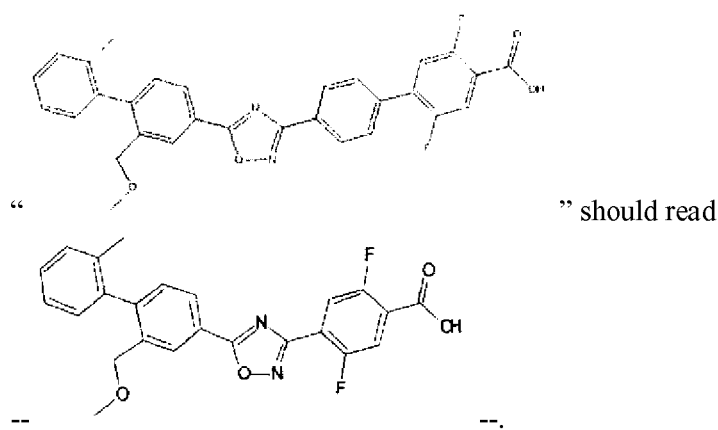

" should read --  --.

Column 191,
Lines 40-43,

" 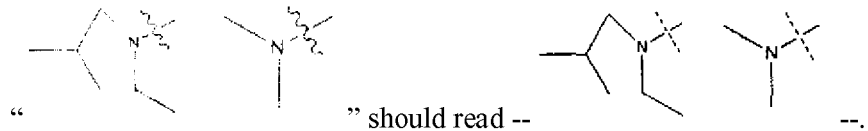 " should read -- --.

Column 192,
Line 10, "germinal" should read --geminal--.

Column 196,
Line 16, "is CH$_2$OCH$_3$" should read --is –CH$_2$OCH$_3$--.
Lines 25-26, "-CH$_2$-O-(CH$_2$)$_n$CO$_2$R$^3$" should read -- -CH$_2$O(CH$_2$)$_n$CO$_2$R$^3$--.

Column 203,
Lines 18-19, "a compounds of" should read --a compound of--.

Column 206,
Line 18, "7.70-7.62, m, 2H)," should read --7.70-7.62 (m, 2H),--.

Column 207,
Line 64, "to obtain get the title" should read --to get the title--.

Column 215,
Line 1, "153-1.54" should read --1.53-1.54--.

Column 216,
Line 45, "3.10-312" should read --3.10-3.12--.

Column 226,
Line 7, "hours The" should read --hours. The--.

Column 228,
Lines 24-25, "Methyl 7-hydroxy-2-methylbiphenyl-4-carboxylate" should read
    --Methyl 2'-hydroxy-2-methylbiphenyl-4-carboxylate--.

Column 239,
Line 66, "(5 mL). sodium" should read --(5 mL). Sodium--.

Column 244,
Line 17, "solvent were removed under reduce" should read
    --solvent was removed under reduced--.

Column 247,
Line 45, "Solvent were" should read --Solvents were-.

Column 249,
Line 6, "(Method 13)" should read --(Method B)--.
Line 42, "tert-Butyl" should read --Tert-Butyl--.

Column 257,
Line 35, "To a solution of solution of" should read --To a solution of--.

Column 260,
Line 33, "glycine-ter-butyl" should read --glycine-tert-butyl--.

Column 270,
Lines 57-58, "3-{[(2-Methoxy-ethyl)-methyl-amino]-methyl}-methyl)" should read
    --3-{[(2-Methoxy-ethyl)-methyl-amino]-methyl}-benzonitrile--.
Line 66, "washed water with" should read --washed with water--.

Column 274,
Line 1, "methyl 4-[3-(2',6'-dimethylbiphenyl-4-yl)-1" should read
    --methyl 4-[5-(2',6'-dimethylbiphenyl-4-yl)-1--.

Column 290.
Lines 8-9, "4-[3-(2',4'-dimethoxy-2-methylbiphenyl-4-yl)-1,2,4-oxadiazol-3-yl]-2-
        fluorobenzoic acid" should read
    --4-[5-(2',4'-dimethoxy-2-methylbiphenyl-4-yl)-1,2,4-oxadiazol-3-yl]-2-
        fluorobenzoic acid--.

Column 294,
Lines 8-9, "4-[3-(2',5'-dimethoxy-2-methylbiphenyl-4-yl)-1,2,4-oxadiazol-3-yl]-2-
        fluorobenzoic acid" should read
    --4-[5-(2',5'-dimethoxy-2-methylbiphenyl-4-yl)-1,2,4-oxadiazol-3-yl]-2-
        fluorobenzoic acid--.

Column 307,
Line 31, "under reduce" should read --under reduced--.

Column 312,
Line 61, "recristalized" should read --recrystallized--.

Column 314,
Lines 59-61, "(2-fluoro-4-{5-[4-(2-methylpiperidin-1-0)-3-(trifluoromethyl)phenyl]-
        1,2,4-oxadiazol-3-yl}phenoxy)acetic acid" should read
    --(2-fluoro-4-{5-[4-(2-methylpiperidin-1-yl)-3-(trifluoromethyl)phenyl]-
        1,2,4-oxadiazol-3-yl}phenoxy)acetic acid--.

Column 322,
Lines 60-61, "dried freezed" should read --dry freezed--.

Column 360,
Lines 21-23, "2,5-di fluoro-4-{5-[2-(methoxymethyl)-2'-methylbiphenyl-4-yl]-1,2,4-oxadiazol-3-yl}benzoic acid" should read
--2,5-difluoro-4-{5-[2-(methoxymethyl)-2'-methylbiphenyl-4-yl]-1,2,4-oxadiazol-3-yl}benzoic acid--.
Lines 42-43, "4-{5-[7-chloro-2-(methoxymethyl)biphenyl-4-yl]-1,2,4-oxadiazol-3-yl}-2-fluorobenzoic acid" should read
--4-{5-[2'-chloro-2-(methoxymethyl)biphenyl-4-yl]-1,2,4-oxadiazol-3-yl}-2-fluorobenzoic acid--.

Column 378,
Line 20, "UPLC/MS" should read --HPLC/MS--.

Column 390,
Line 14, "E4thyl" should read --Ethyl--.
Line 25, "phase were" should read --phase was--.

Column 391,
Line 65, "1.90-166" should read --1.90-1.66--.

Column 473,
Example Nb "66",

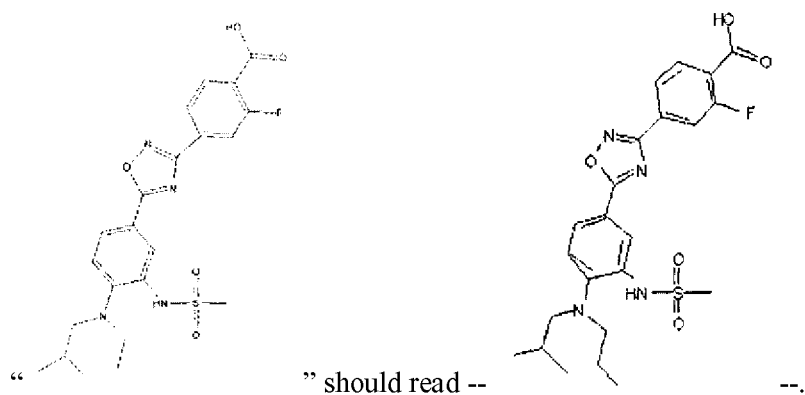

" should read --                --.

CERTIFICATE OF CORRECTION (continued)
U.S. Pat. No. 8,202,865 B2

Column 477,
Example Nb "71",

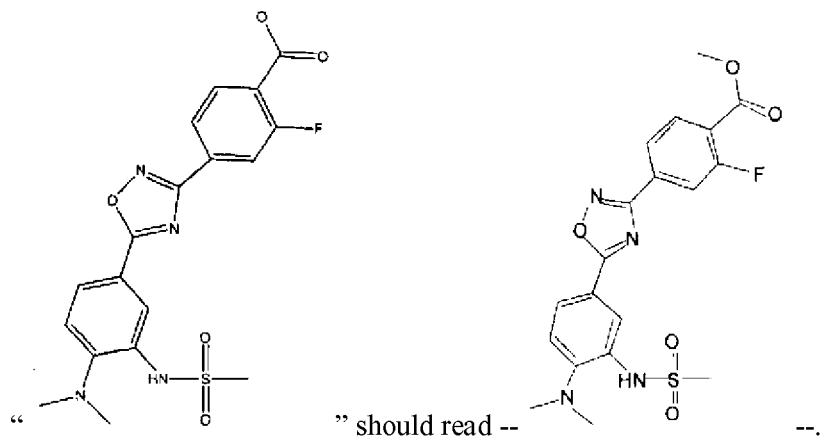
" should read --   --.

Column 527,
Example Nb "140",

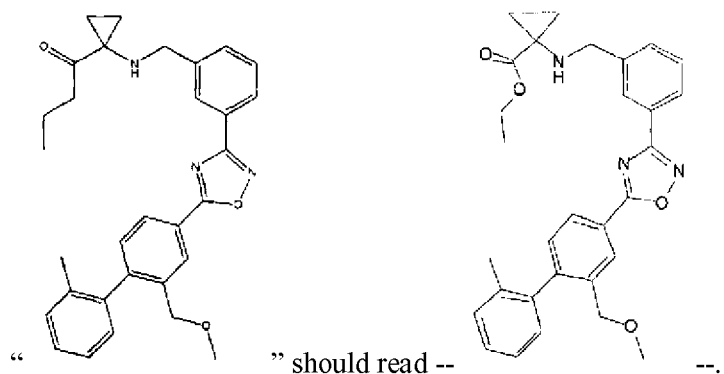
" should read --   --.

Column 545,
Example Nb "167",

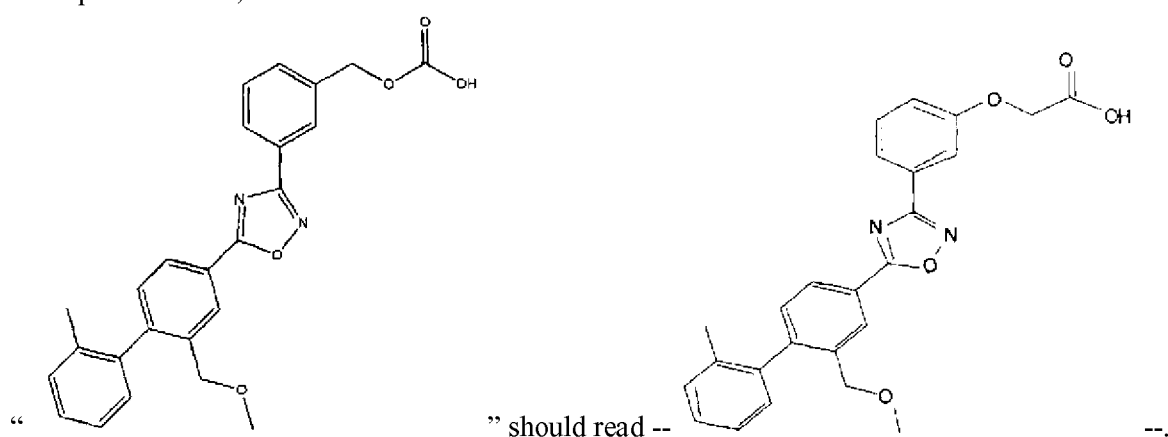
" should read --   --.

CERTIFICATE OF CORRECTION (continued)
U.S. Pat. No. 8,202,865 B2

Column 547,
Example Nb "171",

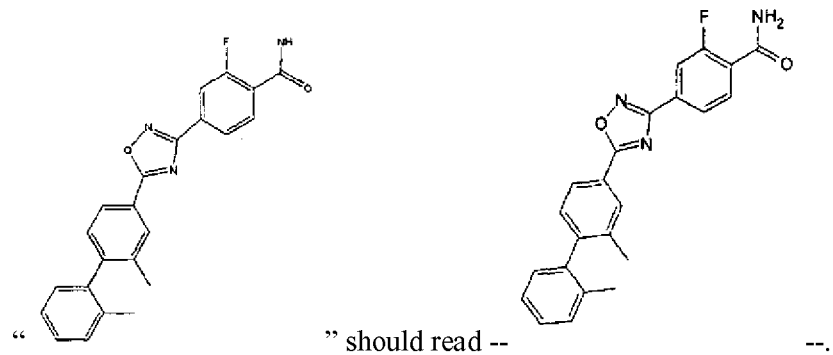

" " should read -- --.

Column 566,
Line 39, "go" should read --go.--.

In the Claims

Column 637, Claim 6,
Example Nb "106",

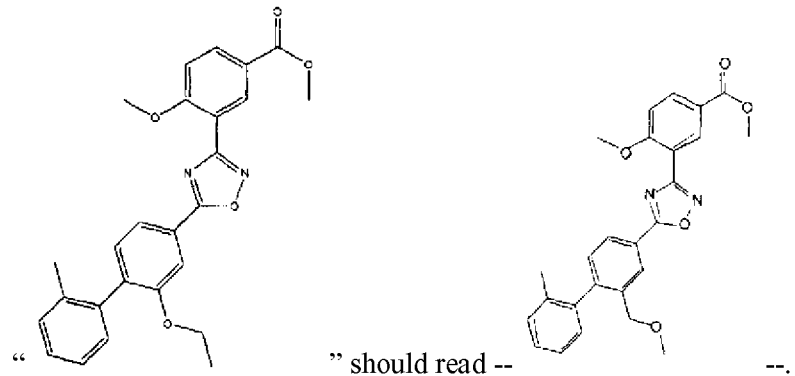

" " should read -- --.

Column 637, Claim 6,
Example Nb "107",

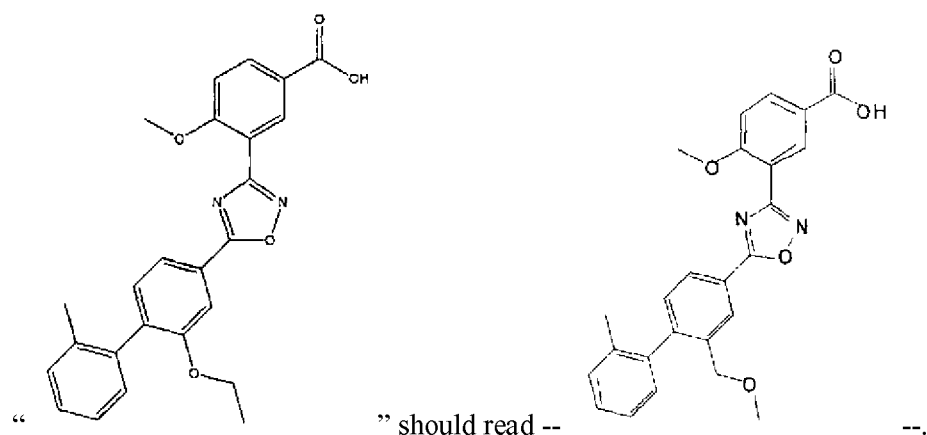

" " should read -- --.

CERTIFICATE OF CORRECTION (continued)
U.S. Pat. No. 8,202,865 B2

Column 639, Claim 6,
Example Nb "108",

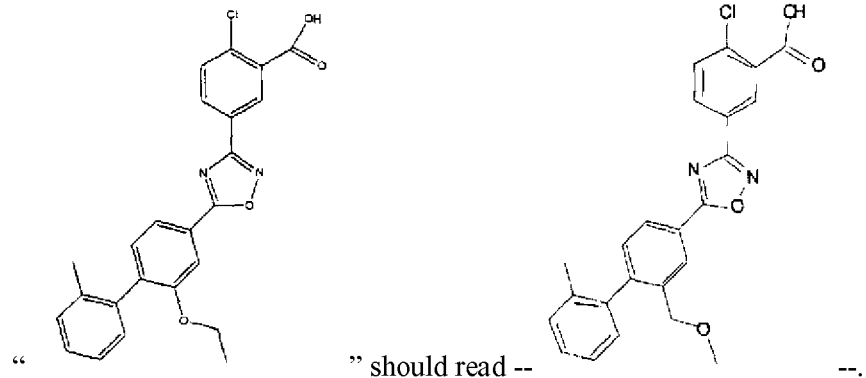

" should read -- [structure] --.

Column 693, Claim 12,
Line 15, "—O—(CH$_2$)$_2$OCH$_3$" should read -- —O(CH$_2$)$_2$OCH$_3$--.

UNITED STATES PATENT AND TRADEMARK OFFICE
CERTIFICATE OF CORRECTION

PATENT NO. : 8,202,865 B2
APPLICATION NO. : 12/675235
DATED : June 19, 2012
INVENTOR(S) : Anna Quattropani et al.

Page 1 of 9

It is certified that error appears in the above-identified patent and that said Letters Patent is hereby corrected as shown below:

In the Specification

Column 2,
Lines 2-3, "—O[C($R^3$)$_2$], —CON($R^3$)$_2$" should read -- —O[C($R^3$)$_2$]$_n$—CON($R^3$)$_2$--.
Lines 11-12, "—[C($R^3$)$_2$], —CON($R^3$)$_2$" should read -- —[C($R^3$)$_2$]$_n$—CON($R^3$)$_2$--.

Column 3,
Line 65, "PyBOPO" should read --PyBOP®--.

Column 4,
Line 64, "consists in" should read --consists of--.

Column 5,
Line 10, "chloride VIa" should read --chloride VIIa--.

Column 9,
Lines 31-32, "methyl 2-fluoro-4-{5-[2-methyl-2-(morpholin-4-ylmethyl)biphenyl-4-yl]-1,2,4-oxadiazol-3-yl}benzoate" should read
--methyl 2-fluoro-4-{5-[2'-methyl-2-(morpholin-4-ylmethyl)biphenyl-4-yl]-1,2,4-oxadiazol-3-yl}benzoate--.

Column 11,
Line 9, "(Miyaura, N." should read --(Miyura, N.--.
Lines 12-13, "temperature" should read --temperatures--.

This certificate supersedes the Certificate of Correction issued December 17, 2013.

Signed and Sealed this
Thirteenth Day of May, 2014

Michelle K. Lee
*Deputy Director of the United States Patent and Trademark Office*

Column 16,
Line 11, "temperature" should read --temperatures--.
Line 60, "(XI) or" should read --(Xi) or--.
Column 17,
Line 52, "2-methyl-1,1':2,1''-terphenyl-4-carboxylic acid" should read
--2-methyl-1,1':2',1''-terphenyl-4-carboxylic acid--.
Column 18,
Line 63, "as it" should read --as is--.
Column 19,
Scheme 9,
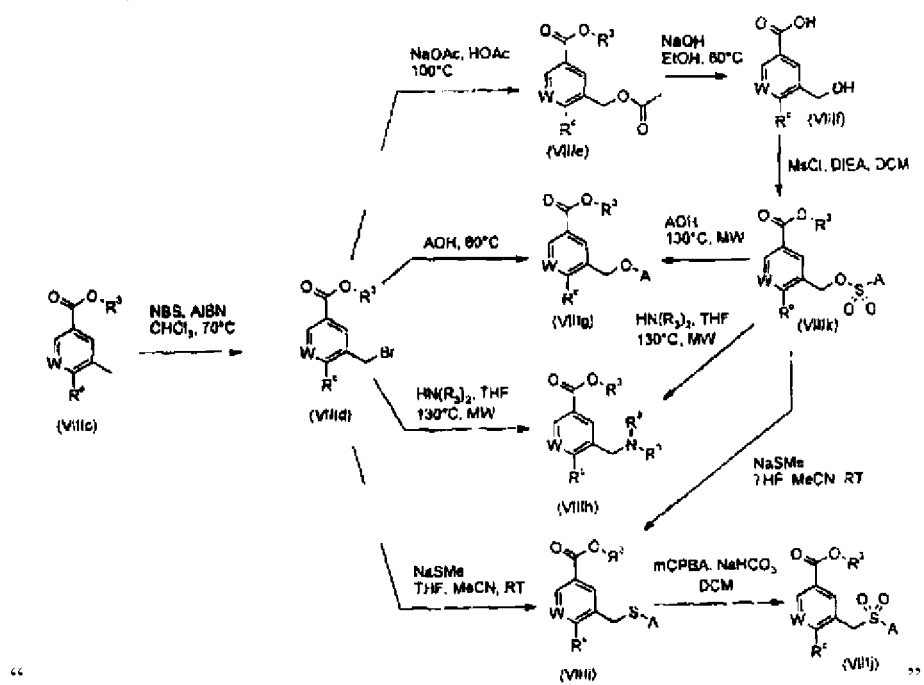
" " should read

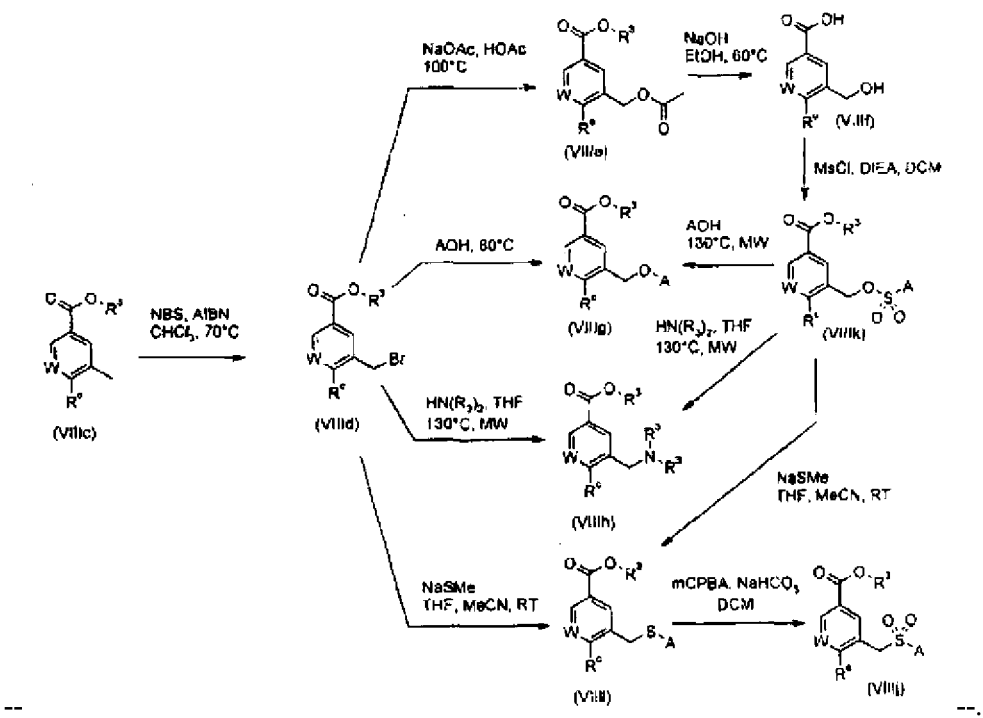

Column 23,
Line 62, "a two steps process" should read --a two-step process--.

Column 27,
Line 49, "temperature" should read --temperatures--.

Column 28,
Lines 4-5, "temperature" should read --temperatures--.
Line 64, "analine" should read --aniline--.

Column 32,
Line 22, "a compounds" should read --a compound--.
Line 40, "a compounds" should read --a compound--.

Column 35,
Lines 36-37, "-CH$_2$-O-(CH$_2$)$_n$CO$_2$H, -CH$_2$-O-(CH$_2$)$_n$CO$_2$CH$_3$" should read
-- -CH$_2$O(CH$_2$)$_n$CO$_2$H, -CH$_2$O(CH$_2$)$_n$CO$_2$CH$_3$--.

Column 35,
Lines 37-38, "-CH$_2$-O-(CH$_2$)$_n$CO$_2$C$_2$H$_5$, -CH$_2$-O-(CH$_2$)$_n$CO$_2$C(CH$_3$)$_3$" should read
-- -CH$_2$O(CH$_2$)$_n$CO$_2$C$_2$H$_5$, -CH$_2$O(CH$_2$)$_n$CO$_2$C(CH$_3$)$_3$--.
Line 55, "defined" should read --defined.--.

CERTIFICATE OF CORRECTION (continued)
U.S. Pat. No. 8,202,865 B2

Column 36,
Line 1, "defined" should read --defined.--.
Line 61, "-CH$_2$N(CH$_3$)-(CH$_2$)$_n$-CO$_2$CH$_3$" should read -- -CH$_2$N(CH$_3$)-(CH$_2$)$_n$CO$_2$CH$_3$--.
Line 67, "-CH$_2$-O-(CH$_2$)$_n$CO$_2$H" should read -- -CH$_2$O(CH$_2$)$_n$CO$_2$H--.

Column 37,
Line 1, "-CH$_2$-O-(CH$_2$)$_n$CO$_2$C$_2$H$_5$" should read -- -CH$_2$O(CH$_2$)$_n$CO$_2$C$_2$H$_5$--.
Line 2, "-O(CH$_2$)$_n$CO$_2$" should read -- -O(CH$_2$)$_n$CO$_2$H--.
Line 39, "-CH$_2$N(CH$_3$)-(CH$_2$)$_n$CO$_2$C(CF$_{13}$)$_3$" should read -- -CH$_2$N(CH$_3$)-(CH$_2$)$_n$CO$_2$C(CH$_3$)$_3$--.
Lines 44-46, "-CH$_2$-O-(CH$_2$)$_n$CO$_2$H, -CH$_2$-O-(CH$_2$)$_n$CO$_2$CH$_3$, -CH$_2$-O-(CH$_2$)$_n$CO$_2$C$_2$H$_5$, -CH$_2$-O-(CH$_2$)$_n$CO$_2$C(CH$_3$)$_3$" should read
-- -CH$_2$O(CH$_2$)$_n$CO$_2$H, -CH$_2$O(CH$_2$)$_n$CO$_2$CH$_3$, -CH$_2$O(CH$_2$)$_n$CO$_2$C$_2$H$_5$, -CH$_2$O(CH$_2$)$_n$CO$_2$C(CH$_3$)$_3$--.
Lines 47-48, "-O(CH$_2$)$_n$CO$_2$C(CF$_{13}$)$_3$" should read -- -O(CH$_2$)$_n$CO$_2$C(CH$_3$)$_3$--.

Column 38,
Line 17, "denotes -COO- or" should read --denotes -NR$^3$-, -COO- or--.

Column 59,
Example Nb "32",

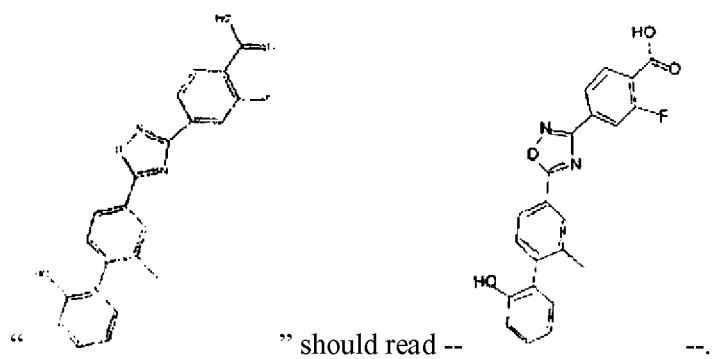 " should read --

Column 101,
Example Nb "97",

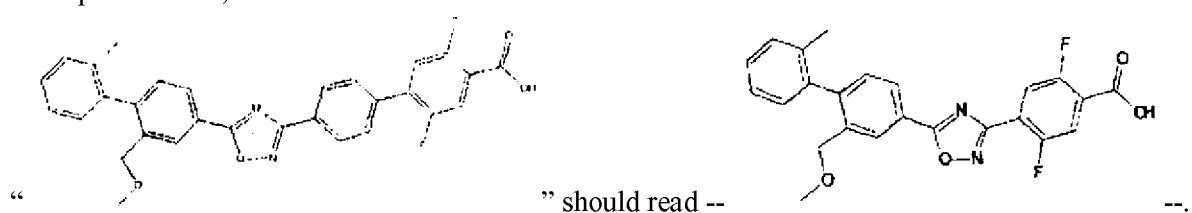 " should read --

Column 191,
Lines 40-43,

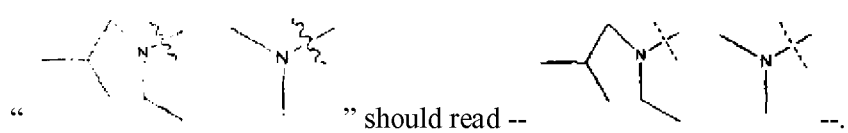 " should read --

Column 192,
Line 10, "germinal" should read --geminal--.

Column 196,
Line 16, "is CH$_2$OCH$_3$" should read --is –CH$_2$OCH$_3$--.
Lines 25-26, "-CH$_2$-O-(CH$_2$)$_n$CO$_2$R$^3$" should read -- -CH$_2$O(CH$_2$)$_n$CO$_2$R$^3$--.

Column 203,
Lines 18-19, "a compounds of" should read --a compound of--.

Column 206,
Line 18, "7.70-7.62, m, 2H)," should read --7.70-7.62 (m, 2H),--.

Column 207,
Line 64, "to obtain get the title" should read --to get the title--.

Column 215,
Line 1, "153-1.54" should read --1.53-1.54--.

Column 216,
Line 45, "3.10-312" should read --3.10-3.12--.

Column 226,
Line 7, "hours The" should read --hours. The--.

Column 228,
Lines 24-25, "Methyl 7-hydroxy-2-methylbiphenyl-4-carboxylate" should read
--Methyl 2'-hydroxy-2-methylbiphenyl-4-carboxylate--.

Column 239,
Line 66, "(5 mL). sodium" should read --(5 mL). Sodium--.

Column 244,
Line 17, "solvent were removed under reduce" should read --solvent was removed under reduced--.

Column 247,
Line 45, "Solvent were" should read --Solvents were--.

Column 249,
Line 6, "(Method 13)" should read --(Method B)--.
Line 42, "tert-Butyl" should read --Tert-Butyl--.

Column 257,
Line 35, "To a solution of solution of" should read --To a solution of--.

Column 260,
Line 33, "glycine-ter-butyl" should read --glycine-tert-butyl--.

Column 270,
Lines 57-58, "3-{[(2-Methoxy-ethyl)-methyl-amino]-methyl}-methyl)" should read
    --3-{[(2-Methoxy-ethyl)-methyl-amino]-methyl}-benzonitrile--.
Line 66, "washed water with" should read --washed with water--.

Column 274,
Line 1, "methyl 4-[3-(2',6'-dimethylbiphenyl-4-yl)-1" should read
    --methyl 4-[5-(2',6'-dimethylbiphenyl-4-yl)-1--.

Column 290,
Lines 8-9, "4-[3-(2',4'-dimethoxy-2-methylbiphenyl-4-yl)-1,2,4-oxadiazol-3-yl]-2-
    fluorobenzoic acid" should read
    --4-[5-(2',4'-dimethoxy-2-methylbiphenyl-4-yl)-1,2,4-oxadiazol-3-yl]-2-
    fluorobenzoic acid--.

Column 294,
Lines 8-9, "4-[3-(2',5'-dimethoxy-2-methylbiphenyl-4-yl)-1,2,4-oxadiazol-3-yl]-2-
    fluorobenzoic acid" should read
    --4-[5-(2',5'-dimethoxy-2-methylbiphenyl-4-yl)-1,2,4-oxadiazol-3-yl]-2-
    fluorobenzoic acid--.

Column 307,
Line 31, "under reduce" should read --under reduced--.

Column 312,
Line 61, "recristalized" should read --recrystallized--.

Column 314,
Lines 59-61, "(2-fluoro-4-{5-[4-(2-methylpiperidin-1-0)-3-(trifluoromethyl)phenyl]-
    1,2,4-oxadiazol-3-yl}phenoxy)acetic acid" should read
    --(2-fluoro-4-{5-[4-(2-methylpiperidin-1-yl)-3-(trifluoromethyl)phenyl]-
    1,2,4-oxadiazol-3-yl}phenoxy)acetic acid--.

Column 322,
Lines 60-61, "dried freezed" should read --dry freezed--.

Column 360,
Lines 21-23, "2,5-di fluoro-4-{5-[2-(methoxymethyl)-2'-methylbiphenyl-4-yl]-1,2,4-
    oxadiazol-3-yl} benzoic acid" should read
    --2,5-difluoro-4-{5-[2-(methoxymethyl)-2'-methylbiphenyl-4-yl]-1,2,4-
    oxadiazol-3-yl}benzoic acid--.

Lines 42-43, "4-{5-[7-chloro-2-(methoxymethyl)biphenyl-4-yl]-1,2,4-oxadiazol-3-yl}-2-fluorobenzoic acid" should read
--4-{5-[2'-chloro-2-(methoxymethyl)biphenyl-4-yl]-1,2,4-oxadiazol-3-yl}-2-fluorobenzoic acid--.

Column 378,
Line 20, "UPLC/MS" should read --HPLC/MS--.

Column 390,
Line 14, "E4thyl" should read --Ethyl--.
Line 25, "phase were" should read --phase was--.

Column 391,
Line 65, "1.90-166" should read --1.90-1.66--.

Column 473,
Example Nb "66",

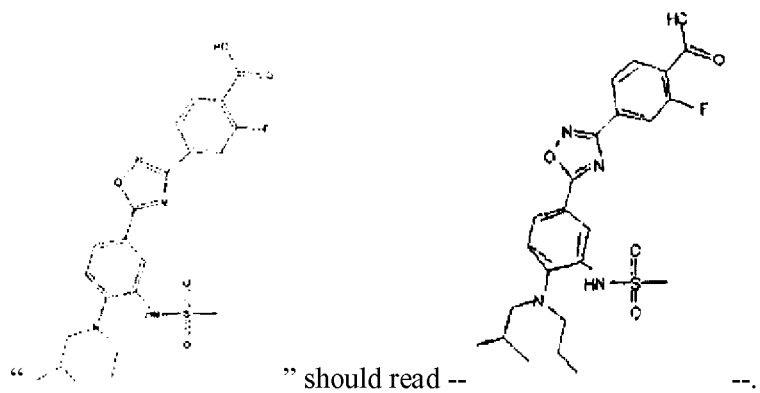 " should read -- --.

Column 477,
Example Nb "71",

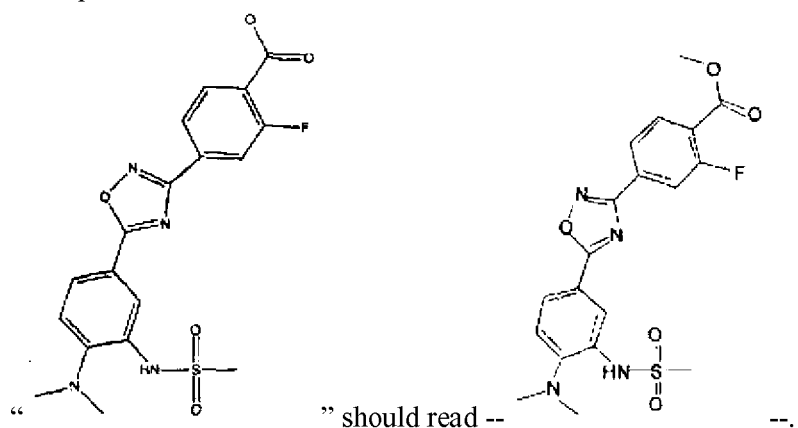 " should read -- --.

CERTIFICATE OF CORRECTION (continued)
U.S. Pat. No. 8,202,865 B2

Column 527,
Example Nb "140",

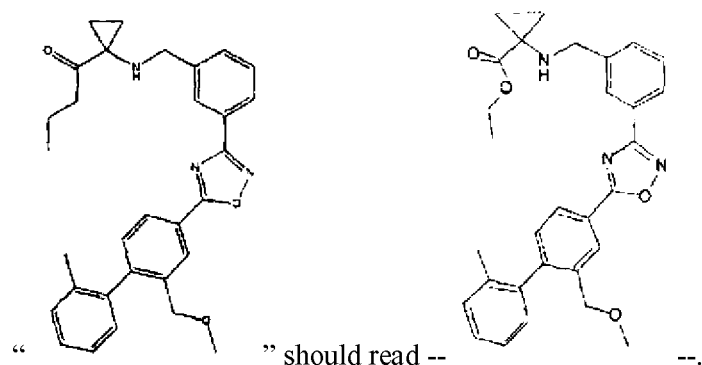

" should read --  --.

Column 545,
Example Nb "167",

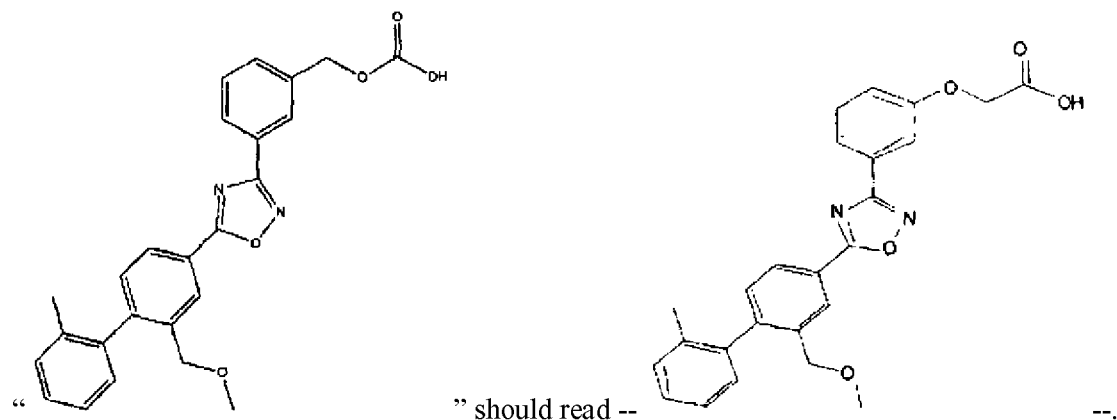

" should read --  --.

Column 547,
Example Nb "171",

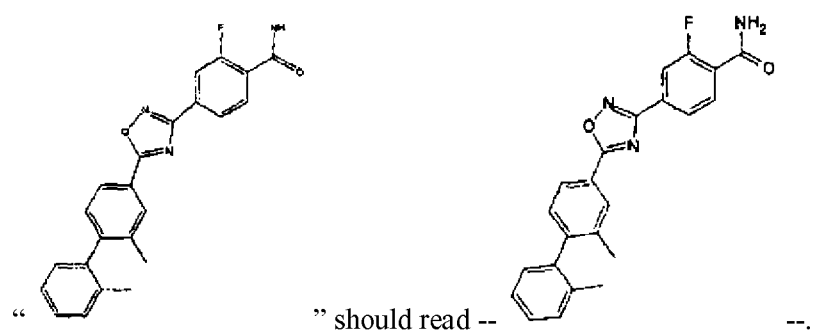

" should read --  --.

Column 566,
Line 39, "go" should read --go.--.

CERTIFICATE OF CORRECTION (continued)
U.S. Pat. No. 8,202,865 B2

In the Claims

Column 637, Claim 6,
Example Nb "106",

" 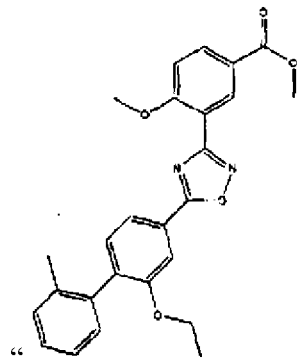 " should read -- 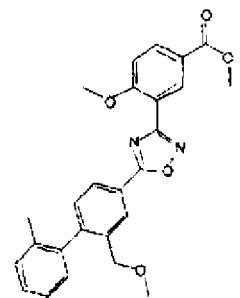 --.

Column 637, Claim 6,
Example Nb "107",

" 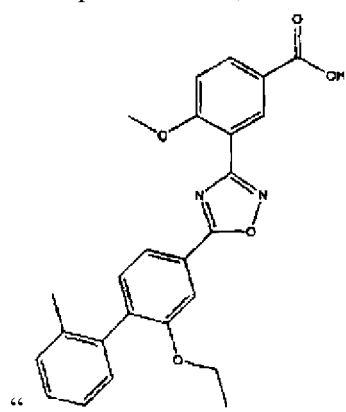 " should read -- 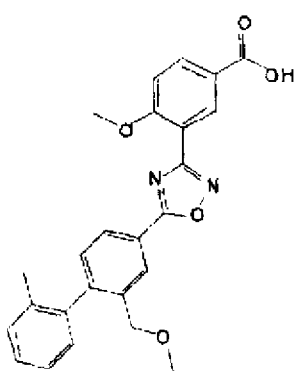 --.

Column 639, Claim 6,
Example Nb "108",

" 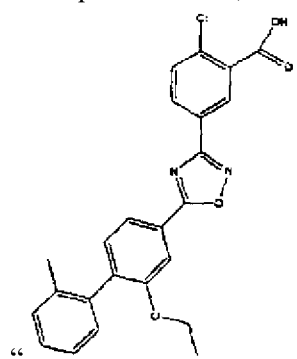 " should read -- 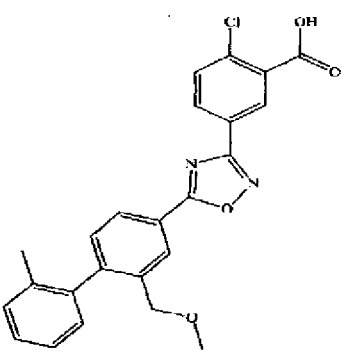 --.

Column 693, Claim 12,
Line 15, "—O—(CH$_2$)$_2$OCH$_3$" should read -- —O(CH$_2$)$_2$OCH$_3$--.